United States Patent
Fyfe et al.

(10) Patent No.: US 9,890,185 B2
(45) Date of Patent: Feb. 13, 2018

(54) UREA DERIVATIVES USEFUL AS KINASE INHIBITORS

(71) Applicants: Respivert Limited, Buckinghamshire (GB); Topivert Pharma Limited, London (GB)

(72) Inventors: Matthew Colin Thor Fyfe, London (GB); Stephen Malcolm Thom, Nottingham (GB); Thomas Matthew Baker, Nottingham (GB); Gareth William Harbottle, Nottingham (GB); Vedran Hasimbegovic, Nottingham (GB); Aaron Rigby, Nottingham (GB)

(73) Assignees: Respivert Limited, Buckinghamshire (GB); Topivert Pharma Limited, London (GB)

( * ) Notice: Subject to any disclaimer, the term of this patent is extended or adjusted under 35 U.S.C. 154(b) by 0 days.

(21) Appl. No.: 15/105,912

(22) PCT Filed: Dec. 19, 2014

(86) PCT No.: PCT/GB2014/053781
§ 371 (c)(1),
(2) Date: Jun. 17, 2016

(87) PCT Pub. No.: WO2015/092423
PCT Pub. Date: Jun. 25, 2015

(65) Prior Publication Data
US 2016/0318958 A1 Nov. 3, 2016

(30) Foreign Application Priority Data
Dec. 20, 2013 (GB) .................................. 1322672.5
Sep. 17, 2014 (GB) .................................. 1416430.5

(51) Int. Cl.
| | | |
|---|---|---|
| C07F 9/6512 | (2006.01) |
| C07D 403/12 | (2006.01) |
| C07D 213/74 | (2006.01) |
| C07D 213/75 | (2006.01) |
| C07D 401/02 | (2006.01) |
| C07D 401/12 | (2006.01) |
| C07D 405/12 | (2006.01) |
| C07D 239/47 | (2006.01) |
| C07D 413/12 | (2006.01) |
| C07F 9/58 | (2006.01) |
| C07F 9/6558 | (2006.01) |
| A61K 31/44 | (2006.01) |
| A61K 31/4427 | (2006.01) |
| A61K 31/4439 | (2006.01) |
| A61K 31/444 | (2006.01) |
| A61K 31/496 | (2006.01) |

(Continued)

(52) U.S. Cl.
CPC .......... *C07F 9/65127* (2013.01); *A61K 31/44* (2013.01); *A61K 31/444* (2013.01); *A61K 31/4427* (2013.01); *A61K 31/4439* (2013.01); *A61K 31/496* (2013.01); *A61K 31/505* (2013.01); *A61K 31/506* (2013.01); *A61K 31/5377* (2013.01); *A61K 31/541* (2013.01); *A61K 31/675* (2013.01); *C07D 213/74* (2013.01); *C07D 213/75* (2013.01); *C07D 239/47* (2013.01); *C07D 401/02* (2013.01); *C07D 401/12* (2013.01); *C07D 403/12* (2013.01); *C07D 405/12* (2013.01); *C07D 413/12* (2013.01); *C07F 9/582* (2013.01); *C07F 9/588* (2013.01); *C07F 9/65122* (2013.01); *C07F 9/65583* (2013.01); *C07F 9/65586* (2013.01)

(58) Field of Classification Search
CPC .. C07D 213/74; C07D 213/75; C07D 239/47; C07D 401/02; C07D 401/12; C07D 403/12; C07D 405/12; C07D 413/12; A61K 31/44; A61K 31/4427; A61K 31/4439; A61K 31/444; A61K 31/496; A61K 31/505; A61K 31/506; A61K 31/5377; A61K 31/541; A61K 31/675; C07F 9/582; C07F 9/588; C07F 9/65122; C07F 9/65127; C07F 9/65583; C07F 9/65586
See application file for complete search history.

(56) References Cited

U.S. PATENT DOCUMENTS 6,319,921 B1 11/2001 Cirillo et al.
6,492,393 B1 12/2002 Breitfelder et al.
(Continued)

FOREIGN PATENT DOCUMENTS

WO  WO 99/23091     5/1999
WO  WO 00/041698    7/2000
(Continued)

OTHER PUBLICATIONS

U.S. Appl. No. 14/561,290, filed Dec. 5, 2014, Murray.
(Continued)

*Primary Examiner* — Sarah Pihonak
(74) *Attorney, Agent, or Firm* — Knobbe, Martens, Olson & Bear, LLP

(57) ABSTRACT

There are provided compounds of formula I, wherein $R^1$, $R^{1A}$, $R^{1C}$ to $R^{1E}$, $R^a$, $R^b$, $X^1$, E and G have meanings given in the description, which compounds have antiinflammatory activity (e.g., through inhibition of one or more of members of: the family of p38 mitogen-activated protein kinase enzymes; Syk kinase; and members of the Src family of tyrosine kinases) and have use in therapy, including in pharmaceutical combinations, especially in the treatment of inflammatory diseases, including inflammatory diseases of the lung, eye and intestines.

18 Claims, No Drawings

(51) Int. Cl.
*A61K 31/505* (2006.01)
*A61K 31/506* (2006.01)
*A61K 31/5377* (2006.01)
*A61K 31/541* (2006.01)
*A61K 31/675* (2006.01)

(56) References Cited

U.S. PATENT DOCUMENTS

| | | |
|---|---|---|
| 6,492,529 B1 | 12/2002 | Kapadia et al. |
| 6,525,046 B1 | 2/2003 | Cirillo et al. |
| 6,852,717 B2 | 2/2005 | Cirillo et al. |
| 6,872,726 B2 | 3/2005 | Cirillo et al. |
| 6,894,173 B2 | 5/2005 | Zhang et al. |
| 6,916,814 B2 | 7/2005 | Moss et al. |
| 7,241,758 B2 | 7/2007 | Hoa et al. |
| 7,279,475 B2 | 10/2007 | Cirillo et al. |
| 7,652,022 B2 | 1/2010 | Floersheimer et al. |
| 7,838,541 B2 | 11/2010 | Dumas et al. |
| 8,080,552 B2 | 12/2011 | Georges et al. |
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,618,140 B2 | 12/2013 | Ito et al. |
| 8,642,773 B2 | 2/2014 | Ito et al. |
| 8,927,563 B2 | 1/2015 | Fyfe |
| 8,933,228 B2 | 1/2015 | Murray et al. |
| 8,975,285 B2 | 3/2015 | Ito et al. |
| 9,024,041 B2 | 5/2015 | King-Underwood |
| 9,079,893 B2 | 7/2015 | Cass |
| 9,108,950 B2 | 8/2015 | Ito et al. |
| 9,242,960 B2 | 1/2016 | Ito et al. |
| 9,249,125 B2 | 2/2016 | Duffy et al. |
| 9,447,076 B2 | 9/2016 | Longshaw et al. |
| 9,475,796 B2 | 10/2016 | Ito et al. |
| 9,481,648 B2 | 11/2016 | Baker et al. |
| 9,499,486 B2 | 11/2016 | Fyfe |
| 9,624,196 B2 | 4/2017 | Longshaw et al. |
| 2001/0011135 A1 | 8/2001 | Riedl et al. |
| 2004/0152725 A1 | 8/2004 | Moss et al. |
| 2008/0312192 A1 | 12/2008 | Bold et al. |
| 2012/0244120 A1 | 9/2012 | Charron et al. |
| 2013/0029990 A1 | 1/2013 | King-Underwood et al. |
| 2013/0040995 A1 | 2/2013 | King-Underwood et al. |
| 2013/0123260 A1 | 5/2013 | Charron et al. |
| 2013/0150343 A1 | 6/2013 | Van Niel et al. |
| 2014/0057915 A1 | 2/2014 | Cariou et al. |
| 2014/0228410 A1 | 8/2014 | Ito et al. |
| 2014/0296208 A1 | 10/2014 | Baker et al. |
| 2015/0166483 A1 | 6/2015 | Fyfe |
| 2015/0210722 A1 | 7/2015 | Fyfe et al. |
| 2015/0218137 A1 | 8/2015 | Cariou et al. |
| 2015/0225373 A1 | 8/2015 | Fyfe et al. |
| 2015/0225427 A1 | 8/2015 | Fyfe et al. |
| 2015/0232450 A1 | 8/2015 | Longshaw et al. |
| 2015/0252024 A1 | 9/2015 | Ito et al. |
| 2015/0329523 A1 | 11/2015 | Frickel et al. |
| 2016/0009695 A1 | 1/2016 | Ito et al. |
| 2016/0016934 A1 | 1/2016 | Fyfe |
| 2016/0039797 A1 | 2/2016 | Fyfe |
| 2016/0045482 A1 | 2/2016 | Charron |
| 2016/0045512 A1 | 2/2016 | Charron |
| 2016/0096805 A1 | 4/2016 | Fyfe |
| 2016/0102059 A1 | 4/2016 | Baker et al. |
| 2016/0115152 A1 | 4/2016 | King-Underwood |
| 2016/0130256 A1 | 5/2016 | King-Underwood et al. |
| 2016/0318909 A1 | 11/2016 | Fyfe |
| 2016/0340343 A1 | 11/2016 | Fyfe et al. |
| 2016/0340375 A1 | 11/2016 | Fyfe et al. |
| 2016/0368896 A1 | 12/2016 | Longshaw et al. |
| 2016/0376232 A1 | 12/2016 | Thom |
| 2017/0007604 A1 | 1/2017 | Ito et al. |
| 2017/0029378 A1 | 2/2017 | Fyfe |
| 2017/0057945 A1 | 3/2017 | Longshaw et al. |
| 2017/0209445 A1 | 7/2017 | Fyfe |
| 2017/0253563 A1 | 9/2017 | Baker |

FOREIGN PATENT DOCUMENTS

| | | |
|---|---|---|
| WO | WO 00/043384 | 7/2000 |
| WO | WO 00/055139 | 9/2000 |
| WO | WO 01/04115 | 1/2001 |
| WO | WO 01/36403 | 5/2001 |
| WO | WO 02/083628 | 10/2002 |
| WO | WO 02/083642 | 10/2002 |
| WO | WO 02/092576 | 11/2002 |
| WO | WO 02/096876 | 12/2002 |
| WO | WO 2003/005999 | 1/2003 |
| WO | WO 2003/068223 | 8/2003 |
| WO | WO 2003/068228 | 8/2003 |
| WO | WO 2003/072569 | 9/2003 |
| WO | WO 2003/099771 | 12/2003 |
| WO | WO 2004/014870 | 2/2004 |
| WO | WO 2005/023761 | 3/2004 |
| WO | WO 2004/113352 | 12/2004 |
| WO | WO 2005/005396 | 1/2005 |
| WO | WO 2005/018624 | 3/2005 |
| WO | WO 2005/044825 | 5/2005 |
| WO | WO 2005/051366 | 6/2005 |
| WO | WO 2005/113494 | 12/2005 |
| WO | WO 2006/015775 | 2/2006 |
| WO | WO 2006/043090 | 4/2006 |
| WO | WO 2007/004749 | 1/2007 |
| WO | WO 2007/053394 | 5/2007 |
| WO | WO 2007/076473 | 7/2007 |
| WO | WO 2008/077548 | 7/2008 |
| WO | WO 2010/038085 | 4/2010 |
| WO | WO 2010/038086 | 4/2010 |
| WO | WO 2010/067130 | 6/2010 |
| WO | WO 2010/067131 | 6/2010 |
| WO | WO 2010/112936 | 10/2010 |
| WO | WO 2011/070368 | 6/2011 |
| WO | WO 2011/070369 | 6/2011 |
| WO | WO 2011/121366 | 10/2011 |
| WO | WO 2011/124923 | 10/2011 |
| WO | WO 2011/124930 | 10/2011 |
| WO | WO 2011/158039 | 12/2011 |
| WO | WO 2011/158042 | 12/2011 |
| WO | WO 2011/158044 | 12/2011 |
| WO | WO 2013/050756 | 4/2013 |
| WO | WO 2013/050757 | 4/2013 |
| WO | WO 2013/083604 A1 | 6/2013 |
| WO | WO 2014/027209 | 2/2014 |
| WO | WO 2014/033446 | 3/2014 |
| WO | WO 2014/033447 | 3/2014 |
| WO | WO 2014/033448 | 3/2014 |
| WO | WO 2014/033449 | 3/2014 |
| WO | WO 2014/076484 | 5/2014 |
| WO | WO 201/140582 | 9/2014 |
| WO | WO 2014/162121 | 10/2014 |
| WO | WO 2014/162122 | 10/2014 |
| WO | WO 2014/162126 | 10/2014 |
| WO | WO 2015/121444 | 8/2015 |
| WO | WO 2015/121660 | 8/2015 |
| WO | WO 2016/051187 | 4/2016 |
| WO | WO 2016/051188 | 4/2016 |

OTHER PUBLICATIONS

Badrinarayan, et al. 2011 "Sequence, structure, and active site analyses of p38 MAP kinase: Exploiting DFG-out conformation as a strategy to design new type II leads" *Journal of Chemical Information and Modeling* 51; 115-129.

Barnes, et al. 2007 "Trimethylsilylpyrazoles as novel inhibitors of p38 MAP kinase: A new use of silicon bioisosteres in medicinal chemistry" *Bioorganic & Medicinal Chemistry* 17; 354-357.

Biancheri, et al. 2016 "Effect of narrow spectrum versus selective kinase inhibitors on the intestinal proinflammatory immune response in ulcerative colitis" *Inflamm Bowel Dis* 22(6): 1306-1315.

(56) References Cited

OTHER PUBLICATIONS

Boehm, et al. 2000 "New inhibitors of p38 kinase" *Expert Opinion on Therapeutic Patents* 10(1): 25-37.
Cirillo, et al. 2009 "Discovery and characterization of the N-phenyl-N'-naphthylurea class of p38 kinase inhibitors" *Bioorganic & Medicinal Chemistry* 19; 2386-2391.
Cogan, et al. 2008 "Structure-based design and subsequent optimization of 2-tolyl-(1,2,3-triazol-1-yl-4-carboxamide) inhibitors of p38 MAP kinase" *Bioorganic & Medicinal Chemistry* 18; 3251-3255.
Dietrich, et al. 2010 "The design, synthesis, and evaluation of 8 hybrid DFG-out allosteric kinase inhibitors: A structural analysis of the binding interactions of Gleevec®, Nexavar®, and BIRB-796" *Bioorganic & Medicinal Chemistry* 18; 5738-5748.
Dodeller, et al. 2006 "The p38 mitogen-activated protein kinase signaling cascade in CD4 T cells" *Arthritis Research & Therapy* 8(2): 1-11.
Dumas, et al. 2004 "Recent developments in the discovery of protein kinase inhibitors from the urea class" *Current Opinion in Drug Discovery & Development* 7(5); 600-616.
Goldberg, et al. 2007 "Discovery and Optimization of p38 Inhibitors via Computer-Assisted Drug Decision" *Journal of Medicinal Chemistry* 50; 4016-4026.
Menard, et al. 2009 "Novel potent BRAF inhibitors: Toward 1 nM compounds through optimization of the Central Phenyl Ring" *Journal of Medicinal Chemistry* 52; 3881-3891.
Montalban, et al. 2010 "KR-003048, a potent, orally active inhibitors of p38 mitogen-activated protein kinase" *European Journal of Pharmacology* 632; 93-102.
Montalban, et al. 2010 "Optimization of α-ketoamide based p38 inhibitors through modifications to the region that binds to the allosteric site" *Bioorganic & Medicinal Chemistry* 20; 4819-4824.
Onions, et al. 2016 "Discovery of narrow spectrum kinase inhibitors: new therapeutic agents for the treatment of COPD and steroid-resistant asthma" *Journal of Medicinal Chemistry* 59: 1727-1746.
Pettus, et al. 2008 "Small Molecule p38 MAP Kinase Inhibitors for the Treatment of Inflammatory Diseases: Novel Structures and Developments During 2006-2008" *Current Topics in Medicinal Chemistry* 8; 1452-1467.
CAS Registry No. 1379397-83-7, Jun. 2012 American Chemical Society.
CAS Registry No. 1384608-34-7, 2012 American Chemical Society.
To, et al. 2015 "Potent anti-inflammatory effects of the narrow spectrum kinase inhibitor RV1088 on rheumatoid arthritis synovial membrane cells" *British Journal of Pharmacology* 172: 3805-3816.
Zambon, et al. 2010 "Novel hinge binder improves activity and pharmacokinetic properties of BRAF inhibitors" *Journal of Medicinal Chemistry* 53; 5639-5655.
U.S. Appl. No. 15/225,377, filed Aug. 1, 2016, Fyfe, et al.
U.S. Appl. No. 15/228,945, filed Aug. 4, 2016, Fyfe, et al.
U.S. Appl. No. 15/253,141, filed Aug. 31, 2016, Longshaw, et al.
U.S. Appl. No. 15/261,174, filed Sep. 9, 2016, Thom.
U.S. Appl. No. 15/291,359, filed Oct. 12, 2016, Fyfe.
Brinkmann, et al. 2010 "Fingolimod (FTY720): discovery and development of an oral drug to treat multiple sclerosis" *Nature Reviews Drug Discovery* 9: 883-897.
Coughlin, et al. 2010 "Approaches and limitations of phosphatidylinositol-3-kinase pathway activation status as a predictive biomarker in the clinical development of targeted therapy" *Breast Cancer Res Treat* 124: 1-11.
Jope, et al. 2007 "Glycogen synthase kinase-3 (GSK3): Inflammation, diseases, and therapeutics" *Neurochem Res* 32: 577-595.
Judge, et al. 2006 "Potassium channel blockers in multiple sclerosis: Neuronal $K_v$ channels and effects of symptomatic treatment" *Pharmacology & Therapeutics* 111: 224-259.
Kim, et al. 2009 "Src family kinases as mediators of endothelial permeability: effects on inflammation and metastasis" *Cell Tissue Res* 335: 249-259.
Kuster "Kinase inhibitors, Methods and Protocols" *Methods in Molecular Biology* 795 Chapters 1 and 2 (in 46 pages).
Lima, et al. 2011 "Anti-inflammatory effects of LASSBio-998, a new drug candidate designed to be a p38 MAPK inhibitor, in an experimental model of acute lung inflammation" *Pharmacological Reports* 63: 1029-1039.
Liu, et al. 2011 "Src phosphorylation of endothelial cell surface intercellular adhesion molecule-1 mediates neutrophil adhesion and contributes to the mechanism of lung inflammation" *Arterioscler Thromb Vasc Biol* 31: 1342-1350.
Masuda, et al. 2008 "Syk inhibitors as treatment for allergic rhinitis" *Pulmonary Pharmacology & Therapeutics* 21: 461-467.
McDermott, et al. 2009 "Personalized cancer therapy with selective kinase inhibitors: An emerging paradigm in medical oncology" *Journal of Clinical Oncology* 27(33): 5650-5659.
Sawyers 2008 "The cancer biomarker problem" *Nature* 452: 548-552.
Singh, et al. 2007 "Spleen tyrosine kinase (Syk) biology, inhibitors and therapeutic applications" *Annual Reports in Medicinal Chemistry* 42: 379-391.
Singh, et al. 2010 "A randomized, placebo-controlled study of the effects of the p38 MAPK inhibitor SB-681323 on blood biomarkers of inflammation in COPD patients" *J Clin Pharmacol* 50: 94-100.
Sutherland, et al. 2004 "Management of chronic obstructive pulmonary disease" *The New England Journal of Medicine* 350: 2689-2697.
Weinblatt, et al. 2010 "An oral spleen tyrosine kinase (Syk) inhibitor for rheumatoid arthritis" *The New England Journal of Medicine* 363(14): 1303-1312.
Yamamoto, et al. 2003 "The orally available spleen tyrosine kinase inhibitor 2-[7-(3,4-Dimethoxyphenyl)-imidazo[1,2-c]pyrimidin-5-ylamino]-nicotinamide dihydrochloride (BAY 61/3606) blocks antigen-induced airway inflammation in rodents" *The Journal of Pharmacology and Experimental Therapeutics* 306(3): 1174-1181.
U.S. Appl. No. 15/457,810, filed Mar. 13, 2017, Lonshaw et al.
U.S. Appl. No. 15/515,079, filed Mar. 28, 2017, Fyfe.

they have become an obvious target for investigation in IBD models. Studies

UREA DERIVATIVES USEFUL AS KINASE INHIBITORS

FIELD OF THE INVENTION

This invention relates, inter alia, to compounds which are antiinflammatory agents (e.g. through inhibition of one or more of members of: the family of p38 mitogen-activated protein kinase enzymes (referred to herein as p38 MAP kinase inhibitors), for example the alpha kinase subtype thereof; Syk kinase; and the Src family of tyrosine kinases). The invention also relates to the use of such compounds in therapy, including in mono- and combination therapies, especially in the treatment of inflammatory diseases, including inflammatory diseases of the lung (such as asthma and chronic obstructive pulmonary disease (COPD)), eye (such as uveitis) and gastrointestinal tract (such as Crohn's disease and ulcerative colitis).

BACKGROUND OF THE INVENTION

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively) have been identified, each displaying different patterns of tissue expression. The p38 MAPK alpha and beta isoforms are found ubiquitously throughout the body; are present in many different cell types and are inhibited by a number of previously described small molecular weight compounds. Early classes of inhibitors were highly toxic due to the broad tissue distribution of these isoforms which resulted in off-target effects of the compounds. Some of the more recently identified inhibitors show improved selectivity for p38 MAPK alpha and beta isoforms and have wider safety margins.

p38 MAP kinase is believed to play a pivotal role in many of the signalling pathways that are involved in initiating and maintaining chronic, persistent inflammation in human disease, for example, in severe asthma, COPD and inflammatory bowel disease (IBD). There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith describes the inhibitory effect of p38 MAP kinase inhibitors on TNFα (but not IL-8) release from human PBMCs (Smith, S. J., *Br. J. Pharmacol.*, 2006, 149:393-404).

The use of inhibitors of p38 MAP kinase in the treatment of COPD and IBD has also been proposed. Small molecule inhibitors targeted to p38 MAPKα/β have proved to be effective in reducing various parameters of inflammation in:
  cells and tissues obtained from patients with COPD, who are generally corticosteroid insensitive (Smith, S. J., *Br. J. Pharmacol.*, 2006, 149:393-404);
  biopsies from IBD patients (Docena, G. et al., *J. of Trans. Immunol.*, 2010, 162:108-115); and
  in vivo animal models (Underwood, D. C. et al., *Am. J. Physiol.*, 2000, 279:L895-902; Nath, P. et al., *Eur. J. Pharmacol.*, 2006, 544:160-167).

Irusen and colleagues also suggested the possibility of involvement of p38 MAPKα/β on corticosteroid insensitivity via the reduction of binding affinity of the glucocorticoid receptor (GR) in nuclei (Irusen, E. et al., *J. Allergy Clin. Immunol.*, 2002, 109:649-657). Clinical investigations in inflammatory diseases with a range of p38 MAP kinase inhibitors, including AMG548, BIRB 796, VX702, SCIO469 and SCIO323, has been described (Lee, M. R. and Dominguez, C., *Current Med. Chem.*, 2005, 12:2979-2994.). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado at al. (2007; *American Thoracic Society Abstract A*56) demonstrates that silencing p38 MAPK γ has the potential to restore sensitivity to corticosteroids. Thus, there may be a dual benefit for patients in the use of a p38 MAP kinase inhibitor for the treatment of COPD.

Many patients diagnosed with asthma or with COPD continue to suffer from uncontrolled symptoms and from exacerbations of their medical condition that can result in hospitalization. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

It has been disclosed previously that compounds that inhibit the activity of both the c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). Taken together with inhibition of p38 MAPK, these are particularly attractive properties for compounds to possess that are intended to treat patients with chronic respiratory diseases.

Certain p38 MAPK inhibitors have also been described as inhibitors of replication of respiratory syncytial virus (Cass L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. Due to the ubiquitous expression of p38 in inflammatory cells it has become an obvious target for investigation in IBD models. Studies investigating the efficacy of p38 inhibitors in animal models of IBD and human biopsies from IBD patients indicated that p38 could be a target for the treatment of IBD (Hove, T. ten et al., *Gut,* 2002, 50:507-512, Docena, G. et al., *J. of Trans. Immunol.* 2010, 162:108-115). However, these findings are not completely consistent with other groups reporting no effect with p38 inhibitors (Malamut G. et al., *Dig. Dis. Sci,* 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology,* 2006, 4:325-334). A small clinical study investigating the efficacy of CNI-1493, a P38 and Jnk inhibitor, in patients with severe Crohn's disease showed significant improvement in clinical score over 8 weeks (Hommes, D. et al. *Gastroenterology.* 2002 122:7-14).

T cells are known to play key role in mediating inflammation of the gastrointestinal tract. Pioneering work by Powrie and colleagues demonstrated that transfer of naive CD4+ cells into severely compromised immunodeficient (SCID) animals results in the development of colitis which is dependent on the presence of commensal bacteria (Powrie F. et al. *Int Immunol.* 1993 5:1461-71). Furthermore, investigation of mucosal membranes from IBD patients showed an upregulation of CD4+ cells which were either Th1 (IFNg/IL-2) or Th2 (IL5/TGFb) biased depending on whether the patient had Crohn's disease or ulcerative colitis (Fuss I J. et al. *J Immunol.* 1996 157:1261-70.). Similarly, T cells are known to play a key role in inflammatory disorders of the eye with several studies reporting increased levels of T cell associated cytokines (IL-17 and IL-23) in sera of Beçhets patients (Chi W. et al. *Invest Ophthalmol Vis Sci.* 2008 49:3058-64). In support, Direskeneli and colleagues demonstrated that Behcets patients have increased Th17 cells and decreased Treg cells in their peripheral blood (Direskeneli H. et al. J Allergy Clin Immunol. 2011 128: 665-6).

One approach to inhibit T cell activation is to target kinases which are involved in activation of the T cell receptor signalling complex. Syk and Src family kinases are known to play a key role in this pathway, where Src family kinases, Fyn and Lck, are the first signalling molecules to be activated downstream of the T cell receptor (Barber E K. et al. *PNAS* 1989 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science.* 1994 10; 264(5165):1599-601).

A clinical trial in rheumatoid arthritis patients with the Syk inhibitor Fostamatinib demonstrated the potential of Syk as an anti-inflammatory target with patients showing improved clinical outcome and reduced serum levels of IL-6 and MMP-3 (Weinblatt M E. et al. *Arthritis Rheum.* 2008 58:3309-18). Syk kinase is widely expressed in cells of the hematopoietic system, most notably in B cells and mature T cells. Through interaction with immunoreceptor tyrosine-based activation (ITAM) motifs it plays an important role in regulating T cell and B cell expansion as well as mediating immune-receptor signalling in inflammatory cells. Syk activation leads to IL-6 and MMP release—inflammatory mediators commonly found upregulated in inflammatory disorders including IBD and rheumatoid arthritis (Wang Y D. et al. *World J Gastroenterol* 2007; 13: 5926-5932, Litinsky I et al. *Cytokine.* 2006 January 33:106-10).

In addition to playing key roles in cell signalling events which control the activity of pro-inflammatory pathways, kinase enzymes are now also recognised to regulate the activity of a range of cellular functions, including the maintenance of DNA integrity (Shilo, Y. *Nature Reviews Cancer,* 2003, 3: 155-168) and co-ordination of the complex processes of cell division. Indeed, certain kinase inhibitors (the so-called "Olaharsky kinases") have been found to alter the frequency of micronucleus formation in vitro (Olaharsky, A. J. et al., *PLoS Comput. Biol.,* 2009, 5(7)). Micronucleus formation is implicated in, or associated with, disruption of mitotic processes and is therefore undesirable. Inhibition of glycogen synthase kinase 3α (GSK3α) was found to be a particularly significant factor that increases the likelihood of a kinase inhibitor promoting micronucleus formation. Also, inhibition of the kinase GSK3β with RNAi has been reported to promote micronucleus formation (Tighe, A. et al., *BMC Cell Biology,* 2007, 8:34).

Whilst it may be possible to attenuate the adverse effects of inhibition of Olaharsky kinases such as GSK3α by optimisation of the dose and/or by changing the route of administration of a molecule, it would be advantageous to identify further therapeutically useful molecules with low or negligible inhibition of Olaharsky kinases, such as GSK 3α and/or have low or negligible disruption of mitotic processes (e.g. as measured in a mitosis assay).

Various compounds, including urea derivatives, are disclosed as inhibiting one or more kinases. Examples of such compounds may be found in WO 99/23091, WO 00/041698, WO 00/043384, WO 00/055139, WO 01/36403, WO 01/4115, WO 02/083628, WO 02/083642, WO 02/092576, WO 02/096876, WO 2003/005999, WO 2003/068223, WO 2003/068228, WO 2003/072569, WO 2004/014870, WO 2004/113352, WO 2005/005396, WO 2005/018624, WO 2005/023761, WO 2005/044825, WO 2006/015775, WO 2006/043090, WO 2007/004749, WO 2007/053394, WO 2013/050756, WO 2013/050757, WO 2014/027209, WO 2014/033446, WO 2014/033447, WO 2014/033448, WO 2014/033449, WO 2014/076484, WO 2014/140582, WO 2014/162126, WO 2014/162122, and WO 2014/162121. Further examples may be found in articles published in:

*Curr. Opin. Drug Devel.* (2004, 7(5), 600-616);
*J. Med. Chem.* (2007, 50, 4016-4026; 2009, 52, 3881-3891; and 2010, 53, 5639-5655);
*Bioorg. Med. Chem. Lett.* (2007, 17, 354-357; 2008, 18, 3251-3255; 2009, 19, 2386-2391; and 2010, 20, 4819-4824);
*Curr. Top. Med. Chem.* (2008, 8, 1452-1467);
*Bioorg. Med. Chem.* (2010, 18, 5738-5748);
*Eur. J. Pharmacol.* (2010, 632, 93-102) and
*J. Chem. Inf. Model.* (2011, 51, 115-129).

Nevertheless, there remains a need to identify and develop new kinase inhibitors, specifically alternative p38 MAP kinase inhibitors that are suitable for the treatment of inflammation. There is particularly a need for such inhibitors that have improved therapeutic potential over currently available treatments or, in particular, that exhibit a superior therapeutic index (e.g. inhibitors that are at least equally efficacious and, in one or more respects, are less toxic at the relevant therapeutic dose than previous agents).

SUMMARY OF THE INVENTION

We have now discovered, surprisingly, that certain phenyl ureas inhibit one or more of p38 MAP kinase, Syk and Src family kinases and therefore possess good anti-inflammatory properties.

Thus, according to a first aspect of the invention, there is provided a compound of formula I,

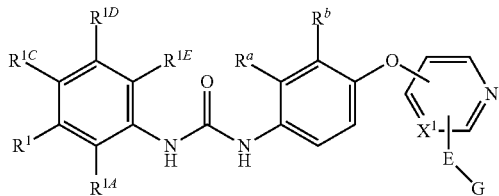

wherein
R$^1$ represents
-L$^1$-C(O)N(R$^{2a}$)R$^{2b}$,
-L$^{2a}$-S(O)$_{0-1}$—R$^{2c1}$,
-L$^{2b}$-S(O)$_2$—R$^{2c2}$,
-L$^3$-P(O)R$^{2d}$R$^{2e}$,
—CH$_2$N(R$^{2d1}$)-Q-R$^{2f}$,
—O—S(O)$_2$—N(R$^{2g}$)R$^{2h}$,
—N=S(O)(CH$_3$)$_2$,
—S(=O)(=NR$^{2i}$)CH$_3$
—O—C(R$^{2x}$)(R$^{2y}$)(R$^{2z}$) or
—CH$_2$-Het$^2$;
L$^1$, L$^{2a}$, L$^{2b}$ and L$^3$ independently represent a bond, —[C(R$^{3a}$)(R$^{3b}$)]$_{1-2}$- or —OC(R$^{3a}$)(R$^{3b}$)—, wherein the O-atom of the latter substituent is attached to the phenyl ring, or L$^1$, L$^{2b}$ or L$^3$ represents O;
R$^{2a}$ represents —[C(R$^{3a}$)(R$^{3b}$)]—[C$_{1-4}$ alkylene]-R$^{3c}$ or, when L$^1$ is not a bond, R$^{2a}$ may alternatively represent H or R$^4$;
R$^{2b}$ represents H or C$_{1-6}$ alkyl,
or, when L$^1$ is not a bond, R$^{2a}$ and R$^{2b}$, together with the N-atom to which they are attached, may alternatively form a 4- to 7-membered heterocyclic group that is fully saturated or partially unsaturated and which heterocyclic group contains one N atom (the atom to which R$^{2a}$ and R$^{2b}$ are attached) and, optionally, one or more further heteroatoms selected from O, S and N, and which heterocyclic group is optionally substituted by one or more substituents selected from halo, OH, oxo, C$_{1-4}$ alkyl and C$_{1-4}$ alkoxy;
R$^{3c}$ represents —[O—CH$_2$(CH$_2$)$_{0-1}$CH$_2$]$_{1-12}$—R$^{5a}$, Het$^1$ or Het$^2$;
R$^{2c1}$ and R$^{2c2}$ independently represent
methyl optionally substituted by one or more halo groups,
Het$^1$,
Het$^2$ or
C$_{3-7}$ cycloalkyl optionally substituted by one or more substituents selected from C$_{1-2}$ alkyl, halo, OH and C$_{1-2}$ alkoxy,
or, when L$^{2a}$ is not a bond, R$^{2c1}$ may alternatively represent R$^{2c3}$,
or, when L$^{2b}$ is not a bond, R$^{2c2}$ may alternatively represent R$^{2c3}$;
R$^{2c3}$ represents C$_{2-7}$ alkyl, C$_{2-7}$ alkenyl, C$_{2-7}$ alkynyl or phenyl, which latter four groups are optionally substituted by one or more substituents selected from C$_{1-2}$ alkyl, halo, OH and C$_{1-2}$ alkoxy;
R$^{2d}$ represents C$_{1-4}$ alkyl;
R$^{2e}$ represents C$_{1-4}$ alkyl, C$_{3-6}$ cycloalkyl, C$_{1-4}$ alkoxy or OH;
or R$^{2d}$ and R$^{2e}$ together combine to form C$_{3-6}$ alkylene;
R$^{2d1}$ represents H or R$^{2d}$;
Q represents C(O) or S(O)$_2$;

R$^{2f}$ represents R$^4$ or, when Q represents C(O), R$^{2f}$ may alternatively represent H;
R$^{2g}$ and R$^{2h}$ independently represent H or R$^4$;
R$^{2i}$ represents H or methyl;
R$^{2x}$ represents C$_{1-6}$ alkyl substituted by one or more OH groups;
R$^{2y}$ and R$^{2z}$ independently represent H or C$_{1-4}$ alkyl optionally substituted by OH;
R$^{3a}$ and R$^{3b}$ represent, independently at each occurrence, H or methyl;
R$^4$ represents, independently at each occurrence, Het$^1$, Het$^2$, C$_{1-6}$ alkyl, C$_{3-7}$ cycloalkyl or phenyl, which latter three groups are optionally substituted by one or more substituents selected from C$_{1-2}$ alkyl, halo, oxo, OH, C$_{1-2}$ alkoxy and N(R$^{4a}$)R$^{4b}$;
R$^{5a}$ represents OR$^{5b}$ or N(R$^{5c}$)R$^{5d}$;
R$^{4a}$, R$^{4b}$ and R$^{5b}$ to R$^{5d}$ independently represent H or C$_{1-4}$ alkyl optionally substituted by one or more halo or OH substituents, or R$^{5c}$ and R$^{5d}$ or R$^{4a}$ and R$^{4b}$, together with the N-atom to which they are attached, form a 4- to 7-membered heterocyclic group that is fully saturated, partially unsaturated or fully aromatic and which heterocyclic group contains one N atom (the atom to which R$^{5c}$ and R$^{5d}$ or R$^{4a}$ and R$^{4b}$ are attached) and, optionally, one or more further heteroatoms selected from O, S and N, and which heterocyclic group is optionally substituted by one or more substituents selected from halo, OH, oxo, C$_{1-4}$ alkyl and C$_{1-4}$ alkoxy;
R$^{1A}$ represents
H, OH, halo, cyano,
C$_{1-6}$ alkyl, C$_{2-6}$ alkenyl, C$_{2-6}$ alkynyl, C$_{1-6}$ alkoxy, which latter four groups are optionally substituted by one or more substituents selected from C$_{1-2}$ alkyl, halo, OH, and C$_{1-2}$ alkoxy,
Het$^1$ or phenyl, which latter group is optionally substituted with one or more substituents selected from halo, C$_{1-2}$ alkyl and C$_{1-2}$ alkoxy;
R$^{1C}$ and R$^{1E}$ independently represent H, halo, cyano or methyl;
R$^{1D}$ represents trimethylsilyl, Het$^1$, Het$^2$, trifluoromethyl, C$_{2-7}$ alkyl, C$_{2-7}$ alkenyl, C$_{2-7}$ alkynyl, C$_{3-7}$ cycloalkyl or phenyl, which latter five groups are optionally substituted by one or more substituents selected from C$_{1-2}$ alkyl, halo, OH and C$_{1-2}$ alkoxy;
Het$^1$ represents, independently at each occurrence, a 5- to 10-membered heterocyclic group that is fully aromatic, which group contains one or more heteroatoms selected from N, O and S and which group is optionally substituted by one or more substituents selected from OH, halo, N(R$^{4a}$)R$^{4b}$, C$_{1-2}$ alkyl and C$_{1-2}$ alkoxy, which latter two groups are optionally substituted by one or more halo atoms;
Het$^2$ represents, independently at each occurrence, a 4- to 8-membered heterocyclic group that is fully saturated or partially unsaturated, which group contains one or more heteroatoms selected from N, O and S and which group is optionally substituted by one or more substituents selected from OH, oxo, N(R$^{4a}$)R$^{4b}$, C$_{1-2}$ alkyl and C$_{1-2}$ alkoxy;
R$^a$ and R$^b$, together with the C-atoms to which they are attached, form a fused phenyl or pyridyl ring, which latter two rings are optionally substituted by one or more substituents selected from C$_{1-3}$ alkyl, C$_{1-3}$ haloalkyl, cyano and halo,
or one of R$^a$ and R$^b$ represents H, halo, cyano, C$_{1-3}$ alkyl or C$_{1-3}$ haloalkyl and the other independently represents halo, cyano, C$_{1-3}$ alkyl or C$_{1-3}$ haloalkyl,
or R$^a$ and R$^b$ together combine to form C$_{3-5}$ alkylene or C$_{3-5}$ alkenylene, which latter two groups are optionally substituted by one or more substituents selected from $C_{1-3}$ alkyl, $C_{1-3}$ haloalkyl, cyano and halo;
$X^1$ represents CH or N;
E represents $N(G^1)$, O or S;
G represents
  phenyl optionally substituted by one or more $Y^1$,
  $Het^3$ optionally substituted by one or more $Y^2$,
  $R^{6a}$ or
  $C(O)R^{6b}$;
$G^1$ represents H or $C_{1-3}$ alkyl;
or G and $G^1$ together combine to form
  $C_{3-6}$ n-alkylene,
  $C_{4-5}$ n-alkylene interrupted between C2 and C3 by —O—, —S(O)$_{0-2}$— or —N(R$^c$)— or
  $C_6$ n-alkylene interrupted between C2 and C3, or between C3 and C4, by —O—, —S(O)$_{0-2}$— or —N(R$^c$)—,
any of which n-alkylene groups are optionally substituted by one or more substituents selected from halo, OH, oxo, $C_{1-4}$ alkyl and $C_{1-4}$ alkoxy, which latter two groups are optionally substituted by one or more halo atoms or by OH;
each $Y^1$ is independently selected from the group consisting of
  halo, OH, cyano, $SF_5$, $CO_2H$, —OC(O)NH$_2$,
  $P(O)R^{6c}R^{6d}$,
  $E^1$-N(R$^{6e}$)R$^{6f}$,
  $E^2$-S(O)$_2$R$^{6g}$,
  $E^3$-[C(R$^{3a}$)(R$^{3b}$)(CH$_2$)$_{0-1}$CH$_2$—O]$_{2-8}$—R$^{6h}$,
  —C≡C—R$^{6i}$,
  —N=S(O)R$^{6j}$R$^{6k}$,
  Het$^a$,
  $C_{1-6}$ alkyl, $C_{3-6}$ cycloalkyl, $C_{1-5}$ alkoxy, $C_{3-6}$ cycloalkoxy, —S(O)$_{0-1}$—$C_{1-6}$ alkyl and —S(O)$_{0-1}$—$C_{3-6}$ cycloalkyl which latter six groups are optionally substituted by one or more substituents selected from halo, OH, $C_{1-3}$ alkyl, $C_{1-3}$ alkoxy and $C_{3-6}$ cycloalkyl;
each $Y^2$ independently represents oxo or $Y^1$;
$E^1$ represents
  a direct bond,
  —C(O)—,
  —S(O)$_2$—,
  —[C(O)]$_p$—$C_{1-8}$ alkylene,
  —C(O)—NR$^{7a}$—CH$_2$—[C$_{1-7}$ alkylene]-,
  -Q$^1$-CH$_2$—[C$_{1-5}$ alkylene]-,
  the alkylene parts of which latter three groups are optionally substituted by one or more substituents selected from halo, $C_{1-3}$ alkyl and OH;
$E^2$ represents
  a direct bond,
  —O—,
  —NR$^{7a}$—
  $C_{1-6}$ alkylene or
  -Q$^2$-CH$_2$—[C$_{1-5}$ alkylene]-,
  the alkylene parts of which latter two groups are optionally substituted by one or more substituents selected from halo, $C_{1-3}$ alkyl and OH;
$E^3$ represents —C(O)NR$^{7a}$, —O— or S(O)$_{0-2}$;
$Q^1$ and $Q^2$ independently represent O or S(O)$_{0-2}$;
p represents 0 or 1;
$R^{6a}$ represents $C_{1-8}$ alkyl, wherein one or two non-adjacent C-atoms of the alkyl group, that are not linked directly to E, are optionally replaced by heteroatoms independently selected from O and N and/or wherein the alkyl group is substituted by one or more $R^8$ substituents;
$R^{6b}$ represents $C_{1-8}$ alkyl, wherein one C-atom of the alkyl group is, or two non-adjacent C-atoms of the alkyl group are, optionally replaced by heteroatoms independently selected from O and N and/or wherein the alkyl group is substituted by one or more $R^8$ substituents;
$R^{6c}$ and $R^{6d}$ independently represent $C_{1-3}$ alkyl or $C_{1-3}$ alkoxy, or $R^{6c}$ and $R^{6d}$ together combine to form $C_{4-6}$ alkylene;
$R^{6e}$ and $R^{6f}$ independently represent H, Het$^4$ or $C_{1-8}$ alkyl, which latter two groups are optionally substituted by $R^{7b}$ and/or one or more substituents selected from $C_{1-2}$ alkyl, halo, N(R$^{7c}$)R$^{7d}$ and OH, or
$R^{6e}$ and $R^{6f}$, together with the N-atom to which they are attached, form a 4- to 7-membered heterocyclic group that is fully saturated, partially unsaturated or fully aromatic and which heterocyclic group contains one N atom (the atom to which $R^{6e}$ and $R^{6f}$ are attached) and, optionally, one or more further heteroatoms selected from O, S and N, and which heterocyclic group is optionally substituted by one or more substituents selected from halo, OH, oxo, $C_{1-4}$ alkyl, $C_{3-7}$ cycloalkyl and $C_{1-4}$ alkoxy;
$R^{6g}$ represents $C_{1-6}$ alkyl, $C_{3-6}$ cycloalkyl or phenyl, which latter three groups are optionally substituted by one or more substituents selected from halo, OH, Het$^5$, $C_{1-3}$ alkyl, $C_{1-3}$ alkoxy and $C_{3-6}$ cycloalkyl;
$R^{6h}$, $R^{6i}$, $R^{6j}$ and $R^{6k}$ independently represent $C_{1-4}$ alkyl optionally substituted by one or more halo atoms, or $R^{6h}$ and $R^{6i}$ independently represent H;
$R^c$, $R^{7a}$, $R^{7c}$ and $R^{7d}$ represent, independently at each occurrence, H or $C_{1-3}$ alkyl;
$R^{7b}$ represents $C_{1-4}$ alkoxy, —(S)$_{0-2}$—$C_{1-4}$ alkyl, —S(O)$_{1-2}$—$C_{1-4}$ alkyl, phenyl or Het$^6$, which latter two groups are optionally substituted by one or more substituents selected from halo, $C_{1-4}$ alkyl, $C_{1-4}$ haloalkyl, $C_{3-7}$ cycloalkyl, $C_{1-4}$ alkoxy, OH, amino and cyano, and which Het$^6$ group may also be substituted by oxo;
$R^8$ represents, independently on each occurrence, halo, OH, oxo, $C_{1-4}$ alkoxy, $C_{3-8}$ cycloalkyl, Het$^7$ or phenyl, which latter four groups are optionally substituted by one or more substituents selected from halo, $C_{1-4}$ alkyl, $C_{1-4}$ haloalkyl, $C_{1-4}$ alkoxy, OH, amino and cyano, and which Het$^7$ group may also be substituted by oxo;
Het$^3$, Het$^4$, Het$^5$, Het$^6$ and Het$^7$ independently represent 4- to 10-membered heterocyclic groups that are fully saturated, partially unsaturated or fully aromatic, which heterocyclic groups contain one or more heteroatoms selected from N, O and S; and
Het$^a$ represents a 5- or 6-membered heterocyclic group that is fully saturated, partially unsaturated or fully aromatic, which group contains one or more heteroatoms selected from N, O and S, and which group is optionally substituted by one or more substituents selected from halo, OH, oxo, $C_{1-3}$ alkyl, $C_{1-3}$ alkoxy and $C_{3-6}$ cycloalkyl;
or a pharmaceutically acceptable salt, solvate or isotopic derivative thereof,
which compounds may be referred to hereinafter as "the compounds of the invention".

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals.

For the avoidance of doubt, compounds of formula I may contain the stated atoms in any of their natural or non-natural isotopic forms. In this respect, embodiments of the invention that may be mentioned include those in which:
(a) the compound of formula I is not isotopically enriched or labelled with respect to any atoms of the compound; and
(b) the compound of formula I is isotopically enriched or labelled with respect to one or more atoms of the compound.

References herein to an "isotopic derivative" relate to the second of these two embodiments. In particular embodiments of the invention, the compound of formula I is isotopically enriched or labelled (with respect to one or more atoms of the compound) with one or more stable isotopes. Thus, the compounds of the invention that may be mentioned include, for example, compounds of formula I that are isotopically enriched or labelled with one or more atoms such as deuterium or the like.

Compounds of formula I may exhibit tautomerism. All tautomeric forms and mixtures thereof are included within the scope of the invention. In particular, the invention includes the keto enol tautomerism existing between indolin-2-one and 2-hydroxyindole.

Unless otherwise specified, alkyl groups and alkoxy groups as defined herein may be straight-chain or, when there is a sufficient number (i.e. a minimum of three) of carbon atoms, be branched. Particular alkyl groups that may be mentioned include, for example, methyl, ethyl, n-propyl, iso-propyl, butyl, n-butyl and tert-butyl. Particular alkoxy groups that may be mentioned include, for example, methoxy, ethoxy, propoxy, and butoxy.

Unless otherwise specified, cycloalkyl groups as defined herein may, when there is a sufficient number (i.e. a minimum of four) of carbon atoms, be part cyclic/acyclic.

Unless otherwise specified, alkylene groups as defined herein may be straight-chain or, when there is a sufficient number (i.e. a minimum of two) of carbon atoms, be branched. In particular embodiments of the invention, alkylene refers to straight-chain alkylene.

Unless otherwise stated, the point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like. Embodiments of the invention that may be mentioned include those in which aryl is phenyl.

For the avoidance of doubt, oxo substituents that may be present on heterocyclic groups represented by $Het^2$, $Het^3$, $Het^4$, $Het^5$, $Het^6$, $Het^7$, $Het^a$, $N(R^{2a})R^{2b}$, $N(R^{4a})R^{4b}$, $N(R^{5c})R^{5d}$ or $N(R^{6e})R^{6f}$ may be attached to any appropriate atoms in the heterocyclic ring including, where valencies allow, to C-, N- and/or S-atoms within the ring (thereby forming keto, N-oxide, S(O) and/or $S(O)_2$ groups).

Values of $Het^2$ that may be mentioned include azetidinyl (e.g. azetidin-1-yl), morpholinyl (e.g. morpholin-4-yl), piperazinyl (e.g. piperazin-1-yl), pyrrolidinyl (e.g. pyrrolidin-1-yl) or thiomorpholinyl (e.g. thiomorpholin-1-yl), such as morpholinyl, piperazinyl or pyrrolidinyl.

Values of $Het^3$ that may be mentioned include 2,3-dihydrobenzo[b][1,4]dioxinyl (e.g. 2,3-dihydrobenzo[b][1,4]dioxin-6-yl), 1,3-dihydrobenzo[c]thiophenyl (e.g. 1,3-dihydrobenzo[c]-thiophen-5-yl), indazolyl (e.g. 1H-indazol-5-yl), indolinyl (e.g. indolin-6-yl), isoxazolyl (e.g. isoxazol-4-yl), isoindolinyl (e.g. isoindolin-5-yl), piperidinyl (e.g. piperidin-4-yl), pyranyl (e.g. pyran-4-yl), pyrazinyl (e.g. pyrazin-2-yl), pyrazolyl (e.g. pyrazol-3-yl or, particularly, pyrazol-4-yl), pyridinyl (e.g. pyridin-2-yl), pyrimidinyl (e.g. pyrimidin-5-yl), tetrahydrofuranyl (e.g. tetrahydrofuran-3-yl) and triazolyl (e.g. triazol-4-yl).

Values of $Het^4$ that may be mentioned include piperidinyl (e.g. piperidin-4-yl).

Values of $Het^6$ that may be mentioned include piperazinyl (e.g. piperazin-1-yl) or piperidinyl (e.g. piperidin-4-yl).

Values of $Het^7$ that may be mentioned include morpholinyl (e.g. morpholin-4-yl), pyrazolyl (e.g. pyrazol-1-yl) and pyridinyl (e.g. pyridin-2-yl).

Unless otherwise specified, the term "halo" includes references to fluoro, chloro, bromo or iodo, in particular to fluoro, chloro or bromo, especially fluoro or chloro.

Embodiments of the invention that may be mentioned include compounds of formula I in which $R^1$ represents:
-$L^1$-C(O)N($R^{2a}$)$R^{2b}$,
-$L^{2a}$-S(O)$_{0-1}$—$R^{2c1}$,
-$L^{2b}$-S(O)$_2$—$R^{2c2}$,
-$L^3$-P(O)$R^{2d}R^{2e}$,
—CH$_2$N($R^{2d1}$)-Q-$R^{2f}$,
—O—S(O)$_2$—N($R^{2g}$)$R^{2h}$,
—N=S(O)(CH$_3$)$_2$,
—S(=O)(=N$R^{2i}$)CH$_3$ or
—O—C($R^{2x}$)($R^{2y}$)($R^{2z}$);

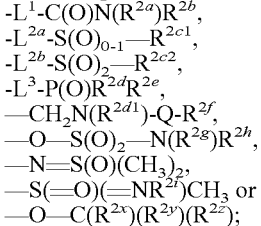

$R^{6e}$ and $R^{6f}$, together with the N-atom to which they are attached, form a 4- to 7-membered heterocyclic group that is fully saturated, partially unsaturated or fully aromatic and which heterocyclic group contains one N atom (the atom to which $R^{6e}$ and $R^{6f}$ are attached) and, optionally, one or more further heteroatoms selected from O, S and N, and which heterocyclic group is optionally substituted by one or more substituents selected from halo, OH, oxo, $C_{1-4}$ alkyl and $C_{1-4}$ alkoxy;

$R^{6g}$ represents $C_{1-6}$ alkyl, $C_{3-6}$ cycloalkyl or phenyl, which latter three groups are optionally substituted by one or more substituents selected from halo, OH, $C_{1-3}$ alkyl, $C_{1-3}$ alkoxy and $C_{3-6}$ cycloalkyl;

$R^{7b}$ represents $C_{1-4}$ alkoxy, —(S)$_{0-2}$—$C_{1-4}$ alkyl, phenyl or $Het^6$, which latter two groups are optionally substituted by one or more substituents selected from halo, $C_{1-4}$ alkyl, $C_{1-4}$ haloalkyl, $C_{1-4}$ alkoxy, OH, amino and cyano, and which $Het^6$ group may also be substituted by oxo;

$Het^1$ represents, independently at each occurrence, a 5- to 10-membered heterocyclic group that is fully aromatic, which group contains one or more heteroatoms selected from N, O and S and which group is optionally substituted by one or more substituents selected from OH, halo, $C_{1-2}$ alkyl and $C_{1-2}$ alkoxy, which latter two groups are optionally substituted by one or more halo atoms; and $Het^2$ represents, independently at each occurrence, a 4- to 8-membered heterocyclic group that is fully saturated or partially unsaturated, which group contains one or more heteroatoms selected from N, O and S and which group is optionally substituted by one or more substituents selected from OH, oxo, $C_{1-2}$ alkyl and $C_{1-2}$ alkoxy.

Other embodiments of the invention that may be mentioned include compounds of formula I in which:
(a) $R^1$ represents:
-$L^1$-C(O)N($R^{2a}$)$R^{2b}$,
-$L^{2a}$-S(O)$_{0-1}$—$R^{2c1}$,
-$L^{2b}$-S(O)$_2$—$R^{2c2}$,
-$L^3$-P(O)$R^{2d}R^{2e}$,
—CH$_2$NH-Q-$R^{2f}$;
—O—S(O)$_2$—N($R^{2g}$)$R^{2h}$,
—N=S(O)(CH$_3$)$_2$ or
—S(=O)(=N$R^{2i}$)CH$_3$;

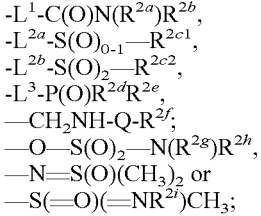

wherein $L^1$, $L^{2a}$, $L^{2b}$, $L^3$, $R^{2a}$, $R^{2b}$, $R^{2c1}$, $R^{2c2}$, $R^{2d}$, $R^{2e}$, $R^{2f}$, $R^{2g}$, $R^{2h}$, $R^{2i}$ and Q are as hereinbefore defined;

(b) $R^4$ represents, independently at each occurrence, $Het^1$, $Het^2$, $C_{1-6}$ alkyl, $C_{3-7}$ cycloalkyl or phenyl, which latter three groups are optionally substituted by one or more substituents selected from $C_{1-2}$ alkyl, halo, oxo, OH and $C_{1-2}$ alkoxy;

(c) $R^{5b}$ to $R^{5d}$ independently represent H or $C_{1-4}$ alkyl optionally substituted by one or more halo atoms, or $R^{5c}$ and $R^{5d}$, together with the N-atom to which they are attached, form a 4- to 7-membered heterocyclic group that is fully saturated, partially unsaturated or fully aromatic and which heterocyclic group contains one N atom (the atom to which $R^{5c}$ and $R^{5d}$ are attached) and, optionally, one or more further heteroatoms selected from O, S and N, and which heterocyclic group is optionally substituted by one or more substituents selected from halo, OH, oxo, $C_{1-4}$ alkyl and $C_{1-4}$ alkoxy;

(d) $R^{14}$ represents
H, halo, cyano,
$C_{1-6}$ alkyl, $C_{2-6}$ alkenyl, $C_{2-6}$ alkynyl, $C_{1-6}$ alkoxy, which latter four groups are optionally substituted by one or more substituents selected from $C_{1-2}$ alkyl, halo, OH and $C_{1-2}$ alkoxy,
$Het^1$ or phenyl, which latter group is optionally substituted with one or more substituents selected from halo, $C_{1-2}$ alkyl and $C_{1-2}$ alkoxy;

(e) $Het^1$ represents, independently at each occurrence, a 5- to 10-membered heterocyclic group that is fully aromatic, which group contains one or more heteroatoms selected from N, O and S and which group is optionally substituted by one or more substituents selected from OH, halo, $C_{1-2}$ alkyl and $C_{1-2}$ alkoxy, which latter two groups are optionally substituted by one or more halo atoms; and (f) $Het^2$ represents, independently at each occurrence, a 4- to 8-membered heterocyclic group that is fully saturated or partially unsaturated, which group contains one or more heteroatoms selected from N, O and S and which group is optionally substituted by one or more substituents selected from OH, oxo, $C_{1-2}$ alkyl and $C_{1-2}$ alkoxy;

(g) G represents
phenyl optionally substituted by one or more $Y^1$,
$Het^3$ optionally substituted by one or more $Y^2$,
$R^{6a}$ or
$C(O)R^{6b}$,
$G^1$ represents H or $C_{1-3}$ alkyl;
or G and $G^1$ together combine to form
$C_{3-6}$ n-alkylene,
$C_{4-5}$ n-alkylene interrupted between C2 and C3 by —O— or —N($R^c$)— or
$C_6$ n-alkylene interrupted between C2 and C3, or between C3 and C4, by —O— or —N($R^c$)—,
any of which n-alkylene groups are optionally substituted by one or more substituents selected from halo, OH, oxo, $C_{1-4}$ alkyl and $C_{1-4}$ alkoxy, which latter two groups are optionally substituted by one or more halo atoms or by OH;

(h) each $Y^1$ is independently selected from the group consisting of
halo, OH, cyano, $SF_5$, —OC(O)$NH_2$,
$P(O)R^{6c}R^{6d}$,
$E^1$—N($R^{6e}$)$R^{6f}$,
$E^2$—S(O)$_2R^{6g}$,
$E^3$—[C($R^{3a}$)($R^{3b}$)(CH$_2$)$_{0-1}$CH$_2$—O]$_{2-8}$—$R^{6h}$,
—C≡C—$R^{6i}$,
—N=S(O)$R^{6j}R^{6k}$,
$Het^a$, $C_{1-6}$ alkyl, $C_{3-6}$ cycloalkyl, $C_{1-6}$ alkoxy, $C_{3-6}$ cycloalkoxy, —S(O)$_{0-1}$—$C_{1-6}$ alkyl and —S(O)$_{0-1}$—$C_{3-6}$ cycloalkyl which latter six groups are optionally substituted by one or more substituents selected from halo, OH, $C_{1-3}$ alkyl, $C_{1-3}$ alkoxy and $C_{3-6}$ cycloalkyl;

(i) $R^{6e}$ and $R^{6f}$ independently represent H or $C_{1-8}$ alkyl, which latter group is optionally substituted by $R^{7b}$ and/or one or more substituents selected from halo and OH, or $R^{6e}$ and $R^{6f}$, together with the N-atom to which they are attached, form a 4- to 7-membered heterocyclic group that is fully saturated, partially unsaturated or fully aromatic and which heterocyclic group contains one N atom (the atom to which $R^{6e}$ and $R^{6f}$ are attached) and, optionally, one or more further heteroatoms selected from O, S and N, and which heterocyclic group is optionally substituted by one or more substituents selected from halo, OH, oxo, $C_{1-4}$ alkyl and $C_{1-4}$ alkoxy;

(j) $R^{6g}$ represents $C_{1-6}$ alkyl, $C_{3-6}$ cycloalkyl or phenyl, which latter three groups are optionally substituted by one or more substituents selected from halo, OH, $C_{1-3}$ alkyl, $C_{1-3}$ alkoxy and $C_{3-6}$ cycloalkyl; and (k) $R^{7b}$ represents $C_{1-4}$ alkoxy, S—$C_{1-4}$ alkyl, phenyl or $Het^6$, which latter two groups are optionally substituted by one or more substituents selected from halo, $C_{1-4}$ alkyl, $C_{1-4}$ haloalkyl, $C_{1-4}$ alkoxy, OH, amino and cyano, and which $Het^6$ group may also be substituted by oxo.

Alternative embodiments of the invention that may be mentioned include compounds of formula I as hereinbefore defined, wherein one or more of the following (e.g. one or more of (a), (b), (e) to (i) and (I) below) applies:

(a) $R^1$ represents
—CH$_2$N($R^{2d}$)-Q-$R^{2f}$,
—O—C($R^{2x}$)($R^{2y}$)($R^{2z}$) or
—CH$_2$-$Het^2$
(e.g. $R^1$ represents —CH$_2$N($R^{2d}$)-Q-$R^{2f}$ or —O—C($R^{2x}$)($R^{2y}$)($R^{2z}$));

(b) $R^4$ represents $C_{1-6}$ alkyl, $C_{3-7}$ cycloalkyl or phenyl, which latter three groups are substituted by N($R^{4a}$)$R^{4b}$ and are optionally further substituted by one or more substituents selected from $C_{1-2}$ alkyl, halo, oxo, OH, $C_{1-2}$ alkoxy and N($R^{4a}$)$R^{4b}$;

(c) $Het^1$ represents, independently at each occurrence, a 5- to 10-membered heterocyclic group that is fully aromatic, which group contains one or more heteroatoms selected from N, O and S and which group is substituted by N($R^{4a}$)$R^{4b}$ and is optionally further substituted by one or more substituents selected from OH, halo, N($R^{4a}$)$R^{4b}$, $C_{1-2}$ alkyl and $C_{1-2}$ alkoxy, which latter two groups are optionally substituted by one or more halo atoms;

(d) $Het^2$ represents, independently at each occurrence, a 4- to 8-membered heterocyclic group that is fully saturated or partially unsaturated, which group contains one or more heteroatoms selected from N, O and S and which group is substituted by N($R^{4a}$)$R^{4b}$ and is optionally further substituted by one or more substituents selected from OH, oxo, N($R^{4a}$)$R^{4b}$, $C_{1-2}$ alkyl and $C_{1-2}$ alkoxy;

(e) $R^{5b}$ or $R^{5c}$ and/or $R^{5d}$ represents $C_{1-4}$ alkyl substituted by OH and optionally further substituted by one or more halo or OH substituents;

(f) G and $G^1$ together combine to form
$C_{4-5}$ n-alkylene interrupted between C2 and C3 by —S(O)$_{0-2}$— or
$C_6$ n-alkylene interrupted between C2 and C3, or between C3 and C4, by —S(O)$_{0-2}$—,
any of which n-alkylene groups are optionally substituted by one or more substituents selected from halo, OH, oxo, $C_{1-4}$ alkyl and $C_{1-4}$ alkoxy, which latter two groups are optionally substituted by one or more halo atoms or by OH;

(g) at least one $Y^1$ is $CO_2H$ and other $Y^1$ groups, if present, are independently selected from the group consisting of halo, OH, cyano, $SF_5$, $CO_2H$, —OC(O)$NH_2$, P(O)$R^{6c}R^{6d}$, $E^1$-N($R^{6e}$)$R^{6f}$, $E^2$-S(O)$_2R^{6g}$, $E^3$-[C($R^{3a}$)($R^{3b}$)(CH$_2$)$_{0-1}$CH$_2$—O]$_{2-8}$—$R^{6h}$, —C≡C—$R^{6i}$, —N=S(O)$R^{6j}R^{6k}$, Het$^a$, $C_{1-6}$ alkyl, $C_{3-6}$ cycloalkyl, $C_{1-6}$ alkoxy, $C_{3-6}$ cycloalkoxy, —S(O)$_{0-1}$—$C_{1-6}$ alkyl and —S(O)$_{0-1}$—$C_{3-6}$ cycloalkyl which latter six groups are optionally substituted by one or more substituents selected from halo, OH, $C_{1-3}$ alkyl, $C_{1-3}$ alkoxy and $C_{3-6}$ cycloalkyl;

(h) $R^{6e}$ and/or $R^{6f}$ represents Het$^4$ optionally substituted by $R^{7b}$ and/or one or more substituents selected from $C_{1-2}$ alkyl, halo, N($R^{7c}$)$R^{7d}$ and OH;

(i) $R^{5e}$ and/or $R^{5f}$ represents $C_{1-8}$ alkyl substituted by $C_{1-2}$ alkyl or N($R^{7c}$)$R^{7d}$ and optionally further substituted by $R^{7b}$ and/or one or more substituents selected from $C_{1-2}$ alkyl, halo, N($R^{7c}$)$R^{7d}$ and OH;

(j) $R^{6e}$ and $R^{6f}$, together with the N-atom to which they are attached, form a 4- to 7-membered heterocyclic group that is fully saturated, partially unsaturated or fully aromatic and which heterocyclic group contains one N atom (the atom to which $R^{6e}$ and $R^{6f}$ are attached) and, optionally, one or more further heteroatoms selected from O, S and N, and which heterocyclic group is substituted by $C_{3-7}$ cycloalkyl and is optionally further substituted by one or more substituents selected from halo, OH, oxo, $C_{1-4}$ alkyl, $C_{3-7}$ cycloalkyl and $C_{1-4}$ alkoxy;

(k) $R^{6g}$ represents $C_{1-6}$ alkyl, $C_{3-6}$ cycloalkyl or phenyl, which latter three groups are substituted by Het$^5$ and are optionally further substituted by one or more substituents selected from halo, OH, Het$^5$, $C_{1-3}$ alkyl, $C_{1-3}$ alkoxy and $C_{3-6}$ cycloalkyl;

(l) $R^{7b}$ represents —S(O)$_{1-2}$—$C_{1-4}$ alkyl, phenyl or Het$^6$, which latter two groups are substituted by $C_{3-7}$ cycloalkyl and are optionally further substituted by one or more substituents selected from halo, $C_{1-4}$ alkyl, $C_{1-4}$ haloalkyl, $C_{3-7}$ cycloalkyl, $C_{1-4}$ alkoxy, OH, amino and cyano, and which Het$^6$ group may also be substituted by oxo, or, particularly, $R^{7b}$ represents $C_{1-4}$ alkyl or —(S)$_2$—$C_{1-4}$ alkyl.

Particular alternative embodiments that may me mentioned include those in which one or more of the following applies:

(a) $R^1$ represents —CH$_2$-Het$^2$;

(b) Het$^1$ represents, independently at each occurrence, a 5- to 10-membered heterocyclic group that is fully aromatic, which group contains one or more heteroatoms selected from N, O and S and which group is substituted by N($R^{4a}$)$R^{4b}$ and is optionally further substituted by one or more substituents selected from OH, halo, N($R^{4e}$)$R^{4b}$, $C_{1-2}$ alkyl and $C_{1-2}$ alkoxy, which latter two groups are optionally substituted by one or more halo atoms;

(c) Het$^2$ represents, independently at each occurrence, a 4- to 8-membered heterocyclic group that is fully saturated or partially unsaturated, which group contains one or more heteroatoms selected from N, O and S and which group is substituted by N($R^{4a}$)$R^{4b}$ and is optionally further substituted by one or more substituents selected from OH, oxo, N($R^{4a}$)$R^{4b}$, $C_{1-2}$ alkyl and $C_{1-2}$ alkoxy;

(d) $R^{6e}$ and $R^{6f}$, together with the N-atom to which they are attached, form a 4- to 7-membered heterocyclic group that is fully saturated, partially unsaturated or fully aromatic and which heterocyclic group contains one N atom (the atom to which $R^{6e}$ and $R^{6f}$ are attached) and, optionally, one or more further heteroatoms selected from O, S and N, and which heterocyclic group is substituted by $C_{3-7}$ cycloalkyl and is optionally further substituted by one or more substituents selected from halo, OH, oxo, $C_{1-4}$ alkyl, $C_{3-7}$ cycloalkyl and $C_{1-4}$ alkoxy;

(e) $R^{6g}$ represents $C_{1-6}$ alkyl, $C_{3-6}$ cycloalkyl or phenyl, which latter three groups are substituted by Het$^5$ and are optionally further substituted by one or more substituents selected from halo, OH, Het$^5$, $C_{1-3}$ alkyl, $C_{1-3}$ alkoxy and $C_{3-6}$ cycloalkyl;

(f) $R^{7b}$ represents —S(O)$_{1-2}$—$C_{1-4}$ alkyl, phenyl or Het$^6$, which latter two groups are substituted by $C_{3-7}$ cycloalkyl and are optionally further substituted by one or more substituents selected from halo, $C_{1-4}$ alkyl, $C_{1-4}$ haloalkyl, $C_{3-7}$ cycloalkyl, $C_{1-4}$ alkoxy, OH, amino and cyano, and which Het$^6$ group may also be substituted by oxo.

Embodiments of the invention that may be mentioned include compounds of formula I in relation to which one or more of the following apply:

(i) $R^1$ represents
-L$^1$-C(O)N($R^{2a}$)$R^{2b}$,
-L$^{2a}$-S(O)—$R^{2c1}$,
-L$^{2b}$-S(O)$_2$—$R^{2c2}$,
-L$^3$-P(O)$R^{2d}R^{2e}$,
—CH$_2$N($R^{2d1}$)-Q-$R^{2f}$,
—O—C($R^{2x}$)($R^{2y}$)($R^{2z}$) or
—CH$_2$-Het$^2$
(e.g. $R^1$ represents —CH$_2$N($R^{2d}$)-Q-$R^{2f}$, —O—C($R^{2x}$)($R^{2y}$)($R^{2z}$) or, particularly, -L$^1$-C(O)N($R^{2a}$)$R^{2b}$, -L$^{2a}$-S(O)—$R^{2c1}$, -L$^{2b}$-S(O)$_2$—$R^{2c2}$, -L$^3$-P(O)$R^{2d}R^{2e}$ or —CH$_2$NH-Q-$R^{2f}$);

(i) $L^1$, $L^{2a}$, $L^{2b}$ and $L^3$ independently represent a bond or —(CH$_2$)$_{1-2}$- or —OCH$_2$— wherein the O-atom is attached to the phenyl ring, or $L^1$, $L^{2b}$ or $L^3$ represents O;

(iii) $R^{2a}$ represents —[C($R^{3a}$)($R^{3b}$)]—[$C_{1-3}$ alkylene]-$R^{3c}$ or, when $L^1$ is not a bond, $R^{2a}$ may alternatively represent H or $C_{1-4}$ alkyl or $R^{2a}$ and $R^{2b}$, together with the N-atom to which they are attached, may form a 4- to 7-membered heterocyclic group that is fully saturated and which heterocyclic group contains one N atom (the atom to which $R^{2a}$ and $R^{2b}$ are attached) and, optionally, one or two further heteroatoms selected from O, S and N, and which heterocyclic group is optionally substituted by one or more substituents selected from OH, oxo, $C_{1-2}$ alkyl and $C_{1-2}$ alkoxy
(e.g. $R^{2a}$ represents —[C($R^{3a}$)($R^{3b}$)]—[$C_{1-3}$ alkylene]-$R^{3c}$ or, when $L^1$ is not a bond, $R^{2a}$ may alternatively represent H or $C_{1-4}$ alkyl);

(iv) $R^{2b}$ represents methyl or, particularly, H;

(v) $R^{3c}$ represents —[O—CH$_2$CH$_2$]$_{2-6}$—$R^{5a}$, Het$^1$ or Het$^2$;

(vi) $R^{2c1}$ and $R^{2c2}$ independently represent methyl optionally substituted by one or more halo groups, or, when $L^{2a}$ is not a bond, $R^{2c1}$ may alternatively represent $R^{2c3}$, or, when $L^{2b}$ is not a bond, $R^{2c2}$ may alternatively represent $R^{2c3}$;

(vii) $R^{2c3}$ represents $C_{2-7}$ alkyl or phenyl, which latter two groups are optionally substituted by one or more substituents selected from $C_{1-2}$ alkyl, halo, OH and $C_{1-2}$ alkoxy;

(viii) $R^{2d}$ represents $C_{1-2}$ alkyl;

(ix) $R^{2e}$ represents $C_{1-2}$ alkyl, $C_{1-2}$ alkoxy or OH, or $R^{2d}$ and $R^{2e}$ together combine to form $C_{4-5}$ alkylene;

(x) $R^{2f}$ represents $C_{1-4}$ alkyl, $C_{5-6}$ cycloalkyl or phenyl, which latter three groups are optionally substituted by one or more substituents selected from $C_{1-2}$ alkyl, halo, OH, $C_{1-2}$ alkoxy and $N(R^{4a})R^{4b}$ (e.g. by one or more substituents selected from $C_{1-2}$ alkyl, halo, OH and $C_{1-2}$ alkoxy) or, when Q represents C(O), $R^{2f}$ may alternatively represent H;

(xi) $R^{2x}$ represents $C_{1-5}$ alkyl substituted by one to three OH groups and $R^{2y}$ and $R^{2z}$ independently represent H or $CH_2OH$;

(xii) $R^{5b}$ represents H or, particularly, $C_{1-2}$ alkyl (such as methyl) optionally substituted by one or more halo atoms;

(xiii) $R^{4a}$, $R^{4b}$, $R^{5c}$ and $R^{5d}$ independently represent H or $C_{1-2}$ alkyl, or $R^{5c}$ and $R^{5d}$ or $R^{4a}$ and $R^{4b}$, together with the N-atom to which they are attached, form a 5- or 6-membered heterocyclic group that is fully saturated, partially unsaturated or fully aromatic and which heterocyclic group contains one N atom (the atom to which $R^{5c}$ and $R^{5d}$ or $R^{4a}$ and $R^{4b}$ are attached) and, optionally, one to three further heteroatoms selected from O, S and N, and which heterocyclic group is optionally substituted by one or more substituents selected from halo, OH, oxo, $C_{1-2}$ alkyl and $C_{1-2}$ alkoxy;

(xiv) $R^{1A}$ represents OH or, particularly, H, halo, $C_{1-4}$ alkyl or $C_{1-4}$ alkoxy, which latter two groups are optionally substituted by one or more fluoro atoms;

(xv) $R^{1C}$ and $R^{1E}$ independently represent halo or, particularly, H;

(xvi) $R^{1D}$ represents trimethylsilyl, $C_{3-7}$ alkyl, $-C(C_{1-2}$ alkyl$)_2$-C≡CH, $C_{3-5}$ cycloalkyl, phenyl or $Het^2$, which latter three groups are optionally substituted by one or more substituents selected from $C_{1-2}$ alkyl, halo and $C_{1-2}$ alkoxy;

(xvii) $Het^1$ represents a 5- or 6-membered heterocyclic group that is fully aromatic, which group contains one to four heteroatoms selected from N, O and S and which group is optionally substituted by one or more substituents selected from halo, $C_{1-2}$ alkyl and $C_{1-2}$ alkoxy;

(xviii) $Het^2$ represents, independently at each occurrence, a 4- to 6-membered (e.g. a 5- or 6-membered) heterocyclic group that is fully saturated or partially unsaturated, which group contains one or two heteroatoms selected from N, O and S and which group is optionally substituted by one or more substituents selected from OH, oxo, $C_{1-2}$ alkyl and $C_{1-2}$ alkoxy;

(xix) $R^a$ and $R^b$, together with the C-atoms to which they are attached, form a fused phenyl ring, or $R^2$ and $R^3$ independently represent halo or $C_{1-2}$ alkyl;

(xx) E represents $N(G^1)$;

(xxi) $G^1$ represents $C_{1-2}$ alkyl (e.g. methyl) or, particularly, H;

(xxii) each $Y^1$ is independently selected from the group consisting of
$-CH_2OH$, $-C(O)OH$ or, particularly,
halo, OH, cyano,
$P(O)R^{6c}R^{6d}$,
$E^1-N(R^{6e})R^{6f}$,
$E^2-S(O)_2R^{6g}$,
$E^3-[C(R^{3a})(R^{3b})CH_2-O]_{2-6}-R^{6h}$,
$-C≡C-H$,
$-N=S(O)(CH_3)_2$ and
$C_{1-4}$ alkyl or $C_{1-4}$ alkoxy, which latter two groups are optionally substituted by one or more fluoro atoms;

(xxiii) each $Y^2$ independently represents oxo or $Y^1$ (e.g. each $Y^2$ independently represents oxo, halo, OH, cyano, $-N(R^{6e})R^{6f}$, $C_{1-4}$ alkoxy or $C_{1-4}$ alkyl, which latter two groups are optionally substituted by one or more fluoro atoms);

(xxiv) $E^1$ represents
$C_{1-3}$ alkylene,
$S(O)_2$,
$-O-CH_2-[C_{1-3}$ alkylene]- or, particularly,
a direct bond,
$-C(O)-$ or
$C(O)-NR^{7a}-CH_2-[C_{1-3}$ alkylene]-,
the alkylene part of which latter group is optionally substituted by one or more substituents selected from fluoro and $C_{1-2}$ alkyl;

(xxv) $E^2$ represents
a direct bond or, particularly, $-O-$;

(xxvi) $E^3$ represents $-C(O)NH$ or $-O-$;

(xxvii) $R^{6a}$ and $R^{6b}$ independently represent $C_{1-4}$ alkyl optionally substituted by one or more substituents selected from halo, OH, $C_{1-2}$ alkoxy, $Het^7$ or phenyl, which latter two groups are optionally substituted by one or more substituents selected from halo, $C_{1-2}$ alkyl, $C_{1-2}$ haloalkyl and $C_{1-2}$ alkoxy;

(xxviii) $R^{6c}$ and $R^{6d}$ independently represent $C_{1-2}$ alkyl or together combine to form $C_{4-5}$ alkylene;

(xxix) $R^{6e}$ and $R^{6f}$ independently represent
H,
$Het^4$ optionally substituted by $C_{1-2}$ alkyl or
$C_{1-6}$ alkyl optionally substituted with one or more OH groups or by phenyl or $Het^6$, which latter two groups are optionally substituted by one or more substituents selected from halo, $C_{1-2}$ alkyl, $C_{1-2}$ haloalkyl and $C_{1-2}$ alkoxy (e.g. $R^{6e}$ and $R^{6f}$ independently represent H or $C_{1-2}$ alkyl, which latter group is optionally substituted by phenyl or $Het^6$, which latter two groups are optionally substituted by one or more substituents selected from halo, $C_{1-2}$ alkyl, $C_{1-2}$ haloalkyl and $C_{1-2}$ alkoxy), or $R^{6e}$ and $R^{6f}$, together with the N-atom to which they are attached, form a 5- or 6-membered heterocyclic group that is fully saturated, partially unsaturated or fully aromatic and which heterocyclic group contains one N atom (the atom to which $R^{6e}$ and $R^{6f}$ are attached) and, optionally, one or two further heteroatoms selected from O, S and N, and which heterocyclic group is optionally substituted by one or more substituents selected from halo, OH, oxo, $C_{1-2}$ alkyl and $C_{1-2}$ alkoxy;

(xxx) $R^{6g}$ represents $C_{3-5}$ cycloalkyl or, particularly, $C_{1-4}$ alkyl or phenyl, which latter two groups are optionally substituted by one or more substituents selected from halo, $C_{1-2}$ alkyl and $C_{1-2}$ alkoxy;

(xxxi) $R^{6h}$ represents H or, particularly, $C_{1-2}$ alkyl;

(xxxii) $R^{7c}$ and $R^{7d}$ independently represent H or methyl;

(xxxiii) $Het^3$ independently represents a 5- to 10-membered heterocyclic group that is fully saturated, partially unsaturated or fully aromatic, which heterocyclic group contains one to four heteroatoms selected from N, O and S;

(xxxiv) $Het^4$, $Het^6$ and $Het^7$ independently represent 5- or 6-membered heterocyclic groups that are fully saturated, partially unsaturated or fully aromatic, which heterocyclic groups contain one to three heteroatoms selected from N, O and S.

Embodiments of the invention that may be mentioned include those in which the compound of formula I is a compound of formula Ia, Ib or Ic,

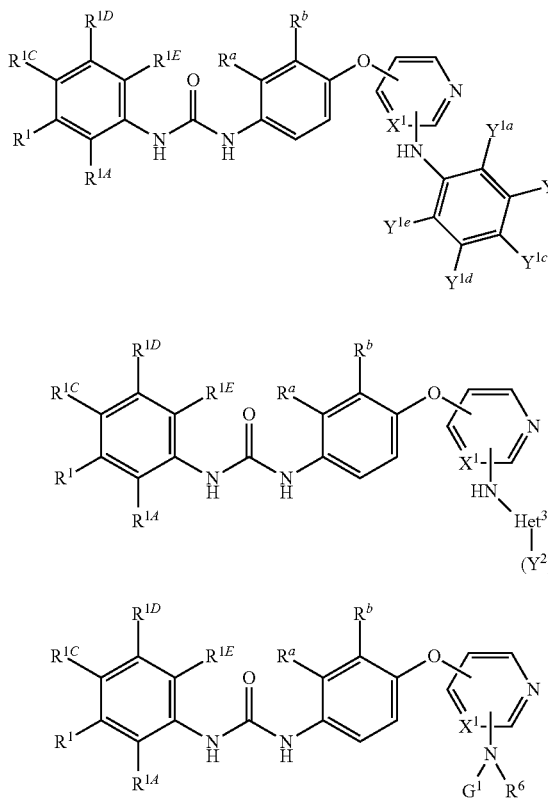

or a pharmaceutically acceptable salt, solvate or isotopic derivative thereof, wherein $R^1$, $R^{1A}$, $R^{1C}$, $R^{1D}$, $R^{1E}$, $R^a$, $R^b$, $X^1$, $Het^3$, $Y^2$ and $G^1$ are as hereinbefore defined and:

$Y^{1a}$ to $Y^{1e}$ each independently represents H or $Y^1$ as defined above;

n represents 0, 1, 2, 3 or 4; and $R^6$ represents $CH_2$-phenyl or, particularly, $C_{1-2}$ alkyl or $—[C(O)]_{0-1}—C_{1-4}$ alkylene-$Het^7$, wherein the $Het^7$ group is as defined above and is optionally substituted by one or more substituents selected from halo, $C_{1-2}$ alkyl, $C_{1-2}$ haloalkyl and $C_{1-2}$ alkoxy.

Embodiments of the invention that may be mentioned include those in which one or more of the following definitions apply to the compounds of formula I, Ia, Ib or Ic:

(i) $R^1$ represents
—$CH_2$-$Het^2$ or, particularly,
-$L^1$-C(O)N($R^{2a}$)$R^{2b}$,
-$L^{2a}$-S(O)—$CH_3$,
-$L^{2b}$-S(O)$_2$—$CH_3$,
-$L^3$-P(O)$R^{2d}R^{2e}$,
—$OCH_2P(O)(CH_3)_2$,
—O—S(O)$_2$—$C_{1-2}$ alkyl,
—$CH_2N(R^{2d1})$-Q-$C_{1-3}$ alkyl,
—$CH_2N(R^{2d1})$-Q-$(CH_2)_{1-3}$—N($R^{4a}$)$R^{4b}$,
—O—$CH_2CH_2$—OH,
—O—CH($CH_2OH$)$_2$ or
—O—$CH_2C(CH_2OH)_3$
(e.g. $R^1$ represents, -$L^1$-C(O)N(H)$R^{2a}$, -$L^{2a}$-S(O)—$CH_3$, -$L^{2b}$-S(O)$_2$—$CH_3$, -$L^3$-P(O)$R^{2d}R^{2e}$, —$OCH_2P(O)(CH_3)_2$, —O—S(O)$_2$—$C_{1-2}$ alkyl, —$CH_2NHC(O)CH_3$ or —$CH_2NHS(O)_2CH_3$);

(ii) $L^1$, $L^{2a}$, $L^{2b}$ and $L^3$ independently represent a bond or —$CH_2$—;

(iii) $R^{2a}$ represents —[C($R^{3a}$)($R^{3b}$)]—[$C_{1-2}$ alkylene]-$R^{3c}$ or, when $L^1$ represents —$CH_2$—, $R^{2a}$ may alternatively represent H or $C_{1-2}$ alkyl, or $R^{2a}$ and $R^{2b}$, together with the N-atom to which they are attached, may form a 5- or 6-membered heterocyclic group that is fully saturated and which heterocyclic group contains one N atom (the atom to which $R^{2a}$ and $R^{2b}$ are attached) and, optionally, a further heteroatom selected from O, S and N, and which heterocyclic group is optionally substituted by one to three substituents selected from oxo and $C_{1-2}$ alkyl,
or $R^{2b}$ represents methyl or, particularly, H;

(iv) $R^{2d1}$ represents methyl or, particularly, H;

(v) $R^{3a}$ and $R^{3b}$ independently represent methyl or, particularly, H;

(vi) $R^{3c}$ represents $Het^1$ or, particularly, [O—$CH_2CH_2$]$_{2-5}$—$R^{5a}$ or $Het^2$;

(vii) $R^{2d}$ represents ethyl or, particularly, methyl;

(viii) $R^{2e}$ represents ethyl or, particularly, methyl,
or $R^{2d}$ and $R^{2e}$ together combine to form —$(CH_2)_{4-5}$—;

(ix) $R^{5a}$ represents N($R^{5c}$)($R^{5d}$) or, particularly, O—$C_{1-2}$ alkyl;

(x) $R^{4a}$, $R^{4b}$, $R^{5c}$ and $R^{5d}$ independently represent H or methyl, or $R^{5c}$ and $R^{5d}$, together with the N-atom to which they are attached, form a 5- or 6-membered heterocyclic group that is fully saturated, partially unsaturated or fully aromatic and which heterocyclic group contains one N atom (the atom to which $R^{5c}$ and $R^{5d}$ are attached) and, optionally, one further heteroatom selected from O, S and N, and which heterocyclic group is optionally substituted by one or more substituents selected from OH, oxo and $C_{1-2}$ alkyl;

(xi) $R^{1A}$ represents H or $C_{1-2}$ alkoxy, which latter group is optionally substituted by one or more fluoro atoms;

(xii) $R^{1C}$ and $R^{1E}$ both represent H;

(xiii) $R^{1D}$ represents trimethylsilyl, —C($CH_3$)$_2$—C≡CH or $C_{3-5}$ cycloalkyl, which latter group is optionally substituted by methyl
or, particularly, $R^{1D}$ represents morpholinyl or $C_{3-6}$ alkyl such as tert-butyl;

(xiv) $Het^1$ represents a 5- or 6-membered heterocyclic group that is fully aromatic, which group contains one N-atom and optionally contains one or two further heteroatoms selected from N, O and S, and which group is optionally substituted by one or more substituents selected from halo, methyl and methoxy;

(xv) $Het^2$ represents a 4- to 6-membered (e.g. a 5- or 6-membered) heterocyclic group that is fully saturated or partially unsaturated, which group contains one or two heteroatoms selected from N, O and S and which group is optionally substituted by one or more substituents selected from oxo, methyl and methoxy;

(xvi) $R^a$ and $R^b$, together with the C-atoms to which they are attached, form a fused phenyl ring;

(xvii) $X^1$ represents N or, particularly, CH;

(xviii) $G^1$ represents H or methyl;

(xix) at least two of $Y^{1a}$ to $Y^{1e}$ are H and the remainder of $Y^{1a}$ to $Y^{1e}$ are independently selected from H, halo, OH, cyano, —$CH_2OH$, —C(O)OH, —S(O)$_2R^{6g}$, —S(O)$_2$N($R^{6e}$)$R^{6f}$, —O—$CH_2$—[$C_{1-2}$ alkylene]-N($R^{6e}$)$R^{6f}$, —P(O)(CH$_3$)$_2$, $E^1$-N($R^{6e}$)$R^{6f}$, —C(O)N($R^{6e}$)$R^{6f}$, —C(O)NH—$CH_2$—[$C_{1-2}$ alkylene]-N($R^{6e}$)$R^{6f}$, —O—S(O)$_2$—$C_{1-4}$ alkyl, $E^3$-[$CH_2CH_2$—O]$_{2-5}$—$R^{6h}$, —C≡C—H, —N═S(O)(CH$_3$)$_2$ and $C_{1-2}$ alkyl or $C_{1-2}$ alkoxy, which latter two groups are optionally substituted by one or more fluoro atoms
(e.g. the remainder of $Y^{1a}$ to $Y^{1e}$ are independently selected from —S(O)$_2$N($R^{6e}$)$R^{6f}$, —O—$CH_2$—[$C_{1-}$ alkylene]-N(R$^{6e}$)R$^{6f}$ or, particularly, H, halo, OH, cyano, —P(O)(CH$_3$)$_2$, —N(R$^{6e}$)R$^{6f}$, —C(O)N(H)R$^{6e}$, —C(O)NH—CH$_2$CH$_2$—N(R$^{6e}$)R$^{6f}$, —O—S(O)$_2$—C$_{1-4}$ alkyl, E$^3$-[CH$_2$CH$_2$—O]$_{2-5}$—R$^{6h}$, —C≡C—H, —N=S(O)(CH$_3$)$_2$ and C$_{1-2}$ alkyl or C$_{1-2}$ alkoxy, which latter two groups are optionally substituted by one or more fluoro atoms);

(xx) E$^1$ represents a direct bond or C$_{1-2}$ alkylene (e.g. CH$_2$);
(xxi) R$^{6e}$ and R$^{6f}$ independently represent
H,
C$_{1-5}$ alkyl (e.g. methyl, ethyl or n-propyl) optionally substituted by one to three OH groups or by Het$^6$ or Het$^4$ optionally substituted by methyl
(e.g. R$^{6e}$ and R$^{6f}$ independently represent H or C$_{1-2}$ alkyl),
or R$^{6e}$ and R$^{6f}$, together with the N-atom to which they are attached, form a 5- or 6-membered heterocyclic group that is fully saturated, partially unsaturated or fully aromatic and which heterocyclic group contains one N atom (the atom to which R$^{6e}$ and R$^{6f}$ are attached) and, optionally, one or two further heteroatoms selected from O, S and N, and which heterocyclic group is optionally substituted by one or more substituents selected from OH, oxo, methyl and methoxy;
(xxii) E$^3$ represents —O— or —C(O)NH;
(xxiii) R$^{6g}$ represents C$_{1-2}$ alkyl (e.g. methyl) or C$_{3-5}$ cycloalkyl (e.g. cyclopropyl);
(xxiv) R$^{6h}$ represents H or, particularly, methyl;
(xxv) Het$^3$ represents a 5- to 10-membered heterocyclic group that is partially unsaturated or fully aromatic, which heterocyclic group contains one to four heteroatoms selected from N, O and S,
or Het$^3$ represents a 5- or 6-membered heterocyclic group that is fully saturated, which heterocyclic group contains one or two heteroatoms selected from N, O and S;
(xxvi) each Y$^2$ independently represents oxo, OH, —N(R$^{6e}$)R$^{6f}$, C$_{1-2}$ alkoxy or C$_{1-2}$ alkyl, which latter two groups are optionally substituted by one or more fluoro atoms;
(xxvii) n represents 0, 1 or 2;
(xxviii) R$^6$ represents C$_{1-2}$ alkyl or —[C(O)]$_{0-1}$—(CH$_2$)$_{1-3}$-Het$^7$, wherein the Het$^7$ group is optionally substituted by one or more substituents selected from methyl and methoxy;
(xxix) Het$^4$, Het$^6$ and Het$^7$ independently represent a 5- or 6-membered heterocyclic group that is fully saturated, partially unsaturated or fully aromatic, which heterocyclic group contains one to three heteroatoms selected from N, O and S.

Particular embodiments of the invention that may be mentioned include those in which the compound of formula I, Ia, Ib or Ic is a compound of formula Ia1, Ib1 or Ic1,

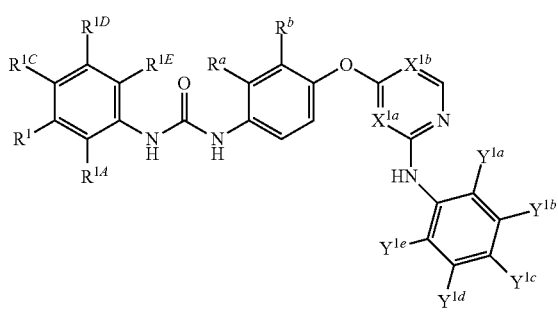

Ia1

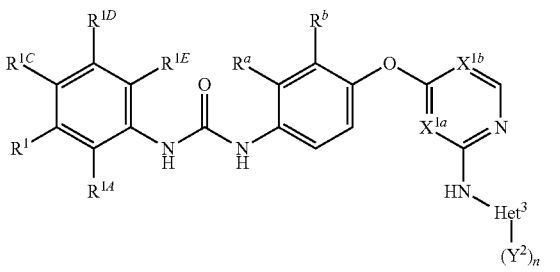

Ib1

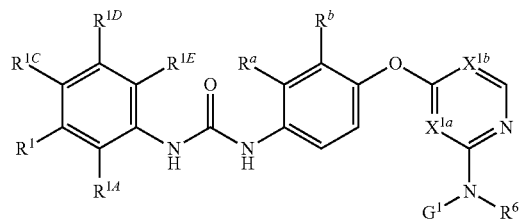

Ic1 or a pharmaceutically acceptable salt, solvate or isotopic derivative thereof, wherein R$^1$, R$^{1A}$, R$^{1C}$, R$^{1D}$, R$^{1E}$, R$^a$, R$^b$, Het$^3$, Y$^{1a}$ to Y$^{1e}$, Y$^2$, R$^6$ and G$^1$ are as hereinbefore defined and:
one of X$^{1a}$ and X$^{1b}$ represents CH and the other represents CH or N.

Particular embodiments of the invention that may be mentioned include those in which the compound of formula Ia or Ia1 is one in which either:
(i) Y$^{1a}$ to Y$^{1e}$ are all H; or
(ii) three or four of Y$^{1a}$ to Y$^{1e}$ are H the remainder of Y$^{1a}$ to Y$^{1e}$ (e.g. Y$^{1b}$ and Y$^{1c}$ or, particularly, Y$^{1b}$ and/or Y$^{1d}$) are independently selected from fluoro, chloro, cyano, —S(O)$_2$N(R$^{6e}$)R$^{6f}$ (e.g. —S(O)$_2$NH$_2$, —S(O)$_2$N(CH$_3$)$_2$ or —S(O)$_2$N(R$^{6e}$)—(CH$_2$)$_{2-3}$-Het$^6$), —S(O)$_2$R$^{6g}$ (e.g. —S(O)$_2$CH$_3$ or —S(O)$_2$-cyclopropyl), —C(O)OH, —C$_{1-2}$ alkylene-N(R$^{6e}$)R$^{6f}$ (e.g. —CH$_2$-(1-methylpiperazin-4-yl)), —C(O)N(R$^{6e}$)R$^{6f}$ (e.g. C(O)N(R$^{6e}$)—(CH$_2$)$_{2-3}$-Het$^6$ or, particularly, —C(O)NH$_2$, —C(O)N(H)CH$_3$, —C(O)N(H)CH$_2$C(CH$_2$OH)$_3$, or —C(O)-(4-methylpiperazin-1-yl)), —C(O)N(H)—CH$_2$(CH$_2$)$_{1-2}$—N(R$^{6e}$)R$^{6f}$ (e.g. —C(O)N(H)—CH$_2$(CH$_2$)$_{1-2}$—N(CH$_3$)$_2$ or —C(O)N(H)—CH$_2$(CH$_2$)$_{1-2}$-(1-methylpiperazin-4-yl or, particularly, morpholin-4-yl or 1-oxo-thiomorpholin-4-yl)), —C(O)N(H)—[CH$_2$CH$_2$—O]$_{2-4}$—CH$_3$, —O—S(O)$_2$—CH$_3$, —O—CH$_2$(CH$_2$)$_{1-2}$—N(R$^{6e}$)R$^{6f}$ (e.g. —O—CH$_2$(CH$_2$)$_{1-2}$-morpholin-4-yl)), —O—[CH$_2$CH$_2$—O]$_{2-4}$—CH$_3$, —P(O)(CH$_3$)$_2$, —N=S(O)(CH$_3$)$_2$, —C≡C—H, —CH$_2$OH, methyl and methoxy, which latter two groups are optionally substituted by one or more fluoro atoms
(e.g. Y$^{1a}$ to Y$^{1e}$, such as Y$^{1b}$ and/or Y$^{1d}$, are independently selected from cyano, —S(O)$_2$N(CH$_3$)$_2$, —C(O)N(H)—CH$_2$CH$_2$—N(R$^{6e}$)R$^{6f}$, —O—CH$_2$CH$_2$—N(R$^{6e}$)R$^{6f}$ or, particularly, fluoro, chloro, —P(O)(CH$_3$)$_2$, —C(O)NH$_2$, —O—S(O)$_2$—CH$_3$, —O—[CH$_2$CH$_2$—O]$_{2-4}$—CH$_3$, —C(O)N(H)—[CH$_2$CH$_2$—O]$_{2-4}$—CH$_3$, —C≡C—H, —N=S(O)(CH$_3$)$_2$, methyl and methoxy, which latter two groups are optionally substituted by one or more fluoro atoms).

More particular embodiments of the invention that may be mentioned include those in which the compound of formula I, Ia, Ib, Ic, Ia1, Ib1 or Ic1 is one in which:

(i) $R^1$ represents —$CH_2$-$Het^2$ or, particularly, —C(O)N(H)—$CH_2CH_2$—$R^{3c}$, —$CH_2$—C(O)$NH_2$, —$CH_2$—C(O)N(H)$CH_3$, —$CH_2$—C(O)N($CH_3$)$_2$, —$CH_2$—C(O)-(morpholin-4-yl)-S(O)—$CH_3$, —S(O)$_2$—$CH_3$, —$CH_2$—S(O)—$CH_3$, —$CH_2$—S(O)$_2$—$CH_3$, —O—S(O)$_2$—$CH_3$, —P(O)($CH_3$)$_2$, —P(O)($CH_2CH_3$)$_2$, —$CH_2$P(O)($CH_3$)$_2$, —O$CH_2$P(O)($CH_3$)$_2$, —$CH_2$NHC(O)$CH_3$, —$CH_2$N($CH_3$)C(O)$CH_3$, —$CH_2$NHC(O)$CH_2$—N($CH_3$)$_2$, —$CH_2$NHS(O)$_2CH_3$, —O—$CH_2CH_2$—OH, —O—CH($CH_2$OH)$_2$ or —O—$CH_2$C($CH_2$OH)$_3$ (e.g. $R^1$ represents —$CH_2$NHC(O)$CH_2$—N($CH_3$)$_2$ or, particularly, —C(O)N(H)—$CH_2CH_2$—$R^{3c}$, —$CH_2$—C(O)$NH_2$, —S(O)—$CH_3$, —S(O)$_2$—$CH_3$, —$CH_2$—S(O)—$CH_3$, —$CH_2$—S(O)$_2$—$CH_3$, —O—S(O)$_2$—$CH_3$, —P(O)($CH_3$)$_2$, —$CH_2$P(O)($CH_3$)$_2$, —O$CH_2$P(O)($CH_3$)$_2$, —$CH_2$NHC(O)$CH_3$, or —$CH_2$NHS(O)$_2CH_3$);

(ii) $R^{3c}$ represents —[O—$CH_2CH_2$]$_{2-4}$—$R^{5a}$ or, particularly, $Het^2$;

(iii) $R^{1A}$ represents H or methoxy, which latter group is optionally substituted by one or more fluoro atoms;

(iv) $R^{1C}$ and $R^{1E}$ both represent H;

(v) $R^{1D}$ represents trimethylsilyl, —C($CH_3$)$_2$—C≡CH, morpholinyl or $C_{3-5}$ alkyl, particularly, tert-butyl; and/or (vi) $Het^2$ represents a 4- or, particularly, a 5- or 6-membered heterocyclic group that is fully saturated, which group contains one or two heteroatoms selected from N, O and S and which group is optionally substituted by oxo or, particularly, by one or more methyl groups.

Other compounds of formula I, Ia, Ib, Ic, Ia1, Ib1 or Ic1 that may be mentioned include the compounds of the examples described hereinafter. Thus, embodiments of the invention that may be mentioned include those in which the compound of formula I, Ia, Ib, Ic, Ia1, Ib1 or Ic1 is a compound selected from the list comprising:

1-(5-(tert-butyl)-3-(dimethylphosphoryl)-2-methoxyphenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

1-(5-(tert-butyl)-3-(dimethylphosphoryl)-2-methoxyphenyl)-3-(4-((2-((3-methoxy-5-(2-(2-(2-methoxyethoxy)ethoxy)ethoxy)phenyl)amino)pyridin-4-yl)oxy)naphthalen-1-yl)urea;

3-((4-((4-(3-(5-(tert-butyl)-3-(dimethylphosphoryl)-2-methoxyphenyl)ureido)naphthalen-1-yl)oxy)pyridin-2-yl)amino)-5-ethynyl-N-(2-(2-(2-methoxyethoxy)ethoxy)ethyl)benzamide;

1-(5-(tert-butyl)-3-(dimethylphosphoryl)-2-methoxyphenyl)-3-(4-((6-((3-methoxy-5-(2-(2-(2-methoxyethoxy)ethoxy)phenyl)amino)pyrimidin-4-yl)oxy)naphthalen-1-yl)urea;

5-(tert-butyl)-2-methoxy-3-(3-(4-((2-((3-methoxy-5-(2-(2-(2-methoxyethoxy)ethoxy)ethoxy)-phenyl)amino)pyrimidin-4-yl)oxy)naphthalen-1-yl)ureido)phenyl methanesulfonate;

1-(5-(tert-butyl)-3-((dimethylphosphoryl)methoxy)-2-methoxyphenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

5-(tert-butyl)-2-methoxy-3-(3-(4-((2-((3-methoxy-5-(2-(2-(2-methoxyethoxy)ethoxy)ethoxy)-phenyl)amino)pyrimidin-4-yl)oxy)naphthalen-1-yl)ureido)-N-(2-(2-(2-methoxyethoxy)ethoxy)ethyl)benzamide;

5-(tert-butyl)-2-methoxy-3-(3-(4-((2-((3-methoxy-5-(2-(2-(2-methoxyethoxy)ethoxy)ethoxy)phenyl)amino)pyrimidin-4-yl)oxy)naphthalen-1-yl)ureido)-N-(2-morpholinoethyl)-benzamide;

1-(5-(tert-butyl)-2-methoxy-3-(methylsulfonyl)phenyl)-3-(4-((2-((3-methoxy-5-(2-(2-(2-methoxyethoxy)ethoxy)ethoxy)phenyl)amino)pyridin-4-yl)oxy)naphthalen-1-yl)urea;

1-(3-(tert-butyl)-5-(dimethylphosphoryl)phenyl)-3-(4-((2-((3-methoxy-5-(2-(2-(2-methoxy-ethoxy)ethoxy)ethoxy)phenyl)amino)pyridin-4-yl)oxy)naphthalen-1-yl)urea;

1-(5-(tert-butyl)-3-(dimethylphosphoryl)-2-methoxyphenyl)-3-(4-((2-(phenylamino)pyridin-4-yl)oxy)naphthalen-1-yl)urea;

1-(5-(tert-butyl)-2-methoxy-3-(methylsulfinyl)phenyl)-3-(4-((2-(phenylamino)pyridin-4-yl)oxy)naphthalen-1-yl)urea;

2-(5-(tert-butyl)-2-methoxy-3-(3-(4-((2-(phenylamino)pyridin-4-yl)oxy)naphthalen-1-yl)ureido)phenyl)acetamide;

5-(tert-butyl)-2-methoxy-N-(2-morpholinoethyl)-3-(3-(4-((2-(phenylamino)pyridin-4-yl)oxy)naphthalen-1-yl)ureido)benzamide;

1-(5-(tert-butyl)-2-methoxy-3-((methylsulfonyl)methyl)phenyl)-3-(4-((2-((3-methoxy-5-(2-(2-(2-methoxyethoxy)ethoxy)ethoxy)phenyl)amino)pyridin-4-yl)oxy)naphthalen-1-yl)urea;

1-(5-(tert-butyl)-3-(dimethylphosphoryl)-2-methoxyphenyl)-3-(4-((2-(phenylamino)pyrimidin-4-yl)oxy)naphthalen-1-yl)urea;

5-(tert-butyl)-2-methoxy-3-(3-(4-((2-((3-methoxy-5-(2-(2-(2-methoxyethoxy)ethoxy)ethoxy)-phenyl)amino)pyridin-4-yl)oxy)naphthalen-1-yl)ureido)-N-(2-morpholinoethyl)benzamide;

2-(5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)acetamide;

1-(5-(tert-butyl)-2-methoxy-3-(methylsulfinyl)phenyl)-3-(4-((2-((3-methoxy-5-(2-(2-(2-methoxyethoxy)ethoxy)ethoxy)phenyl)amino)pyridin-4-yl)oxy)naphthalen-1-yl)urea;

1-(5-(tert-butyl)-3-((dimethylphosphoryl)methoxy)-2-methoxyphenyl)-3-(4-((2-(phenylamino)-pyrimidin-4-yl)oxy)naphthalen-1-yl)urea;

1-(5-(tert-butyl)-3-((dimethylphosphoryl)methoxy)-2-methoxyphenyl)-3-(4-((2-(phenylamino)-pyridin-4-yl)oxy)naphthalen-1-yl)urea;

1-(5-(tert-butyl)-3-(dimethylphosphoryl)-2-methoxyphenyl)-3-(4-((2-((2-methoxyphenyl)-amino)pyrimidin-4-yl)oxy)naphthalen-1-yl)urea;

1-(5-(tert-butyl)-3-(dimethylphosphoryl)-2-methoxyphenyl)-3-(4-((2-((3-methoxyphenyl)-amino)pyrimidin-4-yl)oxy)naphthalen-1-yl)urea;

1-(5-(tert-butyl)-3-(dimethylphosphoryl)-2-methoxyphenyl)-3-(4-((2-((4-methoxyphenyl)-amino)pyrimidin-4-yl)oxy)naphthalen-1-yl)urea;

1-(5-(tert-butyl)-3-(dimethylphosphoryl)-2-methoxyphenyl)-3-(4-((2-((3,4-dimethoxyphenyl)-amino)pyrimidin-4-yl)oxy)naphthalen-1-yl)urea;

1-(5-(tert-butyl)-3-(dimethylphosphoryl)-2-methoxyphenyl)-3-(4-((2-((3,5-dimethoxyphenyl)-amino)pyrimidin-4-yl)oxy)naphthalen-1-yl)urea;

1-(5-(tert-butyl)-3-(dimethylphosphoryl)-2-methoxyphenyl)-3-(4-((2-((7-methyl-1H-indazol-5-yl)amino)pyrimidin-4-yl)oxy)naphthalen-1-yl)urea;

1-(5-(tert-butyl)-2-methoxy-3-(methylsulfinyl)phenyl)-3-(4-((2-(phenylamino)pyrimidin-4-yl)oxy)naphthalen-1-yl)urea;

1-(5-(tert-butyl)-2-methoxy-3-(methylsulfonyl)phenyl)-3-(4-((2-(phenylamino)pyrimidin-4-yl)oxy)naphthalen-1-yl)urea;

1-(5-(tert-butyl)-2-methoxy-3-(methylsulfonyl)phenyl)-3-(4-((2-(phenylamino)pyridin-4-yl)oxy)naphthalen-1-yl)urea;

1-(5-(tert-butyl)-2-methoxy-3-((methylsulfonyl)methyl)phenyl)-3-(4-((2-(phenylamino)-pyrimidin-4-yl)oxy)naphthalen-1-yl)urea;

1-(5-(tert-butyl)-2-methoxy-3-((methylsulfonyl)methyl)phenyl)-3-(4-((2-(phenylamino)pyridin-4-yl)oxy)naphthalen-1-yl)urea;

1-(5-(tert-butyl)-3-(dimethylphosphoryl)-2-methoxyphenyl)-3-(4-((2-(pyridin-2-ylamino)-pyrimidin-4-yl)oxy)naphthalen-1-yl)urea;

1-(5-(tert-butyl)-3-((dimethylphosphoryl)methoxy)-2-methoxyphenyl)-3-(4-((2-((3,5-dimethoxyphenyl)amino)pyrimidin-4-yl)oxy)naphthalen-1-yl)urea;

5-(tert-butyl)-2-methoxy-N-(2-morpholinoethyl)-3-(3-(4-((2-(phenylamino)pyrimidin-4-yl)oxy)naphthalen-1-yl)ureido)benzamide;

1-(5-(tert-butyl)-3-(dimethylphosphoryl)-2-methoxyphenyl)-3-(4-((2-(pyrazin-2-ylamino)-pyrimidin-4-yl)oxy)naphthalen-1-yl)urea;

1-(5-(tert-butyl)-3-(dimethylphosphoryl)-2-methoxyphenyl)-3-(4-((2-(pyrimidin-5-ylamino)-pyrimidin-4-yl)oxy)naphthalen-1-yl)urea;

1-(5-(tert-butyl)-3-(dimethylphosphoryl)-2-methoxyphenyl)-3-(4-((2-((1-methyl-1H-pyrazol-4-yl)amino)pyrimidin-4-yl)oxy)naphthalen-1-yl)urea;

3-((4-((4-(3-(5-(tert-butyl)-3-(dimethylphosphoryl)-2-methoxyphenyl)ureido)naphthalen-1-yl)oxy)pyrimidin-2-yl)amino)phenyl methanesulfonate;

5-(tert-butyl)-2-methoxy-3-(3-(4-((2-(phenylamino)pyrimidin-4-yl)oxy)naphthalen-1-yl)ureido)-N-(2-(pyrrolidin-1-yl)ethyl)benzamide;

1-(5-(tert-butyl)-3-(dimethylphosphoryl)-2-methoxyphenyl)-3-(4-((2-((2-oxoindolin-6-yl)amino)-pyrimidin-4-yl)oxy)naphthalen-1-yl)urea;

1-(5-(tert-butyl)-3-(dimethylphosphoryl)-2-methoxyphenyl)-3-(4-((2-((2,3-dihydrobenzo[b][1,4]dioxin-6-yl)amino)pyrimidin-4-yl)oxy)naphthalen-1-yl)urea;

1-(5-(tert-butyl)-3-(dimethylphosphoryl)-2-methoxyphenyl)-3-(4-((2-((3-(dimethylphosphoryl)-5-methoxyphenyl)amino)pyrimidin-4-yl)oxy)naphthalen-1-yl)urea;

1-(5-(tert-butyl)-3-(dimethylphosphoryl)-2-methoxyphenyl)-3-(4-((2-((3-((dimethyl(oxo)-lambda-6-sulfanylidene)amino)phenyl)amino)pyrimidin-4-yl)oxy)naphthalen-1-yl)urea;

1-(5-(tert-butyl)-3-(dimethylphosphoryl)-2-methoxyphenyl)-3-(4-((2-((2-methyl-2H-1,2,3-triazol-4-yl)amino)pyrimidin-4-yl)oxy)naphthalen-1-yl)urea;

1-(5-(tert-butyl)-3-(dimethylphosphoryl)-2-methoxyphenyl)-3-(4-((2-((2,2-dioxido-1,3-dihydrobenzo[c]thiophen-5-yl)amino)pyrimidin-4-yl)oxy)naphthalen-1-yl)urea;

1-(5-(tert-butyl)-3-(dimethylphosphoryl)-2-methoxyphenyl)-3-(4-((2-(isoxazol-4-ylamino)-pyrimidin-4-yl)oxy)naphthalen-1-yl)urea;

1-(5-(tert-butyl)-3-(dimethylphosphoryl)-2-methoxyphenyl)-3-(4-((2-(pyrazin-2-ylamino)-pyrimidin-4-yl)oxy)naphthalen-1-yl)urea;

5-(tert-butyl)-2-methoxy-3-(3-(4-((2-(phenylamino)pyrimidin-4-yl)oxy)naphthalen-1-yl)ureido)-N-(2-(piperazin-1-yl)ethyl)benzamide;

1-(5-(tert-butyl)-3-(dimethylphosphoryl)-2-methoxyphenyl)-3-(4-((2-((3-oxoisoindolin-5-yl)amino)pyrimidin-4-yl)oxy)naphthalen-1-yl)urea;

1-(5-(tert-butyl)-3-(diethylphosphoryl)-2-methoxyphenyl)-3-(4-((2-(phenylamino)pyridin-4-yl)oxy)naphthalen-1-yl)urea;

1-(5-(tert-butyl)-3-((dimethylphosphoryl)methyl)-2-methoxyphenyl)-3-(4-((2-(phenylamino)-pyridin-4-yl)oxy)naphthalen-1-yl)urea;

1-(5-(tert-butyl)-2-methoxy-3-((methylsulfinyl)methyl)phenyl)-3-(4-((2-(phenylamino)pyridin-4-yl)oxy)naphthalen-1-yl)urea;

1-(5-(tert-butyl)-3-(dimethylphosphoryl)-2-methoxyphenyl)-3-(4-((2-(pyridin-3-ylamino)pyridin-4-yl)oxy)naphthalen-1-yl)urea;

1-(5-(tert-butyl)-3-(dimethylphosphoryl)-2-methoxyphenyl)-3-(4-((2-((6-(dimethylamino)-pyrazin-2-yl)amino)pyridin-4-yl)oxy)naphthalen-1-yl)urea;

N-(4-((4-(3-(5-(tert-butyl)-3-(dimethylphosphoryl)-2-methoxyphenyl)ureido)naphthalen-1-yl)oxy)pyridin-2-yl)-2-((2S,6R)-2,6-dimethylmorpholino)acetamide;

1-(5-(tert-butyl)-3-(dimethylphosphoryl)-2-methoxyphenyl)-3-(4-((2-((3,5-dimethoxyphenyl)-amino)pyridin-4-yl)oxy)naphthalen-1-yl)urea;

1-(5-(tert-butyl)-3-(dimethylphosphoryl)-2-methoxyphenyl)-3-(4-((2-((3-methoxyphenyl)-amino)pyridin-4-yl)oxy)naphthalen-1-yl)urea;

5-(tert-butyl)-2-methoxy-3-(3-(4-((2-(phenylamino)pyridin-4-yl)oxy)naphthalen-1-yl)ureido)-N-(2-(pyrrolidin-1-yl)ethyl)benzamide;

1-(5-(tert-butyl)-3-(dimethylphosphoryl)-2-methoxyphenyl)-3-(4-((2-((1-methylpiperidin-4-yl)amino)pyrimidin-4-yl)oxy)naphthalen-1-yl)urea;

(R)-1-(5-(tert-butyl)-3-(dimethylphosphoryl)-2-methoxyphenyl)-3-(4-((2-(((tetrahydrofuran-3-yl)amino)pyrimidin-4-yl)oxy)naphthalen-1-yl)urea;

(S)-1-(5-(tert-butyl)-3-(dimethylphosphoryl)-2-methoxyphenyl)-3-(4-((2-(((tetrahydrofuran-3-yl)amino)pyrimidin-4-yl)oxy)naphthalen-1-yl)urea;

1-(5-(tert-butyl)-3-(dimethylphosphoryl)-2-methoxyphenyl)-3-(4-((2-(dimethylamino)pyrimidin-4-yl)oxy)naphthalen-1-yl)urea;

1-(5-(tert-butyl)-3-(dimethylphosphoryl)-2-methoxyphenyl)-3-(4-((2-((2-morpholinoethyl)-amino)pyrimidin-4-yl)oxy)naphthalen-1-yl)urea;

1-(5-(tert-butyl)-3-(dimethylphosphoryl)-2-methoxyphenyl)-3-(4-((2-((3,5-dimethylphenyl)-amino)pyridin-4-yl)oxy)naphthalen-1-yl)urea;

1-(5-(tert-butyl)-3-(dimethylphosphoryl)-2-methoxyphenyl)-3-(4-((2-((3-chloro-5-methylmethylphenyl)amino)pyridin-4-yl)oxy)naphthalen-1-yl)urea;

3-((4-((4-(3-(5-(tert-butyl)-3-(dimethylphosphoryl)-2-methoxyphenyl)ureido)naphthalen-1-yl)oxy)pyridin-2-yl)amino)-5-methoxybenzamide;

1-(5-(tert-butyl)-3-(dimethylphosphoryl)-2-methoxyphenyl)-3-(4-((2-((3-fluoro-5-methoxyphenyl)amino)pyridin-4-yl)oxy)naphthalen-1-yl)urea;

1-(5-(tert-butyl)-3-((dimethylphosphoryl)methyl)-2-methoxyphenyl)-3-(4-((2-((3-methoxy-5-(2-(2-(2-methoxyethoxy)ethoxy)ethoxy)phenyl)amino)pyridin-4-yl)oxy)-naphthalen-1-yl)urea;

2-(5-(tert-butyl)-3-(3-(4-((2-((3,5-dimethoxyphenyl)amino)pyridin-4-yl)oxy)naphthalen-1-yl)ureido)-2-methoxyphenyl)acetamide;

1-(5-(tert-butyl)-3-(dimethylphosphoryl)-2-methoxyphenyl)-3-(4-((2-((tetrahydro-2H-pyran-4-yl)amino)pyrimidin-4-yl)oxy)naphthalen-1-yl)urea;

1-(4-((2-((2-(1H-pyrazol-1-yl)ethyl)amino)pyrimidin-4-yl)oxy)naphthalen-1-yl)-3-(5-(tert-butyl)-3-(dimethylphosphoryl)-2-methoxyphenyl)urea;

1-(5-(tert-butyl)-3-(dimethylphosphoryl)-2-methoxyphenyl)-3-(4-((2-((pyridin-2-ylmethyl)-amino)pyrimidin-4-yl)oxy)naphthalen-1-yl)urea;

1-(5-(tert-butyl)-3-(dimethylphosphoryl)-2-methylphenyl)-3-(4-((2-(phenylamino)pyridin-4-yl)oxy)naphthalen-1-yl)urea;

N-(5-(tert-butyl)-2-methoxy-3-(3-(4-((2-(phenylamino)pyridin-4-yl)oxy)naphthalen-1-yl)ureido)benzyl)methanesulfonamide;

2-(5-(tert-butyl)-2-methoxy-3-(3-(4-((2-((3-methoxyphenyl)amino)pyridin-4-yl)oxy)naphthalen-1-yl)ureido)phenyl)acetamide;

1-(5-(tert-butyl)-3-(dimethylphosphoryl)-2-methoxyphenyl)-3-(4-((2-((5-methoxypyridin-3-yl)amino)pyridin-4-yl)oxy)naphthalen-1-yl)urea;

N-(5-(tert-butyl)-2-methoxy-3-(3-(4-((2-(phenylamino)pyridin-4-yl)oxy)naphthalen-1-yl)ureido)benzyl)acetamide;

1-(5-(tert-butyl)-3-(dimethylphosphoryl)-2-methoxyphenyl)-3-(4-((2-((2-methyl-2H-1,2,3-triazol-4-yl)amino)pyridin-4-yl)oxy)naphthalen-1-yl)urea;

1-(5-(tert-butyl)-3-(dimethylphosphoryl)-2-methoxyphenyl)-3-(4-((2-((1-methyl-1H-pyrazol-3-yl)amino)pyridin-4-yl)oxy)naphthalen-1-yl)urea;

N-(2-(azetidin-1-yl)ethyl)-5-(tert-butyl)-2-methoxy-3-(3-(4-((2-(phenylamino)pyridin-4-yl)oxy)naphthalen-1-yl)ureido)benzamide;

(R)-1-(5-(tert-butyl)-2-methoxy-3-(methylsulfinyl)phenyl)-3-(4-((2-(phenylamino)pyridin-4-yl)oxy)naphthalen-1-yl)urea;

(S)-1-(5-(tert-butyl)-2-methoxy-3-(methylsulfinyl)phenyl)-3-(4-((2-(phenylamino)pyridin-4-yl)oxy)naphthalen-1-yl)urea;

1-(5-(tert-butyl)-3-(dimethylphosphoryl)-2-methoxyphenyl)-3-(4-((2-((3-(hydroxymethyl)-5-methoxyphenyl)amino)pyridin-4-yl)oxy)naphthalen-1-yl)urea;

2-(5-(tert-butyl)-2-methoxy-3-(3-(4-((2-((pyridin-2-ylmethyl)amino)pyridin-4-yl)oxy)naphthalen-1-yl)ureido)phenyl)acetamide;

1-(5-(tert-butyl)-3-(dimethylphosphoryl)-2-methoxyphenyl)-3-(4-((2-((pyridin-2-ylmethyl)amino)pyridin-4-yl)oxy)naphthalen-1-yl)urea;

2-(5-(tert-butyl)-3-(3-(4-((2-((3,5-dimethylphenyl)amino)pyridin-4-yl)oxy)naphthalen-1-yl)ureido)-2-methoxyphenyl)acetamide;

1-(4-((2-(benzylamino)pyrimidin-4-yl)oxy)naphthalen-1-yl)-3-(5-(tert-butyl)-3-(dimethylphosphoryl)-2-methoxyphenyl)urea;

2-(5-(tert-butyl)-2-methoxy-3-(3-(4-((2-((3-methoxyphenyl)amino)pyridin-4-yl)oxy)naphthalen-1-yl)ureido)phenyl)-N-methylacetamide;

2-(5-(tert-butyl)-2-methoxy-3-(3-(4-((2-((3-methoxyphenyl)amino)pyridin-4-yl)oxy)naphthalen-1-yl)ureido)phenyl)-N,N-dimethylacetamide;

1-(5-(tert-butyl)-2-methoxy-3-(2-morpholino-2-oxoethyl)phenyl)-3-(4-((2-((3-methoxyphenyl)amino)pyridin-4-yl)oxy)naphthalen-1-yl)urea;

2-(5-(tert-butyl)-2-methoxy-3-(3-(4-((2-((2-methoxypyridin-4-yl)amino)pyridin-4-yl)oxy)naphthalen-1-yl)ureido)phenyl)acetamide;

2-(5-(tert-butyl)-3-(3-(2,3-difluoro-4-((2-(phenylamino)pyridin-4-yl)oxy)phenyl)ureido)-2-methoxyphenyl)acetamide;

2-(5-(tert-butyl)-3-(3-(4-((2-((3-(hydroxymethyl)-5-methoxyphenyl)amino)pyridin-4-yl)oxy)naphthalen-1-yl)ureido)-2-methoxyphenyl)acetamide;

2-(5-(tert-butyl)-2-methoxy-3-(3-(4-((2-((5-methoxypyridin-3-yl)amino)pyridin-4-yl)oxy)naphthalen-1-yl)ureido)phenyl)acetamide;

2-(5-(tert-butyl)-2-methoxy-3-(3-(4-((2-((1-methyl-1H-pyrazol-3-yl)amino)pyridin-4-yl)oxy)naphthalen-1-yl)ureido)phenyl)acetamide;

N-(5-(tert-butyl)-3-(3-(4-((2-((3, 5-di methyl phenyl)amino)pyridin-4-yl)oxy)naphthalen-1-yl) ureido)-2-methoxybenzyl)acetamide;

N-(5-(tert-butyl)-2-methoxy-3-(3-(4-((2-((pyridin-2-ylmethyl)amino)pyridin-4-yl)oxy)naphthalen-1-yl)ureido)benzyl)acetamide;

3-((4-((4-(3-(3-(2-amino-2-oxoethyl)-5-(tert-butyl)-2-methoxyphenyl)ureido)naphthalen-1-yl)oxy)pyridin-2-yl)amino)phenyl methanesulfonate;

2-(5-(tert-butyl)-3-(3-(4-((2-((3-(difluoromethoxy)phenyl)amino)pyridin-4-yl)oxy)naphthalen-1-yl)ureido)-2-methoxyphenyl)acetamide;

3-((4-((4-(3-(3-(acetamidomethyl)-5-(tert-butyl)-2-methoxyphenyl)ureido)naphthalen-1-yl)oxy)pyridin-2-yl)amino)-5-methoxy-N-(2-morpholinoethyl)benzamide;

3-((4-((4-(3-(5-(tert-butyl)-2-methoxy-3-((methylsulfinyl)methyl)phenyl)ureido)naphthalen-1-yl)oxy)pyridin-2-yl)amino)-5-methoxy-N-(2-morpholinoethyl)benzamide;

3-((4-((4-(3-(5-(tert-butyl)-3-((dimethylphosphoryl)methyl)-2-methoxyphenyl)ureido)-naphthalen-1-yl)oxy)pyridin-2-yl)amino)-5-methoxy-N-(2-morpholinoethyl)benzamide;

2-(5-(tert-butyl)-2-methoxy-3-(3-(4-((2-((3-(2-morpholinoethoxy)-5-(trifluoromethyl)-phenyl)amino)pyridin-4-yl)oxy)naphthalen-1-yl)ureido)phenyl)acetamide;

1-(5-(tert-butyl)-2-methoxy-3-(methylsulfinyl)phenyl)-3-(4-((2-((3-(2-morpholinoethoxy)-5-(trifluoromethyl)phenyl)amino)pyridin-4-yl)oxy)naphthalen-1-yl)urea;

3-((4-((4-(3-(3-(acetamidomethyl)-5-(tert-butyl)-2-methoxyphenyl)ureido)naphthalen-1-yl)oxy)pyridin-2-yl)amino)-5-methoxy-N-(2-(2-(2-methoxyethoxy)ethoxy)ethyl)benzamide;

3-((4-((4-(3-(5-(tert-butyl)-2-methoxy-3-((methylsulfinyl)methyl)phenyl) ureido)naphthalen-1-yl)oxy)pyridin-2-yl)amino)-5-methoxy-N-(2-(2-(2-methoxyethoxy)ethoxy)ethyl)benzamide;

N-(5-(tert-butyl)-2-methoxy-3-(3-(4-((2-(phenylamino)pyridin-4-yl)oxy)naphthalen-1-yl)ureido)benzyl)-N-methylacetamide;

3-((4-((4-(3-(5-(tert-butyl)-2-methoxy-3-(methylsulfonyl)phenyl)ureido)naphthalen-1-yl)oxy)pyridin-2-yl)amino)-5-methoxy-N-(2-(2-(2-methoxyethoxy)ethoxy)ethyl)benzamide;

3-((4-((4-(3-(3-(acetamidomethyl)-5-(tert-butyl)-2-methoxyphenyl)ureido)naphthalen-1-yl)oxy)pyridin-2-yl)amino)-5-methoxybenzamide;

2-(5-(tert-butyl)-3-(3-(4-((2-((3-(cyclopropylsulfonyl)-5-methoxyphenyl)amino)pyridin-4-yl)oxy)naphthalen-1-yl)ureido)-2-methoxyphenyl) acetamide;

2-(5-(tert-butyl)-3-(3-(4-((2-((3-(dimethylphosphoryl)-5-methoxyphenyl)amino)pyridin-4-yl)oxy)naphthalen-1-yl)ureido)-2-methoxyphenyl)acetamide;

2-(5-(tert-butyl)-3-(3-(2,3-dichloro-4-((2-((3-methoxyphenyl)amino)pyridin-4-yl)oxy)phenyl)ureido)-2-methoxyphenyl)acetamide;

3-((4-(4-(3-(3-(2-amino-2-oxoethyl)-5-(tert-butyl)-2-methoxyphenyl)ureido)-2,3-dichlorophenoxy)pyridin-2-yl)amino)-5-methoxy-N-(2-(2-(2-methoxyethoxy)ethoxy)ethyl)benzamide;

2-(5-(tert-butyl)-3-(3-(4-((2-((3-cyano-5-methoxyphenyl)
    amino)pyridin-4-yl)oxy)naphthalen-1-yl)ureido)-2-
    methoxyphenyl)acetamide;
2-(5-(tert-butyl)-2-methoxy-3-(3-(4-((2-((3-methoxy-5-sul-
    famoylphenyl)amino)pyridin-4-yl)oxy)naphthalen-1-yl)
    ureido)phenyl)acetamide;
2-(5-(tert-butyl)-3-(3-(4-((2-((3-(N,N-dimethylsulfamoyl)-
    5-methoxyphenyl)amino)pyridin-4-yl)oxy)naphthalen-1-
    yl)ureido)-2-methoxyphenyl)acetamide;
5-(tert-butyl)-2-methoxy-3-(3-(4-((2-((3-methoxy-5-((2-
    morpholinoethyl)carbamoyl)-phenyl)amino)pyrimidin-4-
    yl)oxy)naphthalen-1-yl)ureido)-N-(2-morpholinoethyl)
    benzamide;
3-((4-((4-(3-(3-(2-amino-2-oxoethyl)-5-(tert-butyl)-2-
    methoxyphenyl)ureido)naphthalen-1-yl)oxy)pyridin-2-
    yl)amino)-N-(3-hydroxy-2,2-bis(hydroxymethyl)propyl)-
    5-methoxybenzamide;
3-((4-((4-(3-(5-(tert-butyl)-3-(dimethylphosphoryl)-2-
    methoxyphenyl)ureido)naphthalen-1-yl)oxy)pyridin-2-
    yl)amino)-5-methoxy-N-(2-(1-oxidothiomorpholino)
    ethyl)benzamide;
3-((4-((4-(3-(5-(tert-butyl)-2-methoxy-3-(methylsulfonyl)
    phenyl)ureido)naphthalen-1-yl)oxy)pyridin-2-yl)amino)-
    5-methoxy-N-(2-(1-oxidothiomorpholino)ethyl)benz-
    amide;
4-((4-((4-(3-(5-(tert-butyl)-3-(dimethylphosphoryl)-2-
    methoxyphenyl)ureido)naphthalen-1-yl)oxy)pyridin-2-
    yl)amino)-2-methoxy-N-(2-morpholinoethyl)benzamide
4-((4-((4-(3-(5-(tert-butyl)-2-methoxy-3-(methylsulfonyl)
    phenyl)ureido)naphthalen-1-yl)oxy)pyridin-2-yl)amino)-
    2-methoxy-N-(2-morpholinoethyl)benzamide
1-(5-(tert-butyl)-3-(dimethylphosphoryl)-2-hydroxyphe-
    nyl)-3-(4-((2-(phenylamino)pyridin-4-yl)oxy)naphtha-
    len-1-yl)urea;
1-(5-(tert-butyl)-2-methoxy-3-(methylsulfinyl)phenyl)-3-
    (4-((2-((3,5-dimethoxyphenyl)amino)pyridin-4-yl)oxy)
    naphthalen-1-yl)urea;
1-(5-(tert-butyl)-2-methoxy-3-(methylsulfinyl)phenyl)-3-
    (4-((2-((3-methoxyphenyl)amino)pyridin-4-yl)oxy)naph-
    thalen-1-yl)urea;
1-(5-(tert-butyl)-2-methoxy-3-(methylsulfinyl)phenyl)-3-
    (4-((2-((pyridin-2-ylmethyl)amino)pyridin-4-yl)oxy)
    naphthalen-1-yl)urea;
N-(5-(tert-butyl)-2-methoxy-3-(3-(4-((2-((3-methoxyphe-
    nyl)amino)pyridin-4-yl)oxy)naphthalen-1-yl)ureido)ben-
    zyl)acetamide;
N-(5-(tert-butyl)-3-(3-(4-((2-((3,5-dimethoxyphenyl)
    amino)pyridin-4-yl)oxy)naphthalen-1-yl)ureido)-2-
    methoxybenzyl)acetamide;
3-((4-((4-(3-(3-(2-amino-2-oxoethyl)-5-(tert-butyl)-2-
    methoxyphenyl)ureido)naphthalen-1-yl)oxy)pyridin-2-
    yl)amino)-5-methoxy-N-(2-morpholinoethyl)benzamide;
3-((4-((4-(3-(5-(tert-butyl)-2-methoxy-3-(methylsulfinyl)
    phenyl)ureido)naphthalen-1-yl)oxy)pyridin-2-yl)amino)-
    5-methoxy-N-(2-morpholinoethyl)benzamide;
3-((4-((4-(3-(3-(2-amino-2-oxoethyl)-5-(tert-butyl)-2-
    methoxyphenyl)ureido)naphthalen-1-yl)oxy)pyridin-2-
    yl)amino)-5-methoxybenzamide;
3-((4-((4-(3-(5-(tert-butyl)-2-methoxy-3-(methylsulfinyl)
    phenyl)ureido)naphthalen-1-yl)oxy)pyridin-2-yl)amino)-
    5-methoxy-N-(2-(2-(2-methoxyethoxy)ethoxy)ethyl)ben-
    zamide;
2-(5-(tert-butyl)-3-(3-(4-((2-((3-cyano-5-(2-morpholinoeth-
    oxy)phenyl)amino)pyridin-4-yl)oxy)naphthalen-1-yl)
    ureido)-2-methoxyphenyl)acetamide;

N-(5-(tert-butyl)-3-(3-(4-((2-((3-cyano-5-(2-morpholi-
    noethoxy)phenyl)amino)pyridin-4-yl)oxy)naphthalen-1-
    yl)ureido)-2-methoxybenzyl)acetamide;
1-(5-(tert-butyl)-2-methoxy-3-(methylsulfinyl)phenyl)-3-
    (4-((2-((3-cyano-5-(2-morpholinoethoxy)phenyl)amino)
    pyridin-4-yl)oxy)naphthalen-1-yl)urea;
N-(5-(tert-butyl)-2-methoxy-3-(3-(4-((2-((3-(2-morpholi-
    noethoxy)-5-(trifluoromethyl)phenyl)amino)pyridin-4-
    yl)oxy)naphthalen-1-yl)ureido)benzyl)acetamide;
3-((4-((4-(3-(3-(2-amino-2-oxoethyl)-5-(tert-butyl)-2-
    methoxyphenyl)ureido)naphthalen-1-yl)oxy)pyridin-2-
    yl)amino)-5-methoxy-N-(2-(2-(2-methoxyethoxy)
    ethoxy)ethyl)benzamide;
3-((4-((4-(3-(5-(tert-butyl)-2-methoxy-3-(methylsulfonyl)
    phenyl)ureido)naphthalen-1-yl)oxy)pyridin-2-yl)amino)-
    5-methoxy-N-(2-morpholinoethyl)benzamide;
3-((4-((4-(3-(5-(tert-butyl)-2-methoxy-3-(methylsulfinyl)
    phenyl)ureido)naphthalen-1-yl)oxy)pyridin-2-yl)amino)-
    5-methoxybenzamide;
2-(5-(tert-butyl)-2-methoxy-3-(3-(4-((2-((3-methoxy-5-
    (methylsulfonyl)phenyl)amino)pyridin-4-yl)oxy)naph-
    thalen-1-yl)ureido)phenyl)acetamide;
3-((4-((4-(3-(5-(tert-butyl)-3-(2-hydroxyethoxy)-2-
    methoxyphenyl)ureido)naphthalen-1-yl)oxy)pyridin-2-
    yl)amino)-5-methoxybenzamide;
3-((4-((4-(3-(5-(tert-butyl)-3-(dimethylphosphoryl)-2-
    methoxyphenyl)ureido)naphthalen-1-yl)oxy)pyridin-2-
    yl)amino)-5-methoxy-N,N-dimethylbenzenesulfona-
    mide;
5-(tert-butyl)-2-methoxy-3-(3-(4-((2-((3-methoxy-5-((2-(2-
    (2-methoxyethoxy)ethoxy)ethyl)carbamoyl)phenyl)
    amino)pyridin-4-yl)oxy)naphthalen-1yl)ureido)-N-(2-
    morpholinoethyl)benzamide;
5-(tert-butyl)-2-methoxy-3-(3-(4-((2-((3-methoxy-5-((2-
    morpholinoethyl)carbamoyl)phenyl)amino)pyridin-4-yl)
    oxy)naphthalen-1-yl)ureido)-N-(2-morpholinoethyl)ben-
    zamide;
5-(tert-butyl)-3-(3-(4-((2-((3-carbamoyl-5-methoxyphenyl)
    amino)pyridin-4-yl)oxy)naphthalen-1-yl)ureido)-2-
    methoxy-N-(2-morpholinoethyl)benzamide;
5-(tert-butyl)-3-(3-(4-((2-((3,5-dimethoxyphenyl)amino)
    pyridin-4-yl)oxy)naphthalen-1-yl)ureido)-2-methoxy-N-
    (2-morpholinoethyl)benzamide;
5-(tert-butyl)-2-methoxy-3-(3-(4-((2-((3-methoxyphenyl)
    amino)pyridin-4-yl)oxy)naphthalen-1-yl)ureido)-N-(2-
    morpholinoethyl)benzamide;
5-(tert-butyl)-3-(3-(4-((2-((3,5-dimethoxyphenyl)amino)
    pyridin-4-yl)oxy)naphthalen-1-yl)ureido)-2-methoxy-N-
    (2-(1-oxidothiomorpholino)ethyl)benzamide;
3-((4-((4-(3-(3-(2-amino-2-oxoethyl)-5-(tert-butyl)-2-
    methoxyphenyl)ureido)naphthalen-1-yl)oxy)pyridin-2-
    yl)amino)-5-methoxy-N-(2-(1-oxidothiomorpholino)
    ethyl)benzamide;
3-((4-((4-(3-(5-(tert-butyl)-3-((1,3-dihydroxypropan-2-yl)
    oxy)-2-methoxyphenyl)ureido)naphthalen-1-yl)oxy)pyri-
    din-2-yl)amino)-5-methoxybenzamide;
3-((4-((4-(3-(5-(tert-butyl)-3-(3-hydroxy-2,2-bis(hy-
    droxymethyl)propoxy)-2-methoxyphenyl)ureido)naph-
    thalen-1-yl)oxy)pyridin-2-yl)amino)-5-methoxybenz-
    amide;
3-((4-((4-(3-(3-(2-amino-2-oxoethyl)-5-(tert-butyl)-2-
    methoxyphenyl)ureido)naphthalen-1-yl)oxy)pyridin-2-
    yl)amino)-5-methoxy-N-(3-(1-oxidothiomorpholino)pro-
    pyl)benzamide;

3-((4-((4-(3-(5-(tert-butyl)-2-methoxy-3-(methylsulfinyl)
  phenyl)ureido)naphthalen-1-yl)oxy)pyridin-2-yl)amino)-
  5-methoxy-N-(2-(1-oxidothiomorpholino)ethyl)benz-
  amide;
4-((4-((4-(3-(3-(2-amino-2-oxoethyl)-5-(tert-butyl)-2-
  methoxyphenyl)ureido)naphthalen-1-yl)oxy)pyridin-2-
  yl)amino)-2-methoxy-N-(2-morpholinoethyl)benzamide;
3-((4-((4-(3-(3-(acetamidomethyl)-5-(tert-butyl)-2-
  methoxyphenyl)ureido)naphthalen-1-yl)oxy)pyridin-2-
  yl)amino)-5-methoxy-N-(2-(1-oxidothiomorpholino)
  ethyl)benzamide;
4-((4-((4-(3-(5-(tert-butyl)-2-methoxy-3-(methylsulfinyl)
  phenyl)ureido)naphthalen-1-yl)oxy)pyridin-2-yl)amino)-
  2-methoxy-N-(2-morpholinoethyl)benzamide;
4-((4-((4-(3-(3-(2-amino-2-oxoethyl)-5-(tert-butyl)-2-
  methoxyphenyl)ureido)naphthalen-1-yl)oxy)pyridin-2-
  yl)amino)-N-(3-hydroxy-2,2-bis(hydroxymethyl)propyl)-
  2-methoxybenzamide;
1-(5-(tert-butyl)-2-methoxy-3-(methylsulfinyl)phenyl)-3-
  (4-((2-((7-methyl-1H-indazol-5-yl)amino)pyrimidin-4-
  yl)oxy)naphthalen-1-yl)urea;
3-((4-((4-(3-(5-(tert-butyl)-3-(dimethylphosphoryl)-2-
  methoxyphenyl)ureido)naphthalen-1-yl)oxy)pyridin-2-
  yl)amino)-5-methoxy-N-methyl-N-(2-morpholinoethyl)
  benzenesulfonamide;
4-((4-((4-(3-(5-(tert-butyl)-3-(dimethylphosphoryl)-2-
  methoxyphenyl)ureido)naphthalen-1-yl)oxy)pyridin-2-
  yl)amino)-2-methoxybenzoic acid; 1-(5-tert-butyl-3-dim-
  ethylphosphoryl-2-methoxy-phenyl)-3-[4-[[2-[3-
  methoxy-4-(4-methylpiperazine-1-carbonyl)anilino]-4-
  pyridyl]oxy]-1-naphthyl]urea;
4-[[4-[[4-[(5-tert-butyl-3-dimethylphosphoryl-2-methoxy-
  phenyl)carbamoylamino]-1-naphthyl]oxy]-2-pyridyl]
  amino]-2-methoxy-N-(1-methyl-4-piperidyl)benzamide;
4-[[4-[[4-[(5-tert-butyl-3-dimethylphosphoryl-2-methoxy-
  phenyl)carbamoylamino]-1-naphthyl]oxy]-2-pyridyl]
  amino]-N-(2-dimethylaminoethyl)-2-methoxy-benz-
  amide;
1-(5-tert-butyl-3-dimethylphosphoryl-2-methoxy-phenyl)-
  3-[4-[[2-[3-methoxy-5-[methyl(3-morpholinopropyl)sul-
  famoyl]anilino]-4-pyridyl]oxy]-1-naphthyl]urea;
1-(5-tert-butyl-2-methoxy-3-methylsulfinyl-phenyl)-3-[4-
  [[2-[3-cyano-5-(3-morpholinopropoxy)anilino]-4-
  pyridyl]oxy]-1-naphthyl]urea;
3-[[4-[[4-[(5-tert-butyl-3-dimethylphosphoryl-2-methoxy-
  phenyl)carbamoylamino]-1-naphthyl]oxy]-2-pyridyl]
  amino]-N-methyl-5-(2-morpholinoethoxy)benzamide;
3-((4-((4-(3-(5-(tert-butyl)-3-((2-(dimethylamino)acet-
  amido)methyl)-2-methoxyphenyl)ureido)-naphthalen-1-
  yl)oxy)pyridin-2-yl)amino)-5-methoxy-N-(2-(2-(2-
  methoxyethoxy)ethoxy)ethyl)-benzamide;
3-((4-((4-(3-(5-(tert-butyl)-3-(dimethylphosphoryl)-2-
  methoxyphenyl)ureido)naphthalen-1-yl)oxy)pyridin-2-
  yl)amino)-N-methyl-5-((4-methylpiperazin-1-yl)methyl)
  benzamide;
4-((4-((4-(3-(5-(tert-butyl)-2-methoxy-3-(methylsulfinyl)
  phenyl)ureido)naphthalen-1-yl)oxy)pyridin-2-yl)amino)-
  2-methoxybenzoic acid;
5-(tert-butyl)-3-(3-(4-((2-((3,5-dimethoxyphenyl)amino)
  pyridin-4-yl)oxy)naphthalen-1-yl)ureido)-2-methoxy-N-
  (2-(piperazin-1-yl)ethyl)benzamide;
4-((4-((4-(3-(5-(tert-butyl)-2-methoxy-3-(methylsulfonyl)
  phenyl)ureido)naphthalen-1-yl)oxy)pyrimidin-2-yl)
  amino)-2-methoxybenzoic acid;
4-((4-((4-(3-(5-(tert-butyl)-2-methoxy-3-(methylsulfinyl)
  phenyl)ureido)naphthalen-1-yl)oxy)pyrimidin-2-yl)
  amino)-2-methoxybenzoic acid;
3-((4-((4-(3-(5-(tert-butyl)-3-(dimethylphosphoryl)-2-
  methoxyphenyl)ureido)naphthalen-1-yl)oxy)pyridin-2-
  yl)amino)-5-methoxy-N-methyl-N-(2-(4-methylpiper-
  azin-1-yl)ethyl)benzamide;
3-((4-((4-(3-(5-(tert-butyl)-3-(dimethylphosphoryl)-2-
  methoxyphenyl)ureido)naphthalen-1-yl)oxy)pyridin-2-
  yl)amino)-5-methoxy-N-methyl-N-(2-(1-methylpiperi-
  din-4-yl)ethyl)benzamide;
3-((4-((4-(3-(5-(tert-Butyl)-3-(dimethylphosphoryl)-2-
  methoxyphenyl)ureido)naphthalen-1-yl)oxy)pyridin-2-
  yl)amino)-5-methoxy-N-methyl-N-(2-(4-methylpiper-
  azin-1-yl)ethyl)benzene sulfonamide;
4-((4-((4-(3-(5-(tert-butyl)-2-methoxy-3-(methylsulfonyl)
  phenyl)ureido)naphthalen-1-yl)oxy)pyridin-2-yl)amino)-
  2-methoxybenzoic acid;
3-((4-((4-(3-(5-(tert-butyl)-3-((2-(dimethylamino)acet-
  amido)methyl)-2-methoxyphenyl)ureido)-naphthalen-1-
  yl)oxy)pyrimidin-2-yl)amino)-5-methoxy-N-(2-(2-(2-
  methoxyethoxy)ethoxy)-ethyl)benzamide;
3-((4-((4-(3-(5-(tert-butyl)-2-methoxy-3-((4-methylpiper-
  azin-1-yl)methyl)phenyl)ureido)-naphthalen-1-yl)oxy)
  pyridin-2-yl)amino)-5-methoxy-N-(2-(2-(2-methoxy-
  ethoxy)ethoxy)ethyl)-benzamide;
3-((4-((4-(3-(5-(tert-butyl)-2-methoxy-3-(methylsulfinyl)
  phenyl)ureido)naphthalen-1-yl)oxy)pyrimidin-2-yl)
  amino)-5-methoxy-N-(2-(4-methylpiperazin-1-yl)ethyl)
  benzamide; and
3-((4-((4-(3-(5-(tert-butyl)-2-methoxy-3-(methylsulfinyl)
  phenyl)ureido)naphthalen-1-yl)oxy)pyridin-2-yl)amino)-
  5-methoxy-N-(2-(4-methylpiperazin-1-yl)ethyl)benz-
  amide, or a pharmaceutically acceptable salt, solvate or isotopic derivative thereof.

Examples of salts of compounds of formula I, Ia, Ib, Ic, Ia1, Ib1 or Ic1 include all pharmaceutically acceptable salts, such as, without limitation, acid addition salts of strong mineral acids such as HCl and HBr salts and addition salts of strong organic acids such as methanesulfonic acid.

References herein to a compound of the invention (a compounds of formula I, Ia, Ib, Ic, Ia1, Ib1 or Ic1) are intended to include references to the compound and to all pharmaceutically acceptable salts, solvates and/or tautomers of said compound, unless the context specifically indicates otherwise. In this respect, solvates that may be mentioned include hydrates.

The compounds of the invention (compounds of formula I, Ia, Ib, Ic, Ia1, Ib1 or Ic1) are p38 MAP kinase inhibitors (especially of the alpha subtype) and are therefore useful in medicine, in particular for the treatment of inflammatory diseases. Further aspects of the invention that may be mentioned therefore include the following.

(a) A pharmaceutical formulation comprising compound of formula I, Ia, Ib, Ic, Ia1, Ib1 or Ic1, as hereinbefore defined, or pharmaceutically acceptable salt, solvate or isotopic derivative thereof, in admixture with a pharmaceutically acceptable adjuvant, diluent or carrier.

(b) A combination product comprising
  (A) a compound of formula I, Ia, Ib, Ic, Ia1, Ib1 or Ic1, as hereinbefore defined, or pharmaceutically acceptable salt, solvate or isotopic derivative thereof, and
  (B) another therapeutic agent,
  wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of formula I, Ia, Ib, Ic, Ia1, Ib1 or Ic1, as hereinbefore defined, or pharmaceutically acceptable salt, solvate or isotopic derivative thereof, and another therapeutic agent, in admixture with a pharmaceutically acceptable adjuvant, diluent or carrier (which formulation is hereinafter referred to as a "combined preparation").

It also encompasses a kit of parts comprising components:
(i) a pharmaceutical formulation including a compound of formula I, Ia, Ib, Ic, Ia1, Ib1 or Ic1, as hereinbefore defined, or pharmaceutically acceptable salt, solvate or isotopic derivative thereof, in admixture with a pharmaceutically acceptable adjuvant, diluent or carrier; and
(ii) a pharmaceutical formulation including another therapeutic agent, in admixture with a pharmaceutically-acceptable adjuvant, diluent or carrier,
which components (i) and (ii) are each provided in a form that is suitable for administration in conjunction with the other.
Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.
(c) A process for preparing the pharmaceutical formulation of aspect (a) above, said process comprising the step of admixing the compound of formula I, Ia, Ib, Ic, Ia1, Ib1 or Ic1, as hereinbefore defined, or pharmaceutically acceptable salt, solvate or isotopic derivative thereof, with a pharmaceutically acceptable adjuvant, diluent or carrier.
Embodiments of this aspect of the invention that may be mentioned include those in which the pharmaceutically acceptable adjuvant, diluent or carrier is a topically acceptable adjuvant, diluent or carrier (and/or wherein the process is for preparing a topical pharmaceutical formulation, i.e. a pharmaceutical formulation that is adapted for topical administration).
(d) A compound of formula I, Ia, Ib, Ic, Ia1, Ib1 or Ic1, as hereinbefore defined, or pharmaceutically acceptable salt, solvate or isotopic derivative thereof, for use in medicine (or for use as a medicament or as a pharmaceutical).
(e) A compound of formula I, Ia, Ib, Ic, Ia1, Ib1 or Ic1, as hereinbefore defined, or pharmaceutically acceptable salt, solvate or isotopic derivative thereof, or a pharmaceutical formulation or combination product as defined in connection with aspect (a) or (b) of the invention, for use in the treatment or prevention of an inflammatory disease.
(f) The use of
a compound of formula I, Ia, Ib, Ic, Ia1, Ib1 or Ic1, as hereinbefore defined, or pharmaceutically acceptable salt, solvate or isotopic derivative thereof, or
a pharmaceutical formulation or combination product as defined in connection with aspect (a) or (b) of the invention,
for the preparation of a medicament for the treatment or prevention of an inflammatory disease.
(g) A method of treating or preventing an inflammatory disease, said method comprising administering to a subject an effective amount of
a compound of formula I, Ia, Ib, Ic, Ia1, Ib1 or Ic1, as hereinbefore defined, or pharmaceutically acceptable salt, solvate or isotopic derivative thereof, or
a pharmaceutical formulation or combination product as defined in connection with aspect (a) or (b) of the invention.

(h) A method of sensitizing a subject to the anti-inflammatory effects of a corticosteroid, said method comprising administering to the subject an effective amount of
a compound of formula I, Ia, Ib, Ic, Ia1, Ib1 or Ic1, as hereinbefore defined, or pharmaceutically acceptable salt, solvate or isotopic derivative thereof, or
a pharmaceutical formulation or combination product as defined in connection with aspect (a) or (b) of the invention.
Embodiments of this aspect of the invention that may be mentioned include those in which the subject is one who has become refractory to the anti-inflammatory effects of a corticosteroid.

References herein to "preventing an inflammatory disease" include references to preventing (or reducing the likelihood of) the recurrence of an inflammatory disease in a subject who has previously suffered from such a disease (e.g. a subject who has previously received treatment for that disease, for example treatment according to the method described in (g) above).

Thus, still further aspects of the invention that may be mentioned include the following.
(i) A compound of formula I, Ia, Ib, Ic, Ia1, Ib1 or Ic1, as hereinbefore defined, or pharmaceutically acceptable salt, solvate or isotopic derivative thereof, or a pharmaceutical formulation or combination product as defined in connection with aspect (a) or (b) of the invention, for use in reducing the likelihood of the recurrence of an inflammatory disease in a subject who has previously received treatment for that disease (e.g. treatment with a compound of formula I, Ia, Ib, Ic, Ia1, Ib1 or Ic1, as hereinbefore defined, or pharmaceutically acceptable salt, solvate or isotopic derivative thereof, or a pharmaceutical formulation or combination product as defined in connection with aspect (a) or (b) of the invention).
(j) The use of
a compound of formula I, Ia, Ib, Ic, Ia1, Ib1 or Ic1, as hereinbefore defined, or pharmaceutically acceptable salt, solvate or isotopic derivative thereof, or
a pharmaceutical formulation or combination product as defined in connection with aspect (a) or (b) of the invention,
for the preparation of a medicament for reducing the likelihood of the recurrence of an inflammatory disease in a subject who has previously received treatment for that disease (e.g. treatment with a compound of formula I, Ia, Ib, Ic, Ia1, Ib1 or Ic1, as hereinbefore defined, or pharmaceutically acceptable salt, solvate or isotopic derivative thereof, or a pharmaceutical formulation or combination product as defined in connection with aspect (a) or (b) of the invention).
(k) A method of reducing the likelihood of the recurrence of an inflammatory disease in a subject who has previously received treatment for that disease (e.g. treatment with a compound of formula I, Ia, Ib, Ic, Ia1, Ib1 or Ic1, as hereinbefore defined, or pharmaceutically acceptable salt, solvate or isotopic derivative thereof, or a pharmaceutical formulation or combination product as defined in connection with aspect (a) or (b) of the invention), said method comprising administering to said subject an effective amount of
a compound of formula I, Ia, Ib, Ic, Ia1, Ib1 or Ic1, as hereinbefore defined, or pharmaceutically acceptable salt, solvate or isotopic derivative thereof, or
a pharmaceutical formulation or combination product as defined in connection with aspect (a) or (b) of the invention.

DETAILED DESCRIPTION OF CERTAIN EMBODIMENTS OF THE INVENTION

Formulations

In relation to aspects (a) and (b) above, diluents and carriers that may be mentioned include those suitable for parenteral, oral, topical, mucosal and rectal administration.

The pharmaceutical formulations and combination products of aspects (a) and (b) above may be prepared e.g. for parenteral, subcutaneous, intramuscular, intravenous, intra-articular, intravitreous, periocular, retrobulbar, subconjunctival, sub-Tenon, topical ocular or peri-articular administration, particularly in the form of liquid solutions, emulsions or suspensions; for oral administration, particularly in the form of tablets or capsules, and especially involving technologies aimed at furnishing colon-targeted drug release (Patel, M. M. *Expert Opin. Drug Deliv.* 2011, 8 (10), 1247-1258); for topical e.g. pulmonary or intranasal administration, particularly in the form of powders, nasal drops or aerosols and transdermal administration; for topical ocular administration, particularly in the form of solutions, emulsions, suspensions, ointments, implants/inserts, gels, jellies or liposomal microparticle formulations (Ghate, D.; Edelhauser, H. F. *Expert Opin. Drug Deliv.* 2006, 3 (2), 275-287); for ocular administration, particularly in the form of biodegradable and non-biodegradable implants, liposomes and nanoparticles (Thrimawithana, T. R. et al. *Drug Discov. Today* 2011, 16 (5/6), 270-277); for mucosal administration e.g. to buccal, sublingual or vaginal mucosa, and for rectal administration e.g. in the form of a suppository or enema.

The pharmaceutical formulations and combination products of aspects (a) and (b) above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration typical excipients include sugars, calcium stearate, magnesium stearate, pregelatinated starch, and the like.

Pharmaceutical formulations and combination products suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules. Such two-piece hard shell capsules may be made from, for example, gelatin or hydroxylpropyl methylcellulose (HPMC).

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

A compound of the invention may be administered topically (e.g. to the lung, eye or intestines). Thus, embodiments of aspects (a) and (b) above that may be mentioned include pharmaceutical formulations and combination products that are adapted for topical administration. Such formulations include those in which the excipients (including any adjuvant, diluent and/or carrier) are topically acceptable.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoro methane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. This may be administered by means of a nebuliser e.g. one that can be hand-held and portable or for home or hospital use (ie non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean aerodynamic diameter (MMAD) of 1-10 µm or a $D_{50}$ of 0.5-10 µm e.g. around 1-5 µm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose glucose or mannitol (preferably lactose), usually of large particle size e.g. an MMAD of 50 µm or more, e.g. 100 µm or more or a $D_{50}$ of 40-150 µm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Examples of dry powder delivery systems include SPINHALER, DISKHALER, TURBOHALER, DISKUS and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of the present invention is provided in a micronized dry powder formulation, for example further comprising lactose of a suitable grade optionally together with magnesium stearate, filled into a single dose device such as AEROLISER or filed into a multi dose device such as DISKUS.

The compounds of the present invention may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of inhibitor. The surfactants function to solubilize the inhibitor and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquarternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

Embodiments of the invention that may be mentioned in connection with the combination products described at (b) above include those in which the other therapeutic agent is one or more therapeutic agents that are known by those skilled in the art to be suitable for treating inflammatory diseases (e.g. the specific diseases mentioned below).

For example, for the treatment of respiratory disorders (such as COPD or asthma), the other therapeutic agent is one or more agents selected from the list comprising:
  steroids (e.g. budesonide, beclomethasone dipropionate, fluticasone propionate, mometasone furoate, fluticasone furoate; a further example is ciclesonide);
  beta agonists, particularly beta2 agonists (e.g. terbutaline, salbutamol, salmeterol, formoterol; further examples are vilanterol, olodaterol, reproterol and fenoterol); and
  xanthines (e.g. theophylline).

For example, for the treatment of respiratory disorders (such as COPD or asthma), the other therapeutic agent is one or more agents selected from the list comprising:
  muscarinic antagonists (e.g. tiotropium, umeclidinium, glycopyrronium, aclidinium and daratropium, any of these for example as the bromide salt); and
  phosphodiesterase inhibitors.

Further, for the treatment of gastrointestinal disorders (such as Crohn's disease or ulcerative colitis), the other therapeutic agent may be, for example, one or more agents selected from the list comprising:
  5-aminosalicylic acid, or a prodrug thereof (such as sulfasalazine, olsalazine or bisalazide);
  corticosteroids (e.g. prednisolone, methylprednisolone, or budesonide);
  immunosuppressants (e.g. cyclosporin, tacrolimus, methotrexate, azathioprine or 6-mercaptopurine);
  anti-TNFα antibodies (e.g., infliximab, adalimumab, certolizumab pegol or golimumab);
  anti-IL12/IL23 antibodies (e.g., ustekinumab) or small molecule IL12/IL-23 inhibitors (e.g., apilimod);
  Anti-α4β7 antibodies (e.g., vedolizumab);
  MAdCAM-1 blockers (e.g., PF-00547659);
  antibodies against the cell adhesion molecule α4-integrin (e.g., natalizumab);
  antibodies against the IL2 receptor a subunit (e.g., daclizumab or basiliximab);
  JAK3 inhibitors (e.g., tofacitinib or R348);
  Syk inhibitors and prodrugs thereof (e.g., fostamatinib and R-406);
  Phosphodiesterase-4 inhibitors (e.g., tetomilast);
  HMPL-004;
  probiotics;
  Dersalazine;
  semapimod/CPSI-2364; and
  protein kinase C inhibitors (e.g. AEB-071).

For the treatment of eye disorders (such as uveitis), the other therapeutic agent may be, for example, one or more agents selected from the list comprising:
  corticosteroids (e.g. dexamethasone, prednisolone, triamcinolone acetonide, difluprednate or fluocinolone acetonide);
  immunosuppressants (e.g. cyclosporin, voclosporin, azathioprine, methotrexate, mycophenolate mofetil or tacrolimus);
  anti-TNFα antibodies (e.g., infliximab, adalimumab, certolizumab pegol, ESBA-105 or golimumab);
  anti-IL-17A antibodies (e.g., secukinumab);
  mTOR inhibitors (e.g., sirolimus);
  VGX-1027;
  JAK3 inhibitors (e.g., tofacitinib or R348); and
  protein kinase C inhibitors (e.g. AEB-071).

Medical Uses

The compounds of the invention may be used as monotherapies for inflammatory diseases, or in combination therapies for such diseases.

Thus, embodiments of aspects (e) to (g) above that may be mentioned include those in which the compound of formula I, Ia, Ib, Ic, Ia1, Ib1 or Ic1 (or pharmaceutically acceptable salt, solvate or isotopic derivative thereof) is the sole pharmacologically active ingredient utilised in the treatment.

However, in other embodiments of aspects (e) to (g) above, the compound of formula I, Ia, Ib, Ic, Ia1, Ib1 or Ic1 (or pharmaceutically acceptable salt, solvate or isotopic derivative thereof) is administered to a subject who is also administered one or more other therapeutic agents (e.g. wherein the one or more other therapeutic agents are as defined above in connection with combination products).

When used herein, the term "inflammatory disease" specifically includes references to any one or more of the following:
(i) lung diseases or disorders having an inflammatory component, such as cystic fibrosis, pulmonary hypertension, lung sarcoidosis, idiopathic pulmonary fibrosis or, particularly, COPD (including chronic bronchitis and emphysema), asthma or paediatric asthma;
(ii) skin diseases or disorders having an inflammatory component, such as atopic dermatitis, allergic dermatitis, contact dermatitis or psoriasis;
(iii) nasal diseases or disorders having an inflammatory component, such as allergic rhinitis, rhinitis or sinusitis;

(iv) eye diseases or disorders having an inflammatory component, such as conjunctivitis, allergic conjunctivitis, keratoconjunctivitis sicca (dry eye), glaucoma, diabetic retinopathy, macular oedema (including diabetic macular oedema), central retinal vein occlusion (CRVO), dry and/or wet age related macular degeneration (AMD), post-operative cataract inflammation, or, particularly, uveitis (including posterior, anterior and pan uveitis), corneal graft and limbal cell transplant rejection; and (v) gastrointestinal diseases or disorders having an inflammatory component, such as gluten sensitive enteropathy (coeliac disease), eosinophilic eosophagitis, intestinal graft versus host disease or, particularly, Crohn's disease or ulcerative colitis.

References herein to diseases having an inflammatory component include references to diseases that involve inflammation, whether or not there are other (non-inflammatory) symptoms or consequences of the disease.

According to a further aspect of the invention there is provided a process for the preparation of a compound of formula I which process comprises:

(a) reaction of a compound of formula II,

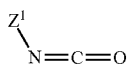

II with a compound of formula III,

III wherein one of $Z^1$ and $Z^2$ is a structural fragment of formula IV

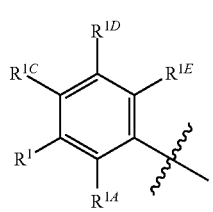

IV and the other of $Z^1$ and $Z^2$ is a structural fragment of formula V

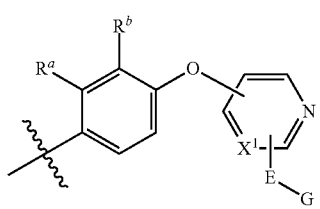

V where $R^1$, $R^{1A}$, $R^{1C}$, $R^{1D}$, $R^{1E}$, $R^a$, $R^b$, $X^1$, E and G are as hereinbefore defined, for example under conditions known to those skilled in the art, for example at a temperature from ambient (e.g. 15 to 30° C.) to about 110° C. in the presence of a suitable organic solvent (e.g. a polar aprotic solvent such as DMF, THF, 1,4-dioxane, or mixtures thereof);

(b) reaction of a compound of formula IIa,

IIa wherein $Z^1$ is as defined above, with a suitable azide-forming agent (i.e. a suitable source of a leaving group and activated azide ion, such as diphenyl phosphorazidate; see, for example, *Tetrahedron* 1974, 30, 2151-2157) under conditions known to those skilled in the art, such as at sub-ambient to ambient temperature (e.g. from an initial temperature of about −5 to 5° C. to ambient temperature post-reaction) in the presence of an amine base (e.g. triethylamine or a sterically hindered base such as N,N-diisopropylethylamine) and a suitable organic solvent (e.g. a polar aprotic solvent such as DMF, THF, 1,4-dioxane, or mixtures thereof), which reaction is followed, without isolation, by thermal rearrangement (e.g. under heating) of the intermediate acyl azide (of formula $Z^1$—C(O)—$N_3$) e.g. at ambient temperature (such as from 15 to 30° C.) to provide, in situ, a compound of formula II, which compound is then reacted with a compound of formula III, as defined above, to provide the compound of formula I;

(c) reaction of a compound of formula IIb,

IIb wherein $LG^1$ represents a suitable leaving group (e.g. imidazolyl, chloro, or aryloxy) and $Z^1$ is as defined above, with a compound of formula III, as defined above, for example under conditions known to those skilled in the art, such as at ambient temperature (e.g. from ambient to 80° C.), optionally in the presence of an amine base (e.g. a sterically hindered base like N,N-diisopropylethylamine) and a suitable organic solvent (e.g. an aprotic solvent, such as dichloromethane);

(d) reaction of a compound of formula VI,

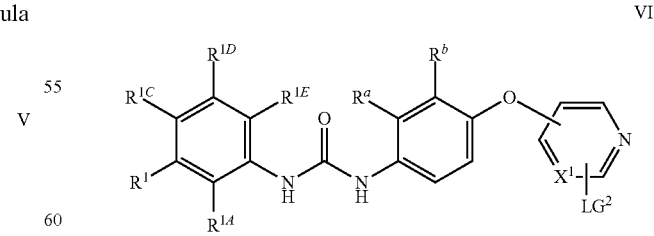

VI wherein $LG^2$ represents a suitable leaving group (e.g. a halo group such as chloro or bromo) and $R^1$, $R^{1A}$, $R^{1C}$, $R^{1D}$, $R^{1E}$, $R^a$, $R^b$ and $X^1$ are as hereinbefore defined with a compound of formula VII,

H-E-G

VII wherein E and G are as hereinbefore defined, for example under conditions known to those skilled in the art (e.g. when E represents N(G¹), as described in *J. Am. Chem. Soc.* 2011, 133, 15686-15696), such as at elevated temperature (e.g. from 50 to 110° C.) in the presence of a suitable organic solvent (e.g. a polar aprotic solvent such as DMF, THF, 1,4-dioxane, or mixtures thereof) and, optionally, an acidic catalyst (e.g. a sulfonic acid such as para-toluenesulfonic acid);

(e) for compounds of formula I in which $R^1$ represents $-L^1-C(O)N(R^{2a})R^{2b}$, reaction of a compound of formula VIII,

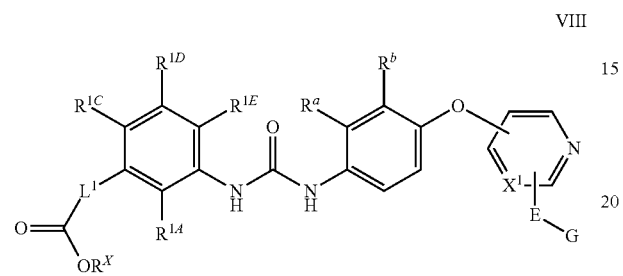

VIII wherein $R^{1A}$, $R^{1C}$, $R^{1D}$, $R^{1E}$, $R^a$, $R^b$, $X^1$, E and G are as hereinbefore defined and $R^X$ represents H or $C_{1-4}$ alkyl, with a compound of formula IX

IX wherein $R^{2a}$ and $R^{2b}$ are as hereinbefore defined, under conditions known to those skilled in the art, for example
 when $R^X$ represents H, reaction in the presence of a suitable solvent, a base (e.g. triethylamine or N,N-diisopropylethylamine) and an amide (peptide) coupling reagent, such as HATU, CD, N,N'-dicyclohexylcarbodiimide, N,N'-diisopropylcarbodiimide, BOP or PyBOP, optionally in combination with an activated ester-forming agent such as HOBt or 1-hydroxy-7-azabenzotriazole,
 when $R^X$ represents H, conversion of the carboxylic acid to an acid halide (e.g. by reaction with a halogenating agent such as thionyl chloride), followed by reaction with the compound of formula (XI) in the presence of a suitable solvent and a base (e.g. triethylamine or N,N-diisopropylethylamine), or
 when $R^X$ represents $C_{1-4}$ alkyl (e.g. methyl), reaction in the presence of a trialkylaluminium (e.g. trimethylaluminium) and an aprotic solvent (e.g. THF); or (f) for compounds of formula I in which $R^1$ represents $CH_2$-$Het^2$, wherein $Het^2$ is connected to the $CH_2$ group via a N-atom, reaction of a compound of formula IXa,

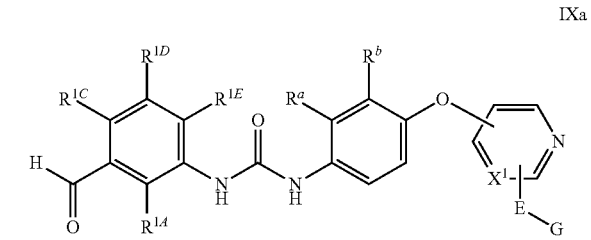

IXa wherein $R^{1A}$, $R^{1C}$, $R^{1D}$, $R^{1E}$, $R^a$, $R^b$, $X^1$, E and G are as hereinbefore defined with (i) a compound of formula IXb, H-$Het^{2a}$   IXb wherein $Het^{2a}$ represents a 4- to 8-membered heterocyclic group that is fully saturated or partially unsaturated, which group contains at least one N-atom (to which the H-atom depicted for the compound of formula IXb is attached), which group optionally contains one or more further heteroatoms selected from N, O and S and which group is optionally substituted by one or more substituents selected from OH, oxo, $C_{1-2}$ alkyl and $C_{1-2}$ alkoxy; and (ii) a reducing agent, for example a boron-based reducing agent (e.g. $NaBH(OAc)_3$, $NaBH_3CN$, a mixture of borane and pyridine, picoline or dimethylsulfide, or a mixture of a metal borohydride such as $NaBH_4$ or $Zn(BH_4)_2$ with a divalent metal salt such as $Mg(ClO_4)_2$, $CoCl_2$ or $ZnCl_2$), a combination of $H_2$ and hydrogenation catalyst (e.g. Pd/C or Pt/C) or a mixture of Zn and $HCO_2NH_4$ or an aqueous base, for example under conditions known to those skilled in the art, such as by reaction at ambient temperature (e.g. when the reducing agent is boron-based, such as $NaBH(OAc)_3$) in the presence of an aprotic organic solvent (e.g. THF).

(g) deprotection of an protected derivative of a compound of formula I, under conditions known to those skilled in the art, wherein the protected derivative bears a protecting group on an O- or N-atom of the compound of formula I (and, for the avoidance of doubt, a protected derivative of one compound of formula I may or may not represent another compound of formula I).

Compounds of formula II may be prepared according to or by analogy with methods known to those skilled in the art, for example by reaction of a compound of formula IIa, as defined above, with an azide-forming agent, followed by rearrangement of the intermediate acyl azide (as described at (b) above; see, for example, *Tetrahedron* 1974, 30, 2151-2157).

Compounds of formula IIb may be prepared by reaction of a compound of formula X,

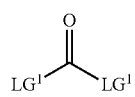

X wherein $LG^1$ is as hereinbefore defined, with a compound of formula XI,

XI wherein $Z^1$ is as hereinbefore defined, for example under conditions known to those skilled in the art.

Amines of formula XI may be prepared from carboxylic acids of formula IIa through the route described in (b) above, where the intermediate isocyanate II is hydrolysed with water to give a carbamic acid that loses carbon dioxide to furnish XI. By the same token, the intermediate isocyanate II can be reacted with an alcohol, such as t-butanol, to generate a protected version of XI. Alternatively, amines of formula XI may be prepared by reduction (under conditions known to those skilled in the art) of the corresponding $NO_2$ compounds.

Certain compounds of formula III in which $Z^2$ represents a structural fragment of formula V, or compounds of formula XI in which $Z^1$ represents a structural fragment of formula V, may be synthesised employing the route outlined in Scheme 1 (see, for example: WO 2003/072569; and WO 2008/046216), wherein $R^a$, $R^b$ and $X^1$ are as hereinbefore defined, $LG^3$ and $LG^4$ represent leaving groups, e.g., halogen or methanesulfonyl, and FG represents a real or latent $NH_2$ group, i.e., a group that is readily transformed into an $NH_2$ group, such as nitro or a protected variant $NH$-$PG^2$, where $PG^2$ is a typical protecting group (see, for example: Greene, T. W.; Wuts, P. G. M. *Protective Groups in Organic Synthesis*; Wiley, 4th revised edition, 2006; ISBN-10: 0471697540), e.g., a carbamate ester or carboxamide. The sequence starts with the base-mediated $S_NAr$ displacement of $LG^3$ in XIII by the aroxides formed when XII is treated with base to generate ethers XIV. The remaining halogen or methanesulfonyl substituents ($LG^4$) of the ether XIV is then displaced i) by an amine, alcohol or thiol of formula VII in a second $S_NAr$ reaction or (ii) via a Buchwald coupling (see, for example, WO 2009/017838) with an amine, alcohol or thiol of formula VII to furnish the desired compound (when FG is $NH_2$), or XV (when FG is nitro or $NH$-$PG^2$). When FG is nitro in XV, the $NH_2$ group may be revealed by a reduction reaction, typically done through hydrogenation employing a suitable catalyst, e.g., palladium on carbon, or employing dissolving metal conditions, such as with iron in glacial acetic acid. Alternatively, when FG is a protecting group, the $NH_2$ group may be revealed by a deprotection reaction. Although only depicted as taking place in the final step of the sequence, it should be noted that the unmasking of the latent $NH_2$ group represented by FG can take place at any stage in the synthetic route shown in Scheme 1.

Compounds of formula VI may be synthesised by analogy with the compounds of formula I (see, for example, alternative processes (a) to (c) above). For example, compounds of formula VI can be prepared by reaction of a compound of formula IIx with a compound of formula IIIx, wherein the compounds of formulae IIx and IIIx take the same definitions as the compounds of formulae II and III, with the exception that one of $Z^1$ and $Z^2$ represents a structural fragment of formula IV, as hereinbefore defined, and the other of $Z^1$ and $Z^2$ represents a structural fragment of formula Va,

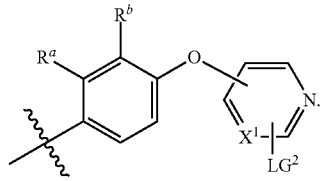

Va

Compounds of formula VII may be prepared according to or by analogy with procedures known to those skilled in the art, for example as described below.

(i) For compounds of formula VII in which G represents phenyl or $Het^3$ substituted by
—O—[C($R^{3a}$)($R^{3b}$)($CH_2$)$_{0-1}$$CH_2$—O]$_{2-8}$—$R^{6h}$,
—O—$CH_2$—[$C_{1-5}$ alkylene]-N($R^{6e}$)$R^{6f}$,
—OS(O)$_2$$R^{6g}$ or
—OC(O)$NH_2$,
reaction of a corresponding compound of formula VII in which G represents phenyl or $Het^3$ substituted by OH and in which the amino group is optionally in protected form (e.g. protected with $PG^2$ or present in masked form, such as a nitro group) with a compound of formula XVIa, XVIb, XVIc or XVId

| | |
|---|---|
| $LG^5$-[C($R^{3a}$)($R^{3b}$)($CH_2$)$_{0-1}$$CH_2$—O]$_{2-8}$—$R^{6h}$ | XVIa |
| $LG^5$-$CH_2$—[$C_{1-5}$ alkylene]-N($R^{6e}$)$R^{6f}$ | XVIb |
| $LG^5$-S(O)$_2$$R^{6g}$ | XVIc |
| O=C=$N^-M^+$ | XVId |

Scheme 1

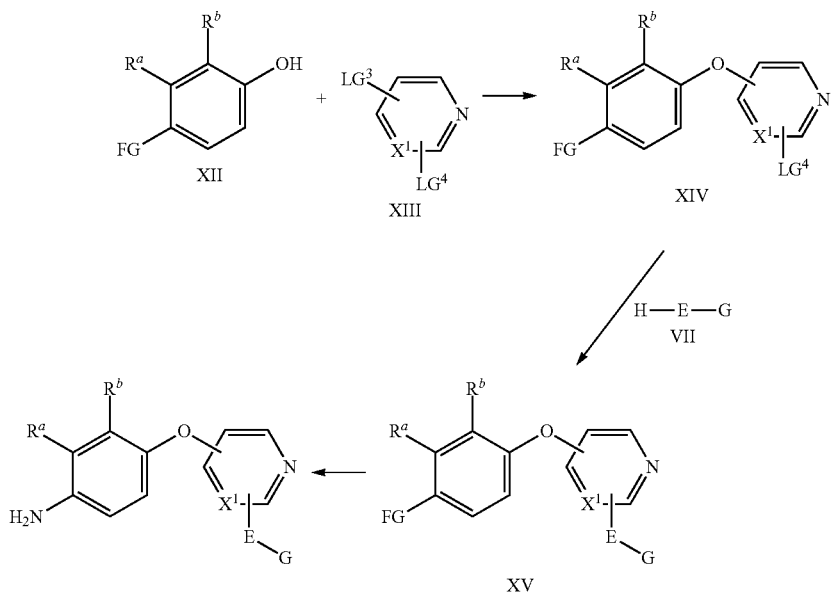

wherein M+ represents a monovalent metal cation (e.g. an alkali metal cation, such as a potassium cation) and LG$^5$ represents a suitable leaving group such as halo, (perfluoro)alkanesulfonate or arylsulfonate (e.g. methanesulfonate or p-toluenesulfonate), R$^{6e}$, R$^{6f}$, R$^{6g}$ and R$^{6h}$ are as hereinbefore defined, under conditions known to those skilled in the art (e.g. in the presence of an organic solvent and either a suitable base or, in the case of reaction with the compound of formula XVId, a suitable acid, such as trifluoroacetic acid), followed by when amino is protected with PG$^2$, removal of the PG$^2$ protecting group or when amino is present in masked form as NO$_2$, reduction of NO$_2$ to NH$_2$.

(ii) For compounds of formula VII in which G represents phenyl or Het$^3$ substituted by
—S—[C(R$^{3a}$)(R$^{3b}$)(CH$_2$)$_{0-1}$CH$_2$—O]$_{2-8}$—R$^{6h}$ or
—S—CH$_2$—[C$_{1-5}$ alkylene]-N(R$^{6e}$)R$^{6f}$
reaction of a corresponding compound of formula VII in which G represents phenyl or Het$^3$ substituted by SH and in which the amino group is optionally in protected form (e.g. protected with PG$^2$ or present in masked form, such as a nitro group) with a compound of formula XVIa or XVIb, as hereinbefore defined, under conditions known to those skilled in the art (e.g. in the presence of a suitable base and an organic solvent), followed by when amino is protected with PG$^2$, removal of the PG$^2$ protecting group or when amino is present in masked form as NO$_2$, reduction of NO$_2$ to NH$_2$.

(iii) For compounds of formula VII in which G represents phenyl or Het$^3$ substituted by
—S(O)$_{1-2}$—[C(R$^{3a}$)(R$^{3b}$)(CH$_2$)$_{0-1}$CH$_2$—O]$_{2-8}$—R$^{6h}$ or
—S(O)$_{1-2}$—CH$_2$—[C$_{1-5}$ alkylene]-N(R$^{6e}$)R$^{6f}$
oxidation of a corresponding compound of formula VII in which G represents phenyl or Het$^3$ substituted by
—S—[C(R$^{3a}$)(R$^{3b}$)(CH$_2$)$_{0-1}$CH$_2$—O]$_{2-8}$—R$^{6h}$ or
—S—CH$_2$—[C$_{1-5}$ alkylene]-N(R$^{6e}$)R$^{6f}$
and in which the amino group is optionally in protected form (e.g. protected with PG$^2$ or present in masked form, such as a nitro group), under conditions known to those skilled in the art (e.g. in the presence of a peracid, such as meta-chloroperbenzoic acid), followed by when amino is protected with PG$^2$, removal of the PG$^2$ protecting group or when amino is present in masked form as NO$_2$, reduction of NO$_2$ to NH$_2$.

(iv) For compounds of formula VII in which G represents phenyl or Het$^3$ substituted by
—S(O)$_2$R$^{6g}$ or
—C≡C—R$^{6i}$,
coupling of a corresponding compound of formula VII in which G represents phenyl or Het$^3$ substituted by LG$^5$ and in which the amino group is optionally in protected form (e.g. protected with PG$^2$ or present in masked form, such as a nitro group), with a compound of formula XVIIa or XVIIb, M$^+$O$^-$—S(O)—R$^{6g}$      XVIIa H—C≡C—R$^{6i}$      XVIIb wherein R$^{6g}$, R$^{6i}$ and M$^+$ are as hereinbefore defined, under conditions known to those skilled in the art (e.g. in the presence of a Pd(0) catalyst, Cu(I) iodide and a suitable base), followed by when amino is protected with PG$^2$, removal of the PG$^2$ protecting group or when amino is present in masked form as NO$_2$, reduction of NO$_2$ to NH$_2$.

(v) For compounds of formula VII in G represents phenyl or Het$^3$ substituted by —N=S(O)R$^{6j}$R$^{6k}$, reaction of a corresponding compound of formula VII in which G represents phenyl or Het$^3$ substituted by NH$_2$ with a compound of formula XVIII, S(O)R$^{6j}$R$^{6k}$      XVIII wherein R$^{6j}$ and R$^{6k}$ are as hereinbefore defined, under conditions known to those skilled in the art (e.g. in the presence of an oxidant such as a C$_{1-6}$ alkyl hypohalite (e.g. tert-butyl hypochlorite)), followed by when amino is protected with PG$^2$, removal of the PG$^2$ protecting group or when amino is present in masked form as NO$_2$, reduction of NO$_2$ to NH$_2$.

(vi) For compounds of formula VII in which G represents phenyl or Het$^3$ substituted by P(O)R$^{6c}$R$^{6d}$, coupling of a corresponding compound of formula VII in which G represents phenyl or Het$^3$ substituted by LG$^5$ with a compound of formula XIX, H—P(O)R$^{6c}$R$^{6d}$      XIX under conditions known to those skilled in the art (e.g. the reaction may be performed by heating in a polar aprotic solvent (e.g. DMF) in the presence of a palladium-containing catalyst (e.g., Pd(II) acetate, optionally in the presence of a bidentate phosphine ligand such as 4,5-bis(diphenylphosphino)-9,9-dimethylxanthene (Xantphos))).

Compounds of formula III in which Z$^2$ represents a structural fragment of formula IV can be prepared using analogous techniques for interconversion of substituents on the phenyl ring.

For example, compounds of formula III in which Z$^2$ represents a structural fragment of formula IV may be prepared as described below.

(a) For compounds of formula III in which Z$^2$ represents a structural fragment of formula IV and L$^3$ represents a bond, cross-coupling of a compound of formula XX,

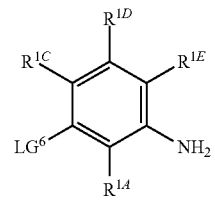

XX wherein R$^{1A}$, R$^{1C}$, R$^{1D}$ and R$^{1E}$ are as hereinbefore defined and LG$^6$ represents a suitable leaving group such as halo (e.g. bromo or iodo), with a compound of formula XXI,

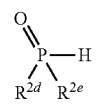

XXI wherein R$^{2d}$ and R$^{2e}$ are as hereinbefore defined, for example under conditions known to those skilled in the art, such as in the presence of a palladium-containing catalyst (e.g., Pd(II) acetate, optionally in the presence of a bidentate phosphine ligand such as 4,5-bis(diphenylphosphino)-9,9-dimethylxanthene (Xantphos); see, for example, WO 2009/143389) to furnish the aryl phosphine oxide.

(b) For compounds of formula III in which $Z^2$ represents a structural fragment of formula IV and $L^3$ represents $-[C(R^{3e})(R^{3b})]_{1-2}-$, cross-coupling of a compound of formula XXII,

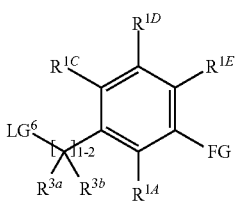

XXII wherein $R^{1A}$, $R^{1C}$, $R^{1D}$, $R^{1E}$, $R^{3a}$, $R^{3b}$, $LG^6$ and FG are as hereinbefore defined, with a compound of formula XXI, as hereinbefore defined, for example under conditions known to those skilled in the art, for example, utilising a transition metal, such as a palladium (see, for example, *Org. Lett.* 2011, 13, 3270-3273 and WO 2009/143389) or nickel (*Bioorg. Med. Chem. Lett.* 2009, 19, 2053-2058), catalyst to generate a phosphoryl-carbon bond, or, alternatively, the compounds of formula XXII are coupled in an Arbuzov-type reaction (WO 2010/141406; *Bioorg. Med. Chem. Lett.* 2009, 19, 2053-2058) with compounds XXIa,

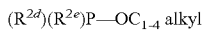

XXIa wherein $R^{2d}$ and $R^{2e}$ are as hereinbefore defined, and XXIa are typically made in situ by reaction of the corresponding chlorophosphine $(R^{2d})(R^{2e})P-Cl$ with a $C_{1-4}$ alkyl alcohol in the presence or a base (e.g. diisopropylethylamine) or with an alkali metal salt of a $C_{1-4}$ alkyl alcohol, followed by,
when FG represents $NH-PG^2$, removal of the $PG^2$ protecting group or,
when FG represents $NO_2$, reduction of $NO_2$ to $NH_2$.

(c) For compounds of formula III in which $Z^2$ represents a structural fragment of formula IV, $L^1$ represents $-[C(R^{3a})(R^{3b})]_{1-2}-$ and $R^{2a}$ and $R^{2b}$ both represent H, hydrolysis of a nitrile of formula XXIII

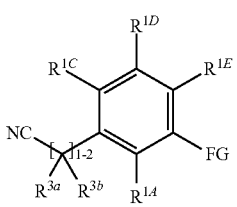

XXIII wherein $R^{1A}$, $R^{1C}$, $R^{1D}$, $R^{1E}$, $R^{3a}$, $R^{3b}$ and FG are as hereinbefore defined, for example under conditions known to those skilled in the art, such as hydrolysis with concentrated hydrochloric acid at elevated temperature, e.g., from 30 to 70° C., to the primary amide followed by
when FG represents $NH-PG^2$, removal of the $PG^2$ protecting group or
when FG represents $NO_2$, reduction of $NO_2$ to $NH_2$.

(d) For compounds of formula III in which $Z^2$ represents a structural fragment of formula IV and $R^1$ represents $-L^1-C(O)N(R^{2a})R^{2b}$ condensation of a carboxylic acid of formula XXIIIa

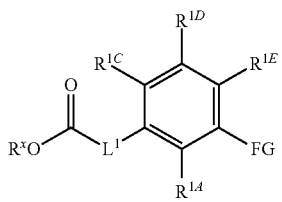

XXIIIa wherein $R^{1A}$, $R^{1C}$, $R^{1D}$, $R^{1E}$, $R^x$, $L^1$ and FG are as hereinbefore defined, with an amine of formula IX, for example under conditions known to those skilled in the art (see, for example, process (e) above in relation to the compounds of formula I), followed by,
when FG represents $NH-PG^2$, by removal of the $PG^2$ protecting group or,
when FG represents $NO_2$, by reduction of $NO_2$ to $NH_2$.

(e) For compounds of formula III in which $Z^2$ represents a structural fragment of formula IV and $R^1$ represents $-S-R^{2c1}$, condensation of the benzenethiol of formula XXIV,

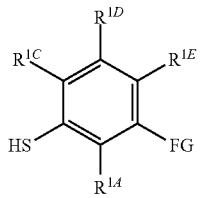

XXIV wherein $R^{1A}$, $R^{1C}$, $R^{1D}$, $R^{1E}$ and FG are as hereinbefore defined, with the compound of formula XXV,

XXV wherein $LG^6$ is as hereinbefore defined, for example under basic (potassium carbonate, sodium ethoxide or triethylamine) conditions when $R^{2c1}$ is methyl, Het² or $C_{3-7}$ cycloalkyl, or under transition metal-catalysed cross-coupling conditions, such as copper(I) iodide (*J. Org. Chem.* 2010, 75, 3626-3643) or a palladium-containing catalyst (WO 2007117381, 18 Oct. 2007), when $R^{2c1}$ is Het¹ followed by,
when FG represents $NH-PG^2$, removal of the $PG^2$ protecting group or,
when FG represents $NO_2$, reduction of $NO_2$ to $NH_2$.

(f) For compounds of formula III in which $Z^2$ represents a structural fragment of formula IV and $R^1$ represents $-[C(R^{3a})(R^{3b})]_{1-2}-S-R^{2c1}$, reaction of a compound of formula XXII, as hereinbefore defined, with a compound of formula XXVI, or the sodium salt—prepared by treatment with base such as sodium hydride or sodium hydroxide—thereof

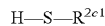

XXVI wherein $R^{2c1}$ is as hereinbefore defined, for example under conditions known to those skilled in the art, e.g., in polar solvents like ethanol or DMF, followed by when FG represents NH-PG², removal of the PG² protecting group or when FG represents NO₂, reduction of NO₂ to NH₂.

(g) For compounds of formula III in which Z² represents a structural fragment of formula IV and R¹ represents —[C(R$^{3a}$)(R$^{3b}$)]$_{0-2}$—S(O)—R$^{2c1}$ or —[C(R$^{3a}$)(R$^{3b}$)]$_{0-2}$—S(O)$_2$—R$^{2c2}$, oxidation of a compound of formula XXVII,

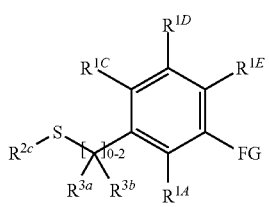

XXVII wherein R$^{2c}$ represents either R$^{2c1}$ or R$^{2c2}$ and R$^{1A}$, R$^{1C}$, R$^{1D}$, R$^{1E}$, R$^{3a}$, R$^{3b}$ and FG are as hereinbefore defined, for example under conditions known to those skilled in the art (e.g. in the presence of a peracid, such as meta-chloroperbenzoic acid) gives the desired sulfoxide or sulfone intermediate. Another route to the sulfone intermediates involves alkylation of the appropriate sodium alkanesulfinate with a compound of the formula XXII. In all cases, the formation of the sulfoxide or sulfone intermediate is followed by, when FG represents NH-PG², removal of the PG² protecting group or, when FG represents NO₂, reduction of NO₂ to NH₂.

(h) For compounds of formula III in which Z² represents a structural fragment of formula IV and R¹ represents CH₂—NH-Q-R$^{2f}$, reaction of a compound of formula XXVIII,

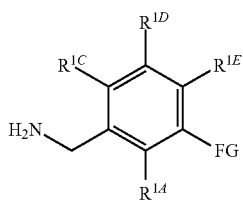

XXVIII wherein R$^{1A}$, R$^{1C}$, R$^{1D}$, R$^{1E}$ and FG are as hereinbefore defined, with a compound of formula XXIX, R$^{2f}$-Q-LG⁶    XXIX Wherein R$^{2f}$, Q and LG⁶ are as hereinbefore defined, for example under conditions known to those skilled in the art—e.g., where XXVIII is condensed with an acid chloride or sulfonyl chloride by condensation in a aprotic solvent, such as dichloromethane or tetrahydrofuran, in the presence of a base, such as diisopropylethylamine—followed by, when FG represents NH-PG², removal of the PG² protecting group or, when FG represents NO₂, reduction of NO₂ to NH₂.

(i) For compounds of formula III in which Z² represents a structural fragment of formula IV wherein R¹ represents —OCH₂—P(O)R$^{2d}$R$^{2e}$, reaction of a compound of formula XXX

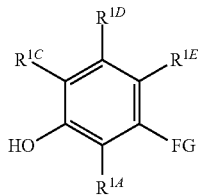

XXX wherein R$^{1A}$, R$^{1C}$, R$^{1E}$, R$^{1D}$ and FG are as hereinbefore defined, with a compound of formula XXXI, LG⁶-CH₂—P(O)R$^{2d}$R$^{2e}$    XXXI wherein R$^{2d}$, R$^{2e}$ and LG⁶ are as hereinbefore defined, for example under conditions known to those skilled in the art (e.g. at elevated temperature in the presence of a base, such as K₂CO₃, and a polar, aprotic solvent, such as DMF), followed by, when FG represents NH-PG², removal of the PG² protecting group or, when FG represents NO₂, reduction of NO₂ to NH₂.

(j) For compounds of formula III in which in which Z² represents a structural fragment of formula IV and L$^{2b}$ is O, reaction of the phenol of formula XXX with a sulfonyl chloride of formula XXXII R$^{2c2}$—SO₂Cl    XXXII wherein R$^{2c2}$ is as hereinbefore defined, for example, in the presence of a base, such as triethylamine, in an aprotic solvent, such as dichloromethane, followed by when FG represents NH-PG², removal of the PG² protecting group or, when FG represents NO₂, reduction of NO₂ to NH₂.

Nitriles of formula XXIII may be prepared by cyanide displacement of LG⁶ in the compound of formula XXII (e.g. with sodium or potassium cyanide in DMSO at ambient temperature). In a similar vein, the amine of formula)(XVIII may be prepared, for example, from the corresponding compounds of formula XXII where —[C(R$^{3a}$)(R$^{3b}$)]$_{1-2}$— represents CH₂ by reaction with an ammonia surrogate, involving, for example, azide displacement followed by Staudinger reduction with triphenylphosphine, or a classical Gabriel amine synthesis comprising reaction with potassium phthalimide followed by cleavage of the imide formed with aqueous or ethanolic hydrazine at reflux.

The compounds of formula XXVIII may also be prepared by reduction of the benzamide XXXIII

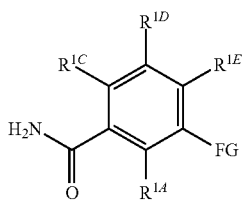

XXXIII wherein R$^{1A}$, R$^{1C}$, R$^{1D}$, R$^{1E}$ and FG are as hereinbefore defined, for example employing conditions known to those skilled in the art (e.g. reduction with borane or lithium aluminium hydride).

Compounds of formula XXII may themselves be prepared by routes known to those skilled in the art, typically from ketone, carboxylic acid or ester precursors. For example, for compounds of formula XXII in which LG⁶ represents halo and —[C(R$^{3a}$)(R$^{3b}$)]$_{1-2}$— represents CH$_2$ may be obtained from the corresponding benzoic acid XXIIa or alkyl benzoate XXIIb. Reduction of the acid XXIIa (e.g., with borane) or the alkyl benzoate XXIIb (e.g., with lithium aluminium hydride or lithium borohydride in an ethereal solvent) furnishes a benzyl alcohol XXIIc that can be transformed into the compound of formula XXII where —[C(R$^{3a}$)(R$^{3b}$)]$_{1-2}$— represents CH$_2$ by a halogenation reaction employing, for example, thionyl chloride when LG⁶ is chloro or triphenylphosphine and bromine when LG⁶ is bromo.

Compounds of formula XXIIIa in which R$^x$ represents H may be prepared by hydrolysis of nitriles of the formula XXIII with aqueous acid or alkali, or with sodium peroxide and water (*J. Chem. Soc., Perkin Trans.* 2 2000, 2399). Compounds of formula XXIIIa in which L¹ represents —OC(R$^{3a}$)(R$^{3b}$)— may be prepared via alkylation of a phenol of formula XXX with a haloester Hal-C(R$^{3a}$)(R$^{3b}$)—C(O)OC$_{1-4}$ alkyl, followed (for compounds of formula XXIIIa in which R$^x$ represents H) by hydrolysis of the ester with aqueous alkali (e.g., lithium hydroxide) or acid (e.g., hydrochloric acid).

It will be understood by persons skilled in the art that compounds represented by formulae II and IIb are generally reactive intermediates. These intermediates may be formed in situ and reacted directly, without isolation, with compounds of formula III to provide compounds of formula I. Furthermore, it will be understood by those skilled in the art that the use of appropriate protective groups may be required during the processes described above for any of the groups Z¹ and Z² which possess chemically-sensitive functional groups, for example, a hydroxyl group or an amino function.

Many of the compounds illustrated in the Schemes are either commercially available, or can be obtained using the cited procedures, or can be readily prepared by conventional methods by those skilled in the art. See for example Regan, J. et al.; *J. Med. Chem.* 2003, 46, 4676-4686, WO 2000/043384, WO 2007/053346, WO 2007/087448, WO 2007/089512 and WO 2009/117080.

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, have a better pharmacokinetic and/or pharmacodynamic profile than, have more suitable solid state morphology than, have better long term stability than, or may have other useful pharmacological properties over, similar compounds, combinations, methods (treatments) or uses known in the prior art for use in the treatment of those conditions or otherwise.

The compounds of the invention may additionally (or alternatively):

exhibit a long duration of action and/or persistence of action (e.g. in comparison to other previously disclosed p38 MAP kinase inhibitors such as, for example, BIRB796); exhibit potent inhibition of Syk (e.g. they may have an IC$_{50}$ against Syk of 500 nM or less, such as 350 nM or less);

not strongly inhibit GSK 3α (e.g. they may have an IC$_{50}$ against GSK 3α of 1,000 nM or greater; such as 1,500, 2,000, 3,000, 4,000, 5,000, 6,000, 7,000, 8,000, 9,000 or 10,000 nM or greater);

target a smaller portion of the kinome, i.e., with improved selectivity, as illustrated by lowered KinomeScan Selectivity Scores;

maintain a relatively high drug concentration between doses (e.g. a high concentration relative to other previously disclosed p38 MAP kinase inhibitors such as, for example, BIRB796);

exhibit properties that are particularly suited to topical/local administration (e.g. following topical/local administration, the generation of high target tissue concentrations but low plasma concentrations of the compounds of formula (I) and/or rapid clearance of the compounds of formula (I) from plasma);

exhibit little or no β-catenin induction and/or inhibition of mitosis in cells;

not produce increases in binucleated cells containing micronuclei in the human lymphocyte in vitro micronucleus test;

exhibit little or no time-dependent inhibition of members of the cytochrome P450 superfamily;

show improved chemical stability in the presence of water (e.g. stability to hydrolysis in aqueous mixtures at elevated temperatures) compared to previously disclosed p38 MAP kinase inhibitors such as, for example, BIRB796;

following administration to a patient, produce metabolites associated with little or no safety (e.g. toxicity) concerns;

exhibit good solubility (for example, solubility in colonic fluids, such as solubility in fasted state simulated colonic fluid [FaSSCoF] of 10 µg/mL or greater (e.g. 20, 30, 50, 100, 200, 300, 500 or 1,000 µg/mL or greater)) and/or cellular permeability, for example relative to known compounds (e.g. the compound disclosed in WO 2014/162122);

have a high degree of crystallinity; and/or exhibit little or no hygroscopicity in the solid state.

Experimental Methods

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under a balloon of hydrogen. Microwave reactions were performed in a CEM Discover and Smithcreator microwave reactor, heating to a constant temperature using variable power microwave irradiation.

Normal phase column chromatography was routinely carried out on an automated flash chromatography system such as CombiFlash Companion or CombiFlash RF system using pre-packed silica (230-400 mesh, 40-63 µm) cartridges. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% NH$_3$ in MeOH.

Analytical Methods

Analytical HPLC was carried out using a Waters Xselect CSH C18, 2.5 µm, 4.6×30 mm column eluting with a gradient of 0.1% Formic Acid in MeCN in 0.1% aqueous Formic Acid; a Waters Xbridge BEH C18, 2.5 µm, 4.6×30 mm column eluting with a gradient of MeCN in aqueous 10 mM Ammonium Bicarbonate. UV spectra of the eluted peaks were measured using either a diode array or variable wavelength detector on an Agilent 1100 system.

Analytical LCMS was carried out using a Waters Xselect CSH C18, 2.5 μm, 4.6×30 mm column eluting with a gradient of 0.1% Formic Acid in MeCN in 0.1% aqueous Formic Acid; a Waters Xbridge BEH C18, 2.5 μm, 4.6×30 mm column eluting with a gradient of MeCN in aqueous 10 mM Ammonium Bicarbonate. UV and mass spectra of the eluted peaks were measured using a variable wavelength detector on either an Agilent 1200 with or an Agilent Infinity 1260 LCMS with 6120 single quadrupole mass spectrometer with positive and negative ion electrospray.

Preparative HPLC was carried out using a Waters Xselect CSH C18, 5 μm, 19×50 mm column using either a gradient of either 0.1% Formic Acid in MeCN in 0.1% aqueous Formic Acid or a gradient of MeCN in aqueous 10 mM Ammonium Bicarbonate; or a Waters Xbridge BEH C18, 5 μm, 19×50 mm column using a gradient MeCN in aqueous 10 mM Ammonium Bicarbonate. Fractions were collected following detection by UV at a single wavelength measured by a variable wavelength detector on a Gilson 215 preparative HPLC or Varian PrepStar preparative HPLC; by mass and UV at a single wavelength measured by a ZQ single quadrupole mass spectrometer, with positive and negative ion electrospray, and a dual wavelength detector on a Waters Fraction Lynx LCMS.

$^1$H NMR Spectroscopy.

$^1$H NMR spectra were acquired on a Bruker Avance III spectrometer at 400 MHz. Either the central peaks of chloroform-d, dimethylsulfoxide-$d_6$ or an internal standard of tetramethylsilane were used as references.

PREPARATION OF COMPOUNDS OF THE INVENTION

Example 1

1-(5-(tert-Butyl)-3-(dimethylphosphoryl)-2-methoxyphenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea

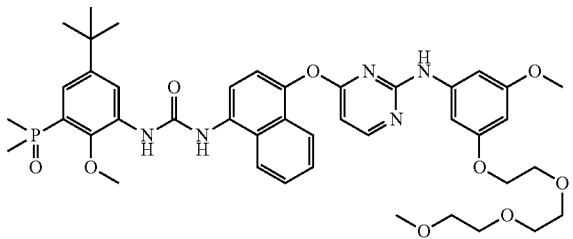 [SMILES: COCCOCCOCCOc1cc(Nc2nccc(Oc3ccc(NC(=O)Nc4cc(C(C)(C)C)cc(P(C)(C)=O)c4OC)c4ccccc34)n2)cc(OC)c1]

(i) 3-Methoxy-5-nitrophenol

A mixture of KOH (29.0 g, 517 mmol) and 1-bromo-3-methoxy-5-nitrobenzene (30 g, 129 mmol) in water (70 mL) and dioxane (70 mL) was degassed for 5 minutes prior to the addition of di-tert-butyl(2',4',6'-triisopropyl-[1,1'-biphenyl]-2-yl)phosphine (1.263 g, 2.97 mmol) and Pd$_2$(dba)$_3$ (1.184 g, 1.293 mmol). The resulting mixture was degassed for a further 2 minutes then heated under a nitrogen atmosphere at 100° C. for 2 h. The mixture was cooled, then acidified with 5M HCl to ~pH 1 and extracted with EtOAc (2×500 mL). The organic layer was washed with saturated brine (200 mL), dried (MgSO$_4$), filtered and concentrated under reduced pressure. The crude product was purified through a pad of silica eluting with 30% EtOAc/isohexane to afford the sub-title compound (20.76 g) as a yellow solid.

$^1$H NMR (400 MHz; DMSO-$d_6$) δ 10.46 (s, 1H), 7.20 (s, 1H), 7.19 (s, 1H), 6.76 (s, 1H), 3.82 (s, 3H). LCMS m/z 168 (M−H)$^−$ (ES$^−$)

(ii) 1-Methoxy-3-(2-(2-(2-methoxyethoxy)ethoxy)ethoxy)-5-nitrobenzene

To a stirred suspension of the product from step (i) above (8.14 g, 45.7 mmol) and K$_2$CO$_3$ (12.64 g, 91 mmol) in acetone (150 mL) was added 1-bromo-2-(2-(2-methoxyethoxy)ethoxy)ethane (8.85 mL, 48.0 mmol). The resulting mixture was refluxed overnight, cooled and filtered. The filtrate was evaporated under reduced pressure and the residue purified by chromatography on silica gel (220 g column, 0-60% EtOAc/isohexane) to afford the sub-title compound (13.41 g) as a yellow oil.

$^1$H NMR (400 MHz, DMSO-$d_6$) δ: 7.34-7.32 (m, 2H), 6.98 (t, 1H), 4.22-4.20 (m, 2H), 3.85 (s, 3H), 3.77-3.74 (m, 2H), 3.60-3.57 (m, 2H), 3.54-3.50 (m, 4H), 3.44-3.40 (m, 2H), 3.23 (s, 3H). LCMS m/z 316 (M+H)$^+$ (ES$^+$)

(iii) 3-Methoxy-5-(2-(2-(2-methoxyethoxy)ethoxy)ethoxy)aniline

The product from step (ii) above (13.4 g, 42.5 mmol) was dissolved in ethanol (150 mL) and Fe powder (13 g, 233 mmol) was added followed by a solution of NH$_4$Cl (2.3 g, 43.0 mmol) in water (150 mL). The resulting suspension was heated at 80° C. for 3 h. The reaction was cooled to rt and filtered through celite. The filtrate was concentrated in vacuo then partitioned between water (250 mL) and EtOAc (400 mL). The organic layer was separated, dried (MgSO$_4$), filtered and concentrated under reduced pressure. The crude product was purified by chromatography on silica gel (120 g column, 0-4% MeOH/DCM) to afford the sub-title compound (10.95 g) as an oil.

$^1$H NMR (400 MHz, DMSO-$d_6$) δ 5.76-5.73 (m, 2H), 5.68 (t, 1H), 5.07 (s, 2H), 3.98-3.89 (m, 2H), 3.72-3.65 (m, 2H), 3.63 (s, 3H), 3.60-3.48 (m, 6H), 3.47-3.40 (m, 2H), 3.24 (s, 3H). LCMS m/z 286 (M+H)$^+$ (ES$^+$)

(iv) tert-Butyl (4-((2-((3-methoxy-5-(2-(2-(2-methoxyethoxy)ethoxy)ethoxy)phenyl)amino)-pyrimidin-4-yl)oxy)naphthalen-1-yl)carbamate tert-Butyl (4-((2-chloropyrimidin-4-yl)oxy)naphthalen-1-yl)carbamate (see, for example, Ito, K. et al., WO 2010/067130, 17 Jun. 2010; 1 g, 2.69 mmol), the product of step (iii) above (1.15 g, 4.03 mmol) and p-TsOH monohydrate (0.100 g, 0.526 mmol) in DMF (10 mL) was heated at 55° C. (internal temperature) for 14 h. The mixture was cooled and added dropwise to sat. aq NaHCO$_3$ (100 mL) then partitioned with EtOAc (2×50 mL). Organics were bulked and washed with 20% w/w NaCl soln. (50 mL), then dried (MgSO$_4$), filtered and solvent evaporated. The crude product was purified by chromatography on silica gel (40 g column) to afford the sub-title compound (1.14 g) as a clear brown oil.

$^1$H NMR (400 MHz, DMSO-$d_6$) δ 9.44 (s, 1H), 9.34 (s, 1H), 8.42 (d, 1H), 8.11 (d, 1H), 7.86-7.76 (m, 1H), 7.66-7.49 (m, 3H), 7.39 (d, 1H), 6.85 (s, 2H), 6.56 (d, 1H), 6.05 (t, 1H), 3.88 (dd, 2H), 3.71-3.63 (m, 2H), 3.59-3.48 (m, 9H), 3.46-3.38 (m, 2H), 3.22 (s, 3H), 1.52 (s, 9H). LCMS m/z 621 (M+H)+ (ES+)

(v) 4-((4-Aminonaphthalen-1-yl)oxy)-N-(3-methoxy-5-(2-(2-(2-methoxyethoxy)ethoxy)-ethoxy)phenyl)pyrimidin-2-amine TFA (2.8 mL, 36.3 mmol) was added dropwise to a stirred solution of the product of step (iv) above (1.1 g, 1.772 mmol) in DCM (5 mL). The reaction was stirred at rt for 2 h. The mixture was added dropwise to stirred water (10 mL) and 1M $K_2CO_3$ solution (35 mL, 35.0 mmol) and stirring continued until effervescence ceased. The mixture was extracted with DCM (2×25 mL) then the combined organic phases were dried ($MgSO_4$) and concentrated under reduced pressure. The crude product was purified by chromatography on silica gel (40 g column, 2% MeOH:DCM to 5%) to afford a brown gum. Recrystallised from iPrOAc (3 mL) afforded the sub-title compound (0.80 g) as a colourless solid.
$^1$H NMR (400 MHz, DMSO-$d_6$) δ 9.42 (s, 1H), 8.33 (d, 1H), 8.22-8.03 (m, 1H), 7.69-7.56 (m, 1H), 7.51-7.35 (m, 2H), 7.11 (d, 1H), 6.87 (d, 2H), 6.68 (d, 1H), 6.35 (d, 1H), 6.04 (t, 1H), 5.79 (s, 2H), 3.94-3.78 (m, 2H), 3.74-3.64 (m, 2H), 3.60-3.47 (m, 9H), 3.46-3.38 (m, 2H), 3.22 (s, 3H). LCMS m/z 521 (M+H)+ (ES+)

(vi) Phenyl (4-((2-((3-methoxy-5-(2-(2-(2-methoxyethoxy)ethoxy)ethoxy)phenyl)amino)-pyrimidin-4-yl)oxy)naphthalen-1-yl)carbamate Phenyl chloroformate (0.730 mL, 5.76 mmol) was added to a stirred solution of the product from step (v) above (3 g, 5.71 mmol) and $NaHCO_3$ (1 g, 11.90 mmol) in THF (30 mL) and DCM (100 mL). The mixture was stirred at rt for 2 h. The mixture was diluted with water (30 mL) and DCM (20 mL) and the mixture passed through a phase-sep cartridge. The resulting filtrate was concentrated in vacuo to afford a pink foam. The material was stirred vigorously in hexane overnight and the resulting solid collected by filtration to afford the sub-title compound (2.83 g) as a pale pink solid.
$^1$H NMR (400 MHz, $CDCl_3$) δ 8.30 (d, 1H), 8.12 (d, 1H), 8.04-7.77 (m, 3H), 7.63-7.59 (m, 1H), 7.54-7.51 (m, 1H), 7.43-7.40 (m, 2H), 7.32-7.23 (m, 4H), 7.03 (s, 1H), 6.64-6.57 (m, 1H), 6.48 (d, 1H), 6.41 (s, 1H), 6.05 (t, 1H), 3.77-3.71 (m, 6H), 3.69-3.61 (m, 7H), 3.58-3.55 (m, 2H), 3.35 (s, 3H).

(vii) 2-Bromo-4-(tert-butyl)-1-methoxybenzene

A mixture of 2-bromo-4-(tert-butyl)phenol (5 g, 21.82 mmol), $K_2CO_3$ (4.52 g, 32.7 mmol) and MeI (1.5 mL, 23.99 mmol) in acetone (70 mL) was stirred at rt for 3 days. The solvent was evaporated and the residue partitioned between DCM (200 mL) and water (200 mL). The organic layer was washed with brine, dried ($MgSO_4$), filtered and evaporated under reduced pressure to afford the sub-title compound (5.29 g) as an oil.
$^1$H NMR (400 MHz, $CDCl_3$) δ: 7.54 (s, 1H), 7.27 (d, 1H), 6.83 (d, 1H), 3.87 (s, 3H), 1.29 (s, 9H).

(viii) 1-Bromo-5-(tert-butyl)-2-methoxy-3-nitrobenzene $HNO_3$ (70%, 2 mL, 31.3 mmol) was added to $Ac_2O$ (2 mL) at 0-5° C. This mixture was added dropwise to a solution of the product from step (vii) above (5.25 g, 21.59 mmol) in $Ac_2O$ (20 mL) at 0° C. over 5 minutes. After 30 minutes the mixture was warmed to rt and stirred for 5 h. The mixture was cooled to 0° C. then $HNO_3$ (2 mL, 31.3 mmol) was added dropwise over 5 minutes. The mixture was warmed to rt, stirred for 20 h then poured into ice cold water (150 mL). The solid was filtered off and dissolved in ether (200 mL), dried ($MgSO_4$), filtered and evaporated under reduced pressure. The crude product was purified by chromatography on silica gel (120 g column, 0-20% EtOAc/isohex) to afford the sub-title compound (4.349 g) as a solid.
$^1$H NMR (400 MHz, $CDCl_3$) δ: 7.78 (s, 1H), 7.74 (s, 1H), 3.99 (s, 3H), 1.33 (s, 9H).

(ix) 3-Bromo-5-(tert-butyl)-2-methoxyaniline

The product from step (viii) above (325 mg, 1.105 mmol) was dissolved in EtOH (6 mL) and iron powder (617 mg, 11.05 mmol) was added, followed by a solution of ammonium chloride (591 mg, 11.05 mmol) in water (3 mL). The resulting suspension was heated at 80° C. for 1 h. The reaction was cooled to rt and filtered through a pad of celite. The filtrate was basified to pH 10 by the addition of sat. aq. $NaHCO_3$, then extracted with EtOAc (3×40 mL). The combined organic extracts were dried ($MgSO_4$), filtered and concentrated in vacuo to afford the sub-title compound (260 mg) as an orange oil.
$^1$H NMR (400 MHz, DMSO-$d_6$) δ: 6.71-6.66 (m, 2H), 5.12 (s, 2H), 3.63 (s, 3H), 1.19 (s, 9H). LCMS m/z 258/260 (M+H)+ (ES+)

(x) (3-Amino-5-(tert-butyl)-2-methoxyphenyl)dimethylphosphine oxide

To a solution of the product from step (ix) above (251 mg, 0.933 mmol) in DMF (3 mL) was added dimethylphosphine oxide (89 mg, 1.027 mmol), palladium(II) acetate (11 mg, 0.049 mmol), potassium phosphate (218 mg, 1.027 mmol) and xantphos (32 mg, 0.055 mmol) and the mixture purged with $N_2$ with sonication for 20 minutes. The reaction mixture was heated in the microwave (CEM, 150° C., 200 W) for 20 min. The reaction was cooled to rt then partitioned between DCM (40 mL) and water (40 mL). The aqueous layer was back extracted with DCM (40 mL). The combined organic extracts were washed with water (50 mL) and brine (50 mL). The mixture was passed through a phase-sep cartridge and the filtrate concentrated in vacuo to afford a dark brown oil (247 mg). The crude product was purified by chromatography on silica gel (40 g column, 0-10% MeOH in EtOAc) to afford the sub-title compound (80 mg) as an orange oil, which solidified on standing.
$^1$H NMR (400 MHz, DMSO-$d_6$) δ: 6.97 (d, 1H), 6.88 (dd, 1H), 4.99 (s, 2H), 3.71 (s, 3H), 1.63 (d, 6H), 1.23 (s, 9H). LCMS m/z 256 (M+H)+ (ES+)

(xi) 1-(5-(tert-Butyl)-3-(dimethylphosphoryl)-2-methoxyphenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea To a stirred solution of the product from step (x) above (76 mg, 0.223 mmol) and the product from step (vi) above (143 mg, 0.223 mmol) in i-PrOAc (3 mL) was added triethylamine (7 µL, 0.050 mmol). The resulting solution was heated at 60° C. overnight. The reaction was cooled to rt and the solvent removed in vacuo to afford an orange oil. The crude product was purified by chromatography on silica gel (40 g column, 0-10% (1% NH₃/MeOH) in DCM) to afford an orange oil, which was triturated with diethyl ether (plus a couple of drops of isohexane) to afford a light, beige solid. The solid was dissolved in the minimum of MeOH and loaded onto SCX.

The column was eluted with MeOH (3 column volumes) then 1% NH₃ in MeOH (3 column volumes). The product containing fraction was concentrated in vacuo to afford a colourless glass, which was triturated with diethyl ether to afford the title compound (35 mg) as a pale beige solid.

¹H NMR (400 MHz, DMSO-d₆) δ: 9.43 (s, 1H), 9.31 (s, 1H), 8.92 (s, 1H), 8.44 (d, 1H), 8.41 (d, 1H), 8.26 (d, 1H), 8.11 (d, 1H), 7.84 (d, 1H), 7.70-7.65 (m, 1H), 7.61-7.57 (m, 1H), 7.41 (d, 1H), 7.36-7.33 (m, 1H), 6.83-6.77 (m, 2H), 6.54 (d, 1H), 6.03 (t, 1H), 3.90 (s, 3H), 3.89-3.84 (m, 2H), 3.67-3.63 (m, 2H), 3.55-3.47 (m, 9H), 3.40-3.37 (m, 2H), 3.20 (s, 3H), 1.74 (d, 6H), 1.30 (s, 9H). LCMS m/z 802 (M+H)⁺ (ES⁺); 800 (M−H)⁻ (ES⁻)

Example 2

1-(5-(tert-Butyl)-3-(dimethylphosphoryl)-2-methoxyphenyl)-3-(4-((2-((3-methoxy-5-(2-(2-(2-methoxyethoxy)ethoxy)ethoxy)phenyl)amino)pyridin-4-yl)oxy)naphthalen-1-yl)urea

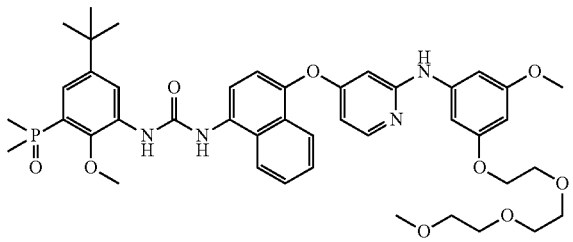 [SMILES: COCCOCCOCCOc1cc(Nc2cc(Oc3ccc(NC(=O)Nc4cc(C(C)(C)C)cc(P(C)(C)=O)c4OC)c4ccccc34)ccn2)cc(OC)c1]

(i) 4-((2-Chloropyridin-4-yl)oxy)naphthalen-1-amine

KOtBu (25.8 g, 230 mmol) was added portionwise to a stirred mixture of 4-aminonaphthalen-1-ol hydrochloride (15 g, 77 mmol) in DMF (250 mL) at −20° C. under N₂. The mixture was stirred for 20 min then 2-chloro-4-fluoropyridine (10.4 mL, 115 mmol) was added and the mixture warmed to 0-5° C. After stirring for 2 h, activated charcoal (20 g) was added, stirred for 30 min then filtered. The filtrate was partitioned between ether (400 mL) and water (400 mL), the ether layer was separated and the aqueous layer washed with ether (300 mL). The combined ether layers were washed with water (200 mL), dried (MgSO₄) and activated charcoal (15 g) added. The mixture was stirred for 30 min then filtered and evaporated under reduced pressure. The residue was triturated with ether (100 mL), filtered and washed with ether (3×50 mL) to afford the sub-title compound (5.44 g).

¹H NMR (400 MHz; CDCl₃) δ 8.18 (d, 1H), 7.88 (d, 1H), 7.77 (d, 1H), 7.56-7.46 (m, 2H), 7.05 (d, 1H), 6.79-6.76 (m, 3H), 4.24 (br s, 2H). LCMS m/z 271 (M+H)⁺ (ES⁺)

(ii) tert-Butyl (4-((2-chloropyridin-4-yl)oxy)naphthalen-1-yl)carbamate

A mixture of the product from step (i) above (1000 mg, 3.69 mmol) and di-tert-butyl dicarbonate (750 mg, 3.44 mmol) in t-BuOH (10 mL) was stirred at reflux for 18 h. The mixture was diluted with water (15 mL) and the solid collected by filtration. The solid was triturated in diethyl ether to yield the sub-title compound (1002 mg) as a pale grey solid.

¹H NMR (400 MHz, DMSO-d₆) δ: 9.37 (s, 1H), 8.28 (d, 1H), 8.16 (d, 1H), 8.82 (dd, 1H), 7.66 (d, 1H), 7.66-7.54 (m, 2H), 7.40 (d, 1H), 7.03 (d, 1H), 6.91 (dd, 1H), 1.52 (s, 9H). LCMS m/z 371 (M+H)⁺ (ES⁺); 369 (M−H)⁻ (ES⁻)

(iii) tert-Butyl (4-((2-((3-methoxy-5-(2-(2-(2-methoxyethoxy)ethoxy)ethoxy)phenyl)amino)-pyridin-4-yl)oxy)naphthalen-1-yl)carbamate Pd₂(dba)₃ (22 mg, 0.024 mmol) and BINAP (30 mg, 0.048 mmol) were stirred in 1,4-dioxane (1 mL) for 10 minutes under N₂. In a separate vessel, purged with N₂, Cs₂CO₃ (455 mg, 1.396 mmol), 3-methoxy-5-(2-(2-(2-methoxyethoxy)ethoxy)ethoxy)aniline (265 mg, 0.930 mmol) and the product from step (ii) above (345 mg, 0.930 mmol) were stirred in 1,4-dioxane (5 mL). The catalyst solution was added to the main reaction mixture and the whole was heated to 90° C. for 48 h. Pd₂(dba)₃ (22 mg, 0.024 mmol) and BINAP (30 mg, 0.048 mmol) were added and the mixture was stirred for a further 18 h. Water was added (15 mL) and the mixture was extracted with EtOAc (3×15 mL). The combined organic phases were washed with saturated brine (15 mL), dried (MgSO₄) and concentrated under reduced pressure. The crude product was purified by chromatography on the Companion (40 g column, 50-100% EtOAc/isohexane) to afford the sub-title compound (194 mg) as a sticky brown oil.

¹H NMR (400 MHz, DMSO-d₆) δ: 9.35 (s, 1H), 8.89 (s, 1H), 8.18-8.08 (m, 2H), 7.84 (d, 1H), 7.67-7.52 (m, 3H), 7.35 (d, 1H), 6.91 (s, 1H), 6.79 (s, 1H), 6.58 (dd, 1H), 6.07-6.02 (m, 2H), 4.01-3.95 (m, 2H), 3.74-6.67 (m, 2H), 3.65 (s, 3H), 3.60-3.48 (m, 6H), 3.46-3.39 (m, 2H), 3.23 (s, 3H), 1.52 (s, 9H). LCMS m/z 620 (M+H)⁺ (ES⁺); 618 (M−H)⁻ (ES⁻)

(iv) 4-((4-Aminonaphthalen-1-yl)oxy)-N-(3-methoxy-5-(2-(2-(2-methoxyethoxy)ethoxy)-ethoxy)phenyl)pyridin-2-amine A solution of the product from step (iii) above (190 mg, 0.307 mmol) in DCM (0.5 mL) was treated with TFA (500 µL, 6.49 mmol) and stirred at rt for 3 h. The mixture was diluted with water (10 mL) and DCM (10 mL). The mixture was neutralised with sat. aq. NaHCO₃ and passed through a phase separation cartridge. The organic phase was dried (MgSO₄) and concentrated to give the sub-title compound (135 mg) as a brown gum.

¹H NMR (400 MHz, DMSO-d₆) δ: 8.08 (s, 1H), 8.20-8.10 (m, 1H), 8.05 (d, 1H), 7.67-7.59 (m, 1H), 7.49-7.39 (m, 2H), 7.09 (d, 1H), 6.89 (s, 1H), 6.76 (s, 1H), 6.71 (d, 1H), 6.52 (dd, 1H), 6.06-5.55 (m, 2H), 5.83 (s, 2H), 4.00-3.90 (m, 2H), 3.74-3.66 (m, 2H), 3.64 (s, 3H), 3.60-3.47 (m, 6H), 3.46-3.38 (m, 2H), 3.23 (s, 3H). LCMS m/z 520 (M+H)⁺ (ES⁺)

(v) Phenyl (4-((2-((3-methoxy-5-(2-(2-methoxyethoxy)ethoxy)ethoxy)phenyl)amino)-pyridin-4-yl)oxy)naphthalen-1-yl)carbamate Phenylchloroformate (76 µL, 0.600 mmol) was added to a stirred solution of the product from step (iv) above (300 mg, 0.572 mmol) and NaHCO₃ (96 mg, 1.143 mmol) in THF (3 mL) and DCM (10 mL). The reaction mixture was stirred at rt overnight. The mixture was diluted with water (10 mL)

and DCM (10 mL) and the mixture passed through a phase-sep cartridge. The resulting filtrate was concentrated in vacuo giving the product as a pale pink foam. The foam was triturated with isohexane, filtered and dried to afford the sub-title compound (182 mg) as a pale pink solid.

LCMS m/z 640 (M+H)$^+$ (ES$^+$)

(vi) 1-(5-(tert-Butyl)-3-(dimethylphosphoryl)-2-methoxyphenyl)-3-(4-((2-((3-methoxy-5-(2-(2-(2-methoxyethoxy)ethoxy)ethoxy)phenyl)amino)pyridin-4-yl)oxy)naphthalen-1-yl)urea Triethylamine (17 µL, 0.122 mmol) was added to a stirred mixture of (3-amino-5-(tert-butyl)-2-methoxyphenyl)dimethylphosphine oxide (see Example 1(x) above; 64 mg, 0.241 mmol) and the product from step (v) above (180 mg, 0.239 mmol) in i-PrOAc (4 mL). The reaction was heated at 60° C. overnight. The reaction was cooled to rt and then concentrated in vacuo. The crude product was purified by chromatography on silica gel (40 g column, 0-10% MeOH in DCM) to afford a colourless glass, which was triturated with diethyl ether, filtered and dried to afford the title compound (69 mg) as a white solid.

$^1$H NMR (400 MHz, DMSO-d$_6$) δ: 9.34 (s, 1H), 8.89 (d, 2H), 8.44 (d, 1H), 8.28 (d, 1H), 8.13-8.09 (m, 2H), 7.86 (d, 1H), 7.72-7.68 (m, 1H), 7.62-7.58 (m, 1H), 7.38 (d, 1H), 7.37-7.33 (m, 1H), 6.90 (t, 1H), 6.77 (t, 1H), 6.58-6.56 (m, 1H), 6.07 (d, 1H), 6.03 (t, 1H), 3.98-3.96 (m, 2H), 3.89 (s, 3H), 3.71-3.68 (m, 2H), 3.64 (s, 3H), 3.57-3.55 (m, 2H), 3.53-3.49 (m, 4H), 3.42-3.40 (m, 2H), 3.22 (s, 3H), 1.74 (d, 6H), 1.30 (s, 9H). LCMS m/z 801 (M+H)$^+$ (ES$^+$); 799 (M-H)$^-$ (ES$^-$)

Example 3

3-((4-((4-(3-(5-(tert-Butyl)-3-(dimethylphosphoryl)-2-methoxyphenyl)ureido)naphthalen-1-yl)oxy)pyridin-2-yl)amino)-5-ethynyl-N-(2-(2-(2-methoxyethoxy)ethoxy)ethyl)benzamide

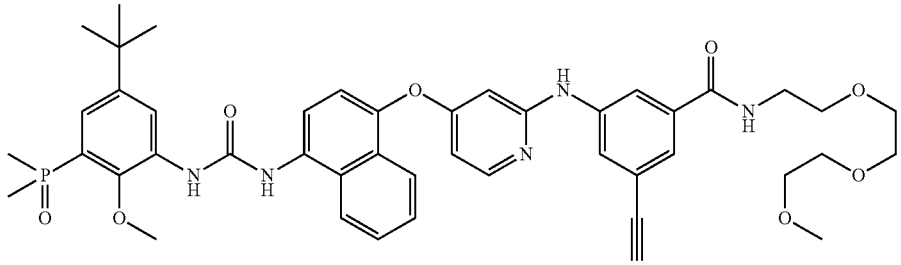 [SMILES: C#Cc1cc(Nc2cc(Oc3ccc(NC(=O)Nc4cc(C(C)(C)C)cc(P(C)(C)=O)c4OC)c4ccccc34)ccn2)cc(C(=O)NCCOCCOCCOC)c1]

(i) 3-Amino-5-((triisopropylsilyl)ethynyl)benzoic acid

Pd(PPh$_3$)$_4$ (9.36 g, 8.10 mmol) was added to a degassed suspension of 3-amino-5-bromobenzoic acid (50 g, 231 mmol), CuI (1.499 g, 7.87 mmol), and ethynyltriisopropylsilane (80 mL, 356 mmol) in triethylamine (300 mL) and DMF (300 mL). The mixture was heated to 90° C. for 2 h. The mixture was cooled and carefully poured into ice-cold HCl (2.0M aq.) (1100 mL, 2200 mmol) and diluted with diethyl ether (500 mL). The biphasic mixture was filtered to remove palladium residues. The layers of the filtrate were separated and the aqueous phase was extracted with a further portion of diethyl ether (300 mL). The organic phases were combined and washed with 20% brine (2×300 mL), 40% brine (300 mL), dried (MgSO$_4$), filtered and concentrated in vacuo affording a pale orange solid. The solid was recrystallised in acetonitrile (250 mL) and collected by filtration, washing with fresh acetonitrile (2×30 mL) affording the product as a yellow solid. The solid was slurried in hexane (250 mL) for 5 h then filtered, washing with more hexane to afford the sub-title compound (45.5 g) as a pale yellow solid.

$^1$H NMR (400 MHz, DMSO-d$_6$) δ: 12.87 (bs, 1H), 7.18 (t, 1H), 7.10 (t, 1H), 6.86 (t, 1H), 5.54 (bs, 2H), 1.10 (s, 21H). LCMS m/z 318 (M+H)$^+$ (ES$^+$); 316 (M-H)$^-$ (ES$^-$)

(ii) 3-((4-((4-((tert-Butoxycarbonyl)amino)naphthalen-1-yl)oxy)pyridin-2-yl)amino)-5-((triisopropylsilyl)ethynyl)benzoic Acid N$_2$ was bubbled through a mixture of tert-butyl (4-((2-chloropyridin-4-yl)oxy)naphthalen-1-yl)carbamate (see Example 2(ii) above; 0.5 g, 1.348 mmol), the product from step (i) above (0.490 g, 1.544 mmol), Cs$_2$CO$_3$ (0.966 g, 2.97 mmol), BINAP (0.078 g, 0.125 mmol) and Pd$_2$dba$_3$ (0.056 g, 0.061 mmol) in dioxane (15 mL) for 10 min then heated at 90° C. for 4 h. The mixture was partitioned between ether (100 mL) and 1M HCl (50 mL), the organic layer separated, washed with water, dried (MgSO$_4$), filtered and evaporated under reduced pressure. The residue was triturated with ether/isohexane, filtered and dried to afford the sub-title compound (760 mg) which was used crude in the next step.

(iii) 3-((4-((4-((tert-Butoxycarbonyl)amino)naphthalen-1-yl)oxy)pyridin-2-yl)amino)-5-ethynylbenzoic Acid 1.0 M TBAF in THF (2.5 mL, 2.500 mmol) was added to a stirred solution of the product from step (ii) above (760 mg) in THF (15 mL). The mixture was stirred for 2 h then water (10 mL) added and acidified to pH-4 with 1M HCl. The mixture was partitioned between EtOAc (70 mL) and water (40 mL), the organic phase washed with sat brine (50 mL), dried (MgSO$_4$), filtered and evaporated under reduced pressure. The crude product was purified by chromatography on silica gel (40 g column, 0-100% EtOAc/isohexane) to afford the sub-title compound (344 mg) as a foam.

$^1$H NMR (400 MHz, DMSO-d$_6$) 400 MHz, δ: 13.07 (s, 1H), 9.39 (s, 1H), 9.29 (s, 1H), 8.18-8.13 (m, 4H), 7.84 (d, 1H), 7.66-7.56 (m, 3H), 7.44 (s, 1H), 7.38 (d, 1H), 6.66 (dd, 1H), 6.07 (d, 1H), 4.22 (s, 1H), 1.53 (s, 9H). LCMS m/z 496 (M+H)$^+$ (ES$^+$)

(iv) tert-Butyl (4-((2-((3-ethynyl-5-((2-(2-(2-methoxyethoxy)ethoxy)ethyl)carbamoyl)-phenyl)amino)pyridin-4-yl)oxy)naphthalen-1-yl)carbamate HATU (500 mg, 1.315 mmol) was added to a stirred solution of the product from step (iii) above (500 mg, 1.009 mmol), 2-(2-(2-methoxyethoxy)ethoxy)ethanamine (277 mg, 1.695 mmol) and triethylamine (250 µL, 1.796 mmol) in N,N-dimethylformamide (10 mL). The mixture was stirred at rt for 18 h. The mixture was diluted with EtOAc (50 mL) and washed with water (50 mL), 20% brine (3×50 mL) and saturated brine (50 mL). The organic phase was dried ($MgSO_4$), filtered and concentrated under reduced pressure. The crude product was purified by chromatography on the Companion (40 g column, EtOAc) to afford the sub-title compound (580 mg) as a tan foam.

LCMS m/z 641 $(M+H)^+$ $(ES^+)$; 639 $(M-H)^-$ $(ES^-)$

(v) 3-((4-((4-Aminonaphthalen-1-yl)oxy)pyridin-2-yl)amino)-5-ethynyl-N-(2-(2-(2-methoxy-ethoxy)ethoxy)ethyl)benzamide TFA (1 mL, 12.98 mmol) was added to a solution of the product from step (iv) above (580 mg, 0.905 mmol) in DCM (5 mL) at rt and stirred overnight. The volatiles were removed under reduced pressure and the residue was redissolved in DCM (20 mL). The organic phase was washed with saturated $NaHCO_3$ solution (20 mL), dried ($MgSO_4$) and concentrated under reduced pressure to yield the sub-title compound (475 mg).

LCMS m/z 541 $(M+H)^+$ $(ES^+)$; 539 $(M-H)^-$ $(ES^-)$

(vi) Phenyl (5-(tert-butyl)-3-(dimethylphosphoryl)-2-methoxyphenyl)carbamate Phenyl chloroformate (66 µL, 0.520 mmol) was added to a stirred solution of (3-amino-5-(tert-butyl)-2-methoxyphenyl)dimethylphosphine oxide (see Example 1(x) above; 125 mg, 0.470 mmol) in THF (2.5 mL) and DCM (8 mL). The reaction mixture was stirred at rt overnight. The mixture was diluted with water (10 mL) and DCM (10 mL) and passed through a phase sep cartridge. The filtrate was concentrated in vacuo then triturated with diethyl ether, filtered and dried to afford the sub-title compound (134 mg) as an off-white solid.

$^1$H NMR (400 MHz, DMSO-$d_6$) δ: 9.71 (s, 1H), 7.76 (s, 1H), 7.57-7.54 (m, 1H), 7.44-7.40 (m, 2H), 7.27-7.20 (m, 3H), 3.87 (s, 3H), 1.68 (d, 6H), 1.28 (s, 9H). LCMS m/z 376 $(M+H)^+$ $(ES^+)$

(vii) 3-((4-((4-(3-(5-(tert-Butyl)-3-(dimethylphosphoryl)-2-methoxyphenyl)ureido)-naphthalen-1-yl)oxy)pyridin-2-yl)amino)-5-ethynyl-N-(2-(2-(2-methoxyethoxy)ethoxy)-ethyl)benzamide To a stirred mixture of the product from step (vi) above (127 mg, 0.321 mmol) and the product from step (v) above (176 mg, 0.321 mmol) in i-PrOAc (6 mL) was added triethylamine (10 µL, 0.072 mmol). The reaction mixture was heated at 60° C. overnight. The reaction was cooled to rt then concentrated in vacuo. The crude product was purified by chromatography on silica gel (40 g column, 0-10% MeOH in DCM) to afford an oil, which was triturated with diethyl ether, filtered and dried to afford the title compound (146 mg) as an off-white solid.

$^1$H NMR (400 MHz, DMSO-$d_6$) δ: 9.35 (s, 1H), 9.21 (s, 1H), 8.90 (s, 1H), 8.45 (t, 1H), 8.44 (d, 1H), 8.29 (d, 1H), 8.15-8.12 (m, 2H), 8.10-8.09 (m, 1H), 7.92-7.91 (m, 1H), 7.88-7.86 (m, 1H), 7.73-7.69 (m, 1H), 7.63-7.59 (m, 1H), 7.42-7.39 (m, 2H), 7.37-7.33 (m, 1H), 6.63-6.61 (m, 1H), 6.13 (d, 1H), 4.18 (s, 1H), 3.90 (s, 3H), 3.52-3.48 (m, 8H), 3.40-3.37 (m, 4H), 3.20 (s, 3H), 1.75 (d, 6H), 1.30 (s, 9H). LCMS m/z 822 $(M+H)^+$ $(ES^+)$

Example 4

1-(5-(tert-Butyl)-3-(dimethylphosphoryl)-2-methoxyphenyl)-3-(4-((6-((3-methoxy-5-(2-(2-(2-methoxyethoxy)ethoxy)ethoxy)phenyl)amino)pyrimidin-4-yl)oxy)naphthalen-1-yl)urea

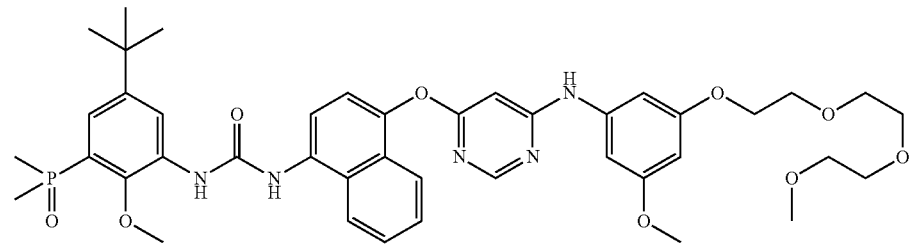 [SMILES: COCCOCCOCCOc1cc(Nc2cc(Oc3ccc(NC(=O)Nc4cc(C(C)(C)C)cc(P(C)(C)=O)c4OC)c4ccccc34)ncn2)cc(OC)c1]

(i) tert-Butyl (4-((6-chloropyrimidin-4-yl)oxy)naphthalen-1-yl)carbamate

DBU (1.7 mL, 11.28 mmol) was added to a mixture of tert-butyl (4-hydroxynaphthalen-1-yl)carbamate (2.45 g, 9.45 mmol) and 4,6-dichloropyrimidine (1.48 g, 9.93 mmol) in MeCN (30 mL) and stirred at rt for 20 h. The mixture was partitioned between EtOAc (150 mL) and aq 2M HCl (150 mL), the organic layer washed with water (150 mL), dried ($MgSO_4$), filtered and evaporated under reduced pressure. The crude product was purified by chromatography on silica gel (120 g column, 0-25% EtOAc/isohexane) to afford the sub-title compound (2.695 g) as a white solid.

$^1$H NMR (400 MHz, $CDCl_3$) δ: 8.56 (s, 1H), 7.94 (br d, 2H), 7.82 (d, 1H), 7.61-7.50 (m, 2H), 7.26 (d, 1H), 6.93 (s, 1H), 6.86 (brs, 1H).

(ii) tert-Butyl(4-((6-((3-methoxy-5-(2-(2-(2-methoxyethoxy)ethoxy)ethoxy)phenyl)amino)-pyrimidin-4-yl)oxy)naphthalen-1-yl)carbamate The product from step (i) above (1.0 g, 2.69 mmol), 3-methoxy-5-(2-(2-(2-methoxyethoxy)ethoxy)ethoxy)aniline (1.0 g, 3.50 mmol) and p-TsOH monohydrate (0.1 g, 0.526 mmol) were stirred in THF (15 mL) at 40° C. (block temperature) for 18 h. The temperature was increased to 50° C. and left to stir another 3 d. then increased to 70° C. and left to stir another 24 h. The mixture was cooled then diluted with water (20 mL) and sat. aq NaHCO$_3$ (20 mL). The aqueous mixture was extracted with EtOAc (3×25 mL) and the organic phases were combined. The organic phase was washed with 0.5 M HCl solution (2×50 mL), saturated brine (50 mL), dried (MgSO$_4$) and concentrated under reduced pressure. The crude product was purified by chromatography on the Companion (40 g column, 50-100% EtOAc/ isohexane) to afford the sub-title compound (0.898 g) as a colourless glass.

$^1$H NMR (400 MHz, DMSO-d$_6$) δ: 9.52 (s, 1H), 9.33 (s, 1H), 9.35 (s, 1H), 8.11 (d, 1H), 7.80 (d, 1H), 7.65-7.51 (m, 3H), 7.36 (d, 1H), 6.88 (dd, 1H), 6.78 (dd, 1H), 6.19 (dd, 1H), 6.10 (s, 1H), 4.06-3.99 (m, 2H), 3.76-6.68 (m, 2H), 3.70 (s, 3H), 3.62-3.56 (m, 2H), 3.56-3.49 (m, 4H), 3.45-3.39 (m, 2H), 3.23 (s, 3H), 1.52 (s, 9H). LCMS m/z 621 (M+H)$^+$ (ES$^+$); 619 (M−H)$^−$ (ES$^−$)

(iii) 6-((4-Aminonaphthalen-1-yl)oxy)-N-(3-methoxy-5-(2-(2-(2-methoxyethoxy)ethoxy)-ethoxy) phenyl)pyrimidin-4-amine Trifluoroacetic acid (600 μL, 7.78 mmol) was added to a stirred solution of the product from step (ii) above (898 mg, 1.447 mmol) in DCM (4 mL) and stirred at rt for 2 h. The mixture was concentrated to remove excess TFA then the residue was redissolved in DCM (25 mL). The organic solution was washed with sat. aq NaHCO$_3$ solution, dried (MgSO$_4$) and concentrated under reduced pressure. The crude product was purified by chromatography on the Companion (12 g column, EtOAc) to afford the sub-title compound (715 mg) as a tan foam.

$^1$H NMR (400 MHz, DMSO-d$_6$) δ: 9.36 (s, 1H), 8.37 (s, 1H), 8.18-8.11 (m, 1H), 7.64-7.57 (m, 1H), 7.49-7.40 (m, 2H), 7.10 (d, 1H), 6.84 (dd, 1H), 6.73 (m, 1H), 6.70 (d, 1H), 6.15 (dd, 1H), 5.89 (s, 1H), 5.81 (br s, 2H), 4.02-3.97 (m, 2H), 3.74-3.68 (m, 2H), 3.67 (s, 3H), 3.60-3.55 (m, 2H), 3.55-3.48 (m, 4H), 3.45-3.39 (m, 2H), 3.23 (s, 3H). LCMS m/z 521 (M+H)$^+$ (ES$^+$); 520 (M−H)$^−$ (ES$^−$)

(iv) 1-(5-(tert-Butyl)-3-(dimethylphosphoryl)-2-methoxyphenyl)-3-(4-((6-((3-methoxy-5-(2-(2-(2-methoxyethoxy)ethoxy)ethoxy)phenyl)amino)pyrimidin-4-yl)oxy)naphthalen-1-yl)urea The product from step (iii) above (150 mg, 0.288 mmol), phenyl (5-(tert-butyl)-3-(dimethylphosphoryl)-2-methoxyphenyl)carbamate (see Example 3(vi) above; 125 mg, 0.333 mmol) and triethylamine (10 μL, 0.072 mmol) were heated to 50° C. (block temp) in iPrOAc (5 mL) and THF (5 mL) for 18 h. The mixture was diluted with EtOAc (25 mL) then washed sequentially with 1 M HCl solution (2×25 mL), water (25 mL), sat. aq NaHCO$_3$ solution (2×25 mL) and saturated brine (25 mL). The organic phase was dried (MgSO$_4$) and filtered. The filtrate was concentrated under reduced pressure to yield the crude product as a brown foam. The crude product was purified by chromatography on the Companion (12 g column, 0-10% MeOH/EtOAc) to afford the title compound (120 mg) as a white foam.

$^1$H NMR (400 MHz, DMSO-d$_6$) δ: 9.50 (s, 1H), 9.33 (s, 1H), 8.89 (s, 1H), 8.44 (d, 1H), 8.36 (s, 1H), 8.27 (s, 1H), 8.09 (d, 1H), 7.84 (d, 1H), 7.69 (ddd, 1H), 7.60 (ddd, 1H), 7.39 (d, 1H), 7.35 (dd, 1H), 6.88 (dd, 1H), 6.77 (dd, 1H), 6.19 (dd, 1H), 6.10 (s, 1H), 4.06-3.97 (m, 2H), 3.90 (s, 3H), 3.77-3.69 (m, 2H), 3.70 (s, 3H), 3.61-3.47 (m, 6H), 3.45-3.38 (m, 2H), 3.23 (s, 3H), 1.75 (d, 6H), 1.31 (s, 9H). LCMS m/z 802 (M+H)$^+$ (ES$^+$); 800 (M−H)$^−$ (ES$^−$)

Example 5

5-(tert-Butyl)-2-methoxy-3-(3-(4-((2-((3-methoxy-5-(2-(2-(2-methoxyethoxy)ethoxy)-ethoxy)phenyl) amino)pyrimidin-4-yl)oxy)naphthalen-1-yl)ureido) phenyl methanesulfonate

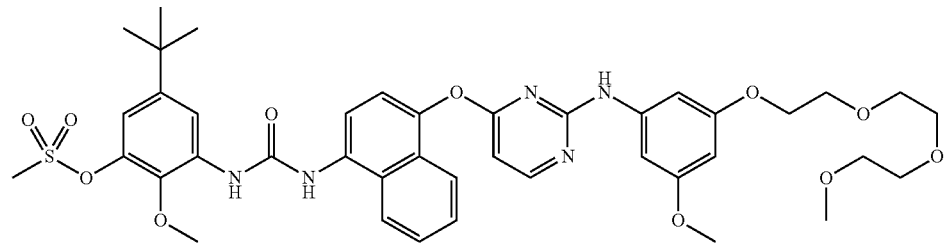 [SMILES: COCCOCCOCCOc1cc(Nc2nccc(Oc3ccc(NC(=O)Nc4cc(C(C)(C)C)cc(OS(C)(=O)=O)c4OC)c4ccccc34)n2)cc(OC)c1]

(i) 5-(tert-Butyl)-2-methoxy-3-nitrophenol

A mixture of KOH (0.5 g, 8.91 mmol) and 1-bromo-5-(tert-butyl)-2-methoxy-3-nitrobenzene (0.5 g, 1.735 mmol) in water (5 mL) and dioxane (5 mL) was degassed for 5 minutes prior to the addition of di-tert-butyl(2',4',6'-triisopropyl-[1,1'-biphenyl]-2-yl)phosphine (0.033 g, 0.078 mmol) and Pd$_2$(dba)$_3$ (0.032 g, 0.035 mmol). The resulting mixture was degassed for a further 2 minutes and then heated under a nitrogen atmosphere at 100° C. for 2 h. The mixture was cooled, partitioned between 1M HCl (50 mL) and EtOAc (60 mL), the organic layer separated, washed with water (20 mL), dried (MgSO$_4$), filtered and evaporated under reduced pressure. The crude product was purified by chromatography on silica gel (40 g column, 0-35% EtOAc/ isohexane) to afford the sub-title compound (344 mg) as a brown oil.

$^1$H NMR (400 MHz, CDCl$_3$) δ: 7.46 (s, 1H), 7.26 (s, 1H), 5.98 (s, 1H), 3.94 (s, 3H), 1.25 (s, 9H). LCMS m/z 226 (M+H)$^+$ (ES$^+$); 224 (M−H)$^−$ (ES$^−$)

(ii) 5-(tert-Butyl)-2-methoxy-3-nitrophenyl methanesulfonate

Methanesulfonyl chloride (130 μL, 1.668 mmol) was added to a mixture of the product from step (i) above (330 mg, 1.465 mmol) and triethylamine (600 μL, 4.30 mmol) in DCM (10 mL) at rt. The mixture was stirred for 3 h then partitioned between DCM (50 mL) and sat. aq NaHCO$_3$ (30 mL). The organic layer was washed with 1M HCl (30 mL), brine (20 mL), dried (MgSO$_4$), filtered and evaporated under reduced pressure to afford the sub-title compound (442 mg) as a gum.

$^1$H NMR (400 MHz, CDCl$_3$) δ: 7.80 (s, 1H), 7.60 (s, 1H), 4.02 (s, 3H), 3.23 (s, 3H), 1.35 (s, 9H).

(iii) 3-Amino-5-(tert-butyl)-2-methoxyphenyl methanesulfonate

A mixture of 5% Pd—C (120 mg, JM type 87L) and the product from step (ii) above (430 mg, 1.418 mmol) in EtOH (8 mL) was hydrogenated under a hydrogen balloon for 64 h then at 5 Bar for 24 h. The mixture was filtered, the filtrate evaporated under reduced pressure and the residue purified by chromatography on silica gel (40 g column, 0-50% EtOAc/isohexane) to afford the sub-title compound (246 mg) as an oil.

$^1$H NMR (400 MHz, CDCl$_3$) δ: 6.71 (s, 2H), 3.88 (s, 2H), 3.84 (s, 3H), 3.16 (s, 3H), 1.26 (s, 9H). LCMS m/z 274 (M+H)$^+$ (ES$^+$)

(iv) 5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl methanesulfonate Triethylamine (5 μL, 0.036 mmol) was added to a mixture of the product from step (iii) above (50 mg, 0.183 mmol) and phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 1(vi) above; 120 mg, 0.187 mmol) in iPrOAc (3 mL) and the mixture heated at 60° C. (block temperature) for 4 h. The reaction was cooled to rt and concentrated in vacuo onto silica gel. The crude product was purified by chromatography on the Companion (12 g column, 1-4% MeOH in DCM) to afford the product as a colourless solid. The material was dissolved in DCM (10 mL) and washed with 1M HCl solution (10 mL). The organic phase was filtered through a hydrophobic frit then concentrated in vacuo affording the title compound (97 mg) as a pale yellow solid.

$^1$H NMR (400 MHz, DMSO-d$_6$) δ: 9.53 (s, 1H), 9.51 (s, 1H), 9.07 (s, 1H), 8.42 (d, 1H), 8.36 (d, 1H), 8.31 (d, 1H), 8.08 (d, 1H), 7.85 (d, 1H), 7.68 (t, 1H), 7.60 (t, 1H), 7.43 (d, 1H), 6.98 (d, 1H), 6.79 (d, 2H), 6.59 (d, 1H), 6.06 (t, 1H), 3.90 (s, 3H), 3.86-3.89 (m, 2H), 3.65-3.67 (m, 2H), 3.47-3.55 (m, 6H), 3.52 (s, 3H), 3.47 (s, 3H), 3.41 (dd, 2H), 3.22 (s, 3H), 1.28 (s, 9H). LCMS m/z 820 (M+H)$^+$ (ES$^+$)

Example 6

1-(5-(tert-Butyl)-3-((dimethylphosphoryl)methoxy)-2-methoxyphenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea

(i) ((5-(tert-Butyl)-2-methoxy-3-nitrophenoxy)methyl)dimethylphosphine oxide A mixture of 5-(tert-butyl)-2-methoxy-3-nitrophenol (350 mg, 1.554 mmol), (chloromethyl)dimethylphosphine oxide (236 mg, 1.865 mmol) and K$_2$CO$_3$ (430 mg, 3.11 mmol) in DMF (8 mL) was heated at 80° C. for 48 h. The mixture was partitioned between EtOAc (80 mL) and water (40 mL), the organic layer washed with brine (40 mL), dried (MgSO$_4$), filtered and evaporated under reduced pressure. The residue was purified by chromatography on silica gel (40 g column, 0-5% MeOH/DCM) to afford the sub-title compound (375 mg) as a white solid.

$^1$H NMR (400 MHz, CDCl$_3$) δ: 7.43 (d, 1H), 7.22 (d, 1H), 4.34 (d, 2H), 3.94 (s, 3H), 1.72 (d, 6H), 1.33 (s, 9H). LCMS m/z 316 (M+H)$^+$ (ES$^+$)

(ii) ((3-Amino-5-(tert-butyl)-2-methoxyphenoxy)methyl)dimethylphosphine oxide A mixture of the product from step (i) above (370 mg, 1.173 mmol) and 5% Pd—C (150 mg) in EtOH (8 mL) was hydrogenated under a balloon of hydrogen for 3 days. The mixture was filtered through celite, the filtrate evaporated, and the residue purified by chromatography on silica gel (40 g column, EtOAc) to afford the sub-title compound (236 mg) as an oil.

$^1$H NMR (400 MHz, CDCl$_3$) δ: 6.50 (d, 1H), 6.40 (d, 1H), 4.32 (d, 2H), 3.85 (s, 2H), 3.80 (s, 3H), 1.70 (d, 6H), 1.28 (s, 9H). LCMS m/z 286 (M+H)$^+$ (ES$^+$)

(iii) 1-(5-(tert-Butyl)-3-((dimethylphosphoryl)methoxy)-2-methoxyphenyl)-3-(4-((2-((3-methoxy-5-(2-(2-(2-methoxyethoxy)ethoxy)ethoxy)phenyl)amino)pyrimidin-4-yl)oxy)-naphthalen-1-yl)urea Triethylamine (5 μL, 0.036 mmol) was added to a mixture of the product from step (ii) above (50 mg, 0.175 mmol) and phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 1(vi) above; 112 mg, 0.175 mmol) in iPrOAc (3 mL) and the mixture heated at 60° C. (block temperature) overnight. The reaction was cooled to rt and concentrated in vacuo onto silica gel. The crude product was purified by chromatography on the Companion (12 g column, 1-5% MeOH in DCM) to afford the title compound (113 mg) as a colourless solid.

$^1$H NMR (400 MHz, DMSO-d$_6$) δ: 9.43 (s, 1H), 9.40 (s, 1H), 8.85 (s, 1H), 8.42 (d, 1H), 8.28 (d, 1H), 8.05-8.08 (m, 2H), 7.85 (d, 1H), 7.68 (t, 1H), 7.59 (t, 1H), 7.41 (d, 1H), 6.81-6.83 (m, 3H), 6.55 (d, 1H), 6.04 (t, 1H), 4.39 (d, 2H), 3.86-3.88 (m, 2H) 3.86 (s, 3H), 3.65-3.67 (m, 2H), 3.48-3.55 (m, 6H), 3.52 (s, 3H), 3.40 (dd, 2H), 3.22 (s, 3H), 1.58 (d, 6H), 1.29 (s, 9H). LCMS m/z 832 (M+H)$^+$ (ES$^+$); 830 (M−H)$^−$ (ES$^−$)

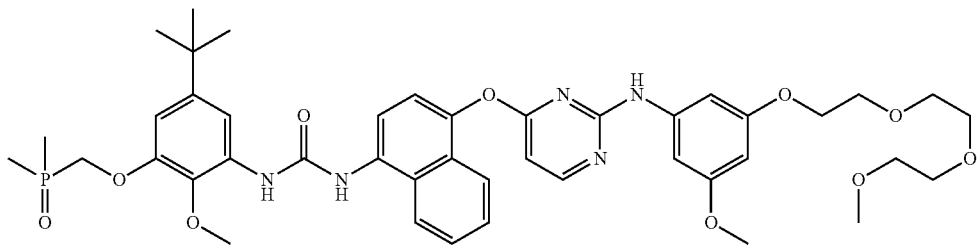 [SMILES: COCCOCCOCCOc1cc(Nc2nccc(Oc3ccc(NC(=O)Nc4cc(C(C)(C)C)cc(OCP(C)(C)=O)c4OC)c4ccccc34)n2)cc(OC)c1]

Example 7

5-(tert-Butyl)-2-methoxy-3-(3-(4-((2-((3-methoxy-5-(2-(2-(2-methoxyethoxy)ethoxy)ethoxy)-phenyl)amino)pyrimidin-4-yl)oxy)naphthalen-1-yl)ureido)-N-(2-(2-(2-methoxyethoxy)ethoxy)-ethyl)benzamide

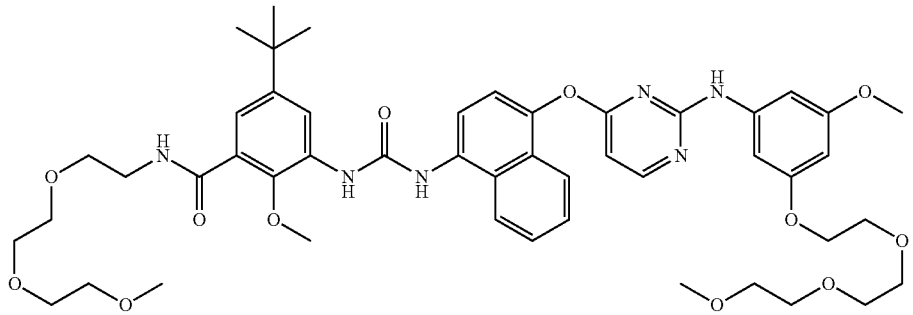 [SMILES: COCCOCCOCCNC(=O)c1cc(C(C)(C)C)cc(NC(=O)Nc2ccc(Oc3ccnc(Nc4cc(OC)cc(OCCOCCOCCOC)c4)n3)c3ccccc23)c1OC]

(i) 3-Amino-5-(tert-butyl)-2-methoxybenzoic acid

5% Pd—C (50 mg) was added to a solution of 5-(tert-butyl)-2-methoxy-3-nitrobenzoic acid (450 mg, 1.777 mmol) in EtOH (3 mL) and acetic acid (2 drops). The reaction was stirred under hydrogen (5 bar) for 2 h. The catalyst was filtered off and the solvent evaporated to give the sub-title compound (380 mg) as a dark brown foam.
LCMS m/z 224 (M+H)+ (ES+)

(ii) 5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)benzoic Acid TEA (30 µL, 0.215 mmol) was added to a solution of phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 1(vi) above; 100 mg, 0.156 mmol) and the product from step (i) above (50 mg, 0.168 mmol) in THF (5 mL) and the reaction heated at 50° C. (block temperature) for 16 h. The solvent was evaporated and the crude product was purified by chromatography on silica gel (40 g column, 5% MeOH:DCM to 10%). This product was purified by preparative HPLC (Varian, Basic (0.1% Ammonium Bicarbonate), Waters X-Bridge Prep-C18, 5 µm, 19×50 mm column, 25-55% MeCN in Water) to afford the sub-title compound (25 mg) as a pale yellow solid.
$^1$H NMR (400 MHz, DMSO-d$_6$) δ 9.52 (s, 1H), 9.42 (s, 1H), 8.97 (s, 1H), 8.48 (d, 1H), 8.41 (d, 1H), 8.30 (d, 1H), 8.08 (d, 1H), 7.85 (d, 1H), 7.72-7.63 (m, 1H), 7.63-7.51 (m, 1H), 7.42 (d, 1H), 7.26 (d, 1H), 6.92-6.70 (m, 2H), 6.55 (d, 1H), 6.04 (t, 1H), 3.86 (s, 5H), 3.72-3.62 (m, 2H), 3.57-3.45 (m, 9H), 3.44-3.35 (m, 2H), 3.21 (s, 3H), 1.28 (s, 9H). LCMS m/z 770 (M+H)+ (ES+)

(iii) 5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)-N-(2-(2-(2-methoxyethoxy)-ethoxy)ethyl)benzamide A stirred mixture of the product from step (ii) above (70 mg, 0.091 mmol), 2-(2-(2-methoxyethoxy)ethoxy)ethanamine (30 mg, 0.184 mmol) and triethylamine (38.0 µL, 0.273 mmol) in DCM (4 mL) was cooled in an ice-bath. 50 wt % T3P in EtOAc (80 µL, 0.134 mmol) was added, the ice-bath was removed and the reaction mixture allowed to warm to rt and stirred at this temperature for 2 h. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford the title compound (41 mg) as a white solid.
$^1$H NMR (400 MHz, DMSO-d$_6$) δ: 9.44 (s, 1H), 9.43 (s, 1H), 8.93 (s, 1H), 8.47 (d, 1H), 8.42 (d, 1H), 8.27-8.31 (m, 2H), 8.09 (d, 1H), 7.85 (d, 1H), 7.68 (t, 1H), 7.59 (t, 1H), 7.42 (d, 1H), 7.20 (d, 1H), 6.81 (d, 2H), 6.55 (d, 1H), 6.03 (t, 1H), 3.86-3.88 (m, 2H), 3.81 (s, 3H), 3.65-3.67 (m, 2H), 3.47-3.61 (m, 16H), 3.51 (s, 3H), 3.39-3.45 (m, 4H), 3.24 (s, 3H), 3.21 (s, 3H), 1.29 (s, 9H). LCMS m/z 458 (M+2H)$^{2+}$ (ES+)

Example 8

5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)-N-(2-morpholinoethyl)-benzamide

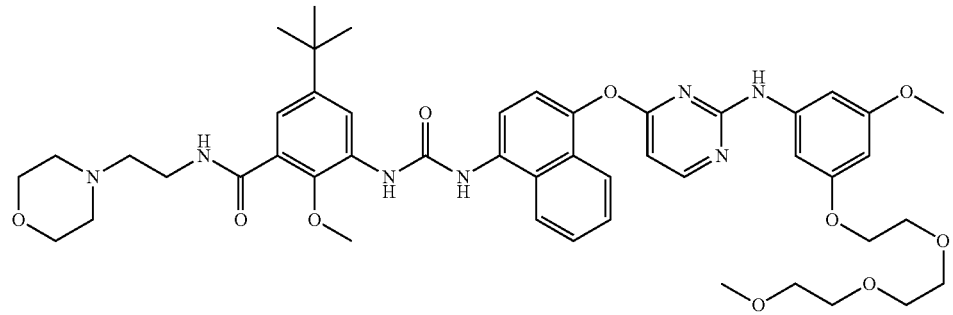 [SMILES: COCCOCCOCCOc1cc(Nc2nccc(Oc3ccc(NC(=O)Nc4cc(C(C)(C)C)cc(C(=O)NCCN5CCOCC5)c4OC)c4ccccc34)n2)cc(OC)c1]

A stirred mixture of 5-(tert-butyl)-2-methoxy-3-(3-(4-((2-((3-methoxy-5-(2-(2-(2-methoxy ethoxy)ethoxy)ethoxy)phenyl)amino)pyrimidin-4-yl)oxy)naphthalen-1-yl)ureido)benzoic acid (see Example 7(ii) above; 60 mg, 0.078 mmol), 2-morpholinoethanamine (20 µL, 0.152 mmol) and triethylamine (35 µL, 0.251 mmol) in DCM (4 mL) was cooled in an ice-bath. 50 wt % T3P in EtOAc (70 µL, 0.118 mmol) was added, the ice-bath was removed and the reaction mixture allowed to warm to rt and stirred at this temperature for 2 h. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford the title compound (41 mg) as an off-white solid.

$^1$H NMR (400 MHz, DMSO-d$_6$) δ: 9.43 (s, 1H), 9.42 (s, 1H), 8.92 (s, 1H), 8.47 (d, 1H), 8.42 (d, 1H), 8.23-8.29 (m, 2H), 8.09 (d, 1H), 7.86 (d, 1H), 7.69 (t, 1H), 7.60 (t, 1H), 7.42 (d, 1H), 7.25 (d, 1H), 6.82 (d, 2H), 6.55 (d, 1H), 6.04 (t, 1H), 3.86-3.88 (m, 2H), 3.84 (s, 3H), 3.65-3.67 (m, 2H), 3.62 (t, 4H), 3.48-3.55 (m, 6H), 3.52 (s, 3H), 3.39-3.45 (m, 4H), 3.22 (s, 3H), 2.51-2.54 (m, 2H), 2.46 (bs, 4H), 1.29 (s, 9H). LCMS m/z 442 (M+2H)2+ (ES$^+$)

Example 9

1-(5-(tert-Butyl)-2-methoxy-3-(methylsulfonyl)phenyl)-3-(4-((2-((3-methoxy-5-(2-(2-(2-methoxyethoxy)ethoxy)ethoxy)phenyl)amino)pyridin-4-yl)oxy)naphthalen-1-yl)urea

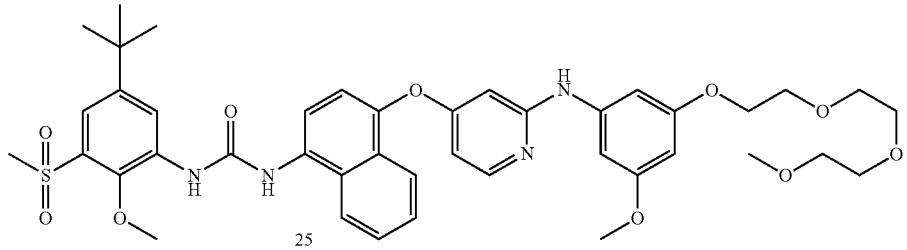

(i) Phenyl (5-(tert-butyl)-2-methoxy-3-(methylsulfonyl)phenyl)carbamate

Phenyl chloroformate (0.5 mL, 3.98 mmol) was added to a stirred suspension of 5-(tert-butyl)-2-methoxy-3-(methylsulfonyl)aniline (see, for example, Wagner, H. et al., WO 2010/026095, 11 Mar. 2010; 1.0 g, 3.89 mmol) and NaHCO$_3$ (700 mg, 8.33 mmol) in THF (10 mL) and DCM (10 mL). The resulting mixture was stirred at rt for 1.5 h. The mixture was diluted with water (40 mL) and DCM (40 mL). The organic phase was separated, washed with saturated brine (50 mL), dried (MgSO$_4$) and concentrated under reduced pressure. The residue was recrystallised in cyclohexane to yield the sub-title compound (1.45 g) as colourless needles. LCMS m/z 378 (M+H)$^+$ (ES$^+$)

(ii) 1-(5-(tert-Butyl)-2-methoxy-3-(methylsulfonyl)phenyl)-3-(4-((2-((3-methoxy-5-(2-(2-(2-methoxyethoxy)ethoxy)ethoxy)phenyl)amino)pyridin-4-yl)oxy)naphthalen-1-yl)urea A solution of the product from step (i) above (125 mg, 0.331 mmol), 4-((4-aminonaphthalen-1-yl)oxy)-N-(3-methoxy-5-(2-(2-(2-methoxyethoxy)ethoxy)ethoxy)-phenyl)pyridin-2-amine (see Example 2(iv) above; 150 mg, 0.289 mmol) and Et$_3$N (20 µL, 0.143 mmol) in isopropyl acetate (5 mL) were heated to 60° C. (block temperature) for 18 h. The mixture was diluted with ethyl acetate (50 mL) and washed with saturated NaHCO$_3$ solution (50 mL) and saturated brine (50 mL). The organic phase was dried (MgSO$_4$), filtered and concentrated. The crude product was purified by chromatography on the Companion (40 g column, EtOAc) to afford a gummy solid. The solid was dissolved in isopropyl acetate (2 mL) then diluted with tert-butyl methyl ether (8 mL) and stirred overnight. The resulting precipitate was collected by filtration to yield the title compound (48 mg) as a white solid.

$^1$H NMR (400 MHz, DMSO-d$_6$) δ: 9.48 (s, 1H), 9.11 (s, 1H), 8.89 (s, 1H), 8.68 (d, 1H), 8.29 (d, 1H), 8.16-8.06 (m, 2H), 7.88 (d, 1H), 7.72 (ddd, 1H), 7.62 (ddd, 1H), 7.44 (d, 1H), 7.41 (d, 1H), 6.91 (s, 1H), 6.78 (s, 1H), 6.58 (dd, 1H), 6.12-5.99 (m, 2H), 4.03-3.94 (m, 2H), 3.95 (s, 3H), 3.75-3.67 (m, 2H), 3.65 (s, 3H), 3.60-3.46 (m, 6H), 3.45-3.39 (m, 2H), 3H under water peak, 3.22 (s, 3H), 1.31 (s, 9H). LCMS m/z 803 (M+H)$^+$ (ES$^+$); 801 (M−H)$^−$ (ES$^−$)

Example 10

1-(3-(tert-Butyl)-5-(dimethylphosphoryl)phenyl)-3-(4-((2-((3-methoxy-5-(2-(2-(2-methoxy-ethoxy)ethoxy)ethoxy)phenyl)amino)pyridin-4-yl)oxy)naphthalen-1-yl)urea

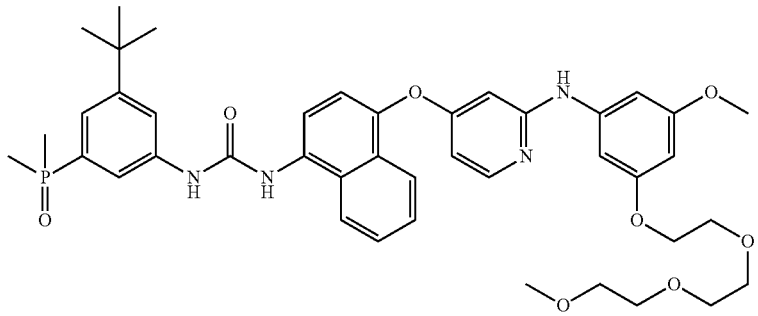 [SMILES: COCCOCCOCCOc1cc(Nc2cc(Oc3ccc(NC(=O)Nc4cc(C(C)(C)C)cc(P(C)(C)=O)c4)c4ccccc34)ccn2)cc(OC)c1]

(i) (5-(tert-butyl)-1,3-phenylene)dicarbamate

To a stirred solution of 5-(tert-butyl)isophthalic acid (1.0 g, 4.50 mmol) and triethylamine (1.38 mL, 9.90 mmol) in dioxane (15 mL) and tBuOH (10 mL, 105 mmol) under $N_2$ at 0° C. was added DPPA (2.15 mL, 9.98 mmol). The mixture was stirred at rt for 10 minutes then heated to 80° C. for 4 h. The reaction was cooled to rt and diluted with EtOAc (100 mL). The organic phase was washed with 1M HCl aq. (50 mL), water (50 mL), sat. $NaHCO_3$ aq. (50 mL) and brine (50 mL), then dried ($MgSO_4$), filtered and concentrated in vacuo onto silica gel. The crude product was purified by chromatography on the Companion (40 g column, 0-15% EtOAc in hexane) to afford the sub-title compound (1.01 g) as a white solid.

$^1$H NMR (400 MHz, DMSO-$d_6$) δ: 9.14 (s, 2H), 7.54 (s, 1H), 7.08 (d, 2H), 1.47 (s, 18H), 1.21 (s, 9H). LCMS m/z 253 (M+H−2×tBu)$^+$ (ES$^+$)

(ii) tert-Butyl (3-amino-5-(tert-butyl)phenyl)carbamate, HCl

2M HCl in $Et_2O$ (100 mL, 200 mmol) was added dropwise to the product from step (i) above (8 g, 21.95 mmol) in ether (100 mL) and the reaction mixture stirred for 16 h. The precipitate was filtered off and washed with diethyl ether to give the sub-title compound (2 g).

$^1$H NMR (400 MHz, DMSO-$d_6$) δ: 10.11 (s, 3H), 9.58 (s, 1H), 7.48 (s, 1H), 7.46 (d, 1H), 7.01 (t, 1H), 1.48 (s, 9H), 1.25 (s, 9H).

(iii) tert-Butyl (3-bromo-5-(tert-butyl)phenyl)carbamate

A solution of the product from step (ii) above (100 mg, 0.378 mmol) free base (free based by partitioning between aq. sat. $NaHCO_3$ and DCM) in MeCN (1 mL) was added dropwise to a solution of copper(I) bromide (80 mg, 0.558 mmol) and isoamyl nitrite (150 μL, 1.114 mmol) in MeCN (2 mL) at 0° C. and the mixture allowed to warm to rt and stirred overnight. The reaction mixture was partitioned between EtOAc (10 mL) and water (10 mL). The organics were separated, dried ($MgSO_4$), filtered, and the solvents evaporated to a dark brown gum. The crude product was purified by chromatography on silica gel (12 g column, 0% EtOAc:isohexane to 20%) to afford the sub-title compound (35 mg) as a yellow solid.

$^1$H NMR (400 MHz, DMSO-$d_6$) δ: 9.45 (s, 1H), 7.58 (s, 1H), 7.45 (t, 1H), 7.13 (t, 1H), 1.48 (s, 9H), 1.24 (s, 9H).

(iv) 3-Bromo-5-(tert-butyl)aniline

TFA (500 μL, 6.49 mmol) was added to a solution of the product from step (iii) above (100 mg, 0.305 mmol) in DCM (3 mL) and the reaction mixture stirred for 2 h. The solvents were evaporated and the residue was partitioned between sat. $NaHCO_3$ soln. (3 mL) and DCM (5 mL) The organics were separated, dried ($MgSO_4$), filtered and solvent evaporated to give the sub-title compound (70 mg) as a brown gum.

LCMS m/z 228/230 (M+H)$^+$ (ES$^+$)

(v) (3-Amino-5-(tert-butyl)phenyl)dimethylphosphine oxide

Dimethylphosphine oxide (50 μL, 0.794 mmol) was added to a degassed suspension of the product from step (iv) above (65 mg, 0.285 mmol), palladium(II) acetate (2 mg, 8.91 μmol), xantphos (10 mg, 0.017 mmol) and potassium phosphate tribasic (150 mg, 0.707 mmol) in DMF (2 mL) under nitrogen and the mixture was heated in a microwave reactor (CEM, 150° C., 200 W) for 1 h. The mixture was filtered and the filtrate evaporated to a dark gum. The crude product was purified by chromatography on silica gel (12 g column, 5% MeOH:DCM to 10%) to afford the sub-title compound (60 mg) as a dark brown gum.

$^1$H NMR (400 MHz, DMSO-$d_6$) δ 6.87 (dt, 1H), 6.79-6.70 (m, 2H), 5.20 (s, 2H), 1.56 (d, 6H), 1.25 (s, 9H). LCMS m/z 226 (M+H)$^+$ (ES$^+$)

(vi) Phenyl (3-(tert-butyl)-5-(dimethylphosphoryl)phenyl)carbamate

Phenyl chloroformate (55 μL, 0.438 mmol) was added to a stirred solution of the product from step (v) above (60 mg, 0.266 mmol) and $NaHCO_3$ (90 mg, 1.071 mmol) in THF (1 mL) and DCM (1 mL). The reaction mixture was stirred for 1 h then filtered and the filtrate evaporated to a brown solid which was stirred in cyclohexane for 1 h. The solid was filtered off and dried to give the sub-title compound (100 mg) as a beige solid.

¹H NMR (400 MHz, CDCl₃) δ: 8.52 (s, 1H), 7.89 (s, 1H), 7.84 (d, 1H), 7.50-7.38 (m, 3H), 7.29-7.24 (m, 1H), 7.23-7.14 (m, 2H), 1.79 (d, 6H), 1.35 (s, 9H).

(vii) 1-(3-(tert-Butyl)-5-(dimethylphosphoryl)phenyl)-3-(4-((2-((3-methoxy-5-(2-(2-(2-methoxyethoxy)ethoxy)ethoxy)phenyl)amino)pyridin-4-yl)oxy)naphthalen-1-yl)urea Triethylamine (10 μL, 0.072 mmol) was added to a solution of the product from step (vi) above (100 mg, 0.290 mmol) and 4-((4-aminonaphthalen-1-yl)oxy)-N-(3-methoxy-5-(2-(2-(2-methoxyethoxy)ethoxy)ethoxy)phenyl)pyridin-2-amine (see Example 2(iv) above; 150 mg, 0.290 mmol) in THF (3 mL) at 60° C. (block temperature) and the mixture stirred for 16 h. The solvent was evaporated under reduced pressure and the residue purified by chromatography on silica gel (40 g column, 0-6% MeOH/DCM) to give a foam at ~93% purity. The crude product was purified by preparative HPLC (Varian, Basic (0.1% Ammonium Bicarbonate), Basic, Waters X-Bridge Prep-C18, 5 μm, 19×50 mm column, 40-80% MeCN in Water) to give a foam that was triturated with ether and filtered to afford the title compound (42 mg) as a solid.

¹H NMR (DMSO-d₆) 400 MHz, δ: 9.25 (s, 1H), 8.89 (s, 1H), 8.87 (s, 1H), 8.21 (d, 1H), 8.11 (d, 1H), 8.05 (d, 1H), 7.87 (d, 1H), 7.75-7.68 (m, 3H), 7.61 (dd, 1H), 7.42-7.38 (m, 2H), 6.91 (s, 1H), 6.79 (s, 1H), 6.58 (dd, 1H), 6.08 (d, 1H), 6.04 (s, 1H), 3.98 (t, 2H), 3.71 (t, 2H), 3.65 (s, 3H), 3.58-3.41 (m, 8H), 3.23 (s, 3H), 1.66 (d, 6H), 1.33 (s, 9H). LCMS m/z 771 (M+H)⁺ (ES⁺)

Example 11

1-(5-(tert-Butyl)-3-(dimethylphosphoryl)-2-methoxyphenyl)-3-(4-((2-(phenylamino)pyridin-4-yl)oxy)naphthalen-1-yl)urea

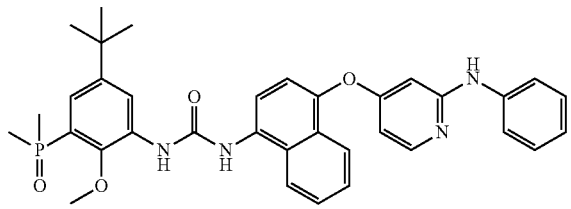 [SMILES: COc1c(NC(=O)Nc2ccc(Oc3ccnc(Nc4ccccc4)c3)c3ccccc23)cc(C(C)(C)C)cc1P(C)(C)=O]

(i) tert-Butyl (4-((2-(phenylamino)pyridin-4-yl)oxy)naphthalen-1-yl)carbamate

Nitrogen was bubbled through a mixture of aniline (1.1 g, 11.81 mmol), tert-butyl (4-((2-chloropyridin-4-yl)oxy)naphthalen-1-yl)carbamate (see Example 2(ii) above; 4 g, 10.79 mmol), 2,2'-bis(diphenylphosphino)-1,1'-binaphthalene (0.441 g, 0.709 mmol), Pd₂dba₃ (0.324 g, 0.354 mmol) and cesium carbonate (6.16 g, 18.90 mmol) in dioxane (50 mL) for 5 min then the mixture heated at 100° C. for 3 h. The mixture was diluted with EtOAc (200 mL), filtered and the solvent evaporated under reduced pressure. Ether (20 mL) was added and the white solid filtered off, washed with ether (5 mL) and dried to afford the product (3.33 g) as a white solid. The filtrate was purified by chromatography on silica gel (220 g column, 0-50% EtOAc/isohexane) to give a solid that was triturated with ether, filtered and dried to afford additional product (608 mg) as a white solid. Materials was combined to afford the sub-title compound (3.938 g) as a white solid.

¹H NMR (400 MHz, CDCl₃) δ: 8.02 (d, 1H), 7.97 (dd, 2H), 7.87 (brd, 1H), 7.63-7.51 (m, 2H), 7.21 (d, 1H), 7.07-7.02 (m, 1H), 6.86 (brs, 2H), 6.41 (d, 1H), 6.34 (dd, 1H), 1.59 (s, 9H). Peaks under CHCl₃. LCMS m/z 428 (M+H)⁺ (ES⁺); 426 (M-H)⁻ (ES⁻)

(ii) 4-((4-Aminonaphthalen-1-yl)oxy)-N-phenylpyridin-2-amine

TFA (10 mL, 130 mmol) was added to a solution of the product from step (ii) above (3.9 g, 9.12 mmol) in DCM (50 mL) and stirred at rt for 1 h. The volatiles were removed under reduced pressure and the residue was redissolved in DCM (75 mL). The solution was washed with saturated NaHCO₃ solution (50 mL) followed by saturated brine (50 mL) and dried (MgSO₄). The drying agent was removed by filtration and the filtrate was concentrated under reduced pressure to yield a pale pink solid. The solid was recrystallised in iPrOAc (60 mL) to yield the sub-title compound (1.1 g) as a white solid. The filtrate was concentrated under reduced pressure and redissolved in refluxing iPrOAc (60 mL). Isohexane (60 mL) was added and the mixture was allowed to cool whilst stirring. The 2nd crop was collected by filtration to yield the sub-title compound (1.2 g) as a pale pink solid. Combined yield of 2.3 g.

¹H NMR (400 MHz, DMSO-d₆) δ: 8.82 (s, 1H), 8.20-8.11 (m, 1H), 8.02 (d, 1H), 7.69-7.61 (m, 1H), 7.61-7.54 (m, 2H), 7.49-7.40 (m, 2H), 7.22-7.14 (m, 2H), 7.10 (d, 1H), 6.82 (ddd, 1H), 6.71 (d, 1H), 6.49 (dd, 1H), 6.02 (d, 1H), 5.81 (br s, 2H). LCMS m/z 328 (M+H)⁺ (ES⁺)

(iii) 1-(5-(tert-Butyl)-3-(dimethylphosphoryl)-2-methoxyphenyl)-3-(4-((2-(phenylamino)-pyridin-4-yl)oxy)naphthalen-1-yl)urea A mixture of the product from step (iii) above (70 mg, 0.214 mmol), phenyl (5-(tert-butyl)-3-(dimethylphosphoryl)-2-methoxyphenyl)carbamate (see Example 3(vi) above; 70 mg, 0.186 mmol) and Et₃N (10 μL, 0.072 mmol) in iPrOAc (6 mL) was heated at 60° C. for 2 h, THF (3 mL) was added and heated for a further 24 h. The mixture was cooled, filtered and washed with MeCN (3 mL) then ether (2 mL). The solid was dissolved in DCM (3 mL), MeCN (1 mL) added, and the DCM evaporated off to give a solid that was filtered, washed with MeCN (1 mL) and dried to afford the title compound (45 mg) as a solid.

¹H NMR (DMSO-d₆) 400 MHz, δ: 9.35 (s, 1H), 8.91 (s, 2H), 8.45 (s, 1H), 8.29 (d, 1H), 8.13 (d, 1H), 8.08 (d, 1H), 7.89 (d, 1H), 7.71 (t, 1H), 7.64-7.59 (m, 3H), 7.41-7.35 (dd, 2H), 7.22-7.18 (dd, 2H), 6.84 (dd, 1H), 6.56 (d, 1H), 6.10 (s, 1H), 3.90 (s, 3H), 1.75 (d, 6H), 1.31 (s, 9H). LCMS m/z 609 (M+H)⁺ (ES⁺); 607 (M-H)⁻ (ES⁻)

Example 12

1-(5-(tert-Butyl)-2-methoxy-3-(methylsulfinyl)phenyl)-3-(4-((2-(phenylamino)pyridin-4-yl)oxy)naphthalen-1-yl)urea

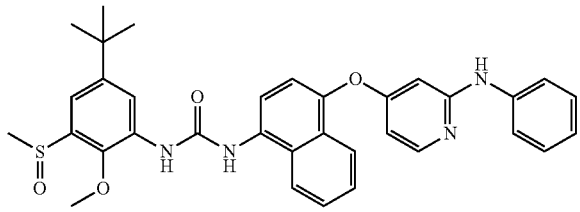 [SMILES: COc1c(NC(=O)Nc2ccc(Oc3ccnc(Nc4ccccc4)c3)c3ccccc23)cc(C(C)(C)C)cc1S(C)=O]

(i) (5-(tert-Butyl)-2-methoxy-3-nitrophenyl)(methyl)sulfane

Isoamyl nitrite (0.901 mL, 6.69 mmol) and 1,2-dimethyldisulfane (0.6 mL, 6.75 mmol) were added sequentially to a stirred solution of 5-(tert-butyl)-2-methoxy-3-nitroaniline (0.5 g, 2.230 mmol) in acetonitrile (30 mL). The mixture was heated to reflux in a vessel fitted with a condenser and bleach scrubber (dreschel bottle) for 2 h. The mixture was concentrated under reduced pressure then co-evaporated with toluene (2×100 mL). The residue was re-dissolved in diethyl ether (100 mL) and washed with water (100 mL), followed by saturated NaHCO$_3$ solution (100 mL) and saturated brine (100 mL). The organic phase was dried (MgSO$_4$), filtered and the filtrate was concentrated under reduced pressure affording the sub-title compound which was used crude in the next step without further purification.

(ii) 5-(tert-Butyl)-2-methoxy-1-(methylsulfinyl)-3-nitrobenzene m-CPBA (0.55 g, 2.390 mmol) was added portionwise to an ice-cooled solution of the product from step (i) above (0.57 g, 2.232 mmol) in DCM (10 mL). The mixture was allowed to warm to rt and stir for 1.5 h. The mixture was added slowly to a 25% solution of sodium sulfite (20 mL) and stirred for 5 minutes. The organic layer was separated and washed with saturated NaHCO$_3$ solution (2×20 mL) and saturated brine (20 mL). The organic layer was dried (MgSO$_4$) and filtered and the filtrate was concentrated onto loose silica. The silicate was purified by chromatography on the Companion (40 g column, EtOAc/CH$_2$Cl$_2$) to afford the sub-title compound (170 mg) as an orange oil.
$^1$H NMR (400 MHz, CDCl$_3$) δ: 8.15 (d, 1H), 8.02 (d, 1H), 3.98 (s, 3H), 2.87 (s, 3H), 1.41 (s, 9H). LCMS m/z 272 (M+H)$^+$ (ES$^+$)

(iii) 5-(tert-Butyl)-2-methoxy-3-(methylsulfinyl)aniline

The product from step (ii) above (170 mg, 0.627 mmol), iron powder (350 mg, 6.27 mmol) and ammonium chloride (35 mg, 0.654 mmol) were heated to reflux in ethanol (4 mL) and water (1 mL) for 1 h. The mixture was filtered through Celite and the filtrate was concentrated under reduced pressure to yield the crude product. The crude product was purified by chromatography on the Companion (40 g column, 75-100% EtOAc/isohexane) to afford the sub-title compound (118 mg) as an orange oil.
$^1$H NMR (400 MHz, CDCl$_3$) δ: 7.29 (d, 1H), 6.96 (d, 1H), 3.81 (s, 3H), 2.76 (s, 3H), 1.29 (s, 9H). LCMS m/z 242 (M+H)$^+$ (ES$^+$)

(iv) Phenyl (5-(tert-butyl)-2-methoxy-3-(methylsulfinyl)phenyl)carbamate

Phenyl chloroformate (70 µL, 0.558 mmol) was added to a stirred suspension of the product from step (iii) above (118 mg, 0.489 mmol) and NaHCO$_3$ (80 mg, 0.952 mmol) in THF (1 mL) and DCM (1 mL) and stirred at it for 18 h. The mixture was diluted with DCM (30 mL) then washed with water (30 mL) and saturated brine (30 mL). The organic phase was dried (MgSO$_4$) then concentrated to yield a solid. The solid was triturated in diethyl ether (50 mL) to yield the sub-title compound (144 mg) as a beige solid.
$^1$H NMR (400 MHz, CDCl$_3$) δ: 8.38 (br s, 1H), 7.61 (d, 1H), 7.48-7.36 (m, 3H), 7.33-7.20 (m, 3H), 3.93 (s, 3H), 2.83 (s, 3H), 1.36 (s, 9H).

(v) 1-(5-(tert-Butyl)-2-methoxy-3-(methylsulfinyl)phenyl)-3-(4-((2-(phenylamino)pyridin-4-yl)oxy)naphthalen-1-yl)urea The product from step (iv) above (35 mg, 0.097 mmol), 4-((4-aminonaphthalen-1-yl)oxy)-N-phenylpyridin-2-amine (see Example 11(ii) above; 31.7 mg, 0.097 mmol) and triethylamine (4 µL, 0.029 mmol) were heated to 60° C. in THF (2 mL) for 18 h. The mixture was concentrated under reduced pressure to remove volatile components then re-dissolved in DCM (10 mL). 1 M sodium carbonate solution (5 mL) was added then the whole was passed through a phase separation cartridge and concentrated under reduced pressure. The crude product was purified by chromatography on the Companion (12 g column, 1.5-5% MeOH/CH$_2$Cl$_2$) to afford a foam. The foam was recrystallised by dissolving in MeCN (5 mL), then adding water (4 mL) and leaving in an open vial over the weekend to yield the title compound (28 mg) as a white crystalline solid.
$^1$H NMR (400 MHz, DMSO-d$_6$) δ: 9.43 (s, 1H), 8.97 (s, 1H), 8.91 (s, 1H), 8.51 (d, 1H), 8.28 (d, 1H), 8.10 (d, 1H), 8.09 (d, 1H), 7.88 (d, 1H), 7.72 (ddd, 1H), 7.62 (ddd, 1H), 7.62-7.56 (m, 2H), 7.40 (d, 1H), 7.36 (d, 1H), 7.24-7.15 (m, 2H), 6.88-6.80 (m, 1H), 6.55 (dd, 1H), 6.10 (d, 1H), 3.86 (s, 3H), 2.79 (s, 3H), 1.32 (s, 9H). LCMS m/z 595 (M+H)$^+$ (ES$^+$); 593 (M−H)$^-$ (ES$^-$)

Example 13

2-(5-(tert-Butyl)-2-methoxy-3-(3-(4-((2-(phenylamino)pyridin-4-yl)oxy)naphthalen-1-yl)ureido)phenyl)acetamide

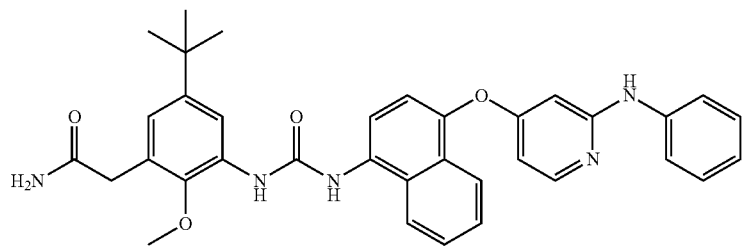 [SMILES: COc1c(CC(N)=O)cc(C(C)(C)C)cc1NC(=O)Nc1ccc(Oc2ccnc(Nc3ccccc3)c2)c2ccccc12]

(i) (5-(tert-Butyl)-2-methoxy-3-nitrophenyl)methanol 2.0 M Lithium borohydride in THF (6.0 mL, 12.00 mmol) was added to an ice-cooled solution of methyl 5-(tert-butyl)-2-methoxy-3-nitrobenzoate (3.2 g, 11.97 mmol) in diethyl ether (20 mL). The mixture was stirred at 0° C. for 15 minutes then allowed to warm to rt and stir for 18 h. The mixture was diluted with diethyl ether (80 mL) then treated slowly with 1 M hydrogen chloride solution (80 mL). Once effervescence had ceased the organic phase was separated off, washed with saturated brine (10 mL), dried (MgSO$_4$) and concentrated under reduced pressure to yield the sub-title compound (3.0 g).

$^1$H NMR (CDCl$_3$) 400 MHz, δ:7.80 (d, 1H), 7.71 (d, 1H), 4.82 (s, 2H), 3.95 (s, 3H), 1.37 (s, 9H). LCMS m/z 222 (M-OH)$^+$ (ES$^+$)

(ii) 5-(tert-Butyl)-1-(chloromethyl)-2-methoxy-3-nitrobenzene

Thionyl chloride (191 µL, 2.61 mmol) was added carefully to a solution of the product from step (i) above (500 mg, 2.090 mmol) in DCM (8 mL) at rt. The mixture was stirred for 18 h at rt. diluted with toluene (200 mL) and concentrated under reduced pressure. The residue was purified by chromatography on the Companion (12 g column, 50% CH$_2$Cl$_2$/isohexane) to afford the sub-title compound (570 mg) as a yellow oil which crystallised on standing.

$^1$H NMR (CDCl$_3$) 400 MHz, δ: 7.84 (d, 1H), 7.69 (d, 1H), 4.70 (s, 2H), 4.00 (s, 3H), 1.37 (s, 9H).

(iii) 2-(5-(tert-Butyl)-2-methoxy-3-nitrophenyl)acetonitrile

A solution of the product from step (ii) above (320 mg, 1.242 mmol) in DMSO (2 mL) was added to a stirred solution of sodium cyanide (60.9 mg, 1.242 mmol) in DMSO (3 mL) at rt and stirred for 18 h. The mixture was diluted with water (20 mL) and extracted with ethyl acetate (25 mL). The organic phase was dried and concentrated under reduced pressure. The residue was recrystallised in cyclohexane to yield the sub-title compound (200 mg) as a yellow solid.

$^1$H NMR (CDCl$_3$) 400 MHz, δ: 7.86 (d, 1H), 7.68 (d, 1H), 3.96 (s, 3H), 3.83 (s, 2H), 1.37 (s, 9H).

(iv) 2-(5-(tert-Butyl)-2-methoxy-3-nitrophenyl)acetamide

The product from step (iii) above (490 mg, 1.974 mmol) was stirred in concentrated hydrogen chloride (5 mL) at 40° C. for 24 h. The mixture was diluted with ice-water (100 mL) and extracted with diethyl ether (50 mL). The organic phase was washed with 1 M sodium carbonate solution (2×50 mL), saturated brine (50 mL) and dried (MgSO$_4$). The solvent was removed under reduced pressure to yield the sub-title compound (368 mg) as an oil which crystallised on standing.

$^1$H NMR (CDCl$_3$) 400 MHz, δ: 7.80 (d, 1H), 7.57 (d, 1H), 5.83 (br s, 1H), 5.48 (br s, 1H), 3.93 (s, 3H), 3.67 (s, 2H), 1.35 (s, 9H). LCMS m/z 267 (M+H)$^+$ (ES$^+$)

(v) 2-(3-Amino-5-(tert-butyl)-2-methoxyphenyl)acetamide

A suspension of the product from step (iv) above (368 mg, 1.382 mmol) and 10% palladium on carbon (50% paste with water) (40 mg) in ethanol (10 mL) was stirred under a balloon of hydrogen at rt for 66 h. Additional 10% palladium on carbon (50% paste with water) (120 mg) was added and the mixture was stirred for a further 18 h. The catalyst was removed by filtration and the filtrate was concentrated under reduced pressure to yield the sub-title compound (310 mg) as a cream solid.

LCMS m/z 237 (M+H)$^+$ (ES$^+$)

(vi) Phenyl (3-(2-amino-2-oxoethyl)-5-(tert-butyl)-2-methoxyphenyl)carbamate Phenyl chloroformate (175 µL, 1.395 mmol) was added to a stirred suspension of the product from step (v) above (310 mg, 1.312 mmol) and NaHCO$_3$ (225 mg, 2.68 mmol) in THF (4 mL) and DCM (4 mL). The mixture was stirred at it for 1.5 h. The mixture was diluted with DCM (15 mL) then washed with water (10 mL) followed by saturated brine (20 mL). The organic phase was dried (MgSO$_4$) and concentrated to yield a sticky solid. The solid was triturated in diethyl ether to yield the sub-title compound (380 mg) as a white solid.

LCMS m/z 357 (M+H)$^+$ (ES$^+$)

(vii) 2-(5-(tert-Butyl)-2-methoxy-3-(3-(4-((2-(phenylamino)pyridin-4-yl)oxy)naphthalen-1-yl)ureido)phenyl)acetamide The product from step (vi) above (149 mg, 0.418 mmol), 4-((4-aminonaphthalen-1-yl)oxy)-N-phenylpyridin-2-amine (see Example 11(ii) above; 137 mg, 0.418 mmol) and triethylamine (20 µL, 0.143 mmol) were heated to 60° C. (block temp) in THF (3 mL) for 18 h. The mixture was concentrated under reduced pressure and the residue was purified by preparative HPLC (Gilson, Acidic (0.1% Formic acid), Acidic, Waters X-Select Prep-C18, 5 µm, 19×50 mm column, 5-95% MeCN in Water) to afford a pink solid. The solid was redissolved in DCM (10 mL) and triethylamine (0.1 mL) added. The mixture was concentrated onto loose silica and the silicate was purified by chromatography on the Companion (12 g column, 2-8% MeOH/DCM) to afford the title compound (35 mg) as a white solid.

$^1$H NMR (DMSO-d$_6$) 400 MHz, δ: 9.40 (s, 1H), 8.92 (s, 1H), 8.80 (s, 1H), 8.30 (d, 1H), 8.21 (d, 1H), 8.12 (d, 1H), 8.08 (d, 1H), 7.87 (d, 1H), 7.71 (ddd, 1H), 7.61 (ddd, 1H), 7.62-7.56 (m, 2H), 7.47 (m, 1H), 7.39 (d, 1H), 7.24-7.15 (m, 2H), 6.97 (br s, 1H), 6.94 (d, 1H), 6.88-6.79 (m, 1H), 6.56 (dd, 1H), 6.08 (d, 1H), 3.77 (s, 3H), 3.45 (s, 2H), 1.27 (s, 9H).

LCMS m/z 590 (M+H)$^+$ (ES$^+$); 588 (M-H)$^-$ (ES$^-$)

Example 14

5-(tert-Butyl)-2-methoxy-N-(2-morpholinoethyl)-3-(3-(4-((2-(phenylamino)pyridin-4-yl)oxy)naphthalen-1-yl)ureido)benzamide

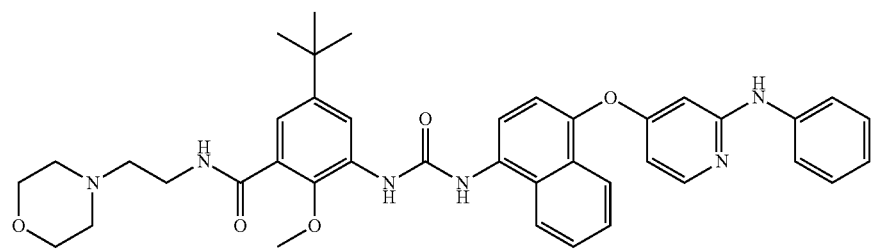 [SMILES: COc1c(NC(=O)Nc2ccc(Oc3ccnc(Nc4ccccc4)c3)c3ccccc23)cc(C(C)(C)C)cc1C(=O)NCCN1CCOCC1]

(i) Methyl 5-(tert-butyl)-2-methoxy-3-((phenoxycarbonyl)amino)benzoate

Phenyl chloroformate (264 µL, 2.107 mmol) was added to a stirred mixture of methyl 3-amino-5-(tert-butyl)-2-methoxybenzoate (500 mg, 2.107 mmol) and NaHCO₃ (354 mg, 4.21 mmol) in DCM (20 mL) and THF (5 mL) at rt. The mixture was stirred overnight then partitioned between DCM (20 mL) and water (20 mL). The organic layer was separated and dried via a hydrophobic frit, affording the sub-title compound (812 mg) as a pale yellow oil which solidified on standing. LCMS m/z 358 (M+H)⁺ (ES⁺)

(ii) Methyl 5-(tert-butyl)-2-methoxy-3-(3-(4-((2-(phenylamino)pyridin-4-yl)oxy)naphthalen-1-yl)ureido)benzoate Triethylamine (48 µL, 0.344 mmol) was added to a mixture of the product from step (i) above (610 mg, 1.707 mmol) and 4-((4-aminonaphthalen-1-yl)oxy)-N-phenylpyridin-2-amine (see Example 11(ii) above; 560 mg, 1.711 mmol) in iPrOAc (20 mL) and the mixture heated at 70° C. (block temperature) overnight. The reaction mixture was diluted with THF and concentrated in vacuo onto silica gel. The crude product was purified by chromatography on the Companion (40 g column, 0.5-3% MeOH in DCM) to afford the sub-title compound (688 mg) as a light brown foam.
LCMS m/z 591 (M+H)⁺ (ES⁺); 589 (M–H)⁻ (ES⁻)

(iii) 5-(tert-Butyl)-2-methoxy-3-(3-(4-((2-(phenylamino)pyridin-4-yl)oxy)naphthalen-1-yl)-ureido)benzoic acid, HCl To a stirred solution of the product from step (ii) above (688 mg, 1.165 mmol) in THF (25 mL) and water (5 mL) was added NaOH (2M aq.) (3500 µL, 7.00 mmol). MeOH (2 mL) was added and stirring continued for 48 h. Additional NaOH was added (1 mL) and stirring continued over a weekend. The reaction was concentrated in vacuo affording a brown gum. The material was suspended in water and acidified with 1M HCl causing a solid to precipitate. The solid was collected by filtration, washing with water and the solid dried at 40° C. under vacuum affording the sub-title compound (590 mg) as a pink solid.
LCMS m/z 577 (M+H)⁺ (ES⁺); 575 (M–H)⁻ (ES⁻)

(iv) 5-(tert-Butyl)-2-methoxy-N-(2-morpholinoethyl)-3-(3-(4-((2-(phenylamino)pyridin-4-yl)oxy)naphthalen-1-yl)ureido)benzamide A stirred mixture of the product from step (iii) above (80 mg, 0.130 mmol), 2-morpholinoethanamine (25.7 µL, 0.196 mmol) and Et₃N (54.6 µL, 0.391 mmol) in DCM (4 mL) was cooled in an ice-bath. T3P (50 wt % in EtOAc) (78 µL, 0.130 mmol) was added, the ice-bath was removed and the reaction mixture allowed to warm to rt and stirred overnight. Further portions of amine (15 µL), Et₃N (25 µL) and T3P (20 µL) were added and stirring continued overnight. The reaction mixture was partitioned between sat. aq. NaHCO₃ (10 mL) and DCM (10 mL). The aqueous phase was back extracted with fresh DCM (10 mL). The combined organic extracts were washed with water (20 mL), brine (20 mL), dried (MgSO₄), filtered and concentrated in vacuo onto silica gel. The crude product was purified by chromatography on the Companion (12 g column, 1-5% MeOH in DCM) to afford the title compound (66 mg) as a pink/brown solid.
¹H NMR (400 MHz, DMSO-d₆) δ: 9.45 (s, 1H), 8.91 (d, 2H), 8.47 (d, 1H), 8.30 (d, 1H), 8.25 (t, 1H), 8.08-8.10 (m, 2H), 7.89 (d, 1H), 7.72 (t, 1H), 7.58-7.64 (m, 3H), 7.39 (d, 1H), 7.25 (d, 1H), 7.20 (t, 2H), 6.84 (t, 1H), 6.55 (dd, 1H), 6.11 (d, 1H), 3.84 (s, 3H), 3.61-3.62 (m, 4H), 3.45 (q, 2H), 2.53-2.54 (m, 2H), 2.46 (bs, 4H), 1.29 (s, 9H). LCMS m/z 689 (M+H)⁺ (ES⁺); 687 (M–H)⁻ (ES⁻)

Example 15

The following compounds were prepared by methods analogous to those described herein (including above and/or the examples below). Where chemical shifts from ¹H NMR spectra are reported, these were obtained in DMSO-d₆ at 400 MHz and ambient temperature, unless otherwise specified.

(a) 1-(5-(tert-butyl)-2-methoxy-3-((methylsulfonyl)methyl)phenyl)-3-(4-((2-((3-methoxy-5-(2-(2-(2-methoxyethoxy)ethoxy)ethoxy)phenyl)amino)pyridin-4-yl)oxy)naphthalen-1-yl)urea

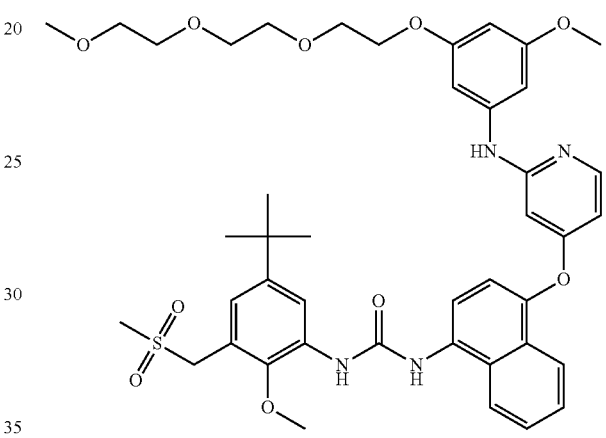

¹H NMR δ: 9.38 (s, 1H), 8.91 (s, 1H), 8.87 (s, 1H), 8.34 (d, 1H), 8.30 (d, 1H), 8.12 (d, 1H), 8.11 (d, 1H), 7.87 (d, 1H), 7.71 (ddd, 1H), 7.61 (ddd, 1H), 7.39 (d, 1H), 7.14 (d, 1H), 6.91 (dd, 1H), 6.78 (dd, 1H), 6.58 (dd, 1H), 6.08 (d, 1H), 6.04 (dd, 1H), 4.51 (s, 2H), 4.01-3.94 (m, 2H), 3.82 (s, 3H), 3.74-3.68 (m, 2H), 3.36 (s, 3H), 3.60-3.55 (m, 2H), 3.55-3.49 (m, 4H), 3.44-3.39 (m, 2H), 3.23 (s, 3H), 3.02 (s, 3H), 1.29 (s, 9H). LCMS m/z 817 (M+H)⁺ (ES⁺)

(b) 1-(5-(tert-butyl)-3-(dimethylphosphoryl)-2-methoxyphenyl)-3-(4-((2-(phenylamino)-pyrimidin-4-yl)oxy)naphthalen-1-yl)urea

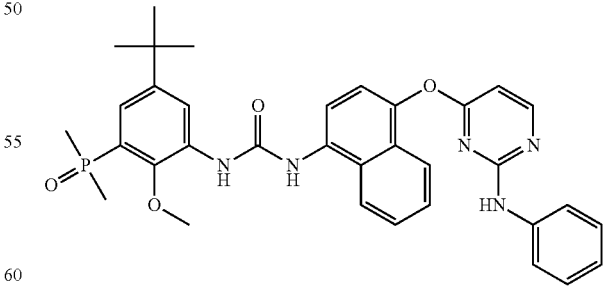

¹H NMR δ: 9.52 (s, 1H), 9.36 (s, 1H), 8.89 (s, 1H), 8.46 (d, 1H), 8.40 (d, 1H), 8.28 (d, 1H), 8.10 (d, 1H), 7.84 (d, 1H), 7.68 (dd, 1H), 7.58 (dd, 1H), 7.43 (d, 1H), 7.35 (dd, 1H), 7.28 (brd, 2H), 6.99 (dd, 2H), 6.77 (dd, 1H), 6.59 (d, 1H), 3.92 (s, 3H), 1.76 (d, 6H), 1.31 (s, 9H). LCMS m/z 610 (M+H)⁺ (ES⁺)

(c) 2-(5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)acetamide

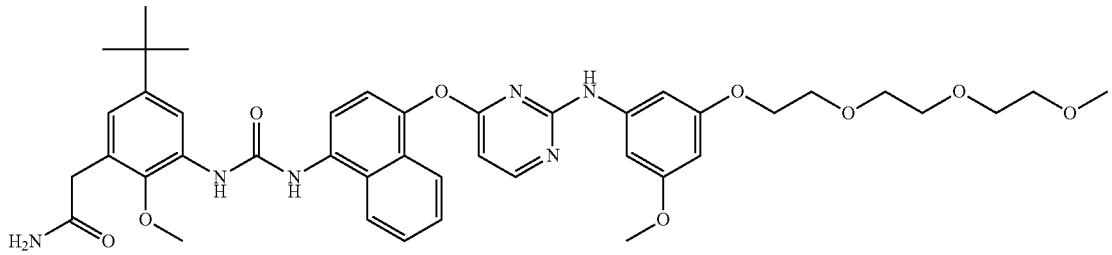 [SMILES: COCCOCCOCCOc1cc(Nc2nccc(Oc3ccc(NC(=O)Nc4cc(C(C)(C)C)cc(CC(N)=O)c4OC)c4ccccc34)n2)cc(OC)c1]

¹H NMR δ: 9.42 (s, 1H), 9.35 (s, 1H), 8.80 (s, 1H), 8.41 (d, 1H), 8.28 (d, 1H), 8.21 (d, 1H), 8.10 (d, 1H), 7.85 (d, 1H), 7.68 (ddd, 1H), 7.59 (ddd, 1H), 7.44 (br s, 1H), 7.41 (d, 1H), 6.99-6.90 (m, 2H), 6.87-6.75 (m, 2H), 6.55 (d, 1H), 6.04 (dd, 1H), 3.92-3.82 (m, 2H), 3.78 (s, 3H), 3.70-3.61 (m, 2H), 3.58-3.36 (m, 13H), 3.22 (s, 3H), 1.27 (s, 9H). LCMS m/z 783 (M+H)⁺ (ES⁺)

(d) 1-(5-(tert-butyl)-3-((dimethylphosphoryl)methoxy)-2-methoxyphenyl)-3-(4-((2-(phenylamino)pyrimidin-4-yl)oxy)naphthalen-1-yl)urea

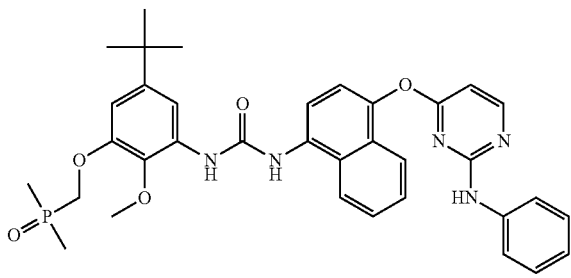

¹H NMR δ: 9.51 (s, 1H), 9.44 (s, 1H), 8.83 (s, 1H), 8.41 (d, 1H), 8.29 (d, 1H), 8.03-8.06 (m, 2H), 7.84 (d, 1H), 7.67 (t, 1H), 7.58 (t, 1H), 7.41 (d, 1H), 7.29 (bd, 2H), 6.99 (t, 2H), 6.83 (d, 1H), 6.78 (t, 1H), 6.60 (d, 1H), 4.40 (d, 2H), 3.87 (s, 3H), 1.58 (d, 6H), 1.29 (s, 9H). LCMS m/z 640 (M+H)⁺ (ES⁺)

(e) 1-(5-(tert-butyl)-3-((dimethylphosphoryl)methoxy)-2-methoxyphenyl)-3-(4-((2-(phenylamino)pyridin-4-yl)oxy)naphthalen-1-yl)urea

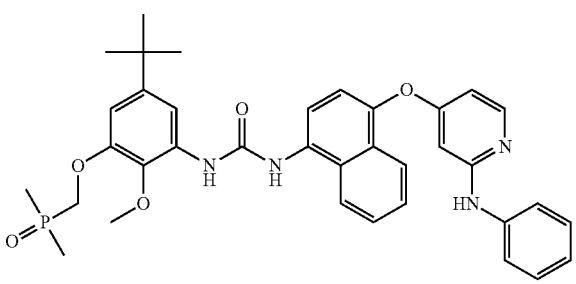 [SMILES: COc1c(NC(=O)Nc2ccc(Oc3ccnc(Nc4ccccc4)c3)c3ccccc23)cc(C(C)(C)C)cc1OCP(C)(C)=O]

¹H NMR δ: 9.43 (s, 1H), 8.90 (s, 1H), 8.84 (s, 1H), 8.30 (d, 1H), 8.04-8.09 (m, 3H), 7.88 (d, 1H), 7.71 (t, 1H), 7.58-7.63 (m, 3H), 7.38 (d, 1H), 7.20 (t, 2H), 6.83-6.86 (m, 2H), 6.56 (d, 1H), 6.10 (d, 1H), 4.39 (d, 2H), 3.86 (s, 3H), 1.58 (d, 6H), 1.29 (s, 9H). LCMS m/z 639 (M+H)⁺ (ES⁺)

(f) 1-(5-(tert-butyl)-3-(dimethylphosphoryl)-2-methoxyphenyl)-3-(4-((2-((2-methoxy-phenyl)amino)pyrimidin-4-yl)oxy)naphthalen-1-yl)urea

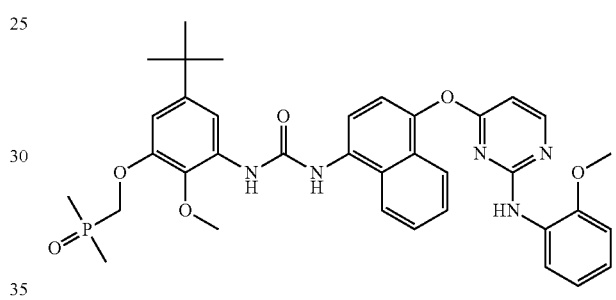

¹H NMR δ 9.29 (s, 1H), 8.83 (s, 1H), 8.39 (d, 1H), 8.31 (d, 1H), 8.22 (d, 1H), 8.04 (d, 1H), 7.85-7.70 (m, 2H), 7.66-7.57 (m, 1H), 7.57-7.45 (m, 1H), 7.41-7.32 (m, 2H), 7.29 (dd, 1H), 6.89-6.81 (m, 1H), 6.78 (td, 1H), 6.55-6.44 (m, 2H), 3.84 (s, 3H), 3.70 (s, 3H), 1.68 (d, 6H), 1.24 (s, 9H). LCMS m/z 640 (M+H)⁺ (ES⁺)

(g) 1-(5-(tert-butyl)-3-(dimethylphosphoryl)-2-methoxyphenyl)-3-(4-((2-((3-methoxy-phenyl)amino)pyrimidin-4-yl)oxy)naphthalen-1-yl)urea

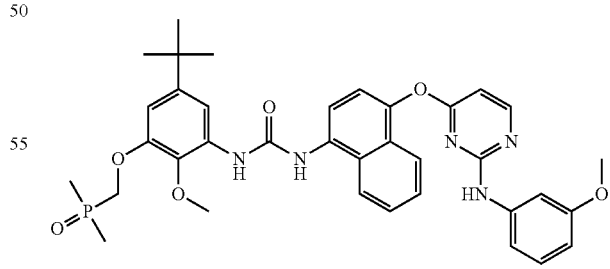

¹H NMR δ 9.40 (s, 1H), 9.25 (s, 1H), 8.82 (s, 1H), 8.38 (d, 1H), 8.33 (d, 1H), 8.20 (d, 1H), 8.03 (d, 1H), 7.77 (dd, 1H), 7.66-7.56 (m, 1H), 7.56-7.47 (m, 1H), 7.34 (d, 1H), 7.28 (dd, 1H), 7.02 (s, 1H), 6.93-6.78 (m, 2H), 6.50 (d, 1H), 6.31 (dt, 1H), 3.84 (s, 3H), 3.46 (s, 3H), 1.68 (d, 6H), 1.23 (s, 9H). LCMS m/z 640 (M+H)⁺ (ES⁺)

(h) 1-(5-(tert-butyl)-3-(dimethylphosphoryl)-2-methoxyphenyl)-3-(4-((2-((4-methoxy-phenyl)amino)pyrimidin-4-yl)oxy)naphthalen-1-yl)urea

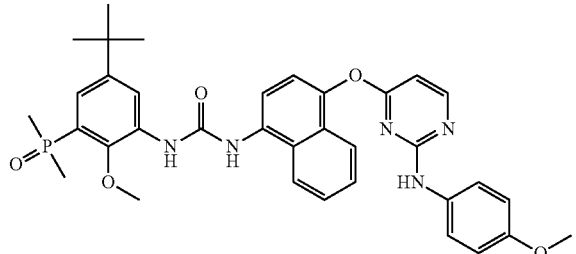

¹H NMR δ 9.28 (s, 1H), 9.26 (s, 1H), 8.82 (s, 1H), 8.38 (d, 1H), 8.27 (d, 1H), 8.21 (d, 1H), 8.03 (d, 1H), 7.76 (dd, 1H), 7.65-7.55 (m, 1H), 7.55-7.45 (m, 1H), 7.34 (d, 1H), 7.28 (dd, 1H), 7.09 (s, 2H), 6.56-6.47 (m, 2H), 6.46 (d, 1H), 3.83 (s, 3H), 3.53 (s, 3H), 1.68 (d, 6H), 1.23 (s, 9H). LCMS m/z 640 (M+H)⁺ (ES⁺)

(i) 1-(5-(tert-butyl)-3-(dimethylphosphoryl)-2-methoxyphenyl)-3-(4-((2-((3,4-dimethoxyphenyl)amino)pyrimidin-4-yl)oxy)naphthalen-1-yl)urea

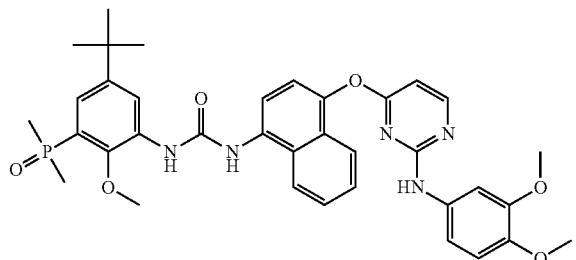

¹H NMR δ 9.26 (s, 1H), 9.21 (s, 1H), 8.81 (s, 1H), 8.37 (d, 1H), 8.29 (d, 1H), 8.20 (d, 1H), 8.02 (d, 1H), 7.77 (dd, 1H), 7.66-7.56 (m, 1H), 7.56-7.47 (m, 1H), 7.34 (d, 1H), 7.28 (dd, 1H), 6.98 (s, 1H), 6.89-6.70 (m, 1H), 6.53 (d, 1H), 6.46 (d, 1H), 3.83 (s, 3H), 3.54 (s, 3H), 3.38 (s, 3H), 1.68 (d, 6H), 1.23 (s, 9H). LCMS m/z 670 (M+H)⁺ (ES⁺)

(j) 1-(5-(tert-butyl)-3-(dimethylphosphoryl)-2-methoxyphenyl)-3-(4-((2-((7-methyl-1H-indazol-5-yl)amino)pyrimidin-4-yl)oxy)naphthalen-1-yl)urea

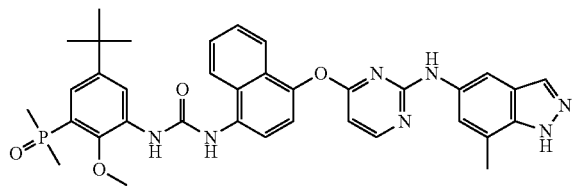 [SMILES: COc1c(NC(=O)Nc2ccc(Oc3ccnc(Nc4cc(C)c5[nH]ncc5c4)n3)c3ccccc23)cc(C(C)(C)C)cc1P(C)(C)=O]

¹H NMR δ 12.84 (s, 1H), 9.48 (s, 1H), 9.43 (s, 1H), 9.01 (s, 1H), 8.45 (d, 1H), 8.40 (d, 1H), 8.34 (d, 1H), 8.26 (d, 1H), 7.85 (d, 1H), 7.72-7.64 (m, 1H), 7.65-7.52 (m, 2H), 7.45 (d, 1H), 7.41-7.32 (m, 2H), 7.01 (s, 1H), 6.60 (d, 1H), 3.94 (s, 3H), 2.29 (s, 3H), 1.77 (d, 6H), 1.31 (s, 9H). LCMS m/z 664 (M+H)⁺ (ES⁺)

(k) 1-(5-(tert-butyl)-2-methoxy-3-(methylsulfinyl)phenyl)-3-(4-((2-(phenylamino)pyrimidin-4-yl)oxy)naphthalen-1-yl)urea

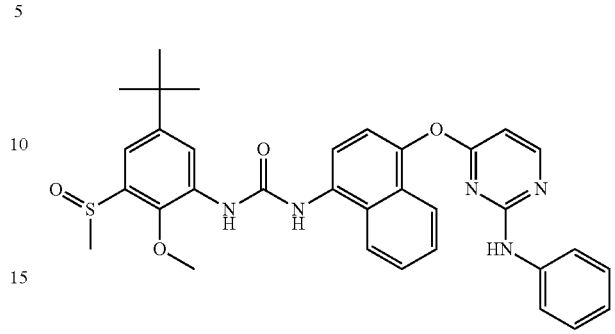

¹H NMR δ:9.53 (s, 1H), 9.44 (s, 1H), 8.95 (s, 1H), 8.53 (d, 1H), 8.41 (d, 1H), 8.28 (d, 1H), 8.07 (d, 1H), 7.84 (d, 1H), 7.68 (ddd, 1H), 7.59 (ddd, 1H), 7.41 (d, 1H), 7.36 (d, 1H), 7.34-7.20 (m, 2H), 6.99 (t, 2H), 6.77 (t, 1H), 6.60 (d, 1H), 3.88 (s, 3H), 2.79 (s, 3H), 1.32 (s, 9H). LCMS m/z 596 (M+H)⁺ (ES⁺)

(l) 1-(5-(tert-butyl)-2-methoxy-3-(methylsulfonyl)phenyl)-3-(4-((2-(phenylamino)pyrimidin-4-yl)oxy)naphthalen-1-yl)urea

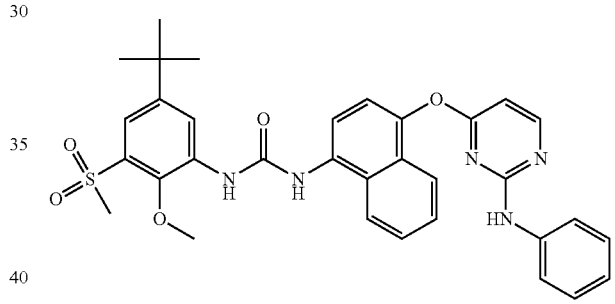

¹H NMR δ: 9.53 (s, 1H), 9.48 (s, 1H), 9.06 (s, 1H), 8.71 (d, 1H), 8.40 (d, 1H), 8.28 (d, 1H), 8.08 (d, 1H), 7.85 (d, 1H), 7.69 (ddd, 1H), 7.59 (ddd, 1H), 7.45 (s, 1H), 7.43 (d, 1H), 7.37-7.17 (m, 2H), 6.99 (t, 2H), 6.77 (t, 1H), 6.60 (d, 1H), 3.97 (s, 3H), 3.35 (s, 3H), 1.32 (s, 9H). LCMS m/z 612 (M+H)⁺ (ES⁺)

(m) 1-(5-(tert-butyl)-2-methoxy-3-(methylsulfonyl)phenyl)-3-(4-((2-(phenylamino)pyridin-4-yl)oxy)naphthalen-1-yl)urea

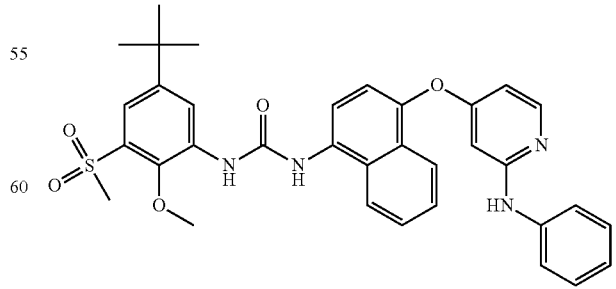

¹H NMR δ: 9.46 (s, 1H), 9.09 (s, 1H), 8.91 (s, 1H), 8.68 (d, 1H), 8.29 (d, 1H), 8.11 (d, 1H), 8.08 (d, 1H), 7.89 (d, 1H), 7.73 (ddd, 1H), 7.62 (ddd, 1H), 7.63-7.57 (m, 2H), 7.44 (d, 1H), 7.41 (d, 1H), 7.23-7.16 (m, 2H), 6.88-6.81 (m, 1H), 6.55 (dd, 1H), 6.10 (d, 1H), 3.95 (s, 3H), 3.35 (s, 3H), 1.31 (s, 9H). LCMS m/z 611 (M+H)⁺ (ES⁺)

(n) 1-(5-(tert-butyl)-2-methoxy-3-((methylsulfonyl)methyl)phenyl)-3-(4-((2-(phenylamino)-pyrimidin-4-yl)oxy)naphthalen-1-yl)urea

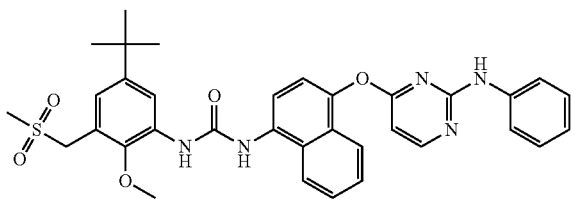 [SMILES: COc1c(CS(C)(=O)=O)cc(C(C)(C)C)cc1NC(=O)Nc1ccc(Oc2ccnc(Nc3ccccc3)n2)c2ccccc12]

¹H NMR δ: 9.53 (s, 1H), 9.40 (s, 1H), 8.90 (s, 1H), 8.40 (d, 1H), 8.36 (d, 1H), 8.29 (d, 1H), 8.09 (d, 1H), 7.84 (d, 1H), 7.60 (ddd, 1H), 7.58 (ddd, 1H), 7.42 (d, 1H), 7.36-7.22 (m, 2H), 7.13 (d, 1H), 6.99 (t, 2H), 6.77 (t, 1H), 6.59 (d, 1H), 4.51 (s, 2H), 3.83 (s, 3H), 3.02 (s, 3H), 1.29 (s, 9H). LCMS m/z 626 (M+H)⁺ (ES⁺)

(o) 1-(5-(tert-butyl)-3-(dimethylphosphoryl)-2-methoxyphenyl)-3-(4-((2-(pyridin-2-ylamino)pyrimidin-4-yl)oxy)naphthalen-1-yl)urea

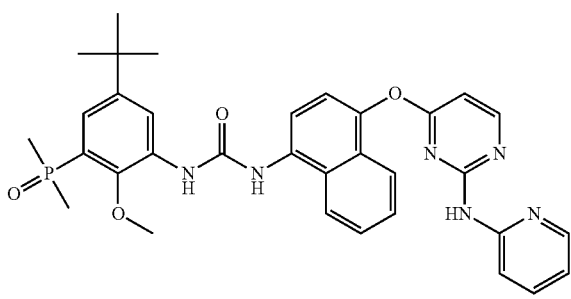 [SMILES: COc1c(NC(=O)Nc2ccc(Oc3ccnc(Nc4ccccn4)n3)c3ccccc23)cc(C(C)(C)C)cc1P(C)(C)=O]

¹H NMR δ 9.71 (s, 1H), 9.30 (s, 1H), 8.82 (s, 1H), 8.51-8.31 (m, 2H), 8.22 (d, 1H), 8.10-8.05 (m, 1H), 8.03 (d, 1H), 7.77 (d, 1H), 7.65-7.56 (m, 1H), 7.55-7.47 (m, 1H), 7.38 (d, 1H), 7.28 (dd, 1H), 7.25-7.13 (m, 2H), 6.78-6.68 (m, 1H), 6.61 (d, 1H), 3.84 (s, 3H), 1.68 (d, 6H), 1.23 (s, 9H). LCMS m/z 611 (M+H)⁺ (ES⁺)

(p) 5-(tert-butyl)-2-methoxy-N-(2-morpholinoethyl)-3-(3-(4-((2-(phenylamino)pyrimidin-4-yl)oxy)naphthalen-1-yl)ureido)benzamide

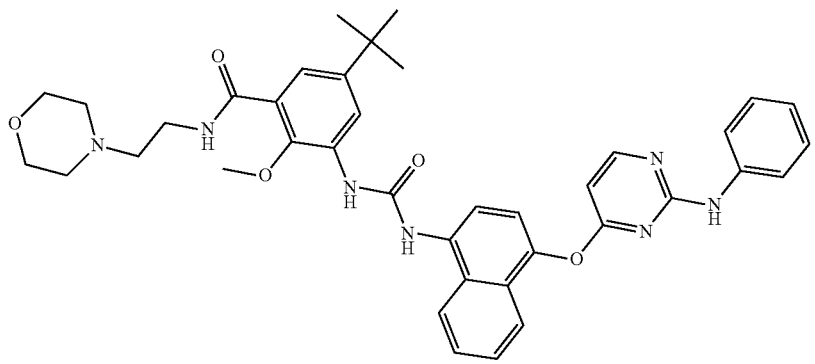 [SMILES: COc1c(NC(=O)Nc2ccc(Oc3ccnc(Nc4ccccc4)n3)c3ccccc23)cc(C(C)(C)C)cc1C(=O)NCCN1CCOCC1]

¹H NMR δ: 9.53 (s, 1H), 9.48 (s, 1H), 8.91 (s, 1H), 8.49 (d, 1H), 8.41 (d, 1H), 8.26-8.30 (m, 2H), 8.07 (d, 1H), 7.84 (d, 1H), 7.69 (t, 1H), 7.59 (t, 1H), 7.43 (d, 1H), 7.29 (bd, 2H), 7.25 (d, 1H), 6.99 (t, 2H), 6.77 (t, 1H), 6.60 (d, 1H), 3.85 (s, 3H), 3.61-3.63 (m, 4H), 3.45 (q, 2H), 2.51-2.54 (m, 2H), 2.46 (bs, 4H), 1.29 (s, 9H). LCMS m/z 690 (M+H)⁺ (ES⁺)

(q) 1-(5-(tert-butyl)-3-(dimethylphosphoryl)-2-methoxyphenyl)-3-(4-((2-(pyrazin-2-ylamino)pyrimidin-4-yl)oxy)naphthalen-1-yl)urea

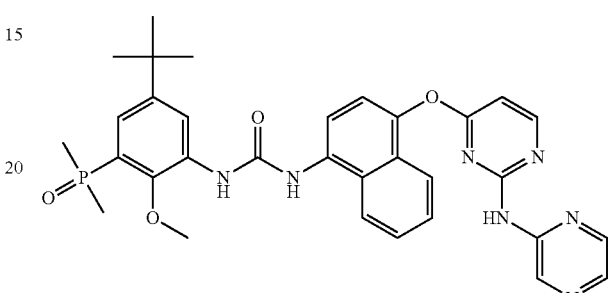

¹H NMR δ 10.24 (s, 1H), 9.40 (s, 1H), 8.92 (s, 1H), 8.84 (d, 1H), 8.50 (d, 1H), 8.46 (d, 1H), 8.30 (d, 1H), 8.22 (dd, 1H), 8.15 (d, 1H), 8.09 (d, 1H), 7.85 (d, 1H), 7.75-7.64 (m, 1H), 7.64-7.53 (m, 1H), 7.47 (d, 1H), 7.36 (dd, 1H), 6.68 (d, 1H), 3.91 (s, 3H), 1.75 (d, 6H), 1.30 (s, 9H). LCMS m/z 612 (M+H)⁺ (ES⁺)

(r) 1-(5-(tert-butyl)-3-(dimethylphosphoryl)-2-methoxyphenyl)-3-(4-((2-(pyrimidin-5-ylamino)pyrimidin-4-yl)oxy)naphthalen-1-yl)urea

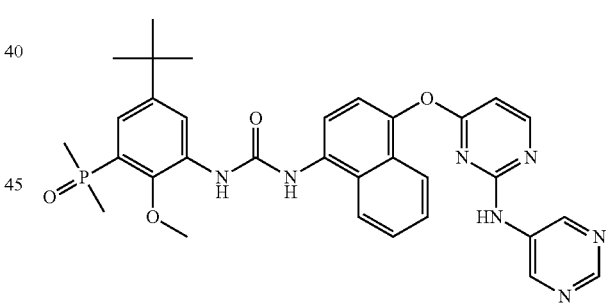

¹H NMR δ 9.87 (s, 1H), 9.38 (s, 1H), 8.91 (s, 1H), 8.83 (s, 2H), 8.65 (s, 1H), 8.49 (d, 1H), 8.45 (d, 1H), 8.28 (d, 1H), 8.12 (d, 1H), 7.84 (d, 1H), 7.73-7.64 (m, 1H), 7.64-7.54 (m, 1H), 7.45 (d, 1H), 7.35 (dd, 1H), 6.72 (d, 1H), 3.91 (s, 3H), 1.75 (d, 6H), 1.30 (s, 9H). LCMS m/z 612 (M+H)⁺ (ES⁺)

(s) 1-(5-(tert-butyl)-3-(dimethylphosphoryl)-2-methoxyphenyl)-3-(4-((2-((1-methyl-1H-pyrazol-4-yl)amino)pyrimidin-4-yl)oxy)naphthalen-1-yl)urea

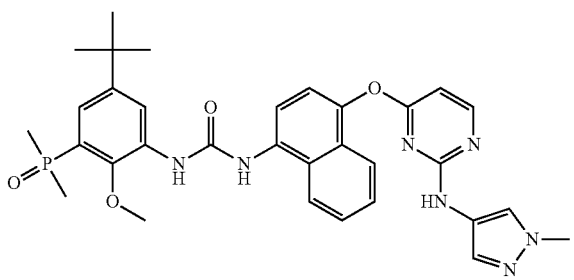 [SMILES: COc1c(NC(=O)Nc2ccc(Oc3ccnc(Nc4cnn(C)c4)n3)c3ccccc23)cc(C(C)(C)C)cc1P(C)(C)=O]

¹H NMR (373K) δ 9.12 (s, 1H), 9.01 (s, 1H), 8.60 (s, 1H), 8.36 (d, 1H), 8.33 (d, 1H), 8.31-8.26 (m, 1H), 8.07 (d, 1H), 7.88 (dt, 1H), 7.66 (ddd, 1H), 7.57 (ddd, 1H), 7.42 (dd, 1H), 7.38 (d, 1H), 7.17 (s, 1H), 6.99 (s, 1H), 6.47 (d, 1H), 3.94 (s, 3H), 3.56 (s, 3H), 1.75 (d, 6H), 1.34 (s, 9H). LCMS m/z 614 (M+H)⁺ (ES⁺)

(t) 3-((4-((4-(3-(5-(tert-butyl)-3-(dimethylphosphoryl)-2-methoxyphenyl)ureido)-naphthalen-1-yl)oxy)pyrimidin-24)amino)phenyl methanesulfonate

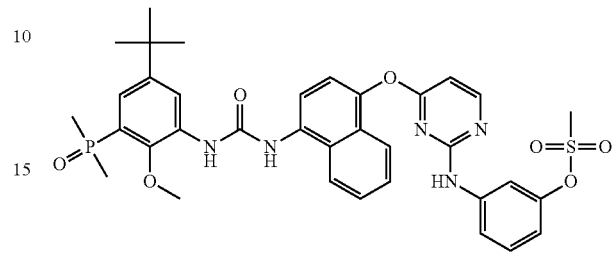

¹H NMR δ 9.77 (s, 1H), 9.36 (s, 1H), 8.91 (s, 1H), 8.54-8.37 (m, 2H), 8.28 (d, 1H), 8.11 (d, 1H), 7.91-7.79 (m, 1H), 7.72-7.63 (m, 1H), 7.63-7.56 (m, 1H), 7.52 (s, 1H), 7.44 (d, 1H), 7.41-7.28 (m, 2H), 7.10 (t, 1H), 6.86-6.73 (m, 1H), 6.64 (d, 1H), 3.91 (s, 3H), 3.28 (s, 3H), 1.75 (d, 6H), 1.30 (s, 9H). LCMS m/z 704 (M+H)⁺ (ES⁺)

(u) 5-(tert-butyl)-2-methoxy-3-(3-(4-((2-(phenylamino)pyrimidin-4-yl)oxy)naphthalen-1-yl)ureido)-N-(2-(pyrrolidin-1-yl)ethyl)benzamide

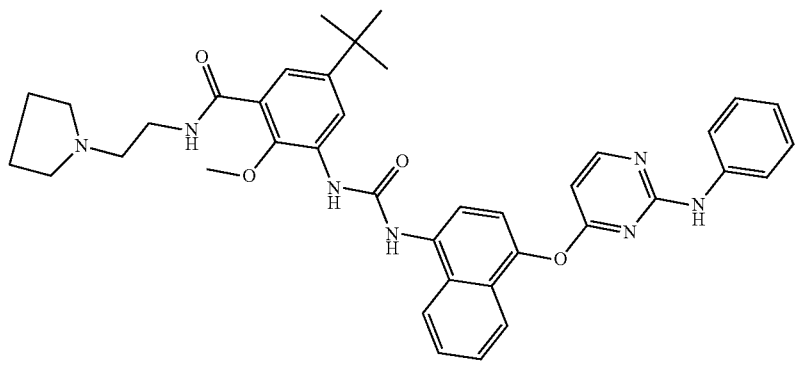 [SMILES: COc1c(NC(=O)Nc2ccc(Oc3ccnc(Nc4ccccc4)n3)c3ccccc23)cc(C(C)(C)C)cc1C(=O)NCCN1CCCC1]

¹H NMR δ: 9.53 (s, 1H), 9.46 (s, 1H), 8.94 (s, 1H), 8.49 (d, 1H), 8.40 (d, 1H), 8.28-8.33 (m, 2H), 8.07 (d, 1H), 7.84 (d, 1H), 7.68 (t, 1H), 7.59 (t, 1H), 7.43 (d, 1H), 7.26-7.29 (m, 3H), 6.99 (t, 2H), 6.77 (t, 1H), 6.60 (d, 1H), 3.82 (s, 3H), 3.43 (q, 2H), 2.64 (t, 2H), 2.53-2.55 (m, 4H), 1.73 (bs, 4H), 1.29 (s, 9H). LCMS m/z 674 (M+H)⁺ (ES⁺)

(v) 1-(5-(tert-butyl)-3-(dimethylphosphoryl)-2-methoxyphenyl)-3-(4-((2-((2-oxoindolin-6-yl)amino)pyrimidin-4-yl)oxy)naphthalen-1-yl)urea

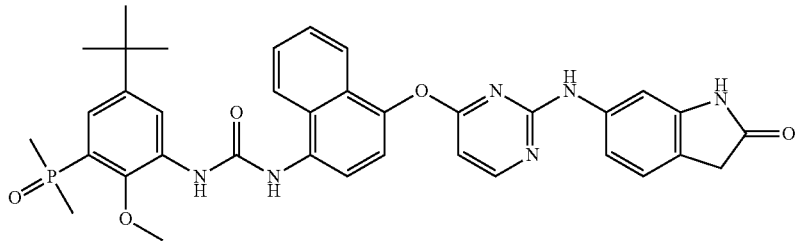 [SMILES: COc1c(NC(=O)Nc2ccc(Oc3ccnc(Nc4ccc5c(c4)NC(=O)C5)n3)c3ccccc23)cc(C(C)(C)C)cc1P(C)(C)=O]

¹H NMR δ 10.22 (s, 1H), 9.52 (s, 1H), 9.36 (s, 1H), 8.90 (s, 1H), 8.46 (d, 1H), 8.38 (d, 1H), 8.27 (d, 1H), 8.10 (d, 1H), 7.91-7.78 (m, 1H), 7.74-7.65 (m, 1H), 7.65-7.53 (m, 1H), 7.43 (d, 1H), 7.36 (dd, 1H), 7.16 (s, 1H), 7.03-6.88 (m, 1H), 6.80 (d, 1H), 6.50 (d, 1H), 3.91 (s, 3H), 3.31 (s, 2H), 1.75 (d, 6H), 1.31 (s, 9H). LCMS m/z 665 (M+H)⁺ (ES⁺)

(w) 1-(5-(tert-butyl)-3-(dimethylphosphoryl)-2-methoxyphenyl)-3-(4-((2-((2,3-dihydrobenzo[b][1,4]dioxin-6-yl)amino)pyrimidin-4-yl)oxy)naphthalen-1-yl)urea

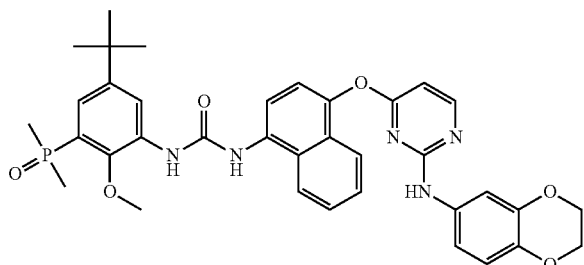

¹H NMR δ 9.47-9.23 (m, 2H), 8.93 (s, 1H), 8.46 (d, 1H), 8.35 (d, 1H), 8.28 (d, 1H), 8.11 (d, 1H), 7.94-7.74 (m, 1H), 7.74-7.62 (m, 1H), 7.62-7.51 (m, 1H), 7.41 (d, 1H), 7.36 (dd, 1H), 6.96 (s, 1H), 6.75 (s, 1H), 6.57-6.38 (m, 2H), 4.22-3.98 (m, 4H), 3.91 (s, 3H), 1.76 (d, 6H), 1.30 (s, 9H). LCMS m/z 668 (M+H)⁺ (ES⁺)

(x) 1-(5-(tert-butyl)-3-(dimethylphosphoryl)-2-methoxyphenyl)-3-(4-((2-((2-methyl-2H-1,2,3-triazol-4-yl)amino)pyrimidin-4-yl)oxy)naphthalen-1-yl)urea

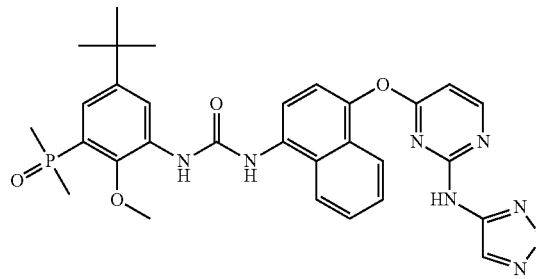

¹H NMR δ 10.24 (s, 1H), 9.39 (s, 1H), 8.91 (s, 1H), 8.47 (d, 1H), 8.41 (d, 1H), 8.30 (d, 1H), 8.16 (d, 1H), 7.82 (d, 1H), 7.68 (t, 1H), 7.58 (t, 1H), 7.42 (d, 1H), 7.35 (dd, 1H), 6.62 (d, 1H), 3.92 (s, 3H), 3.90 (s, 3H), 1.76 (d, 6H), 1.31 (s, 9H). One exchangeable proton not visible. LCMS m/z 615 (M+H)⁺ (ES⁺)

(y) 1-(5-(tert-butyl)-3-(dimethylphosphoryl)-2-methoxyphenyl)-3-(4-((2-((2,2-dioxido-1,3-dihydrobenzo[c]thiophen-5-yl)amino)pyrimidin-4-yl)oxy)naphthalen-1-yl)urea

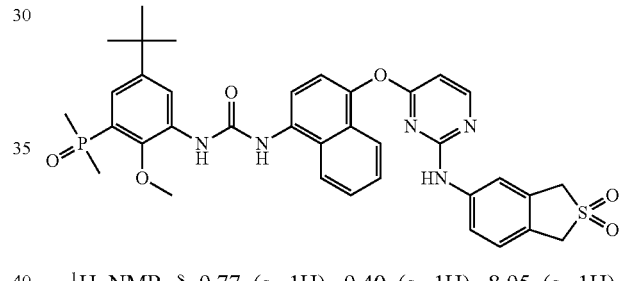

¹H NMR δ 9.77 (s, 1H), 9.40 (s, 1H), 8.95 (s, 1H), 8.50-8.41 (m, 2H), 8.31 (d, 1H), 8.21 (d, 1H), 7.89-7.80 (m, 1H), 7.70 (m, 1H), 7.63-7.55 (m, 1H), 7.45 (d, 1H), 7.36 (m, 2H), 7.19 (s, 1H), 7.04 (d, 1H), 6.69 (d, 1H), 4.27 (s, 2H), 4.05 (s, 2H), 3.91 (s, 3H), 1.75 (d, 6H), 1.31 (s, 9H). LCMS m/z 700 (M+H)⁺ (ES⁺)

(z) 1-(5-(tert-butyl)-3-(dimethylphosphoryl)-2-methoxyphenyl)-3-(4-((2-(isoxazol-4-ylamino)pyrimidin-4-yl)oxy)naphthalen-1-yl)urea

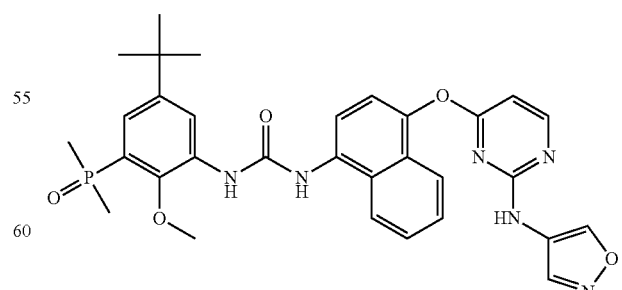

¹H NMR δ 9.32 (s, 1H), 8.87 (s, 1H), 8.43 (d, 1H), 8.38 (d, 1H), 8.26 (d, 1H), 8.07 (d, 1H), 7.92-7.79 (m, 1H), 7.75 (s, 1H), 7.73-7.65 (m, 1H), 7.66-7.55 (m, 1H), 7.45 (d, 1H), 7.35 (dd, 1H), 7.03 (d, 1H), 6.53 (d, 1H), 3.90 (s, 3H), 1.75

(d, 6H), 1.30 (s, 9H). One exchangeable proton not visible. LCMS m/z 601 (M+H)⁺ (ES⁺)

(aa) 1-(5-(tert-butyl)-3-(dimethylphosphoryl)-2-methoxyphenyl)-3-(4-((2-(pyrazin-2-ylamino)pyridin-4-yl)oxy)naphthalen-1-yl)urea

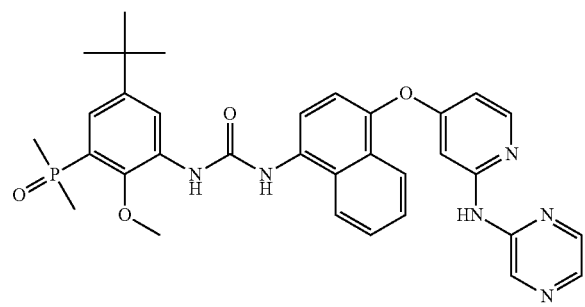 [SMILES: COc1c(NC(=O)Nc2ccc(Oc3ccnc(Nc4cnccn4)c3)c3ccccc23)cc(C(C)(C)C)cc1P(C)(C)=O]

¹H NMR δ 9.99 (s, 1H), 9.35 (s, 1H), 9.07 (d, 1H), 8.91 (s, 1H), 8.44 (d, 1H), 8.29 (d, 1H), 8.23-8.08 (m, 3H), 8.06 (d, 1H), 7.97-7.82 (m, 1H), 7.77-7.66 (m, 1H), 7.66-7.53 (m, 1H), 7.41-7.33 (m, 2H), 7.30 (d, 1H), 6.51 (dd, 1H), 3.91 (s, 3H), 1.75 (d, 6H), 1.31 (s, 9H). LCMS m/z 611 (M+H)⁺ (ES⁺)

(ab) 1-(5-(tert-butyl)-3-(dimethylphosphoryl)-2-methoxyphenyl)-3-(4-((2-((3-oxoisoindolin-5-yl)amino)pyrimidin-4-yl)oxy)naphthalen-1-yl)urea

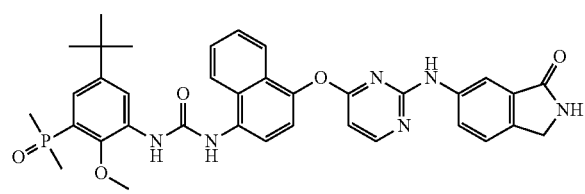 [SMILES: COc1c(NC(=O)Nc2ccc(Oc3ccnc(Nc4ccc5c(c4)C(=O)NC5)n3)c3ccccc23)cc(C(C)(C)C)cc1P(C)(C)=O]

¹H NMR δ 9.73 (s, 1H), 9.35 (s, 1H), 8.88 (s, 1H), 8.48-8.41 (m, 3H), 8.28 (m, 1H), 8.08 (d, 1H), 7.94 (s, 1H), 7.89-7.83 (m, 1H), 7.69 (m, 1H), 7.65-7.57 (m, 2H), 7.45 (d, 1H), 7.36 (dd, 1H), 7.21 (d, 1H), 6.55 (d, 1H), 4.23 (s, 2H), 3.91 (s, 3H), 1.75 (d, 6H), 1.31 (s, 9H). LCMS m/z 665 (M+H)⁺ (ES⁺)

(ac) 1-(5-(tert-butyl)-3-(diethylphosphoryl)-2-methoxyphenyl)-3-(4-((2-(phenylamino)-pyridin-4-yl)oxy)naphthalen-1-yl)urea

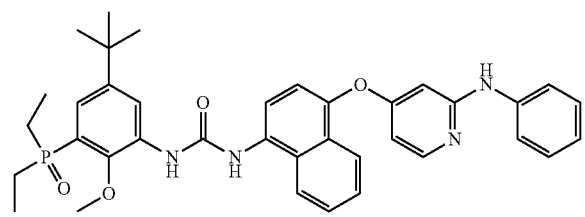 [SMILES: CCP(=O)(CC)c1cc(C(C)(C)C)cc(NC(=O)Nc2ccc(Oc3ccnc(Nc4ccccc4)c3)c3ccccc23)c1OC]

¹H NMR δ: 9.31 (br s, 1H), 8.91 (s, 1H), 8.89 (s, 1H), 8.41 (d, 1H), 8.28 (d, 1H), 8.13 (d, 1H), 8.08 (d, 1H), 7.88 (d, 1H), 7.71 (ddd, 1H), 7.65-7.54 (m, 3H), 7.40 (d, 1H), 7.38 (dd, 1H), 7.20 (ddd, 1H), 6.84 (tt, 1H), 6.55 (dd, 1H), 6.08 (d, 1H), 3.86 (s, 3H), 2.12-1.87 (m, 4H), 1.30 (s, 9H), 1.01 (dt, 6H). LCMS m/z 637 (M+H)⁺ (ES⁺)

(ad) 1-(5-(tert-butyl)-3-(dimethylphosphoryl)-2-methoxyphenyl)-3-(4-((2-(pyridin-3-ylamino)pyridin-4-yl)oxy)naphthalen-1-yl)urea

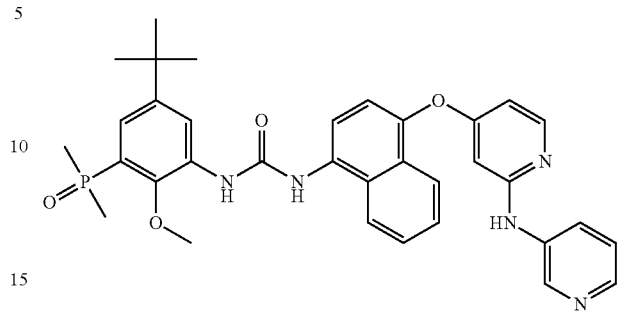

¹H NMR δ 9.28 (s, 1H), 9.03 (s, 1H), 8.83 (s, 1H), 8.61 (dd, 1H), 8.37 (d, 1H), 8.22 (d, 1H), 8.14-8.02 (m, 3H), 7.98 (dd, 1H), 7.81 (d, 1H), 7.71-7.60 (m, 1H), 7.59-7.51 (m, 1H), 7.33 (d, 1H), 7.29 (dd, 1H), 7.16 (dd, 1H), 6.55 (dd, 1H), 6.04 (d, 1H), 3.83 (s, 3H), 1.68 (d, 6H), 1.23 (s, 9H). LCMS m/z 610 (M+H)⁺ (ES⁺)

(ae) 1-(5-(tert-butyl)-3-(dimethylphosphoryl)-2-methoxyphenyl)-3-(4-((2-((6-(dimethylamino)pyrazin-2-yl)amino)pyridin-4-yl)oxy)naphthalen-1-yl)urea

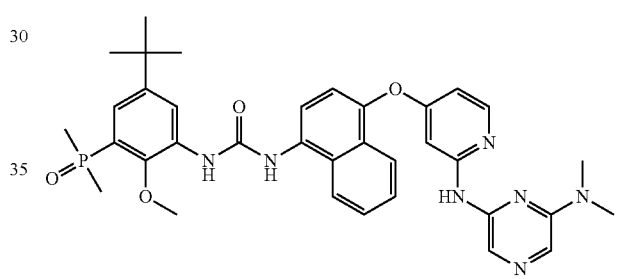

¹H NMR δ 9.64 (s, 1H), 9.36 (s, 1H), 8.90 (s, 1H), 8.45 (d, 1H), 8.28 (d, 1H), 8.18 (d, 1H), 8.08 (d, 1H), 7.87 (d, 1H), 7.80 (s, 1H), 7.77-7.65 (m, 1H), 7.65-7.53 (m, 1H), 7.45 (d, 1H), 7.41 (s, 1H), 7.40-7.33 (m, 2H), 6.74 (dd, 1H), 3.92 (s, 3H), 2.55 (s, 6H), 1.75 (d, 6H), 1.30 (s, 9H). LCMS m/z 654 (M+H)⁺ (ES⁺)

(af) 1-(5-(tert-butyl)-3-(dimethylphosphoryl)-2-methoxyphenyl)-3-(4-((2-((3-methoxy-phenyl)amino)pyridin-4-yl)oxy)naphthalen-1-yl)urea

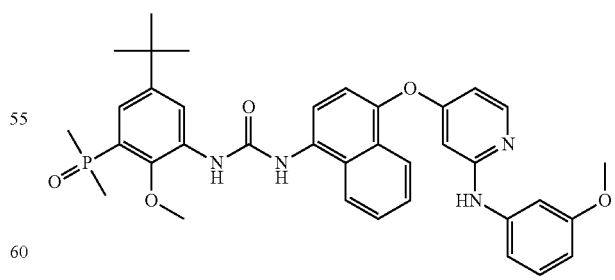

¹H NMR δ 9.33 (s, 1H), 8.90 (s, 2H), 8.44 (d, 1H), 8.29 (d, 1H), 8.13 (d, 1H), 8.10 (d, 1H), 7.88 (d, 1H), 7.79-7.66 (m, 1H), 7.67-7.55 (m, 1H), 7.44-7.27 (m, 3H), 7.20-6.99 (m, 2H), 6.56 (dd, 1H), 6.49-6.37 (m, 1H), 6.10 (d, 1H), 3.90 (s, 3H), 3.68 (s, 3H), 1.75 (d, 6H), 1.31 (s, 9H). LCMS m/z 639 (M+H)⁺ (ES⁺)

(ag) 5-(tert-butyl)-2-methoxy-3-(3-(4-((2-(phenylamino)pyridin-4-yl)oxy)naphthalen-1-yl)ureido)-N-(2-(pyrrolidin-1-yl)ethyl)benzamide

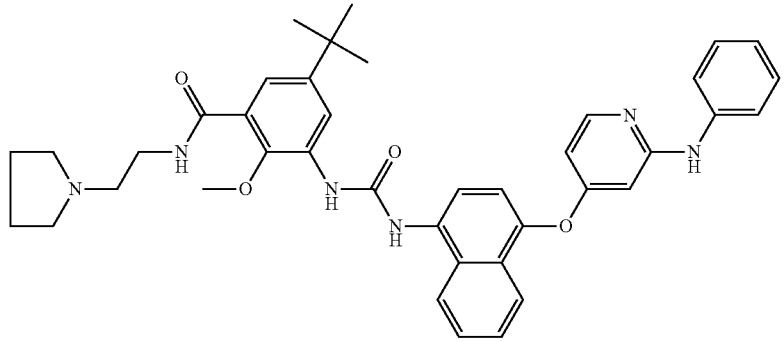 [SMILES: COc1c(NC(=O)Nc2ccc(Oc3ccnc(Nc4ccccc4)c3)c3ccccc23)cc(C(C)(C)C)cc1C(=O)NCCN1CCCC1]

$^1$H NMR δ: 9.47 (s, 1H), 8.94 (s, 1H), 8.90 (s, 1H), 8.47 (d, 1H), 8.29-8.32 (m, 2H), 8.08-8.10 (m, 2H), 7.89 (d, 1H), 7.71 (t, 1H), 7.58-7.64 (m, 3H), 7.39 (d, 1H), 7.27 (d, 1H), 7.20 (t, 2H), 6.84 (t, 1H), 6.56 (dd, 1H), 6.11 (d, 1H), 3.82 (s, 3H), 3.45 (q, 2H), 2.70 (bs, 2H), 2.60 (bs, 4H), 1.75 (bs, 4H), 1.29 (s, 9H). LCMS m/z 673 (M+H)$^+$ (ES$^+$)

(ah) 1-(5-(tert-butyl)-3-(dimethylphosphoryl)-2-methoxyphenyl)-3-(4-((2-((1-methylpiperidin-4-yl)amino)pyrimidin-4-yl)oxy)naphthalen-1-yl)urea

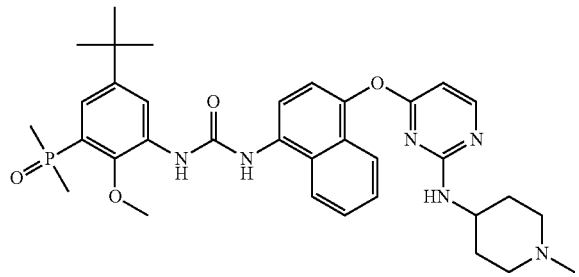 [SMILES: COc1c(NC(=O)Nc2ccc(Oc3ccnc(NC4CCN(C)CC4)n3)c3ccccc23)cc(C(C)(C)C)cc1P(C)(C)=O]

$^1$H NMR (100° C.) δ 9.05 (s, 1H), 8.55 (s, 1H), 8.36 (d, 1H), 8.24 (m, 1H), 8.17 (d, 1H), 7.97 (d, 1H), 7.86 (m, 1H), 7.63 (ddd, 1H), 7.56 (ddd, 1H), 7.41 (dd, 1H), 7.31 (d, 1H), 6.48 (d, 1H), 6.20 (d, 1H), 3.93 (s, 3H), 3.40 (s, 1H), 2.62 (m, 2H), 2.12 (s, 3H), 1.91-1.79 (m, 2H), 1.75 (d, 6H), 1.65 (m, 2H), 1.49-1.37 (m, 2H), 1.33 (s, 9H). LCMS m/z 631 (M+H)$^+$ (ES$^+$)

(ai) (R)-1-(5-(tert-butyl)-3-(dimethylphosphoryl)-2-methoxyphenyl)-3-(4-((2-((tetrahydrofuran-3-yl)amino)pyrimidin-4-yl)oxy)naphthalen-1-yl)urea

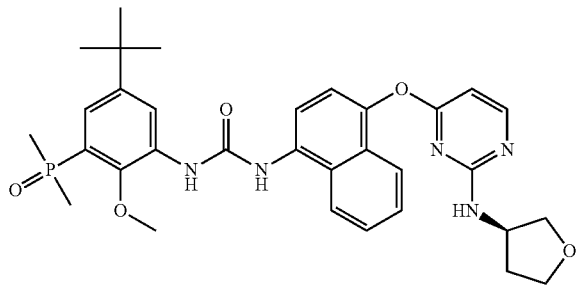 [SMILES: COc1c(NC(=O)Nc2ccc(Oc3ccnc(N[C@@H]4CCOC4)n3)c3ccccc23)cc(C(C)(C)C)cc1P(C)(C)=O]

$^1$H NMR (100° C.) δ 9.05 (s, 1H), 8.54 (s, 1H), 8.36 (d, 1H), 8.24 (m, 1H), 8.20 (d, 1H), 7.98 (d, 1H), 7.89-7.83 (m, 1H), 7.64 (ddd, 1H), 7.57 (ddd, 1H), 7.41 (dd, 1H), 7.33 (d, 1H), 6.88 (m, 1H), 6.26 (d, 1H), 4.13 (m, 1H), 3.93 (s, 3H), 3.77-3.69 (m, 1H), 3.62 (m, 2H), 3.39 (dd, 1H), 2.04-1.92 (m, 1H), 1.83-1.77 (m, 1H), 1.75 (d, 6H), 1.33 (s, 9H). LCMS m/z 604 (M+H)$^+$ (ES$^+$)

(aj) (S)-1-(5-(tert-butyl)-3-(dimethylphosphoryl)-2-methoxyphenyl)-3-(4-((2-((tetrahydrofuran-3-yl)amino)pyrimidin-4-yl)oxy)naphthalen-1-yl)urea

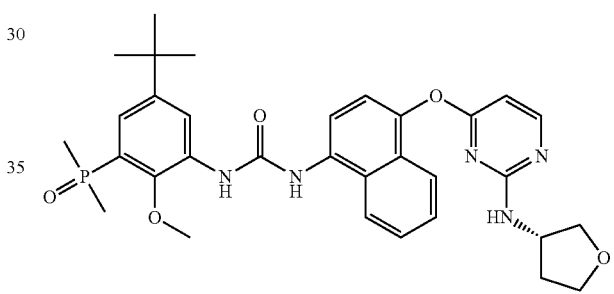

$^1$H NMR (100° C.) δ 9.05 (s, 1H), 8.54 (s, 1H), 8.36 (d, 1H), 8.24 (m, 1H), 8.20 (d, 1H), 7.98 (d, 1H), 7.86 (m, 1H), 7.64 (ddd, 1H), 7.57 (ddd, 1H), 7.41 (dd, 1H), 7.33 (d, 1H), 6.88 (m, 1H), 6.26 (d, 1H), 4.14 (m, 1H), 3.93 (s, 3H), 3.73 (m, 1H), 3.62 (m, 2H), 3.39 (dd, 1H), 2.03-1.92 (m, 1H), 1.83-1.77 (m, 1H), 1.75 (d, 6H), 1.33 (s, 9H). LCMS m/z 604 (M+H)$^+$ (ES$^+$)

(ak) 1-(5-(tert-butyl)-3-(dimethylphosphoryl)-2-methoxyphenyl)-3-(4-((2-(dimethylamino)-pyrimidin-4-yl)oxy)naphthalen-1-yl)urea

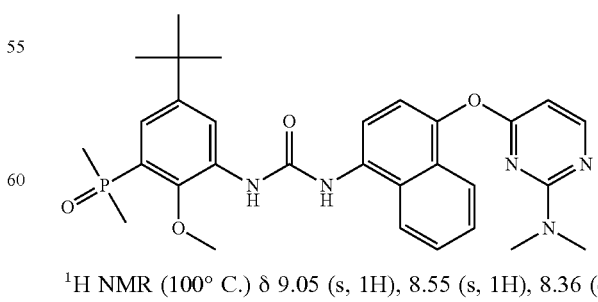

$^1$H NMR (100° C.) δ 9.05 (s, 1H), 8.55 (s, 1H), 8.36 (d, 1H), 8.31-8.20 (m, 2H), 8.02 (d, 1H), 7.94-7.85 (m, 1H), 7.64 (ddd, 1H), 7.57 (ddd, 1H), 7.41 (dd, 1H), 7.35 (d, 1H), 6.16 (d, 1H), 3.92 (s, 3H), 1.75 (d, 6H), 1.33 (s, 9H). (note at 2.95 ppm comes —N(Me)₂ (dimethylamino group) signal of which overlaps with water peak.) LCMS m/z 562 (M+H)⁺ (ES⁺)

(al) 1-(5-(tert-butyl)-3-(dimethylphosphoryl)-2-methoxyphenyl)-3-(4-((2-((2-morpholinoethyl)amino)pyrimidin-4-yl)oxy)naphthalen-1-yl)urea

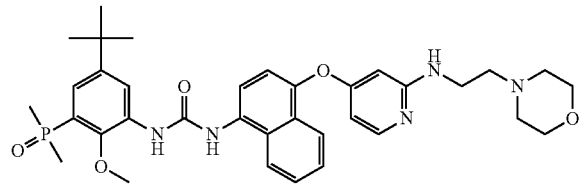 [SMILES: COc1c(NC(=O)Nc2ccc(Oc3ccnc(NCCN4CCOCC4)c3)c3ccccc23)cc(C(C)(C)C)cc1P(C)(C)=O]

¹H NMR (100° C.) δ 9.03 (s, 1H), 8.56 (s, 1H), 8.36 (d, 1H), 8.24 (m, 1H), 8.18 (d, 1H), 8.00 (d, 1H), 7.86 (m, 1H), 7.64 (ddd, 1H), 7.56 (ddd, 1H), 7.41 (dd, 1H), 7.32 (d, 1H), 6.53 (s, 1H), 6.23 (d, 1H), 3.93 (s, 3H), 3.56-3.42 (m, 4H), 3.19 (q, 2H), 2.37-2.27 (m, 2H), 2.24 (s, 4H), 1.75 (d, 6H), 1.34 (s, 9H). LCMS m/z 647 (M+H)⁺ (ES⁺)

(am) 1-(5-(tert-butyl)-3-(dimethylphosphoryl)-2-methoxyphenyl)-3-(4-((2-((3-chloro-5-methylmethylphenyl)amino)pyridin-4-yl)oxy)naphthalen-1-yl)urea

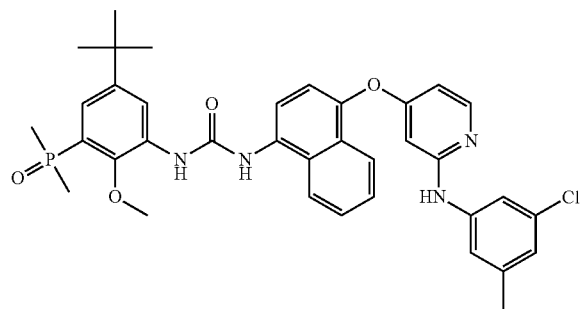 [SMILES: COc1c(NC(=O)Nc2ccc(Oc3ccnc(Nc4cc(C)cc(Cl)c4)c3)c3ccccc23)cc(C(C)(C)C)cc1P(C)(C)=O]

¹H NMR δ 9.34 (s, 1H), 9.04 (s, 1H), 8.90 (s, 1H), 8.44 (d, 1H), 8.29 (d, 1H), 8.18-8.06 (m, 2H), 7.87 (d, 1H), 7.79-7.68 (m, 2H), 7.66-7.57 (m, 1H), 7.40 (d, 1H), 7.36 (dd, 1H), 7.17 (s, 1H), 6.71 (s, 1H), 6.62 (dd, 1H), 6.09 (d, 1H), 3.90 (s, 3H), 2.21 (s, 3H), 1.75 (d, 6H), 1.31 (s, 9H). LCMS m/z 657/659 (M+H)⁺ (ES⁺)

(an) 1-(5-(tert-butyl)-3-(dimethylphosphoryl)-2-methoxyphenyl)-3-(4-((2-((3-fluoro-5-methoxyphenyl)amino)pyridin-4-yl)oxy)naphthalen-1-yl)urea

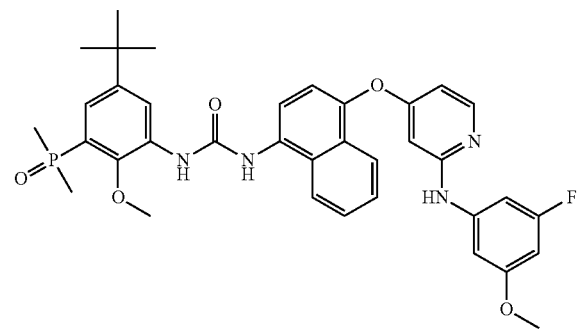 [SMILES: COc1cc(F)cc(Nc2cc(Oc3ccc(NC(=O)Nc4cc(C(C)(C)C)cc(P(C)(C)=O)c4OC)c4ccccc34)ccn2)c1]

¹H NMR δ 9.34 (s, 1H), 9.11 (s, 1H), 8.90 (s, 1H), 8.44 (d, 1H), 8.29 (d, 1H), 8.14 (d, 1H), 8.13 (d, 1H), 7.87 (d, 1H), 7.79-7.67 (m, 1H), 7.67-7.55 (m, 1H), 7.40 (d, 1H), 7.36 (dd, 1H), 7.26 (dt, 1H), 6.95 (s, 1H), 6.63 (dd, 1H), 6.29 (dt, 1H), 6.08 (d, 1H), 3.91 (s, 3H), 3.69 (s, 3H), 1.75 (d, 6H), 1.31 (s, 9H). LCMS m/z 657 (M+H)⁺ (ES⁺)

(ao) 1-(4-((2-((2-(1H-pyrazol-1-yl)ethyl)amino)pyrimidin-4-yl)oxy)naphthalen-1-yl)-3-(5-(tert-butyl)-3-(dimethylphosphoryl)-2-methoxyphenyl)urea

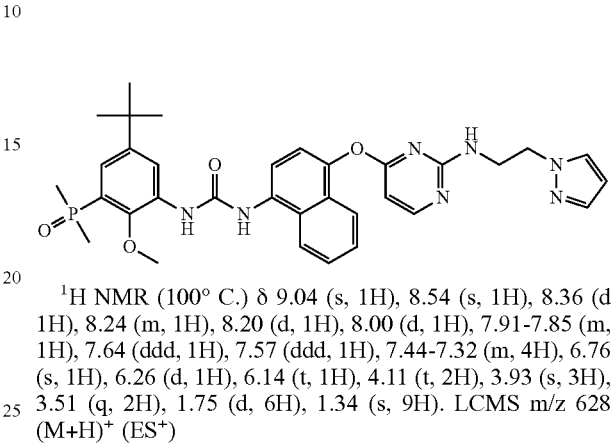

¹H NMR (100° C.) δ 9.04 (s, 1H), 8.54 (s, 1H), 8.36 (d 1H), 8.24 (m, 1H), 8.20 (d, 1H), 8.00 (d, 1H), 7.91-7.85 (m, 1H), 7.64 (ddd, 1H), 7.57 (ddd, 1H), 7.44-7.32 (m, 4H), 6.76 (s, 1H), 6.26 (d, 1H), 6.14 (t, 1H), 4.11 (t, 2H), 3.93 (s, 3H), 3.51 (q, 2H), 1.75 (d, 6H), 1.34 (s, 9H). LCMS m/z 628 (M+H)⁺ (ES⁺)

(ap) 1-(5-(tert-butyl)-3-(dimethylphosphoryl)-2-methylphenyl)-3-(4-((2-(phenylamino)pyridin-4-yl)oxy)naphthalen-1-yl)urea

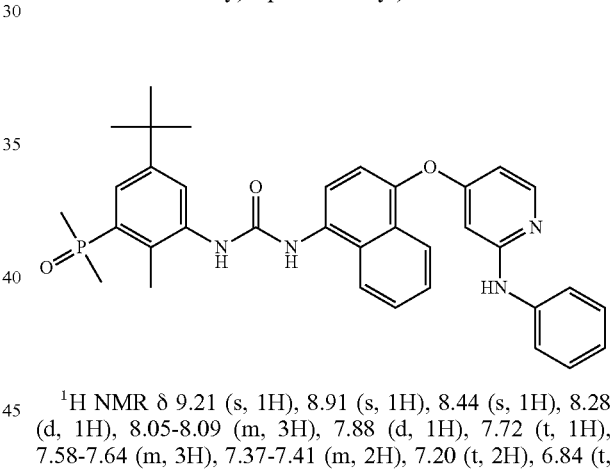

¹H NMR δ 9.21 (s, 1H), 8.91 (s, 1H), 8.44 (s, 1H), 8.28 (d, 1H), 8.05-8.09 (m, 3H), 7.88 (d, 1H), 7.72 (t, 1H), 7.58-7.64 (m, 3H), 7.37-7.41 (m, 2H), 7.20 (t, 2H), 6.84 (t, 1H), 6.56 (dd, 1H), 6.11 (d, 1H), 2.58 (s, 3H), 1.77 (d, 6H), 1.30 (s, 9H).
LCMS m/z 593 (M+H)⁺ (ES⁺); 591 (M−H)⁻ (ES⁻)

(aq) N-(5-(tert-butyl)-2-methoxy-3-(3-(4-((2-(phenylamino)pyridin-4-yl)oxy)naphthalen-1-yl)ureido)benzyl)methanesulfonamide

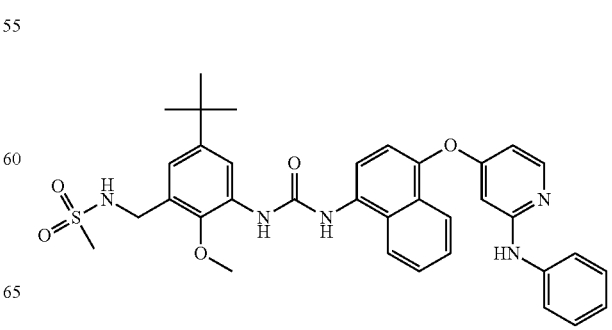

¹H NMR δ 9.41 (s, 1H), 8.90 (s, 1H), 8.84 (s, 1H), 8.30 (d, 1H), 8.28 (d, 1H), 8.10 (d, 1H), 8.09 (d, 1H), 7.89 (d, 1H), 7.76 (ddd, 1H), 7.66 (ddd, 1H), 7.62-7.56 (m, 2H), 7.52 (t, 1H), 7.38 (d, 1H), 7.23-7.16 (m, 2H), 7.13 (d, 1H), 6.84 (ddd, 1H), 6.55 (dd, 1H), 6.10 (d, 1H), 4.25 (d, 2H), 3.80 (s, 3H), 2.91 (s, 3H), 1.29 (s, 9H). LCMS m/z 640 (M+H)⁺ (ES⁺); 638 (M–H)⁻ (ES⁻)

(ar) 1-(5-(tert-butyl)-3-(dimethylphosphoryl)-2-methoxyphenyl)-3-(4-((2-((2-methyl-2H-1,2,3-triazol-4-yl)amino)pyridin-4-yl)oxy)naphthalen-1-yl)urea

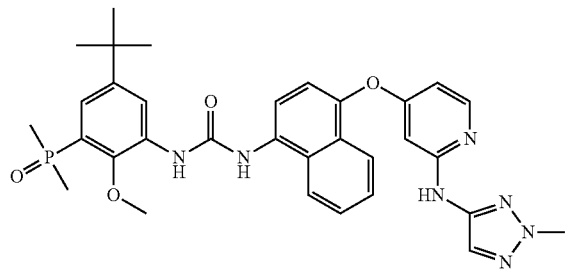

¹H NMR δ 9.53 (s, 1H), 9.35 (s, 1H), 8.90 (s, 1H), 8.44 (d, 1H), 8.29 (d, 1H), 8.11 (d, 1H), 8.09-8.06 (m, 1H), 7.88 (d, 1H), 7.82 (s, 1H), 7.76-7.66 (m, 1H), 7.66-7.56 (m, 1H), 7.45-7.27 (m, 2H), 6.53-6.40 (m, 2H), 3.98 (s, 3H), 3.90 (s, 3H), 1.75 (d, 6H), 1.31 (s, 9H). LCMS m/z 614 (M+H)⁺ (ES⁺); 612 (M–H)⁻ (ES⁻)

Example 16

5-(tert-Butyl)-2-methoxy-3-(3-(4-((2-((3-methoxy-5-(2-(2-(2-methoxyethoxy)ethoxy)ethoxy)-phenyl)amino)pyridin-4-yl)oxy)naphthalen-1-yl)ureido)-N-(2-morpholinoethyl)benzamide (i) 5-(tert-Butyl)-2-methoxy-N-(2-morpholinoethyl)-3-nitrobenzamide To a stirred solution of 5-(tert-butyl)-2-methoxy-3-nitrobenzoyl chloride (100 mg, 0.368 mmol) and triethylamine (155 μL, 1.112 mmol) in DCM (5 mlL was added 2-morpholinoethanamine (48 μL, 0.366 mmol) and the reaction stirred overnight. 50 wt % T3P in EtOAc (175 μL, 0.294 mmol) was added and the reaction stirred over the weekend. The mixture was diluted with DCM (10 mL) and quenched with sat. NaHCO₃ solution. The aqueous phase was extracted with more DCM and the combined organic phases were washed with water and brine, then dried (MgSO₄), filtered and concentrated in vacuo. The crude product was purified by chromatography on the Companion (12 g column, 1-5% MeOH in DCM) to afford the sub-title compound (91 mg) as a pale yellow oil.

LCMS m/z 366 (M+H)⁺ (ES⁺)

(ii) 3-Amino-5-(tert-butyl)-2-methoxy-N-(2-morpholinoethyl)benzamide

The product from step (i) above (91 mg, 0.249 mmol) was dissolved in ethanol (3 mL) and Fe powder (139 mg, 2.490 mmol) was added followed by a solution of NH₄Cl (133 mg, 2.490 mmol) in water (1 mL). The resulting suspension was heated at 80° C. for 2 h. The reaction was cooled to rt and filtered. The filtrate was concentrated in vacuo then partitioned between water (10 mL) and EtOAc (10 mL). The aqueous phase was extracted with EtOAc (10 mL). The combined organic extracts were washed with brine (15 mL), dried (MgSO₄), filtered and concentrated in vacuo affording the sub-title compound (74 mg) as a pale yellow oil.

LCMS m/z 336 (M+H)⁺ (ES⁺)

(iii) Phenyl (5-(tert-butyl)-2-methoxy-3-((2-morpholinoethyl)carbamoyl)phenyl)carbamate Phenyl chloroformate (30 μL, 0.240 mmol) was added to a stirred mixture of the product from step (ii) above (74 mg, 0.221 mmol) and NaHCO₃ (40 mg, 0.476 mmol) in DCM (3 mL) and THF (1 mL) at rt. The mixture was stirred overnight then partitioned between DCM (10 mL) and water (10 mL). The organic layer was separated, washed with brine (10 mL), dried (MgSO₄) and evaporated under reduced pressure.

LCMS m/z 456 (M+H)⁺ (ES⁺)

(iv) 5-(tert-Butyl)-2-methoxy-3-(3-(4-((2-((3-methoxy-5-(2-(2-(2-methoxyethoxy)ethoxy)-ethoxy)phenyl)amino)pyridin-4-yl)oxy)naphthalen-1-yl)ureido)-N-(2-morpholinoethyl)-benzamide Triethylamine (5 μL, 0.036 mmol) was added to a mixture of the product from step (iii) above (81 mg, 0.178 mmol) and 4-((4-aminonaphthalen-1-yl)oxy)-N-(3-methoxy-5-(2-(2-(2-methoxyethoxy)ethoxy)ethoxy)phenyl)pyridin-2-amine

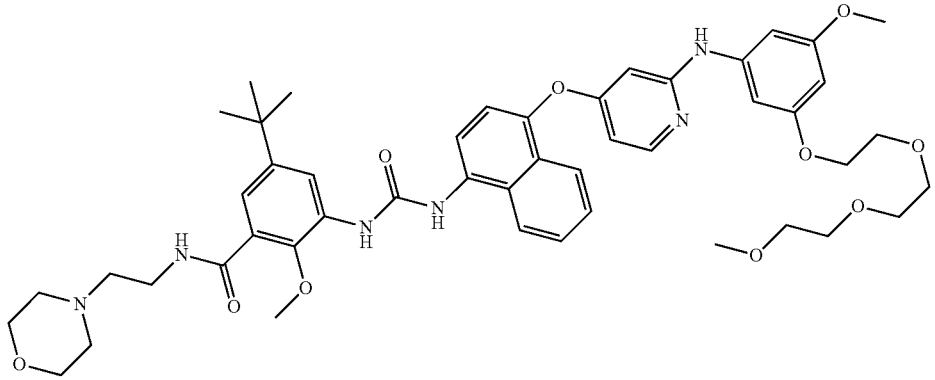 [SMILES: COCCOCCOCCOc1cc(Nc2cc(Oc3ccc(NC(=O)Nc4cc(C(C)(C)C)cc(C(=O)NCCN5CCOCC5)c4OC)c4ccccc34)ccn2)cc(OC)c1]

(see Example 2(iv) above; 93 mg, 0.178 mmol) in isopropyl acetate (3 mL) and the mixture heated at 60° C. (block temperature) overnight. The reaction was cooled to rt and concentrated in vacuo onto silica gel. The crude product was purified by chromatography on the Companion (12 g column, 1-5% MeOH in DCM) to afford a pale pink solid. The crude product was purified by preparative HPLC (Varian, Basic (0.1% Ammonium Bicarbonate), Basic, Waters X-Bridge Prep-C18, 5 μm, 19×50 mm column, 50-75% MeCN in Water) to afford the title compound (43 mg) as a white solid.

$^1$H NMR (400 MHz, DMSO-d$_6$) δ: 9.46 (s, 1H), 8.92 (s, 1H), 8.88 (s, 1H), 8.47 (d, 1H), 8.30 (d, 1H), 8.25 (t, 1H), 8.08-8.12 (m, 2H), 7.88 (d, 1H), 7.72 (t, 1H), 7.62 (t, 1H), 7.39 (d, 1H), 7.25 (d, 1H), 6.91 (s, 1H), 6.79 (s, 1H), 6.58 (dd, 1H), 6.10 (d, 1H), 6.04 (t, 1H), 3.97-3.99 (m, 2H), 3.84 (s, 3H), 2.70-2.72 (m, 2H), 3.66 (s, 3H), 3.61-3.63 (m, 4H), 3.50-3.58 (m, 6H), 3.41-3.47 (m, 4H), 3.23 (s, 3H), 2 protons under DMSO, 2.46-2.50 (m, 4H), 1.29 (s, 9H). LCMS m/z 881 (M+H)$^+$ (ES$^+$); 441 (M+2H)$^{2+}$ (ES$^+$)

Example 17

1-(5-(tert-Butyl)-2-methoxy-3-(methylsulfinyl)phenyl)-3-(4-((2-((3-methoxy-5-(2-(2-(2-methoxyethoxy)ethoxy)ethoxy)phenyl)amino)pyridin-4-yl)oxy)naphthalen-1-yl)urea

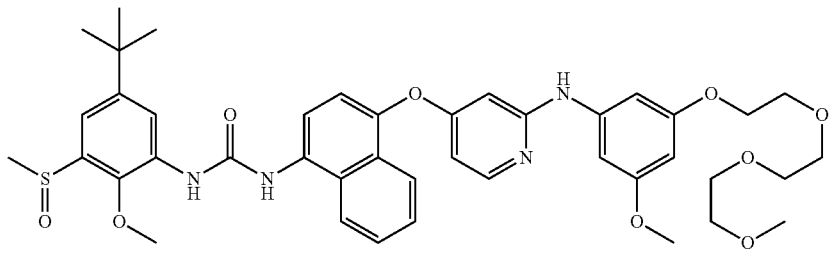 [SMILES: COCCOCCOCCOc1cc(Nc2cc(Oc3ccc(NC(=O)Nc4cc(C(C)(C)C)cc(S(C)=O)c4OC)c4ccccc34)ccn2)cc(OC)c1]

A stirred solution of phenyl (5-(tert-butyl)-2-methoxy-3-(methylsulfinyl)phenyl)carbamate (see Example 12(iv) above; 70 mg, 0.194 mmol), 4-((4-aminonaphthalen-1-yl)oxy)-N-(3-methoxy-5-(2-(2-(2-methoxyethoxy)-ethoxy)ethoxy)phenyl)pyridin-2-amine (see Example 2(iv) above; 101 mg, 0.194 mmol) and triethylamine (10 μl, 0.072 mmol) was heated to 60° C. (block temperature) in isopropyl acetate (2 mL) for 18 h. The mixture was concentrated under reduced pressure and the residue was purified by preparative HPLC (Gilson, Acidic (0.1% Formic acid), Acidic, Waters X-Select Prep-C18, 5 μm, 19×50 mm column, 20-60% MeCN in Water). Fractions containing product were combined and the bulk of the acetonitrile was removed under reduced pressure. The aqueous mixture was then basified with saturated NaHCO$_3$ solution (10 mL) and extracted with ethyl acetate (20 mL). The organic phase was washed with saturated brine (10 mL), dried (MgSO$_4$) and concentrated under reduced pressure to yield the title compound (63 mg) as a tan foam.

$^1$H NMR (400 MHz, DMSO-d$_6$) δ: 9.40 (s, 1H), 8.95 (s, 1H), 8.87 (s, 1H), 8.50 (d, 1H), 8.28 (d, 1H), 8.11 (d, 1H), 8.09 (d, 1H), 7.87 (d, 1H), 7.71 (ddd, 1H), 7.61 (ddd, 1H), 7.39 (d, 1H), 7.36 (d, 1H), 6.90 (dd, 1H), 6.78 (dd, 1H), 6.57 (dd, 1H), 6.09 (d, 1H), 6.04 (dd, 1H), 4.01-3.94 (m, 2H), 3.87 (s, 3H), 3.74-3.68 (m, 2H), 3.66 (s, 3H), 3.60-3.55 (m, 2H), 3.55-3.49 (m, 4H), 3.45-3.38 (m, 2H), 3.23 (s, 3H), 2.79 (s, 3H), 1.32 (s, 9H).

LCMS m/z 787 (M+H)$^+$ (ES-'); 785 (M−H)$^-$ (ES$^-$)

Example 18

1-(5-(tert-Butyl)-3-(dimethylphosphoryl)-2-methoxyphenyl)-3-(4-((2-((3,5-dimethoxyphenyl)-amino)pyrimidin-4-yl)oxy)naphthalen-1-yl)urea

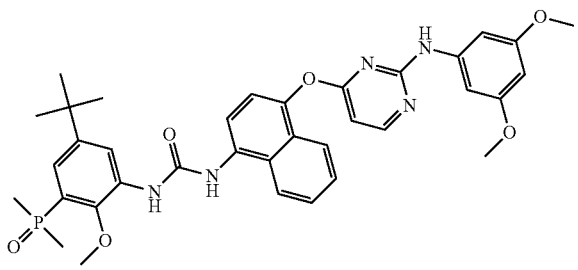 [SMILES: COc1cc(Nc2nccc(Oc3ccc(NC(=O)Nc4cc(C(C)(C)C)cc(P(C)(C)=O)c4OC)c4ccccc34)n2)cc(OC)c1]

(i) Phenyl (4-((2-chloropyrimidin-4-yl)oxy)naphthalen-1-yl)carbamate

In a 250 mL flask, a solution of 4-((2-chloropyrimidin-4-yl)oxy)naphthalen-1-amine (see, for example, Cirillo, P. F. et al., WO 2002/92576, 21 Nov. 2000; 4 g, 14.72 mmol) and NaHCO$_3$ (2.473 g, 29.4 mmol) in THF (31 mL) and DCM (98 mL) was treated dropwise with phenyl chloroformate (3.51 mL, 28.0 mmol). The resultant brown suspension was stirred at it for 20 h. The mixture was filtered and the filtrate diluted with DCM (50 mL). The filtrate was washed with water (120 mL) and the DCM phase was filtered through phase-sep cartridge. The resulting filtrate was concentrated in vacuo giving the product as a dark pink solid. The material was triturated with cyclohexane (60 mL) and filtered to afford the sub-title compound (5.54 g).

$^1$H NMR (400 MHz, Acetonitrile-d3) δ 8.57 (d, 1H), 8.25 (m, 2H), 7.90 (m, 1H), 7.83 (d, 1H), 7.72 (ddd, 1H), 7.62 (ddd, 1H), 7.53-7.43 (m, 2H), 7.39 (d, 1H), 7.35-7.27 (m, 3H), 7.16 (d, 1H). LCMS m/z 392/394 (M+H)$^+$ (ES$^+$)

(ii) 1-(5-(tert-Butyl)-3-(dimethylphosphoryl)-2-methoxyphenyl)-3-(4-((2-chloropyrimidin-4-yl)oxy)naphthalen-1-yl)urea TEA (150 μL, 1.076 mmol) was added to a solution of the product from step (i) above (2 g, 5.10 mmol) and (3-amino-5-(tert-butyl)-2-methoxyphenyl)dimethylphosphine oxide (see Example 1(x) above; 1.4 g, 5.48 mmol) in THF (30 mL) and the reaction heated at 60° C. (block temperature) for 16 h. The resultant precipitate was filtered off to give 1.5 g as a pale pink solid. The solid was stirred in MeOH for 72 h and filtered. The filtrate was evaporated to give the sub-title compound (500 mg) as a colourless solid.

$^1$H NMR (400 MHz, DMSO-d$_6$) δ 9.37 (s, 1H), 8.92 (s, 1H), 8.67 (d, 1H), 8.44 (d, 1H), 8.30 (d, 1H), 8.13 (d, 1H), 7.82 (d, 1H), 7.77-7.67 (m, 1H), 7.65-7.57 (m, 1H), 7.45 (d, 1H), 7.36 (dd, 1H), 7.28 (d, 1H), 3.90 (s, 3H), 1.75 (d, 6H), 1.30 (s, 9H). LCMS m/z 553/555 (M+H)$^+$ (ES$^+$)

(iii) 1-(5-(tert-Butyl)-3-(dimethylphosphoryl)-2-methoxyphenyl)-3-(4-((2-((3,5-dimethoxyphenyl)amino)pyrimidin-4-yl)oxy)naphthalen-1-yl)urea The product from step (ii) above (100 mg, 0.181 mmol) was dissolved in DMF (3 mL) and added to 3,5-dimethoxyaniline (50 mg, 0.326 mmol) and p-TsOH monohydrate (15 mg, 0.079 mmol). The reaction was stirred at 70° C. (block temperature) for 7 h. The reaction was cooled to rt and poured into sat. NaHCO$_3$ solution (20 mL) and the product extracted with EtOAc (2×20 mL). Organics bulked and washed with 20% w/w brine solution (20 mL) separated and dried (MgSO4), filtered and evaporated. The crude product was purified by preparative HPLC (Varian, Basic (0.1% Ammonium Bicarbonate), Basic, Waters X-Bridge Prep-C18, 5 μm, 19×50 mm column, 25-70% MeCN in Water) to afford the title compound (100 mg) as a colourless solid.

$^1$H NMR (400 MHz, DMSO-d$_6$) δ 9.36 (s, 1H), 9.23 (s, 1H), 8.84 (s, 1H), 8.37 (d, 1H), 8.34 (d, 1H), 8.19 (d, 1H), 8.05 (d, 1H), 7.77 (d, 1H), 7.65-7.56 (m, 1H), 7.55-7.48 (m, 1H), 7.34 (d, 1H), 7.28 (dd, 1H), 6.69 (s, 2H), 6.49 (d, 1H), 5.92 (t, 1H), 3.83 (s, 3H), 3.44 (s, 6H), 1.68 (d, 6H), 1.23 (s, 9H). LCMS m/z 670 (M+H)$^+$ (ES$^+$)

Example 19

1-(5-(tert-Butyl)-2-methoxy-3-((methylsulfonyl)methyl)phenyl)-3-(4-((2-(phenylamino)pyridin-4-yl)oxy)naphthalen-1-yl)urea

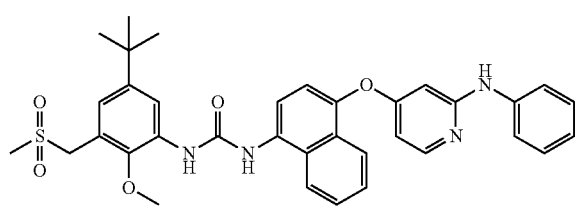 [SMILES: COc1c(CS(C)(=O)=O)cc(C(C)(C)C)cc1NC(=O)Nc1ccc(Oc2ccnc(Nc3ccccc3)c2)c2ccccc12]

(i) Phenyl (5-(tert-butyl)-2-methoxy-3-((methylsulfonyl)methyl)phenyl)carbamate

Phenyl chloroformate (90 μL, 0.717 mmol) was added to a stirred suspension of 5-(tert-butyl)-2-methoxy-3-((methylsulfonyl)methyl)aniline (see, for example, Wagner, H. et al., WO 2010/026096, 11 Mar. 2010; 180 mg, 0.663 mmol) and NaHCO$_3$ (120 mg, 1.428 mmol) in THF (1 mL) and DCM (1 mL) and stirred at rt for 2 h. The mixture was diluted with DCM (30 mL) then washed with water (30 mL) and saturated brine (30 mL). The organic phase was dried (MgSO$_4$) then concentrated to yield an oil. The oil was crystallised from cyclohexane (20 mL) to afford the sub-title compound (210 mg) as a white solid.

LCMS m/z 392 (M+H)$^+$ (ES$^+$); 296 (M-PhOH)$^-$ (ES$^-$)

(ii) 1-(5-(tert-Butyl)-2-methoxy-3-((methylsulfonyl)methyl)phenyl)-3-(4-((2-(phenylamino)-pyridin-4-yl)oxy)naphthalen-1-yl)urea The product from step (i) above (70 mg, 0.179 mmol), 4-((4-aminonaphthalen-1-yl)oxy)-N-phenylpyridin-2-amine (see Example 11(ii) above; 58.5 mg, 0.179 mmol) and Et$_3$N (8 μL, 0.057 mmol) were heated to 60° C. in THF (2 mL) for 18 h. The mixture was concentrated under reduced pressure to remove volatile components then redissolved in DCM (10 mL). 1 M Na$_2$CO$_3$ solution (5 mL) was added then the whole was passed through a phase separation cartridge and concentrated under reduced pressure. The crude product was purified by chromatography on the Companion (12 g column, 0.5-2.5% MeOH/DCM) to afford a foam. The foam was recrystallised by dissolving in acetonitrile (5 mL), then adding water (4 mL) and leaving in an open vial over the weekend to afford the title compound (57 mg) as a white crystalline solid.

$^1$H NMR (400 MHz, DMSO-d$_6$) δ: 9.39 (s, 1H), 8.92 (s, 1H), 8.91 (s, 1H), 8.34 (d, 1H), 8.30 (d, 1H), 8.12 (d, 1H), 8.08 (d, 1H), 7.88 (d, 1H), 7.71 (ddd, 1H), 7.61 (ddd, 1H), 7.61-7.56 (m, 2H), 7.39 (d, 1H), 7.25-7.16 (m, 2H), 7.13 (d, 1H), 6.87-6.81 (m, 1H), 6.56 (dd, 1H), 6.09 (d, 1H), 4.51 (s, 2H), 3.82 (s, 3H), 3.02 (s, 3H), 1.29 (s, 9H). LCMS m/z 625 (M+H)$^+$ (ES$^+$); 623 (M-H)$^-$ (ES$^-$)

Example 20

1-(5-(tert-Butyl)-3-((dimethylphosphoryl)methoxy)-2-methoxyphenyl)-3-(4-((2-((3,5-dimethoxyphenyl)amino)pyrimidin-4-yl)oxy)naphthalen-1-yl)urea

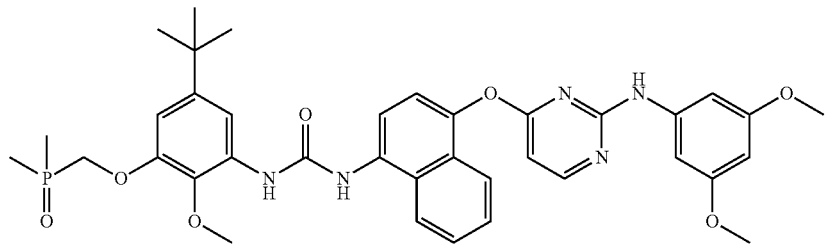

(i) tert-Butyl (4-((2-((3,5-dimethoxyphenyl)amino)pyrimidin-4-yl)oxy)naphthalen-1-yl)carbamate tert-Butyl (4-((2-chloropyrimidin-4-yl)oxy)naphthalen-1-yl)carbamate (see, for example, Ito, K. et al., WO 2010/067130, 17 Jun. 2010; 300 mg, 0.807 mmol) was dissolved in DMF (10 mL) and added to 3,5-dimethoxyaniline (200 mg, 1.306 mmol) and p-TsOH monohydrate (62 mg, 0.326 mmol). The reaction was stirred at 70° C. (block temperature) for 7 h. The reaction was cooled to rt and poured into sat. NaHCO$_3$ solution (100 mL) resulting in the precipitation of a beige solid. The solid was collected by filtration, washing with additional water. The solid was dissolved in DCM and concentrated in vacuo onto silica gel. The crude product was purified by chromatography on the Companion (40 g column, 20-50% EtOAc in hexane) to afford the sub-title compound (275 mg) as a white solid.

$^1$H NMR (400 MHz, DMSO-d$_6$) δ: 9.44 (s, 1H), 9.34 (s, 1H), 8.42 (d, 1H), 8.11 (d, 1H), 7.82 (d, 1H), 7.53-7.63 (m, 3H), 7.39 (d, 1H), 6.82 (s, 2H), 6.57 (d, 1H), 6.02 (t, 1H), 3.50 (s, 6H), 1.52 (s, 9H). LCMS m/z 489 (M+H)$^+$ (ES$^+$), 487 (M–H)$^-$ (ES$^-$)

(ii) 4-((4-Aminonaphthalen-1-yl)oxy)-N-(3,5-dimethoxyphenyl)pyrimidin-2-amine TFA (1 mL, 12.98 mmol) was added to a stirred solution of the product from step (i) above (275 mg, 0.563 mmol) in DCM (10 mL) at rt then stirred overnight. The reaction mixture was concentrated in vacuo then the residue partitioned between DCM/THF (4:1) and NaHCO$_3$ aq. solution. The organic phase was dried (MgSO$_4$), filtered and concentrated in vacuo to afford the sub-title compound (200 mg) as a pale pink foam.

LCMS m/z 389 (M+H)$^+$ (ES$^+$)

(iii) Phenyl (5-(tert-butyl)-3-((dimethylphosphoryl)methoxy)-2-methoxyphenyl)carbamate Phenyl chloroformate (360 μL, 2.87 mmol) was added to a stirred mixture of ((3-amino-5-(tert-butyl)-2-methoxyphenoxy)methyl)dimethylphosphine oxide (see Example 6(ii) above; 820 mg, 2.87 mmol) and NaHCO$_3$ (483 mg, 5.75 mmol) in DCM (25 mL) and THF (8 mL) at rt for 5 h. The mixture was diluted with DCM (20 mL) and water (20 mL). The organic layer was separated and dried via a hydrophobic frit, affording a white foam. The material was suspended in cyclohexane (20 mL) and stirred for 2 h. The product was isolated by filtration washing with hexane to afford the sub-title compound (1.06 g) as a white solid.

LCMS m/z 406 (M+H)$^+$ (ES$^+$)

(iv) 1-(5-(tert-Butyl)-3-((dimethylphosphoryl)methoxy)-2-methoxyphenyl)-3-(4-((2-((3,5-dimethoxyphenyl)amino)pyrimidin-4-yl)oxy)naphthalen-1-yl)urea A mixture of the product from step (ii) above (100 mg, 0.257 mmol), the product from step (iii) above (104 mg, 0.257 mmol) and Et$_3$N (8 μL, 0.057 mmol) in iPrOAc (6 mL) was heated at 60° C. overnight. The reaction was diluted with DCM and concentrated in vacuo onto silica gel. The crude product was purified by chromatography on the Companion (40 g column, 3-6% MeOH in DCM) to afford a pink solid. The crude product was purified by preparative HPLC (Gilson, Acidic (0.1% Formic acid), Acidic, Waters X-Select Prep-C18, 5 μm, 19×50 mm column, 25-70% MeCN in Water) to afford the title compound (63 mg) as an off-white solid.

$^1$H NMR (400 MHz, DMSO-d$_6$) δ: 9.45 (s, 1H), 9.38 (s, 1H), 8.87 (s, 1H), 8.42 (d, 1H), 8.28 (d, 1H), 8.05-8.08 (m, 2H), 7.94 (d, 1H), 7.67 (t, 1H), 7.59 (t, 1H), 7.40 (d, 1H), 6.83 (d, 1H), 6.77 (s, 2H), 6.57 (d, 1H), 6.00 (s, 1H), 4.39 (d, 2H), 3.86 (s, 3H), 3.51 (s, 6H), 1.58 (d, 6H), 1.29 (s, 9H). LCMS m/z 700 (M+H)$^+$ (ES$^+$); 698 (M–H)$^-$ (ES$^-$)

Example 21

1-(5-(tert-Butyl)-3-(dimethylphosphoryl)-2-methoxyphenyl)-3-(4-((2-((3-(dimethylphosphoryl)-5-methoxyphenyl)amino)pyrimidin-4-yl)oxy)naphthalen-1-yl)urea

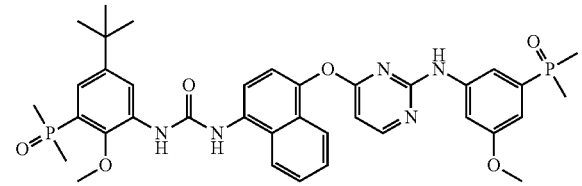 [SMILES: COc1cc(Nc2nccc(Oc3ccc(NC(=O)Nc4cc(C(C)(C)C)cc(P(C)(C)=O)c4OC)c4ccccc34)n2)cc(P(C)(C)=O)c1]

(i) (3-Methoxy-5-nitrophenyl)dimethylphosphine oxide

1-Bromo-3-methoxy-5-nitrobenzene (500 mg, 2.155 mmol), xantphos (125 mg, 0.215 mmol), Pd(OAc)$_2$ (24.19 mg, 0.108 mmol) and potassium phosphate tribasic monohydrate (503 mg, 2.155 mmol) were combined under N$_2$ in a microwave tube containing a magnetic stirrer. Dimethylphosphine oxide (181 μL, 2.59 mmol) was dissolved in degassed anhydrous DMF (4 mL). Reactants were combined under nitrogen and the reaction was heated at 120° C. for 40 min. The mixture was filtered and the solvents evaporated. The crude product was purified by chromatography on the Companion (40 g column, 2% MeOH:DCM to 5%) to afford the sub-title compound (310 mg) as a pale yellow solid.

$^1$H NMR (400 MHz, CDCl$_3$) δ 8.02 (ddd, 1H), 7.87 (t, 1H), 7.73 (ddd, 1H), 3.96 (s, 3H), 1.80 (d, 6H).

(ii) (3-Amino-5-methoxyphenyl)dimethylphosphine oxide

Pd—C, 10% w/w (30 mg) was added to a solution of the product from step (i) above (300 mg, 1.309 mmol) in ethanol (3 mL) and stirred under hydrogen for 16 h. The mixture was filtered and solvents evaporated to give a yellow gum. The product was redissolved in EtOH (3 mL) and Pd—C, 10% w/w (30 mg) added before stirring for an additional 3 h. The mixture was filtered and solvent evaporated to afford the sub-title compound (250 mg) as a yellow gum.

$^1$H NMR (400 MHz, DMSO) δ 6.54 (dt, 1H), 6.40 (d, 1H), 6.27 (t, 1H), 5.37 (s, 2H), 3.70 (s, 3H), 1.56 (d, 6H). LCMS m/z 200 (M+H)$^+$ (ES$^+$)

(iii) 1-(5-(tert-Butyl)-3-(dimethylphosphoryl)-2-methoxyphenyl)-3-(4-((2-((3-(dimethylphosphoryl)-5-methoxyphenyl)amino)pyrimidin-4-yl)oxy)naphthalen-1-yl)urea In a 20 mL vial, a solution of 1-(5-(tert-butyl)-3-(dimethylphosphoryl)-2-methoxyphenyl)-3-(4-((2-chloropyrimidin- 4-yl)oxy)naphthalen-1-yl)urea (see Example 18(ii) above; 100 mg, 0.181 mmol) and the product from step (ii) above (100 mg, 0.502 mmol) in DMF (3 mL) was treated with p-TsOH monohydrate (15 mg, 0.079 mmol). The reaction was stirred at 70° C. (block temperature) for 7 h then cooled to rt and poured into sat. NaHCO$_3$ solution (20 mL) and the product extracted with EtOAc (2×20 mL). Organics combined and washed with 20% w/w brine solution (20 mL) separated, dried (Na$_2$SO$_4$), filtered and evaporated. The crude product was purified by chromatography on silica gel (40 g column, 2-10% MeOH in DCM) to afford the title compound (95 mg) as a solid.

$^1$H NMR (400 MHz, DMSO-d$_6$) δ 9.66 (s, 1H), 9.36 (s, 1H), 8.97 (s, 1H), 8.54-8.37 (m, 2H), 8.28 (d, 1H), 8.14 (d, 1H), 7.91-7.77 (m, 1H), 7.74-7.63 (m, 1H), 7.63-7.54 (m, 1H), 7.50-7.39 (m, 2H), 7.40-7.28 (m, 2H), 6.84-6.70 (m, 1H), 6.60 (d, 1H), 3.90 (s, 3H), 3.58 (s, 3H), 1.75 (d, 6H), 1.51 (d, 6H), 1.30 (s, 9H). LCMS m/z 716 (M+H)$^+$ (ES$^+$)

Example 22

1-(5-(tert-Butyl)-3-(dimethylphosphoryl)-2-methoxyphenyl)-3-(4-((2-((3-((dimethyl(oxo)-lambda-6-sulfanylidene)amino)phenyl)amino)pyrimidin-4-yl)oxy)naphthalen-1-yl)urea

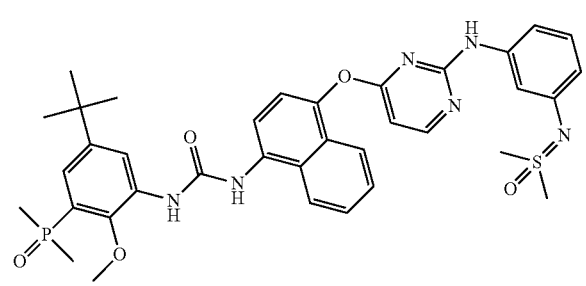 [SMILES: COc1c(NC(=O)Nc2ccc(Oc3ccnc(Nc4cccc(N=S(C)(C)=O)c4)n3)c3ccccc23)cc(C(C)(C)C)cc1P(C)(C)=O]

(i) S,S-Dimethyl-N-(3-nitrophenyl)-sulfoximine

A solution of DMSO (5 mL, 70.5 mmol) in DCM (15 mL) was added slowly to a stirred solution of tert-butyl hypochlorite (2.61 g, 24 mmol) in DCM (40 mL) at −60° C. under N$_2$. The mixture was stirred for 1 h then a mixture of 3-nitroaniline (2.76 g, 20 mmol) in DCM (80 mL) was added. After stirring for 6 h at −50° C., a solution of Et$_3$N (5 mL, 35.9 mmol) in DCM (10 mL) was added and the mixture allowed to warm to rt. The solvent was evaporated under reduced pressure and the residue partitioned between EtOAc (200 mL) and water (200 mL). The organic layer was separated, washed with brine, dried (MgSO$_4$) and evaporated under reduced pressure. The crude product was purified by chromatography on silica gel (80 g column, 10-80% EtOAc/isohexane) to afford the sub-title compound (1.237 g) as a yellow solid.

$^1$H NMR (400 MHz; CDCl$_3$) δ 7.89-7.88 (m, 1H), 7.83-7.81 (m, 1H), 7.41-7.35 (m, 2H), 3.21 (s, 6H). LCMS m/z 215 (M+H)$^+$ (ES$^+$)

(ii) S,S-Dimethyl-N-(3-aminophenyl)-sulfoximine

A stirred mixture of the product from step (i) above (1.23 g, 5.74 mmol) and 10% Pd/C (200 mg) in EtOH (25 mL) was hydrogenated under a balloon of hydrogen for 5 h. The mixture was flushed with nitrogen, filtered and evaporated under reduced pressure to afford the sub-title compound (1.006 g) as solid.

$^1$H NMR (DMSO-de) 400 MHz, δ: 6.80 (t, 1H), 6.22 (s, 1H), 6.12-6.09 (m, 2H), 4.86 (s, 2H), 3.15 (s, 6H).

(iii) 1-(5-(tert-butyl)-3-(dimethylphosphoryl)-2-methoxyphenyl)-3-(4-((2-((3-((dimethyl(oxo)-lambda-6-sulfanylidene)amino)phenyl)amino)pyrimidin-4-yl)oxy)naphthalen-1-yl)urea In a 20 mL vial, a solution of 1-(5-(tert-butyl)-3-(dimethylphosphoryl)-2-methoxyphenyl)-3-(4-((2-chloropyrimidin-4-yl)oxy)naphthalen-1-yl)urea (see Example 18(ii) above; 100 mg, 0.181 mmol) and the product from step (ii) above (66 mg, 0.358 mmol) in DMF (3 mL) was treated with p-TsOH monohydrate (15 mg, 0.079 mmol). The reaction was stirred at 70° C. (block temperature) for 7 h. The reaction was cooled to it and poured into sat. NaHCO$_3$ solution (20 mL) and the product extracted with EtOAc (2×20 mL). Organics were combined and washed with 20% w/w brine solution (20 mL), separated, dried (Na$_2$SO$_4$), filtered and evaporated. The crude product was purified by chromatography on silica gel (40 g column, 2-20% MeOH in DCM) to afford the title compound (75 mg) as a solid.

$^1$H NMR (400 MHz, DMSO-d$_6$) δ 9.37 (s, 2H), 8.92 (s, 1H), 8.46 (d, 1H), 8.37 (d, 1H), 8.28 (d, 1H), 8.10 (d, 1H), 7.90-7.77 (m, 1H), 7.73-7.64 (m, 1H), 7.64-7.55 (m, 1H), 7.43 (d, 1H), 7.36 (dd, 1H), 7.09 (s, 1H), 6.93 (d, 1H), 6.79 (t, 1H), 6.49 (d, 1H), 6.47-6.39 (m, 1H), 3.91 (s, 3H), 3.36 (s, 6H), 1.75 (d, 6H), 1.30 (s, 9H). LCMS m/z 701 (M+H)$^+$ (ES$^+$)

Example 23

5-(tert-Butyl)-2-methoxy-3-(3-(4-((2-(phenylamino) pyridin-4-yl)oxy)naphthalen-1-yl)ureido)-N-(2-(piperazin-1-yl)ethyl)benzamide

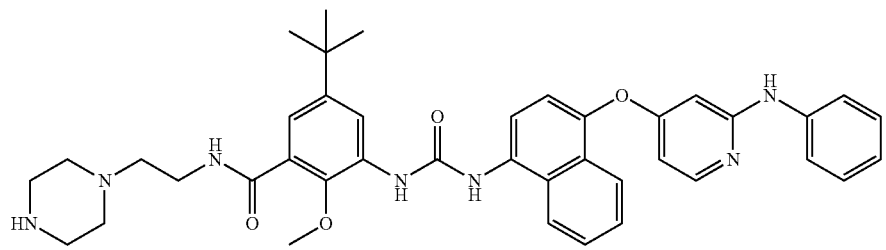 [SMILES: COc1c(NC(=O)Nc2ccc(Oc3ccnc(Nc4ccccc4)c3)c3ccccc23)cc(C(C)(C)C)cc1C(=O)NCCN1CCNCC1]

(i) tert-Butyl 4-(2-(5-(tert-butyl)-2-methoxy-3-(3-(4-((2-(phenylamino)pyridin-4-yl)oxy)-naphthalen-1-yl)ureido)benzamido)ethyl)piperazine-1-carboxylate A stirred mixture of 5-(tert-butyl)-2-methoxy-3-(3-(4-((2-(phenylamino)pyridin-4-yl)oxy)naphthalen-1-yl)ureido)benzoic acid, HCl (see Example 14(iii) above; 80 mg, 0.130 mmol), tert-butyl 4-(2-aminoethyl)piperazine-1-carboxylate (59.8 mg, 0.261 mmol) and triethylamine (72.7 μL, 0.522 mmol) in DCM (4 mL) was cooled in an ice-bath. 50 wt % T3P in EtOAc (93 μL, 0.157 mmol) was added, the ice-bath was removed and the reaction mixture allowed to warm to rt and stirred for 36 h. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford the sub-title compound (52 mg) as a pink/brown solid.

LCMS m/z 788 (M+H)$^+$ (ES$^+$); 786 (M−H)$^−$ (ES$^−$)

(ii) 5-(tert-Butyl)-2-methoxy-3-(3-(4-((2-(phenylamino)pyridin-4-yl)oxy)naphthalen-1-yl)ureido)-N-(2-(piperazin-1-yl)ethyl)benzamide TFA (100 μL, 1.298 mmol) was added dropwise to a stirred solution of the product from step (i) above (52 mg, 0.066 mmol) in DCM (2 mL). The reaction was stirred at rt overnight then concentrated in vacuo and the residue partitioned between DCM (3 mL) and sat. NaHCO$_3$ soln. (4 mL). The aqueous phase was separated and extracted with DCM (2 mL). The combined organics were dried (MgSO$_4$), filtered and concentrated in vacuo to afford the title compound (49 mg) as a pink/brown solid.

$^1$H NMR (400 MHz, DMSO-d$_6$) δ: 9.46 (s, 1H), 8.91 (d, 2H), 8.47 (d, 1H), 8.30 (d, 1H), 8.24 (t, 1H), 8.08-8.10 (m, 2H), 7.89 (d, 1H), 7.72 (t, 1H), 7.58-7.64 (m, 3H), 7.39 (d, 1H), 7.27 (d, 1H), 7.20 (t, 2H), 6.84 (t, 1H), 6.55 (dd, 1H), 6.11 (d, 1H), 3.84 (s, 3H), 3.43 (q, 2H), 1H under H$_2$O, 2.77-2.80 (m, 4H), 2H under DMSO, 2.42 (bs, 4H), 1.29 (s, 9H).

LCMS m/z 345 (M+2H)$^{2+}$ (ES$^+$)

Example 24

1-(5-(tert-Butyl)-3-((dimethylphosphoryl)methyl)-2-methoxyphenyl)-3-(4-((2-(phenylamino)-pyridin-4-yl)oxy)naphthalen-1-yl)urea

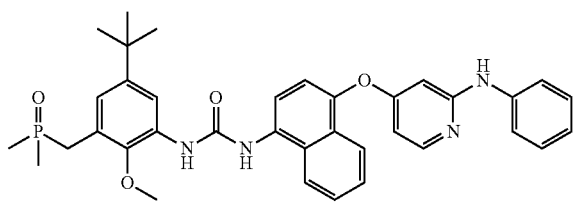 [SMILES: COc1c(CP(C)(C)=O)cc(C(C)(C)C)cc1NC(=O)Nc1ccc(Oc2ccnc(Nc3ccccc3)c2)c2ccccc12]

(i) 5-(tert-Butyl)-1-(chloromethyl)-2-methoxy-3-nitrobenzene

SOCl$_2$ (2.0 mL, 27.4 mmol) was added carefully to a solution of (5-(tert-butyl)-2-methoxy-3-nitrophenyl)methanol (see Example 13(i) above; 5.5 g, 22.99 mmol) in DCM (80 mL) at rt. The mixture was stirred for 18 h then diluted with toluene (200 mL) and concentrated under reduced pressure. The residue was purified by chromatography on silica gel (50 g column, 50% DCM/isohexane) to afford the sub-title compound (5.05 g) as a yellow oil which crystallised on standing.

$^1$H NMR (CDCl$_3$) 400 MHz, δ: 7.84 (d, 1H), 7.69 (d, 1H), 4.70 (s, 2H), 4.00 (s, 3H), 1.37 (s, 9H).

(ii) (5-(tert-Butyl)-2-methoxy-3-nitrobenzyl)dimethylphosphine oxide

Chlorodimethylphosphine (4.10 mL, 51.8 mmol) was added dropwise to a stirred solution of Hünig's Base (10 mL, 57.3 mmol) and methanol (2.2 mL, 54.4 mmol) in THF (50 mL) at 0-5° C. under N$_2$. The mixture was warmed to rt, stirred for 1 h then the solid filtered and washed with THF (10 mL). A solution of the product from step (i) above (3.5 g, 13.58 mmol) in THF (15 mL) was added to the filtrate and the solution heated at 100° C. for 24 h in a sealed vessel. The mixture was cooled and evaporated under reduced pressure. The crude product was purified by chromatography on silica gel (220 g column, 2-8% MeOH/DCM) to afford the sub-title compound (0.91 g) as a yellow oil.

$^1$H NMR (400 MHz; CDCl$_3$) δ 7.77 (dd, 1H), 7.66 (dd, 1H), 3.91 (s, 3H), 3.72 (d, 6H), 3.64 (d, 2H), 1.35 (s, 9H). LCMS m/z 300 (M+H)$^+$ (ES$^+$), 85% purity (iii) (3-Amino-5-(tert-butyl)-2-methoxybenzyl)dimethylphosphine oxide The product from step (ii) above (910 mg, 2.58 mmol), iron powder (1.5 g, 26.9 mmol) and NH$_4$Cl (150 mg, 2.80 mmol) were heated to reflux in ethanol (16 mL) and water (4 mL) for 1 h. The mixture was filtered through celite and the filtrate was concentrated under reduced pressure to yield the crude product. The crude product was purified by chromatography on the Companion (40 g column, 1-5% MeOH/DCM) to afford the sub-title compound (300 mg) as a yellow oil which crystallised on standing.

LCMS m/z 270 (M+H)$^+$ (ES$^+$)

(iv) Phenyl (5-(tert-butyl)-3-((dimethylphosphoryl)methyl)-2-methoxyphenyl)carbamate Phenyl chloroformate (150 μL, 1.196 mmol) was added to a stirred suspension of the product from step (iii) above (300 mg, 1.114 mmol) and NaHCO$_3$ (200 mg, 2.381 mmol) in THF (5 mL) and DCM (5 mL) and stirred at it for 2 h. The mixture was diluted with DCM (50 mL) then washed with water (50 mL) and saturated brine (50 mL). The organic phase was dried (MgSO$_4$) then concentrated to yield a solid. The solid was triturated in diethyl ether (20 mL) to yield the sub-title compound (285 mg) as a white solid.

$^1$H NMR (400 MHz, CDCl$_3$) δ: 8.12 (br s, 1H), 7.44-7.35 (m, 3H), 7.27-7.22 (m, 1H), 7.22-7.16 (m, 2H), 6.97-6.91 (m, 1H), 3.81 (s, 3H), 3.29 (d, 2H), 1.48 (d, 6H), 1.26 (s, 9H).

LCMS m/z 390 (M+H)$^+$ (ES$^+$)

(v) 1-(5-(tert-Butyl)-3-((dimethylphosphoryl)methyl)-2-methoxyphenyl)-3-(4-((2-(Phenylamino)pyridin-4-yl)oxy)naphthalen-1-yl)urea The product from step (iv) above (90 mg, 0.231 mmol), 4-((4-aminonaphthalen-1-yl)oxy)-N-phenylpyridin-2-amine (see Example 11(ii) above; 76 mg, 0.231 mmol) and Et₃N (10 µL, 0.072 mmol) were heated to 60° C. (block temp) in THF (3 mL) for 18 h. The volatiles were removed under reduced pressure and the crude product was purified by chromatography on the Companion (40 g column, 3-10% MeOH/DCM) to afford the title compound (70 mg) as a pale pink solid.

¹H NMR (400 MHz, DMSO-d₆) δ: 9.38 (s, 1H), 8.90 (s, 1H), 8.84 (s, 1H), 8.30 (s, 1H), 8.21 (dd, 1H), 8.11 (d, 1H), 8.08 (d, 1H), 7.86 (dd, 1H), 7.69 (ddd, 1H), 7.64-7.54 (m, 3H), 7.38 (d, 1H), 7.19 (ddd, 2H), 6.97 (dd, 1H), 6.84 (ddd, 1H), 6.55 (dd, 1H), 6.09 (d, 1H), 3.79 (s, 3H), 3.19 (d, 2H), 1.40 (d, 6H), 1.26 (s, 9H). LCMS m/z 623 (M+H)⁺ (ES⁺); 621 (M−H)⁻ (ES⁻)

Example 25

1-(5-(tert-Butyl)-2-methoxy-3-((methylsulfinyl)methyl)phenyl)-3-(4-((2-(phenylamino)pyridin-4-yl)oxy)naphthalen-1-yl)urea

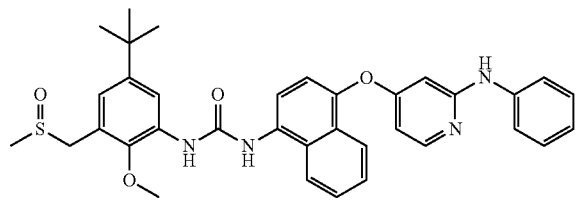 [SMILES: COc1c(CS(C)=O)cc(C(C)(C)C)cc1NC(=O)Nc1ccc(Oc2ccnc(Nc3ccccc3)c2)c2ccccc12]

(i) Phenyl (5-(tert-butyl)-2-methoxy-3-((methylsulfinyl)methyl)phenyl)carbamate

Phenyl chloroformate (115 µL, 0.917 mmol) was added to a stirred suspension of 5-(tert-butyl)-2-methoxy-3-((methylsulfinyl)methyl)aniline (see, for example, Wagner, H. et al., WO 2010/026096, 11 Mar. 2010; 220 mg, 0.861 mmol) and NaHCO₃ (150 mg, 1.786 mmol) in THF (3 mL) and DCM (3 mL) and stirred at rt for 18 h. The mixture was diluted with DCM (10 mL) then washed with water (10 mL) and saturated brine (10 mL). The organic phase was dried (MgSO₄) then concentrated to yield a gum. The gum was crystallised from cyclohexane (20 mL) to yield the sub-title compound (215 mg) as a cream-white solid.

LCMS m/z 376 (M+H)⁺ (ES⁺).

(ii) 1-(5-(tert-Butyl)-2-methoxy-3-((methylsulfinyl)methyl)phenyl)-3-(4-((2-(phenylamino)-pyridin-4-yl)oxy)naphthalen-1-yl)urea The product from step (i) above (70 mg, 0.186 mmol), 4-((4-aminonaphthalen-1-yl)oxy)-N-phenylpyridin-2-amine (see Example 11(ii) above; 62 mg, 0.189 mmol) and Et₃N (8 µL, 0.057 mmol) were heated to 60° C. (block temp) in THF (3 mL) for 18 h. The crude product was purified by chromatography on the Companion (40 g column, 3-7% MeOH/DCM) to afford a pale yellow solid. The solid was further purified by chromatography on the Companion (12 g column, 0-25% acetone/EtOAc) to afford a sticky pink gum. The gum was redissolved in tert-butyl acetate (3 mL) and diluted with isohexane (6 mL). The resulting precipitate was collected by filtration to afford the title compound (45 mg) as a pale pink solid.

¹H NMR (400 MHz, DMSO-d₆) δ: 9.40 (s, 1H), 8.91 (s, 1H), 8.89 (s, 1H), 8.31 (s, 1H), 8.30 (d, 1H), 8.12 (d, 1H), 8.09 (d, 1H), 7.87 (d, 1H), 7.71 (ddd, 1H), 7.65-7.55 (m, 3H), 7.39 (d, 1H), 7.20 (ddd, 2H), 7.03 (d, 1H), 6.84 (ddd, 1H), 6.56 (dd, 1H), 6.08 (d, 1H), 4.13 (d, 1H), 4.05 (d, 1H), 3.81 (s, 3H), 2.61 (s, 3H), 1.28 (s, 9H). LCMS m/z 609 (M+H)⁺ (ES⁺); 607 (M−H)⁻ (ES⁻)

Example 26

N-(4-((4-(3-(5-(tert-Butyl)-3-(dimethylphosphoryl)-2-methoxyphenyl)ureido)naphthalen-1-yl)oxy)pyridin-2-yl)-2-(cis-2,6-dimethylmorpholino)acetamide

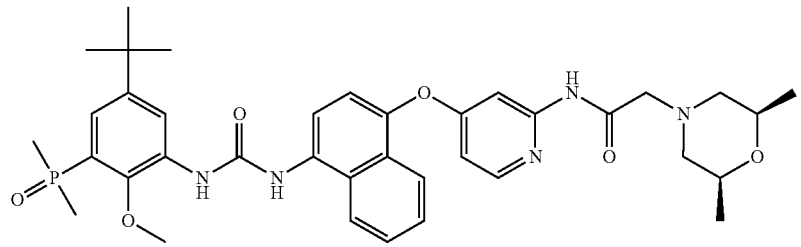 [SMILES: COc1c(NC(=O)Nc2ccc(Oc3ccnc(NC(=O)CN4C[C@@H](C)O[C@@H](C)C4)c3)c3ccccc23)cc(C(C)(C)C)cc1P(C)(C)=O]

(i) 2-(cis)-2,6-Dimethylmorpholino)-N-(4-((4-nitronaphthalen-1-yl)oxy)pyridin-2-yl)acetamide Chloroacetyl chloride (290 µL, 3.62 mmol) was added to a solution of 4-((4-nitronaphthalen-1-yl)oxy)pyridin-2-amine (see, for example, King-Underwood, J. et al., WO 2011/124930, 13 Oct. 2011; 1 g, 3.56 mmol) and Et₃N (1 mL, 7.17 mmol) in DCM (20 mL) at 0-5° C. under N₂. The mixture was stirred for 30 min then a further portion of chloroacetyl chloride (200 µL) was added. After 10 min cis-2,6-dimethylmorpholine (825 mg, 7.16 mmol) was added, the mixture warmed to rt and stirred for 24 h. The mixture was partitioned between DCM (100 mL) and water (100 mL), the organic layer washed with brine (50 mL), dried (MgSO₄), filtered and evaporated under reduced pressure. The crude product was purified by chromatography on silica gel (80 g column, 0-80% EtOAc/isohexane) to afford the sub-title compound (886 mg) as a foam.

LCMS m/z 437 (M+H)⁺ (ES⁺); 435 (M−H)⁻ (ES⁻)

(ii) N-(4-((4-aminonaphthalen-1-yl)oxy)pyridin-2-yl)-2-(cis-2,6-dimethylmorpholino)acetamide A mixture of the product from step (i) above (880 mg, 2.016 mmol), Fe powder (1.2 g, 21.49 mmol) and NH$_4$Cl (55 mg, 1.028 mmol) in EtOH (20 mL) and water (5 mL) was heated at 80° C. for 1 h. The mixture was filtered through celite, washing with EtOAc (120 mL). The filtrate was washed with sat aq NaHCO$_3$ (50 mL), brine (50 mL), dried (MgSO$_4$), filtered and evaporated under reduced pressure. The crude product was purified by chromatography on silica gel (40 g column, 0-70% EtOAc-isohexane) to afford the sub-title compound (564 mg) as a foam.

$^1$H NMR (CDCl$_3$) 400 MHz, δ: 8.08 (d, 1H), 7.96 (s, 1H), 7.90-7.84 (m, 2H), 7.55-7.46 (m, 2H), 7.09 (d, 1H), 6.69 (d, 1H), 6.58 (dd, 1H), 3.91-3.81 (brm, 2H), 3.13 (s, 2H), 2.77 (d, 2H), 2.03 (t, 2H), 1.18 (d, 6H). LCMS m/z 407 (M+H)$^+$ (ES$^+$)

(iii) N-(4-((4-(3-(5-(tert-butyl)-3-(dimethylphosphoryl)-2-methoxyphenyl)ureido)naphthalen-1-yl)oxy)pyridin-2-yl)-2-(cis-2,6-dimethylmorpholino)acetamide Et$_3$N (10 μL, 0.072 mmol) was added to a solution of phenyl (5-(tert-butyl)-3-(dimethylphosphoryl)-2-methoxyphenyl)carbamate (see Example 3(vi) above; 75 mg, 0.200 mmol) and the product from step (ii) above (80 mg, 0.197 mmol) in THF (2 mL) and the reaction heated at 65° C. (block temperature) for 16 h. The reaction mixture was cooled and the resulting solid filtered off and washed with THF (1 mL) to afford the title compound (65 mg) as a colourless solid.

$^1$H NMR (400 MHz, DMSO-d$_6$) δ 9.90 (s, 1H), 9.27 (s, 1H), 8.85 (s, 1H), 8.36 (d, 1H), 8.23 (d, 1H), 8.13 (d, 1H), 8.07 (d, 1H), 7.79 (d, 1H), 7.69-7.60 (m, 1H), 7.59 (d, 1H), 7.57-7.45 (m, 1H), 7.33-7.25 (m, 2H), 6.67 (dd, 1H), 3.83 (s, 3H), 3.61-3.41 (m, 2H), 3.02 (s, 2H), 2.65 (dt, 2H), 1.76 (t, 2H), 1.67 (d, 6H), 1.23 (s, 9H), 0.96 (d, 6H). LCMS m/z 688 (M+H)$^+$ (ES$^+$); 686 (M−H)$^−$ (ES$^−$)

Example 27

1-(5-(tert-Butyl)-3-(dimethylphosphoryl)-2-methoxyphenyl)-3-(4-((2-((3,5-dimethoxyphenyl)amino)pyridin-4-yl)oxy)naphthalen-1-yl)urea

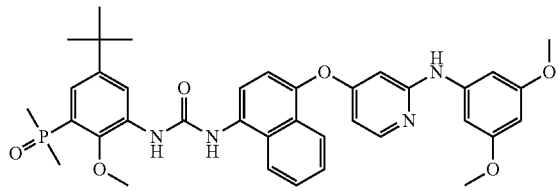 [SMILES: COc1cc(Nc2cc(Oc3ccc(NC(=O)Nc4cc(C(C)(C)C)cc(P(C)(C)=O)c4OC)c4ccccc34)ccn2)cc(OC)c1]

(i) tert-Butyl (4-((2-((3,5-dimethoxyphenyl)amino)pyridin-4-yl)oxy)naphthalen-1-yl)carbamate Pd$_2$(dba)$_3$ (120 mg, 0.131 mmol) was added to a degassed suspension of tert-butyl (4-((2-chloropyridin-4-yl)oxy)naphthalen-1-yl)carbamate (see Example 2(ii) above; 1 g, 2.70 mmol), 3,5-dimethoxyaniline (0.45 g, 2.94 mmol), xantphos (150 mg, 0.259 mmol) and Cs$_2$CO$_3$ (1.4 g, 4.30 mmol) in 1,4-dioxane (10 mL) and the reaction heated under nitrogen at 85° C. for 5 h. The reaction mixture was filtered and the solvent evaporated. The crude product was purified by chromatography on silica gel (80 g column, 1% MeOH: DCM to 4%) to give a brown foam. This product was dissolved in DCM (20 mL) partitioned with 15% w/w citric acid (20 mL). The organics were separated, dried (MgSO$_4$) filtered and evaporated to afford the sub-title compound (1.2 g) as a tan foam.

$^1$H NMR (400 MHz, DMSO-d$_6$) δ 9.36 (s, 1H), 8.95 (s, 1H), 8.13 (d, 1H), 8.10 (d, 1H), 7.87-7.80 (m, 1H), 7.67-7.52 (m, 3H), 7.35 (d, 1H), 6.83 (d, 2H), 6.58 (dd, 1H), 6.07 (d, 1H), 6.04 (t, 1H), 3.66 (s, 6H), 1.52 (s, 9H).

(ii) 4-((4-Aminonaphthalen-1-yl)oxy)-N-(3,5-dimethoxyphenyl)pyridin-2-amine

TFA (1 mL, 12.98 mmol) was added to a solution of the product from step (i) above (1.2 g, 2.461 mmol) in DCM (3 mL) and the reaction left stirring overnight. The solvents were evaporated and the residue partitioned between sat NaHCO$_3$ soln. (10 mL) and DCM (10 mL). The organics were separated, dried (MgSO$_4$), filtered and the solvent evaporated to afford the sub-title compound (930 mg) as a brown foam.

$^1$H NMR (400 MHz, DMSO-d$_6$) δ 8.82 (s, 1H), 8.20-8.09 (m, 1H), 8.04 (d, 1H), 7.70-7.55 (m, 1H), 7.53-7.35 (m, 2H), 7.10 (d, 1H), 6.82 (d, 2H), 6.71 (d, 1H), 6.52 (dd, 1H), 6.01 (d, 2H), 5.84 (s, 2H), 3.64 (s, 6H). LCMS m/z 388 (M+H)$^+$ (ES$^+$)

(iii) 1-(5-(tert-Butyl)-3-(dimethylphosphoryl)-2-methoxyphenyl)-3-(4-((2-((3,5-dimethoxyphenyl)amino)pyridin-4-yl)oxy)naphthalen-1-yl)urea Et$_3$N (10 μL, 0.072 mmol) was added to a solution of phenyl (5-(tert-butyl)-3-(dimethylphosphoryl)-2-methoxyphenyl)carbamate (see Example 3(vi) above; 75 mg, 0.200 mmol) and the product from step (ii) above (75 mg, 0.194 mmol) in THF (2 mL) and the reaction heated at 65° C. (block temperature) for 16 h. The solvents were evaporated and the crude product was purified by preparative HPLC (Gilson, Basic (0.1% Ammonium Bicarbonate), Basic, Waters X-Bridge Prep-C18, 5 μm, 19×50 mm column, 25-70% MeCN in Water) to afford a colourless solid which was triturated with MeCN (1 mL) to afford the title compound (60 mg) as a colourless solid.

$^1$H NMR (400 MHz, DMSO-d$_6$) δ 9.34 (s, 1H), 8.89 (d, 2H), 8.44 (d, 1H), 8.29 (d, 1H), 8.13 (d, 1H), 8.10 (d, 1H), 7.87 (d, 1H), 7.77-7.67 (m, 1H), 7.67-7.55 (m, 1H), 7.47-7.25 (m, 2H), 6.84 (d, 2H), 6.57 (dd, 1H), 6.09 (d, 1H), 6.02 (t, 1H), 3.90 (s, 3H), 3.66 (s, 6H), 1.75 (d, 6H), 1.31 (s, 9H). LCMS m/z 669 (M+H)$^+$ (ES$^+$); 667 (M−H)$^−$ (ES$^−$)

Example 28

1-(5-(tert-Butyl)-3-(dimethylphosphoryl)-2-methoxyphenyl)-3-(4-((2-((3,5-dimethylphenyl)amino)pyridin-4-yl)oxy)naphthalen-1-yl)urea

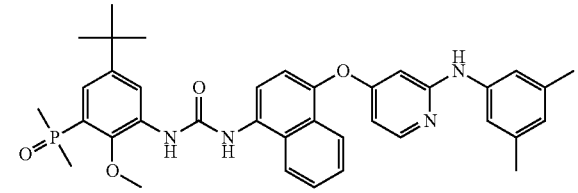 [SMILES: COc1c(NC(=O)Nc2ccc(Oc3ccnc(Nc4cc(C)cc(C)c4)c3)c3ccccc23)cc(C(C)(C)C)cc1P(C)(C)=O]

(i) tert-Butyl (4-((2-((3,5-dimethylphenyl)amino)pyridin-4-yl)oxy)naphthalen-1-yl)carbamate Pd$_2$(dba)$_3$ (40 mg, 0.044 mmol) was added to a degassed suspension of tert-butyl (4-((2-chloropyridin-4-yl)oxy)naphthalen-1-yl)carbamate (see Example 2(ii) above; 300 mg, 0.809 mmol), 3,5-dimethylaniline (100 µL, 0.802 mmol), xantphos (50 mg, 0.086 mmol) and Cs$_2$CO$_3$ (400 mg, 1.228 mmol) in 1,4-dioxane (2 mL) and the reaction heated under nitrogen at 85° C. for 5 h. The reaction mixture was filtered and the solvent evaporated. The crude product was purified by chromatography on silica gel (40 g column, 10% EtOAc:isohexane to 50%) to afford a brown foam. This product was dissolved in DCM (20 mL) partitioned with 15% w/w citric acid (20 mL). The organics were separated, dried (MgSO$_4$) filtered and evaporated to afford the sub-title compound (85 mg).

$^1$H NMR (400 MHz, DMSO-d$_6$) δ 9.38 (s, 1H), 8.78 (s, 1H), 8.13 (d, 1H), 8.08 (d, 1H), 7.89-7.78 (m, 1H), 7.64-7.52 (m, 3H), 7.35 (d, 1H), 7.21-7.07 (m, 2H), 6.54 (dd, 1H), 6.48 (s, 1H), 6.05 (d, 1H), 2.16 (s, 6H), 1.52 (s, 9H). LCMS m/z 456 (M+H)$^+$ (ES$^+$); 454 (M–H)$^-$ (ES$^-$)

(ii) 4-((4-Aminonaphthalen-1-yl)oxy)-N-(3,5-dimethylphenyl)pyridin-2-amine

TFA (500 µL, 6.49 mmol) was added to a solution of the product from step (i) above (85 mg, 0.187 mmol) in DCM (3 mL) and the reaction left stirring overnight. The solvents were evaporated and the residue partitioned between sat NaHCO$_3$ soln. (10 mL) and DCM (10 mL). The organics were separated, dried (MgSO$_4$), filtered and the solvent evaporated to afford the sub-title compound (50 mg).

LCMS m/z 356 (M+H)$^+$ (ES$^+$)

(iii) 1-(5-(tert-Butyl)-3-(dimethylphosphoryl)-2-methoxyphenyl)-3-(4-((2-((3,5-dimethylphenyl)amino)pyridin-4-yl)oxy)naphthalen-1-yl)urea Et$_3$N (5 µL, 0.036 mmol) was added to a solution of phenyl (5-(tert-butyl)-3-(dimethylphosphoryl)-2-methoxyphenyl)carbamate (see Example 3(vi) above; 55 mg, 0.147 mmol) and the product from step (ii) above (50 mg, 0.141 mmol) in THF (1 mL) and the reaction heated at 65° C. (block temperature) for 16 h. The solvent was evaporated and the crude product was purified by chromatography on silica gel (12 g column, 2% MeOH:DCM to 10%) to afford a tan foam which was stirred in MeCN (2 mL) at 50° C. for 1 h after which time a colourless solid had precipitated. The solid was filtered off and washed with MeCN (1 mL) to afford the title compound (40 mg) as a colourless solid.

$^1$H NMR (400 MHz, DMSO-d$_6$) δ 9.33 (s, 1H), 8.90 (s, 1H), 8.75 (s, 1H), 8.44 (d, 1H), 8.28 (d, 1H), 8.12 (d, 1H), 8.08 (d, 1H), 7.88 (d, 1H), 7.76-7.66 (m, 1H), 7.66-7.57 (m, 1H), 7.47-7.29 (m, 2H), 7.22-7.05 (m, 2H), 6.53 (dd, 1H), 6.49 (s, 1H), 6.09 (d, 1H), 3.90 (s, 3H), 2.16 (s, 6H), 1.75 (d, 6H), 1.31 (s, 9H). LCMS m/z 637 (M+H)$^+$ (ES$^+$); 635 (M–H)$^-$ (ES$^-$)

Example 29

1-(5-(tert-Butyl)-3-((dimethylphosphoryl)methyl)-2-methoxyphenyl)-3-(4-((2-((3-methoxy-5-(2-(2-(2-methoxyethoxy)ethoxy)ethoxy)phenyl)amino)pyridin-4-yl)oxy)naphthalen-1-yl)urea

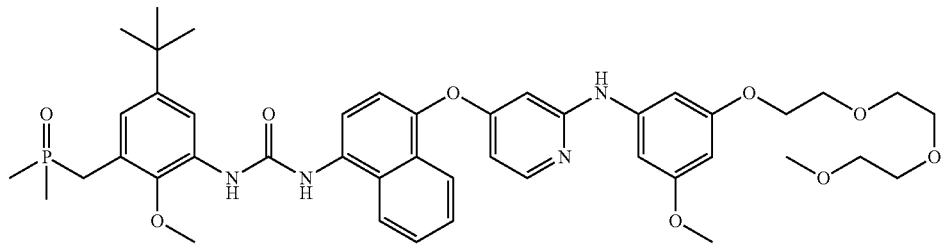 [SMILES: COCCOCCOCCOc1cc(Nc2cc(Oc3ccc(NC(=O)Nc4cc(C(C)(C)C)cc(CP(C)(C)=O)c4OC)c4ccccc34)ccn2)cc(OC)c1]

Phenyl (5-(tert-butyl)-3-((dimethylphosphoryl)methyl)-2-methoxyphenyl)carbamate (see Example 24(iv) above; 90 mg, 0.231 mmol), 4-((4-aminonaphthalen-1-yl)oxy)-N-(3-methoxy-5-(2-(2-(2-methoxyethoxy)ethoxy)ethoxy)phenyl)pyridin-2-amine (see Example 2(iv) above; 120 mg, 0.231 mmol) and Et$_3$N (10 µL, 0.072 mmol) were heated to 60° C. (block temp) in THF (3 mL) for 18 h. The volatiles were removed under reduced pressure and the residue was purified by chromatography on the Companion (40 g column, 5-8% MeOH/DCM) to afford a colourless foam which was triturated in diethyl ether to afford the title compound (87 mg) as a white solid.

$^1$H NMR (400 MHz, DMSO-d$_6$) δ: 9.39 (s, 1H), 8.86 (s, 1H), 8.85 (s, 1H), 8.30 (d, 1H), 8.21 (dd, 1H), 8.11 (d, 1H), 8.09 (d, 1H), 7.85 (d, 1H), 7.69 (ddd, 1H), 7.60 (ddd, 1H), 7.37 (d, 1H), 6.97 (dd, 1H), 6.90 (dd, 1H), 6.78 (dd, 1H), 6.57 (dd, 1H), 6.07 (d, 1H), 6.03 (dd, 1H), 4.01-3.91 (m, 2H), 3.79 (s, 3H), 3.73-3.67 (m, 2H), 3.65 (s, 3H), 3.59-3.54 (m, 2H), 3.54-3.48 (m, 4H), 3.44-3.39 (m, 2H), 3.22 (s, 3H), 3.18 (d, 2H), 1.40 (d, 6H), 1.29 (s, 9H).

LCMS m/z 815 (M+H)$^+$ (ES$^+$); 813 (M–H)$^-$ (ES$^-$)

Example 30

2-(5-(tert-Butyl)-3-(3-(4-((2-((3,5-dimethoxyphenyl)amino)pyridin-4-yl)oxy)naphthalen-1-yl)ureido)-2-methoxyphenyl)acetamide

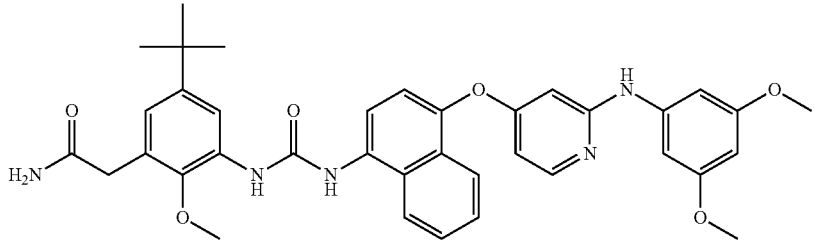 [SMILES: COc1cc(Nc2cc(Oc3ccc(NC(=O)Nc4cc(C(C)(C)C)cc(CC(N)=O)c4OC)c4ccccc34)ccn2)cc(OC)c1]

Et₃N (10 μL, 0.072 mmol) was added to a solution of phenyl (3-(2-amino-2-oxoethyl)-5-(tert-butyl)-2-methoxyphenyl)carbamate (see Example 13(vi) above; 100 mg, 0.281 mmol) and 4-((4-aminonaphthalen-1-yl)oxy)-N-(3,5-dimethoxyphenyl)pyridin-2-amine (see Example 27(ii) above; 100 mg, 0.258 mmol) in THF (2 mL) and the reaction heated at 65° C. (block temperature) for 48 h. The solvent was evaporated and the crude product was purified by chromatography on silica gel (12 g column, 2% MeOH:DCM to 10%) to give a pink glass which was stirred in MeCN (2 mL) at 50° C. for 1 h. The resulting solid was filtered off and washed with MeCN (1 mL) to afford the title compound (100 mg) as a colourless solid.

¹H NMR (400 MHz, DMSO-d₆) δ 9.38 (s, 1H), 8.88 (s, 1H), 8.79 (s, 1H), 8.30 (d, 1H), 8.21 (d, 1H), 8.12 (d, 1H), 8.10 (d, 1H), 7.87 (d, 1H), 7.77-7.65 (m, 1H), 7.65-7.55 (m, 1H), 7.45 (s, 1H), 7.38 (d, 1H), 6.98-6.89 (m, 2H), 6.84 (d, 2H), 6.58 (dd, 1H), 6.09 (d, 1H), 6.02 (t, 1H), 3.78 (s, 3H), 3.66 (s, 6H), 3.45 (s, 2H), 1.27 (s, 9H). LCMS m/z 650 (M+H)⁺ (ES⁺); 648 (M−H)⁻ (ES⁻)

Example 31

1-(5-(tert-Butyl)-3-(dimethylphosphoryl)-2-methoxyphenyl)-3-(4-((2-((tetrahydro-2H-pyran-4-yl)amino)pyrimidin-4-yl)oxy)naphthalen-1-yl)urea

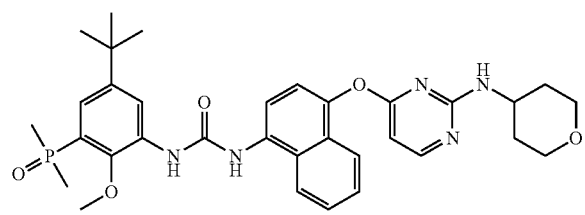 [SMILES: COc1c(NC(=O)Nc2ccc(Oc3ccnc(NC4CCOCC4)n3)c3ccccc23)cc(C(C)(C)C)cc1P(C)(C)=O]

In a 20 mL vial, a solution of 1-(5-(tert-butyl)-3-(dimethylphosphoryl)-2-methoxyphenyl)-3-(4-((2-chloropyrimidin-4-yl)oxy)naphthalen-1-yl)urea (see Example 18(ii) above; 100 mg, 0.181 mmol) and tetrahydro-2H-pyran-4-amine (37.3 μL, 0.362 mmol) in NMP (3 mL) was treated with TEA (126 μL, 0.904 mmol). The resultant yellow solution was heated at 65° C. (block) for 40 h. The reaction was cooled to rt and poured into water (20 mL) and the product extracted with EtOAc (2×20 mL). Organics were bulked and washed with 20% w/w brine solution (20 mL), separated, dried (MgSO₄), filtered and evaporated. The crude product was purified by chromatography on silica gel (40 g column, 2% MeOH:DCM to 8%) followed by preparative HPLC (Varian, Basic (0.1% Ammonium Bicarbonate), Basic, Waters X-Bridge Prep-C18, 5 μm, 19×50 mm column, 25-70% MeCN in Water) to afford the title compound (23 mg) as a white solid.

¹H NMR (400 MHz, DMSO-d₆, 50° C.) δ 9.20 (s, 1H), 8.74 (s, 1H), 8.41 (d, 1H), 8.23 (d, 1H), 8.19 (d, 1H), 8.01 (d, 1H), 7.82 (d, 1H), 7.70-7.62 (m, 1H), 7.61-7.52 (m, 1H), 7.37 (dd, 1H), 7.33 (d, 1H), 6.91 (br s, 1H), 6.23 (d, 1H), 3.91 (s, 3H), 3.73 (br s, 2H), 3.22 (peak under water) 1.75 (d, 6H), 1.60 (br m, 2H), 1.40-130 (br s, 2H) 1.31 (s, 9H).
LCMS m/z 618 (M+H)⁺ (ES⁺); 616 (M−H)⁻ (ES⁻)

Example 32

1-(5-(tert-Butyl)-3-(dimethylphosphoryl)-2-methoxyphenyl)-3-(4-((2-((pyridin-2-ylmethyl)amino)pyrimidin-4-yl)oxy)naphthalen-1-yl)urea

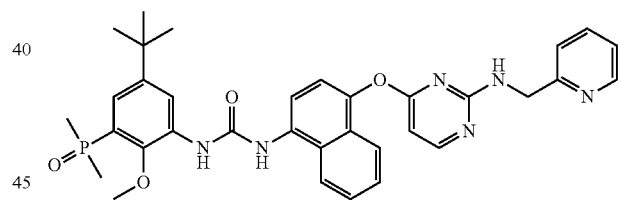

In a 20 mL vial, a solution of 1-(5-(tert-butyl)-3-(dimethylphosphoryl)-2-methoxyphenyl)-3-(4-((2-chloropyrimidin-4-yl)oxy)naphthalen-1-yl)urea (see Example 18(ii) above; 100 mg, 0.181 mmol) and pyridin-2-ylmethanamine (55.9 μL, 0.543 mmol) in NMP (3 mL) was treated with TEA (126 μL, 0.904 mmol). The resultant yellow solution was heated at 65° C. (block) for 16 h in total. The reaction was cooled to rt and poured into water (20 mL) and the product extracted with EtOAc (2×20 mL). Organics were bulked and washed with brine solution (20 mL), separated, dried (MgSO₄), filtered and evaporated. The residue was purified by preparative HPLC (Varian, Basic (0.1% Ammonium Bicarbonate), Basic, Waters X-Bridge Prep-C18, 5 μm, 19×50 mm column, 25-70% MeCN in Water) to afford the title compound (37 mg).

¹H NMR (400 MHz, DMSO-d₆, 100° C.) δ 9.03 (s, 1H), 8.53 (s, 1H), 8.43 (m, 1H), 8.36 (d, 1H), 8.24 (m, 1H), 8.19 (d, 1H), 7.96 (d, 1H), 7.89-7.83 (m, 1H), 7.68-7.52 (m, 3H), 7.41 (dd, 1H), 7.29 (d, 1H), 7.24-7.13 (m, 2H), 7.09 (m, 1H), 6.24 (d, 1H), 4.43 (d, 2H), 3.93 (s, 3H), 1.75 (d, 6H), 1.33 (s, 9H). LCMS m/z 625 (M+H)⁺ (ES⁺); 623 (M−H)⁻ (ES⁻)

Example 33

2-(5-(tert-Butyl)-2-methoxy-3-(3-(4-((2-((3-methoxyphenyl)amino)pyridin-4-yl)oxy)naphthalen-1-yl)ureido)phenyl)acetamide

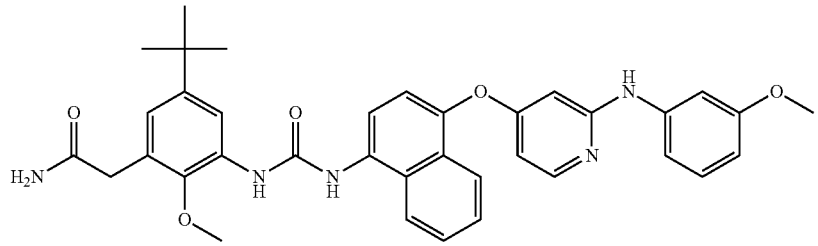 [SMILES: COc1cccc(Nc2cc(Oc3ccc(NC(=O)Nc4cc(C(C)(C)C)cc(CC(N)=O)c4OC)c4ccccc34)ccn2)c1]

(i) tert-Butyl (4-((2-((3-methoxyphenyl)amino)pyridin-4-yl)oxy)naphthalen-1-yl)carbamate Pd$_2$(dba)$_3$ (120 mg, 0.131 mmol) was added to a degassed suspension of tert-butyl (4-((2-chloropyridin-4-yl)oxy)naphthalen-1-yl)carbamate (see Example 2(ii) above; 1 g, 2.70 mmol), 3-methoxyaniline (0.32 mL, 2.85 mmol), xantphos (150 mg, 0.259 mmol) and Cs$_2$CO$_3$ (1.4 g, 4.30 mmol) in 1,4-dioxane (10 mL) and the reaction heated under nitrogen at 85° C. for 5 h. The reaction mixture was filtered and the solvent evaporated. The crude product was purified by chromatography on silica gel (80 g column, 1% MeOH:DCM to 4%) to afford a brown foam. This product was dissolved in DCM (20 mL) partitioned with 15% w/w citric acid (20 mL). The organics were separated, dried (MgSO$_4$), filtered and evaporated to afford the sub-title compound (1 g).

$^1$H NMR (400 MHz, DMSO-d$_6$) δ 9.36 (s, 1H), 8.93 (s, 1H), 8.14 (d, 1H), 8.10 (d, 1H), 7.88-7.81 (m, 1H), 7.67-7.53 (m, 3H), 7.43-7.25 (m, 2H), 7.16-6.96 (m, 2H), 6.57 (dd, 1H), 6.49-6.36 (m, 1H), 6.07 (d, 1H), 3.68 (s, 3H), 1.53 (s, 9H). LCMS m/z 458 (M+H)$^+$ (ES$^+$)

(ii) 4-((4-Aminonaphthalen-1-yl)oxy)-N-(3-methoxyphenyl)pyridin-2-amine

TFA (1 mL, 12.98 mmol) was added to a solution of the product from step (i) above (1 g, 2.186 mmol) in DCM (3 mL) and the reaction left stirring overnight. The solvents were evaporated and the residue partitioned between sat NaHCO$_3$ soln. (10 mL) and DCM (10 mL). The organics were separated, dried (MgSO$_4$), filtered and the solvent evaporated to afford the sub-title compound (800 mg).

$^1$H NMR (400 MHz, DMSO-d$_6$) δ 8.90 (s, 1H), 8.21-8.10 (m, 1H), 8.03 (d, 1H), 7.69-7.57 (m, 1H), 7.52-7.39 (m, 2H), 7.35-7.28 (m, 1H), 7.14-7.00 (m, 3H), 6.71 (d, 1H), 6.53 (dd, 1H), 6.43 (dt, 1H), 6.02 (d, 1H), 5.91 (s, 2H), 3.67 (s, 3H). LCMS m/z 358 (M+H)$^+$ (ES$^+$).

(iii) 2-(5-(tert-Butyl)-2-methoxy-3-(3-(4-((2-((3-methoxyphenyl)amino)pyridin-4-yl)oxy)naphthalen-1-yl)ureido)phenyl)acetamide Et$_3$N (10 μL, 0.072 mmol) was added to a solution of phenyl (3-(2-amino-2-oxoethyl)-5-(tert-butyl)-2-methoxyphenyl)carbamate (see Example 13(vi) above; 100 mg, 0.281 mmol) and the product from step (ii) above (100 mg, 0.280 mmol) in THF (2 mL) and the reaction heated at 65° C. (block temperature) for 16 h. The solvent was evaporated and the crude product was purified by chromatography on silica gel (12 g column, 2% MeOH:DCM to 10%) to give a pink glass which was stirred in MeCN (2 mL) at 50° C. for 1 h. The resulting solid was filtered off and washed with MeCN (1 mL) to afford the title compound (75 mg) as a colourless solid.

$^1$H NMR (400 MHz, DMSO-d$_6$) δ 9.38 (s, 1H), 8.90 (s, 1H), 8.79 (s, 1H), 8.30 (d, 1H), 8.21 (d, 1H), 8.16-8.04 (m, 2H), 7.87 (d, 1H), 7.77-7.67 (m, 1H), 7.65-7.58 (m, 1H), 7.45 (s, 1H), 7.38 (d, 1H), 7.36-7.31 (m, 1H), 7.17-7.03 (m, 2H), 6.99-6.85 (m, 2H), 6.57 (dd, 1H), 6.49-6.38 (m, 1H), 6.09 (d, 1H), 3.78 (s, 3H), 3.68 (s, 3H), 3.46 (s, 2H), 1.27 (s, 9H).

LCMS m/z 620 (M+H)$^+$ (ES$^+$); 618 (M−H)$^−$ (ES$^−$).

Example 34

1-(5-(tert-Butyl)-3-(dimethylphosphoryl)-2-methoxyphenyl)-3-(4-((2-((5-methoxypyridin-3-yl)amino)pyridin-4-yl)oxy)naphthalen-1-yl)urea

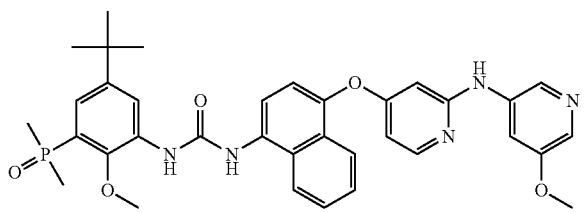 [SMILES: COc1cncc(Nc2cc(Oc3ccc(NC(=O)Nc4cc(C(C)(C)C)cc(P(C)(C)=O)c4OC)c4ccccc34)ccn2)c1]

(i) tert-Butyl (4-((2-((5-methoxypyridin-3-yl)amino)pyridin-4-yl)oxy)naphthalen-1-yl)carbamate Pd$_2$(dba)$_3$ (25 mg, 0.027 mmol) was added to a degassed suspension of tert-butyl (4-((2-chloropyridin-4-yl)oxy)naphthalen-1-yl)carbamate (see Example 2(ii) above; 200 mg, 0.539 mmol), 5-methoxypyridin-3-amine (75 mg, 0.604 mmol), xantphos (30 mg, 0.052 mmol) and Cs$_2$CO$_3$ (275 mg, 0.844 mmol) in 1,4-dioxane (2 mL) and the reaction heated under nitrogen at 85° C. for 5 h. The reaction mixture was filtered and the solvent evaporated. The crude product was purified by chromatography on silica gel (40 g column, 2% MeOH:DCM to 6%) to afford the sub-title compound (90 mg).

$^1$H NMR (400 MHz, DMSO-d$_6$) δ 9.37 (s, 1H), 9.16 (s, 1H), 8.25 (d, 1H), 8.19-8.06 (m, 2H), 7.97-7.89 (m, 1H), 7.88-7.76 (m, 2H), 7.71-7.52 (m, 3H), 7.37 (d, 1H), 6.65 (dd, 1H), 6.08 (d, 1H), 3.78 (s, 3H), 1.53 (s, 9H). LCMS m/z 459 (M+H)+ (ES+)

(ii) 4-((4-Aminonaphthalen-1-yl)oxy)-N-(5-methoxypyridin-3-yl)pyridin-2-amine TFA (500 μL, 6.49 mmol) was added to a solution of the product from step (i) above (90 mg, 0.196 mmol) in DCM (3 mL) and the reaction left stirring overnight. The solvents were evaporated and the residue partitioned between sat NaHCO$_3$ soln. (10 mL) and DCM (10 mL). The organics were separated, dried (MgSO$_4$), filtered and the solvent evaporated to afford the sub-title compound (70 mg) as a tan foam.
LCMS m/z 359 (M+H)+ (ES+)

(iii) 1-(5-(tert-Butyl)-3-(dimethylphosphoryl)-2-methoxyphenyl)-3-(4-((2-((5-methoxypyridin-3-yl)amino)pyridin-4-yl)oxy)naphthalen-1-yl)urea Et$_3$N (10 μL, 0.072 mmol) was added to a solution of phenyl (5-(tert-butyl)-3-(dimethylphosphoryl)-2-methoxyphenyl)carbamate (see Example 3(vi) above; 80 mg, 0.213 mmol) and the product from step (ii) above (80 mg, 0.223 mmol) in THF (1 mL) and the reaction heated at 65° C. (block temperature) for 16 h. The solvent was evaporated and the crude product was purified by chromatography on silica gel (12 g column, 5% MeOH:DCM to 10%) to afford a pink solid which was stirred in MeCN (2 mL) at 50° C. for 30 minutes, cooled, and the resultant solid filtered off to afford the title compound (70 mg) as a colourless solid.
$^1$H NMR (400 MHz, DMSO-d$_6$) δ 9.35 (s, 1H), 9.14 (s, 1H), 8.91 (s, 1H), 8.44 (d, 1H), 8.29 (d, 1H), 8.25 (d, 1H), 8.15 (d, 1H), 8.13 (d, 1H), 7.93 (t, 1H), 7.87 (d, 1H), 7.80 (d, 1H), 7.76-7.68 (m, 1H), 7.67-7.57 (m, 1H), 7.41 (d, 1H), 7.36 (dd, 1H), 6.64 (dd, 1H), 6.12 (d, 1H), 3.91 (s, 3H), 3.78 (s, 3H), 1.75 (d, 6H), 1.31 (s, 9H). LCMS m/z 640 (M+H)+ (ES-'); 638 (M-H)- (ES-)

Example 35

N-(5-(tert-Butyl)-2-methoxy-3-(3-(4-((2-(phenylamino)pyridin-4-yl)oxy)naphthalen-1-yl)ureido)benzyl)acetamide

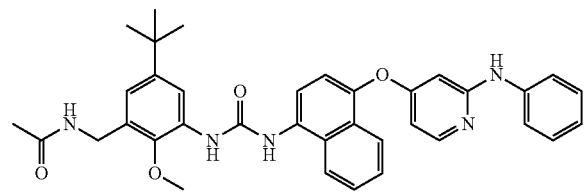 [SMILES: COc1c(CNC(C)=O)cc(C(C)(C)C)cc1NC(=O)Nc1ccc(Oc2ccnc(Nc3ccccc3)c2)c2ccccc12]

(i) 2-(5-(tert-Butyl)-2-methoxy-3-nitrobenzyl)isoindoline-1,3-dione

Potassium phthalate (1.5 g, 8.10 mmol) was added to a stirred solution of 5-(tert-butyl)-1-(chloromethyl)-2-methoxy-3-nitrobenzene (see Example 24(i) above; 1.1 g, 4.27 mmol) in DMF (10 mL) and stirred at rt for 4 h. The mixture was diluted with water (150 mL) and extracted with ethyl acetate (2×70 mL). The combined organic phases were washed with 20% brine (2×70 mL), saturated brine (70 mL) and dried (MgSO$_4$). The solvent was removed under reduced pressure to yield an oil which was crystallised from cyclohexane to afford the sub-title compound (1.23 g) as a white solid.
LCMS m/z 369 (M+H)+ (ES+)

(ii) (5-(tert-Butyl)-2-methoxy-3-nitrophenyl)methanamine

A solution of the product from step (i) above (1.20 g, 3.26 mmol) and 1.0 M hydrazine in THF (7.0 mL, 7.00 mmol) in EtOH (100 mL) was heated to reflux for 10 h. The solid was removed by filtration and the filtrate was concentrated under reduced pressure. The resulting solid/oil mixture was resuspended in diethyl ether (50 mL) and washed with 0.5 M sodium hydroxide solution (2×50 mL) followed by saturated brine (50 mL). The organic phase was dried (MgSO$_4$), filtered and concentrated under reduced pressure to afford the sub-title compound (630 mg) which was used in the next step without further purification.
LCMS m/z 239 (M+H)+ (ES+)

(iii) N-(5-(tert-Butyl)-2-methoxy-3-nitrobenzyl)acetamide

AcCl (75 μL, 1.055 mmol) was added to a stirred solution of the product from step (ii) above (200 mg, 0.755 mmol) and pyridine (100 μL, 1.236 mmol) in DCM (3 mL). The mixture was stirred for 18 h, diluted with DCM (5 mL) and 1 M aqueous HCl (5 mL) then poured through a phase separation cartridge. The organic phase was loaded directly onto a silica gel column and purified on the Companion (12 g column, 50-100% Et$_2$O/isohexane) to afford the sub-title compound (162 mg) as a yellow oil which crystallised on standing.
LCMS m/z 281 (M+H)+ (ES+); 279 (M-H)- (ES-)

(iv) N-(3-Amino-5-(tert-butyl)-2-methoxybenzyl)acetamide

A mixture of the product from step (iii) above (160 mg, 0.571 mmol) and 5% Pd/C (50 mg) in ethanol (5 mL) was stirred under a balloon of hydrogen at rt for 2 h. The catalyst was removed by filtration and the filtrate was concentrated under reduced pressure to yield the sub-title compound (132 mg) as a colourless oil which crystallised on standing.
LCMS m/z 192 (M-AcNH)+ (ES+)

(v) Phenyl (3-(acetamidomethyl)-5-(tert-butyl)-2-methoxyphenyl)carbamate

Phenyl chloroformate (75 μL, 0.597 mmol) was added to a stirred mixture of the product from step (iv) above (132 mg, 0.506 mmol) and NaHCO$_3$ (100 mg, 1.190 mmol) in THF (2 mL) and DCM (2 mL). The mixture was stirred at it for 2 h. The mixture was diluted with DCM (10 mL) and water (10 mL). The organic phase was separated, dried (MgSO$_4$) and concentrated under reduced pressure. The residue was triturated in diethyl ether:isohexane (1:1) to afford the sub-title compound (163 mg) as a white solid.
$^1$H NMR (400 MHz, CDCl$_3$) δ: 8.14 (brs, 1H), 7.42 (brs, 1H), 7.45-7.33 (m, 2H), 7.27-7.21 (m, 2H), 7.21-7.16 (m, 2H), 6.98 (d, 1H), 4.48 (d, 2H), 3.82 (s, 3H), 2.02 (s, 3H), 1.27 (s, 9H).

(vi) N-(5-(tert-Butyl)-2-methoxy-3-(3-(4-((2-(phenylamino)pyridin-4-yl)oxy)naphthalen-1-yl)ureido)benzyl)acetamide A solution of the product from step (v) above (75 mg, 0.202 mmol), 4-((4-aminonaphthalen-1-yl)oxy)-N-phenylpyridin-2-amine (see Example 11(ii) above; 66 mg, 0.202 mmol) and Et₃N (10 μl, 0.072 mmol) was heated to 60° C. (block temp) in isopropyl acetate (3 mL) for 18 h. The mixture was concentrated under reduced pressure and the residue was purified by chromatography on the Companion (12 g column, 50-100% EtOAc/isohexane) to afford a beige solid. The solid was purified by preparative HPLC (Gilson, Acidic (0.1% Formic acid), Acidic, Waters X-Select Prep-C18, 5 μm, 19×50 mm column, 15-75% MeCN in Water). Pure fractions were combined then evaporated to remove acetonitrile then saturated NaHCO₃ (5 mL) added. The mixture was extracted with ethyl acetate (25 mL) then washed with saturated brine (15 mL) and dried (MgSO₄). The solvent was removed under reduced pressure to yield the title compound (25 mg) as a white solid.

$^1$H NMR (400 MHz, DMSO-d₆) δ: 9.39 (s, 1H), 8.89 (s, 1H), 8.81 (s, 1H), 8.33-8.21 (m, 3H), 8.12-8.05 (m, 2H), 7.87 (d, 1H), 7.70 (ddd, 1H), 7.60 (ddd, 1H), 7.61-7.55 (m, 2H), 7.37 (d, 1H), 7.19 (ddd, 2H), 6.94 (d, 1H), 6.83 (ddd, 1H), 6.54 (dd, 1H), 6.09 (d, 1H), 4.32 (d, 2H), 3.78 (s, 3H), 1.89 (s, 3H), 1.26 (s, 9H). LCMS m/z 604 (M+H)$^+$ (ES$^+$), 602 (M−H)$^−$ (ES$^−$)

Example 36

1-(5-(tert-Butyl)-3-(dimethylphosphoryl)-2-methoxyphenyl)-3-(4-((2-((1-methyl-1H-pyrazol-3-yl)amino)pyridin-4-yl)oxy)naphthalen-1-yl)urea

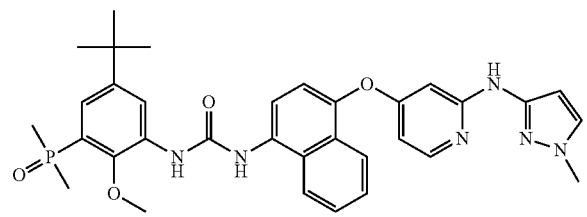 [SMILES: COc1c(NC(=O)Nc2ccc(Oc3ccnc(Nc4ccn(C)n4)c3)c3ccccc23)cc(C(C)(C)C)cc1P(C)(C)=O]

(i) 4-((4-Aminonaphthalen-1-yl)oxy)-N-(1-methyl-1H-pyrazol-3-yl)pyridin-2-amine BrettPhos G1 precatalyst (25 mg, 0.031 mmol) was added to a degassed solution of tert-butyl (4-((2-chloropyridin-4-yl)oxy)naphthalen-1-yl)carbamate (see Example 2(ii) above; 300 mg, 0.809 mmol), 1-methyl-1H-pyrazol-3-amine (100 mg, 1.030 mmol) and NaOtBu (120 mg, 1.249 mmol) in tBuOH (5 mL) and the mixture heated under nitrogen at 80° C. block temperature for 1 h. The mixture was diluted with DCM (10 mL) and filtered. The filtrate was evaporated to yield a tan foam which was redissolved in DCM (10 mL) and TFA (1 mL, 12.98 mmol) added. The reaction mixture was stirred at rt for 16 h then the solvent evaporated and the residue was azeotroped with toluene (10 mL) before partitioning between DCM (10 mL) and sat NaHCO₃ (10 mL). The organics were separated, dried (MgSO₄), filtered and evaporated to a brown glass. The crude product was purified by chromatography on silica gel (40 g column, 1% MeOH:DCM to 6%) to afford the sub-title compound (130 mg) as a tan glass.

$^1$H NMR (400 MHz, DMSO-d₆) δ 9.03 (s, 1H), 8.20-8.09 (m, 1H), 7.92 (d, 1H), 7.69-7.57 (m, 1H), 7.50-7.34 (m, 3H), 7.06 (d, 1H), 6.78 (d, 1H), 6.70 (d, 1H), 6.22 (dd, 1H), 6.16 (d, 1H), 5.78 (s, 2H), 3.64 (s, 3H). LCMS m/z 332 (M+H)$^+$ (ES$^+$)

(ii) 1-(5-(tert-Butyl)-3-(dimethylphosphoryl)-2-methoxyphenyl)-3-(4-((2-((1-methyl-1H-pyrazol-3-yl)amino)pyridin-4-yl)oxy)naphthalen-1-yl)urea Et₃N (10 μL, 0.072 mmol) was added to a solution of phenyl (5-(tert-butyl)-3-(dimethylphosphoryl)-2-methoxyphenyl)carbamate (see Example 3(vi) above; 100 mg, 0.266 mmol) and the product from step (i) above (75 mg, 0.226 mmol) in THF (2 mL) and heated at 65° C. (block temperature) for 48 h. The solvent was evaporated and the crude product was purified by chromatography on silica gel (12 g column, 2% MeOH:DCM to 10%) to afford a colourless glass which was stirred in MeCN (3 mL) at 50° C. until a colourless solid precipitated. The suspension was cooled to rt, filtered and washed with MeCN (1 mL) to afford the title compound (75 mg) as a colourless solid.

$^1$H NMR (400 MHz, DMSO-d₆) δ 9.32 (s, 1H), 9.15 (s, 1H), 8.89 (s, 1H), 8.44 (d, 1H), 8.28 (d, 1H), 8.10 (d, 1H), 7.99 (d, 1H), 7.90 (d, 1H), 7.77-7.65 (m, 1H), 7.66-7.55 (m, 1H), 7.45 (d, 1H), 7.40-7.28 (m, 2H), 6.88 (d, 1H), 6.32 (dd, 1H), 6.16 (d, 1H), 3.90 (s, 3H), 3.64 (s, 3H), 1.75 (d, 6H), 1.31 (s, 9H). LCMS m/z 613 (M+H)$^+$ (ES$^+$); 611 (M−H)$^−$ (ES$^−$)

Example 37

3-((4-((4-(3-(5-(tert-butyl)-3-(dimethylphosphoryl)-2-methoxyphenyl)ureido)-naphthalen-1-yl)oxy)pyridin-2-yl)amino)-5-methoxybenzamide

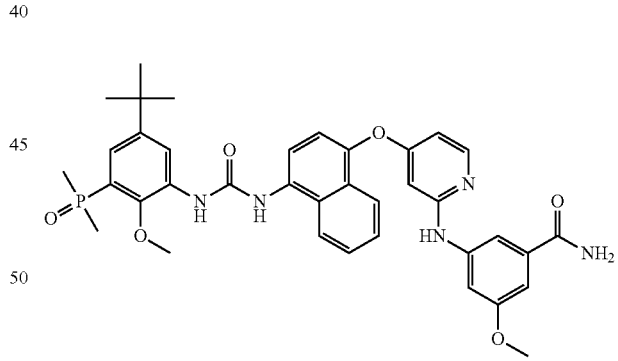

(i) tert-Butyl (4-((2-((3-carbamoyl-5-methoxyphenyl)amino)pyridin-4-yl)oxy)naphthalen-1-yl)carbamate Pd₂(dba)₃ (15 mg, 0.016 mmol) was added to a degassed suspension of tert-butyl (4-((2-chloropyridin-4-yl)oxy)naphthalen-1-yl)carbamate (see Example 2(ii) above; 130 mg, 0.351 mmol), 3-amino-5-methoxybenzamide (60 mg, 0.361 mmol), xantphos (20 mg, 0.035 mmol) and Cs₂CO₃ (175 mg, 0.537 mmol) in 1,4-dioxane (2 mL) and the reaction heated under nitrogen at 85° C. for 5 h. The reaction mixture was filtered and the solvent evaporated. The crude product was purified by chromatography on silica gel (12 g column, 1% MeOH:DCM to 4%) to afford the sub-title compound (68 mg).

$^1$H NMR (400 MHz, DMSO-$d_6$) δ 9.39 (s, 1H), 9.08 (s, 1H), 8.23-8.01 (m, 2H), 7.94-7.74 (m, 2H), 7.67-7.47 (m, 4H), 7.36 (d, 1H), 7.27 (s, 1H), 7.00-6.84 (m, 1H), 6.58 (dd, 1H), 6.10 (d, 1H), 5.77 (s, 1H), 3.74 (s, 3H), 1.52 (s, 9H). LCMS m/z 501 (M+H)$^+$ (ES$^+$); 499 (M−H)$^−$ (ES$^−$)

(ii) 3-((4-((4-Aminonaphthalen-1-yl)oxy)pyridin-2-yl)amino)-5-methoxybenzamide

TFA (500 μL, 6.49 mmol) was added to a solution of the product from step (i) above (65 mg, 0.130 mmol) in DCM (3 mL) and the reaction left stirring overnight. The solvents were evaporated and the residue partitioned between sat NaHCO$_3$ soln. (10 mL) and DCM (10 mL). The organics were separated, dried (MgSO$_4$), filtered and the solvent evaporated to afford the sub-title compound (40 mg).
LCMS m/z 401 (M+H)$^+$ (ES$^+$)

(iii) 3-((4-((4-(3-(5-(tert-Butyl)-3-(dimethylphosphoryl)-2-methoxyphenyl)ureido)naphthalen-1-yl)oxy)pyridin-2-yl)amino)-5-methoxybenzamide Triethylamine (3 μL, 0.022 mmol) was added to a solution of phenyl (5-(tert-butyl)-3-(dimethylphosphoryl)-2-methoxyphenyl)carbamate (see Example 3(vi) above; 40 mg, 0.107 mmol) and the product from step (ii) above (40 mg, 0.100 mmol) in THF (1 mL) and the reaction heated at 65° C. (block temperature) for 16 h. The solvent was evaporated and the crude product was purified by preparative HPLC (Gilson, Basic (0.1% Ammonium Bicarbonate), Basic, Waters X-Bridge Prep-C18, 5 μm, 19×50 mm column, 25-70% MeCN in Water) to afford the title compound (20 mg) as a colourless solid.

$^1$H NMR (400 MHz, DMSO-$d_6$) δ 9.34 (s, 1H), 9.04 (s, 1H), 8.90 (s, 1H), 8.43 (d, 1H), 8.37-8.22 (m, 1H), 8.20-8.05 (m, 2H), 7.87 (d, 1H), 7.81 (s, 1H), 7.77-7.66 (m, 1H), 7.64-7.58 (m, 1H), 7.57 (t, 1H), 7.51 (t, 1H), 7.43-7.31 (m, 2H), 7.24 (s, 1H), 6.92 (dd, 1H), 6.56 (dd, 1H), 6.13 (d, 1H), 3.90 (s, 3H), 3.73 (s, 3H), 1.74 (d, 6H), 1.30 (s, 9H).
LCMS m/z 682 (M+H)$^+$ (ES$^+$); 680 (M−H)$^−$ (ES$^−$)

Example 38

The following compounds were prepared by methods analogous to those described herein (including above and/or the examples below). Where chemical shifts from $^1$H NMR spectra are reported, these were obtained at 400 MHz and ambient temperature, unless otherwise specified.

(a) N-(2-(Azetidin-1-yl)ethyl)-5-(tert-butyl)-2-methoxy-3-(3-(4-((2-(phenylamino)pyridin-4-yl)oxy)naphthalen-1-yl)ureido)benzamide $^1$H NMR (400 MHz, DMSO-$d_6$) δ: 9.45 (s, 1H), 8.96 (s, 1H), 8.90 (s, 1H), 8.47 (d, 1H), 8.30 (d, 1H), 8.25 (t, 1H), 8.08-8.11 (m, 2H), 7.89 (d, 1H), 7.72 (t, 1H), 7.58-7.64 (m, 3H), 7.39 (d, 1H), 7.24 (d, 1H), 7.20 (t, 2H), 6.84 (t, 1H), 6.56 (dd, 1H), 6.11 (d, 1H), 3.83 (s, 3H), 3.25 (q, 2H), 3.19 (t, 4H), 2.54-2.57 (m, 2H), 2.01 (quint, 2H), 1.29 (s, 9H).
LCMS m/z 330 (M+2H)$^{2+}$ (ES$^+$); 657 (M−H)$^−$ (ES$^−$)

(b) 1-(5-(tert-Butyl)-2-methoxy-3-(methylsulfinyl)phenyl)-3-(4-((2-(phenylamino)pyridin-4-yl)oxy)naphthalen-1-yl)urea

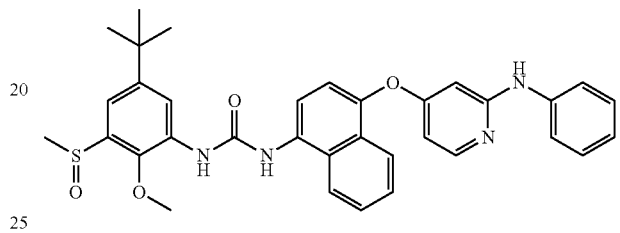

Chiral prep HPLC separation of the racemate (Example 12) was performed using the conditions; Chiral IA column, 45-min run, 15% EtOH in hexane.

(b1) Enantiomer 1

Chiral retention time: 24.95 min.
LCMS m/z 595 (M+H)$^+$ (ES$^+$); 593 (M−H)$^−$ (ES$^−$)
$^1$H NMR (400 MHz, DMSO-$d_6$) δ: 9.43 (s, 1H), 8.97 (s, 1H), 8.90 (s, 1H), 8.51 (d, 1H), 8.29 (d, 1H), 8.08-8.10 (m, 2H), 7.89 (d, 1H), 7.71 (t, 1H), 7.58-7.64 (m, 3H), 7.36-7.40 (m, 2H), 7.20 (t, 2H), 6.84 (t, 1H), 6.56 (dd, 1H), 6.11 (d, 1H), 3.87 (s, 3H), 2.79 (s, 3H), 1.32 (s, 9H).

(b2) Enantiomer 2

Chiral retention time: 28.80 min.
LCMS m/z 595 (M+H)$^+$ (ES$^+$); 593 (M−H)$^−$ (ES$^−$)
$^1$H NMR (400 MHz, DMSO-$d_6$) δ: 9.41 (s, 1H), 8.96 (s, 1H), 8.90 (s, 1H), 8.51 (d, 1H), 8.28 (d, 1H), 8.08-8.11 (m, 2H), 7.89 (d, 1H), 7.72 (t, 1H), 7.58-7.64 (m, 3H), 7.36-7.41 (m, 2H), 7.20 (t, 2H), 6.84 (t, 1H), 6.56 (dd, 1H), 6.10 (d, 1H), 3.87 (s, 3H), 2.79 (s, 3H), 1.32 (s, 9H).

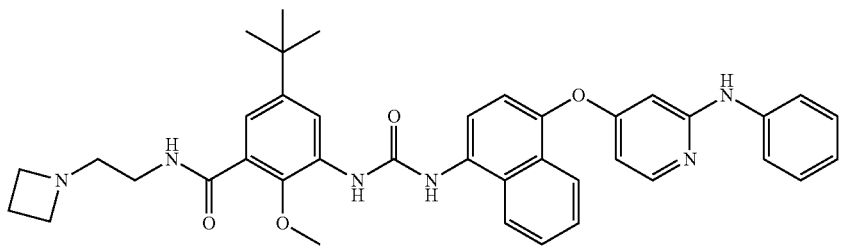 [SMILES: COc1c(NC(=O)Nc2ccc(Oc3ccnc(Nc4ccccc4)c3)c3ccccc23)cc(C(C)(C)C)cc1C(=O)NCCN1CCC1]

(c) 1-(5-(tert-Butyl)-3-(dimethylphosphoryl)-2-methoxyphenyl)-3-(4-((2-((3-(hydroxymethyl)-5-methoxyphenyl)amino)pyridin-4-yl)oxy)naphthalen-1-yl)urea

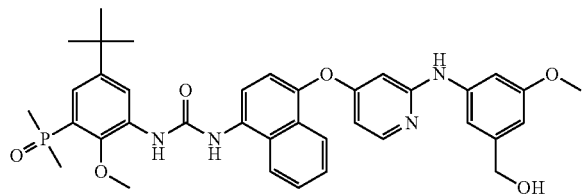 [SMILES: COc1cc(CO)cc(Nc2cc(Oc3ccc(NC(=O)Nc4cc(C(C)(C)C)cc(P(C)(C)=O)c4OC)c4ccccc34)ccn2)c1]

$^1$H NMR (400 MHz, DMSO-d$_6$) δ 9.35 (s, 1H), 8.90 (s, 1H), 8.87 (s, 1H), 8.43 (d, 1H), 8.29 (d, 1H), 8.18-8.02 (m, 2H), 7.88 (d, 1H), 7.77-7.66 (m, 1H), 7.65-7.56 (m, 1H), 7.44-7.31 (m, 2H), 7.23 (t, 1H), 7.02 (s, 1H), 6.54 (dd, 1H), 6.41 (s, 1H), 6.13 (d, 1H), 5.07 (s, 1H), 4.38 (s, 2H), 3.91 (s, 3H), 3.68 (s, 3H), 1.75 (d, 6H), 1.31 (s, 9H). LCMS m/z 669 (M+H)$^+$ (ES$^+$)

(d) 2-(5-(tert-Butyl)-2-methoxy-3-(3-(4-((2-((pyridin-2-ylmethyl)amino)pyridin-4-yl)oxy)naphthalen-1-yl)ureido)phenyl)acetamide

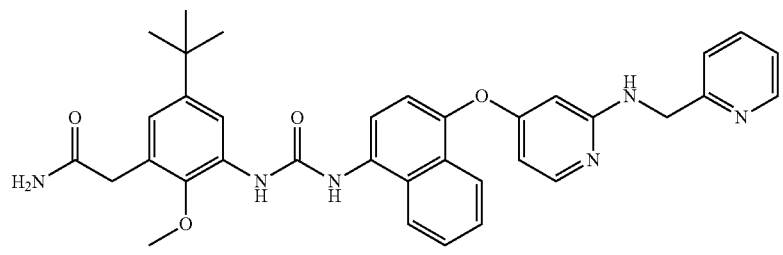 [SMILES: COc1c(CC(N)=O)cc(C(C)(C)C)cc1NC(=O)Nc1ccc(Oc2ccnc(NCc3ccccn3)c2)c2ccccc12]

$^1$H NMR (400 MHz, DMSO-d$_6$) δ: 9.36 (s, 1H), 8.78 (s, 1H), 8.45 (ddd, 1H), 8.28 (d, 1H), 8.20 (d, 1H), 8.07 (d, 1H), 7.89-7.82 (m, 2H), 7.73-7.64 (m, 2H), 7.59 (ddd, 1H), 7.45 (br s, 1H), 7.30 (d, 1H), 7.27-7.16 (m, 2H), 7.10 (t, 1H), 6.95 (br s, 1H), 6.93 (d, 1H), 6.25 (dd, 1H), 5.92 (d, 1H), 4.49 (d, 2H), 3.77 (s, 3H), 3.45 (s, 2H), 1.27 (s, 9H).
LCMS m/z 605 (M+H)$^+$ (ES$^+$); 603 (M−H)$^−$ (ES$^−$)

(e) 1-(5-(tert-Butyl)-3-(dimethylphosphoryl)-2-methoxyphenyl)-3-(4-((2-((pyridin-2-ylmethyl)amino)pyridin-4-yl)oxy)naphthalen-1-yl)urea

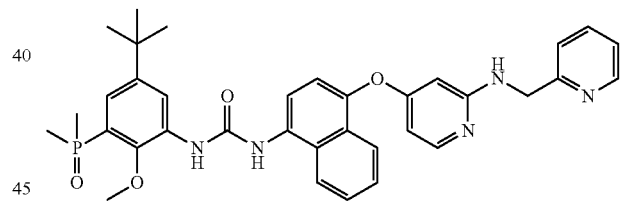

$^1$H NMR (400 MHz, DMSO-d$_6$) δ: 9.32 (s, 1H), 8.90 (s, 1H), 8.45 (ddd, 1H), 8.44 (d, 1H), 8.27 (d, 1H), 8.09 (d, 1H), 7.90-7.82 (m, 2H), 7.74-7.65 (m, 2H), 7.60 (ddd, 1H), 7.35 (dd, 1H), 7.31 (d, 1H), 7.24 (d, 1H), 7.20 (ddd, 1H), 7.10 (t, 1H), 6.25 (dd, 1H), 5.93 (d, 1H), 4.49 (d, 2H), 3.90 (s, 3H), 1.74 (d, 6H), 1.30 (s, 9H). LCMS m/z 624 (M+H)$^+$ (ES$^+$); 622 (M−H)$^−$ (ES$^−$)

(f) 2-(5-(tert-Butyl)-3-(3-(4-((2-((3,5-dimethylphenyl)amino)pyridin-4-yl)oxy)naphthalen-1-yl)ureido)-2-methoxyphenyl)acetamide

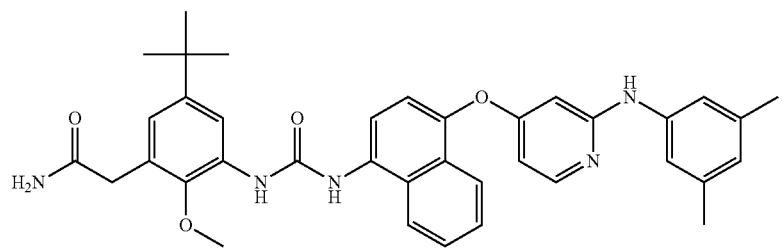 [SMILES: COc1c(CC(N)=O)cc(C(C)(C)C)cc1NC(=O)Nc1ccc(Oc2ccnc(Nc3cc(C)cc(C)c3)c2)c2ccccc12]

¹H NMR (400 MHz, DMSO-d₆) δ 9.37 (s, 1H), 8.78 (s, 1H), 8.75 (s, 1H), 8.29 (d, 1H), 8.19 (d, 1H), 8.14-8.01 (m, 2H), 7.86 (d, 1H), 7.73-7.64 (m, 1H), 7.64-7.56 (m, 1H), 7.49-7.42 (m, 1H), 7.37 (d, 1H), 7.12 (s, 2H), 7.00-6.85 (m, 2H), 6.53 (dd, 1H), 6.48 (s, 1H), 6.08 (d, 1H), 3.76 (s, 3H), 3.44 (s, 2H), 2.15 (s, 6H), 1.26 (s, 9H). LCMS m/z 618 (M+H)⁺ (ES⁺); 616 (M−H)⁻ (ES⁻)

(g) 1-(4-((2-(Benzylamino)pyrimidin-4-yl)oxy)naphthalen-1-yl)-3-(5-(tert-butyl)-3-(dimethylphosphoryl)-2-methoxyphenyl)urea

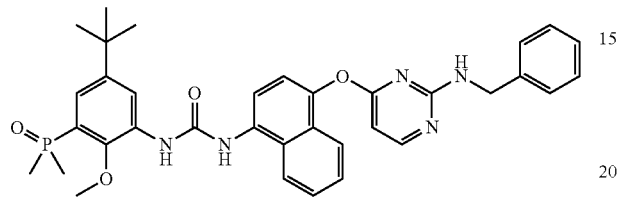

¹H NMR (400 MHz, DMSO-d₆) δ: 9.08 (s, 1H), 8.58 (s, 1H), 8.38 (d, 1H), 8.25 (d, 1H), 8.19 (d, 1H), 7.99 (d, 1H), 7.85 (d, 1H), 7.65 (t, 1H), 7.56 (t, 1H), 7.40 (dd, 1H), 7.29-7.31 (m, 2H), 7.08-7.20 (m, 5H), 6.24 (d, 1H), 4.28 (d, 2H), 3.93 (s, 3H), 1.75 (d, 6H), 1.33 (s, 9H). LCMS m/z 624 (M+H)⁺ (ES⁺)

(h) 2-(5-(tert-Butyl)-2-methoxy-3-(3-(4-((2-((3-methoxyphenyl)amino)pyridin-4-yl)oxy)naphthalen-1-yl)ureido)phenyl)-N-methylacetamide

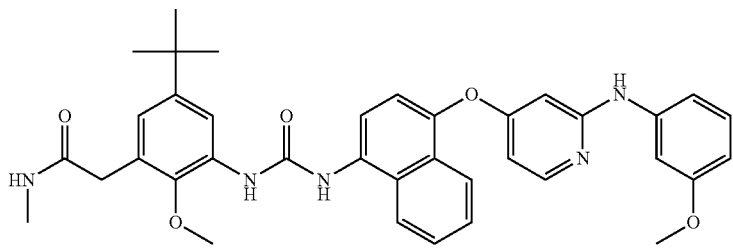 [SMILES: CNC(=O)Cc1cc(C(C)(C)C)cc(NC(=O)Nc2ccc(Oc3ccnc(Nc4cccc(OC)c4)c3)c3ccccc23)c1OC]

¹H NMR (400 MHz, DMSO-d₆) δ 9.37 (s, 1H), 8.90 (s, 1H), 8.79 (s, 1H), 8.30 (d, 1H), 8.21 (d, 1H), 8.10 (t, 2H), 7.96-7.82 (m, 2H), 7.77-7.66 (m, 1H), 7.66-7.57 (m, 1H), 7.38 (d, 1H), 7.36-7.29 (m, 1H), 7.15-7.04 (m, 2H), 6.92 (d, 1H), 6.57 (dd, 1H), 6.47-6.37 (m, 1H), 6.09 (d, 1H), 3.76 (s, 3H), 3.68 (s, 3H), 3.46 (s, 2H), 2.63 (d, 3H), 1.27 (s, 9H). LCMS m/z 634 (M+H)⁺ (ES⁺); 632 (M−H)⁻ (ES⁻)

(i) 2-(5-(tert-Butyl)-2-methoxy-3-(3-(4-((2-((3-methoxyphenyl)amino)pyridin-4-yl)oxy)naphthalen-1-yl)ureido)phenyl)-N,N-dimethylacetamide

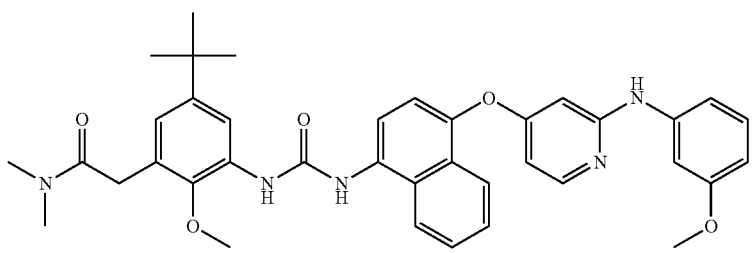 [SMILES: COc1cccc(Nc2cc(Oc3ccc(NC(=O)Nc4cc(C(C)(C)C)cc(CC(=O)N(C)C)c4OC)c4ccccc34)ccn2)c1]

¹H NMR (400 MHz, DMSO-d₆) δ 9.37 (s, 1H), 8.90 (s, 1H), 8.79 (s, 1H), 8.30 (d, 1H), 8.21 (d, 1H), 8.15-8.05 (m, 2H), 7.87 (d, 1H), 7.76-7.65 (m, 1H), 7.65-7.57 (m, 1H), 7.38 (d, 1H), 7.36-7.29 (m, 1H), 7.15-7.03 (m, 2H), 6.82 (d, 1H), 6.57 (dd, 1H), 6.48-6.39 (m, 1H), 6.09 (d, 1H), 3.73 (s, 3H), 3.70 (s, 2H), 3.68 (s, 3H), 3.07 (s, 3H), 2.88 (s, 3H), 1.26 (s, 9H).
LCMS m/z 648 (M+H)⁺ (ES⁺); 646 (M−H)⁻ (ES⁻)

(j) 1-(5-(tert-Butyl)-2-methoxy-3-(2-morpholino-2-oxoethyl)phenyl)-3-(4-((2-((3-methoxyphenyl)amino)pyridin-4-yl)oxy)naphthalen-1-yl)urea

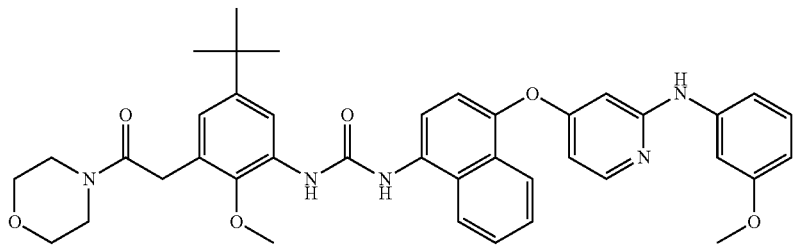 [SMILES: COc1cccc(Nc2cc(Oc3ccc(NC(=O)Nc4cc(C(C)(C)C)cc(CC(=O)N5CCOCC5)c4OC)c4ccccc34)ccn2)c1]

¹H NMR (400 MHz, DMSO-d₆) δ 9.38 (s, 1H), 8.90 (s, 1H), 8.80 (s, 1H), 8.30 (d, 1H), 8.23 (d, 1H), 8.17-8.01 (m, 2H), 7.87 (d, 1H), 7.77-7.66 (m, 1H), 7.65-7.54 (m, 1H), 7.38 (d, 1H), 7.36-7.27 (m, 1H), 7.17-6.99 (m, 2H), 6.83 (d, 1H), 6.57 (dd, 1H), 6.49-6.36 (m, 1H), 6.10 (d, 1H), 3.74 (s, 3H), 3.73 (s, 2H), 3.68 (s, 3H), 3.61-3.55 (m, 2H), 3.55-3.45 (m, 6H), 1.27 (s, 9H).
LCMS m/z 690 (M+H)⁺ (ES⁺); 688 (M−H)⁻ (ES⁻)

(k) 2-(5-(tert-Butyl)-2-methoxy-3-(3-(4-((2-((2-methoxypyridin-4-yl)amino)pyridin-4-yl)oxy)naphthalen-1-yl)ureido)phenyl)acetamide

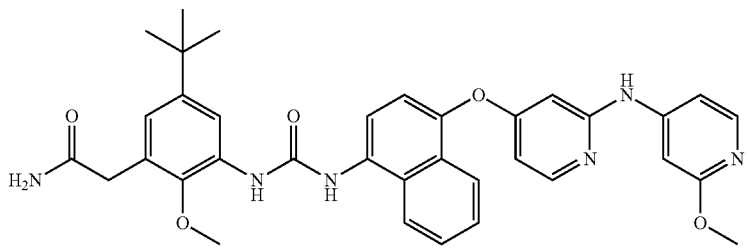 [SMILES: COc1cc(Nc2cc(Oc3ccc(NC(=O)Nc4cc(C(C)(C)C)cc(CC(N)=O)c4OC)c4ccccc34)ccn2)ccn1]

¹H NMR (400 MHz, DMSO-d₆) δ: 9.39 (s, 1H), 9.34 (s, 1H), 8.79 (s, 1H), 8.31 (d, 1H), 8.18-8.21 (m, 2H), 8.12 (d, 1H), 7.84-7.87 (m, 2H), 7.71 (t, 1H), 7.61 (t, 1H), 7.45 (bs, 1H), 7.40 (d, 1H), 7.32 (d, 1H), 6.98 (dd, 1H), 6.94 (d, 2H), 6.72 (dd, 1H), 6.15 (d, 1H), 3.78 (s, 6H), 3.45 (s, 2H), 1.27 (s, 9H). LCMS m/z 621 (M+H)⁺ (ES⁺); 311 (M+2H)²⁺ (ES⁺)

(l) 2-(5-(tert-Butyl)-3-(3-(2,3-difluoro-4-((2-(phenylamino)pyridin-4-yl)oxy)phenyl)ureido)-2-methoxyphenyl)acetamide

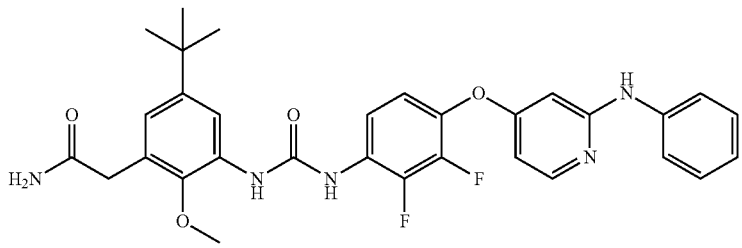 [SMILES: COc1c(CC(N)=O)cc(C(C)(C)C)cc1NC(=O)Nc1ccc(Oc2ccnc(Nc3ccccc3)c2)c(F)c1F]

¹H NMR (DMSO-d₆) 400 MHz, δ: 9.47 (s, 1H), 9.00 (s, 1H), 8.80 (s, 1H), 8.15 (d, 1H), 8.11 (ddd, 1H), 8.09 (d, 1H), 7.67-7.60 (m, 2H), 7.44 (br s, 1H), 7.28-7.16 (m, 3H), 6.95 (d, 1H), 6.94 (br s, 1H), 6.88 (ddd, 1H), 6.50 (dd, 1H), 6.24 (d, 1H), 3.72 (s, 3H), 3.43 (s, 2H), 1.27 (s, 9H). LCMS m/z 576 (M+H)⁺ (ES⁺); 574 (M–H)⁻ (ES⁻)

(m) 2-(5-(tert-Butyl)-3-(3-(4-((2-((3-(hydroxymethyl)-5-methoxyphenyl)amino)pyridin-4-yl)oxy)naphthalen-1-yl)ureido)-2-methoxyphenyl)acetamide

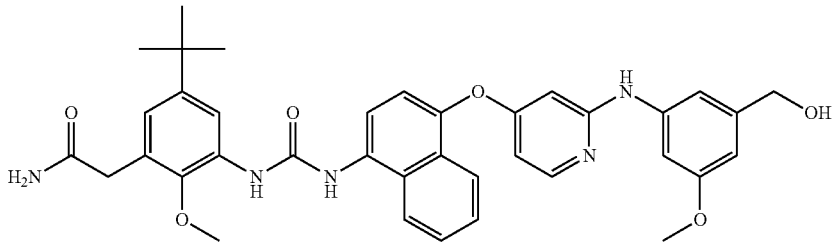 [SMILES: COc1cc(CO)cc(Nc2cc(Oc3ccc(NC(=O)Nc4cc(C(C)(C)C)cc(CC(N)=O)c4OC)c4ccccc34)ccn2)c1]

¹H NMR (400 MHz, DMSO-d₆) δ 9.40 (s, 1H), 8.89 (s, 1H), 8.80 (s, 1H), 8.31 (d, 1H), 8.21 (d, 1H), 8.16-8.04 (m, 2H), 7.87 (d, 1H), 7.76-7.67 (m, 1H), 7.66-7.57 (m, 1H), 7.52-7.42 (m, 1H), 7.38 (d, 1H), 7.24 (t, 1H), 7.07-7.00 (m, 1H), 7.00-6.89 (m, 2H), 6.55 (dd, 1H), 6.47-6.34 (m, 1H), 6.12 (d, 1H), 5.10 (s, 1H), 4.38 (s, 2H), 3.78 (s, 3H), 3.67 (s, 3H), 3.45 (s, 2H), 1.27 (s, 9H). LCMS m/z 650 (M+H)⁺ (ES⁺)

(n) 2-(5-(tert-butyl)-2-methoxy-3-(3-(4-((2-((5-methoxypyridin-3-yl)amino)pyridin-4-yl)oxy)naphthalen-1-yl)ureido)phenyl)acetamide

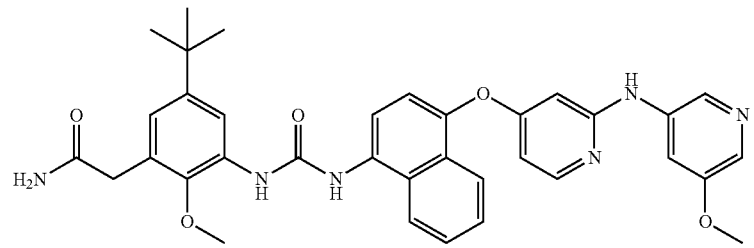 [SMILES: COc1cncc(Nc2cc(Oc3ccc(NC(=O)Nc4cc(C(C)(C)C)cc(CC(N)=O)c4OC)c4ccccc34)ccn2)c1]

¹H NMR (400 MHz, DMSO-d₆) δ: 9.40 (s, 1H), 9.14 (s, 1H), 8.79 (s, 1H), 8.31 (d, 1H), 8.25 (d, 1H), 8.20 (d, 1H), 8.11-8.15 (m, 2H), 7.92 (t, 1H), 7.87 (d, 1H), 7.80 (d, 1H), 7.71 (t, 1H), 7.61 (t, 1H), 7.45 (bs, 1H), 7.40 (d, 1H), 6.94 (d, 2H), 6.65 (dd, 1H), 6.11 (d, 1H), 3.78 (s, 6H), 3.45 (s, 2H), 1.27 (s, 9H). LCMS m/z 621 (M+H)⁺ (ES⁺); 311 (M+2H)²⁺ (ES⁺)

(o) 2-(5-(tert-Butyl)-2-methoxy-3-(3-(4-((2-((1-methyl-1H-pyrazol-3-yl)amino)pyridin-4-yl)oxy)naphthalen-1-yl)ureido)phenyl)acetamide

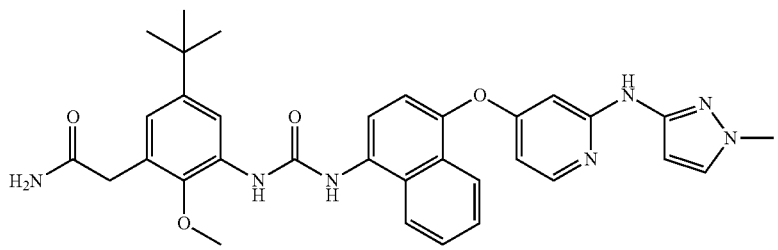 [SMILES: COc1c(CC(N)=O)cc(C(C)(C)C)cc1NC(=O)Nc1ccc(Oc2ccnc(Nc3ccn(C)n3)c2)c2ccccc12]

¹H NMR (400 MHz, DMSO-d₆) δ: 9.36 (s, 1H), 9.13 (s, 1H), 8.77 (s, 1H), 8.29 (d, 1H), 8.20 (d, 1H), 8.08 (d, 1H), 7.99 (d, 1H), 7.89 (d, 1H), 7.69 (t, 1H), 7.59 (t, 1H), 7.44-7.45 (m, 2H), 7.33 (d, 1H), 6.94 (d, 2H), 6.88 (d, 1H), 6.32 (dd, 1H), 6.17 (d, 1H), 3.77 (s, 3H), 3.64 (s, 3H), 3.45 (s, 2H), 1.27 (s, 9H). LCMS m/z 594 (M+H)⁺ (ES⁺)

(p) N-(5-(tert-Butyl)-3-(3-(4-((2-((3,5-dimethylphenyl)amino)pyridin-4-yl)oxy)naphthalen-1-yl)ureido)-2-methoxybenzyl)acetamide

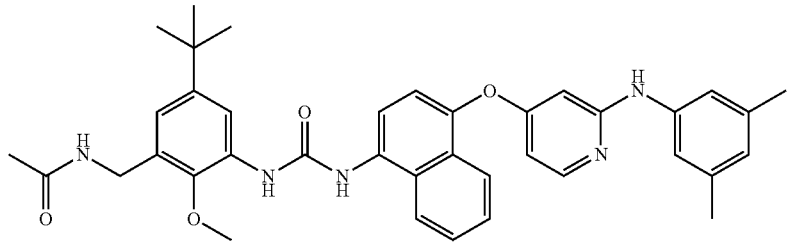 [SMILES: COc1c(CNC(C)=O)cc(C(C)(C)C)cc1NC(=O)Nc1ccc(Oc2ccnc(Nc3cc(C)cc(C)c3)c2)c2ccccc12]

¹H NMR (400 MHz, DMSO-d₆) δ: 9.40 (s, 1H), 8.82 (s, 1H), 8.74 (s, 1H), 8.30 (d, 1H), 8.26 (dd, 1H), 8.24 (d, 1H), 8.10 (d, 1H), 8.09 (d, 1H), 7.87 (d, 1H), 7.71 (ddd, 1H), 7.61 (ddd, 1H), 7.37 (d, 1H), 7.14 (s, 2H), 6.95 (d, 1H), 6.53 (dd, 1H), 6.48 (s, 1H), 6.09 (d, 1H), 4.33 (d, 2H), 3.78 (s, 3H), 2.17 (s, 6H), 1.90 (s, 3H), 1.27 (s, 9H). LCMS m/z 632 (M+H)⁺ (ES⁺); 630 (M–H)⁻ (ES⁻)

(q) N-(5-(tert-Butyl)-2-methoxy-3-(3-(4-((2-((pyridin-2-ylmethyl)amino)pyridin-4-yl)oxy)naphthalen-1-yl)ureido)benzyl)acetamide

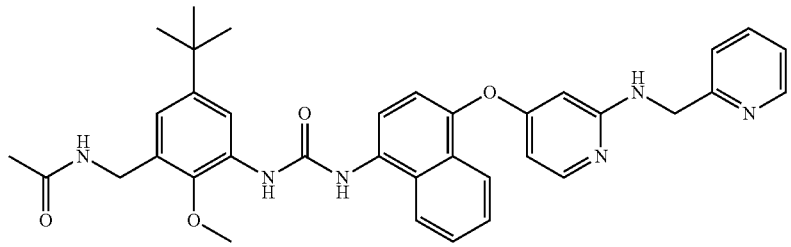 [SMILES: COc1c(CNC(C)=O)cc(C(C)(C)C)cc1NC(=O)Nc1ccc(Oc2ccnc(NCc3ccccn3)c2)c2ccccc12]

¹H NMR (400 MHz, DMSO-d₆) δ 9.38 (s, 1H), 8.80 (s, 1H), 8.44 (d, 1H), 8.32-8.21 (m, 3H), 8.06 (d, 1H), 7.86 (d, 1H), 7.86 (d, 1H), 7.74-7.65 (m, 2H), 7.59 (ddd, 1H), 7.30 (d, 1H), 7.25 (d, 1H), 7.20 (dd, 1H), 7.10 (dd, 1H), 6.94 (d, 1H), 6.25 (dd, 1H), 5.92 (d, 1H), 4.49 (d, 2H), 4.32 (d, 2H), 3.78 (s, 3H), 1.90 (s, 3H), 1.27 (s, 9H). LCMS m/z 619 (M+H)⁺ (ES⁺); 617 (M–H)⁻ (ES⁻)

(r) 3-((4-((4-(3-(3-(2-Amino-2-oxoethyl)-5-(tert-butyl)-2-methoxyphenyl)ureido)naphthalen-1-yl)oxy)pyridin-2-yl)amino)phenyl methanesulfonate

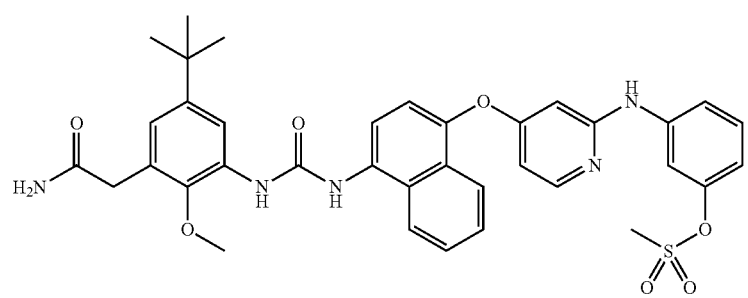 [SMILES: COc1c(CC(N)=O)cc(C(C)(C)C)cc1NC(=O)Nc1ccc(Oc2ccnc(Nc3cccc(OS(C)(=O)=O)c3)c2)c2ccccc12]

$^1$H NMR (400 MHz, DMSO-d$_6$) δ: 9.42 (s, 1H), 9.20 (s, 1H), 8.81 (s, 1H), 8.31 (d, 1H), 8.20 (d, 1H), 8.10-8.14 (m, 2H), 7.86 (d, 1H), 7.81 (t, 1H), 7.71 (t, 1H), 7.61 (t, 1H), 7.45-7.49 (m, 2H), 7.39 (d, 1H), 7.29 (t, 1H), 6.94 (d, 2H), 6.82 (dd, 1H), 6.64 (dd, 1H), 6.11 (d, 1H), 3.78 (s, 3H), 3.45 (s, 2H), 3.35 (s, 3H), 1.27 (s, 9H). LCMS m/z 684 (M+H)$^+$ (ES$^+$)

(s) 2-(5-(tert-Butyl)-3-(3-(4-((2-((3-(difluoromethoxy)phenyl)amino)pyridin-4-yl)oxy)naphthalen-1-yl)ureido)-2-methoxyphenyl)acetamide

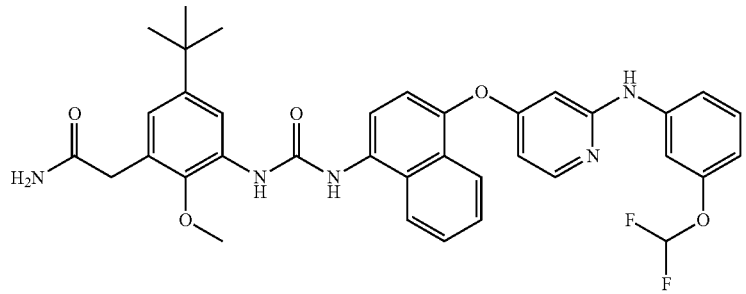 [SMILES: COc1c(CC(N)=O)cc(C(C)(C)C)cc1NC(=O)Nc1ccc(Oc2ccnc(Nc3cccc(OC(F)F)c3)c2)c2ccccc12]

$^1$H NMR (400 MHz, DMSO-d$_6$) δ: 9.40 (s, 1H), 9.12 (s, 1H), 8.79 (s, 1H), 8.31 (d, 1H), 8.20 (d, 1H), 8.10-8.14 (m, 2H), 7.87 (d, 1H), 7.68-7.73 (m, 2H), 7.59-7.63 (m, 1H), 7.40 (s, 1H), 7.39 (d, 1H), 7.33-7.35 (m, 1H), 7.22 (t, 1H), 7.15 (bt, 1H), 6.94-6.96 (m, 2H), 6.62-6.65 (m, 2H), 6.10 (d, 1H), 3.78 (s, 3H), 3.45 (s, 2H), 1.27 (s, 9H). LCMS m/z 656 (M+H)$^+$ (ES$^+$)

(t) 3-((4-((4-(3-(3-(Acetamidomethyl)-5-(tert-butyl)-2-methoxyphenyl)ureido)naphthalen-1-yl)oxy)pyridin-2-yl)amino)-5-methoxy-N-(2-morpholinoethyl)benzamide

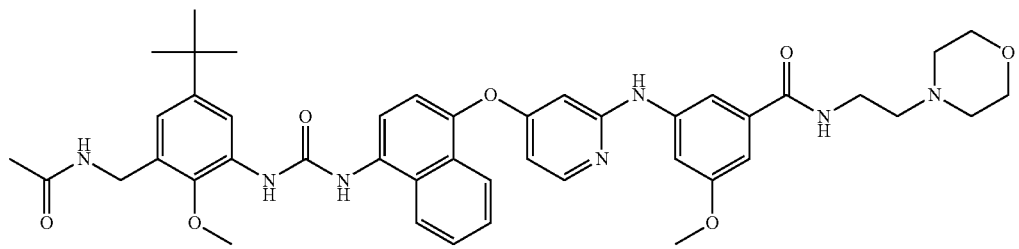 [SMILES: COc1cc(Nc2cc(Oc3ccc(NC(=O)Nc4cc(C(C)(C)C)cc(CNC(C)=O)c4OC)c4ccccc34)ccn2)cc(C(=O)NCCN2CCOCC2)c1]

$^1$H NMR (400 MHz, DMSO-d$_6$) δ 9.42 (s, 1H), 9.08 (s, 1H), 8.84 (s, 1H), 8.34-8.22 (m, 4H), 8.12 (d, 1H), 8.11 (s, 1H), 7.87 (d, 1H), 7.75-7.68 (m, 1H), 7.66-7.58 (m, 1H), 7.56 (t, 1H), 7.50 (t, 1H), 7.39 (d, 1H), 6.95 (d, 1H), 6.86 (dd, 1H), 6.58 (dd, 1H), 6.13 (d, 1H), 4.33 (d, 2H), 3.78 (s, 3H), 3.74 (s, 3H), 3.56 (t, 4H), 2.45-2.39 (m, 6H), 1.90 (s, 3H), 1.27 (s, 9H). (CH$_2$ under water peak). LCMS m/z 790 (M+H)$^+$ (ES$^+$); 788 (M−H)$^-$ (ES$^-$)

(u) 3-((4-((4-(3-(5-(tert-Butyl)-2-methoxy-3-((methylsulfinyl)methyl)phenyl)ureido)naphthalen-1-yl)oxy)pyridin-2-yl)amino)-5-methoxy-N-(2-morpholinoethyl)benzamide

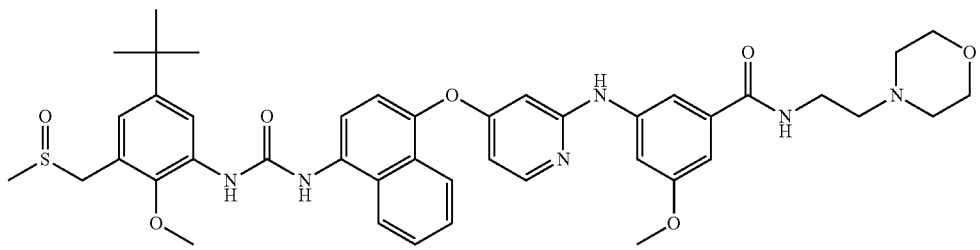 [SMILES: COc1cc(Nc2cc(Oc3ccc(NC(=O)Nc4cc(C(C)(C)C)cc(CS(C)=O)c4OC)c4ccccc34)ccn2)cc(C(=O)NCCN2CCOCC2)c1]

¹H NMR (400 MHz, DMSO-d₆) δ 9.41 (s, 1H), 9.08 (s, 1H), 8.89 (s, 1H), 8.34-8.28 (m, 2H), 8.25 (t, 1H), 8.13 (d, 1H), 8.11 (d, 1H), 7.87 (d, 1H), 7.75-7.67 (m, 1H), 7.66-7.58 (m, 1H), 7.56 (t, 1H), 7.50 (t, 1H), 7.39 (d, 1H), 7.04 (d, 1H), 6.86 (dd, 1H), 6.59 (dd, 1H), 6.12 (d, 1H), 4.13 (d, 1H), 4.05 (d, 1H), 3.81 (s, 3H), 3.74 (s, 3H), 3.56 (t, 4H), 2.61 (s, 3H), 2.48-2.33 (m, 6H), 1.28 (s, 9H). (CH₂ under water peak). LCMS m/z 795 (M+H)⁺ (ES⁺); 793 (M−H)⁻ (ES⁻)

(v) 3-((4-((4-(3-(5-(tert-Butyl)-3-((dimethylphosphoryl)methyl)-2-methoxyphenyl)ureido)-naphthalen-1-yl)oxy)pyridin-2-yl)amino)-5-methoxy-N-(2-morpholinoethyl)benzamide

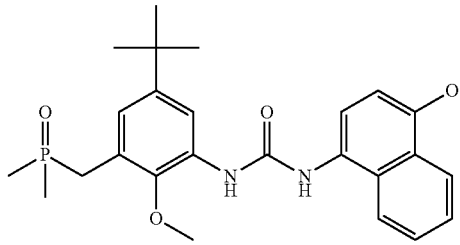
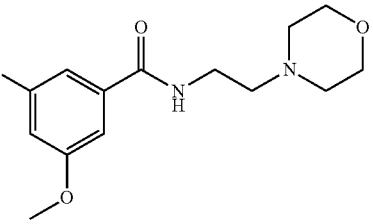

¹H NMR (400 MHz, DMSO-d₆) δ 9.41 (s, 1H), 9.08 (s, 1H), 8.87 (s, 1H), 8.31 (d, 1H), 8.25 (t, 1H), 8.22 (t, 1H), 8.13 (d, 1H), 8.11 (d, 1H), 7.87 (d, 1H), 7.77-7.66 (m, 1H), 7.66-7.58 (m, 1H), 7.56 (t, 1H), 7.53-7.46 (m, 1H), 7.39 (d, 1H), 6.98 (t, 1H), 6.86 (dd, 1H), 6.59 (dd, 1H), 6.12 (d, 1H), 3.80 (s, 3H), 3.74 (s, 3H), 3.56 (t, 4H), 3.19 (d, 2H), 2.48-2.33 (m, 6H), 1.41 (d, 6H), 1.27 (s, 9H). (CH₂ under water peak). LCMS m/z 809 (M+H)⁺ (ES⁺); 807 (M−H)⁻ (ES⁻)

(w) 2-(5-(tert-Butyl)-2-methoxy-3-(3-(4-((2-((3-(2-morpholinoethoxy)-5-(trifluoromethyl)-phenyl)amino)pyridin-4-yl)oxy)naphthalen-1-yl)ureido)phenyl)acetamide

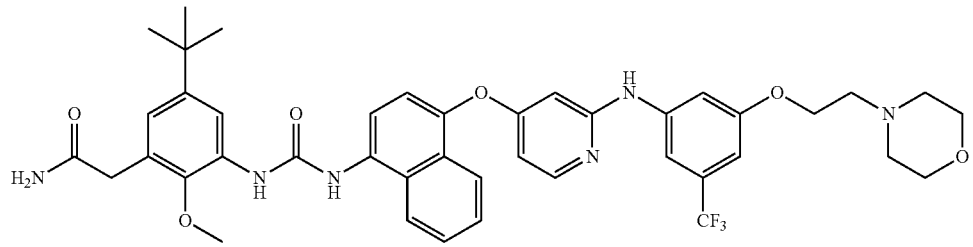

¹H NMR (400 MHz, DMSO-d₆) δ 9.40 (s, 1H), 9.24 (s, 1H), 8.80 (s, 1H), 8.31 (d, 1H), 8.20 (d, 1H), 8.17 (d, 1H), 8.10 (d, 1H), 7.86 (d, 1H), 7.71 (ddd, 1H), 7.61 (dd, 1H), 7.60-7.54 (m, 2H), 7.49-7.40 (m, 1H), 7.40 (d, 1H), 6.99-6.91 (m, 1H), 6.94 (d, 1H), 6.72 (dd, 1H), 6.66 (dd, 1H), 6.08 (d, 1H), 4.10 (t, 2H), 3.78 (s, 3H), 3.61-3.54 (m, 4H), 3.46 (s, 2H), 2.68 (t, 2H), 2.48-2.42 (m, 4H), 1.27 (s, 9H). LCMS m/z 394 (M+2H)²⁺ (ES⁺)

(x) 1-(5-(tert-Butyl)-2-methoxy-3-(methylsulfinyl)phenyl)-3-(4-((2-((3-(2-morpholinoethoxy)-5-(trifluoromethyl)phenyl)amino)pyridin-4-yl)oxy)naphthalen-1-yl)urea

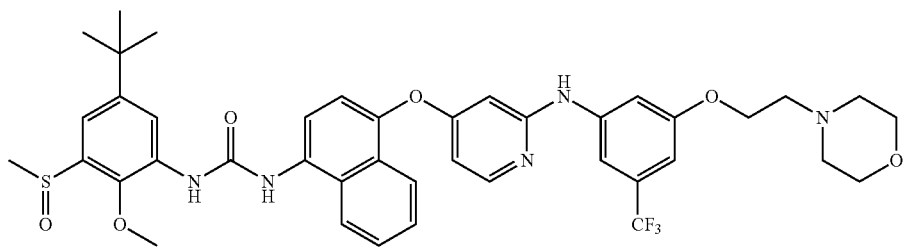 [SMILES: COc1c(NC(=O)Nc2ccc(Oc3ccnc(Nc4cc(OCCN5CCOCC5)cc(C(F)(F)F)c4)c3)c3ccccc23)cc(C(C)(C)C)cc1S(C)=O]

¹H NMR (400 MHz, DMSO-d₆) δ 9.44 (s, 1H), 9.25 (s, 1H), 8.98 (s, 1H), 8.50 (d, 1H), 8.29 (d, 1H), 8.17 (d, 1H), 8.11 (d, 1H), 7.87 (d, 1H), 7.72 (ddd, 1H), 7.62 (ddd, 1H), 7.60-7.54 (m, 2H), 7.41 (d, 1H), 7.36 (d, 1H), 6.72 (dd, 1H), 6.66 (dd, 1H), 6.10 (d, 1H), 4.10 (t, 2H), 3.87 (s, 3H), 3.61-3.51 (m, 4H), 2.79 (s, 3H), 2.68 (t, 2H), 2.49-2.41 (m, 4H), 1.32 (s, 9H).
LCMS m/z 396 (M+2H)²⁺ (ES⁺)

(y) 3-((4-((4-(3-(3-(Acetamidomethyl)-5-(tert-butyl)-2-methoxyphenyl)ureido)naphthalen-1-yl)oxy)pyridin-2-yl)amino)-5-methoxy-N-(2-(2-(2-methoxyethoxy)ethoxy)ethyl)benzamide

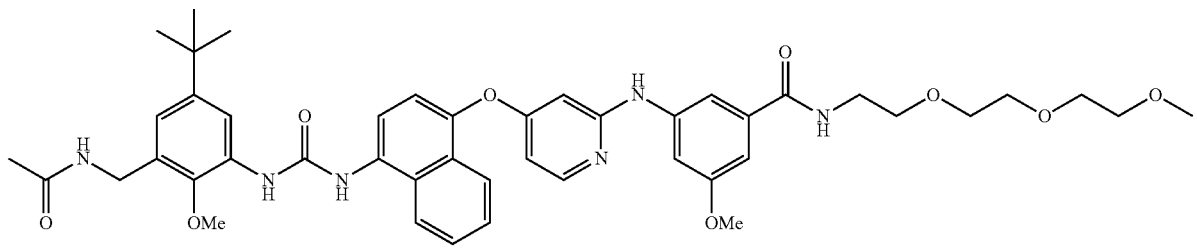 [SMILES: COCCOCCOCCNC(=O)c1cc(Nc2cc(Oc3ccc(NC(=O)Nc4cc(C(C)(C)C)cc(CNC(C)=O)c4OC)c4ccccc34)ccn2)cc(OC)c1]

¹H NMR (400 MHz, DMSO-d₆) δ 9.43 (s, 1H), 9.07 (s, 1H), 8.83 (s, 1H), 8.37-8.29 (m, 2H), 8.29-8.23 (m, 2H), 8.12 (s, 1H), 8.10 (d, 1H), 7.87 (d, 1H), 7.74-7.67 (m, 1H), 7.64-7.59 (m, 1H), 7.58 (t, 1H), 7.51 (t, 1H), 7.38 (d, 1H), 6.95 (d, 1H), 6.89 (dd, 1H), 6.57 (dd, 1H), 6.14 (d, 1H), 4.33 (d, 2H), 3.78 (s, 3H), 3.75 (s, 3H), 3.55-3.47 (m, 8H), 3.44-3.35 (m, 4H), 3.21 (s, 3H), 1.90 (s, 3H), 1.27 (s, 9H).
LCMS m/z 412 (M+2H)²⁺ (ES⁺)

(z) 3-((4-((4-(3-(5-(tert-Butyl)-2-methoxy-3-((methylsulfinyl)methyl)phenyl)ureido)naphthalen-1-yl)oxy)pyridin-2-yl)amino)-5-methoxy-N-(2-(2-(2-methoxyethoxy)ethoxy)ethyl)benzamide

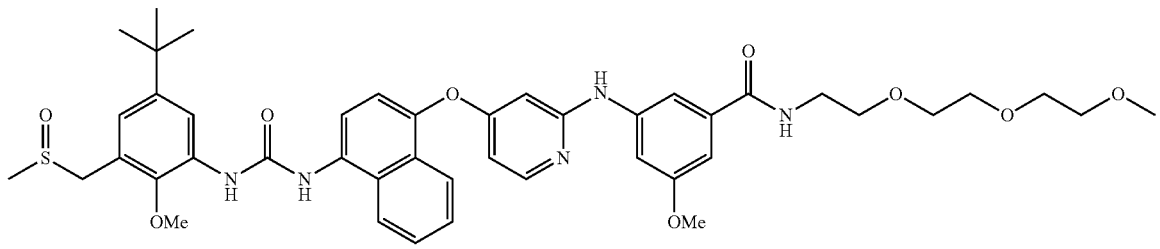

¹H NMR (400 MHz, DMSO-d₆) δ 9.42 (s, 1H), 9.07 (s, 1H), 8.89 (s, 1H), 8.42-8.22 (m, 3H), 8.13 (d, 1H), 8.11 (s, 1H), 7.88 (d, 1H), 7.75-7.66 (m, 1H), 7.65-7.55 (m, 2H), 7.55-7.49 (m, 1H), 7.39 (d, 1H), 7.04 (d, 1H), 6.93-6.85 (m, 1H), 6.58 (dd, 1H), 6.14 (d, 1H), 4.13 (d, 1H), 4.05 (d, 1H), 3.81 (s, 3H), 3.75 (s, 3H), 3.62-3.46 (m, 8H), 3.45-3.36 (m, 4H), 3.21 (s, 3H), 2.60 (s, 3H), 1.28 (s, 9H). LCMS m/z 414 (M+2H)²⁺ (ES⁺)

(aa) N-(5-(tert-Butyl)-2-methoxy-3-(3-(4-((2-(phenylamino)pyridin-4-yl)oxy)naphthalen-1-yl)ureido)benzyl)-N-methylacetamide

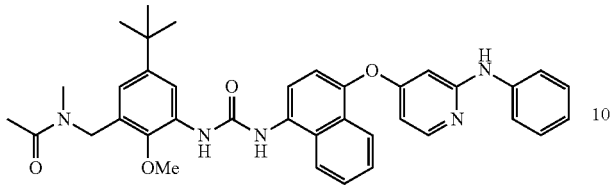

1H NMR 373K (400 MHz, DMSO-d$_6$) δ 9.13 (s, 1H), 8.59 (s, 1H), 8.53 (s, 1H), 8.38-8.24 (m, 1H), 8.20 (d, 1H), 8.08 (d, 1H), 8.01 (d, 1H), 7.95 (d, 1H), 7.72-7.64 (m, 1H), 7.63-7.53 (m, 3H), 7.32 (d, 1H), 7.25-7.16 (m, 2H), 6.87 (tt, 1H), 6.82 (d, 1H), 6.50 (dd, 1H), 6.27 (d, 1H), 4.61 (s, 2H), 3.80 (s, 3H), 2.91 (s, 3H), 2.10 (s, 3H), 1.29 (s, 9H). LCMS m/z 618 (M+H)$^+$ (ES$^+$)

(ab) 3-((4-((4-(3-(5-(tert-Butyl)-2-methoxy-3-(methylsulfonyl)phenyl)ureido)naphthalen-1-yl)oxy)pyridin-2-yl)amino)-5-methoxy-N-(2-(2-(2-methoxyethoxy)ethoxy)ethyl)benzamide

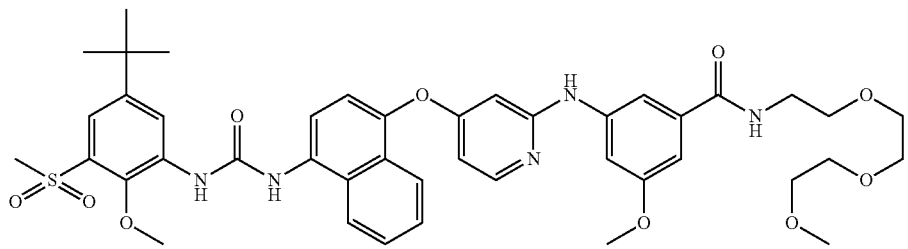 [SMILES: COCCOCCOCCNC(=O)c1cc(Nc2cc(Oc3ccc(NC(=O)Nc4cc(C(C)(C)C)cc(S(C)(=O)=O)c4OC)c4ccccc34)ccn2)cc(OC)c1]

$^1$H NMR (400 MHz, DMSO-d$_6$) δ 9.46 (s, 1H), 9.07 (d, 2H), 8.69 (d, 1H), 8.34 (t, 1H), 8.29 (d, 1H), 8.12 (s, 1H), 8.11 (d, 1H), 7.89 (d, 1H), 7.79-7.67 (m, 1H), 7.67-7.60 (m, 1H), 7.58 (t, 1H), 7.51 (t, 1H), 7.45 (d, 1H), 7.40 (d, 1H), 6.89 (dd, 1H), 6.57 (dd, 1H), 6.15 (d, 1H), 3.96 (s, 3H), 3.75 (s, 3H), 3.55-3.47 (m, 8H), 3.42-3.37 (m, 4H), 3.35 (s, 3H), 3.21 (s, 3H), 1.32 (s, 9H). LCMS m/z 830 (M+H)$^+$ (ES$^+$)

(ac) 3-((4-((4-(3-(3-(Acetamidomethyl)-5-(tert-butyl)-2-methoxyphenyl)ureido)naphthalen-1-yl)oxy)pyridin-2-yl)amino)-5-methoxybenzamide

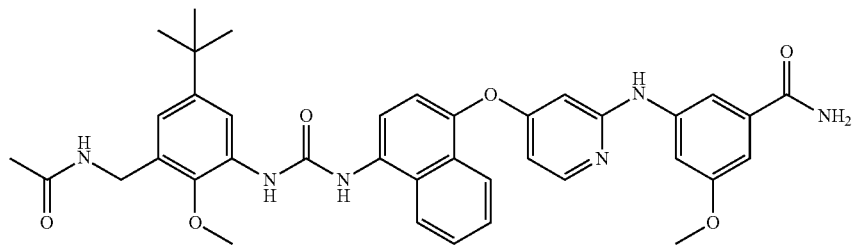 [SMILES: COc1cc(Nc2cc(Oc3ccc(NC(=O)Nc4cc(C(C)(C)C)cc(CNC(C)=O)c4OC)c4ccccc34)ccn2)cc(C(N)=O)c1]

$^1$H NMR (400 MHz, DMSO-d$_6$) δ 9.41 (s, 1H), 9.04 (s, 1H), 8.82 (s, 1H), 8.30 (d, 1H), 8.26 (t, 1H), 8.24 (d, 1H), 8.12 (d, 1H), 8.10 (d, 1H), 7.87 (d, 1H), 7.81 (s, 1H), 7.71 (ddd, 1H), 7.61 (ddd, 1H), 7.57 (dd, 1H), 7.52 (dd, 1H), 7.38 (d, 1H), 7.24 (s, 1H), 6.95 (d, 1H), 6.92 (dd, 1H), 6.56 (dd, 1H), 6.14 (d, 1H), 4.33 (d, 2H), 3.78 (s, 3H), 3.74 (s, 3H), 1.90 (s, 3H), 1.27 (s, 9H). LCMS m/z 677 (M+H)$^+$ (ES$^+$)

(ad) 2-(5-(tert-Butyl)-3-(3-(4-((2-((3-(cyclopropyl-sulfonyl)-5-methoxyphenyl)amino)pyridin-4-yl)oxy)naphthalen-1-yl)ureido)-2-methoxyphenyl)acetamide

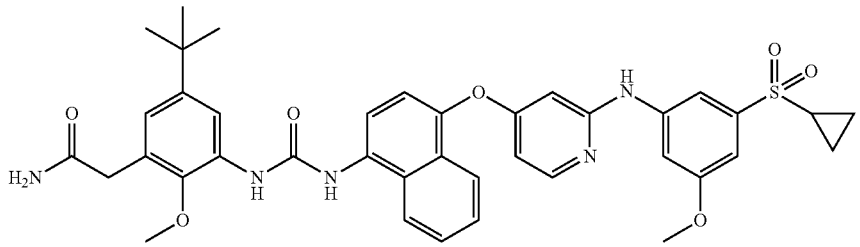 [SMILES: COc1cc(Nc2cc(Oc3ccc(NC(=O)Nc4cc(C(C)(C)C)cc(CC(N)=O)c4OC)c4ccccc34)ccn2)cc(S(=O)(=O)C2CC2)c1]

¹H NMR (400 MHz, DMSO-d₆) δ: 9.40 (s, 1H), 9.33 (s, 1H), 8.79 (s, 1H), 8.31 (d, 1H), 8.20 (d, 1H), 8.15 (d, 1H), 8.12 (d, 1H), 7.85 (d, 1H), 7.72-7.67 (m, 3H), 7.62-7.58 (m, 1H), 7.44 (bs, 1H), 7.39 (d, 1H), 6.93 (d, 2H), 6.85 (dd, 1H), 6.65 (dd, 1H), 6.10 (d, 1H), 3.78 (s, 3H), 3.77 (s, 3H), 3.45 (s, 2H), 2.81-2.77 (m, 1H), 1.26 (s, 9H), 1.08-1.01 (m, 4H). LCMS m/z 724 (M+H)⁺ (ES⁺).

(ae) 2-(5-(tert-Butyl)-3-(3-(4-((2-((3-(dimethylphos-phoryl)-5-methoxyphenyl)amino)pyridin-4-yl)oxy)naphthalen-1-yl)ureido)-2-methoxyphenyl)acetamide

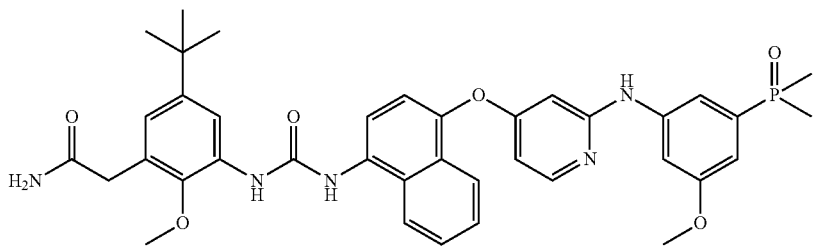 [SMILES: COc1cc(Nc2cc(Oc3ccc(NC(=O)Nc4cc(C(C)(C)C)cc(CC(N)=O)c4OC)c4ccccc34)ccn2)cc(P(C)(C)=O)c1]

¹H NMR (400 MHz, DMSO-d₆) δ: 9.38 (s, 1H), 9.12 (s, 1H), 8.79 (s, 1H), 8.30 (d, 1H), 8.20 (d, 1H), 8.12 (s, 1H), 8.10 (d, 1H), 7.86 (d, 1H), 7.70-7.68 (m, 1H), 7.63-7.58 (m, 2H), 7.44 (bs, 1H), 7.40-7.37 (m, 2H), 6.93 (d, 2H), 6.76-6.72 (m, 1H), 6.58 (dd, 1H), 6.11 (d, 1H), 3.77 (s, 3H), 3.74 (s, 3H), 3.44 (s, 2H), 1.58 (d, 6H), 1.26 (s, 9H). LCMS m/z 696 (M+H)⁺ (ES⁺)

(af) 2-(5-(tert-Butyl)-3-(3-(2,3-dichloro-4-((2-((3-methoxyphenyl)amino)pyridin-4-yl)oxy)phenyl)ureido)-2-methoxyphenyl)acetamide

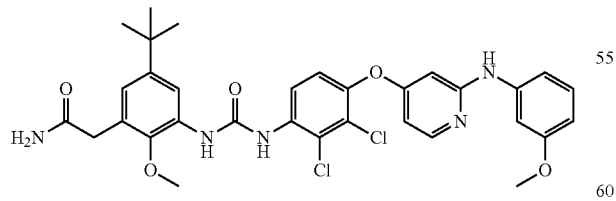

¹H NMR (400 MHz, DMSO-d₆) δ 9.16 (s, 1H), 9.10 (s, 1H), 9.00 (s, 1H), 8.24 (d, 1H), 8.16-8.00 (m, 2H), 7.46 (s, 1H), 7.40 (d, 1H), 7.39-7.35 (m, 1H), 7.18-7.09 (m, 2H), 7.00-6.90 (m, 2H), 6.50 (dd, 1H), 6.48-6.43 (m, 1H), 6.10 (d, 1H), 3.72 (s, 3H), 3.71 (s, 3H), 3.44 (s, 2H), 1.26 (s, 9H). LCMS m/z 638/640 (M+H)⁺ (ES⁺)

(ag) 3-((4-(4-(3-(3-(2-Amino-2-oxoethyl)-5-(tert-butyl)-2-methoxyphenyl)ureido)-2,3-dichlorophenoxy)pyridin-2-yl)amino)-5-methoxy-N-(2-(2-(2-methoxyethoxy)ethoxy)ethyl)benzamide

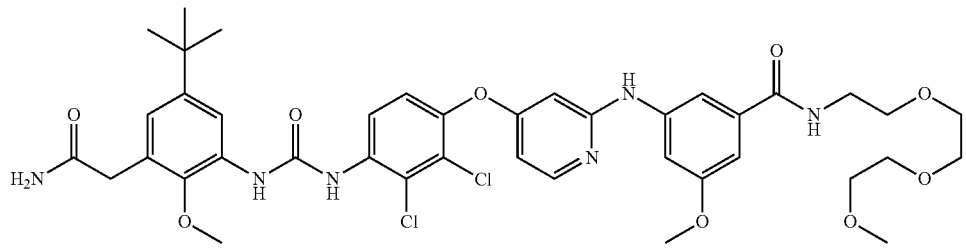 [SMILES: COCCOCCOCCNC(=O)c1cc(Nc2cc(Oc3ccc(NC(=O)Nc4cc(C(C)(C)C)cc(CC(N)=O)c4OC)c(Cl)c3Cl)ccn2)cc(OC)c1]

$^1$H NMR (400 MHz, DMSO-d$_6$) δ 9.15 (d, 2H), 9.10 (s, 1H), 8.37 (t, 1H), 8.24 (d, 1H), 8.17-8.04 (m, 2H), 7.62 (t, 1H), 7.54 (t, 1H), 7.44 (s, 1H), 7.40 (d, 1H), 6.96 (d, 1H), 6.95-6.85 (m, 2H), 6.51 (dd, 1H), 6.15 (d, 1H), 3.77 (s, 3H), 3.72 (s, 3H), 3.58-3.48 (m, 8H), 3.46-3.36 (m, 6H), 3.22 (s, 3H), 1.26 (s, 9H). LCMS m/z 827/829 (M+H)$^+$ (ES$^+$)

(ah) 2-(5-(tert-Butyl)-3-(3-(4-((2-((3-cyano-5-methoxyphenyl)amino)pyridin-4-yl)oxy)naphthalen-1-yl)ureido)-2-methoxyphenyl)acetamide

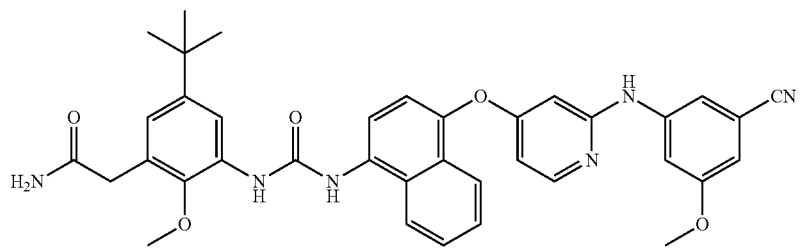 [SMILES: COc1cc(C#N)cc(Nc2cc(Oc3ccc(NC(=O)Nc4cc(C(C)(C)C)cc(CC(N)=O)c4OC)c4ccccc34)ccn2)c1]

$^1$H NMR (400 MHz, DMSO-d$_6$) δ: 9.41 (s, 1H), 9.27 (s, 1H), 8.80 (s, 1H), 8.31 (d, 1H), 8.19 (d, 1H), 8.18 (d, 1H), 8.12 (d, 1H), 7.86 (d, 1H), 7.75 (s, 1H), 7.71 (t, 1H), 7.61 (t, 1H), 7.48 (t, 1H), 7.45 (bs, 1H), 7.40 (d, 1H), 6.94 (d, 2H), 6.89 (s, 1H), 6.68 (dd, 1H), 6.07 (d, 1H), 3.78 (s, 3H), 3.75 (s, 3H), 3.45 (s, 2H), 1.27 (s, 9H). LCMS m/z 323 (M+2H)$^{2+}$ (ES$^+$)

(ai) 2-(5-(tert-Butyl)-2-methoxy-3-(3-(4-((2-((3-methoxy-5-sulfamoylphenyl)amino)pyridin-4-yl)oxy)naphthalen-1-yl)ureido)phenyl)acetamide

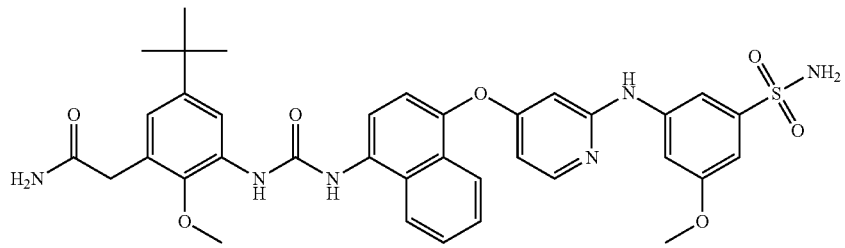 [SMILES: COc1cc(Nc2cc(Oc3ccc(NC(=O)Nc4cc(C(C)(C)C)cc(CC(N)=O)c4OC)c4ccccc34)ccn2)cc(S(N)(=O)=O)c1]

$^1$H NMR (400 MHz, DMSO-d$_6$) δ 9.40 (s, 1H), 9.25 (s, 1H), 8.80 (s, 1H), 8.31 (d, 1H), 8.21 (d, 1H), 8.18-8.06 (m, 2H), 7.87 (d, 1H), 7.75-7.68 (m, 1H), 7.66 (t, 1H), 7.64-7.59 (m, 1H), 7.58 (t, 1H), 7.45 (s, 1H), 7.39 (d, 1H), 7.26 (s, 2H), 7.01-6.91 (m, 2H), 6.88 (dd, 1H), 6.63 (dd, 1H), 6.13 (d, 1H), 3.78 (s, 3H), 3.76 (s, 3H), 3.45 (s, 2H), 1.27 (s, 9H). LCMS m/z 699 (M+H)$^+$ (ES$^+$)

(aj) 2-(5-(tert-Butyl)-3-(3-(4-((2-((3-(N,N-dimethyl-sulfamoyl)-5-methoxyphenyl)amino)pyridin-4-yl)oxy)naphthalen-1-yl)ureido)-2-methoxyphenyl)acetamide

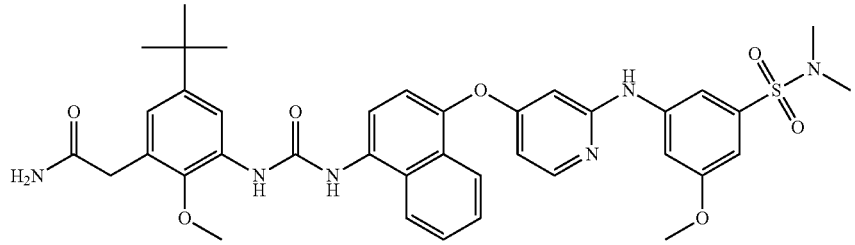 [SMILES: COc1cc(Nc2cc(Oc3ccc(NC(=O)Nc4cc(C(C)(C)C)cc(CC(N)=O)c4OC)c4ccccc34)ccn2)cc(S(=O)(=O)N(C)C)c1]

$^1$H NMR (400 MHz, DMSO-d$_6$) δ 9.40 (s, 1H), 9.31 (s, 1H), 8.80 (s, 1H), 8.31 (d, 1H), 8.21 (d, 1H), 8.18-8.07 (m, 2H), 7.86 (d, 1H), 7.76-7.66 (m, 2H), 7.66-7.58 (m, 1H), 7.57 (t, 1H), 7.45 (s, 1H), 7.40 (d, 1H), 7.03-6.87 (m, 2H), 6.73-6.61 (m, 2H), 6.10 (d, 1H), 3.78 (s, 3H), 3.78 (s, 3H), 3.45 (s, 2H), 2.61 (s, 6H), 1.27 (s, 9H). LCMS m/z 727 (M+H)$^+$ (ES$^+$)

(ak) 5-(tert-Butyl)-2-methoxy-3-(3-(4-((2-((3-methoxy-5-((2-morpholinoethyl)carbamoyl)-phenyl)amino)pyrimidin-4-yl)oxy)naphthalen-1-yl)ureido)-N-(2-morpholinoethyl)benzamide

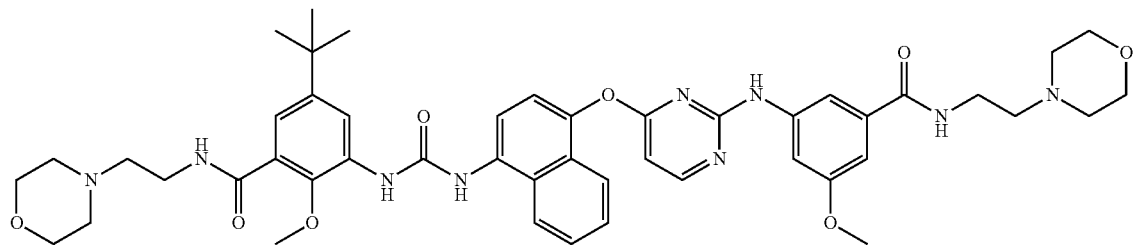 [SMILES: COc1cc(Nc2nccc(Oc3ccc(NC(=O)Nc4cc(C(C)(C)C)cc(C(=O)NCCN5CCOCC5)c4OC)c4ccccc34)n2)cc(C(=O)NCCN2CCOCC2)c1]

$^1$H NMR (400 MHz, DMSO-d$_6$) δ: 9.61 (s, 1H), 9.42 (s, 1H), 8.92 (s, 1H), 8.47 (d, 1H), 8.42 (d, 1H), 8.23-8.29 (m, 2H), 8.18 (t, 1H), 8.08 (d, 1H), 7.86 (d, 1H), 7.67-7.71 (m, 1H), 7.56-7.62 (m, 2H), 7.44 (d, 1H), 7.34 (s, 1H), 7.25 (d, 1H), 6.86 (s, 1H), 6.55 (d, 1H), 3.84 (s, 3H), 3.61-3.63 (m, 4H), 3.59 (s, 3H), 3.54-3.56 (m, 4H), 3.45 (q, 2H), 3.32-3.37 (m, 2H), 2.40-2.46 (m, 12H), 1.29 (s, 9H). LCMS m/z 877 (M+H)$^+$ (ES$^+$)

(al) 3-((4-((4-(3-(3-(2-Amino-2-oxoethyl)-5-(tert-butyl)-2-methoxyphenyl)ureido)naphthalen-1-yl)oxy)pyridin-2-yl)amino)-N-(3-hydroxy-2,2-bis(hydroxymethyl)propyl)-5-methoxybenzamide

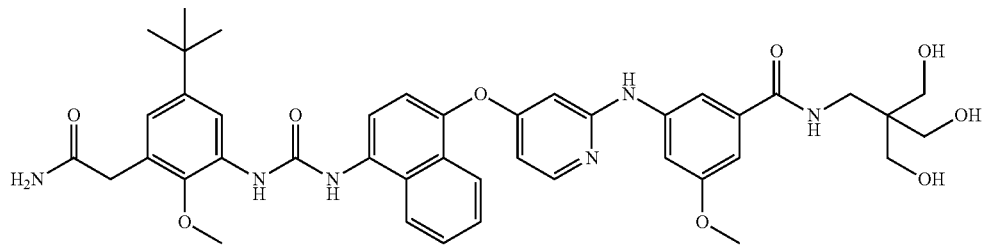 [SMILES: COc1cc(Nc2cc(Oc3ccc(NC(=O)Nc4cc(C(C)(C)C)cc(CC(N)=O)c4OC)c4ccccc34)ccn2)cc(C(=O)NCC(CO)(CO)CO)c1]

¹H NMR (400 MHz, DMSO-d₆) δ 9.39 (s, 1H), 9.10 (s, 1H), 8.79 (s, 1H), 8.31 (d, 1H), 8.24 (t, 1H), 8.21 (d, 1H), 8.17-8.07 (m, 2H), 7.87 (d, 1H), 7.75-7.66 (m, 1H), 7.65-7.59 (m, 1H), 7.60-7.57 (m, 1H), 7.55-7.52 (m, 1H), 7.45 (s, 1H), 7.39 (d, 1H), 7.01-6.89 (m, 2H), 6.88-6.78 (m, 1H), 6.59 (dd, 1H), 6.12 (d, 1H), 4.46 (t, 3H), 3.78 (s, 3H), 3.75 (s, 3H), 3.46 (s, 2H), 3.24 (d, 2H), 1.27 (s, 9H). (6H under water peak at 3.32 ppm). LCMS m/z 781 (M+H)⁺ (ES⁺)

(am) 3-((4-((4-(3-(5-(tert-Butyl)-3-(dimethylphosphoryl)-2-methoxyphenyl)ureido)naphthalen-1-yl)oxy)pyridin-2-yl)amino)-5-methoxy-N-(2-(1-oxidothiomorpholino)ethyl)benzamide

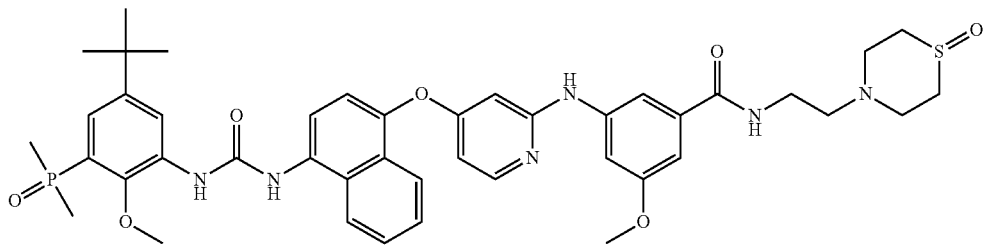 [SMILES: COc1cc(Nc2cc(Oc3ccc(NC(=O)Nc4cc(C(C)(C)C)cc(P(C)(C)=O)c4OC)c4ccccc34)ccn2)cc(C(=O)NCCN2CCS(=O)CC2)c1]

¹H NMR (400 MHz, DMSO-d₆) δ 9.35 (s, 1H), 9.06 (s, 1H), 8.91 (s, 1H), 8.44 (d, 1H), 8.29 (d, 1H), 8.27-8.20 (m, 1H), 8.18-8.06 (m, 2H), 7.88 (d, 1H), 7.77-7.68 (m, 1H), 7.65-7.58 (m, 1H), 7.56 (t, 1H), 7.51 (s, 1H), 7.42-7.32 (m, 2H), 6.90-6.81 (m, 1H), 6.58 (dd, 1H), 6.14 (d, 1H), 3.91 (s, 3H), 3.75 (s, 3H), 3.01-2.79 (m, 4H), 2.71 (q, 4H), 2.59-2.52 (m, 2H), 1.75 (d, 6H), 1.31 (s, 9H). (CH₂ under water peak at 3.32 ppm). LCMS m/z 827 (M+H)⁺ (ES⁺); 825 (M−H)⁻ (ES⁻)

(an) 3-((4-((4-(3-(5-(tert-Butyl)-2-methoxy-3-(methylsulfonyl)phenyl)ureido)naphthalen-1-yl)oxy)pyridin-2-yl)amino)-5-methoxy-N-(2-(1-oxidothiomorpholino)ethyl)benzamide

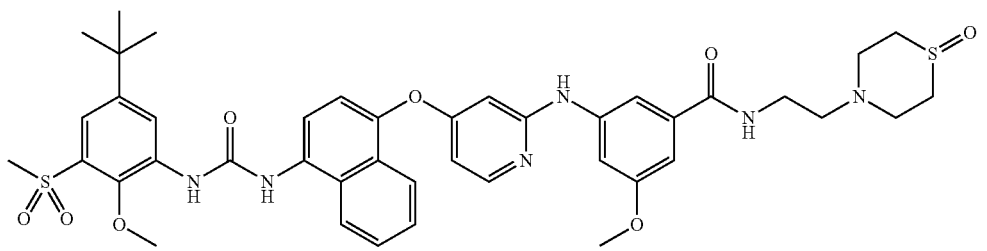 [SMILES: COc1cc(Nc2cc(Oc3ccc(NC(=O)Nc4cc(C(C)(C)C)cc(S(C)(=O)=O)c4OC)c4ccccc34)ccn2)cc(C(=O)NCCN2CCS(=O)CC2)c1]

¹H NMR (400 MHz, DMSO-d₆) δ 9.47 (s, 1H), 9.18-8.99 (m, 2H), 8.68 (d, 1H), 8.29 (d, 1H), 8.25 (t, 1H), 8.17-8.06 (m, 2H), 7.89 (d, 1H), 7.79-7.68 (m, 1H), 7.68-7.59 (m, 1H), 7.56 (t, 1H), 7.51 (s, 1H), 7.45 (d, 1H), 7.40 (d, 1H), 6.93-6.81 (m, 1H), 6.58 (dd, 1H), 6.15 (d, 1H), 3.96 (s, 3H), 3.75 (s, 3H), 3.02-2.80 (m, 4H), 2.79-2.62 (m, 4H), 2.59-2.53 (m, 2H), 1.32 (s, 9H). (CH₂ and —SO₂CH₃ under water peak at 3.32 ppm). LCMS m/z 829 (M+H)⁺ (ES⁺); 827 (M−H)⁻ (ES⁻)

(ao) 4-((4-((4-(3-(5-(tert-Butyl)-3-(dimethylphosphoryl)-2-methoxyphenyl)ureido)naphthalen-1-yl)oxy)pyridin-2-yl)amino)-2-methoxy-N-(2-morpholinoethyl)benzamide

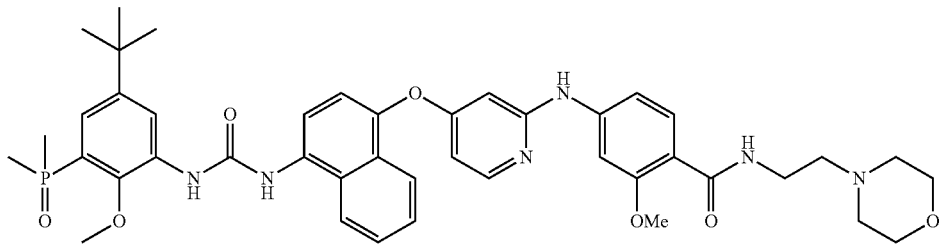 [SMILES: COc1cc(Nc2cc(Oc3ccc(NC(=O)Nc4cc(C(C)(C)C)cc(P(C)(C)=O)c4OC)c4ccccc34)ccn2)ccc1C(=O)NCCN1CCOCC1]

¹H NMR (DMSO-d₆, 400 MHz) δ 9.35 (s, 1H), 9.25 (s, 1H), 8.91 (s, 1H), 8.43 (d, 1H), 8.29 (d, 1H), 8.20 (t, 1H), 8.16 (d, 1H), 8.13 (d, 1H), 7.86 (dd, 1H), 7.76 (d, 1H), 7.73-7.69 (m, 1H), 7.63-7.59 (m, 1H), 7.57 (d, 1H), 7.40 (d, 1H), 7.35 (dd, 1H), 7.22 (dd, 1H), 6.64 (dd, 1H), 6.15 (d, 1H), 3.90 (s, 3H), 3.87 (s, 3H), 3.61-3.59 (m, 4H), 3.40-3.35 (m, 2H), 2.47-2.41 (m, 6H), 1.74 (d, 6H), 1.30 (s, 9H). LCMS m/z 795 (M+H)⁺ (ES⁺); 793 (M−H)⁻ (ES⁻)

(ap) 4-((4-((4-(3-(5-(tert-Butyl)-2-methoxy-3-(methylsulfonyl)phenyl)ureido)naphthalen-1-yl)oxy)pyridin-2-yl)amino)-2-methoxy-N-(2-morpholinoethyl)benzamide

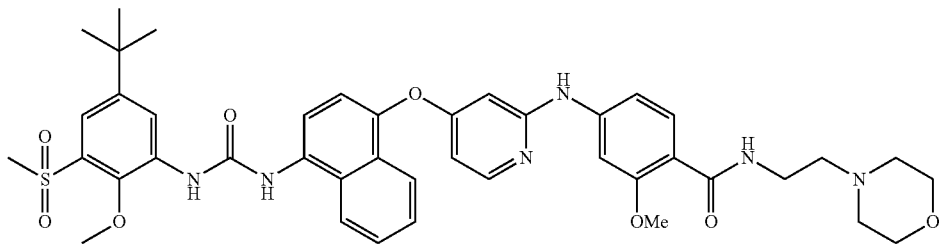

¹H NMR (400 MHz, DMSO-d₆) δ 9.47 (s, 1H), 9.27 (s, 1H), 9.09 (s, 1H), 8.68 (d, 1H), 8.29 (d, 1H), 8.21 (t, 1H), 8.16 (d, 1H), 8.12 (d, 1H), 7.88 (d, 1H), 7.76 (d, 1H), 7.74-7.70 (m, 1H), 7.64-7.60 (m, 1H), 7.57 (d, 1H), 7.44 (d, 1H), 7.41 (d, 1H), 7.22 (dd, 1H), 6.66 (dd, 1H), 6.15 (d, 1H), 3.94 (s, 3H), 3.87 (s, 3H), 3.61-3.59 (m, 4H), 3.38-3.37 (m, 2H), 3.34 (s, 3H), 2.45-2.41 (m, 6H), 1.31 (s, 9H). LCMS m/z 797 (M+H)⁺ (ES⁺); 795 (M−H)⁻ (ES⁻)

Example 39

1-(5-(tert-Butyl)-3-(dimethylphosphoryl)-2-hydroxyphenyl)-3-(4-((2-(phenylamino)pyridin-4-yl)oxy)naphthalen-1-yl)urea

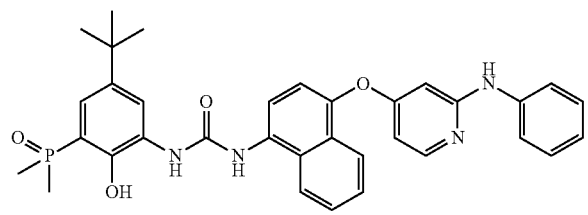 [SMILES: CC(C)(C)c1cc(NC(=O)Nc2ccc(Oc3ccnc(Nc4ccccc4)c3)c3ccccc23)c(O)c(P(C)(C)=O)c1]

BBr₃ (60 μL, 0.635 mmol) was added to a solution of 1-(5-(tert-butyl)-3-(dimethylphosphoryl)-2-methoxyphenyl)-3-(4-((2-(phenylamino)pyridin-4-yl)oxy)naphthalen-1-yl)urea (see Example 11 above; 184 mg, 0.302 mmol) in DCM (10 mL) at 0-5° C. The mixture was warmed to rt and stirred for 24 h. The mixture was quenched carefully with MeOH (1 mL), then partitioned between DCM (15 mL) and water (15 mL). The organic layer was separated, washed with brine (10 mL) and dried via hydrophibic frit. The crude product was purified by chromatography on silica gel (12 g column, 2-10% MeOH/DCM) to afford the title compound (21 mg) as an off-white solid.

¹H NMR (400 MHz, DMSO-d₆) δ: 12.08 (s, 1H), 9.44 (s, 1H), 8.90 (s, 1H), 8.81 (s, 1H), 8.39 (d, 1H), 8.30 (d, 1H), 8.07-8.09 (m, 2H), 7.87 (d, 1H), 7.69 (t, 1H), 7.58-7.62 (m, 3H), 7.38 (d, 1H), 7.20 (t, 2H), 7.07 (dd, 1H), 6.84 (t, 1H), 6.56 (dd, 1H), 6.09 (d, 1H), 1.85 (d, 6H), 1.28 (s, 9H). LCMS m/z 595 (M+H)⁺ (ES⁺); 593 (M−H)⁻ (ES⁻)

Example 40

1-(5-(tert-Butyl)-2-methoxy-3-(methylsulfinyl)phenyl)-3-(4-((2-((3,5-dimethoxyphenyl)amino)pyridin-4-yl)oxy)naphthalen-1-yl)urea

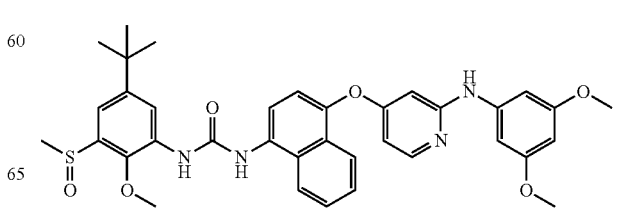

Triethylamine (5 μL, 0.036 mmol) was added to a mixture of phenyl (5-(tert-butyl)-2-methoxy-3-(methylsulfinyl)phenyl)carbamate (see Example 12(iv) above; 60 mg, 0.166 mmol) and 4-((4-aminonaphthalen-1-yl)oxy)-N-(3,5-dimethoxyphenyl)pyridin-2-amine (see Example 27(ii) above; 60 mg, 0.155 mmol) in THF (3 mL) and the mixture heated at 65° C. (block temperature) for 16 h. The reaction was cooled to rt and the mixture concentrated in vacuo onto silica gel. The crude product was purified by chromatography on the Companion (12 g column, 1-5% MeOH in DCM) to afford a pink solid. The crude product was purified by preparative HPLC (Gilson, Acidic (0.1% Formic acid), Acidic, Waters X-Select Prep-C18, 5 μm, 19×50 mm column, 25-75% MeCN in Water) to afford the title compound (51 mg) as a white solid.

$^1$H NMR (400 MHz, DMSO-$d_6$) δ: 9.41 (s, 1H), 8.96 (s, 1H), 8.89 (s, 1H), 8.51 (d, 1H), 8.28 (d, 1H), 8.11 (s, 1H), 8.09 (d, 1H), 7.88 (d, 1H), 7.71 (t, 1H), 7.62 (t, 1H), 7.39 (d, 1H), 7.37 (d, 1H), 6.85 (d, 2H), 6.58 (dd, 1H), 6.09 (d, 1H), 6.02 (t, 1H), 3.87 (s, 3H), 3.66 (s, 6H), 2.79 (s, 3H), 1.32 (s, 9H). LCMS m/z 655 (M+H)$^+$ (ES$^+$)

Example 41

1-(5-(tert-Butyl)-2-methoxy-3-(methylsulfinyl)phenyl)-3-(4-((2-((3-methoxyphenyl)amino)pyridin-4-yl)oxy)naphthalen-1-yl)urea

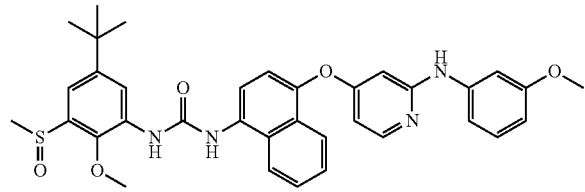

Triethylamine (5 μL, 0.036 mmol) was added to a mixture of phenyl (5-(tert-butyl)-2-methoxy-3-(methylsulfinyl)phenyl)carbamate (see Example 12(iv) above; 60 mg, 0.166 mmol) and 4-((4-aminonaphthalen-1-yl)oxy)-N-(3-methoxyphenyl)pyridin-2-amine (see Example 33 (ii) above; 60 mg, 0.168 mmol) in THF (3 mL) and the mixture heated at 65° C. (block temperature) for 16 h. The reaction was cooled to rt and the mixture concentrated in vacuo onto silica gel. The crude product was purified by chromatography on the Companion (12 g column, 1-10% MeOH in DCM) to afford a pale pink solid. The crude product was purified by preparative HPLC (Gilson, Acidic (0.1% Formic acid), Acidic, Waters X-Select Prep-C18, 5 μm, 19×50 mm column, 25-75% MeCN in Water) to afford the title compound (53 mg) as a white solid.

$^1$H NMR (400 MHz, DMSO-$d_6$) δ: 9.41 (s, 1H), 8.96 (s, 1H), 8.91 (s, 1H), 8.51 (d, 1H), 8.28 (d, 1H), 8.09-8.11 (m, 2H), 7.88 (d, 1H), 7.72 (t, 1H), 7.62 (t, 1H), 7.40 (d, 1H), 7.37 (d, 1H), 7.34 (s, 1H), 7.09-7.10 (m, 2H), 6.57 (dd, 1H), 6.41-6.46 (m, 1H), 6.10 (d, 1H), 3.87 (s, 3H), 3.68 (s, 3H), 2.79 (s, 3H), 1.32 (s, 9H). LCMS m/z 625 (M+H)$^+$ (ES-F); 623 (M−H)$^−$ (ES$^−$)

Example 42

1-(5-(tert-Butyl)-2-methoxy-3-(methylsulfinyl)phenyl)-3-(4-((2-((pyridin-2-ylmethyl)amino)pyridin-4-yl)oxy)naphthalen-1-yl)urea

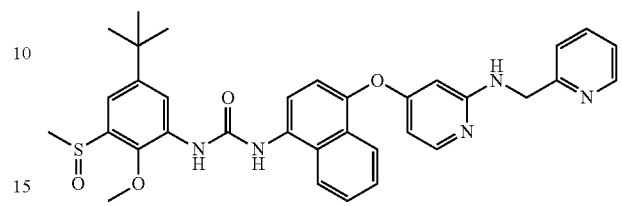

(i) tert-Butyl (4-((2-((pyridin-2-ylmethyl)amino) pyridin-4-yl)oxy)naphthalen-1-yl)carbamate A mixture of tert-butyl (4-((2-chloropyridin-4-yl)oxy) naphthalen-1-yl)carbamate (see Example 2(ii) above; 1.0 g, 2.70 mmol), pyridin-2-ylmethanamine (0.350 g, 3.24 mmol), Pd$_2$(dba)$_3$ (0.150 g, 0.164 mmol), Cs$_2$CO$_3$ (1.5 g, 4.60 mmol) and BINAP (0.200 g, 0.321 mmol) in 1,4-dioxane (15 mL) was purged with nitrogen for 10 minutes. The mixture was then heated to 90° C. for 18 h. The mixture was diluted with DCM (50 mL) and filtered. The filtrate was concentrated under reduced pressure and purified by chromatography on the Companion (80 g column, 50-100% EtOAc/isohexane) to afford the sub-title compound (390 mg) as an orange glass.
LCMS m/z 443 (M+H)$^+$ (ES$^+$); 441 (M−H)$^−$ (ES$^−$)

(ii) 4-((4-Aminonaphthalen-1-yl)oxy)-N-(pyridin-2-ylmethyl)pyridin-2-amine

The product from step (i) above (390 mg, 0.749 mmol) and TFA (1.0 mL, 12.98 mmol) were stirred in DCM (5 mL) at rt for 1 h. The mixture was co-evaporated in toluene (40 mL) then redissolved in DCM (15 mL). The solution was washed with saturated NaHCO$_3$ solution (15 mL) then loaded directly onto the Companion (40 g column, 50-100% EtOAc/isohexane) to afford the sub-title compound (235 mg) as a brown foam.
LCMS m/z 343 (M+H)$^+$ (ES$^+$); 341 (M−H)$^−$ (ES$^−$)

(iii) 1-(5-(tert-Butyl)-2-methoxy-3-(methylsulfinyl) phenyl)-3-(4-((2-((pyridin-2-ylmethyl)amino)pyridin-4-yl)oxy)naphthalen-1-yl)urea Phenyl (5-(tert-butyl)-2-methoxy-3-(methylsulfinyl)phenyl)carbamate (see Example 12(iv) above; 60 mg, 0.166 mmol), the product from step (ii) above (50 mg, 0.146 mmol) and Et$_3$N (5 μL, 0.036 mmol) were heated to 70° C. (block temperature) in isopropyl acetate/THF (1:1, 5 mL) for 18 h. The volatiles were removed under reduced pressure and the residue was purified by preparative HPLC (Varian, Acidic (0.1% Formic acid), Acidic, Waters X-Select Prep-C18, 5 μm, 19×50 mm column, 15-60% MeCN in Water) to afford the formate salt. The salt was loaded onto a column of SCX (250 mg) in MeOH. The column was washed with MeOH and then the product was eluted with 0.7 M ammonia in MeOH. The resultant mixture was concentrated in vacuo then purified by preparative HPLC (Varian, Basic (0.1% Ammonium Bicarbonate), Basic, Waters X-Bridge Prep-C18, 5 μm, 19×50 mm column, 20-95% MeCN in 0.1% ammonium bicarbonate/water) to afford the title compound (31 mg) as a white solid.

¹H NMR (400 MHz, DMSO-d₆) δ:9.39 (s, 1H), 8.95 (s, 1H), 8.50 (d, 1H), 8.45 (ddd, 1H), 8.26 (d, 1H), 8.06 (d, 1H), 7.90-7.83 (m, 2H), 7.74-7.65 (m, 2H), 7.60 (ddd, 1H), 7.36 (d, 1H), 7.31 (d, 1H), 7.25 (d, 1H), 7.20 (ddd, 1H), 7.11 (t, 1H), 7.25 (dd, 1H), 5.93 (d, 1H), 4.49 (d, 2H), 3.86 (s, 3H), 2.79 (s, 3H), 1.32 (s, 9H). LCMS m/z 610 (M+H)⁺ (ES⁺); 608 (M−H)⁻ (ES⁻)

Example 43

N-(5-(tert-Butyl)-2-methoxy-3-(3-(4-((2-((3-methoxyphenyl)amino)pyridin-4-yl)oxy)naphthalen-1-yl)ureido)benzyl)acetamide

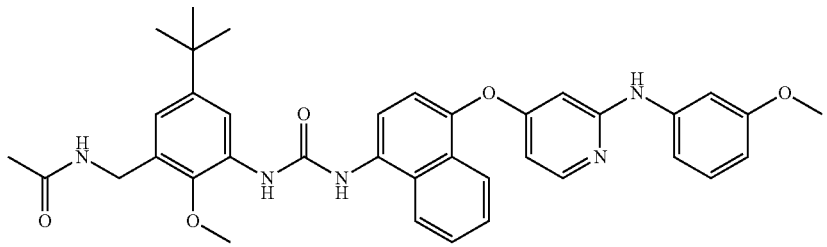 [SMILES: COc1cccc(Nc2cc(Oc3ccc(NC(=O)Nc4cc(C(C)(C)C)cc(CNC(C)=O)c4OC)c4ccccc34)ccn2)c1]

A solution of phenyl (3-(acetamidomethyl)-5-(tert-butyl)-2-methoxyphenyl)carbamate (see Example 35(v) above; 100 mg, 0.270 mmol), 4-((4-aminonaphthalen-1-yl)oxy)-N-(3-methoxyphenyl)pyridin-2-amine (see Example 33 (ii) above; 100 mg, 0.280 mmol) and Et₃N (10 μL, 0.072 mmol) was heated to 60° C. (block temp) in isopropyl acetate (3 mL) for 24 h. The mixture was diluted with ethyl acetate (10 mL) then washed with saturated NaHCO₃ solution (10 mL) followed by saturated brine (10 mL). The organic phase was dried (MgSO₄), filtered and concentrated under reduced pressure. The crude product was purified by chromatography on the Companion (40 g column, 2-5% MeOH/DCM) to afford the title compound (100 mg) as a pale pink solid.

¹H NMR (400 MHz, DMSO-d₆) δ: 9.40 (s, 1H), 8.90 (s, 1H), 8.82 (s, 1H), 8.30 (d, 1H), 8.26 (dd, 1H), 8.25 (d, 1H), 8.10 (d, 1H), 8.09 (d, 1H), 7.86 (d, 1H), 7.71 (ddd, 1H), 7.61 (ddd, 1H), 7.38 (d, 1H), 7.35-7.31 (m, 1H), 7.13-7.05 (m, 2H), 6.95 (d, 1H), 6.56 (dd, 1H), 6.47-6.39 (m, 1H), 6.09 (d, 1H), 4.33 (d, 2H), 3.78 (s, 3H), 3.68 (s, 3H), 1.90 (s, 3H), 1.27 (s, 9H).

LCMS m/z 634 (M+H)⁺ (ES⁺); 632 (M−H)⁻ (ES⁻)

Example 44

N-(5-(tert-Butyl)-3-(3-(4-((2-((3,5-dimethoxyphenyl)amino)pyridin-4-yl)oxy)naphthalen-1-yl)ureido)-2-methoxybenzyl)acetamide

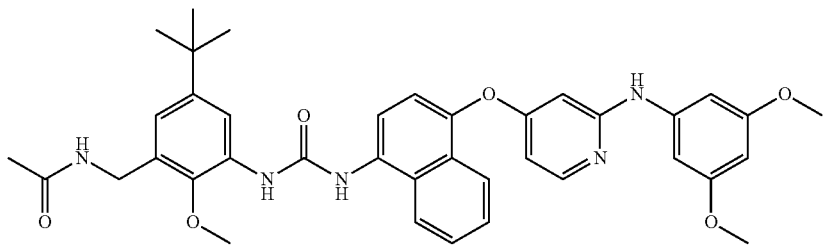 [SMILES: COc1cc(Nc2cc(Oc3ccc(NC(=O)Nc4cc(C(C)(C)C)cc(CNC(C)=O)c4OC)c4ccccc34)ccn2)cc(OC)c1]

A solution of phenyl (3-(acetamidomethyl)-5-(tert-butyl)-2-methoxyphenyl)carbamate (see Example 35(v) above; 100 mg, 0.270 mmol), 4-((4-aminonaphthalen-1-yl)oxy)-N-(3,5-dimethoxyphenyl)pyridin-2-amine (see Example 27(ii) above; 100 mg, 0.258 mmol) and Et₃N (10 μL, 0.072 mmol) was heated to 60° C. (block temp) in isopropyl acetate (3 mL) for 24 h. The mixture was diluted with ethyl acetate (10 mL) then washed with saturated NaHCO₃ solution (10 mL) followed by saturated brine (10 mL). The organic phase was dried (MgSO₄), filtered and concentrated under reduced pressure. The crude product was purified by chromatography on the Companion (40 g column, 2-5% MeOH/DCM) then purified further by chromatography on the Companion (40 g column, 0-40% Acetone/PhMe) to afford the title compound (90 mg) as a white solid.

¹H NMR (400 MHz, DMSO-d₆) δ: 9.14 (s, 1H), 8.88 (s, 1H), 8.82 (s, 1H), 8.30 (d, 1H), 8.26 (dd, 1H), 8.24 (d, 1H), 8.11 (d, 1H), 8.09 (d, 1H), 7.87 (d, 1H), 7.71 (ddd, 1H), 7.61 (ddd, 1H), 7.38 (d, 1H), 6.95 (d, 1H), 6.84 (d, 2H), 6.57 (dd, 1H), 6.09 (d, 1H), 6.02 (dd, 1H), 4.33 (d, 2H), 3.79 (s, 3H), 3.06 (s, 6H), 1.90 (s, 3H), 1.27 (s, 9H).

LCMS m/z 664 (M+H)⁺ (ES⁺); 662 (M−H)⁻ (ES⁻)

Example 45

3-((4-((4-(3-(3-(2-Amino-2-oxoethyl)-5-(tert-butyl)-2-methoxyphenyl)ureido)naphthalen-1-yl)oxy)pyridin-2-yl)amino)-5-methoxy-N-(2-morpholinoethyl)benzamide

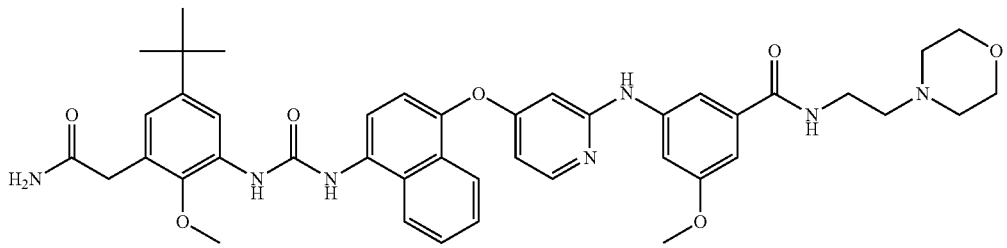 [SMILES: COc1cc(Nc2cc(Oc3ccc(NC(=O)Nc4cc(C(C)(C)C)cc(CC(N)=O)c4OC)c4ccccc34)ccn2)cc(C(=O)NCCN2CCOCC2)c1]

(i) tert-Butyl (4-((2-((3-methoxy-5-((2-morpholinoethyl)carbamoyl)phenyl)amino)pyridin-4-yl)oxy)naphthalen-1-yl)carbamate A mixture of 3-amino-5-methoxy-N-(2-morpholinoethyl)benzamide (see, for example, Cariou, C. A. M. et al., WO 2014/027209, 20 Feb. 2014; 0.8 g, 2.86 mmol), tert-butyl (4-((2-chloropyridin-4-yl)oxy)naphthalen-1-yl)carbamate (see Example 2(ii) above; 1 g, 2.70 mmol), $K_2CO_3$ (0.75 g, 5.43 mmol), BrettPhos G1 precatalyst (0.05 g, 0.063 mmol) and tBuBrettPhos (0.03 g, 0.062 mmol) were degassed under vacuum back filling with nitrogen 3 times. tBuOH (20 mL) was added and the suspension degassed under vacuum back filling with nitrogen 3 times. The reaction was then heated under nitrogen at 90° C. for 1 h. The reaction mixture was cooled and diluted with DCM (50 mL) filtered and the filtrate evaporated to a pink glass. The crude product was purified by chromatography on silica gel (40 g column, 2% MeOH:DCM to 8%) to afford the sub-title compound (1.75 g) as a tan glass.

$^1$H NMR (400 MHz, DMSO-$d_6$) δ 9.36 (s, 1H), 9.08 (s, 1H), 8.22 (t, 1H), 8.18-8.06 (m, 2H), 7.84 (d, 1H), 7.67-7.54 (m, 4H), 7.51 (t, 1H), 7.36 (d, 1H), 6.95-6.80 (m, 1H), 6.58 (dd, 1H), 6.11 (d, 1H), 3.74 (s, 3H), 3.66-3.48 (m, 4H), 3.39-3.33 (m, 2H), 2.47-2.34 (m, 6H), 1.53 (s, 9H). LCMS m/z 614 (M+H)$^+$ (ES$^+$)

(ii) 3-((4-((4-Aminonaphthalen-1-yl)oxy)pyridin-2-yl)amino)-5-methoxy-N-(2-morpholinoethyl)benzamide TFA (2 mL, 26.0 mmol) was added to a solution of the product from step (i) above (1.75 g, 2.65 mmol) in DCM (30 mL) and the reaction stirred for 16 h. The solvents were evaporated and the residue azeotroped with toluene (2×100 mL). The residue was partitioned between sat NaHCO$_3$ soln. (200 mL) and DCM (200 mL). The organics were separated, dried (MgSO$_4$), filtered and the solvent evaporated to afford the sub-title compound (1.5 g).

$^1$H NMR (400 MHz, DMSO-$d_6$) δ 8.99 (s, 1H), 8.22 (t, 1H), 8.19-8.10 (m, 1H), 8.06 (d, 1H), 7.72-7.60 (m, 1H), 7.55 (t, 1H), 7.50 (t, 1H), 7.48-7.39 (m, 2H), 7.10 (d, 1H), 6.84 (s, 1H), 6.71 (d, 1H), 6.52 (dd, 1H), 6.06 (d, 1H), 5.83 (s, 2H), 3.74 (s, 3H), 3.65-3.51 (m, 4H), 3.36 (d, 2H), 2.43 (dd, 6H). LCMS m/z 514 (M+H)$^+$ (ES$^+$)

(iii) 3-((4-((4-(3-(3-(2-Amino-2-oxoethyl)-5-(tert-butyl)-2-methoxyphenyl)ureido)naphthalen-1-yl)oxy)pyridin-2-yl)amino)-5-methoxy-N-(2-morpholinoethyl)benzamide A solution of phenyl (3-(2-amino-2-oxoethyl)-5-(tert-butyl)-2-methoxyphenyl)carbamate (see Example 13(vi) above; 100 mg, 0.281 mmol) and the product from step (ii) above (115 mg, 0.224 mmol) and TEA (10 µL, 0.072 mmol) in 2-Me-THF (2 mL) was heated at 65° C. (block temperature) for 16 h. The solvent was evaporated and the crude product was purified by chromatography on silica gel (12 g column, 2% MeOH:DCM to 15%) to give a brown glass which was further purified by preparative HPLC (Varian, Basic (0.1% Ammonium Bicarbonate), Basic, Waters X-Bridge Prep-C18, 5 µm, 19×50 mm column, 25-70% MeCN in Water) to afford the title compound (75 mg) as a colourless solid.

$^1$H NMR (400 MHz, DMSO-$d_6$) δ 9.41 (s, 1H), 9.08 (s, 1H), 8.81 (s, 1H), 8.31 (d, 1H), 8.26 (t, 1H), 8.21 (d, 1H), 8.13 (d, 1H), 8.11 (d, 1H), 7.93-7.82 (m, 1H), 7.76-7.66 (m, 1H), 7.66-7.56 (m, 1H), 7.56 (t, 1H), 7.51 (t, 1H), 7.48 (s, 1H), 7.39 (d, 1H), 6.97 (s, 1H), 6.94 (d, 1H), 6.86 (dd, 1H), 6.59 (dd, 1H), 6.12 (d, 1H), 3.77 (s, 3H), 3.74 (s, 3H), 3.57 (t, 4H), 3.45 (s, 2H), 2.48-2.33 (m, 6H), 1.27 (s, 9H). (CH$_2$ under water peak). LCMS m/z 776 (M+H)$^+$ (ES$^+$); 774 (M−H)$^-$ (ES$^-$)

Example 46

3-((4-((4-(3-(5-(tert-Butyl)-2-methoxy-3-(methylsulfinyl)phenyl)ureido)naphthalen-1-yl)oxy)pyridin-2-yl)amino)-5-methoxy-N-(2-morpholinoethyl)benzamide

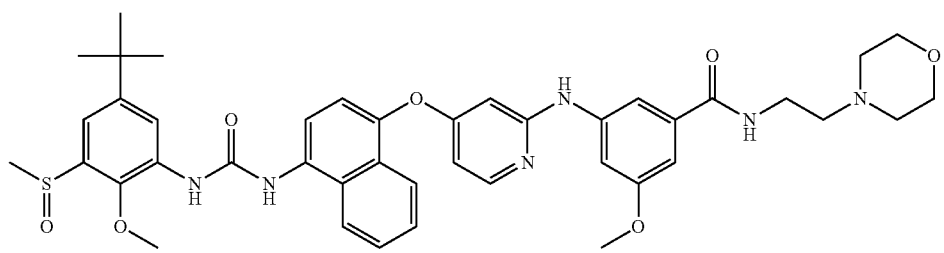 [SMILES: COc1cc(Nc2cc(Oc3ccc(NC(=O)Nc4cc(C(C)(C)C)cc(S(C)=O)c4OC)c4ccccc34)ccn2)cc(C(=O)NCCN2CCOCC2)c1]

A solution of phenyl (5-(tert-butyl)-2-methoxy-3-(methylsulfinyl)phenyl)carbamate (see Example 12(iv) above; 100 mg, 0.277 mmol), 3-((4-((4-aminonaphthalen-1-yl)oxy)pyridin-2-yl)amino)-5-methoxy-N-(2-morpholinoethyl)benzamide (see Example 45(ii) above; 115 mg, 0.224 mmol) and TEA (10 µL, 0.072 mmol) in 2-Me-THF (2 mL) was heated at 65° C. (block temperature) for 16 h. The solvent was evaporated and the crude product was purified by chromatography on silica gel (12 g column, 2% MeOH: DCM to 15%) to give a brown glass which was further purified by preparative HPLC (Varian, Basic (0.1% Ammonium Bicarbonate), Basic, Waters X-Bridge Prep-C18, 5 µm, 19×50 mm column, 25-70% MeCN in Water) to afford the title compound (36 mg).

$^1$H NMR (400 MHz, DMSO-$d_6$) δ 9.44 (s, 1H), 9.08 (s, 1H), 8.99 (s, 1H), 8.51 (d, 1H), 8.36-8.22 (m, 2H), 8.12 (d, 1H), 8.10 (d, 1H), 7.88 (d, 1H), 7.77-7.67 (m, 1H), 7.66-7.58 (m, 1H), 7.56 (t, 1H), 7.50 (t, 1H), 7.40 (d, 1H), 7.36 (d, 1H), 6.86 (dd, 1H), 6.58 (dd, 1H), 6.13 (d, 1H), 3.86 (s, 3H), 3.74 (s, 3H), 3.56 (t, 4H), 2.79 (s, 3H), 2.46-2.40 (m, 6H), 1.32 (s, 9H). (CH$_2$ under water peak). LCMS m/z 781 (M+H)$^+$ (ES$^+$); 779 (M−H)$^−$ (ES$^−$)

Example 47

3-((4-((4-(3-(3-(2-Amino-2-oxoethyl)-5-(tert-butyl)-2-methoxyphenyl)ureido)naphthalen-1-yl)oxy)pyridin-2-yl)amino)-5-methoxybenzamide

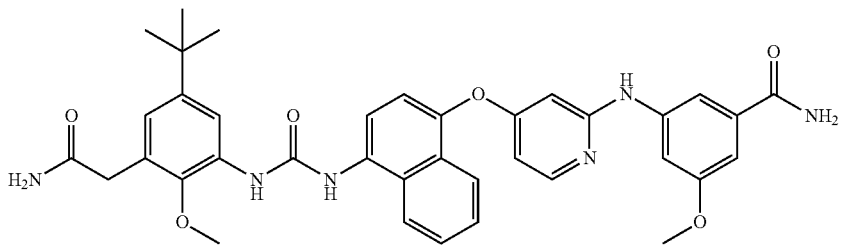 [SMILES: COc1cc(Nc2cc(Oc3ccc(NC(=O)Nc4cc(C(C)(C)C)cc(CC(N)=O)c4OC)c4ccccc34)ccn2)cc(C(N)=O)c1]

Et$_3$N (9 µL, 0.065 mmol) was added to a solution of phenyl (3-(2-amino-2-oxoethyl)-5-(tert-butyl)-2-methoxyphenyl)carbamate (see Example 13(vi) above; 90 mg, 0.253 mmol) and 3-((4-((4-aminonaphthalen-1-yl)oxy)pyridin-2-yl)amino)-5-methoxybenzamide (see Example 37(ii) above; 100 mg, 0.250 mmol) in THF (3 mL) and the reaction heated at 65° C. (block temperature) for 16 h. The crude product was purified by preparative HPLC (Varian, Basic (0.1% Ammonium Bicarbonate), Basic, Waters X-Bridge Prep-C18, 5 µm, 19×50 mm column, 25-70% MeCN in Water) to afford the title compound (62 mg) as a colourless solid.

$^1$H NMR (400 MHz, DMSO-$d_6$) δ: 9.39 (s, 1H), 9.04 (s, 1H), 8.79 (s, 1H), 8.31 (d, 1H), 8.21 (d, 1H), 8.12 (d, 1H), 8.11 (s, 1H), 7.87 (d, 1H), 7.81 (s, 1H), 7.71 (t, 1H), 7.61 (t, 1H), 7.57 (t, 1H), 7.52 (t, 1H), 7.45 (s, 1H), 7.38 (d, 1H), 7.24 (s, 1H), 6.94 (d, 2H), 6.92 (t, 1H), 6.58 (dd, 1H), 6.14 (d, 1H), 3.78 (s, 3H), 3.74 (s, 3H), 3.45 (s, 2H), 9.02 (s, 9H). LCMS m/z 332 (M+2H)$^{2+}$ (ES$^+$)

Example 48

3-((4-((4-(3-(5-(tert-Butyl)-2-methoxy-3-(methylsulfinyl)phenyl)ureido)naphthalen-1-yl)oxy)pyridin-2-yl)amino)-5-methoxy-N-(2-(2-(2-methoxyethoxy)ethoxy)ethyl)benzamide

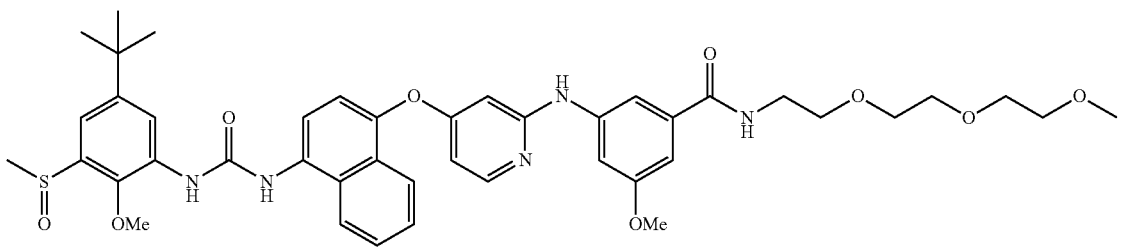

(i) Methyl 3-((4-((4-((tert-butoxycarbonyl)amino)naphthalen-1-yl)oxy)pyridin-2-yl)amino)-5-methoxybenzoate A flask charged with tert-butyl (4-((2-chloropyridin-4-yl)oxy)naphthalen-1-yl)carbamate (see Example 2(ii) above; 20.1 g, 54.2 mmol), methyl 3-amino-5-methoxybenzoate (10.80 g, 59.6 mmol), BrettPhos G1 Precatalyst (550 mg, 0.689 mmol) and $K_2CO_3$ (14.98 g, 108 mmol) in anhydrous tBuOH (300 mL) was back filled with nitrogen (×3) and then placed on a heating block (preheated to 90° C.). The suspension was degassed with nitrogen, stirred for 8 h and then cooled to it and stirred for 8 h. Reaction mixture was warmed to 50° C. then cooled to it and diluted with DCM (1 L), the suspension was filtered through Celite and the solvent evaporated. The brown oil was sonicated with diethyl ether (500 mL) and the solid filtered under suction, washing with further diethylether, to afford the sub-title compound (21.55 g) as a beige solid.

$^1$H NMR (400 MHz, DMSO-$d_6$) δ 9.37 (s, 1H), 9.19 (s, 1H), 8.15 (s, 1H), 8.13 (s, 1H), 7.85 (dd, 1H), 7.76 (dd, 1H), 7.69 (dd, 1H), 7.66-7.54 (m, 3H), 7.37 (d, 1H), 6.96 (dd, 1H), 6.62 (dd, 1H), 6.09 (d, 1H), 3.82 (s, 3H), 3.75 (s, 3H), 1.53 (s, 9H). (90% purity)

LCMS m/z 516 (M+H)$^+$ (ES$^+$); 514 (M–H)$^-$ (ES$^-$)

(ii) 3-((4-((4-((tert-Butoxycarbonyl)amino)naphthalen-1-yl)oxy)pyridin-2-yl)amino)-5-methoxybenzoic acid Lithium hydroxide (0.103 g, 4.31 mmol) then water (5 mL, 3.59 mmol) were added consecutively to a stirred solution of the product from step (i) above (1.85 g, 3.59 mmol) in THF (10 mL) and MeOH (5 mL). The mixture was stirred at it for 23 h then the solvents were removed in vacuo. The residue was dissolved in water (75 mL) then washed with ether (50 mL). The organic layer was extracted with water (25 mL) then the combined aqueous layers were washed with ether (50 mL), then acidified to pH=1 with 1M HCl. The white solid precipitate was collected by filtration, then washed with water (20 mL), ether (20 mL) before drying by suction then in vacuo to afford the sub-title compound (1.076 g).

A further crop of product was obtained by extraction of the aqueous layer to afford a further 516 mg. Combined yield of 1.592 g.

$^1$H NMR (DMSO-$d_6$) 400 MHz, δ: 12.9 (s, 1H), 9.04 (s, 1H), 9.02 (s, 1H), 8.14-8.12 (m, 2H), 7.83 (dd, 1H), 7.74-7.72 (m, 1H), 7.66-7.53 (m, 4H), 7.36 (d, 1H), 6.96-6.93 (m, 1H), 6.61 (dd, 1H), 6.06 (d, 1H), 3.74 (s, 3H), 1.52 (s, 9H). LCMS m/z 502 (M+H)$^+$ (ES$^+$)

(iii) tert-Butyl (4-((2-((3-methoxy-5-((2-(2-(2-methoxyethoxy)ethoxy)ethyl)carbamoyl)phenyl)amino)pyridin-4-yl)oxy)naphthalen-1-yl)carbamate Et$_3$N (0.840 mL, 6.02 mmol) was added to a stirred solution of the product from step (ii) above (1.59 g, 3.01 mmol) and HATU (1.374 g, 3.61 mmol) in DMF (16 mL) under an atmosphere of nitrogen. The mixture was stirred for 5 minutes then 2-(2-(2-methoxyethoxy)ethoxy)ethanamine (0.521 g, 3.16 mmol) was added in DMF (4 mL). After 1 hour the majority of the solvents were removed in vacuo, the residue dissolved in EtOAc (250 mL), then washed with saturated NaHCO$_3$ (75 mL), water (75 mL), brine (75 mL), dried (MgSO$_4$), filtered then reduced in vacuo to leave a pink foam. The crude product was purified by chromatography on the Companion (80 g column, 0-100%, 10% MeOH in DCM:DCM) to afford the sub-title compound (1.83 g) as a foam.

$^1$H NMR (DMSO-$d_6$) 400 MHz, δ: 9.39 (s, 1H), 9.10 (s, 1H), 8.36 (t, 1H), 8.14-8.10 (m, 2H), 7.83 (bdd, 1H), 7.64-7.54 (m, 4H), 7.50 (bt, 1H), 7.35 (d, 1H), 6.89-6.87 (m, 1H), 6.57 (dd, 1H), 6.09 (d, 1H), 3.74 (s, 3H), 3.54-3.47 (m, 8H), 3.40-3.34 (m, 4H), 3.20 (s, 3H), 1.52 (s, 9H). LCMS m/z 647 (M+H)$^+$ (ES$^+$); 645 (M–H)$^-$ (ES$^-$)

(iv) 3-((4-((4-Aminonaphthalen-1-yl)oxy)pyridin-2-yl)amino)-5-methoxy-N-(2-(2-(2-methoxyethoxy)ethoxy)ethyl)benzamide TFA (3 mL, 38.9 mmol) was added to a stirred solution of the product from step (iii) above (1.83 g, 2.72 mmol) in DCM (15 mL). The solution was placed under nitrogen, stirred for 4 h then concentrated in vacuo. The residue was dissolved in DCM (100 mL), washed with sat. NaHCO$_3$ (50 mL), brine (50 mL), dried (MgSO$_4$), filtered then concentrated in vacuo to obtain a residue which was azeotroped with ether (2×20 mL) to afford the sub-title compound (1.347 g) as a pale pink foam.

$^1$H NMR (DMSO-$d_6$) 400 MHz, δ: 8.99 (s, 1H), 8.33 (t, 1H), 8.17-8.13 (m, 1H), 8.05 (d, 1H), 7.65-7.60 (m, 1H), 7.56 (bt, 1H), 7.49 (bt, 1H), 7.47-7.41 (m, 2H), 7.10 (d, 1H), 6.86 (dd, 1H), 6.71 (d, 1H), 6.51 (dd, 1H), 6.05 (d, 1H), 5.83 (brs, 2H), 3.74 (s, 3H), 3.55-3.47 (m, 8H), 3.41-3.33 (m, 4H), 3.20 (s, 3H). LCMS m/z 547 (M+H)$^+$ (ES$^+$)

(v) 3-((4-((4-(3-(5-(tert-Butyl)-2-methoxy-3-(methylsulfinyl)phenyl)ureido)naphthalen-1-yl)oxy)pyridin-2-yl)amino)-5-methoxy-N-(2-(2-(2-methoxyethoxy)ethoxy)ethyl)benzamide TEA (8.92 μL, 0.064 mmol) was added to a stirred suspension of the product from step (iv) above (100 mg, 0.183 mmol) and phenyl (5-(tert-butyl)-2-methoxy-3-(methylsulfinyl)phenyl)-carbamate (see Example 12(iv) above; 81 mg, 0.220 mmol) in iPrOAc (2.5 mL). The mixture was placed under nitrogen then heated at 70° C. overnight. After 19 hours the reaction was concentrated in vacuo using DCM to transfer the reaction mixture and the crude product was purified by chromatography on the Companion (12 g column, 0-70% of 10% MeOH in DCM:DCM) to afford the title compound (123 mg) as a white solid.

$^1$H NMR (DMSO-$d_6$) 400 MHz, δ: 9.40 (s, 1H), 9.06 (s, 1H), 8.95 (s, 1H), 8.50 (d, 1H), 8.34 (t, 1H), 8.28 (d, 1H), 8.11 (d, 1H), 8.10 (d, 1H), 7.87 (d, 1H), 7.71 (ddd, 1H), 7.61 (ddd, 1H), 7.57 (bt, 1H), 7.50 (bt, 1H), 7.39 (d, 1H), 7.36 (d, 1H), 6.88-6.87 (m, 1H), 6.57 (dd, 1H), 6.14 (d, 1H), 3.86 (s, 3H), 3.74 (s, 3H), 3.54-3.47 (m, 8H), 3.41-3.34 (m, 4H), 3.20 (s, 3H), 2.79 (s, 3H), 1.31 (s, 9H). LCMS m/z 814 (M+H)$^+$ (ES$^+$)

Example 49

2-(5-(tert-Butyl)-3-(3-(4-((2-((3-cyano-5-(2-morpholinoethoxy)phenyl)amino)pyridin-4-yl)oxy)naphthalen-1-yl)ureido)-2-methoxyphenyl)acetamide

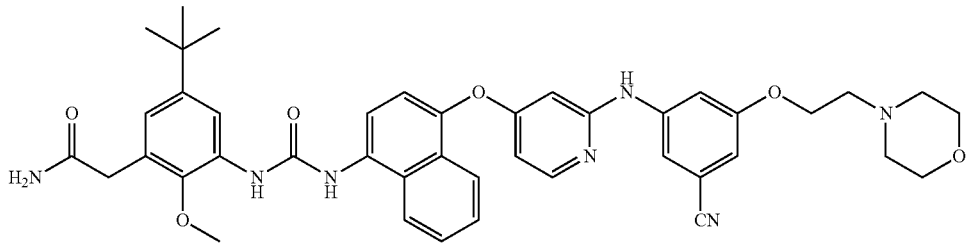

(i) tert-Butyl (4-((2-((3-cyano-5-(2-morpholinoethoxy)phenyl)amino)pyridin-4-yl)oxy)naphthalen-1-yl)carbamate A flask was charged with tert-butyl (4-((2-chloropyridin-4-yl)oxy)naphthalen-1-yl)carbamate (see Example 2(ii) above; 400 mg, 1.079 mmol), 3-amino-5-(2-morpholinoethoxy)benzonitrile (Fyfe, M. C. T. et al., WO 2014/033446, 6 Mar. 2014; 280 mg, 1.132 mmol), BrettPhos Pd G1 methyl-t-Butyl ether adduct (30 mg, 0.034 mmol) and $K_2CO_3$ (300 mg, 2.171 mmol) then purged with nitrogen. To this was added degassed tert-butanol (10 mL) and the mixture was heated to reflux for 3 h. The mixture was diluted with DCM (40 mL) then filtered and concentrated under reduced pressure. The crude product was purified by chromatography on the Companion (40 g column, 2-4% MeOH/DCM) to afford the sub-title compound (640 mg) as a tan foam.
LCMS m/z 582 $(M+H)^+$ $(ES^+)$ (ii) 3-((4-((4-Aminonaphthalen-1-yl)oxy)pyridin-2-yl)amino)-5-(2-morpholinoethoxy)-benzonitrile A solution of the product from step (i) above (640 mg, 1.100 mmol) in isopropanol (4 mL), was treated with 5 M hydrogen chloride in isopropanol (8 mL) and stirred at rt overnight. The resulting precipitate was collected by filtration and washed with diethyl ether (20 mL). The filter cake was redissolved in methanol (10 mL) and water (30 mL), then added to a stirred solution of saturated $NaHCO_3$ (20 mL) and water (20 mL). The resulting solid was extracted with ethyl acetate (40 mL) then the organic phase was washed with saturated brine (40 mL) and dried ($MgSO_4$). The solvent was removed under reduced pressure then the residue was redissolved in isopropyl acetate and added dropwise to a vigorously stirred flask of isohexane (150 mL). The resulting precipitate was collected by filtration to yield the sub-title compound (350 mg) as a pale pink solid.
LCMS m/z 482 $(M+H)^+$ $(ES^+)$ (iii) 2-(5-(tert-Butyl)-3-(3-(4-((2-((3-cyano-5-(2-morpholinoethoxy)phenyl)amino)pyridin-4-yl)oxy)naphthalen-1-yl)ureido)-2-methoxyphenyl)acetamide Phenyl (3-(2-amino-2-oxoethyl)-5-(tert-butyl)-2-methoxyphenyl)carbamate (see Example 13(vi) above; 74.0 mg, 0.208 mmol), the product from step (ii) above (100 mg, 0.208 mmol) and $Et_3N$ (10 µL, 0.072 mmol) were heated to 70° C. (block temperature) in isopropyl acetate (3 mL) for 18 h. The mixture was cooled, $Et_3N$ (40 µL, 0.287 mmol) added and purified directly on the Companion (40 g column, 2-8% MeOH/DCM) to afford a colourless solid. The solid was dissolved in isopropyl acetate (3 mL) then diluted with isohexane (10 mL). The resulting precipitate was collected by filtration and washed with isohexane to afford the title compound (87 mg) as a white solid.
$^1$H NMR (400 MHz, DMSO-$d_6$) δ 9.40 (s, 1H), 9.25 (s, 1H), 8.79 (s, 1H), 8.31 (d, 1H), 8.20 (d, 1H), 8.18 (d, 1H), 8.12 (d, 1H), 7.86 (d, 1H), 7.71 (ddd, 1H), 7.68 (dd, 1H), 7.61 (ddd, 1H), 7.53 (dd, 1H), 7.48-7.42 (m, 1H), 7.40 (d, 1H), 6.97-6.91 (m, 1H), 6.94 (d, 1H), 6.91 (dd, 1H), 6.69 (dd, 1H), 6.07 (d, 1H), 4.08 (t, 2H), 3.78 (s, 3H), 3.61-3.53 (m, 4H), 3.45 (s, 2H), 2.67 (t, 2H), 2.48-2.41 (m, 4H), 1.27 (s, 9H). LCMS m/z 744 $(M+H)^+$ $(ES^+)$; 742 $(M-H)^-$ $(ES^-)$ Example 50

N-(5-(tert-Butyl)-3-(3-(4-((2-((3-cyano-5-(2-morpholinoethoxy)phenyl)amino)pyridin-4-yl)oxy)naphthalen-1-yl)ureido)-2-methoxybenzyl)acetamide

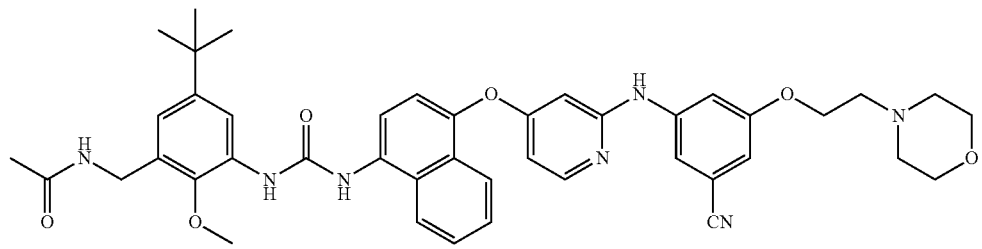 [SMILES: COc1c(CNC(C)=O)cc(C(C)(C)C)cc1NC(=O)Nc1ccc(Oc2ccnc(Nc3cc(C#N)cc(OCCN4CCOCC4)c3)c2)c2ccccc12]

Phenyl (3-(acetamidomethyl)-5-(tert-butyl)-2-methoxyphenyl)carbamate (see Example 35(v) above; 77 mg, 0.208 mmol), 3-((4-((4-aminonaphthalen-1-yl)oxy)pyridin-2-yl)amino)-5-(2-morpholinoethoxy)benzonitrile (see Example 49(ii) above; 100 mg, 0.208 mmol) and Et$_3$N (10 μL, 0.072 mmol) were heated to 70° C. (block temperature) in isopropyl acetate for 18 h. The resulting precipitate was collected by filtration and washed with a further portion of isopropyl acetate (3 mL) to afford the title compound (92 mg) as a colourless solid.

$^1$H NMR (400 MHz, DMSO-d$_6$) δ 9.41 (s, 1H), 9.25 (s, 1H), 8.82 (s, 1H), 8.31 (d, 1H), 8.26 (t, 1H), 8.24 (d, 1H), 8.18 (d, 1H), 8.11 (d, 1H), 7.86 (d, 1H), 7.71 (ddd, 1H), 7.68 (dd, 1H), 7.61 (ddd, 1H), 7.53 (dd, 1H), 7.40 (d, 1H), 6.95 (d, 1H), 6.91 (dd, 1H), 6.69 (dd, 1H), 6.07 (d, 1H), 4.33 (d, 2H), 4.08 (t, 2H), 3.79 (s, 3H), 3.60-3.54 (m, 4H), 2.67 (t, 2H), 2.48-2.41 (m, 4H), 1.90 (s, 3H), 1.27 (s, 9H). LCMS m/z 758 (M+H)$^+$ (ES$^+$)

Example 51

1-(5-(tert-Butyl)-2-methoxy-3-(methylsulfinyl)phenyl)-3-(4-((2-((3-cyano-5-(2-morpholinoethoxy)phenyl)amino)pyridin-4-yl)oxy)naphthalen-1-yl)urea

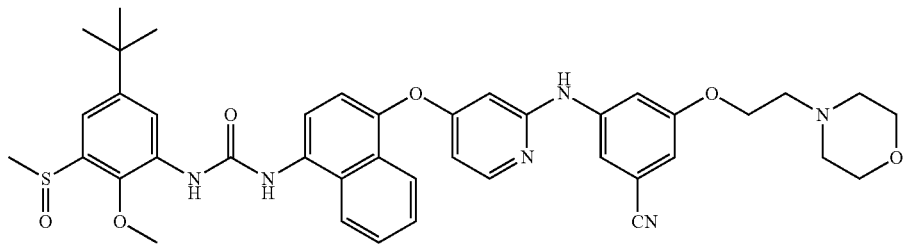

Phenyl (5-(tert-butyl)-2-methoxy-3-(methylsulfinyl)phenyl)carbamate (see Example 12(iv) above; 75 mg, 0.208 mmol), 3-((4-((4-aminonaphthalen-1-yl)oxy)pyridin-2-yl)amino)-5-(2-morpholinoethoxy)benzonitrile (see Example 49(ii) above; 100 mg, 0.208 mmol) and Et$_3$N (10 μL, 0.072 mmol) were heated to 70° C. (block temperature) in isopropyl acetate (3 mL) for 18 h. The mixture was cooled, triethylamine (40 uL) added and purified directly on the Companion (40 g column, 2-8% MeOH/DCM) to afford a colourless solid. The solid was dissolved in isopropyl acetate (3 mL) then diluted with isohexane (10 mL). The resulting precipitate was collected by filtration and washed with isohexane to afford the title compound (55 mg) as a colourless solid.

$^1$H NMR (400 MHz, DMSO-d$_6$) δ9.43 (s, 1H), 9.25 (s, 1H), 8.96 (s, 1H), 8.49 (d, 1H), 8.28 (d, 1H), 8.17 (d, 1H), 8.10 (d, 1H), 7.86 (d, 1H), 7.71 (ddd, 1H), 7.67 (dd, 1H), 7.61 (ddd, 1H), 7.53 (dd, 1H), 7.41 (d, 1H), 7.36 (d, 1H), 6.90 (dd, 1H), 6.68 (dd, 1H), 6.07 (d, 1H), 4.08 (t, 2H), 3.86 (s, 3H), 3.61-3.49 (m, 4H), 2.78 (s, 3H), 2.66 (t, 2H), 2.48-2.39 (m, 4H), 1.31 (s, 9H). LCMS m/z 749 (M+H)+, 375 (M+2H)$^{2+}$ (ES$^+$)

Example 52

N-(5-(tert-butyl)-2-methoxy-3-(3-((4-((2-((3-(2-morpholinoethoxy)-5-(trifluoromethyl)phenyl)amino)pyridin-4-yl)oxy)naphthalen-1-yl)ureido)benzyl)acetamide

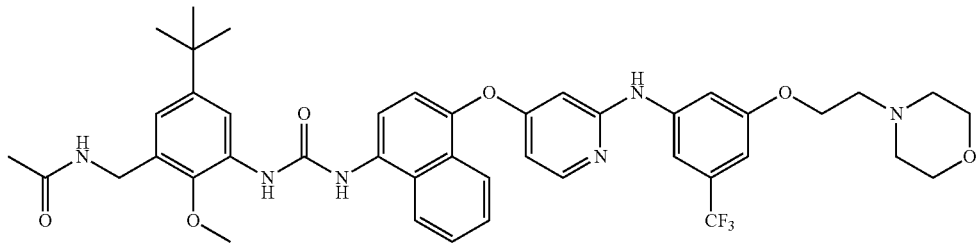 [SMILES: COc1c(CNC(C)=O)cc(C(C)(C)C)cc1NC(=O)Nc1ccc(Oc2ccnc(Nc3cc(OCCN4CCOCC4)cc(C(F)(F)F)c3)c2)c2ccccc12]

167

(i) tert-Butyl (4-((2-((3-(2-morpholinoethoxy)-5-(trifluoromethyl)phenyl)amino)pyridin-4-yl)oxy)naphthalen-1-yl)carbamate A flask was charged with tert-butyl (4-((2-chloropyridin-4-yl)oxy)naphthalen-1-yl)carbamate (see Example 2(ii) above; 400 mg, 1.079 mmol), 3-(2-morpholinoethoxy)-5-(trifluoromethyl)aniline (Adams, R. S. et al., WO 2006/076706, 20 Jul. 2006; 310 mg, 1.068 mmol), BrettPhos Pd G1 methyl-t-Butyl ether adduct (30 mg, 0.034 mmol) and $K_2CO_3$ (300 mg, 2.171 mmol) then purged with nitrogen. To this was added degassed tert-butanol (10 mL) and the mixture was heated to reflux for 3 h. The mixture was diluted with DCM (40 mL) then filtered and concentrated under reduced pressure. The crude product was purified by chromatography on the Companion (40 g column, 2-4% MeOH/DCM) to afford the sub-title compound (616 mg) as a tan foam.

LCMS m/z 625 (M+H)$^+$ (ES$^+$)

(ii) 4-((4-Aminonaphthalen-1-yl)oxy)-N-(3-(2-morpholinoethoxy)-5-(trifluoromethyl)phenyl)pyridin-2-amine A solution of the product from step (i) above (610 mg, 0.977 mmol) in isopropanol (4 mL), was treated with 5 M hydrogen chloride in isopropanol (8 mL) and stirred at rt overnight. The mixture was diluted with diethyl ether (50 mL) and the resulting solid was collected by filtration. The solid was redissolved in methanol (10 mL) and water (30 mL) then added slowly to a stirred flask of 5% sodium bicarbonate solution (50 mL). The resulting solid was collected by filtration to afford the sub-title compound (412 mg) as a pale pink solid.

LCMS m/z 525 (M+H)$^+$ (ES$^+$)

(iii) N-(5-(tert-Butyl)-2-methoxy-3-(3-(4-((2-((3-(2-morpholinoethoxy)-5-(trifluoromethyl)phenyl)amino)pyridin-4-yl)oxy)naphthalen-1-yl)ureido)benzyl)acetamide Phenyl (3-(acetamidomethyl)-5-(tert-butyl)-2-methoxyphenyl)carbamate (see Example 35(v) above; 75 mg, 0.202 mmol), the product from step (ii) above (105 mg, 0.200 mmol) and Et$_3$N (10 μL, 0.072 mmol) were heated to 70° C. (block temperature) in isopropyl acetate (3 mL) for 18 h. The mixture was cooled, Et$_3$N (40 uL) added and purified directly on the Companion (40 g column, 2-8% MeOH/DCM) then purified by preparative HPLC (Gilson, Acidic

168

(0.1% Formic acid), Acidic, Waters X-Select Prep-C18, 5 μm, 19×50 mm column, 25-75% MeCN in Water) to afford a colourless solid (partial formate salt). The solid was dissolved methanol (5 mL) then added to a stirred solution of 4% aqueous sodium bicarbonate (25 mL). The resulting precipitate was collected by filtration and washed with water (2×2 mL) to afford the title compound (70 mg) as a colourless solid.

$^1$H NMR (400 MHz, DMSO-d$_6$) δ 9.47 (s, 1H), 9.25 (s, 1H), 8.85 (s, 1H), 8.32 (d, 1H), 8.26 (t, 1H), 8.24 (d, 1H), 8.17 (d, 1H), 8.11 (d, 1H), 7.86 (d, 1H), 7.71 (ddd, 1H), 7.61 (ddd, 1H), 7.60-7.54 (m, 2H), 7.40 (d, 1H), 6.95 (d, 1H), 6.72 (dd, 1H), 6.66 (dd, 1H), 6.09 (d, 1H), 4.33 (d, 2H), 4.10 (t, 2H), 3.79 (s, 3H), 3.61-3.53 (m, 4H), 2.68 (t, 2H), 2.48-2.43 (m, 4H), 1.90 (s, 3H), 1.27 (s, 9H). LCMS m/z 401 (M+2H)$^{2+}$ (ES$^+$)

Example 53

3-((4-((4-(3-(3-(2-Amino-2-oxoethyl)-5-(tert-butyl)-2-methoxyphenyl)ureido)naphthalen-1-yl)oxy)pyridin-2-yl)amino)-5-methoxy-N-(2-(2-(2-methoxyethoxy)ethoxy)ethyl)benzamide

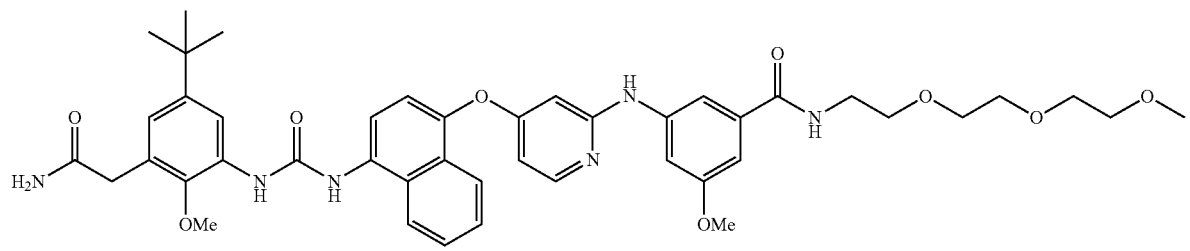 [SMILES: COCCOCCOCCNC(=O)c1cc(Nc2cc(Oc3ccc(NC(=O)Nc4cc(C(C)(C)C)cc(CC(N)=O)c4OC)c4ccccc34)ccn2)cc(OC)c1]

TEA (8.92 μL, 0.064 mmol) was added to a stirred suspension of 3-((4-((4-aminonaphthalen-1-yl)oxy)pyridin-2-yl)amino)-5-methoxy-N-(2-(2-(2-methoxyethoxy)ethoxy)ethyl)benzamide (see Example 48(iv) above; 100 mg, 0.183 mmol) and phenyl (3-(2-amino-2-oxoethyl)-5-(tert-butyl)-2-methoxyphenyl)carbamate (see Example 13(vi) above; 90 mg, 0.220 mmol) in iPrOAc (2.5 mL). The mixture was placed under nitrogen then heated at 70° C. overnight. After 19 hours the reaction was concentrated in vacuo and the crude product was purified by chromatography on the Companion (12 g column, 0-70% of 10% MeOH in DCM:DCM) then by preparative HPLC (Varian, Basic (0.1% Ammonium Bicarbonate), Basic, Waters X-Bridge Prep-C18, 5 μm, 19×50 mm column, 40-65% MeCN in Water) to afford the title compound (68 mg) as a colourless solid.

$^1$H NMR (400 MHz, DMSO-d$_6$) δ 9.42 (s, 1H), 9.07 (s, 1H), 8.81 (s, 1H), 8.34 (t, 1H), 8.31 (d, 1H), 8.21 (d, 1H), 8.12 (d, 1H), 8.11 (s, 1H), 7.87 (d, 1H), 7.75-7.66 (m, 1H), 7.64-7.60 (m, 1H), 7.58 (t, 1H), 7.54-7.49 (m, 1H), 7.45 (s, 1H), 7.38 (d, 1H), 7.00-6.92 (m, 2H), 6.92-6.84 (m, 1H), 6.58 (dd, 1H), 6.14 (d, 1H), 3.78 (s, 3H), 3.75 (s, 3H), 3.57-3.47 (m, 8H), 3.46 (s, 2H), 3.43-3.36 (m, 4H), 3.21 (s, 3H), 1.27 (s, 9H). LCMS m/z 405 (M+2H)$^{2+}$ (ES$^+$)

Example 54

3-((4-((4-(3-(5-(tert-Butyl)-2-methoxy-3-(methylsulfonyl)phenyl)ureido)naphthalen-1-yl)oxy)pyridin-2-yl)amino)-5-methoxy-N-(2-morpholinoethyl)benzamide

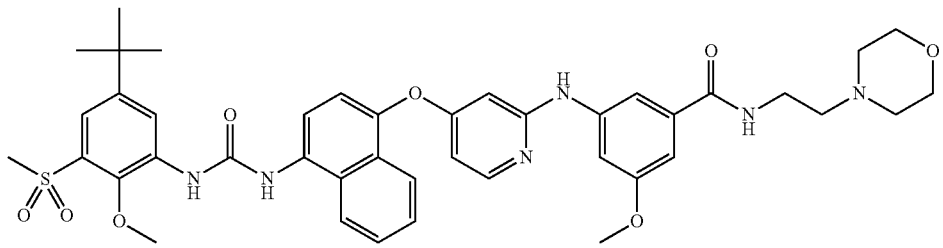 [SMILES: COc1cc(Nc2cc(Oc3ccc(NC(=O)Nc4cc(C(C)(C)C)cc(S(C)(=O)=O)c4OC)c4ccccc34)ccn2)cc(C(=O)NCCN2CCOCC2)c1]

A solution of phenyl (5-(tert-butyl)-2-methoxy-3-(methylsulfonyl)phenyl)carbamate (see Example 9(i) above; 100 mg, 0.265 mmol), 3-((4-((4-aminonaphthalen-1-yl)oxy)pyridin-2-yl)amino)-5-methoxy-N-(2-morpholinoethyl)benzamide (see Example 45(ii) above; 120 mg, 0.234 mmol) and TEA (10 µL, 0.072 mmol) in THF (2 mL) was heated at 65° C. (block temperature) for 16 h. The solvent was evaporated and the crude product was purified by chromatography on silica gel (12 g column, 2% MeOH:DCM to 15%) to give a brown glass which was further purified by preparative HPLC (Varian, Basic (0.1% Ammonium Bicarbonate), Basic, Waters X-Bridge Prep-C18, 5 µm, 19×50 mm column, 30-65% MeCN in Water) to afford the title compound (49 mg).

$^1$H NMR (400 MHz, DMSO-d$_6$) δ 9.47 (s, 1H), 9.07 (d, 2H), 8.68 (d, 1H), 8.29 (d, 1H), 8.23 (t, 1H), 8.12 (s, 1H), 8.11 (d, 1H), 7.89 (d, 1H), 7.76-7.69 (m, 1H), 7.66-7.59 (m, 1H), 7.56 (t, 1H), 7.51 (t, 1H), 7.45 (d, 1H), 7.40 (d, 1H), 6.86 (dd, 1H), 6.58 (dd, 1H), 6.15 (d, 1H), 3.96 (s, 3H), 3.75 (s, 3H), 3.62-3.53 (m, 4H), 2.48-2.35 (m, 6H), 1.32 (s, 9H). (—CH$_2$ and —SO$_2$CH$_3$ under water peak 3.37-3.31 ppm). LCMS m/z 797 (M+H)$^+$ (ES$^+$)

Example 55

3-((4-((4-(3-(5-(tert-Butyl)-2-methoxy-3-(methylsulfinyl)phenyl)ureido)naphthalen-1-yl)oxy)pyridin-2-yl)amino)-5-methoxybenzamide

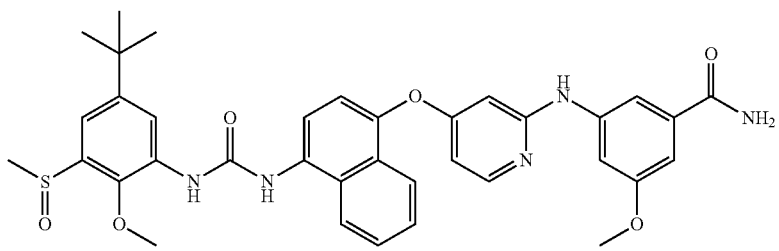 [SMILES: COc1cc(Nc2cc(Oc3ccc(NC(=O)Nc4cc(C(C)(C)C)cc(S(C)=O)c4OC)c4ccccc34)ccn2)cc(C(N)=O)c1]

Triethylamine (9 µL, 0.065 mmol) was added to a solution of phenyl (5-(tert-butyl)-2-methoxy-3-(methylsulfinyl)phenyl)carbamate (see Example 12(iv) above; 95 mg, 0.263 mmol) and 3-((4-((4-aminonaphthalen-1-yl)oxy)pyridin-2-yl)amino)-5-methoxybenzamide (see Example 37(ii) above; 100 mg, 0.250 mmol) in THF (3 mL) and the reaction heated at 65° C. (block temperature) for 16 h. The crude product was purified by preparative HPLC (Varian, Basic (0.1% Ammonium Bicarbonate), Basic, Waters X-Bridge Prep-C18, 5 µm, 19×50 mm column, 25-70% MeCN in Water) to afford a white solid which was re-purified by preparative HPLC (Waters, Acidic (0.1% Formic acid), Acidic, Waters X-Select Prep-C18, 5 µm, 19×50 mm column, 20-50% MeCN in Water). The solid was dissolved in a mixture of MeOH and DCM and partitioned with sat. NaHCO$_3$ solution. The organic phase was dried via hydrophobic frit and concentrated in vacuo to give a solid that was recrystallised form acetonitrile (5 mL) to afford the title compound (60 mg) as a white solid.

$^1$H NMR (400 MHz, DMSO-d$_6$) δ 9.50 (s, 1H), 9.05 (s, 1H), 9.02 (s, 1H), 8.49 (d, 1H), 8.30 (d, 1H), 8.12 (d, 1H), 8.11 (d, 1H), 7.87 (d, 1H), 7.81 (s, 1H), 7.71 (ddd, 1H), 7.61 (ddd, 1H), 7.57 (dd, 1H), 7.53 (dd, 1H), 7.39 (d, 1H), 7.36 (d, 1H), 7.24 (s, 1H), 6.92 (dd, 1H), 6.57 (dd, 1H), 6.14 (d, 1H), 3.78 (s, 3H), 3.74 (s, 3H), 2.79 (s, 3H), 1.32 (s, 9H). LCMS m/z 668 (M+H)$^+$ (ES$^+$)

Example 56

2-(5-(tert-Butyl)-2-methoxy-3-(3-(4-((2-((3-methoxy-5-(methylsulfonyl)phenyl)amino)pyridin-4-yl)oxy)naphthalen-1-yl)ureido)phenyl)acetamide (i) tert-Butyl (4-((2-((3-methoxy-5-(methylsulfonyl)phenyl)amino)pyridin-4-yl)oxy)naphthalen-1-yl) carbamate A mixture of 3-methoxy-5-(methylsulfonyl)aniline (Casillas, L. N. et al., WO 2011/120026, 29 Sep. 2011; 300 mg, 1.491 mmol), tert-butyl (4-((2-chloropyridin-4-yl)oxy)naphthalen-1-yl)carbamate (see Example 2(ii) above; 553 mg, 1.491 mmol), K$_2$CO$_3$ (412 mg, 2.98 mmol) and BrettPhos G1 precatalyst (23.82 mg, 0.030 mmol) were degassed under vacuum, back filling with nitrogen 3 times. tBuOH (3 mL) was added and the suspension degassed an additional 3 times. The reaction was heated under nitrogen at 85° C. for 16 hours. The reaction mixture was diluted with DCM (20 mL), filtered through celite and concentrated in vacuo. The crude product was purified by chromatography on the Companion (12 g column, 0-100% ethyl acetate in iso-hexane) to afford the sub-title compound (698 mg) as a thick yellow gum.

LCMS m/z 536 (M+H)$^+$ (ES$^+$); 534 (M–H)$^-$ (ES$^-$)

(ii) 4-((4-Aminonaphthalen-1-yl)oxy)-N-(3-methoxy-5-(methylsulfonyl)phenyl)pyridin-2-amine A solution of the product from step (i) above (698 mg, 1.238 mmol) in DCM (20 mL) and HCl (5 mL, 5N in iPrOH) was stirred over the week-end at rt. Diethyl ether (50 mL) was added, and the newly formed white precipitate was filtered and washed with diethyl ether to afford an off-white solid. The solid was diluted in DCM and washed with a saturated solution of NaHCO$_3$. The organic layer was concentrated in vacuo to afford the sub-title compound (482 mg) as a burgundy gum.

LCMS m/z 436 (M+H)$^+$ (ES$^+$)

(iii) 2-(5-(tert-Butyl)-2-methoxy-3-(3-(4-((2-((3-methoxy-5-(methylsulfonyl)phenyl)amino)pyridin-4-yl)oxy)naphthalen-1-yl)ureido)phenyl)acetamide Triethylamine (7 µL, 0.050 mmol) was added to a mixture of phenyl (3-(2-amino-2-oxoethyl)-5-(tert-butyl)-2-methoxyphenyl)carbamate (see Example 13(vi) above; 98 mg, 0.276 mmol) and the product from step (ii) above (100 mg, 0.230 mmol) in isopropyl acetate (2 mL) and the mixture heated at 70° C. (block temperature) overnight (17 hours). The reaction mixture was concentrated in vacuo and the crude product was purified by preparative HPLC (Waters, Acidic (0.1% Formic acid), Acidic, Waters X-Select Prep-C18, 5 µm, 19×50 mm column, 35-60% MeCN in Water) to afford a white solid which was diluted in DCM (2 mL) and washed with a saturated solution of NaHCO$_3$ (2 mL). The organic layer was dried via a hydrophobic phase separator and concentrated in vacuo to afford a white solid. The residue was triturated with MeCN (3 mL). The resultant solid was filtered, and dried in vacuo to afford the title compound (54 mg) as a light colourless solid.

$^1$H NMR (400 MHz, DMSO-d$_6$) δ: 9.39 (s, 1H), 9.34 (s, 1H), 8.79 (s, 1H), 8.30 (d, 1H), 8.20 (d, 1H), 8.16 (d, 1H), 8.12 (d, 1H), 7.86 (d, 1H), 7.74-7.66 (m, 3H), 7.62-7.58 (m, 1H), 7.44 (bs, 1H), 7.39 (d, 1H), 6.93-6.90 (m, 3H), 6.64 (dd, 1H), 6.11 (d, 1H), 3.79 (s, 3H), 3.77 (s, 3H), 3.44 (s, 2H), 3.15 (s, 3H), 1.26 (s, 9H). LCMS m/z 698 (M+H)$^+$ (ES$^+$)

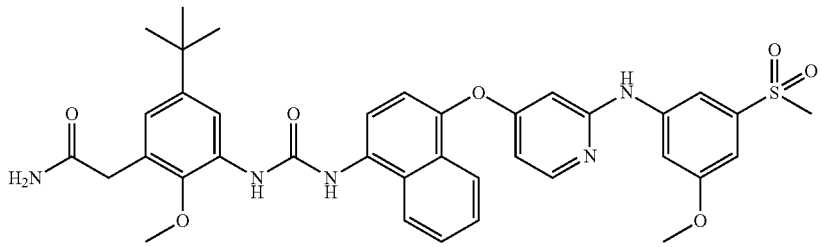 [SMILES: COc1cc(Nc2cc(Oc3ccc(NC(=O)Nc4cc(C(C)(C)C)cc(CC(N)=O)c4OC)c4ccccc34)ccn2)cc(S(C)(=O)=O)c1]

Example 57

3-((4-((4-(3-(5-(tert-Butyl)-3-(2-hydroxyethoxy)-2-methoxyphenyl)ureido)naphthalen-1-yl)oxy)pyridin-2-yl)amino)-5-methoxybenzamide

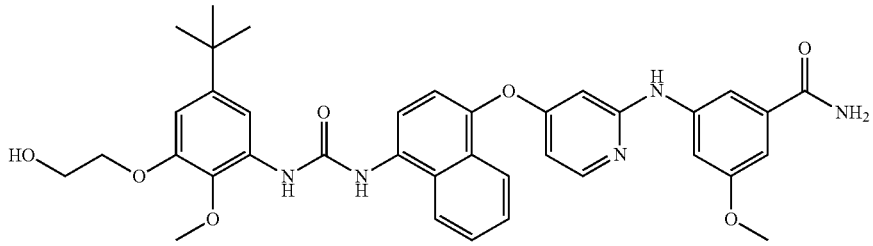 [SMILES: COc1cc(Nc2cc(Oc3ccc(NC(=O)Nc4cc(C(C)(C)C)cc(OCCO)c4OC)c4ccccc34)ccn2)cc(C(N)=O)c1]

(i) tert-Butyl(2-(5-(tert-butyl)-2-methoxy-3-nitrophenoxy)ethoxy)dimethylsilane A mixture of 5-(tert-butyl)-2-methoxy-3-nitrophenol (600 mg, 2.66 mmol), (2-bromoethoxy)(tert-butyl)dimethylsilane (700 mg, 2.93 mmol) and $K_2CO_3$ (736 mg, 5.33 mmol) in DMF was heated at 60° C. for 4 h. The mixture was partitioned between ether (80 mL) and water (80 mL), the organic layer separated, washed with water (50 mL), dried ($MgSO_4$), filtered and evaporated under reduced pressure. The residue was purified by chromatography on silica gel (40 g column, 0-10% EtOAc/isohexane) to afford the sub-title compound (918 mg) as an oil.

$^1$H NMR (400 MHz, $CDCl_3$) δ 7.32 (d, 1H), 7.14 (d, 1H), 4.13 (t, 2H), 4.01 (t, 2H), 3.97 (s, 3H), 1.31 (s, 9H), 0.91 (s, 9H), 0.10 (s, 6H).

(ii) 5-(tert-Butyl)-3-(2-((tert-butyldimethylsilyl)oxy)ethoxy)-2-methoxyaniline A mixture of 10% Pd/C (150 mg) and the product from step (i) above (910 mg, 2.373 mmol) in EtOH (15 mL) was hydrogenated under a balloon of hydrogen for 24 h. The mixture was filtered through Celite and the filtrate evaporated under reduced pressure. The crude product was purified by chromatography on silica gel (40 g column, 0-25% EtOAc/isohexane) to afford the sub-title compound (694 mg) as an oil.

$^1$H NMR (400 MHz, $CDCl_3$) δ 6.49 (d, 1H), 6.42 (d, 1H), 4.09 (t, 2H), 4.00 (t, 2H), 3.86 (s, 3H), 1.28 (s, 9H), 0.93 (s, 9H), 0.13 (s, 6H). LCMS m/z 354 (M+H)$^+$ (ES$^+$)

(iii) Phenyl (5-(tert-butyl)-3-(2-((tert-butyldimethylsilyl)oxy)ethoxy)-2-methoxyphenyl)-carbamate Phenyl chloroformate (265 µL, 2.116 mmol) was added to a mixture of the product from step (ii) above (680 mg, 1.923 mmol) and $NaHCO_3$ (323 mg, 3.85 mmol) in DCM (7 mL) and THF (7 mL). The mixture was stirred for 3 h then partitioned between DCM (50 mL) and water (30 mL). The organic layer was separated, dried ($MgSO_4$), filtered and evaporated under reduced pressure to afford the sub-title compound (895 mg) as an oil.

LCMS m/z 474 (M+H)$^+$ (ES$^+$), 92% purity.

(iv) 3-((4-((4-(3-(5-(tert-Butyl)-3-(2-((tert-butyldimethylsilyl)oxy)ethoxy)-2-methoxyphenyl)ureido)naphthalen-1-yl)oxy)pyridin-2-yl)amino)-5-methoxybenzamide A mixture of the product from step (iii) above (445 mg, 0.939 mmol), 3-((4-((4-aminonaphthalen-1-yl)oxy)pyridin-2-yl)amino)-5-methoxybenzamide (see Example 37(ii) above; 376 mg, 0.939 mmol) and $Et_3N$ (40 µL, 0.287 mmol) in THF (5 mL) was heated at 60° C. for 48 h. The mixture was cooled, partitioned between EtOAc (30 mL) and brine (20 mL), the organic layer separated, dried ($MgSO_4$), filtered and evaporated under reduced pressure. The residue was purified by chromatography on silica gel (40 g column, 0-100% EtOAc/isohexane) to afford the sub-title compound (320 mg) as a foam.

LCMS m/z 780 (M+H)$^+$ (ES$^+$), 77% purity.

(v) 3-((4-((4-(3-(5-(tert-Butyl)-3-(2-hydroxyethoxy)-2-methoxyphenyl)ureido)naphthalen-1-yl)oxy)pyridin-2-yl)amino)-5-methoxybenzamide A solution of 1M TBAF (500 µL, 0.500 mmol) in THF was added to a solution of the product from step (iv) above (310 mg, 0.306 mmol) in THF (5 mL) and the mixture stirred at rt for 4 h. The mixture was partitioned between EtOAc (40 mL) and water (20 mL), the organic layer separated, washed with brine (20 mL), dried ($MgSO_4$), filtered and evaporated under reduced pressure. The residue was triturated with MeCN, filtered and dried to afford the title compound (85 mg) as an off white solid.

$^1$H NMR (400 MHz, DMSO-$d_6$) δ 9.46 (s, 1H), 9.08 (s, 1H), 8.86 (s, 1H), 8.34 (d, 1H), 8.15 (d, 1H), 8.11 (d, 1H), 8.03 (d, 1H), 7.91 (d, 1H), 7.84 (s, 1H), 7.73 (t, 1H), 7.66-7.60 (m, 2H), 7.56 (s, 1H), 7.41 (d, 1H), 7.28 (s, 1H), 6.96 (s, 1H), 6.74 (d, 1H), 6.60 (dd, 1H), 6.18 (d, 1H), 4.90 (t, 1H), 4.11 (t, 2H), 3.89 (s, 3H), 3.82 (q, 2H), 3.77 (s, 3H), 1.31 (s, 9H).

LCMS m/z 666 (M+H)$^+$ (ES$^+$)

Example 58

3-((4-((4-(3-(5-(tert-Butyl)-3-(dimethylphosphoryl)-2-methoxyphenyl)ureido)naphthalen-1-yl)oxy)pyridin-2-yl)amino)-5-methoxy-N,N-dimethylbenzenesulfonamide

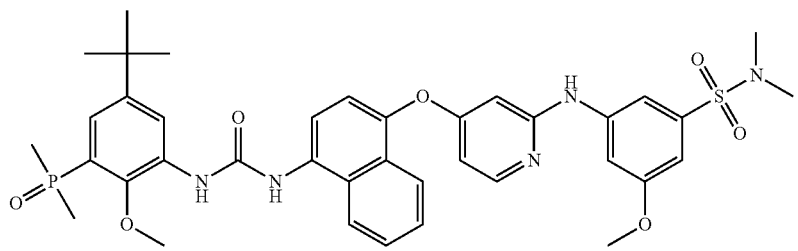 [SMILES: COc1cc(Nc2cc(Oc3ccc(NC(=O)Nc4cc(C(C)(C)C)cc(P(C)(C)=O)c4OC)c4ccccc34)ccn2)cc(S(=O)(=O)N(C)C)c1]

(i) 3-Methoxy-N,N-dimethyl-5-nitrobenzenesulfonamide

A solution of 3-methoxy-5-nitrobenzene-1-sulfonyl chloride (300 mg, 1.192 mmol) in MeCN (3 mL) was added dropwise to stirring ice cold dimethylamine 33% w/w in water (2 mL, 13.03 mmol). The reaction was allowed to warm to rt then diluted with water (10 mL). The resulting crystalline solid was filtered off, washed with water and dried to constant weight to afford the sub-title compound (250 mg) as pale brown plates.

$^1$H NMR (400 MHz, DMSO-$d_6$) δ 8.04 (t, 1H), 7.97 (dd, 1H), 7.63 (dd, 1H), 3.99 (s, 3H), 2.70 (s, 6H). LCMS m/z 261 (M+H)$^+$ (ES$^+$)

(ii) 3-Amino-5-methoxy-N,N-dimethylbenzenesulfonamide

5% Pd/C (50% paste with water) (150 mg) was added to a solution of the product from step (i) above (300 mg, 1.153 mmol) in MeOH (8 mL) and the reaction stirred under hydrogen (5 bar) for 1 h. The reaction mixture was filtered and the solvent evaporated to afford the sub-title compound (220 mg) as a colourless crystalline solid.

$^1$H NMR (400 MHz, DMSO-$d_6$) δ 6.54 (t, 1H), 6.39 (dd, 1H), 6.32 (t, 1H), 5.65 (s, 2H), 3.73 (s, 3H), 2.60 (s, 6H). LCMS m/z 231 (M+H)$^+$ (ES$^+$)

(iii) 3-((4-((4-Aminonaphthalen-1-yl)oxy)pyridin-2-yl)amino)-5-methoxy-N,N-dimethylbenzenesulfonamide BrettPhos G1 Precatalyst (20 mg, 0.023 mmol) was added to a degassed suspension of tert-butyl (4-((2-chloropyridin-4-yl)oxy)naphthalen-1-yl)carbamate (see Example 2(ii) above; 170 mg, 0.458 mmol), the product from step (ii) above (120 mg, 0.521 mmol) and K$_2$CO$_3$ (100 mg, 0.724 mmol) in tBuOH (5 mL) and the reaction heated under nitrogen at 85° C. for 2 h. The reaction mixture was diluted with DCM (10 mL), filtered and the solvent evaporated. The crude product was purified by chromatography on silica gel (40 g column, 0% MeOH:DCM to 5%) to afford a brown glass. This material was dissolved in DCM (2 mL) then TFA (500 μL, 6.49 mmol) was added. The reaction was stirred at rt for 72 h, the solvents were evaporated and the residue azeotroped with toluene (2×10 mL). The residue was partitioned between sat NaHCO$_3$ soln. (10 mL) and DCM (10 mL). The organics were separated, dried (MgSO$_4$), filtered and the solvent evaporated to afford the sub-title compound (200 mg) as a brown glass.

$^1$H NMR (400 MHz, DMSO-$d_6$) δ 9.24 (s, 1H), 8.22-8.13 (m, 1H), 8.09 (d, 1H), 7.70 (t, 1H), 7.66-7.58 (m, 1H), 7.56 (t, 1H), 7.50-7.38 (m, 2H), 7.11 (d, 1H), 6.72 (d, 1H), 6.66 (dd, 1H), 6.59 (dd, 1H), 6.03 (d, 1H), 5.84 (s, 2H), 3.77 (s, 3H), 2.61 (s, 6H). LCMS m/z 465 (M+H)$^+$ (ES$^+$)

(iv) 3-((4-((4-(3-(5-(tert-Butyl)-3-(dimethylphosphoryl)-2-methoxyphenyl)ureido)naphthalen-1-yl)oxy)pyridin-2-yl)amino)-5-methoxy-N,N-dimethylbenzenesulfonamide A solution of phenyl (5-(tert-butyl)-3-(dimethylphosphoryl)-2-methoxyphenyl)carbamate (see Example 3(vi) above; 100 mg, 0.266 mmol), the product from step (iii) above (100 mg, 0.215 mmol) and TEA (10 μL, 0.072 mmol) in THF (2 mL) was heated at 65° C. (block temperature) for 4 days. The solvent was evaporated and the crude product was purified by chromatography on silica gel (40 g column, 2% MeOH:DCM to 10%) to give a tan glass which was further purified by preparative HPLC (Gilson, Basic (0.1% Ammonium Bicarbonate), Basic, Waters X-Bridge Prep-C18, 5 μm, 19×50 mm column, 25-70% MeCN in Water) to afford the title compound (50 mg).

$^1$H NMR (400 MHz, DMSO-$d_6$) δ 9.37 (s, 1H), 9.32 (s, 1H), 8.92 (s, 1H), 8.44 (d, 1H), 8.30 (d, 1H), 8.20-8.07 (m, 2H), 7.87 (d, 1H), 7.77-7.67 (m, 2H), 7.66-7.59 (m, 1H), 7.57 (t, 1H), 7.40 (d, 1H), 7.36 (dd, 1H), 6.68 (dd, 1H), 6.65 (dd, 1H), 6.11 (d, 1H), 3.90 (s, 3H), 3.78 (s, 3H), 2.61 (s, 6H), 1.75 (d, 6H), 1.31 (s, 9H). LCMS m/z 746 (M+H)$^+$ (ES$^+$)

Example 59

5-(tert-Butyl)-2-methoxy-3-(3-(4-((2-((3-methoxy-5-((2-(2-(2-methoxyethoxy)ethoxy)ethyl)carbamoyl)phenyl)amino)pyridin-4-yl)oxy)naphthalen-1-yl)ureido)-N-(2-morpholinoethyl)benzamide

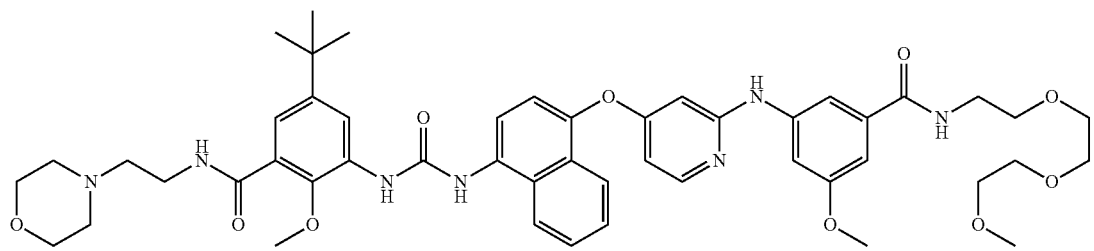 [SMILES: COCCOCCOCCNC(=O)c1cc(Nc2cc(Oc3ccc(NC(=O)Nc4cc(C(C)(C)C)cc(C(=O)NCCN5CCOCC5)c4OC)c4ccccc34)ccn2)cc(OC)c1]

(i) Methyl 5-(tert-butyl)-2-methoxy-3-(3-(4-((2-((3-methoxy-5-((2-(2-(2-methoxyethoxy)ethoxy)ethyl)carbamoyl)phenyl)amino)pyridin-4-yl)oxy)naphthalen-1-yl)ureido)benzoate Methyl 5-(tert-Butyl)-2-methoxy-3-((phenoxycarbonyl)amino)benzoate (see Example 14(i) above; 157 mg, 0.439 mmol), 3-((4-((4-aminonaphthalen-1-yl)oxy)pyridin-2-yl)amino)-5-methoxy-N-(2-(2-(2-methoxyethoxy)ethoxy)ethyl)benzamide (see Example 48(iv) above; 200 mg, 0.366 mmol) and triethylamine (11 µL, 0.079 mmol) were heated to 70° C. in iPrOAc (5 mL) for 18 h during which time a

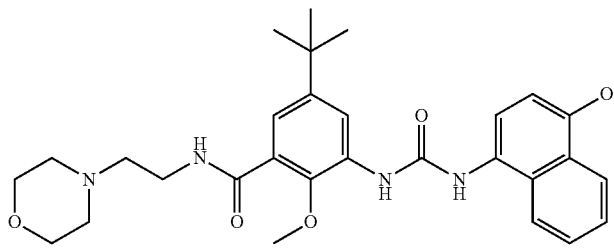

solid precipitated from solution. The solid was isolated by filtration to afford the sub-title compound (255 mg) as a pale pink solid.

LCMS m/z 405 (M+2H)²⁺ (ES⁺)

(ii) 5-(tert-Butyl)-2-methoxy-3-(3-(4-((2-((3-methoxy-5-((2-(2-(2-methoxyethoxy)ethoxy)ethyl)carbamoyl)phenyl)amino)pyridin-4-yl)oxy)naphthalen-1-yl)ureido)benzoic acid, HCl To a stirred solution of the product from step (i) above (255 mg, 0.315 mmol) in THF (10 mL) was added NaOH (2M aq.) (3.0 mL, 6.00 mmol). MeOH (2 mL) was added and stirring continued overnight. The reaction was concentrated in vacuo affording a brown solid. The material was suspended in water and acidified with 1M HCl causing a solid to precipitate. The solid was collected by filtration, washing with water and the solid dried at 40° C. under vacuum to afford the sub-title compound (240 mg) as a pink solid.

LCMS m/z 399 (M+2H)²⁺ (ES⁺)

(iii) 5-(tert-Butyl)-2-methoxy-3-(3-(4-((2-((3-methoxy-5-((2-(2-(2-methoxyethoxy)ethoxy)ethyl)carbamoyl)phenyl)amino)pyridin-4-yl)oxy)naphthalen-1-yl)ureido)-N-(2-morpholinoethyl)-benzamide HATU (50 mg, 0.131 mmol) was added to a stirred solution of the product from step (ii) above (100 mg, 0.120 mmol), 2-morpholinoethanamine (20 µL, 0.152 mmol) and Hünig's Base (75 µL, 0.429 mmol) in DMF (2 mL) at rt. The mixture was stirred for 2 h then poured into water (30 mL) and extracted with EtOAc (2×20 mL). The organic phase was washed with brine (20 mL) then dried (MgSO₄), filtered and concentrated in vacuo affording a red oil. The crude product was purified by preparative HPLC (Gilson, Basic (0.1% Ammonium Bicarbonate), Basic, Waters X-Bridge Prep-C18, 5 µm, 19×50 mm column, 35%-65% MeCN in Water) to afford the title compound (56 mg) as a white solid.

¹H NMR (400 MHz, DMSO-d₆) δ: 9.46 (s, 1H), 9.07 (s, 1H), 8.92 (s, 1H), 8.47 (d, 1H), 8.34 (t, 1H), 8.30 (d, 1H), 8.25 (t, 1H), 8.09-8.12 (m, 2H), 7.88 (d, 1H), 7.72 (t, 1H), 7.62 (t, 1H), 7.58 (t, 1H), 7.51 (s, 1H), 7.39 (d, 1H), 7.25 (d, 1H), 6.89 (s, 1H), 6.58 (dd, 1H), 6.15 (d, 1H), 3.84 (s, 3H), 3.75 (s, 3H), 3.61-3.63 (m, 4H), 3.49-3.52 (m, 8H), 3.37-3.47 (m, 6H), 3.21 (s, 3H), 2 protons under DMSO, 2.46 (bs, 4H), 1.29 (s, 9H). LCMS m/z 909 (M+H)⁺ (ES⁺)

Example 60

5-(tert-Butyl)-2-methoxy-3-(3-(4-((2-((3-methoxy-5-((2-morpholinoethyl)carbamoyl)phenyl)amino)pyridin-4-yl)oxy)naphthalen-1-yl)ureido)-N-(2-morpholinoethyl)benzamide

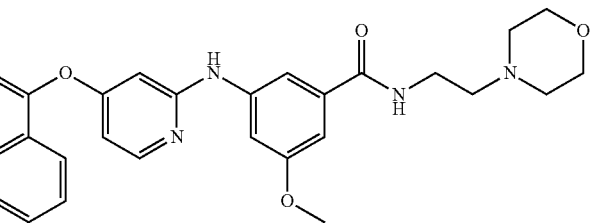

(i) Methyl 5-(tert-butyl)-2-methoxy-3-(3-(4-((2-((3-methoxy-5-((2-morpholinoethyl)carbamoyl)phenyl)amino)pyridin-4-yl)oxy)naphthalen-1-yl)ureido)benzoate Methyl 5-(tert-Butyl)-2-methoxy-3-((phenoxycarbonyl)amino)benzoate (see Example 14(i) above; 167 mg, 0.467 mmol), 3-((4-((4-aminonaphthalen-1-yl)oxy)pyridin-2-yl)amino)-5-methoxy-N-(2-morpholinoethyl)benzamide (see Example 45(ii) above; 200 mg, 0.389 mmol) and triethylamine (11 µL, 0.079 mmol) were heated to 70° C. in iPrOAc (5 mL) for 18 h. The mixture was concentrated under reduced pressure onto silica gel and purified by chromatography on the Companion (12 g column, 1-6% MeOH in EtOAc) to afford the sub-title compound (226 mg) as a pale yellow glass.

LCMS m/z 389 (M+2H)²⁺ (ES⁺)

(ii) 5-(tert-Butyl)-2-methoxy-3-(3-(4-((2-((3-methoxy-5-((2-morpholinoethyl)carbamoyl)-phenyl)amino)pyridin-4-yl)oxy)naphthalen-1-yl)ureido) benzoic acid, 2HCl To a stirred solution of the product from step (i) above (226 mg, 0.291 mmol) in THF (10 mL) was added NaOH (2M aq.) (1.5 mL, 3.00 mmol). MeOH (1 mL) was added and stirring continued overnight. Additional NaOH (2M, 1.0 mL) was added and stirring continued overnight. The reaction was concentrated in vacuo affording a beige solid. The material was suspended in water and acidified with 1M HCl causing a solid to precipitate. The solid was collected by filtration, washing with water and the solid dried at 40° C. under vacuum to afford the sub-title compound (200 mg) as a pale pink solid.

LCMS m/z 382 (M+2H)²⁺ (ES⁺)

(iii) 5-(tert-Butyl)-2-methoxy-3-(3-(4-((2-((3-methoxy-5-((2-morpholinoethyl)carbamoyl)-phenyl)amino)pyridin-4-yl)oxy)naphthalen-1-yl)ureido)-N-(2-morpholinoethyl)benzamide HATU (50.0 mg, 0.132 mmol) was added to a stirred solution of the product from step (ii) above (100 mg, 0.120 mmol), 2-morpholinoethanamine (20 μL, 0.152 mmol) and Hünig's Base (96 μL, 0.549 mmol) in DMF (2 mL) at rt. The mixture was stirred for 2 h then poured into water (30 mL) resulting in the precipitation of a pale pink solid. The solid was recovered by filtration, washing with water and the resulting material was dried at 40° C. under vacuum for 2 h. The crude product was purified by preparative HPLC (Gilson, Basic (0.1% Ammonium Bicarbonate), Basic, Waters X-Bridge Prep-C18, 5 μm, 19×50 mm column, 35%-65% MeCN in Water) to afford a white solid. The solid was dissolved in MeCN and concentrated in vacuo to afford the title compound (49 mg) as a white solid.

$^1$H NMR (400 MHz, DMSO-$d_6$) δ: 9.46 (s, 1H), 9.07 (s, 1H), 8.92 (s, 1H), 8.47 (d, 1H), 8.30 (d, 1H), 8.25 (t, 1H), 8.23 (t, 1H), 8.09-8.12 (m, 2H), 7.88 (d, 1H), 7.70-7.74 (m, 1H), 7.60-7.64 (m, 1H), 7.56 (t, 1H), 7.51 (s, 1H), 7.39 (d, 1H), 7.25 (d, 1H), 6.86 (s, 1H), 6.58 (dd, 1H), 6.15 (d, 1H), 3.84 (s, 3H), 3.75 (s, 3H), 3.62 (t, 4H), 3.57 (t, 4H), 3.45 (q, 2H), 3.35 (q, 2H), 2H under DMSO, 2.41-2.46 (m, 10H), 1.29 (s, 9H). LCMS m/z 876 (M+H)$^+$ (ES$^+$)

Example 61

5-(tert-Butyl)-3-(3-(4-((2-((3-carbamoyl-5-methoxyphenyl)amino)pyridin-4-yl)oxy)naphthalen-1-yl)ureido)-2-methoxy-N-(2-morpholinoethyl)benzamide (ii) 5-(tert-Butyl)-3-(3-(4-((2-((3-carbamoyl-5-methoxyphenyl)amino)pyridin-4-yl)oxy)naphthalen-1-yl)ureido)-2-methoxybenzoic acid, HCl To a stirred solution of the product from step (i) above (265 mg, 0.399 mmol) in THF (10 mL) was added NaOH (2M aq.) (4.0 mL, 8.00 mmol). MeOH (2 mL) was added and stirring continued overnight. The reaction was concentrated in vacuo affording a beige solid. The material was suspended in water and acidified with 1M HCl causing a solid to precipitate. The solid was collected by filtration, washing with water and the solid dried at 40° C. under vacuum to afford the sub-title compound (244 mg) as an off-white solid.

LCMS m/z 326 (M+2H)$^{2+}$ (ES$^+$)

(iii) 5-(tert-Butyl)-3-(3-(4-((2-((3-carbamoyl-5-methoxyphenyl)amino)pyridin-4-yl)oxy)naphthalen-1-yl)ureido)-2-methoxy-N-(2-morpholinoethyl)benzamide HATU (60 mg, 0.158 mmol) was added to a stirred solution of the product from step (ii) above (100 mg, 0.146 mmol), 2-morpholinoethanamine (25 μL, 0.190 mmol) and Hünig's Base (90 μL, 0.515 mmol) in DMF (2 mL) at rt. The mixture was stirred for 2 h then poured into water (30 mL) resulting in the precipitation of an off-white solid. The solid was recovered by filtration, washing with water and the

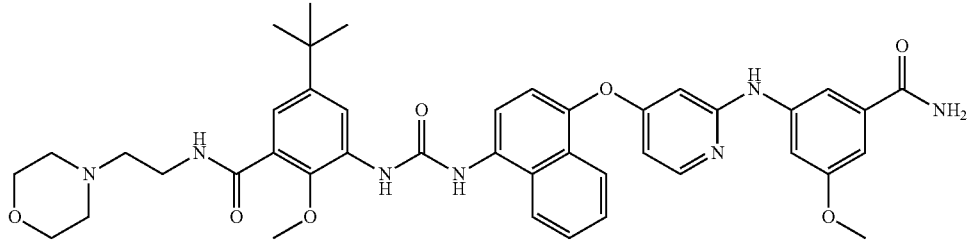 [SMILES: COc1cc(Nc2cc(Oc3ccc(NC(=O)Nc4cc(C(C)(C)C)cc(C(=O)NCCN5CCOCC5)c4OC)c4ccccc34)ccn2)cc(C(N)=O)c1]

(i) Methyl 5-(tert-butyl)-3-(3-(4-((2-((3-carbamoyl-5-methoxyphenyl)amino)pyridin-4-yl)oxy)naphthalen-1-yl)ureido)-2-methoxybenzoate Methyl 5-(tert-butyl)-2-methoxy-3-((phenoxycarbonyl)amino)benzoate (see Example 14(i) above; 214 mg, 0.599 mmol), 3-((4-((4-aminonaphthalen-1-yl)oxy)pyridin-2-yl)amino)-5-methoxybenzamide (see Example 37(ii) above; 200 mg, 0.499 mmol) and triethylamine (15 μL, 0.108 mmol) were heated to 70° C. in iPrOAc (5 mL) for 18 h. The mixture was concentrated under reduced pressure onto silica gel and purified by chromatography on the Companion (12 g column, 1-6% MeOH in DCM) to afford the sub-title compound (265 mg) as a pale yellow glass.

LCMS m/z 333 (M+2H)$^{2+}$ (ES$^+$)

resulting material was dried at 40° C. under vacuum for 2 h. The crude product was purified by preparative HPLC (Gilson, Basic (0.1% Ammonium Bicarbonate), Basic, Waters X-Bridge Prep-C18, 5 μm, 19×50 mm column, 35%-65% MeCN in Water) to afford a white solid. The product was re-purified by preparative HPLC (Waters, Acidic (0.1% Formic acid), Acidic, Waters X-Select Prep-C18, 5 μm, 19×50 mm column, 20-50% MeCN in Water) to afford the title compound (27 mg) as a white solid.

$^1$H NMR (400 MHz, DMSO-$d_6$) δ: 9.48 (s, 1H), 9.05 (s, 1H), 8.93 (s, 1H), 8.47 (d, 1H), 8.31 (d, 1H), 8.25 (t, 1H), 8.08-8.12 (m, 2H), 7.88 (d, 1H), 7.81 (s, 1H), 7.71 (t, 1H), 7.62 (t, 1H), 7.57 (t, 1H), 7.52 (s, 1H), 7.39 (d, 1H), 7.25 (d, 2H), 6.92 (s, 1H), 6.57 (dd, 1H), 6.15 (d, 1H), 3.84 (s, 3H), 3.74 (s, 3H), 3.61-3.63 (m, 4H), 3.45 (q, 2H), 2H under DMSO, 2.46 (bs, 4H), 1.29 (s, 9H). LCMS m/z 762 (M+H)$^+$ (ES$^+$)

Example 62

5-(tert-Butyl)-3-(3-(4-((2-((3,5-dimethoxyphenyl)amino)pyridin-4-yl)oxy)naphthalen-1-yl)ureido)-2-methoxy-N-(2-morpholinoethyl)benzamide

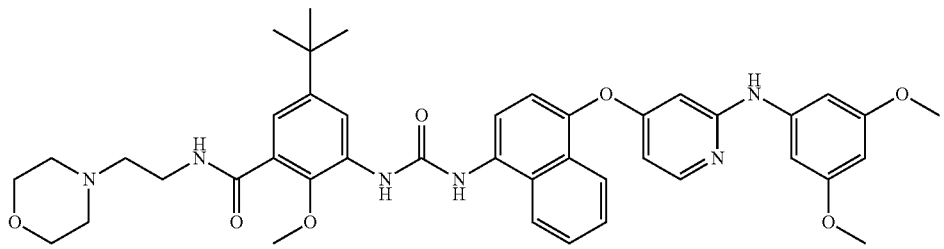 [SMILES: COc1cc(Nc2cc(Oc3ccc(NC(=O)Nc4cc(C(C)(C)C)cc(C(=O)NCCN5CCOCC5)c4OC)c4ccccc34)ccn2)cc(OC)c1]

(i) Methyl 5-(tert-butyl)-3-(3-(4-((2-((3,5-dimethoxyphenyl)amino)pyridin-4-yl)oxy)naphthalen-1-yl)ureido)-2-methoxybenzoate Methyl 5-(tert-butyl)-2-methoxy-3-((phenoxycarbonyl)amino)benzoate (see Example 14(i) above; 221 mg, 0.619 mmol), 4-((4-aminonaphthalen-1-yl)oxy)-N-(3,5-dimethoxyphenyl)-pyridin-2-amine (see Example 27(ii) above; 200 mg, 0.516 mmol) and triethylamine (15 µL, 0.108 mmol) were heated to 70° C. in iPrOAc (5 mL) for 18 h. The mixture was concentrated under reduced pressure onto silica gel and purified by chromatography on the Companion (12 g column, 1-6% MeOH in DCM) to afford the sub-title compound (230 mg) as a pale pink foam. LCMS m/z 326 (M+2H)$^{2+}$ (ES$^+$)

(ii) 5-(tert-Butyl)-3-(3-(4-((2-((3,5-dimethoxyphenyl)amino)pyridin-4-yl)oxy)naphthalen-1-yl)ureido)-2-methoxybenzoic acid, HCl To a stirred solution of the product from step (i) above (230 mg, 0.353 mmol) in THF (10 mL) was added NaOH (2M aq.) (4.0 mL, 8.00 mmol). MeOH (2 mL) was added and stirring continued overnight. The reaction was concentrated in vacuo affording a beige solid. The material was suspended in water and acidified with 1M HCl causing a solid to precipitate. The solid was collected by filtration, washing with water and the solid dried at 40° C. under vacuum to afford the sub-title compound (209 mg) as an off-white solid.
LCMS m/z 637 (M+H)$^+$ (ES$^+$)

(iii) 5-(tert-Butyl)-3-(3-(4-((2-((3,5-dimethoxyphenyl)amino)pyridin-4-yl)oxy)naphthalen-1-yl)ureido)-2-methoxy-N-(2-morpholinoethyl)benzamide HATU (60 mg, 0.158 mmol) was added to a stirred solution of the product from step (ii) above (100 mg, 0.149 mmol), 2-morpholinoethanamine (25 µL, 0.190 mmol) and Hünig's Base (90 µL, 0.515 mmol) in DMF (2 mL) at rt. The mixture was stirred for 2 h then poured into water (30 mL) resulting in the precipitation of an off-white solid. The solid was recovered by filtration, washing with water and the resulting material was dried at 40° C. under vacuum for 2 h. The crude product was purified by chromatography on the Companion (12 g column, 1-10% MeOH in DCM) to afford the title compound (70 mg) as a white solid.

$^1$H NMR (400 MHz, DMSO-d$_6$) δ: 9.45 (s, 1H), 8.92 (s, 1H), 8.89 (s, 1H), 8.47 (d, 1H), 8.30 (d, 1H), 8.25 (t, 1H), 8.11 (d, 1H), 8.09 (d, 1H), 7.88 (d, 1H), 7.72 (t, 1H), 7.62 (t, 1H), 7.39 (d, 1H), 7.25 (d, 1H), 6.85 (d, 2H), 6.58 (dd, 1H), 6.10 (d, 1H), 6.03 (t, 1H), 3.84 (s, 3H), 3.66 (s, 6H), 3.61-3.63 (m, 4H), 3.45 (q, 2H), 2H under DMSO, 2.46 (bs, 4H), 1.29 (s, 9H). LCMS m/z 749 (M+H)$^+$ (ES$^+$)

Example 63

5-(tert-Butyl)-2-methoxy-3-(3-(4-((2-((3-methoxyphenyl)amino)pyridin-4-yl)oxy)naphthalen-1-yl)ureido)-N-(2-morpholinoethyl)benzamide

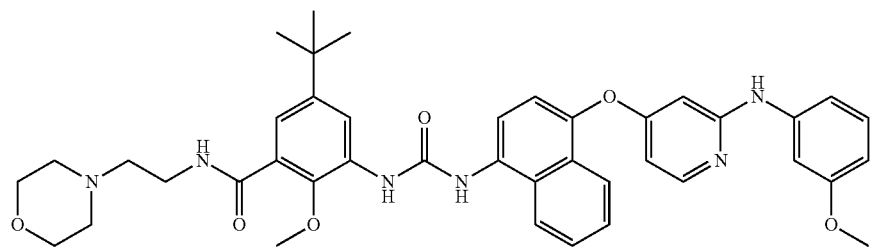 [SMILES: COc1cccc(Nc2cc(Oc3ccc(NC(=O)Nc4cc(C(C)(C)C)cc(C(=O)NCCN5CCOCC5)c4OC)c4ccccc34)ccn2)c1]

(i) Methyl 5-(tert-butyl)-2-methoxy-3-(3-(4-((2-((3-methoxyphenyl)amino)pyridin-4-yl)oxy)naphthalen-1-yl)ureido)benzoate Methyl 5-(tert-butyl)-2-methoxy-3-((phenoxycarbonyl)amino)benzoate (see Example 14(i) above; 180 mg, 0.504 mmol), 4-((4-aminonaphthalen-1-yl)oxy)-N-(3-methoxyphenyl)pyridin-2-amine (see Example 33 (ii) above; 150 mg, 0.420 mmol) and triethylamine (8 µL, 0.057 mmol) were heated to 70° C. in iPrOAc (5 mL) for 18 h. The mixture was concentrated under reduced pressure onto silica gel and purified by chromatography on the Companion (12 g column, 1-6% MeOH in DCM) to afford the sub-title compound (140 mg) as a pale pink glass.
LCMS m/z 311 (M+2H)²⁺ (ES⁺)

(ii) 5-(tert-Butyl)-2-methoxy-3-(3-(4-((2-((3-methoxyphenyl)amino)pyridin-4-yl)oxy)naphthalen-1-yl)ureido)benzoic acid, HCl To a stirred solution of the product from step (i) above (140 mg, 0.226 mmol) in THF (10 mL) was added NaOH (2M aq.) (3.0 mL, 6.00 mmol). MeOH (2 mL) was added and stirring continued overnight. The reaction was concentrated in vacuo affording a beige solid. The material was suspended in water and acidified with 1M HCl causing a solid to precipitate. The solid was collected by filtration, washing with water and the solid dried at 40° C. under vacuum to afford the sub-title compound (120 mg) as an off-white solid.
LCMS m/z 607 (M+H)⁺ (ES⁺)

(iii) 5-(tert-Butyl)-2-methoxy-3-(3-(4-((2-((3-methoxyphenyl)amino)pyridin-4-yl)oxy)naphthalen-1-yl)ureido)-N-(2-morpholinoethyl)benzamide HATU (60 mg, 0.158 mmol) was added to a stirred solution of the product from step (ii) above (100 mg, 0.155 mmol), 2-morpholinoethanamine (25 µL, 0.190 mmol) and Hünig's Base (90 µL, 0.515 mmol) in DMF (2 mL) at rt. The mixture was stirred for 2 h then poured into water (30 mL) and extracted with EtOAc (2×20 mL). The combined organic phase was washed with brine then dried (MgSO₄), filtered and concentrated in vacuo. The crude product was purified by chromatography on the Companion (12 g column, 1-10% MeOH in DCM) to afford the title compound (72 mg) as a white solid.

¹H NMR (400 MHz, DMSO-d₆) δ: 9.45 (s, 1H), 8.91 (s, 1H), 8.91 (s, 1H), 8.47 (d, 1H), 8.30 (d, 1H), 8.25 (t, 1H), 8.11 (d, 1H), 8.09 (d, 1H), 7.88 (d, 1H), 7.72 (t, 1H), 7.62 (t, 1H), 7.39 (d, 1H), 7.34 (s, 1H), 7.25 (d, 1H), 7.07-7.10 (m, 2H), 6.57 (dd, 1H), 6.42-6.46 (m, 1H), 6.11 (d, 1H), 3.84 (s, 3H), 3.68 (s, 3H), 3.61-3.63 (m, 4H), 3.45 (q, 2H), 2H under DMSO, 2.46 (bs, 4H), 1.29 (s, 9H). LCMS m/z 719 (M+H)⁺ (ES⁺)

Example 64

5-(tert-Butyl)-3-(3-(4-((2-((3,5-dimethoxyphenyl)amino)pyridin-4-yl)oxy)naphthalen-1-yl)ureido)-2-methoxy-N-(2-(1-oxidothiomorpholino)ethyl)benzamide

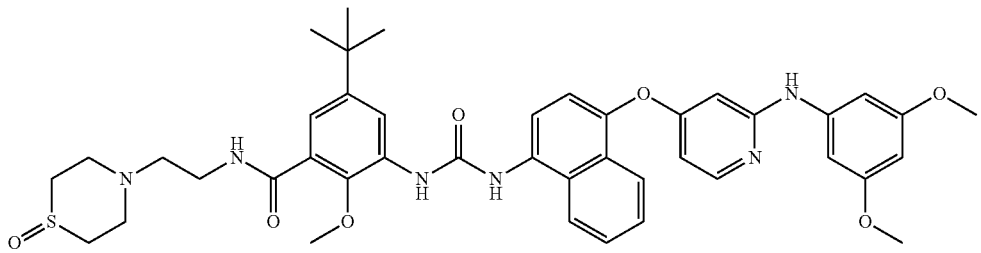 [SMILES: COc1cc(Nc2cc(Oc3ccc(NC(=O)Nc4cc(C(C)(C)C)cc(C(=O)NCCN5CCS(=O)CC5)c4OC)c4ccccc34)ccn2)cc(OC)c1]

HATU (60 mg, 0.158 mmol) was added to a stirred solution of 5-(tert-butyl)-3-(3-(4-((2-((3,5-dimethoxyphenyl)amino)pyridin-4-yl)oxy)naphthalen-1-yl)ureido)-2-methoxybenzoic acid, HCl (see Example 62(ii) above; 100 mg, 0.149 mmol), 4-(2-aminoethyl)thiomorpholine 1-oxide (35 mg, 0.216 mmol) and Hünig's Base (90 µL, 0.515 mmol) in DMF (2 mL) at rt. The mixture was stirred for 2 h then poured into water (30 mL) and extracted with EtOAc (2×20 mL). The combined organic phase was washed with brine then dried (MgSO₄), filtered and concentrated in vacuo. The crude product was purified by chromatography on the Companion (12 g column, 1-10% MeOH in DCM) to afford the title compound (76 mg) as a white solid.

¹H NMR (400 MHz, DMSO-d₆) δ: 9.45 (s, 1H), 8.92 (s, 1H), 8.89 (s, 1H), 8.46 (d, 1H), 8.30 (d, 1H), 8.23 (t, 1H), 8.11 (d, 1H), 8.09 (d, 1H), 7.88 (d, 1H), 7.72 (t, 1H), 7.61 (t, 1H), 7.39 (d, 1H), 7.22 (d, 1H), 6.85 (d, 2H), 6.58 (dd, 1H), 6.10 (d, 1H), 6.03 (t, 1H), 3.83 (s, 3H), 3.66 (s, 6H), 3.45 (q, 2H), 2.87-3.03 (m, 4H), 2.73-2.78 (m, 4H), 2.62 (t, 2H), 1.29 (s, 9H). LCMS m/z 781 (M+H)⁺ (ES⁺)

Example 65

3-((4-((4-(3-(3-(2-Amino-2-oxoethyl)-5-(tert-butyl)-2-methoxyphenyl)ureido)naphthalen-1-yl)oxy)pyridin-2-yl)amino)-5-methoxy-N-(2-(1-oxidothiomorpholino)ethyl)benzamide

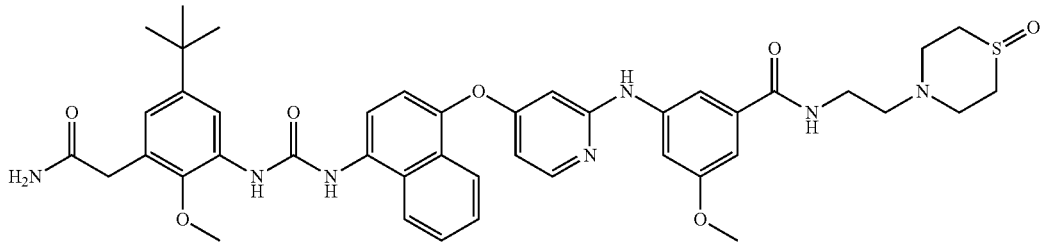 [SMILES: COc1cc(Nc2cc(Oc3ccc(NC(=O)Nc4cc(C(C)(C)C)cc(CC(N)=O)c4OC)c4ccccc34)ccn2)cc(C(=O)NCCN2CCS(=O)CC2)c1]

(i) Methyl 3-((4-((4-aminonaphthalen-1-yl)oxy)pyridin-2-yl)amino)-5-methoxybenzoate 5M HCl in IPA (10 mL) was added to a solution of methyl 3-((4-((4-((tert-butoxycarbonyl)amino)naphthalen-1-yl)oxy)pyridin-2-yl)amino)-5-methoxybenzoate (see Example 48(i) above; 1 g, 1.940 mmol) in DCM (10 mL) and the reaction left stirring for 2 hours. Diethyl ether (20 mL) was added, and the white precipitate was filtered off. The solid was partitioned between DCM (50 mL) and a saturated solution of NaHCO$_3$ (50 mL). The organic layer was dried over MgSO$_4$, filtered and concentrated in vacuo to afford a pale pink foam (700 mg).

LCMS m/z 416 (M+H)$^+$ (ES$^+$)

(ii) Methyl 3-((4-((4-(3-(3-(2-amino-2-oxoethyl)-5-(tert-butyl)-2-methoxyphenyl)ureido)-naphthalen-1-yl)oxy)pyridin-2-yl)amino)-5-methoxybenzoate A solution of phenyl (3-(2-amino-2-oxoethyl)-5-(tert-butyl)-2-methoxyphenyl)carbamate (see Example 13(vi) above; 200 mg, 0.561 mmol), the product from step (i) above (200 mg, 0.481 mmol) and TEA (15 μL, 0.108 mmol) in THF (2 mL) was heated at 65° C. (block temperature) for 4 days. The solvent was evaporated and the crude product was purified by chromatography on silica gel (12 g column, 2% MeOH:DCM to 8%) to afford the sub-title compound (238 mg) as a pale pink solid.

$^1$H NMR (400 MHz, DMSO-d$_6$) δ 9.39 (s, 1H), 9.17 (s, 1H), 8.80 (s, 1H), 8.31 (d, 1H), 8.21 (d, 1H), 8.18-8.08 (m, 2H), 7.87 (d, 1H), 7.76 (dd, 1H), 7.75-7.66 (m, 2H), 7.66-7.57 (m, 1H), 7.45 (s, 1H), 7.39 (d, 1H), 6.96 (dd, 1H), 6.95-6.92 (m, 2H), 6.62 (dd, 1H), 6.11 (d, 1H), 3.82 (s, 3H), 3.78 (s, 3H), 3.76 (s, 3H), 3.46 (s, 2H), 1.27 (s, 9H). LCMS m/z 678 (M+H)$^+$ (ES$^+$)

(iii) 3-((4-((4-(3-(3-(2-Amino-2-oxoethyl)-5-(tert-butyl)-2-methoxyphenyl)ureido)naphthalen-1-yl)oxy)pyridin-2-yl)amino)-5-methoxybenzoic acid LiOH (9 mg, 0.376 mmol) was added to a solution of the product from step (ii) above (225 mg, 0.332 mmol) in THF (2 mL) and a few drops of water added. The reaction was left stirring overnight. LiOH (9 mg, 0.376 mmol) was added and stirring continued for a further 24 h. The reaction mixture was partitioned between water (5 mL) and EtOAc (5 mL), the aqueous layer was separated and acidified to ~pH 5 with conc. HCl. The resulting precipitated was filtered and dried to afford the sub-title compound (170 mg) as a tan solid.

$^1$H NMR (400 MHz, DMSO-d$_6$) δ 12.97 (s, 1H), 9.79-9.36 (m, 2H), 8.87 (s, 1H), 8.36 (d, 1H), 8.20 (d, 1H), 8.13 (d, 1H), 8.10 (d, 1H), 7.86 (d, 1H), 7.77-7.67 (m, 1H), 7.67-7.57 (m, 2H), 7.50 (s, 1H), 7.46 (s, 1H), 7.42 (d, 1H), 7.08 (s, 1H), 7.01-6.86 (m, 2H), 6.71 (dd, 1H), 6.19 (d, 1H), 3.78 (s, 3H), 3.76 (s, 3H), 3.45 (s, 2H), 1.27 (s, 9H). LCMS m/z 664 (M+H)$^+$ (ES$^+$)

(iv) 3-((4-((4-(3-(3-(2-Amino-2-oxoethyl)-5-(tert-butyl)-2-methoxyphenyl)ureido)naphthalen-1-yl)oxy)pyridin-2-yl)amino)-5-methoxy-N-(2-(1-oxidothiomorpholino)ethyl)benzamide HATU (75 mg, 0.197 mmol) was added to a solution of the product from step (iii) above (82 mg, 0.124 mmol), 4-(2-aminoethyl)thiomorpholine 1-oxide (30 mg, 0.185 mmol) and Hünig's Base (70 μL, 0.401 mmol) in DMF (2 mL) and stirred at rt for 2 h. The mixture was diluted with water (10 mL) then the precipitate was collected by filtration and washed with water (2×3 mL). The filter cake was purified by chromatography on silica gel (12 g column, 5% MeOH:DCM to 15%) to afford the title compound (65 mg) as a tan solid.

$^1$H NMR (400 MHz, DMSO-d$_6$) δ 9.40 (s, 1H), 9.06 (s, 1H), 8.80 (s, 1H), 8.31 (d, 1H), 8.25 (t, 1H), 8.21 (d, 1H), 8.15-8.06 (m, 2H), 7.87 (d, 1H), 7.76-7.66 (m, 1H), 7.65-7.58 (m, 1H), 7.58-7.53 (m, 1H), 7.53-7.48 (m, 1H), 7.45 (s, 1H), 7.38 (d, 1H), 7.00-6.90 (m, 2H), 6.90-6.81 (m, 1H), 6.58 (dd, 1H), 6.13 (d, 1H), 3.78 (s, 3H), 3.75 (s, 3H), 3.46 (s, 2H), 2.99-2.79 (m, 4H), 2.77-2.63 (m, 4H), 2.54 (t, 2H), 1.27 (s, 9H). (CH$_2$ under water peak). LCMS m/z 808 (M+H)$^+$ (ES$^+$)

Example 66

3-((4-((4-(3-(5-(tert-Butyl)-3-((1,3-dihydroxypropan-2-yl)oxy)-2-methoxyphenyl)ureido) naphthalen-1-yl)oxy)pyridin-2-yl)amino)-5-methoxybenzamide

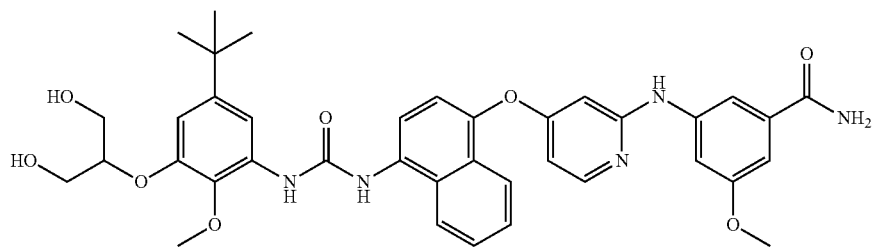 [SMILES: COc1cc(Nc2cc(Oc3ccc(NC(=O)Nc4cc(C(C)(C)C)cc(OC(CO)CO)c4OC)c4ccccc34)ccn2)cc(C(N)=O)c1]

(i) 1,3-Bis(benzyloxy)propan-2-yl methanesulfonate

Ms-Cl (300 µL, 3.86 mmol) was added to a solution of 1,3-bis(benzyloxy)propan-2-ol (1 g, 3.67 mmol) and Et₃N (560 µL, 4.02 mmol) in DCM (15 mL) at 0-5° C. The mixture was stirred for 3 h then partitioned between DCM (50 mL) and water (30 mL). The organic layer was separated, washed with water (30 mL), dried (MgSO₄), filtered and evaporated under reduced pressure to afford the sub-title compound (1.27 g) as an oil which was used crude in the next step.

(ii) (((2-(5-(tert-Butyl)-2-methoxy-3-nitrophenoxy) propane-1,3-diyl)bis(oxy))bis(methylene))-dibenzene A mixture of 5-(tert-butyl)-2-methoxy-3-nitrophenol (600 mg, 2.66 mmol), the product from step (i) above (1.2 g, 3.42 mmol) and K₂CO₃ (800 mg, 5.79 mmol) in DMF (10 mL) was heated at 100° C. for 10 h, cooled and partitioned between ether (70 mL) and water (50 mL). The organic layer was dried (MgSO₄), filtered and evaporated under reduced pressure. The crude product was purified by chromatography on silica gel (40 g column, 0-10% EtOAc/isohexane) to afford the sub-title compound (870 mg) as an oil.

¹H NMR (400 MHz, CDCl₃) δ 7.37-7.29 (m, 12H), 4.64 (pent, 1H), 4.58 (s, 4H), 3.96 (s, 3H), 3.79 (d, 4H), 1.25 (s, 9H).

(iii) 3-((1,3-Bis(benzyloxy)propan-2-yl)oxy)-5-(tert-butyl)-2-methoxyaniline A mixture of the product from step (ii) above (860 mg, 1.793 mmol), Fe powder (900 mg, 16.12 mmol) and NH₄Cl (50 mg, 0.935 mmol) in EtOH (15 mL) and water (5 mL) was heated at 65° C. for 4 h. The mixture was cooled, filtered through Celite and evaporated under reduced pressure. The residue was partitioned between EtOAc (50 mL) and sat aq NaHCO₃ soln (30 mL), the organic layer separated, washed with water (20 mL), dried (MgSO₄), filtered and evaporated under reduced pressure. The crude product was purified by chromatography on silica gel (40 g column, 0-30% EtOAc/isohexane) to afford the sub-title compound (650 mg) as an oil.

¹H NMR (400 MHz, CDCl₃) δ 7.36-7.28 (m, 10H), 6.56 (d, 1H), 6.53 (d, 1H), 4.63-4.59 (m, 5H), 3.85 (s, 3H), 3.80 (d, 4H), 1.25 (s, 9H). LCMS m/z 450 (M+H)⁺ (ES⁺)

(iv) Phenyl (3-((1,3-bis(benzyloxy)propan-2-yl) oxy)-5-(tert-butyl)-2-methoxyphenyl)-carbamate Phenyl chloroformate (200 µL, 1.594 mmol) was added to a mixture of the product from step (iii) above (640 mg, 1.424 mmol) and NaHCO₃ (243 mg, 2.90 mmol) in DCM (7 mL) and THF (7 mL). The mixture was stirred for 3 h then partitioned between DCM (50 mL) and water (30 mL). The organic layer was separated, dried (MgSO₄), filtered and evaporated under reduced pressure to afford the sub-title compound (815 mg) as an oil.

LCMS m/z 570 (M+H)⁺ (ES⁺)

(v) 3-((4-((4-(3-(5-(tert-Butyl)-3-((1, 3-di hydroxypropan-2-yl)oxy)-2-methoxyphenyl) ureido)-naphthalen-1-yl)oxy)pyridin-2-yl)amino)-5-methoxybenzamide A mixture of the product from step (iv) above (385 mg, 0.676 mmol) and 10% Pd—C (100 mg) in THF (10 mL) was hydrogenated at 5 bar for 4 h then filtered. 3-((4-((4-Aminonaphthalen-1-yl)oxy)pyridin-2-yl)amino)-5-methoxybenzamide (see Example 37(ii) above; 200 mg, 0.499 mmol) and Et₃N (45 µL, 0.323 mmol) were added and the mixture heated at 60° C. for 48 h. The solvent was evaporated under reduced pressure and the residue purified by chromatography on silica gel (40 g column, 0-10% MeOH/DCM) then purified by preparative HPLC (Waters, Acidic (0.1% Formic acid), Acidic, Waters X-Select Prep-C18, 5 µm, 19×50 mm column, 20-50% MeCN in Water) to afford the title compound (50 mg) as a colourless solid.

¹H NMR (400 MHz, DMSO-d₆) δ 9.42 (s, 1H), 9.05 (s, 1H), 8.81 (s, 1H), 8.30 (d, 1H), 8.11 (d, 1H), 8.08 (d, 1H), 7.98 (d, 1H), 7.87 (d, 1H), 7.81 (s, 1H), 7.75-7.66 (m, 1H), 7.66-7.58 (m, 1H), 7.57 (t, 1H), 7.52 (t, 1H), 7.38 (d, 1H), 7.24 (s, 1H), 6.99-6.87 (m, 1H), 6.78 (d, 1H), 6.57 (dd, 1H), 6.14 (d, 1H), 4.80 (s, 2H), 4.31 (p, 1H), 3.86 (s, 3H), 3.74 (s, 3H), 3.71-3.58 (m, 4H), 1.27 (s, 9H). LCMS m/z 696 (M+H)⁺ (ES⁺)

Example 67

3-((4-((4-(3-(5-(tert-Butyl)-3-(3-hydroxy-2,2-bis(hydroxymethyl)propoxy)-2-methoxyphenyl)ureido)naphthalen-1-yl)oxy)pyridin-24)amino)-5-methoxybenzamide

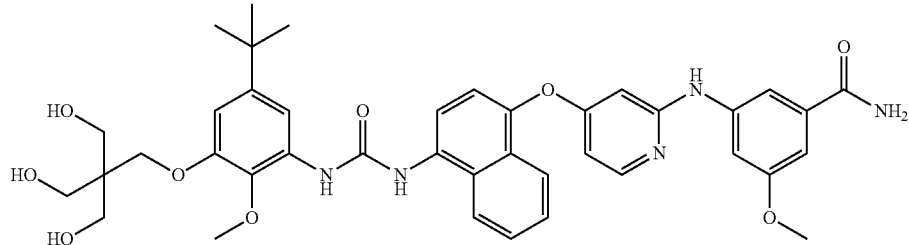 [SMILES: COc1cc(Nc2cc(Oc3ccc(NC(=O)Nc4cc(C(C)(C)C)cc(OCC(CO)(CO)CO)c4OC)c4ccccc34)ccn2)cc(C(N)=O)c1]

(i) (5-((5-(tert-Butyl)-2-methoxy-3-nitrophenoxy)methyl)-2,2-dimethyl-1,3-dioxan-5-yl)methanol A mixture of 5-(tert-butyl)-2-methoxy-3-nitrophenol (1 g, 4.44 mmol), (5-(bromomethyl)-2,2-dimethyl-1,3-dioxan-5-yl)methanol (1.2 g, 5.02 mmol) and $K_2CO_3$ (2 g, 14.47 mmol) in DMF (20 mL) was heated at 100° C. for 24 h. The mixture was partitioned between ether (100 mL) and water (60 mL), the organic layer washed with brine (60 mL), dried ($MgSO_4$), filtered and evaporated under reduced pressure. The crude product was purified by chromatography on silica gel (40 g column, 0-70% EtOAc/isohexane) to afford the sub-title compound (955 mg) as a yellow oil.

LCMS m/z 384 $(M+H)^+$ $(ES^+)$

1H NMR in $CDCl_3$ was consistent with product structure at 70% purity. Deprotection of acetonide had occurred, ~5:2, product:deprotected product (ii) (5-((3-Amino-5-(tert-butyl)-2-methoxyphenoxy)methyl)-2,2-dimethyl-1,3-dioxan-5-yl)methanol A mixture of the crude product from step (i) above (500 mg) and 10% Pd—C (100 mg) in THF (8 mL) was hydrogenated at 5 bar for 20 h. The mixture was filtered and the filtrate evaporated under reduced pressure to afford the sub-title compound (460 mg) as a brown oil.

LCMS m/z 354 $(M+H)^+$ $(ES^+)$ (iii) 3-((4-((4-(3-(5-(tert-Butyl)-3-(3-hydroxy-2,2-bis(hydroxymethyl)propoxy)-2-methoxyphenyl)ureido)naphthalen-1-yl)oxy)pyridin-2-yl)amino)-5-methoxybenzamide Phenyl chloroformate (180 µL, 1.435 mmol) was added to a mixture of the crude product from step (ii) above (455 mg) and $NaHCO_3$ (324 mg, 3.86 mmol) in THF (5 mL) and DCM (5 mL) at rt. The mixture was stirred for 2 h then partitioned between DCM (30 mL) and water (30 mL). The organic layer was separated, dried ($MgSO_4$), filtered and evaporated under reduced pressure to afford the crude carbamate as a foam (541 mg). A mixture of 3-((4-((4-aminonaphthalen-1-yl)oxy)pyridin-2-yl)amino)-5-methoxybenzamide (see Example 37(ii) above; 300 mg, 0.749 mmol), the crude carbamate (535 mg) and $Et_3N$ (80 µL, 0.574 mmol) in THF (5 mL) was heated at 60° C. for 24 h. The mixture was cooled then MeOH (5 mL) and aq 1M HCl (5 mL) added and stirred for 3 h at rt. Sat. aq. $NaHCO_3$ soln (5 mL) was added, stirred for 5 min and the solvent decanted from the gum that formed. The gum was pre-adsorbed onto silica and purified by chromatography on silica gel (40 g column, 5-15% MeOH/DCM) then purified by preparative HPLC (Waters, Acidic (0.1% Formic acid), Acidic, Waters X-Select Prep-C18, 5 µm, 19×50 mm column, 20-50% MeCN in Water) to afford the title compound (40 mg) as a colourless solid.

$^1$H NMR (400 MHz, DMSO-$d_6$) δ 9.43 (s, 1H), 9.05 (s, 1H), 8.80 (s, 1H), 8.30 (d, 1H), 8.11 (d, 1H), 8.07 (d, 1H), 7.97 (d, 1H), 7.87 (d, 1H), 7.82 (s, 1H), 7.75-7.65 (m, 1H), 7.65-7.58 (m, 1H), 7.57 (t, 1H), 7.52 (t, 1H), 7.38 (d, 1H), 7.24 (s, 1H), 6.92 (dd, 1H), 6.68 (d, 1H), 6.57 (dd, 1H), 6.14 (d, 1H), 4.43 (s, 3H), 3.92 (s, 2H), 3.85 (s, 3H), 3.74 (s, 3H), 3.56 (s, 6H), 1.27 (s, 9H). LCMS m/z 740 $(M+H)^+$ $(ES^+)$

Example 68

3-((4-((4-(3-(3-(2-Amino-2-oxoethyl)-5-(tert-butyl)-2-methoxyphenyl)ureido)naphthalen-1-yl)oxy)pyridin-2-yl)amino)-5-methoxy-N-(3-(1-oxidothiomorpholino)propyl)benzamide

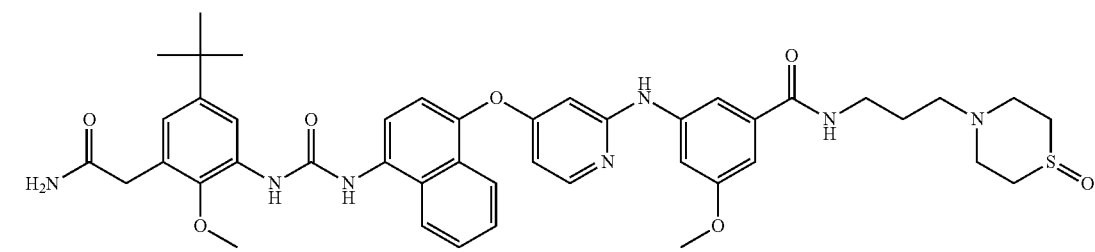 [SMILES: COc1cc(Nc2cc(Oc3ccc(NC(=O)Nc4cc(C(C)(C)C)cc(CC(N)=O)c4OC)c4ccccc34)ccn2)cc(C(=O)NCCCN2CCS(=O)CC2)c1]

(i) 3-((4-((4-((tert-Butoxycarbonyl)amino)naphthalen-1-yl)oxy)pyridin-2-yl)amino)-5-methoxybenzoic acid, lithium salt A solution of LiOH (0.28 g, 11.69 mmol) in water (5 mL) was added to a solution of methyl 3-((4-((4-((tert-butoxycarbonyl)amino)naphthalen-1-yl)oxy)pyridin-2-yl)amino)-5-methoxy-benzoate (see Example 48(i) above; 3 g, 5.82 mmol) in THF (30 mL). The reaction was left stirring for 16 h then a further portion of LiOH (0.28 g, 11.69 mmol) in water (5 mL) was added and stirring continued for 24 h. The reaction mixture was partitioned between water (50 mL) and EtOAc (100 mL). The organic layer was separated, dried (MgSO$_4$), filtered, and the solvent evaporated to afford the title compound (3 g) as a tan solid.

$^1$H NMR (400 MHz, DMSO-d$_6$) δ 9.35 (s, 1H), 8.96 (s, 1H), 8.13 (d, 1H), 8.08 (d, 1H), 7.92-7.76 (m, 1H), 7.72-7.52 (m, 4H), 7.48 (s, 1H), 7.34 (d, 1H), 7.05 (s, 1H), 6.51 (dd, 1H), 6.12 (s, 1H), 3.69 (s, 3H), 1.52 (s, 9H). LCMS m/z 502 (M+H)$^+$ (ES$^+$)

(ii) tert-Butyl (4-((2-((3-methoxy-5-((3-(1-oxidothiomorpholino)propyl)carbamoyl)phenyl)amino)pyridin-4-yl)oxy)naphthalen-1-yl)carbamate HATU (0.5 g, 1.315 mmol) was added to a solution of the product from step (i) above (0.6 g, 1.180 mmol), 4-(3-aminopropyl)thiomorpholine 1-oxide (0.25 g, 1.418 mmol) and Hünig's Base (0.5 mL, 2.86 mmol) in DMF (5 mL) and stirred at rt for 2 h. The mixture was diluted with water (50 mL) then the precipitate was collected by filtration and washed with water (2×3 mL). The filter cake was purified by chromatography on silica gel (12 g column, 2% MeOH:DCM to 10%) to afford the sub-title compound (545 mg) as a tan solid.

$^1$H NMR (400 MHz, DMSO-d$_6$) δ 9.36 (s, 1H), 9.08 (s, 1H), 8.31 (t, 1H), 8.23-8.04 (m, 2H), 7.84 (d, 1H), 7.74-7.52 (m, 4H), 7.49 (s, 1H), 7.35 (d, 1H), 6.86 (s, 1H), 6.58 (dd, 1H), 6.11 (d, 1H), 3.74 (s, 3H), 3.25 (q, 2H), 2.92-2.78 (m, 4H), 2.76-2.57 (m, 4H), 2.41 (t, 2H), 1.67 (p, 2H), 1.53 (s, 9H). LCMS m/z 660 (M+H)$^+$ (ES$^+$)

(iii) 3-((4-((4-Aminonaphthalen-1-yl)oxy)pyridin-2-yl)amino)-5-methoxy-N-(3-(1-oxidothiomorpholino)propyl)benzamide TFA (750 μL, 9.73 mmol) was added to a solution of the product from step (ii) above (545 mg, 0.826 mmol) in DCM (3 mL) and the reaction stirred for 16 h. The solvent was evaporated and the residue dissolved in 5% MeOH:DCM (10 mL) before partitioning with sat. NaHCO$_3$ soln. (10 mL). The organics were separated, dried (MgSO$_4$), filtered and the solvent evaporated to afford the sub-title compound (370 mg).

$^1$H NMR (400 MHz, DMSO-d$_6$) δ 8.98 (s, 1H), 8.31 (s, 1H), 8.20-8.12 (m, 1H), 8.06 (d, 1H), 7.69-7.60 (m, 1H), 7.55 (t, 1H), 7.52-7.39 (m, 3H), 7.10 (d, 1H), 6.84 (dd, 1H), 6.71 (d, 1H), 6.52 (dd, 1H), 6.06 (d, 1H), 5.82 (s, 2H), 3.73 (s, 3H), 3.25 (q, 2H), 2.95-2.77 (m, 4H), 2.78-2.56 (m, 4H), 2.48-2.35 (m, 2H), 1.68 (s, 2H). LCMS m/z 560 (M+H)$^+$ (ES$^+$)

(iv) 3-((4-((4-(3-(3-(2-Amino-2-oxoethyl)-5-(tert-butyl)-2-methoxyphenyl)ureido)naphthalen-1-yl)oxy)pyridin-2-yl)amino)-5-methoxy-N-(3-(1-oxidothiomorpholino)propyl)benzamide A solution of phenyl (3-(2-amino-2-oxoethyl)-5-(tert-butyl)-2-methoxyphenyl)carbamate (see Example 13(vi) above; 80 mg, 0.224 mmol), the product from step (iii) above (100 mg, 0.179 mmol) and TEA (5 μL, 0.036 mmol) in THF (2 mL) was heated at 65° C. (block temperature) for 4 days. The solvent was evaporated and the crude product was purified by chromatography on silica gel (12 g column, 5% MeOH:DCM to 20%) to afford the title compound (85 mg) as a colourless solid.

$^1$H NMR (400 MHz, DMSO-d$_6$) δ 9.39 (s, 1H), 9.06 (s, 1H), 8.79 (s, 1H), 8.38-8.27 (m, 2H), 8.21 (d, 1H), 8.12 (d, 1H), 8.11 (s, 1H), 7.87 (d, 1H), 7.75-7.66 (m, 1H), 7.65-7.58 (m, 1H), 7.56 (t, 1H), 7.49 (t, 1H), 7.45 (s, 1H), 7.38 (d, 1H), 7.00-6.90 (m, 2H), 6.86 (dd, 1H), 6.58 (dd, 1H), 6.13 (d, 1H), 3.78 (s, 3H), 3.75 (s, 3H), 3.46 (s, 2H), 3.25 (q, 2H), 2.93-2.78 (m, 4H), 2.76-2.56 (m, 4H), 2.41 (t, 2H), 1.67 (p, 2H), 1.27 (s, 9H). LCMS m/z 822 (M+H)$^+$ (ES$^+$); 820 (M−H)$^−$ (ES$^−$)

Example 69

3-((4-((4-(3-(5-(tert-Butyl)-2-methoxy-3-(methylsulfinyl)phenyl)ureido)naphthalen-1-yl)oxy)pyridin-2-yl)amino)-5-methoxy-N-(2-(1-oxidothiomorpholino)ethyl)benzamide

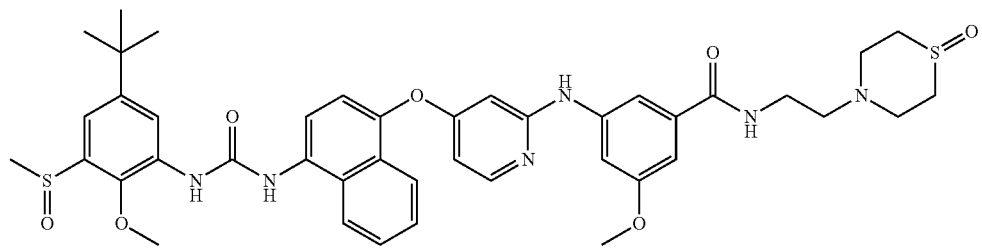 [SMILES: COc1cc(Nc2cc(Oc3ccc(NC(=O)Nc4cc(C(C)(C)C)cc(S(C)=O)c4OC)c4ccccc34)ccn2)cc(C(=O)NCCN2CCS(=O)CC2)c1]

(i) tert-Butyl (4-((2-((3-methoxy-5-((2-(1-oxidothiomorpholino)ethyl)carbamoyl)phenyl)-amino)pyridin-4-yl)oxy)naphthalen-1-yl)carbamate HATU (2 g, 5.26 mmol) was added to a solution of 3-((4-((4-((tert-butoxycarbonyl)amino)naphthalen-1-yl)oxy)pyridin-2-yl)amino)-5-methoxybenzoic acid, lithium salt (see Example 68(i) above; 2 g, 3.93 mmol), 4-(2-aminoethyl)thiomorpholine 1-oxide (0.8 g, 4.93 mmol) and Hünig's Base (1.2 mL, 6.87 mmol) in DMF (20 mL) and stirred at rt for 2 h. The mixture was diluted with water (200 mL) then the precipitate was collected by filtration and washed with water (2×100 mL). The filter cake was preabsorbed onto silica (10 g) and purified by chromatography on silica gel (80 g column, 2% MeOH:DCM to 10%) to afford the sub-title compound (2.45 g) as a tan solid.

$^1$H NMR (400 MHz, DMSO-$d_6$) δ 9.36 (s, 1H), 9.08 (s, 1H), 8.24 (t, 1H), 8.18-8.08 (m, 2H), 7.88-7.80 (m, 1H), 7.68-7.54 (m, 4H), 7.51 (t, 1H), 7.36 (d, 1H), 6.86 (dd, 1H), 6.58 (dd, 1H), 6.11 (d, 1H), 3.75 (s, 3H), 3.41-3.34 (m, 2H), 2.99-2.79 (m, 4H), 2.76-2.64 (m, 4H), 2.54 (t, 2H), 1.53 (s, 9H). LCMS m/z 646 (M+H)$^+$ (ES$^+$)

(ii) 3-((4-((4-Aminonaphthalen-1-yl)oxy)pyridin-2-yl)amino)-5-methoxy-N-(2-(1-oxidothiomorpholino)ethyl)benzamide TFA (2 mL, 26.0 mmol) was added to a solution of the product from step (i) above (2.4 g, 3.72 mmol) in DCM (20 mL) and the reaction stirred for 16 h. The solvent was evaporated and the residue dissolved in 5% MeOH:DCM (100 mL) before partitioning with sat. NaHCO$_3$ soln. (50 mL). The organics were separated, dried (MgSO$_4$), filtered and solvent evaporated to afford the sub-title compound (1.8 g) as a tan foam.

$^1$H NMR (400 MHz, DMSO-$d_6$) δ 8.99 (s, 1H), 8.23 (t, 1H), 8.20-8.11 (m, 1H), 8.06 (d, 1H), 7.70-7.59 (m, 1H), 7.55 (t, 1H), 7.49 (t, 1H), 7.48-7.41 (m, 2H), 7.10 (d, 1H), 6.84 (dd, 1H), 6.71 (d, 1H), 6.52 (dd, 1H), 6.06 (d, 1H), 5.82 (s, 2H), 3.73 (s, 3H), 3.42-3.34 (m, 2H), 3.04-2.80 (m, 4H), 2.79-2.61 (m, 4H), 2.60-2.52 (m, 2H). LCMS m/z 546 (M+H)$^+$ (ES$^+$); 544 (M−H)$^-$ (ES$^-$)

(iii) 3-((4-((4-(3-(5-(tert-Butyl)-2-methoxy-3-(methylsulfinyl)phenyl)ureido)naphthalen-1-yl)oxy)pyridin-2-yl)amino)-5-methoxy-N-(2-(1-oxidothiomorpholino)ethyl)benzamide A solution of phenyl (5-(tert-butyl)-2-methoxy-3-(methylsulfinyl)phenyl)carbamate (see Example 12(iv) above; 80 mg, 0.221 mmol) and the product from step (ii) above (100 mg, 0.183 mmol) and TEA (5 µL, 0.036 mmol) in THF (2 mL) was heated at 65° C. (block temperature) for 4 days. The solvent was evaporated and the crude product was purified by chromatography on silica gel (12 g column, 5% MeOH:DCM to 20%) to afford the title compound (120 mg) as a colourless solid.

$^1$H NMR (400 MHz, DMSO-$d_6$) δ 9.42 (d, 1H), 9.07 (s, 1H), 8.96 (s, 1H), 8.55-8.45 (m, 1H), 8.34-8.19 (m, 2H), 8.16-8.04 (m, 2H), 7.88 (d, 1H), 7.76-7.67 (m, 1H), 7.67-7.59 (m, 1H), 7.58-7.48 (m, 2H), 7.40 (d, 1H), 7.37 (d, 1H), 6.86 (s, 1H), 6.58 (dd, 1H), 6.14 (d, 1H), 3.87 (d, 3H), 3.75 (s, 3H), 3.00-2.82 (m, 4H), 2.79 (s, 3H), 2.76-2.63 (m, 4H), 2.59-2.53 (m, 2H), 1.32 (s, 9H) (CH$_2$ under water peak 3.32 ppm). LCMS m/z 813 (M+H)$^+$ (ES$^+$); 811 (M−H)$^-$ (ES$^-$)

Example 70

4-((4-((4-(3-(3-(2-Amino-2-oxoethyl)-5-(tert-butyl)-2-methoxyphenyl)ureido)naphthalen-1-yl)oxy)pyridin-2-yl)amino)-2-methoxy-N-(2-morpholinoethyl)benzamide

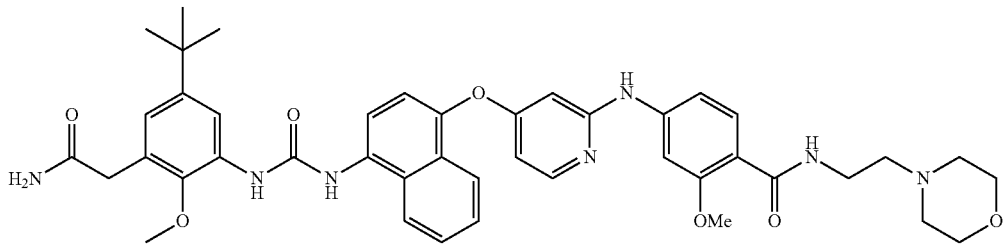 [SMILES: COc1cc(Nc2cc(Oc3ccc(NC(=O)Nc4cc(C(C)(C)C)cc(CC(N)=O)c4OC)c4ccccc34)ccn2)ccc1C(=O)NCCN1CCOCC1]

(i) Methyl 4-((4-((4-((tert-butoxycarbonyl)amino)naphthalen-1-yl)oxy)pyridin-2-yl)amino)-2-methoxybenzoate A suspension of tert-butyl (4-((2-chloropyridin-4-yl)oxy)naphthalen-1-yl)carbamate (see Example 2(ii) above; 2.8 g, 7.55 mmol), methyl 4-amino-2-methoxybenzoate (1.4 g, 7.73 mmol), BINAP (375 mg, 0.602 mmol) and cesium carbonate (4.90 g, 15.03 mmol) in 1,4-dioxane (45 mL) was degassed with nitrogen for 10 minutes. Pd$_2$dba$_3$ (275 mg, 0.300 mmol) was added and the mixture was heated to 9° C. overnight. The mixture was diluted with diethyl ether (60 mL) and filtered through Celite. The filtrate was then washed with water (2×100 mL), and saturated brine (50 mL). The organic phase was dried (MgSO$_4$), filtered and concentrated under reduced pressure to yield the crude product as an orange foam which was purified by chromatography on the Companion (80 g column, 20-50% EtOAc in hexane) to afford the sub-title compound (3.05 g) as a yellow foam.

$^1$H NMR (400 MHz, DMSO-$d_6$) δ: 9.38 (s, 1H), 9.36 (s, 1H), 8.18 (d, 1H), 8.14 (d, 1H), 7.83 (d, 1H), 7.54-7.66 (m, 5H), 7.37 (d, 1H), 7.22 (dd, 1H), 6.69 (dd, 1H), 6.15 (d, 1H), 3.74 (s, 3H), 3.71 (s, 3H), 1.53 (s, 9H). LCMS m/z 516 (M+H)$^+$ (ES$^+$)

(ii) 4-((4-((4-((tert-Butoxycarbonyl)amino)naphthalen-1-yl)oxy)pyridin-2-yl)amino)-2-methoxybenzoic acid, HCl To a stirred solution of the product from step (i) above (2.3 g, 4.46 mmol) in THF (20 mL) was added NaOH (2M aq.) (20 mL, 40.0 mmol). MeOH (4 mL) was added and stirring continued overnight. The reaction was concentrated in vacuo affording a tan gum. The material was suspended in water and acidified with 1M HCl causing a brown solid to precipitate. The solid was collected by filtration and dried at 40° C. under vacuum to afford the sub-title compound (1.29 g) as a brown solid.

LCMS m/z 502 (M+H)$^+$ (ES$^+$)

(iii) tert-Butyl (4-((2-((3-methoxy-4-((2-morpholinoethyl)carbamoyl)phenyl)amino)pyridin-4-yl)oxy)naphthalen-1-yl)carbamate Et$_3$N (1 mL, 7.17 mmol) was added to a stirred mixture of the product from step (ii) above (1.29 g, 2.398 mmol) and HATU (1.094 g, 2.88 mmol) in DMF (10 mL) under an atmosphere of nitrogen. The mixture was stirred for 3 minutes then 2-morpholinoethanamine (0.405 mL, 3.09 mmol) was added. After 2 hours the majority of the solvents were removed in vacuo then the residue was dissolved in EtOAc (50 mL), washed with saturated NaHCO$_3$ (20 mL), followed by brine (20 mL), dried (MgSO$_4$), filtered then reduced in vacuo to leave a brown foam. The crude product was purified by chromatography on the Companion (40 g column, 0-10% methanol in DCM) to afford the sub-title compound (1.15 g) as a flocculent off-white powder.

LCMS m/z 307 (M+2H)$^{2+}$ (ES$^+$)

(iv) 4-((4-((4-Aminonaphthalen-1-yl)oxy)pyridin-2-yl)amino)-2-methoxy-N-(2-morpholinoethyl)benzamide TFA (5 mL, 64.9 mmol) was added to a solution of the product from step (iii) above (1.15 g, 1.874 mmol) in DCM (100 mL) and stirred at rt for 1 h. The volatiles were removed under reduced pressure and the residue was redissolved in DCM (50 mL). The solution was washed with saturated NaHCO$_3$ solution (20 mL). The two layers were separated via a hydrophobic phase separator. The organic layer was concentrated in vacuo to afford the sub-title compound (921 mg) as a pale pink solid.

$^1$H NMR (400 MHz, DMSO-d$_6$) δ 9.18 (s, 1H), 8.19-8.15 (m, 2H), 8.11 (d, 1H), 7.75 (d, 1H), 7.65-7.61 (m, 1H), 7.56 (s, 1H), 7.46-7.43 (m, 2H), 7.27-7.14 (m, 1H), 7.10 (d, 1H), 6.71 (d, 1H), 6.59 (dd, 1H), 6.08 (d, 1H), 5.83 (bs, 2H), 3.85 (s, 3H), 3.60 (bs, 4H), 3.38 (bs, 2H), 2.50-2.41 (m, 4H) (2H proton under DMSO peak). LCMS m/z 257 (M+2H)$^{2+}$ (ES$^+$)

(v) 4-((4-((4-(3-(3-(2-Amino-2-oxoethyl)-5-(tert-butyl)-2-methoxyphenyl)ureido)naphthalen-1-yl)oxy)pyridin-2-yl)amino)-2-methoxy-N-(2-morpholinoethyl)benzamide Triethylamine (7.15 µL, 0.051 mmol) was added to a mixture of phenyl (3-(2-amino-2-oxoethyl)-5-(tert-butyl)-2-methoxyphenyl)carbamate (see Example 13(vi) above; 91 mg, 0.254 mmol) and the product from step (iv) above (150 mg, 0.254 mmol) in isopropyl acetate (5 mL) and the mixture heated at 70° C. (block temperature) overnight (17 hours). A second aliquot of triethylamine (7.15 µL, 0.051 mmol) was added, and the reaction was heated at 70° C. for 24 hours. The reaction mixture was concentrated in vacuo. The crude product was purified by chromatography on the Companion (12 g column, 0.5-2% MeOH in DCM, flushed with 20% MeOH in DCM) to afford a tan powder. The crude product was purified by preparative HPLC (Gilson, Basic (0.1% Ammonium Bicarbonate), Basic, Waters X-Bridge Prep-C18, 5 µm, 19×50 mm column, 25-70% MeCN in Water) to afford the title compound (40 mg) as a light colourless powder.

$^1$H NMR (DMSO-d$_6$, 400 MHz) δ 9.39 (s, 1H), 9.25 (s, 1H), 8.79 (s, 1H), 8.30 (d, 1H), 8.20-8.18 (m, 2H), 8.16 (d, 1H), 8.12 (d, 1H), 7.86 (d, 1H), 7.76 (d, 1H), 7.70 (ddd, 1H), 7.60 (ddd, 1H), 7.57 (d, 1H), 7.44 (bs, 1H), 7.39 (d, 1H), 7.22 (dd, 1H), 6.93 (d, 2H), 6.65 (dd, 1H), 6.14 (d, 1H), 3.87 (s, 3H), 3.77 (s, 3H), 3.60 (t, 4H), 3.45 (s, 2H), 3.40-3.35 (m, 2H), 2.47-2.41 (m, 6H), 1.26 (s, 9H). LCMS m/z 776 (M+H)$^+$ (ES$^+$); 774 (M−H)$^-$ (ES$^-$)

Example 71

3-((4-((4-(3-(3-(Acetamidomethyl)-5-(tert-butyl)-2-methoxyphenyl)ureido)naphthalen-1-yl)oxy)pyridin-2-yl)amino)-5-methoxy-N-(2-(1-oxidothiomorpholino)ethyl)benzamide

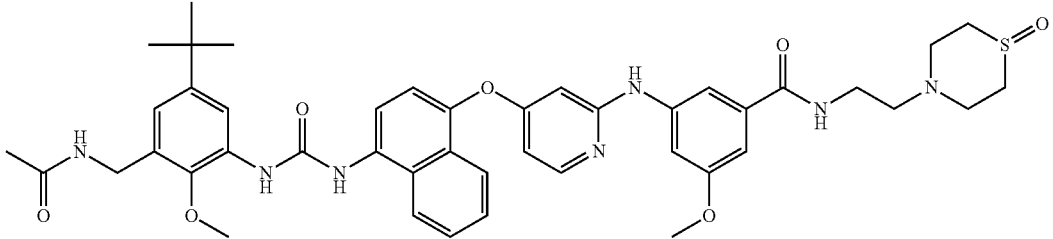 [SMILES: COc1cc(Nc2cc(Oc3ccc(NC(=O)Nc4cc(C(C)(C)C)cc(CNC(C)=O)c4OC)c4ccccc34)ccn2)cc(C(=O)NCCN2CCS(=O)CC2)c1]

A solution of phenyl (3-(acetamidomethyl)-5-(tert-butyl)-2-methoxyphenyl)carbamate (see Example 35(v) above; 85 mg, 0.229 mmol) and 3-((4-((4-aminonaphthalen-1-yl)oxy)pyridin-2-yl)amino)-5-methoxy-N-(2-(1-oxidothiomorpholino)ethyl)benzamide (see Example 69(ii) above; 100 mg, 0.183 mmol) and TEA (5 µL, 0.036 mmol) in THF (2 mL) was heated at 65° C. (block temperature) for 4 days. The solvent was evaporated and the crude product was purified by chromatography on silica gel (12 g column, 5% MeOH:DCM to 20%) to a tan solid which was further purified by preparative HPLC (Varian, Basic (0.1% Ammonium Bicarbonate), Basic, Waters X-Bridge Prep-C18, 5 µm, 19×50 mm column, 20-50% MeCN in Water) to afford the title compound (70 mg) as a colourless solid.

$^1$H NMR (400 MHz, DMSO-d$_6$) δ 9.42 (s, 1H), 9.07 (s, 1H), 8.83 (s, 1H), 8.39-8.18 (m, 4H), 8.19-8.03 (m, 2H), 7.87 (d, 1H), 7.78-7.67 (m, 1H), 7.65-7.58 (m, 1H), 7.56 (t, 1H), 7.50 (t, 1H), 7.39 (d, 1H), 6.95 (d, 1H), 6.86 (dd, 1H), 6.58 (dd, 1H), 6.13 (d, 1H), 4.33 (d, 2H), 3.78 (s, 3H), 3.74 (s, 3H), 3.02-2.79 (m, 4H), 2.77-2.60 (m, 4H), 2.59-2.52 (m, 2H), 1.90 (s, 3H), 1.27 (s, 9H). (CH$_2$ under water peak at 3.32 ppm). LCMS m/z 822 (M+H)$^+$ (ES$^+$); 820 (M−H)$^-$ (ES$^-$)

Example 72

4-((4-((4-(3-(5-(tert-Butyl)-2-methoxy-3-(methylsulfinyl)phenyl)ureido)naphthalen-1-yl)oxy)pyridin-2-yl)amino)-2-methoxy-N-(2-morpholinoethyl)benzamide

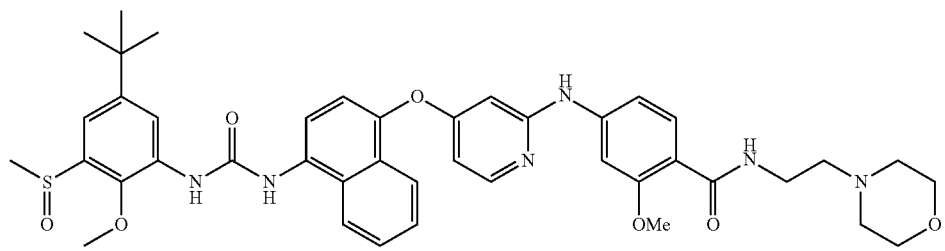 [SMILES: COc1cc(Nc2cc(Oc3ccc(NC(=O)Nc4cc(C(C)(C)C)cc(S(C)=O)c4OC)c4ccccc34)ccn2)ccc1C(=O)NCCN1CCOCC1]

Triethylamine (7.15 µL, 0.051 mmol) was added to a mixture of phenyl (5-(tert-butyl)-2-methoxy-3-(methylsulfinyl)phenyl)carbamate (see Example 12(iv) above; 92 mg, 0.254 mmol) and 4-((4-((4-aminonaphthalen-1-yl)oxy)pyridin-2-yl)amino)-2-methoxy-N-(2-morpholinoethyl)benzamide (see Example 70(iv) above; 150 mg, 0.254 mmol) in isopropyl acetate (5 mL) and the mixture heated at 70° C. (block temperature) overnight (17 hours). The reaction mixture was concentrated in vacuo. The crude product was purified by chromatography on the Companion (12 g column, 0.5-10% MeOH in DCM) then purified by preparative HPLC (Gilson, Basic (0.1% Ammonium Bicarbonate), Basic, Waters X-Bridge Prep-C18, 5 µm, 19×50 mm column, 35-60% MeCN in Water) to afford the title compound (30 mg) as a tan powder.

$^1$H NMR (400 MHz, DMSO-$d_6$) δ 9.42 (s, 1H), 9.27 (s, 1H), 8.97 (s, 1H), 8.50 (d, 1H), 8.28 (d, 1H), 8.21-8.20 (m, 1H), 8.16 (d, 1H), 8.11 (d, 1H), 7.86 (d, 1H), 7.74 (d, 1H), 7.72-7.70 (m, 1H), 7.63-7.57 (m, 2H), 7.40 (d, 1H), 7.35 (d, 1H), 7.22 (d, 1H), 6.65 (dd, 1H), 6.14 (d, 1H), 3.86 (2×s, 6H), 3.61-3.62 (m, 4H), 3.38-3.36 (m, 2H), 2.78 (s, 3H), 2.45-2.41 (m, 6H), 1.31 (s, 9H). LCMS m/z 781 (M+H)$^+$ (ES$^+$); 779 (M−H)$^-$ (ES$^-$)

Example 73

4-((4-((4-(3-(3-(2-Amino-2-oxoethyl)-5-(tert-butyl)-2-methoxyphenyl)ureido)naphthalen-1-yl)oxy)pyridin-2-yl)amino)-N-(3-hydroxy-2,2-bis(hydroxymethyl)propyl)-2-methoxybenzamide

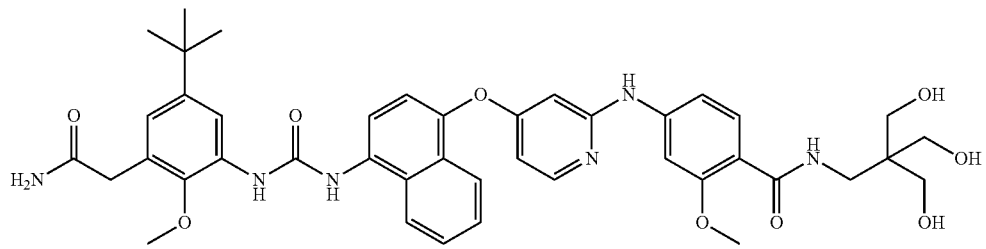 [SMILES: COc1cc(Nc2cc(Oc3ccc(NC(=O)Nc4cc(C(C)(C)C)cc(CC(N)=O)c4OC)c4ccccc34)ccn2)ccc1C(=O)NCC(CO)(CO)CO]

(i) Methyl 4-((4-((4-aminonaphthalen-1-yl)oxy)pyridin-2-yl)amino)-2-methoxybenzoate TFA (7 mL, 91 mmol) was added to a solution of methyl 4-((4-((4-((tert-butoxycarbonyl)-amino)naphthalen-1-yl)oxy)pyridin-2-yl)amino)-2-methoxybenzoate (see Example 70(i) above; 2.34 g, 4.08 mmol, 90% purity) in DCM (50 mL) and the reaction stirred for 2 h. The solvents were evaporated and the residue partitioned between sat NaHCO$_3$ soln. (100 mL) and DCM (60 mL). The organics were separated, dried (MgSO$_4$), filtered and the solvent evaporated to afford the sub-title compound (1.5 g) as a pale brown foam.

LCMS m/z 416 (M+H)$^+$ (ES$^+$)

(ii) Methyl 4-((4-((4-(3-(3-(2-amino-2-oxoethyl)-5-(tert-butyl)-2-methoxyphenyl)ureido)-naphthalen-1-yl)oxy)pyridin-2-yl)amino)-2-methoxybenzoate A mixture of phenyl (3-(2-amino-2-oxoethyl)-5-(tert-butyl)-2-methoxyphenyl)carbamate (see Example 13(vi) above; 70 mg, 0.196 mmol), the product from step (i) above (82 mg, 0.196 mmol) and Et₃N (10 µL, 0.072 mmol) in THF (3 mL) was heated at 60° C. for 24 h. The solvent was evaporated under reduced pressure and the residue purified by chromatography on silica gel (12 g column, 0-7% MeOH/DCM) to afford the sub-title compound (103 mg) as a foam. LCMS m/z 678 (M+H)⁺ (ES⁺); 676 (M−H)⁻ (ES⁻)

(iii) 4-((4-((4-(3-(3-(2-Amino-2-oxoethyl)-5-(tert-butyl)-2-methoxyphenyl)ureido)naphthalen-1-yl)oxy)pyridin-2-yl)amino)-2-methoxybenzoic acid, HCl A mixture of the product from step (ii) above (100 mg, 0.148 mmol) and LiOH (15 mg, 0.626 mmol) in MeOH (2 mL), water (2 mL) and THF (2 mL) was stirred at rt for 24 h. 1M NaOH (1 mL) was added, stirred for 20 h then evaporated under reduced pressure. The residue was stirred in 1M HCl (6 mL) for 1 h, filtered, washed with water then ether to afford the sub-title compound (82 mg) as a white solid.
LCMS m/z 664 (M+H)⁺ (ES⁺); 662 (M−H)⁻ (ES⁻)

(iv) 4-((4-((4-(3-(3-(2-Amino-2-oxoethyl)-5-(tert-butyl)-2-methoxyphenyl)ureido)naphthalen-1-yl)oxy)pyridin-2-yl)amino)-N-(3-hydroxy-2,2-bis(hydroxymethyl)propyl)-2-methoxybenzamide HATU (50 mg, 0.131 mmol) was added to a mixture of the product from step (iii) above (81 mg, 0.116 mmol), 2-(aminomethyl)-2-(hydroxymethyl)propane-1,3-diol (25 mg, 0.185 mmol) and Hünig's Base (60 µL, 0.344 mmol) in DMF (2 mL) and stirred at it for 20 h. HATU (50 mg, 0.131 mmol) was added, stirred for 3 h then water (8 mL) added. The solid was filtered then purified by preparative HPLC (Varian, Basic (0.1% Ammonium Bicarbonate), Basic, Waters X-Bridge Prep-C18, 5 µm, 19×50 mm column, 20-50% MeCN in Water) to afford the title compound (16 mg) as a solid.
¹H NMR (400 MHz, DMSO-d₆) δ 9.42 (s, 1H), 9.28 (s, 1H), 8.82 (s, 1H), 8.50 (t, 1H), 8.32 (d, 1H), 8.21 (d, 1H), 8.17 (d, 1H), 8.13 (d, 1H), 7.86 (d, 1H), 7.77 (d, 1H), 7.73-7.69 (m, 1H), 7.63-7.59 (m, 2H), 7.48 (s, 1H), 7.40 (d, 1H), 7.22 (dd, 1H), 6.97 (s, 1H), 6.94 (d, 1H), 6.66 (dd, 1H), 6.14 (d, 1H), 4.52 (t, 3H), 3.84 (s, 3H), 3.78 (s, 3H), 3.45 (s, 2H), 3.28 (d, 2H), 1.27 (s, 9H). 6H under H₂O peak. LCMS m/z 781 (M+H)⁺ (ES⁺); 779 (M−H)⁻ (ES⁻)

Example 74

1-(5-(tert-Butyl)-2-methoxy-3-(methylsulfinyl)phenyl)-3-(4-((2-((7-methyl-1H-indazol-5-yl)amino)pyrimidin-4-yl)oxy)naphthalen-1-yl)urea

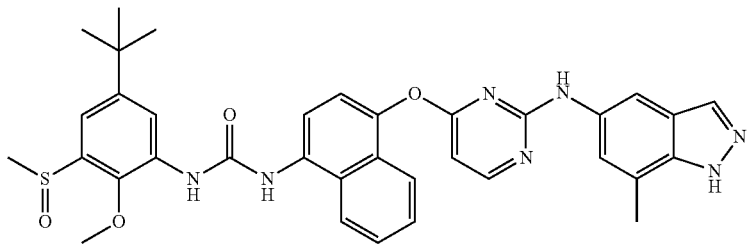 [SMILES: COc1c(NC(=O)Nc2ccc(Oc3ccnc(Nc4cc(C)c5[nH]ncc5c4)n3)c3ccccc23)cc(C(C)(C)C)cc1S(C)=O]

Triethylamine (8 µL, 0.057 mmol) was added to a solution of phenyl (5-(tert-butyl)-2-methoxy-3-(methylsulfinyl)phenyl)carbamate (see Example 12(iv) above; 105 mg, 0.290 mmol) and N-(4-((4-aminonaphthalen-1-yl)oxy)pyrimidin-2-yl)-7-methyl-1H-indazol-5-amine (see WO 2014/033448; 100 mg, 0.261 mmol) in iPrOAc (4 mL) at 70° C. (block temperature) and the mixture stirred for 24 h. The reaction was cooled to rt and the resulting suspended solid collected by filtration. The crude product was purified by chromatography on the Companion (12 g column, 2-5% MeOH in DCM) to afford the title compound (54 mg) as a pale pink solid.
¹H NMR (400 MHz, DMSO-de) δ: 12.84 (s, 1H), 9.49 (bs, 2H), 9.06 (s, 1H), 8.52 (d, 1H), 8.40 (d, 1H), 8.33 (d, 1H), 8.22 (d, 1H), 7.86 (d, 1H), 7.56-7.70 (m, 3H), 7.46 (d, 1H), 7.38 (d, 1H), 7.38 (bs, 1H), 7.01 (s, 1H), 6.61 (d, 1H), 3.90 (s, 3H), 2.81 (s, 3H), 2.29 (s, 3H), 1.33 (s, 9H). LCMS m/z 650 (M+H)⁺ (ES⁺)

Example 75

3-((4-((4-(3-(5-(tert-Butyl)-3-(dimethylphosphoryl)-2-methoxyphenyl)ureido)naphthalen-1-yl)oxy)pyridin-2-yl)amino)-5-methoxy-N-methyl-N-(2-morpholinoethyl)benzenesulfonamide

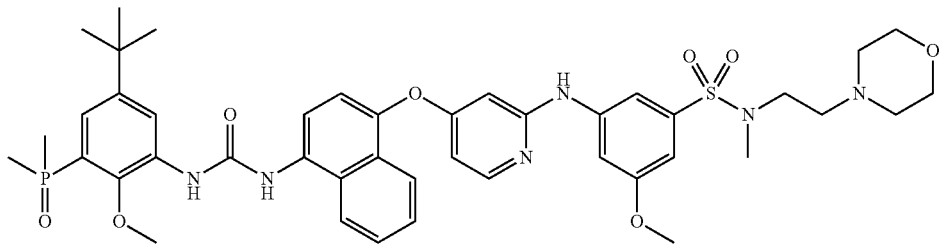 [SMILES: COc1cc(Nc2cc(Oc3ccc(NC(=O)Nc4cc(C(C)(C)C)cc(P(C)(C)=O)c4OC)c4ccccc34)ccn2)cc(S(=O)(=O)N(C)CCN2CCOCC2)c1]

(i) 3-Methoxy-N-methyl-N-(2-morpholinoethyl)-5-nitrobenzenesulfonamide

A solution of 3-methoxy-5-nitrobenzene-1-sulfonyl chloride (300 mg, 1.192 mmol) in MeCN (3 mL) was added dropwise to stirring ice cold solution of N-methyl-2-morpholinoethanamine (172 mg, 1.192 mmol) and triethylamine (500 µL, 3.59 mmol) in MeCN (3 mL). The reaction was stirred for 5 mins then warmed to rt and stirred for 1 h. The reaction was concentrated in vacuo. The residue was slurried in EtOAc (15 mL) and the resulting suspension filtered. The filter cake was washed with EtOAc (5 mL) and the filtrate concentrated in vacuo affording a brown oil. The crude product was purified by chromatography on the Companion (40 g column, 0.5-2.5% MeOH in DCM) to afford the sub-title compound (268 mg) as a yellow oil.

LCMS m/z 360 (M+H)$^+$ (ES$^+$)

(ii) 3-Amino-5-methoxy-N-methyl-N-(2-morpholinoethyl)benzenesulfonamide

5% Pd/C (50% paste with water) (150 mg) was added to a degassed solution of the product from step (i) above (268 mg, 0.746 mmol) in MeOH (8 mL). The reaction was degassed with $H_2$ and stirred under a $H_2$ atmosphere for 2 h. The reaction mixture was filtered through Celite and the filtrate concentrated in vacuo to afford the sub-title compound (251 mg) as a colourless oil.

LCMS m/z 330 (M+H)$^+$ (ES$^+$)

(iii) 1-(5-(tert-Butyl)-3-(dimethylphosphoryl)-2-methoxyphenyl)-3-(4-((2-chloropyridin-4-yl)oxy)naphthalen-1-yl)urea Triethylamine (90 µL, 0.646 mmol) was added to a solution of phenyl (5-(tert-butyl)-3-(dimethylphosphoryl)-2-methoxyphenyl)carbamate (see Example 3(vi) above; 1.30 g, 3.46 mmol) and 4-((2-chloropyridin-4-yl)oxy)naphthalen-1-amine (see Example 2(i) above; 830 mg, 3.07 mmol) in iPrOAc (40 mL) at 70° C. (block temperature) and the mixture stirred for 24 h. An additional 500 mg of phenyl carbamate was added and stirring continued overnight. The reaction was cooled to it and concentrated in vacuo. The crude product was purified by chromatography on the Companion (80 g column, 2-7% MeOH in DCM) to afford the sub-title compound (1.38 g) as a pink foam.

LCMS m/z 277 (M+2H)$^{2+}$ (ES$^+$)

(iv) 3-((4-((4-(3-(5-(tert-Butyl)-3-(dimethylphosphoryl)-2-methoxyphenyl)ureido)naphthalen-1-yl)oxy)pyridin-2-yl)amino)-5-methoxy-N-methyl-N-(2-morpholinoethyl)benzenesulfonamide A mixture of the product from step (ii) above (125 mg, 0.379 mmol), the product from step (iii) above (200 mg, 0.362 mmol), $K_2CO_3$ (150 mg, 1.085 mmol), and BrettPhos G1 precatalyst (15 mg, 0.019 mmol) were degassed under vacuum, back filling with nitrogen 3 times. DMF (2 mL) was added and the suspension degassed under vacuum back filling with nitrogen 3 times. The reaction was then heated under nitrogen at 85° C. (block temperature) for 2 h. The reaction was cooled and quenched with water affording a beige suspension. The solid was recovered by filtration, washing with more water, then dried in vacuo. The crude product was purified by chromatography on the Companion (12 g column, 2-8% MeOH in DCM) to afford a pale beige solid which was triturated in $Et_2O$ (5 mL) then recovered by filtration, washing with more $Et_2O$. The solid was purified by preparative HPLC (Gilson, Acidic (0.1% Formic acid), Acidic, Waters X-Select Prep-C18, 5 µm, 19×50 mm column, 20-50% MeCN in Water) to afford a white foam. The material was partitioned between DCM and $NaHCO_3$ solution. The organic phase was dried via hydrophobic frit then concentrated in vacuo. The residue was re-concentrated in vacuo from MeCN then dried at 40° C. under vacuum. The crude product was purified by preparative HPLC (Varian, Basic (0.1% Ammonium Bicarbonate), Basic, Waters X-Bridge Prep-C18, 5 µm, 19×50 mm column, 25-70% MeCN in Water) to afford the title compound (33 mg) as a white solid.

$^1$H NMR (400 MHz, DMSO-d$_6$) δ: 9.38 (s, 1H), 9.30 (s, 1H), 8.94 (s, 1H), 8.4 (d, 1H), 8.30 (d, 1H), 8.15 (s, 1H), 8.14 (d, 1H), 7.86 (d, 1H), 7.72 (t, 1H), 7.61-7.67 (m, 3H), 7.41 (d, 1H), 7.36 (dd, 1H), 6.71 (t, 1H), 6.66 (dd, 1H), 6.09 (d, 1H), 3.90 (s, 3H), 3.77 (s, 3H), 3.51-3.53 (m, 4H), 3.07 (t, 2H), 2.72 (s, 3H), 2.42 (t, 2H), 2.34 (bs, 4H), 1.75 (d, 6H), 1.30 (s, 9H).

LCMS m/z 845 (M+H)$^+$ (ES$^+$)

Example 76

4-((4-((4-(3-(5-(tert-Butyl)-3-(dimethylphosphoryl)-2-methoxyphenyl)ureido)naphthalen-1-yl)oxy)pyridin-2-yl)amino)-2-methoxybenzoic acid

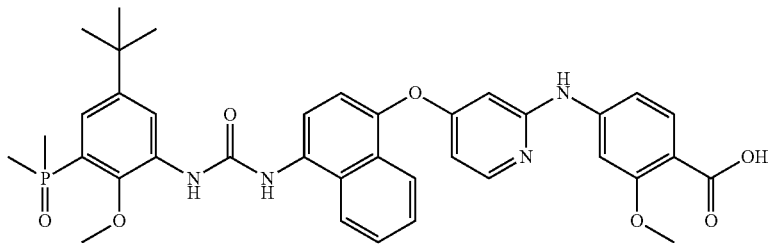 [SMILES: COc1cc(Nc2cc(Oc3ccc(NC(=O)Nc4cc(C(C)(C)C)cc(P(C)(C)=O)c4OC)c4ccccc34)ccn2)ccc1C(=O)O]

(i) Methyl 4-((4-((4-(3-(5-(tert-butyl)-3-(dimethylphosphoryl)-2-methoxyphenyl)ureido) naphthalen-1-yl)oxy)pyridin-2-yl)amino)-2-methoxybenzoate A mixture of methyl 4-amino-2-methoxybenzoate (200 mg, 1.104 mmol), 1-(5-(tert-butyl)-3-(dimethylphosphoryl)-2-methoxyphenyl)-3-(4-((2-chloropyridin-4-yl)oxy)naphthalen-1-yl)urea (see Example 75(iii) above; 600 mg, 1.087 mmol), $K_2CO_3$ (450 mg, 3.26 mmol), and BrettPhos G1 precatalyst (45 mg, 0.056 mmol) were degassed under vacuum, back filling with nitrogen 3 times. DMF (5 mL) was added and the suspension degassed under vacuum back filling with nitrogen 3 times. The reaction was then heated under nitrogen at 75° C. (block temperature) for 2 h. The reaction was cooled and partitioned between EtOAc and water. The biphasic mixture was filtered. The organic component of the filtrate was dried ($MgSO_4$), filtered and concentrated in vacuo onto silica gel. The crude product was purified by chromatography on the Companion (40 g column, 2-10% MeOH in DCM) to afford the sub-title compound (313 mg) as a pale pink glass.
LCMS m/z 349 $(M+2H)^{2+}$ $(ES^+)$ (ii) 4-((4-((4-(3-(5-(tert-Butyl)-3-(dimethylphosphoryl)-2-methoxyphenyl)ureido)naphthalen-1-yl)oxy)pyridin-2-yl)amino)-2-methoxybenzoic acid To a stirred solution of the product from step (i) above (313 mg, 0.449 mmol) in THF (18 mL) was added NaOH (2M aq.) (6.0 mL, 12.00 mmol). MeOH (3 mL) was added and stirring continued over the weekend. The reaction was concentrated in vacuo affording a yellow solid. The material was suspended in water and acidified with 1M HCl causing a pink solid to precipitate. The solid was collected by filtration, washing with water. The wet solid was dissolved in MeCN and concentrated in vacuo. The resulting solid was dried at 40° C. under vacuum to afford 4-((4-((4-(3-(5-(tert-butyl)-3-(dimethylphosphoryl)-2-methoxyphenyl)ureido)-naphthalen-1-yl)oxy)pyridin-2-yl)amino)-2-methoxybenzoic acid, HCl (270 mg) as a beige solid. 40 mg was purified by prep-HPLC (Varian, basic) to afford the title compound (28 mg) as a white solid.

$^1$H NMR (400 MHz, DMSO-$d_6$) δ: 11.75 (bs, 1H), 9.39 (s, 1H), 9.30 (s, 1H), 8.93 (s, 1H), 8.44 (s, 1H), 8.30 (d, 1H), 8.13-8.18 (m, 2H), 7.87 (d, 1H), 7.72 (t, 1H), 7.61-7.64 (m, 2H), 7.50 (s, 1H), 7.41 (d, 1H), 7.37 (d, 1H), 7.22 (d, 1H), 6.67 (d, 1H), 6.17 (s, 1H), 3.91 (s, 3H), 3.74 (s, 3H), 1.76 (d, 6H), 1.31 (s, 9H). LCMS m/z 683 $(M+H)^+$ $(ES^+)$

Example 77

3-((4-((4-(3-(5-(tert-Butyl)-3-((2-(dimethylamino)acetamido)methyl)-2-methoxyphenyl)ureido)naphthalen-1-yl)oxy)pyridin-2-yl)amino)-5-methoxy-N-(2-(2-(2-methoxyethoxy)ethoxy)ethyl)benzamide

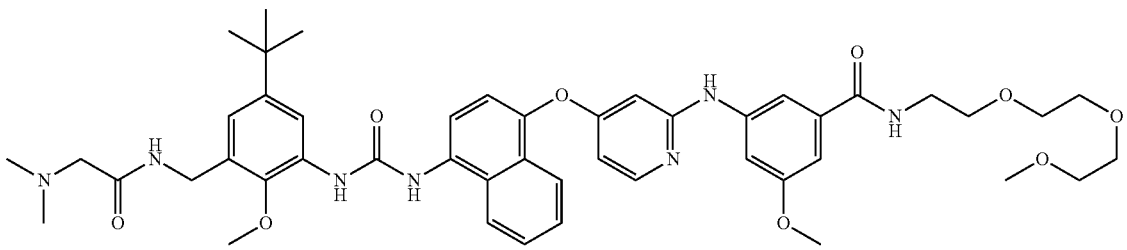 [SMILES: COCCOCCOCCNC(=O)c1cc(Nc2cc(Oc3ccc(NC(=O)Nc4cc(C(C)(C)C)cc(CNC(=O)CN(C)C)c4OC)c4ccccc34)ccn2)cc(OC)c1]

(i) 5-(tert-Butyl)-1-(chloromethyl)-2-methoxy-3-nitrobenzene

Thionyl chloride (2.0 mL, 27.4 mmol) was added carefully to a solution of (5-(tert-butyl)-2-methoxy-3-nitrophenyl)methanol (4.9 g, 20.48 mmol) in DCM (80 mL) at rt. The mixture was stirred for 18 h at rt then diluted with toluene (200 mL) and concentrated under reduced pressure. The residue was purified by chromatography on silica gel (50 g column, 50% $CH_2Cl_2$/isohexane) to afford the sub-title compound (3.96 g) as a yellow oil which crystallised on standing.

$^1$H NMR (400 MHz, $CDCl_3$) δ: 7.84 (d, 1H), 7.69 (d, 1H), 4.70 (s, 2H), 4.00 (s, 3H), 1.37 (s, 9H).

(ii) (5-(tert-Butyl)-2-methoxy-3-nitrophenyl)methan-amine

Sodium azide (0.6 g, 9.23 mmol) was added to a solution of the product from step (i) above (2.5 g, 8.25 mmol) in DMSO (100 mL) at 45° C. and stirring continued for 16 h. The reaction mixture was partitioned with water (500 mL) and Et$_2$O (250 mL). The aqueous was separated and extracted with fresh Et$_2$O (50 mL). The organics were bulked and washed with 20% w/w NaCl soln. (250 mL). The organics were separated and triphenylphosphine (2.6 g, 9.91 mmol) and water (5 mL) added. The mixture was stirred at rt for 2 h. The solvent was evaporated and the crude product was loaded onto a column of SCX (40 g) in MeOH. The column was washed with MeOH and then the product was eluted with 0.7 M ammonia in MeOH. The resultant mixture was concentrated in vacuo to afford the sub-title compound (1.0 g) as a thick yellow oil.

$^1$H NMR (400 MHz, DMSO-d$_6$) δ 7.87 (d, 1H), 7.69 (d, 1H), 3.81 (s, 2H), 3.81 (s, 3H), 1.31 (s, 9H). —NH$_2$ not visible. LCMS m/z 239 (M+H)$^+$ (ES$^+$)

(iii) N-(5-(tert-butyl)-2-methoxy-3-nitrobenzyl)-2-(dimethylamino)acetamide

HATU (1.2 g, 3.16 mmol) was added to a solution of the product from step (ii) above (500 mg, 2.098 mmol), 2-(dimethylamino)acetic acid (260 mg, 2.52 mmol) and Hünig's Base (1 mL, 5.73 mmol) in EtOAc (10 mL). The reaction mixture was stirred at rt for 72 h. The solid was filtered off and the filtrate partitioned with EtOAc (20 mL) and water (50 mL). The organics were separated, dried (MgSO$_4$), filtered and the solvent evaporated to a yellow oil. The crude product was purified by chromatography on silica gel (12 g column, EtOAc:isohexane). The resulting material was purified again by chromatography on silica gel (12 g column, 0.1% 0.88 ammonia in MeCN) to afford the sub-title compound (400 mg) as a thick yellow oil.

$^1$H NMR (400 MHz, DMSO-d$_6$) δ 8.44 (t, 1H), 7.74 (d, 1H), 7.63 (d, 1H), 4.39 (d, 2H), 3.84 (s, 3H), 2.95 (s, 2H), 2.24 (s, 6H), 1.27 (s, 9H). LCMS m/z 324 (M+H)$^+$ (ES$^+$)

(iv) N-(3-amino-5-(tert-butyl)-2-methoxybenzyl)-2-(dimethylamino)acetamide

A solution of the product from step (iii) above (400 mg, 1.237 mmol) and 5% palladium on carbon (50% paste with water) (50 mg, 0.012 mmol) in EtOH (5 mL) was stirred under hydrogen (5 bar) for 2 h. The catalyst was removed by filtration and the filtrate was concentrated under reduced pressure to yield the sub-title compound (310 mg) as a thick grey oil.

$^1$H NMR (400 MHz, DMSO-d$_6$) δ 7.99 (t, 1H), 6.64 (d, 1H), 6.45 (d, 1H), 4.76 (s, 2H), 4.26 (d, 2H), 3.62 (s, 3H), 2.91 (s, 2H), 2.23 (s, 6H), 1.19 (s, 9H)

(v) Phenyl (5-(tert-butyl)-3-((2-(dimethylamino)acetamido)methyl)-2-methoxyphenyl)-carbamate Phenyl chloroformate (130 μL, 1.038 mmol) was added to a mixture of the product from step (iv) above (300 mg, 1.022 mmol) and NaHCO$_3$ (180 mg, 2.143 mmol) in DCM (3 mL) and THF (1 mL) and stirred at rt for 1 h. The reaction was dosed again with phenyl chloroformate (130 μL, 1.038 mmol) and stirred for a further 1 h. The mixture was partitioned between DCM (10 mL) and water (10 mL). The organic layer was separated, dried (MgSO$_4$), filtered and the solvent evaporated to give a brown oil. The crude oil was triturated with cyclohexane to give a brown solid which was filtered and washed with cyclohexane to afford the sub-title compound (180 mg) as white solid.

$^1$H NMR (400 MHz, CDCl$_3$) δ 8.18 (s, 1H), 7.50 (s, 1H), 7.47-7.37 (m, 2H), 7.34-7.16 (m, 4H), 7.03 (d, 1H), 4.58 (d, 2H), 3.87 (s, 3H), 3.10 (s, 2H), 2.37 (s, 6H), 1.31 (s, 9H)

(vi) 3-((4-((4-(3-(5-(tert-Butyl)-3-((2-(dimethylamino)acetamido)methyl)-2-methoxyphenyl)-ureido)naphthalen-1-yl)oxy)pyridin-2-yl)amino)-5-methoxy-N-(2-(2-(2-methoxyethoxy)-ethoxy)ethyl)benzamide A solution of the product from step (v) above (80 mg, 0.193 mmol) and 3-((4-((4-aminonaphthalen-1-yl)oxy)pyridin-2-yl)amino)-5-methoxy-N-(2-(2-(2-methoxyethoxy)ethoxy)-ethyl)benzamide (see Example 48(iv) above; 100 mg, 0.183 mmol) and Et$_3$N (5 μL, 0.036 mmol) in THF (2 mL) was heated at 60° C. (block temperature) for 16 h. The solvent was evaporated and the crude product was purified by chromatography on silica gel (12 g column, 5% MeOH:DCM to 20%) to give a tan solid which was further purified by preparative HPLC (Waters, Acidic (0.1% Formic acid), Acidic, Waters X-Select Prep-C18, 5 μm, 19×50 mm column, 20-50% MeCN in Water) to afford a colourless gum which was partitioned between DCM (5 mL) and sat. NaHCO$_3$ (5 mL). The organics were separated, dried, filtered and the solvent evaporated to give the title compound (35 mg) as a colourless glass.

$^1$H NMR (400 MHz, DMSO-d$_6$) δ 9.41 (s, 1H), 9.06 (s, 1H), 8.83 (s, 1H), 8.40-8.27 (m, 2H), 8.27-8.18 (m, 2H), 8.12 (s, 1H), 8.10 (d, 1H), 7.87 (d, 1H), 7.75-7.66 (m, 1H), 7.66-7.59 (m, 1H), 7.58 (t, 1H), 7.51 (t, 1H), 7.38 (d, 1H), 6.94 (d, 1H), 6.89 (dd, 1H), 6.57 (dd, 1H), 6.14 (d, 1H), 4.39 (d, 2H), 3.81 (s, 3H), 3.75 (s, 3H), 3.55-3.46 (m, 8H), 3.43-3.35 (m, 4H), 3.21 (s, 3H), 2.96 (s, 2H), 2.26 (s, 6H), 1.26 (s, 9H). LCMS m/z 866 (M+H)$^+$ (ES$^+$)

Example 78

3-((4-((4-(3-(5-(tert-Butyl)-3-(dimethylphosphoryl)-2-methoxyphenyl)ureido)naphthalen-1-yl)oxy)pyridin-2-yl)amino)-N-methyl-5-((4-methylpiperazin-1-yl)methyl)benzamide

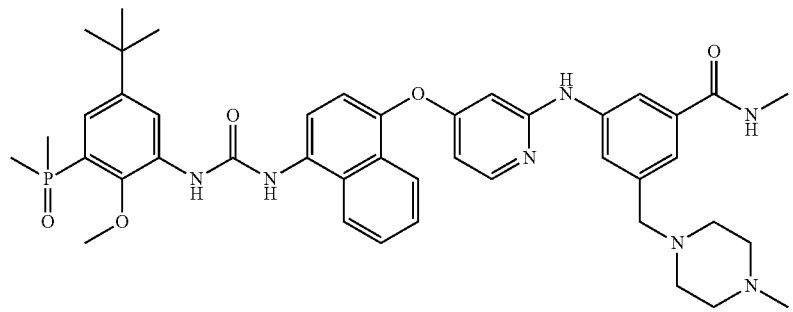

(i) Methyl 3-(hydroxymethyl)-5-nitrobenzoate

BH$_3$-THF (1M in THF) (9 mL, 9.00 mmol) was added over 10 min to a solution of 3-(methoxycarbonyl)-5-nitrobenzoic acid (2.0 g, 8.88 mmol) in THF (20 mL) at rt. The mixture was stirred for 40 h. The reaction was heated to 60° C. and stirring continued for 4 h. Further BH$_3$-THF (1M in THF) (9 mL, 9.00 mmol) was added dropwise over 10 minutes and the resulting solution re-heated to 60° C. for 5 h. The reaction was quenched carefully with MeOH (5 mL), stirring for 2 h, and the mixture partitioned between Et$_2$O (100 mL) and 1 M HCl (50 mL). The organic layer washed with brine (25 mL), dried (MgSO$_4$), filtered and evaporated under reduced pressure affording a yellow oil. The crude product was purified by chromatography on the Companion (80 g column, 0-50% EtOAc/isohexane) to afford the sub-title compound (1.4 g) as a colourless oil which slowly solidified on standing.

$^1$H NMR (400 MHz, DMSO-d$_6$) δ: 8.50 (s, 1H), 8.42 (s, 1H), 8.32 (s, 1H), 5.68 (t, 1H), 4.71 (d, 2H), 3.93 (s, 3H). LCMS m/z 212 (M+H)$^+$ (ES$^+$)

(ii) Methyl 3-(bromomethyl)-5-nitrobenzoate

To a stirred solution of the product from step (i) above (400 mg, 1.894 mmol) in THF (5 mL) at 0° C. was added triphenylphosphine (994 mg, 3.79 mmol). N-Bromosuccinimide (708 mg, 3.98 mmol) was added in portions and the reaction was allowed to warm to rt and stirred overnight. The reaction was diluted with EtOAc (50 mL) and washed with NaHCO$_3$ (50 mL) solution and brine (30 mL), then dried (MgSO$_4$), filtered and concentrated in vacuo affording a dark brown solid. The crude product was purified by chromatography on the Companion (40 g column, 0-25% EtOAc in hexane) to afford the sub-title compound (470 mg) as a white solid.

$^1$H NMR (400 MHz, DMSO-d$_6$) δ: 8.62 (t, 1H), 8.55 (t, 1H), 8.47 (t, 1H), 4.96 (s, 2H), 3.95 (s, 3H).

(iii) Methyl 3-((4-methylpiperazin-1-yl)methyl)-5-nitrobenzoate

To a stirred solution of the product from step (ii) above (470 mg, 1.715 mmol) and Et$_3$N (480 μL, 3.44 mmol) in DCM (15 mL) was added 1-methylpiperazine (285 μL, 2.57 mmol). The reaction was stirred overnight. The reaction was diluted with DCM (15 mL) and washed with sat. aq. NaHCO$_3$ solution (20 mL) and water (20 mL). The organic phase was dried via hydrophobic frit and concentrated in vacuo affording the sub-title compound (400 mg) as a yellow oil.

$^1$H NMR (400 MHz, DMSO-d$_6$) δ: 8.52 (s, 1H), 8.40 (s, 1H), 8.29 (s, 1H), 3.93 (s, 3H), 3.67 (s, 2H), 2.23-2.50 (m, 8H), 2.16 (s, 3H). LCMS m/z 294 (M+H)$^+$ (ES$^+$)

(iv) Methyl 3-amino-5-((4-methylpiperazin-1-yl)methyl)benzoate

The product from step (iii) above (400 mg, 1.364 mmol) was dissolved in EtOH (15 mL) and iron powder (700 mg, 12.53 mmol) was added followed by a solution of NH$_4$Cl (70 mg, 1.309 mmol) in water (5 mL). The resulting suspension was heated at 80° C. for 2 h. The reaction was cooled to rt and filtered through Celite. The filtrate was concentrated in vacuo affording a yellow oil. The material was dissolved in MeOH and loaded onto a pre-conditioned cartridge of SCX resin. The resin was washed with MeOH then the product released in 1% NH$_3$ in MeOH. The NH$_3$ solution was concentrated in vacuo affording the sub-title compound (228 mg) as a colourless oil.

LCMS m/z 264 (M+H)$^+$ (ES$^+$)

(v) Methyl 3-((4-((4-((tert-butoxycarbonyl)amino) naphthalen-1-yl)oxy)pyridin-2-yl)amino)-5-((4-methylpiperazin-1-yl)methyl)benzoate A mixture of the product from step (iv) above (228 mg, 0.866 mmol), tert-butyl (4-((2-chloropyridin-4-yl)oxy)naphthalen-1-yl)carbamate (see Example 2(ii) above; 321 mg, 0.866 mmol), potassium carbonate (320 mg, 2.315 mmol), and BrettPhos G1 precatalyst (14 mg, 0.018 mmol) were degassed under vacuum back filling with nitrogen 3 times. DMF (4 mL) was added and the suspension degassed under vacuum back filling with nitrogen 3 times. The reaction was then heated under nitrogen at 85° C. (block temperature) for 1 h. The reaction was cooled and partitioned between EtOAc (40 mL) and water (100 mL). The organic phase was dried (MgSO$_4$), filtered and concentrated in vacuo affording a dark brown oil. The crude product was purified by chromatography on the Companion (12 g column, 3-10% MeOH in DCM) to afford the sub-title compound (432 mg) as a yellow oil.

LCMS m/z 598 (M+H)$^+$ (ES$^+$)

(vi) Methyl 3-((4-((4-aminonaphthalen-1-yl)oxy) pyridin-2-yl)amino)-5-((4-methylpiperazin-1-yl) methyl)benzoate TFA (1.0 mL, 12.98 mmol) was added to a solution of the product from step (v) above (432 mg, 0.723 mmol) in DCM (10 mL) and the reaction stirred overnight. The solvents were evaporated and the residue partitioned between sat NaHCO$_3$ soln. (40 mL) and DCM (40 mL). The organics were separated, dried (MgSO$_4$), filtered and the solvent evaporated to give the sub-title compound (375 mg) as a brown gum.

$^1$H NMR (400 MHz, DMSO-d$_6$) δ: 9.07 (s, 1H), 8.23 (s, 1H), 8.15-8.17 (m, 1H), 8.07 (d, 1H), 7.71 (s, 1H), 7.63-7.65 (m, 1H), 7.44-7.46 (m, 2H), 7.36 (s, 1H), 7.10 (d, 1H), 6.71 (d, 1H), 6.53 (d, 1H), 6.06 (s, 1H), 5.83 (s, 2H), 3.82 (s, 3H), 3.41 (s, 2H), 2.24-2.42 (m, 8H), 2.14 (s, 3H). LCMS m/z 250 (M+2H)$^{2+}$ (ES$^+$)

(vii) Methyl 3-((4-((4-(3-(5-(tert-butyl)-3-(dimethylphosphoryl)-2-methoxyphenyl)ureido)-naphthalen-1-yl)oxy)pyridin-2-yl)amino)-5-((4-methylpiperazin-1-yl)methyl)benzoate Et$_3$N (30 μL, 0.215 mmol) was added to a solution of phenyl (5-(tert-butyl)-3-(dimethylphosphoryl)-2-methoxyphenyl)carbamate (see Example 3(vi) above; 300 mg, 0.799 mmol) and the product from step (vi) above (375 mg, 0.754 mmol) in THF (10 mL) at 70° C. (block temperature) and the mixture stirred for 2 h. The reaction was cooled to rt and concentrated in vacuo affording a brown foam. The crude product was dissolved in MeOH and loaded onto a pre-conditioned cartridge of SCX resin. The resin was washed with MeOH then the product released with 1% NH$_3$ in MeOH. The ammonia solution was concentrated in vacuo affording the sub-title compound (523 mg) as a brown oil at 82% purity which was used crude in the next reaction.

LCMS m/z 390 (M+2H)$^{2+}$ (ES$^+$)

(viii) 3-((4-((4-(3-(5-(tert-Butyl)-3-(dimethylphosphoryl)-2-methoxyphenyl)ureido)naphthalen-1-yl)oxy)pyridin-2-yl)amino)-5-((4-methylpiperazin-1-yl)methyl)benzoic acid, 2HCl To a stirred solution of the product from step (vii) above (523 mg, 0.551 mmol) in THF (20 mL) was added NaOH (2M aq.) (6.0 mL, 12.00 mmol). MeOH (3 mL) was added and stirring continued overnight. The reaction was concentrated in vacuo affording a beige solid. The material was acidified with 1M HCl and the resulting solution re-concentrated in vacuo affording a pink solid. The material was slurried in DMF (5 mL) and filtered. The filtrate was concentrated in vacuo affording a red gum. The gum was suspended in MeCN (10 mL) and stirred for 30 mins. The resulting suspended solid was isolated by filtration, washing with further MeCN to afford the sub-title compound (507 mg) as a beige solid.
LCMS m/z 765 (M+H)+ (ES+)

(ix) 3-((4-((4-(3-(5-(tert-Butyl)-3-(dimethylphosphoryl)-2-methoxyphenyl)ureido)naphthalen-1-yl)oxy)pyridin-2-yl)amino)-N-methyl-5-((4-methylpiperazin-1-yl)methyl)benzamide HATU (130 mg, 0.342 mmol) was added to a stirred solution of the product from step (viii) above (200 mg, 0.239 mmol), methylamine hydrochloride (20 mg, 0.296 mmol) and Hünig's Base (250 µL, 1.431 mmol) in DMF (4 mL) at rt. The mixture was stirred over the weekend. The mixture was poured into water (10 mL) and partitioned with EtOAc (10 mL). The organic phase was concentrated in vacuo. The crude product was purified by preparative HPLC (Waters, Acidic (0.1% Formic acid), Acidic, Waters X-Select Prep-C18, 5 µm, 19×50 mm column, 10-35% MeCN in Water) to afford an orange solid. The solid was partitioned between sat. aq. $NaHCO_3$ solution and 10% MeOH in DCM. The organic phase was dried via hydrophobic frit and concentrated in vacuo. The residue was re-concentrated from MeCN and the residue dried in vacuo at 45° C. affording the title compound (75 mg) as a pale orange solid.
$^1$H NMR (400 MHz, DMSO-$d_6$) δ: 9.35 (s, 1H), 9.03 (s, 1H), 8.92 (s, 1H), 8.45 (d, 1H), 8.25-8.31 (m, 2H), 8.10-8.14 m (m, 2H), 7.97 (s, 1H), 7.88 (d, 1H), 7.71 (t, 1H), 7.59-7.63 (m, 2H), 7.34-7.40 (m, 2H), 7.19 (s, 1H), 6.56 (dd, 1H), 6.15 (d, 1H), 3.91 (s, 3H), 3.39 (s, 2H), 2.75 (d, 3H), 2.21-2.41 (m, 8H), 2.13 (s, 3H), 1.75 (d, 6H), 1.31 (s, 9H). LCMS m/z 778 (M+H)+ (ES+)

Example 79

The following compounds were prepared by methods analogous to those described herein (including above and/or the examples below). Where chemical shifts from $^1$H NMR spectra are reported, these were obtained at 400 MHz and ambient temperature, unless otherwise specified.

(a) 1-(5-tert-Butyl-3-dimethylphosphoryl-2-methoxy-phenyl)-3-[4-[[2-[3-methoxy-4-(4-methyl-piperazine-1-carbonyl)anilino]-4-pyridyl]oxy]-1-naphthyl]urea

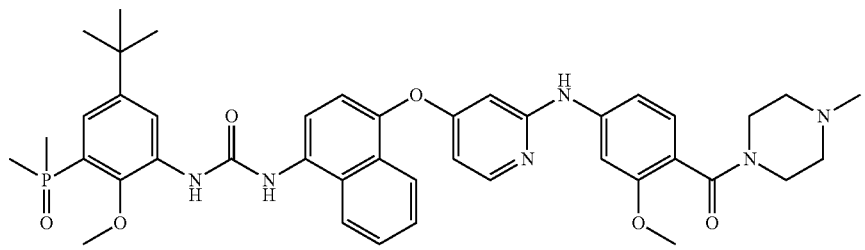

$^1$H NMR (400 MHz, DMSO-$d_6$) δ: 9.35 (s, 1H), 9.09 (s, 1H), 8.91 (s, 1H), 8.44 (d, 1H), 8.29 (d, 1H), 8.12-8.14 (m, 2H), 7.88 (d, 1H), 7.72 (t, 1H), 7.62 (t, 1H), 7.34-7.41 (m, 3H), 7.21 (dd, 1H), 6.99 (d, 1H), 6.62 (dd, 1H), 6.12 (d, 1H), 3.91 (s, 3H), 3.70 (s, 3H), 3.52-3.59 (m, 2H), 3.13 (bs, 2H), 2.17-2.33 (m, 4H), 2.17 (s, 3H), 1.75 (d, 6H), 1.31 (s, 9H).
LCMS m/z 765 (M+H)+ (ES+)

(b) 4-[[4-[[4-[(5-tert-Butyl-3-dimethylphosphoryl-2-methoxy-phenyl)carbamoylamino]-1-naphthyl]oxy]-2-pyridyl]amino]-2-methoxy-N-(1-methyl-4-piperidyl)benzamide

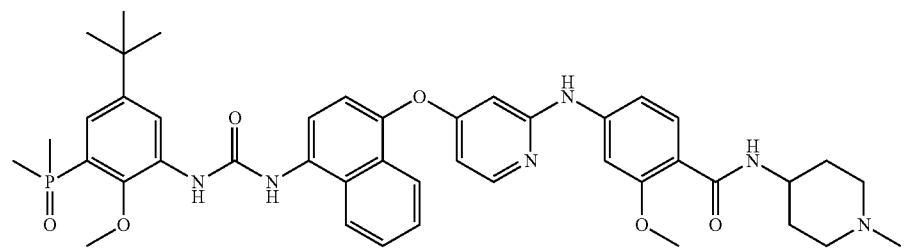

211

$^1$H NMR (400 MHz, DMSO-d$_6$) δ: 9.36 (s, 1H), 9.25 (s, 1H), 8.92 (s, 1H), 8.44 (d, 1H), 8.30 (d, 1H), 8.13-8.17 (m, 2H), 7.87 (d, 1H), 7.79 (d, 1H), 7.69-7.74 (m, 2H), 7.58-7.64 (m, 2H), 7.41 (d, 1H), 7.36 (dd, 1H), 7.22 (dd, 1H), 6.66 (dd, 1H), 6.16 (d, 1H), 3.91 (s, 3H), 3.85 (s, 3H), 3.71-3.78 (m, 1H), 2.61-2.67 (m, 2H), 2.16 (s, 3H), 2.04 (t, 2H), 1.73-1.82 (m, 2H), 1.75 (s, 6H), 1.46-1.56 (m, 2H), 1.31 (s, 9H). LCMS m/z 779 (M+H)$^+$ (ES$^+$)

(c) 4-[[4-[[4-[(5-tert-Butyl-3-dimethylphosphoryl-2-methoxy-phenyl)carbamoylamino]-1-naphthyl]oxy]-2-pyridyl]amino]-N-(2-dimethylaminoethyl)-2-methoxy-benzamide

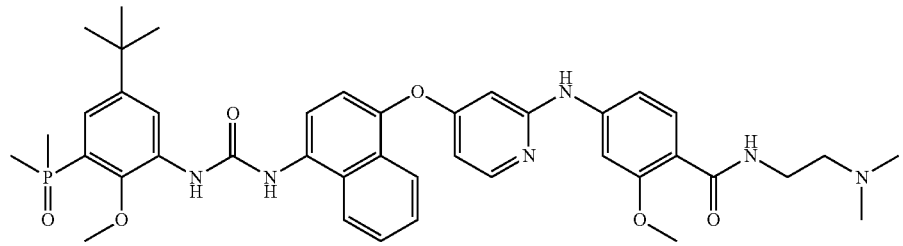

$^1$H NMR (400 MHz, DMSO-d$_6$) δ: 9.36 (s, 1H), 9.25 (s, 1H), 8.92 (s, 1H), 8.44 (d, 1H), 8.30 (d, 1H), 8.13-8.17 (m, 3H), 7.87 (d, 1H), 7.76 (d, 1H), 7.72 (t, 1H), 7.62 (t, 1H), 7.58 (d, 1H), 7.41 (d, 1H), 7.36 (dd, 1H), 7.21 (dd, 1H), 6.66 (dd, 1H), 6.16 (d, 1H), 3.91 (s, 3H), 3.84 (s, 3H), 2H underwater, 2.38 (t, 2H), 2.19 (s, 6H), 1.75 (d, 6H), 1.31 (s, 9H). LCMS m/z 753 (M+H)$^+$ (ES$^+$)

(d) 1-(5-tert-Butyl-3-dimethylphosphoryl-2-methoxy-phenyl)-3-[4-[[2-[3-methoxy-5-[methyl(3-morpholinopropyl)sulfamoyl]anilino]-4-pyridyl]oxy]-1-naphthyl]urea

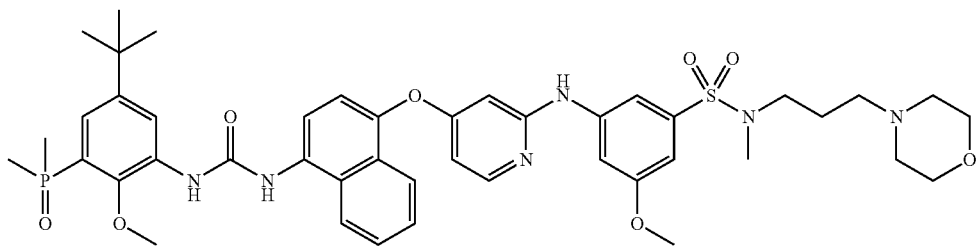 [SMILES: COc1cc(Nc2cc(Oc3ccc(NC(=O)Nc4cc(C(C)(C)C)cc(P(C)(C)=O)c4OC)c4ccccc34)ccn2)cc(S(=O)(=O)N(C)CCCN2CCOCC2)c1]

$^1$H NMR (400 MHz, DMSO-d$_6$) δ: 9.35 (s, 1H), 9.30 (s, 1H), 8.91 (s, 1H), 8.45 (d, 1H), 8.30 (d, 1H), 8.13-8.16 (m, 2H), 7.87 (d, 1H), 7.72 (t, 1H), 7.60-7.65 (m, 3H), 7.40 (d, 1H), 7.36 (dd, 1H), 6.69 (s, 1H), 6.66 (dd, 1H), 6.11 (d, 1H), 3.91 (s, 3H), 3.78 (s, 3H), 3.51-3.53 (m, 4H), 2.98 (t, 2H), 2.68 (s, 3H), 2.22-2.28 (m, 6H), 1.76 (d, 6H), 1.59 (quint, 2H), 1.31 (s, 9H).
LCMS m/z 859 (M+H)$^+$ (ES$^+$)

(e) 1-(5-tert-Butyl-2-methoxy-3-methylsulfinyl-phenyl)-3-[4-[[2-[3-cyano-5-(3-morpholinopropoxy)anilino]-4-pyridyl]oxy]-1-naphthyl]urea

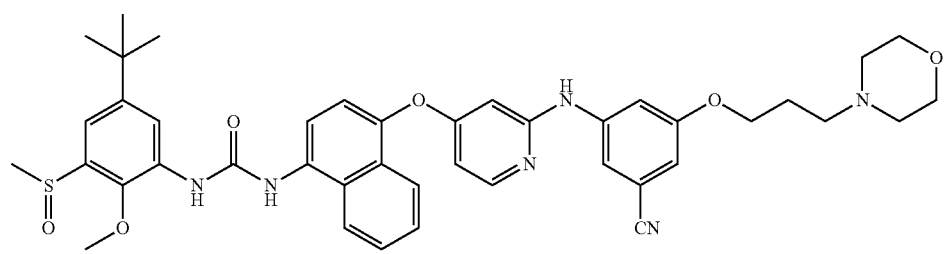 [SMILES: COc1c(NC(=O)Nc2ccc(Oc3ccnc(Nc4cc(C#N)cc(OCCCN5CCOCC5)c4)c3)c3ccccc23)cc(C(C)(C)C)cc1S(C)=O]

¹H NMR (400 MHz, DMSO-d₆) δ: 9.42 (s, 1H), 9.26 (s, 1H), 8.96 (s, 1H), 8.51 (d, 1H), 8.29 (d, 1H), 8.18 (d, 1H), 8.11 (d, 1H), 7.87 (d, 1H), 7.70-7.74 (m, 2H), 7.60-7.64 (m, 1H), 7.50 (t, 1H), 7.42 (d, 1H), 7.37 (d, 1H), 6.88 (s, 1H), 6.69 (dd, 1H), 6.09 (d, 1H), 4.00 (t, 2H), 3.87 (s, 3H), 3.55-3.57 (m, 4H), 2.79 (s, 3H), 2.35-2.41 (m, 6H), 1.86 (quint, 2H), 1.32 (s, 9H).

LCMS m/z 763 (M+H)⁺ (ES⁺)

(f) 3-[[4-[[4-[(5-tert-Butyl-3-dimethylphosphoryl-2-methoxy-phenyl)carbamoylamino]-1-naphthyl]oxy]-2-pyridyl]amino]-N-methyl-5-(2-morpholinoethoxy)benzamide

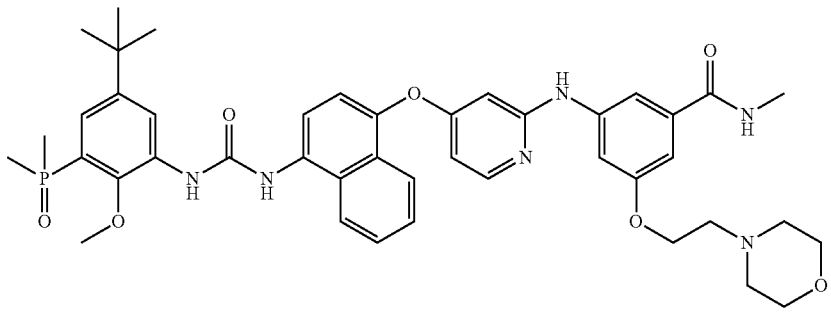 [SMILES: CNC(=O)c1cc(Nc2cc(Oc3ccc(NC(=O)Nc4cc(C(C)(C)C)cc(P(C)(C)=O)c4OC)c4ccccc34)ccn2)cc(OCCN2CCOCC2)c1]

¹H NMR (400 MHz, DMSO-d₆) δ: 9.34 (s, 1H), 9.05 (s, 1H), 8.91 (s, 1H), 8.45 (d, 1H), 8.25-8.30 (m, 2H), 8.11-8.15 (m, 2H), 7.88 (d, 1H), 7.71 (t, 1H), 7.60-7.63 (m, 2H), 7.46 (s, 1H), 7.39 (d, 1H), 7.36 (dd, 1H), 6.88 (s, 1H), 6.58 (dd, 1H), 6.14 (d, 1H), 4.07 (t, 2H), 3.91 (s, 3H), 3.57-3.59 (m, 4H), 2.75 (d, 3H), 2.70 (t, 2H), 2.46-2.48 (m, 4H), 1.75 (d, 6H), 1.31 (s, 9H).

LCMS m/z 795 (M+H)⁺ (ES⁺)

(g) 4-((4-((4-(3-(5-(tert-Butyl)-2-methoxy-3-(methylsulfinyl)phenyl)ureido)naphthalen-1-yl)oxy)pyridin-2-yl)amino)-2-methoxybenzoic acid

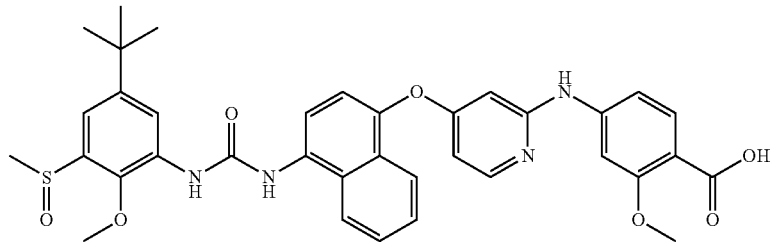 [SMILES: COc1cc(Nc2cc(Oc3ccc(NC(=O)Nc4cc(C(C)(C)C)cc(S(C)=O)c4OC)c4ccccc34)ccn2)ccc1C(=O)O]

¹H NMR (400 MHz, DMSO-d₆) δ 9.51 (s, 1H), 9.31 (s, 1H), 9.03 (s, 1H), 8.50 (d, 1H), 8.30 (d, 1H), 8.18 (d, 1H), 8.11 (d, 1H), 7.87 (d, 1H), 7.73-7.69 (m, 1H), 7.60-7.64 (m, 2H), 7.49 (d, 1H), 7.42 (d, 1H), 7.36 (d, 1H), 7.22 (dd, 1H), 6.67 (dd, 1H), 6.16 (d, 1H), 3.86 (s, 3H), 3.74 (s, 3H), 2.79 (s, 3H), 1.32 (s, 3H). LCMS m/z 669 (M+H)⁺ (ES⁺); 667 (M−H)⁻ (ES⁻)

(h) 5-(tert-Butyl)-3-(3-(4-((2-((3,5-dimethoxyphenyl)amino)pyridin-4-yl)oxy)naphthalen-1-yl)ureido)-2-methoxy-N-(2-(piperazin-1-yl)ethyl)benzamide

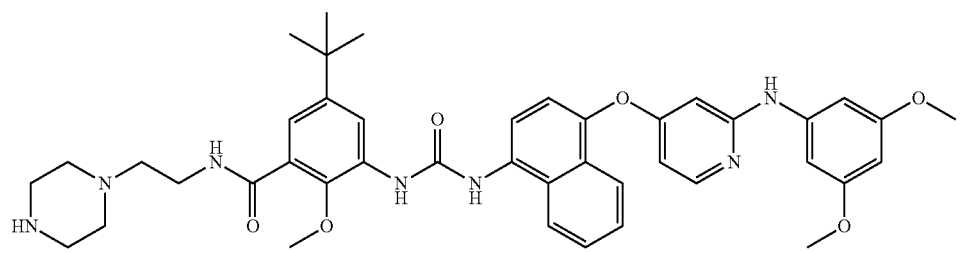 [SMILES: COc1cc(Nc2cc(Oc3ccc(NC(=O)Nc4cc(C(C)(C)C)cc(C(=O)NCCN5CCNCC5)c4OC)c4ccccc34)ccn2)cc(OC)c1]

¹H NMR (400 MHz, DMSO-d₆) δ 9.47 (s, 1H), 8.94 (s, 1H), 8.89 (s, 1H), 8.46 (d, 1H), 8.30 (d, 1H), 8.25 (t, 1H), 8.10 (s, 1H), 8.08 (d, 1H), 7.85 (d, 1H), 7.71 (ddd, 1H), 7.61 (ddd, 1H), 7.38 (d, 1H), 7.26 (d, 1H), 6.84 (d, 2H), 6.57 (dd, 1H), 6.08 (d, 1H), 6.02 (t, 1H), 3.83 (s, 3H), 3.65 (s, 6H), 3.42 (q, 2H), 2.72 (t, 4H), 2.48 (m, 2H), 2.37 (bs, 4H), 1.28 (s, 9H).
LCMS m/z 748 (M+H)⁺ (ES⁺); 746 (M−H)⁻ (ES⁻)

(i) 4-((4-((4-(3-(5-(tert-Butyl)-2-methoxy-3-(methylsulfonyl)phenyl)ureido)naphthalen-1-yl)oxy)pyrimidin-2-yl)amino)-2-methoxybenzoic acid

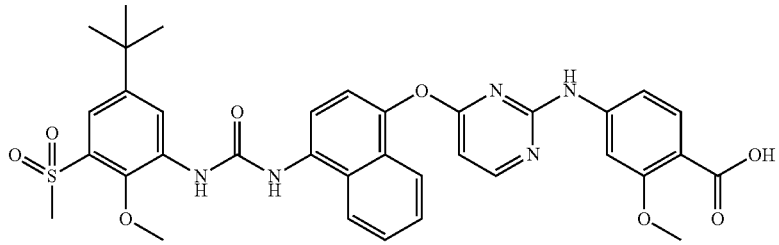 [SMILES: COc1cc(Nc2nccc(Oc3ccc(NC(=O)Nc4cc(C(C)(C)C)cc(S(C)(=O)=O)c4OC)c4ccccc34)n2)ccc1C(=O)O]

¹H NMR (400 MHz, DMSO-d₆) δ 9.79 (s, 1H), 9.54 (s, 1H), 9.11 (s, 1H), 8.67 (d, 1H), 8.47 (d, 1H), 8.29 (d, 1H), 8.09 (d, 1H), 7.84 (d, 1H), 7.71-7.67 (m, 1H), 7.61-7.57 (m, 1H), 7.44-7.42 (m, 2H), 7.37 (d, 1H), 7.28 (s, 1H), 7.02 (d, 1H), 6.68 (d, 1H), 3.95 (s, 3H), 3.44 (s, 3H), 3.34 (s, 3H), 1.31 (s, 9H). LCMS m/z 686 (M+H)⁺ (ES⁺)

(j) 4-((4-((4-(3-(5-(tert-Butyl)-2-methoxy-3-(methylsulfinyl)phenyl)ureido)naphthalen-1-yl)oxy)pyrimidin-2-yl)amino)-2-methoxybenzoic acid

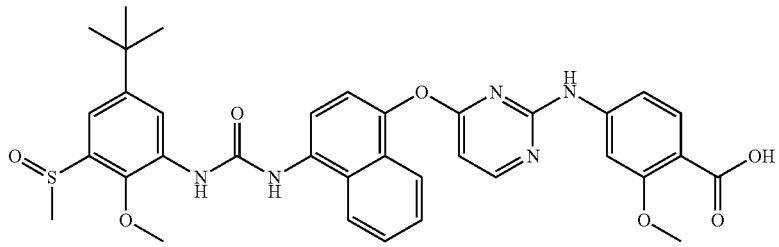 [SMILES: COc1cc(Nc2nccc(Oc3ccc(NC(=O)Nc4cc(C(C)(C)C)cc(S(C)=O)c4OC)c4ccccc34)n2)ccc1C(=O)O]

¹H NMR (400 MHz, DMSO-d₆) δ 9.79 (s, 1H), 9.50 (s, 1H), 9.00 (s, 1H), 8.49 (d, 1H), 8.47 (d, 1H), 8.28 (d, 1H), 8.08 (d, 1H), 7.84 (d, 1H), 7.70-7.65 (m, 1H), 7.61-7.57 (m, 1H), 7.42 (d, 1H), 7.38 (d, 1H), 7.35 (d, 1H), 7.29 (s, 1H), 7.02 (d, 1H), 6.68 (d, 1H), 3.86 (s, 3H), 3.43 (s, 3H), 2.78 (s, 3H), 1.31 (s, 9H). LCMS m/z 670 (M+H)⁺ (ES⁺)

(k) 3-((4-((4-(3-(5-(tert-Butyl)-3-(dimethylphosphoryl)-2-methoxyphenyl)ureido)naphthalen-1-yl)oxy)pyridin-2-yl)amino)-5-methoxy-N-methyl-N-(2-(4-methylpiperazin-1-yl)ethyl)benzamide

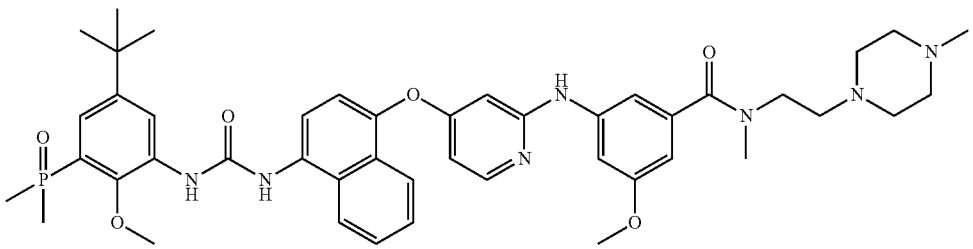

¹H NMR (400 MHz, DMSO-d₆, 298K) δ 9.39 (s, 1H), 9.02 (s, 1H), 8.94 (s, 1H), 8.42 (d, 1H), 8.29 (d, 1H), 8.13-8.10 (m, 2H), 7.86 (d, 1H), 7.68 (dd, 1H), 7.60 (dd, 1H), 7.39-7.33 (m, 2H), 7.29 (bs, 1H), 7.19 (bs, 1H), 6.59 (dd, 1H), 6.36 (s, 1H), 6.08 (d, 1H), 3.90 (s, 3H), 3.70 (s, 3H), 3.51 (bs, 1H), 3.26 (bs, 1H), 2.92-2.86 (m, 3H), 2.41-2.05 (m, 11H), 1.74 (d, 6H), 1.30 (s, 9H). (2H under DMSO). LCMS m/z 822 (M+H)⁺ (ES⁺)

(l) 3-((4-((4-(3-(5-(tert-Butyl)-3-(dimethylphosphoryl)-2-methoxyphenyl)ureido)naphthalen-1-yl)oxy)pyridin-2-yl)amino)-5-methoxy-N-methyl-N-(2-(1-methylpiperidin-4-yl)ethyl)benzamide

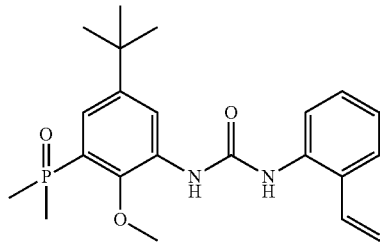
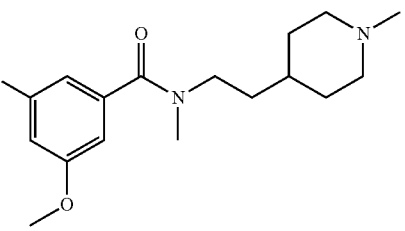

¹H NMR (400 MHz, DMSO-d₆, 333K) δ 9.21 (s, 1H), 8.88 (s, 1H), 8.74 (s, 1H), 8.39 (d, 1H), 8.28 (d, 1H), 8.11 (d, 1H), 8.07 (d, 1H), 7.90 (d, 1H), 7.71-7.66 (m, 1H), 7.62-7.58 (m, 1H), 7.40-7.34 (m, 2H), 7.26 (bs, 1H), 7.21 (bs, 1H), 6.57 (dd, 1H), 6.37 (s, 1H), 6.18 (d, 1H), 3.92 (s, 3H), 3.72 (s, 3H), 3.31 (bs, 2H), 2.88 (s, 3H), 2.64 (bs, 2H), 2.10 (s, 3H), 1.77-1.73 (m, 8H), 1.49-1.46 (m, 4H), 1.31 (s, 9H), 1.10 (bs, 3H). LCMS m/z 821 (M+H)⁺ (ES⁺)

(m) 3-((4-((4-(3-(5-(tert-Butyl)-3-(dimethylphosphoryl)-2-methoxyphenyl)ureido)naphthalen-1-yl)oxy)pyridin-2-yl)amino)-5-methoxy-N-methyl-N-(2-(4-methylpiperazin-1-yl)ethyl)benzene sulfonamide

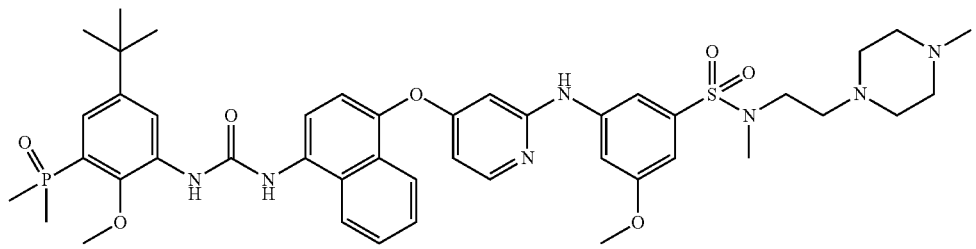

¹H NMR (400 MHz, DMSO-d₆) δ 9.37 (s, 1H), 9.28 (s, 1H), 8.92 (s, 1H), 8.42 (d, 1H), 8.29 (d, 1H), 8.14 (d, 1H), 8.12 (d, 1H), 7.86 (d, 1H), 7.71 (dd, 1H), 7.65-7.58 (m, 3H), 7.39 (d, 1H), 7.35 (dd, 1H), 6.70 (dd, 1H), 6.64 (dd, 1H), 6.09 (d, 1H), 3.90 (s, 3H), 3.77 (s, 3H), 3.05 (t, 2H), 2.71 (s, 3H), 2.49-2.21 (m, 10H), 2.10 (s, 3H), 1.74 (d, 6H), 1.30 (s, 9H).
LCMS m/z 858 (M+H)⁺ (ES⁺)

Example 80

4-((4-((4-(3-(5-(tert-Butyl)-2-methoxy-3-(methylsulfonyl)phenyl)ureido)naphthalen-1-yl)oxy)pyridin-2-yl)amino)-2-methoxybenzoic acid

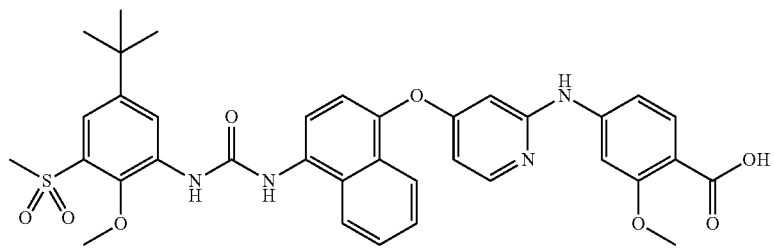 [SMILES: COc1cc(Nc2cc(Oc3ccc(NC(=O)Nc4cc(C(C)(C)C)cc(S(C)(=O)=O)c4OC)c4ccccc34)ccn2)ccc1C(=O)O]

(i) Methyl 4-((4-((4-(3-(5-(tert-butyl)-2-methoxy-3-(methylsulfonyl)phenyl)ureido)naphthalen-1-yl)oxy)pyridin-2-yl)amino)-2-methoxybenzoate A mixture of phenyl (5-(tert-butyl)-2-methoxy-3-(methylsulfonyl)phenyl)carbamate (see Example 9(i) above; 200 mg, 0.530 mmol), methyl 4-((4-((4-aminonaphthalen-1-yl)oxy)pyridin-2-yl)amino)-2-methoxybenzoate (see Example 73(i) above; 150 mg, 0.361 mmol) and Et$_3$N (15 μL, 0.108 mmol) in THF (4 mL) was heated at 60° C. for 48 h. The solvent was evaporated and the residue purified by chromatography on silica gel (40 g column, 0-5% MeOH/DCM) then purified further by chromatography on silica gel (40 g column, 0-100% EtOAc/isohexane) to afford the subtitle compound (195 mg) as a foam.

LCMS m/z 699 (M+H)$^+$ (ES$^+$) at 2.39 min (85% purity).

(ii) 4-((4-((4-(3-(5-(tert-Butyl)-2-methoxy-3-(methylsulfonyl)phenyl)ureido)naphthalen-1-yl)oxy)pyridin-2-yl)amino)-2-methoxybenzoic acid A mixture of the product from step (i) above (193 mg, 0.276 mmol) and aq 2M NaOH (600 μL, 1.200 mmol) in THF (3 mL) and MeOH (1 mL) was stirred at rt for 72 h then evaporated under reduced pressure. Aqueous 1M HCl (15 mL) was added, the mixture stirred for 1 h then filtered. The solid was washed with ether and purified by preparative HPLC (Gilson, Basic (0.1% Ammonium Bicarbonate), Basic, Waters X-Bridge Prep-C18, 5 μm, 19×50 mm column, MeCN in Water) to afford the title compound (38 mg) as an off white solid.

$^1$H NMR (400 MHz, DMSO-d$_6$) δ 9.55 (s, 1H), 9.31 (s, 1H), 9.14 (s, 1H), 8.68 (d, 1H), 8.30 (d, 1H), 8.18 (d, 1H), 8.12 (d, 1H), 7.88 (d, 1H), 7.75-7.70 (m, 1H), 7.64-7.60 (m, 2H), 7.50 (d, 1H), 7.44 (d, 1H), 7.42 (d, 1H), 7.22 (dd, 1H), 6.68 (dd, 1H), 6.16 (d, 1H), 3.95 (s, 3H), 3.74 (s, 3H), 3.35 (s, 3H, under water peak), 1.31 (s, 3H). LCMS m/z 685 (M+H)$^+$ (ES$^+$); 683 (M-H)$^-$ (ES$^-$)

Example 81

3-((4-((4-(3-(5-(tert-Butyl)-3-((2-(dimethylamino)acetamido)methyl)-2-methoxyphenyl)ureido)-naphthalen-1-yl)oxy)pyrimidin-2-yl)amino)-5-methoxy-N-(2-(2-(2-methoxyethoxy)ethoxy)-ethyl)benzamide

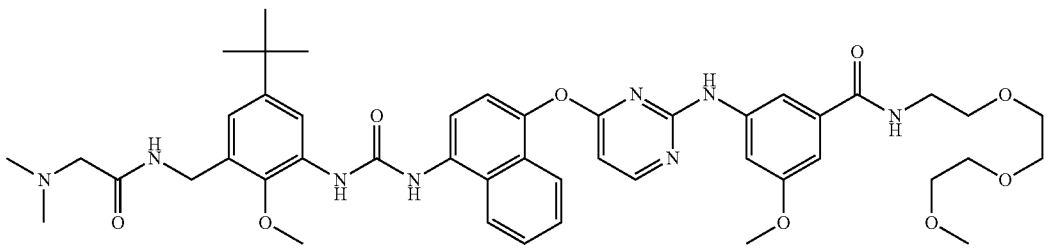 [SMILES: COCCOCCOCCNC(=O)c1cc(Nc2nccc(Oc3ccc(NC(=O)Nc4cc(C(C)(C)C)cc(CNC(=O)CN(C)C)c4OC)c4ccccc34)n2)cc(OC)c1]

A solution of phenyl (5-(tert-butyl)-3-((2-(dimethylamino)acetamido)methyl)-2-methoxy-phenyl)carbamate (see Example 77(v) above; 80 mg, 0.193 mmol), 3-((4-((4-aminonaphthalen-1-yl)oxy)pyrimidin-2-yl)amino)-5-methoxy-N-(2-(2-(2-methoxyethoxy)-ethoxy)ethyl)benzamide (see Fyfe, M. C. T., WO 2014/140582; 100 mg, 0.183 mmol) and TEA (5 μL, 0.036 mmol) in THF (2 mL) was heated at 60° C. (block temperature) for 48 h. The solvent was evaporated and the crude product was purified by chromatography on silica gel (12 g column, 2-10% MeOH in DCM) to give a pale yellow solid which was further purified by preparative HPLC (Varian, Basic (0.1% Ammonium Bicarbonate), Basic, Waters X-Bridge Prep-C18, 5 μm, 19×50 mm column, 35-65% MeCN in Water) to afford the title compound (62 mg) as a pale yellow solid.

$^1$H NMR (400 MHz, DMSO-d$_6$) δ: 9.60 (s, 1H), 9.37 (s, 1H), 8.84 (s, 1H), 8.42 (d, 1H), 8.28-8.32 (m, 2H), 8.22-8.25 (m, 2H), 8.10 (d, 1H), 7.85 (d, 1H), 7.66-7.70 (m, 1H), 7.57-7.61 (m, 2H), 7.43 (d, 1H), 7.35 (s, 1H), 6.94 (d, 1H), 6.89 (s, 1H), 6.54 (d, 1H), 4.39 (d, 2H), 3.80 (s, 3H), 3.59 (s, 3H), 3.47-3.54 (m, 8H), 3.36-3.40 (m, 4H), 3.20 (s, 3H), 2.95 (s, 2H), 2.26 (s, 6H), 1.25 (s, 9H). LCMS m/z 868 (M+H)$^+$ (ES$^+$)

Example 82

3-((4-((4-(3-(5-(tert-Butyl)-2-methoxy-3-((4-methyl-piperazin-1-yl)methyl)phenyl)ureido)-naphthalen-1-yl)oxy)pyridin-2-yl)amino)-5-methoxy-N-(2-(2-(2-methoxyethoxy)ethoxy)ethyl)-benzamide

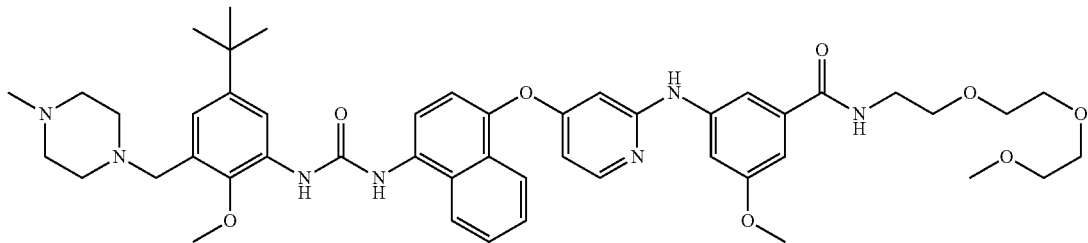 [SMILES: COCCOCCOCCNC(=O)c1cc(Nc2cc(Oc3ccc(NC(=O)Nc4cc(C(C)(C)C)cc(CN5CCN(C)CC5)c4OC)c4ccccc34)ccn2)cc(OC)c1]

(i) 3-Amino-5-(tert-butyl)-2-methoxybenzaldehyde 5-(tert-Butyl)-2-methoxy-3-nitrobenzaldehyde (1.0 g, 4.21 mmol) was dissolved in ethanol (30 mL) and iron powder (2.3 g, 41.2 mmol) was added followed by a solution of ammonium chloride (300 mg, 5.61 mmol) in water (10 mL). The resulting suspension was heated at 80° C. for 2 h. The reaction was cooled to rt and filtered. The filtrate was concentrated in vacuo affording a pale yellow solid. The solid was suspended in EtOAc (30 mL) and the suspension sonicated for 5 mins. The mixture was filtered and the pale yellow filtrate concentrated in vacuo affording the subtitle compound (856 mg) as a pale-yellow glass.

LCMS m/z 208 (M+H)$^+$ (ES$^+$)

(ii) Phenyl (5-(tert-butyl)-3-formyl-2-methoxyphenyl)carbamate

Phenyl chloroformate (0.70 ml, 5.58 mmol) was added to a stirred solution of the product from step (i) above (856 mg, 4.13 mmol) and sodium bicarbonate (1.1 g, 13.09 mmol) in THF (15 mL) and DCM (30 mL). The mixture was stirred for 6 h. The reaction was diluted with DCM (30 mL) and water (50 mL) and the organic phase dried via hydrophobic frit then concentrated in vacuo affording yellow oil. The oil was suspended in cyclohexane (20 mL) and re-concentrated affording the product as a pale yellow foam. The foam was stirred in cyclohexane overnight and the product recovered by filtration to afford the subtitle compound (1.13 g) as a white solid which was dried at 40° C. in a dessicator for 2 h.

LCMS m/z 328 (M+H)$^+$ (ES$^+$)

(iii) 3-((4-((4-(3-(5-(tert-Butyl)-3-formyl-2-methoxyphenyl)ureido)naphthalen-1-yl)oxy)pyridin-2-yl)amino)-5-methoxy-N-(2-(2-(2-methoxyethoxy)ethoxy)ethyl)benzamide A mixture of the product from step (ii) above (700 mg, 2.138 mmol), 3-((4-((4-aminonaphthalen-1-yl)oxy)pyridin-2-yl)amino)-5-methoxy-N-(2-(2-(2-methoxyethoxy)ethoxy)ethyl)benzamide (see Example 48(iv) above; 974 mg, 1.782 mmol) and Et$_3$N (75 µL, 0.538 mmol) in THF (10 mL) was heated at 60° C. for 24 h. The solvent was evaporated, the residue was triturated with ether/DCM, the solid filtered and dried to afford the subtitle compound (1.19 g) as a solid.

$^1$H NMR (400 MHz, DMSO-d$_6$) δ 10.31 (s, 1H), 8.49 (s, 1H), 9.08 (s, 1H), 9.05 (s, 1H), 8.72 (d, 1H), 8.37-8.30 (m, 2H), 8.12 (d, 1H), 8.10 (d, 1H), 7.89 (d, 1H), 7.70-7.74 (m, 1H), 7.64-7.58 (m, 2H), 7.51 (s, 1H), 7.42 (d, 1H), 7.40 (d, 1H), 6.89 (s, 1H), 6.58 (dd, 1H), 6.15 (d, 1H), 3.96 (s, 3H), 3.75 (s, 3H), 3.54-3.48 (m, 8H), 3.41-3.36 (m, 4H), 3.21 (s, 3H), 1.31 (s, 9H). LCMS m/z 780 (M+H)$^+$ (ES$^+$); 778 (M−H)$^-$ (ES$^-$)

(iv) 3-((4-((4-(3-(5-(tert-Butyl)-2-methoxy-3-((4-methylpiperazin-1-yl)methyl)phenyl)ureido)naphthalen-1-yl)oxy)pyridin-2-yl) amino)-5-methoxy-N-(2-(2-(2-methoxyethoxy)ethoxy)ethyl)benzamide A mixture of the product from step (iii) above (200 mg, 0.256 mmol), 1-methylpiperazine (50 µL, 0.449 mmol) and sodium triacetoxyborohydride (70 mg, 0.330 mmol) in THF (2 mL) was stirred at rt for 24 h. A further portion of 1-methylpiperazine (50 µL, 0.449 mmol) and sodium triacetoxyborohydride (70 mg, 0.330 mmol) were added and stirred for a further 4 h. The mixture was partitioned between DCM (50 mL) and aq sat NaHCO$_3$ soln (50 mL), the organic layer washed with brine (30 mL), dried (MgSO$_4$), filtered and evaporated under reduced pressure. The residue was purified by chromatography on silica gel (40 g column, 0-10% MeOH/DCM) to afford the title compound (122 mg) as an off-white solid.

$^1$H NMR (400 MHz, DMSO-d$_6$) δ 9.40 (s, 1H), 9.06 (s, 1H), 8.80 (s, 1H), 8.35-8.30 (m, 2H), 8.24 (d, 1H), 8.12 (d, 1H), 8.10 (d, 1H), 7.87 (d, 1H), 7.72-7.57 (m, 3H), 7.51 (s, 1H), 7.38 (d, 1H), 7.01 (d, 1H), 6.89 (s, 1H), 6.58 (dd, 1H), 6.14 (d, 1H), 3.80 (s, 3H), 3.75 (s, 3H), 3.55-3.48 (m, 10H), 3.42-3.36 (m, 4H), 3.21 (s, 3H), 2.50-2.24 (br m, 8H), 2.17 (s, 3H), 1.27 (s, 9H). LCMS m/z 864 (M+H)$^+$ (ES$^+$); 862 (M−H)$^-$ (ES$^-$)

Example 83

3-((4-((4-(3-(5-(tert-Butyl)-2-methoxy-3-(methyl-sulfinyl)phenyl)ureido)naphthalen-1-yl)oxy)pyrimi-din-2-yl)amino)-5-methoxy-N-(2-(4-methylpiper-azin-1-yl)ethyl)benzamide

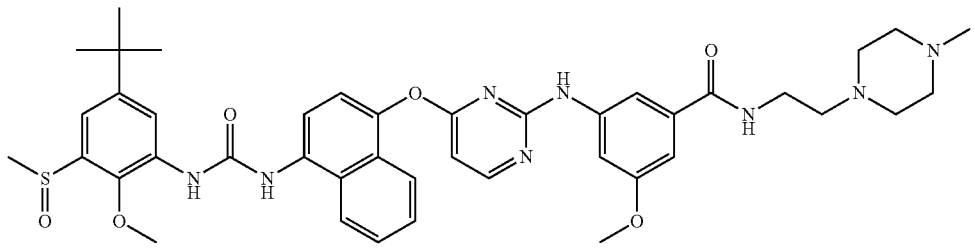

(i) 3-((4-((4-Aminonaphthalen-1-yl)oxy)pyrimidin-2-yl)amino)-5-methoxy-N-(2-(4-methylpiperazin-1-yl)ethyl)benzamide HATU (200 mg, 0.526 mmol) was added to a solution of 3-((4-((4-((tert-butoxycarbonyl)amino)naphthalen-1-yl)oxy)pyrimidin-2-yl)amino)-5-methoxybenzoic acid (see Fyfe, M. C. T. et al., WO 2014/162126; 200 mg, 0.398 mmol), 2-(4-methylpiperazin-1-yl)ethanamine (100 mg, 0.698 mmol) and Hünig's Base (200 µL, 1.145 mmol) in DMF (2 mL). The reaction mixture was stirred at rt for 72 h. The reaction mixture was partitioned between water (10 mL) and DCM (20 mL). The organics were separated, dried (MgSO$_4$), filtered and evaporated to give a brown gum. This material was dissolved in IPA (2 mL) and HCl, 6N in IPA (2 mL, 12.00 mmol) was added. The reaction mixture was stirred overnight. The solvent was evaporated and the residue partitioned between sat. NaHCO$_3$ (10 mL) and DCM (20 mL). The organics were separated, dried (MgSO$_4$), filtered and evaporated to afford the subtitle compound (200 mg) as a tan glass.

LCMS m/z 528 (M+H)$^+$ (ES$^+$)

(ii) 3-((4-((4-(3-(5-(tert-Butyl)-2-methoxy-3-(methylsulfinyl)phenyl)ureido)naphthalen-1-yl)oxy)pyrimidin-2-yl)amino)-5-methoxy-N-(2-(4-methylpiperazin-1-yl)ethyl)benzamide A solution of phenyl (5-(tert-butyl)-2-methoxy-3-(methylsulfinyl)phenyl)carbamate (see Example 12(iv) above; 200 mg, 0.553 mmol), the product from step (i) above (200 mg, 0.379 mmol) and TEA (10 µL, 0.072 mmol) in THF (10 mL) was heated at 60° C. (block temperature) for 16 h. The solvent was evaporated and the crude product was purified by chromatography on silica gel (40 g column, 2% MeOH:DCM to 8%) to afford a tan glass. This was further purified by preparative HPLC (Varian, Basic (0.1% Ammonium Bicarbonate), Basic, Waters X-Bridge Prep-C18, 5 µm, 19×50 mm column, 20-50% MeCN in Water) to afford the title compound (150 mg) as a colourless solid.

$^1$H NMR (400 MHz, DMSO-d$_6$) δ 9.60 (s, 1H), 9.38 (s, 1H), 8.97 (s, 1H), 8.51 (d, 1H), 8.42 (d, 1H), 8.26 (d, 1H), 8.15 (t, 1H), 8.09 (d, 1H), 7.86 (d, 1H), 7.68 (ddd, 1H), 7.64-7.52 (m, 2H), 7.44 (d, 1H), 7.36 (d, 1H), 7.33 (s, 1H), 6.85 (t, 1H), 6.55 (d, 1H), 3.87 (s, 3H), 3.59 (s, 3H), 2.79 (s, 3H), 2.47-2.17 (m, 10H), 2.13 (s, 3H), 1.32 (s, 9H). (2H under water peak at 3.32 ppm). LCMS m/z 795 (M+H)$^+$ (ES$^+$)

Example 84

3-((4-((4-(3-(5-(tert-Butyl)-2-methoxy-3-(methyl-sulfinyl)phenyl)ureido)naphthalen-1-yl)oxy)pyridin-2-yl)amino)-5-methoxy-N-(2-(4-methylpiperazin-1-yl)ethyl)benzamide

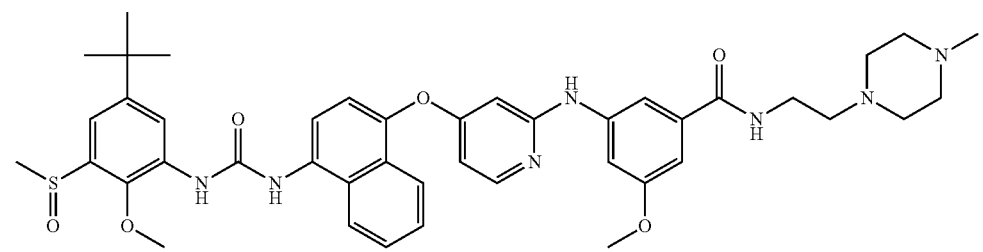

(i) Methyl 3-((4-((4-(3-(5-(tert-butyl)-2-methoxy-3-(methylsulfinyl)phenyl)ureido)naphthalen-1-yl)oxy)pyridin-2-yl)amino)-5-methoxybenzoate A solution of phenyl (5-(tert-butyl)-2-methoxy-3-(methylsulfinyl)phenyl)carbamate (see Example 12(iv) above; 500 mg, 1.383 mmol), methyl 3-((4-((4-aminonaphthalen-1-yl)oxy)pyridin-2-yl)amino)-5-methoxybenzoate (see Example 65(i) above; 440 mg, 1.059 mmol) and TEA (30 µL, 0.215 mmol) in THF (10 mL) was heated at 60° C. (block temperature) for 16 h. The solvent was evaporated and the crude product was purified by chromatography on silica gel (40 g column, 2% MeOH:DCM to 8%) to afford the subtitle compound (660 mg, 82% purity) as a colourless solid.

$^1$H NMR (400 MHz, DMSO-d$_6$) δ 9.41 (s, 1H), 9.17 (s, 1H), 8.96 (s, 1H), 8.50 (d, 1H), 8.28 (d, 1H), 8.14 (d, 1H), 8.10 (d, 1H), 7.91-7.85 (m, 1H), 7.76 (dd, 1H), 7.74-7.67 (m, 2H), 7.62 (ddd, 1H), 7.40 (d, 1H), 7.37 (d, 1H), 6.96 (dd, 1H), 6.61 (dd, 1H), 6.12 (d, 1H), 3.87 (s, 3H), 3.82 (s, 3H), 3.75 (s, 3H), 2.79 (s, 3H), 1.32 (s, 9H). LCMS m/z 683 (M+H)$^+$ (ES$^+$)

(ii) 3-((4-((4-(3-(5-(tert-Butyl)-2-methoxy-3-(methylsulfinyl)phenyl)ureido)naphthalen-1-yl)oxy)pyridin-2-yl)amino)-5-methoxybenzoic acid, HCl To a stirred solution of the product from step (i) above (650 mg, 0.952 mmol) in THF (5 mL) and MeOH (1 mL) was added LiOH (50 mg, 2.088 mmol) and water (1 mL) and the reaction stirred at 40° C. for 4 h. The solvents were evaporated and the residue dissolved in water (50 mL). The resulting solution was made to pH 1 with 1N HCl and the suspension partitioned between 20% MeOH:DCM (150 mL) and water (50 mL). The organics were separated, dried (MgSO$_4$), filtered and evaporated to afford the subtitle compound (660 mg) as a tan solid.

$^1$H NMR (400 MHz, DMSO-d$_6$) δ 9.83 (s, 1H), 9.68 (s, 1H), 9.11 (s, 1H), 8.48 (d, 1H), 8.38 (d, 1H), 8.13 (d, 1H), 8.08 (d, 1H), 7.87 (d, 1H), 7.80-7.68 (m, 1H), 7.69-7.61 (m, 1H), 7.56 (s, 1H), 7.45 (d, 1H), 7.42 (s, 1H), 7.36 (d, 1H), 7.15 (s, 1H), 6.77 (dd, 1H), 6.24 (d, 1H), 3.87 (s, 3H), 3.77 (s, 3H), 2.79 (s, 3H), 1.32 (s, 9H). LCMS m/z 669 (M+H)$^+$ (ES$^+$)

(iii) 3-((4-((4-(3-(5-(tert-Butyl)-2-methoxy-3-(methylsulfinyl)phenyl)ureido)naphthalen-1-yl)oxy)pyridin-2-yl)amino)-5-methoxy-N-(2-(4-methylpiperazin-1-yl)ethyl)benzamide HATU (150 mg, 0.394 mmol) was added to a solution of the product from step (ii) above (200 mg, 0.284 mmol), 2-(4-methylpiperazin-1-yl)ethanamine (60 mg, 0.419 mmol) and diisopropylethylamine (150 µL, 0.859 mmol) in DMF (2 mL). The reaction mixture was stirred at rt for 72 h. Water (10 mL) added and the resulting solid filtered off, washed with water (2 mL) and dried to afford the title compound (0.19 g).

$^1$H NMR (400 MHz, DMSO-d$_6$) δ 9.41 (s, 1H), 9.07 (s, 1H), 8.96 (s, 1H), 8.51 (d, 1H), 8.28 (d, 1H), 8.21 (t, 1H), 8.12 (d, 1H), 8.10 (d, 1H), 7.88 (d, 1H), 7.77-7.67 (m, 1H), 7.66-7.58 (m, 1H), 7.56 (t, 1H), 7.50 (t, 1H), 7.40 (d, 1H), 7.36 (d, 1H), 6.86 (dd, 1H), 6.58 (dd, 1H), 6.14 (d, 1H), 3.87 (s, 3H), 3.74 (s, 3H), 2.79 (s, 3H), 2.43 (t, 2H), 2.32 (s, br, 10H), 2.15 (s, 3H), 1.32 (s, 9H). LCMS m/z 794 (M+H)$^+$ (ES$^+$)

Biological Testing: Experimental Methods
Enzyme Binding Assays (Kinomescan)

Kinase enzyme binding activities of compounds disclosed herein may be determined using a proprietary assay which measures active site-directed competition binding to an immobilized ligand (Fabian, M. A. et al., *Nature Biotechnol.*, 2005, 23:329-336). These assays may be conducted by DiscoverX (formerly Ambit; San Diego, Calif.). The percentage inhibition produced by incubation with a test compound may be calculated relative to the non-inhibited control.

Enzyme Inhibition Assays

The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition

The following two assay variants can be used for determination of p38 MAPKα inhibition.

Method 1

The inhibitory activities of test compounds against the p38 MAPKα isoform (MAPK14: Invitrogen), are evaluated indirectly by determining the level of activation/phosphorylation of the down-stream molecule, MAPKAP-K2. The p38 MAPKα protein (80 ng/mL, 2.5 µL) is mixed with the test compound (2.5 µL of either 4 µg/mL, 0.4 µg/mL, 0.04 µg/mL or 0.004 µg/mL) for 2 hr at RT. The mix solution (2.5 µL) of the p38a inactive target MAPKAP-K2 (Invitrogen, 600 ng/mL) and FRET peptide (8 µM; a phosphorylation target for MAPKAP-K2) is then added and the kinase reaction is initiated by adding ATP (40 µM, 2.5 µL). The mixture is incubated for 1 hr at RT. Development reagent (protease, 5 µL) is added for 1 hr prior to detection in a fluorescence microplate reader (Varioskan® Flash, Thermo-Fisher Scientific).

Method 2

This method follows the same steps as Method 1 above, but utilises a higher concentration of the p38 MAPKα protein (2.5 µL of 200 ng/mL protein instead of 2.5 µL of 80 ng/mL protein) for mixing with the test compound.

p38 MAPKγ Enzyme Inhibition

The inhibitory activities of compounds of the invention against p38MAPKγ (MAPK12: Invitrogen), are evaluated in a similar fashion to that described hereinabove. The enzyme (800 ng/mL, 2.5 µL) is incubated with the test compound (2.5 µL at either 4 µg/mL, 0.4 µg/mL, 0.04 µg/mL, or 0.004 µg/mL) for 2 hr at RT. The FRET peptides (8 µM, 2.5 µL), and appropriate ATP solution (2.5 µL, 400 µM) is then added to the enzymes/compound mixtures and incubated for 1 hr. Development reagent (protease, 5 µL) is added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), are evaluated in a similar fashion to that described hereinabove. The relevant enzyme (3000 ng/mL or 2000 ng/mL respectively, 2.5 µL) is incubated with the test compound (either 4 µg/mL, 0.4 µg/mL, 0.04 µg/mL, or 0.004 µg/mL, 2.5 µL each) for 2 hr at RT. The FRET peptides (8 µM, 2.5 µL), and appropriate ATP solutions (2.5 µL, 800 µM for c-Src, and 60 µM ATP for Syk) are then added to the enzymes/compound mixtures and incubated for 1 hr. Development reagent (protease, 5 µL) is added for 1 hr prior to detection in a fluorescence microplate reader (Varioskan® Flash, ThermoFisher Scientific).

GSK 3α Enzyme Inhibition

The following two assay variants can be used for determination of GSK 3α inhibition.

Method 1

The inhibitory activities of compounds of the invention against the GSK 3α enzyme isoform (Invitrogen), are evaluated by determining the level of activation/phosphorylation of the target peptide. The GSK3-α protein (500 ng/mL, 2.5 µL) is mixed with the test compound (2.5 µL at either 4

μg/mL, 0.4 μg/mL, 0.04 μg/mL, or 0.004 μg/mL) for 2 hr at RT. The FRET peptide (8 μM, 2.5 μL), which is a phosphorylation target for GSK3α, and ATP (40 μM, 2.5 μL) are then added to the enzyme/compound mixture and the resulting mixture incubated for 1 hr. Development reagent (protease, 5 μL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction are calculated using the ratio of coumarin emission (donor) over fluorescein emission (acceptor), for which high ratios indicate high phosphorylation and low ratios indicate low phosphorylation levels. The percentage inhibition of each reaction is calculated relative to non-inhibited control and the 50% inhibitory concentration ($IC_{50}$ value) is then calculated from the concentration-response curve.

Method 2

This method follows the same steps as Method 1 above, but utilises a shorter period of mixing of the test compound (105 minutes instead of 2 hours) with the GSK3-α protein.

Cellular Assays

The compounds of the invention were studied using one or more of the following assays.

(a) LPS-Induced TNFα/IL-8 Release in d-U937 Cells

U937 cells, a human monocytic cell line, are differentiated to macrophage-type cells by incubation with phorbol myristate acetate (PMA; 100 ng/mL) for 48 to 72 hr. Cells are pre-incubated with final concentrations of test compound for 2 hr and are then stimulated with 0.1 μg/mL of LPS (from *E. Coli*: O111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 μg/mL of BIRB796 at each concentration of test compound by comparison against vehicle control. The relative 50% effective concentration ($REC_{50}$) is determined from the resultant concentration-response curve. The inhibition of IL-8 production is calculated at each concentration of test compound by comparison with vehicle control. The 50% inhibitory concentration ($IC_{50}$) is determined from the resultant concentration-response curve.

(b) LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 hours before addition of 1 ng/mL LPS (*Escherichia Coli* 0111:B4 from Sigma Aldrich) for 24 hours under normal tissue culture conditions (37° C., 5% $CO_2$). The supernatant is harvested for determination of IL-8 and TNFα concentrations by sandwich ELISA (Duo-set, R&D systems) and read on the fluorescence microplate reader (Varioskan® Flash, ThermoFisher Scientific). The concentration at 50% inhibition ($IC_{50}$) of IL-8 and TNFα production is calculated from the dose response curve.

(c) IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD28 monoclonal antibodies (0.3 μg/mL eBioscience and 3 μg/mL BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

(d) IL-1β-Induced IL-8 Release in HT29 Cells

HT29 cells, a human colon adenocarcinoma cell line, are plated in a 96 well plate (24 hrs) and pre-treated with compounds at the desired concentration for 2 hours before addition of 5 ng/mL of IL-1β (Abcam) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells are incubated for 2 hrs and non-adherent cells removed by washing. To differentiate the cells to macrophages the cells are incubated with 5 ng/mL of GM-CSF (Peprotech) for 7 days under normal tissue culture conditions. Compounds are then added to the cells at the desired concentration for a 2 hour pre-treatment before stimulation with 10 ng/mL LPS for 24 hours. Supernatants are harvested and IL-8 and TNFα release determined by Sandwich ELISA (Duo-set, R&D System). The $IC_{50}$ is determined from the dose response curve.

(f) Poly I:C-Induced ICAM-1 Expression in BEAS2B Cells

Poly I:C is used in these studies as a simple, RNA virus mimic. Poly I:C-Oligofectamine mixture (1 μg/mL Poly I:C, ±2% Oligofectamine, 25 μL; Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of test compounds for 2 hr and the level of ICAM1 expression on the cell surface is determined by cell-based ELISA. At a time point 18 hr after poly I:C transfection, cells are fixed with 4% formaldehyde in PBS and then endogenous peroxidase is quenched by the addition of washing buffer (100 μL, 0.05% Tween in PBS: PBS-Tween) containing 0.1% sodium azide and 1% hydrogen peroxide. Cells are washed with wash-buffer (3×200 μL) and after blocking the wells with 5% milk in PBS-Tween (100 μL) for 1 hr, the cells are incubated with anti-human ICAM-1 antibody (50 μL; Cell Signalling Technology, Danvers, Mass.) in 1% BSA PBS overnight at 4° C.

The cells are washed with PBS-Tween (3×200 μL) and incubated with the secondary antibody (100 μL; HRP-conjugated anti-rabbit IgG, Dako Ltd., Glostrup, Denmark). The cells are then incubated with of substrate (50 μL) for 2-20 min, followed by the addition of stop solution (50 μL, 1N $H_2SO_4$). The ICAM-1 signal is detected by reading the absorbance at 450 nm against a reference wavelength of 655 nm using a spectrophotometer. The cells are then washed with PBS-Tween (3×200 μL) and total cell numbers in each well are determined by reading absorbance at 595 nm after Crystal Violet staining (50 μL of a 2% solution in PBS) and elution by 1% SDS solution (100 μL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) Cell Mitosis Assay

Peripheral blood mononucleocytes (PBMCs) from healthy subjects are separated from whole blood (Quintiles, London, UK) using a density gradient (Histopaque®-1077, Sigma-Aldrich, Poole, UK). The PBMCs (3 million cells per sample) are subsequently treated with 2% PHA (phytohaemagglutinin, Sigma-Aldrich, Poole, UK) for 48 hr, followed by a 20 hr exposure to varying concentrations of test compounds. At 2 hr before collection, PBMCs are treated with demecolcine (0.1 µg/mL; Invitrogen, Paisley, UK) to arrest cells in metaphase. To observe mitotic cells, PBMCs are permeabilised and fixed by adding Intraprep (50 µL; Beckman Coulter, France), and stained with anti-phosphohistone 3 (0.26 ng/L; #9701; Cell Signalling, Danvers, Mass.) and propidium iodide (1 mg/mL; Sigma-Aldrich, Poole, UK) as previously described (Muehlbauer P. A. and Schuler M. J., *Mutation Research*, 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(h) Rhinovirus-Induced IL-8 Release and ICAM-1 Expression

Human rhinovirus RV16 is obtained from the American Type Culture Collection (Manassas, Va.). Viral stocks are generated by infecting Hela cells with HRV until 80% of the cells are cytopathic.

BEAS2B cells are infected with HRV at an MOI of 5 and incubated for 2 hr at 33° C. with gentle shaking for to promote absorption. The cells are then washed with PBS, fresh media added and the cells are incubated for a further 72 hr. The supernatant is collected for assay of IL-8 concentrations using a Duoset ELISA development kit (R&D systems, Minneapolis, Minn.).

The level of ICAM1 expressing cell surface is determined by cell-based ELISA. At 72 hr after infection, cells are fixed with 4% formaldehyde in PBS. After quenching endogenous peroxidase by adding 0.1% sodium azide and 1% hydrogen peroxide, wells are washed with wash-buffer (0.05% Tween in PBS:PBS-Tween). After blocking well with 5% milk in PBS-Tween for 1 hr, the cells are incubated with anti-human ICAM-1 antibody in 5% BSA PBS-Tween (1:500) overnight. Wells are washed with PBS-Tween and incubated with the secondary antibody (HRP-conjugated anti-rabbit IgG, Dako Ltd.). The ICAM-1 signal is detected by adding substrate and reading at 450 nm with a reference wavelength of 655 nm using a spectrophotometer. The wells are then washed with PBS-Tween and total cell numbers in each well are determined by reading absorbance at 595 nm after Crystal Violet staining and elution by 1% SDS solution. The measured $OD_{450-655}$ readings are corrected for cell number by dividing with the $OD_{595}$ reading in each well. Compounds are added 2 hr before HRV infection and 2 hr after infection when non-infected HRV is washed out.

(i) Assessment of HRV16 Induced CPE in MRC5

MRC-5 cells are infected with HRV16 at an MOI of 1 in DMEM containing 5% FCS and 1.5 mM $MgCl_2$, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 µL, 2% formaldehyde, 10% methanol and 0.175% Methylene Blue) for 2 hr at RT. After washing, 1% SDS in distilled water (100 µL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(j) In Vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at an MOI of 0.001 in the LHC8 Media: RPMI-1640 (50:50) containing 15 mM magnesium chloride and incubated for 1 hr at 37° C. for adsorption. The cells are then washed with PBS (3×200 µL), fresh media (200 µL) is added and incubation continued for 4 days. Where appropriate, cells are pre-incubated with the compound or DMSO for 2 hr, and then added again after washout of the virus.

The cells are fixed with 4% formaldehyde in PBS solution (50 µL) for 20 min, washed with WB (3×200 µL), (washing buffer, PBS including 0.5% BSA and 0.05% Tween-20) and incubated with blocking solution (5% condensed milk in PBS) for 1 hr. Cells are then washed with WB (3×200 µL) and incubated for 1 hr at RT with anti-RSV (2F7) F-fusion protein antibody (40 µL; mouse monoclonal, lot 798760, Cat. No. ab43812, Abcam) in 5% BSA in PBS-tween. After washing, cells are incubated with an HRP-conjugated secondary antibody solution (50 µL) in 5% BSA in PBS-Tween (lot 00053170, Cat.No. P0447, Dako) and then TMB substrate added (50 µL; substrate reagent pack, lot 269472, Cat. No. DY999, R&D Systems, Inc.). This reaction is stopped by the addition of $2N\ H_2SO_4$ (50 µL) and the resultant signal is determined colourimetrically (OD: 450 nm with a reference wavelength of 655 nm) in a microplate reader (Varioskan® Flash, ThermoFisher Scientific).

Cells are then washed and a 2.5% crystal violet solution (50 µL; lot 8656, Cat. No. PL7000, Pro-Lab Diagnostics) is applied for 30 min. After washing with WB, 1% SDS in distilled water (100 µL) is added to each well, and plates are shaken lightly on the shaker for 1 hr prior to reading the absorbance at 595 nm. The measured $OD_{450-655}$ readings are corrected to the cell number by dividing the $OD_{450-655}$ by the $OD_{595}$ readings. The percentage inhibition for each well is calculated and the $IC_{50}$ value is calculated from the concentration-response curve generated from the serial dilutions of compound.

(k) Cell Viability Assay: MTT Assay

Differentiated U937 cells are pre-incubated with each test compound (final concentration 1 µg/mL or 10 µg/mL in 200 µL media indicated below) under two protocols: the first for 4 hr in 5% FCS RPMI 1640 media and the second in 10% FCS RPMI 1640 media for 24 h. The supernatant is replaced with new media (200 µL) and MTT stock solution (10 µL, 5 mg/mL) is added to each well. After incubation for 1 hr the media are removed, DMSO (200 µL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(l) Human Biopsy Assay

Intestinal mucosa biopsies are obtained from the inflamed regions of the colon of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 hr in the organ culture chamber. The supernatant is harvested for determination of IL-6, IL-8, IL-1β and TNFα levels by R&D ELISA. Percentage inhibition of cytokine release by the test compounds is calculated relative to the cytokine release determined for the DMSO control (100%).

(m) Accumulation of β Catenin in d-U937 Cells

U937 cells, a human monocytic cell line, are differentiated into macrophage-type cells by incubation with PMA; (100 ng/mL) for between 48 to 72 hr. The cells are then incubated with either final concentrations of test compound or vehicle for 18 hr. The induction of β-catenin by the test compounds is stopped by replacing the media with 4% formaldehyde solution. Endogenous peroxide activity is neutralised by incubating with quenching buffer (100 µL, 0.1% sodium azide, 1% $H_2O_2$ in PBS with 0.05% Tween-20) for 20 min. The cells are washed with washing buffer (200 µL; PBS containing 0.05% Tween-20) and incubated with blocking solution (200 µL; 5% milk in PBS) for 1 hr, re-washed with washing buffer (200 µL) and then incubated overnight with anti-β-catenin antibody solution (50 µL) in 1% BSA/PBS (BD, Oxford, UK).

After washing with washing buffer (3×200 µL; PBS containing 0.05% Tween-20), cells are incubated with an HRP-conjugated secondary antibody solution (100 µL) in 1% BSA/PBS (Dako, Cambridge, UK) and the resultant signal is determined colourimetrically (OD: 450 nm with a reference wavelength of 655 nm) using TMB substrate (50 µL; R&D Systems, Abingdon, UK). This reaction is stopped by addition of 1N $H_2SO_4$ solution (50 µL). Cells are then washed with washing buffer and 2% crystal violet solution (50 µL) is applied for 30 min. After washing with washing buffer (3×200 µL), 1% SDS (100 µL) is added to each well and the plates are shaken lightly for 1 hr prior to measuring the absorbance at 595 nm (Varioskan® Flash, Thermo-Fisher Scientific).

The measured $OD_{450-655}$ readings are corrected for cell number by dividing the $OD_{450-655}$ by the $OD_{595}$ readings. The percentage induction for each well is calculated relative to vehicle, and the ratio of induction normalized in comparison with the induction produced by a standard control comprising of Reference Compound (N-(4-(4-(3-(3-tert-butyl-1-p-tolyl-1H-pyrazol-5-yl)ureido)naphthalen-1-yloxy) pyridin-2-yl)-2-methoxyacetamide) (1 µg/mL) which is defined as 100%.

(n) T Cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at $2×10^5$ cells per well in 100 µL RPMI/10% FBS on 96 well flat bottomed plate (Corning Costar). 25 µL of test compound are diluted to the appropriate concentration (8× final conc.) in normal medium and added to duplicate wells on the plate to achieve a dose response range of 0.03 ng/mL 250 ng/mL. DMSO is added as a negative control. Plates are allowed to pre-incubate for 2 hours before stimulation with 1 µg/mL anti-CD3 (OKT3; eBioscience). After 72 h, the medium in each well is replaced with 150 µL of fresh medium containing 10 µM BrdU (Roche). After 16 h, the supernatant is removed, the plate is dried and the cells fixed by adding 100 µL of fix/denature solution to each well for 20 min as per the manufacturer's instructions (Roche). Plates are washed once with PBS before addition of the anti-BrdU detection antibody and incubated for 90 mins at room temperature. Plates are then washed gently 3× with the wash buffer supplied and developed by addition of 100 µL of substrate solution. The reaction is stopped by addition of 50 µL of 1 M $H_2SO_4$, and read for absorbance at 450 nm on a plate reader (Varioskan® Flash, ThermoFisher Scientific). The $IC_{50}$ is determined from the dose response curve.

(o) IL-2 and IFNγ Release in CD3/CD28 Stimulated LPMC Cells from IBD Patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments 3-4 mm size. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 µm cell strainer, washed twice, resuspended in RPMI-1640 medium (Sigma-Aldrich) containing 10% fetal calf serum, 100 U/mL penicillin and 100 µg/mL streptomycin, and used for cell culture.

Freshly isolated LPMCs ($2×10^5$ cells/well) are stimulated with 1 µg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

(p) Inhibition of Cytokine Release from Myofibroblasts Isolated from IBD Patients Myofibroblasts from inflamed IBD mucosa are isolated as follows:

The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 µg/mL streptomycin, 50 µg/mL gentamycin, and 1 µg/mL amphotericin (Sigma-Aldrich). Established colonies of myofibroblasts are seeded into 25-cm² culture flasks and cultured in DMEM supplemented with 20% FBS and antibiotics to at least passage 4 to provide a sufficient quantity for use in stimulation experiments.

Subconfluent monolayers of myofibroblasts are then seeded in 12-well plates at $3×10^5$ cells per well are starved in serum-free medium for 24 h at 37° C., 5% $CO_2$ before being cultured for 24 h in the presence of either DMSO control or appropriate concentrations of compound. After 24 h the supernatant is removed and assayed for the presence of IL-8 and IL-6 by R&D ELISA. Percentage inhibition of cytokine release by the test compounds is calculated relative to the cytokine release determined for the DMSO control (100%).

(q) Human Neutrophil Degranulation

Neutrophils are isolated from human peripheral blood as follows:

Blood is collected by venepuncture and anti-coagulated by addition of 1:1 EDTA:sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis-Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+ (Hanks buffered salt solution (without phenol red) containing cytochalasin B (5 µg/mL) and 1 mM $CaCl_2$) to achieve $5 \times 10^6$ cells/mL.

$5 \times 10^4$ cells are added to each well of a V-bottom 96 well plate and incubated (30 mins, 37° C.) with the appropriate concentration of test compound (0.3-1000 ng/mL) or vehicle (DMSO, 0.5% final conc). Degranulation is stimulated by addition of fMLP (final conc 1 µM) which after a further incubation (30 mins, 37° C.) the cells are removed by centrifugation (5 mins, 1500 rpm) and the supernatants transferred to a flat bottom 96 well plate. An equal volume of tetramethylbenzidine (TMB) is added and after 10 mins the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

(r) Cell Cytotoxicity Assay $5 \times 10^4$ TK6 cells (lymphoblastic T cell line) are added to the appropriate number of wells of a 96 well plate in 195 µL of media (RPMI supplemented with 10% foetal bovine serum). 5 µL of DMSO control (final concentration 0.5% v/v) or test compound (final concentration either 5 or 1 µg/mL) is added to the wells and incubated at 37° C., 5% $CO_2$. After 24 hours, the plate is centrifuged at 1300 rpm for 3 minutes and the supernatant discarded. Cells are then resuspended in 7.5 µg/mL propidium iodide (PI) in PBS. After 15 minutes, cells are analysed by flow cytometry (BD accuri). The % viability is calculated as the % of cells that are PI negative in the test wells normalized to the DMSO control.

In Vivo Screening: Pharmacodynamics and Anti-Inflammatory Activity (i) LPS-Induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min. After a further 8 hr the animals are anesthetized, their tracheas cannulated and BALF extracted by infusing and then withdrawing from their lungs 1.0 mL of PBS via the tracheal catheter. Total and differential white cell counts in the BALF samples are measured using a Neubaur haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are shown as mean±S.E.M. (standard error of the mean). The percentage inhibition of neutrophil accumulation is calculated for each treatment relative to vehicle treatment.

(ii) Cigarette Smoke Model

A/J mice (males, 5 weeks old) are exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances are administered intra-nasally (35 µL of solution in 50% DMSO/PBS) once daily for 3 days after the final cigarette smoke exposure. At 12 hr after the last dosing, each of the animals is anesthetized, the trachea cannulated and bronchoalveolar lavage fluid (BALF) is collected. The numbers of alveolar macrophages and neutrophils are determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

(iii) DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with dextran sodium sulphate (DSS). On Day 0 of the study DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study animals are weighed every day and stool observations are made and recorded as a score, based on stool consistency. At the time of sacrifice on Day +6 the large intestine is removed and the length and weight are recorded. Sections of the colon are taken for either MPO analysis to determine neutrophil infiltration or for histopathology scoring to determine disease severity.

(iv) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1 or 5 mg/kg) one day before (Day −1) stimulation of the inflammatory response by treatment with 2,4,6-trinitrobenzenesulphonic acid (TNBS) (15 mg/mL in 50% ethanol/50% saline). On Day 0 of the study TNBS (200 µL) is administered intra-colonically via a plastic catheter with BID dosing of the vehicle, reference or test compound continuing for 2 or 4 days. During the study animals are weighed every day and stool observations are made and recorded as a score, based on stool consistency. At the time of sacrifice on Day 2 (or Day 4) the large intestine is removed and the length and weight recorded. Sections of the colon are taken for histopathology scoring to determine disease severity.

(v) Adoptive Transfer in Mice

On Study day 0, female Balb/C mice are terminated and spleens obtained for $CD45RB^{high}$ cell isolation (Using SCID IBD cell Separation protocol). Approximately $4 \times 10^5$ cells/mL $CD45RB^{high}$ cells are then injected IP (100 µL/mouse) into female SCID animals. On study day 14, mice are weighed and random/zed into treatment groups based on body weight. On Day 14, compounds are administered BID, via oral gavage, in a peanut oil vehicle at the dose levels outlined below and a dose volume of 5 mL/kg. Treatment continues until study day 42, at which point the animals are necropsied 4 hours after am administration. The colon length and weight is recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between naïve animals and vehicle animals, where higher inhibition implies closer to the non-diseased, naïve, phenotype.

(vi) Endotoxin-Induced Uveitis in Rats

Male, Lewis rats (6-8 weeks old, Charles River UK Limited) are housed in cages of 3 at 19-21° C. with a 12 h light/dark cycle (07:00/19:00) and fed a standard diet of rodent chow and water ad libitum. Non-fasted rats are weighed, individually identified on the tail with a permanent marker and receive a single intravitreal administration into the right vitreous humor (5 µL dose volume) of 100 ng/animal, i.v.t. of LPS (*Escherichia coli* 0111:B4 prepared in PBS, Sigma Aldrich, UK) using a 32-gauge needle. Untreated rats are injected with PBS. Test compound, dexamethasone (Dex) or vehicle (20% hydroxypropyl-□-cyclodextrin, 0.1% HPMC, 0.01% Benzalconium chloride, 0.05% EDTA, 0.7% NaCl in deionised water) are administered by the topical route onto the right eye (10 μL) of animals 30 minutes prior to LPS, at the time of LPS administration, and 1, 2 and 4 hours post LPS administration. Before administration, the solution or suspension to be administered is agitated for 5 minutes to ensure a uniform suspension. 6 hours after LPS dosing, animals are euthanized by overdose with pentobarbitone (i.v.). Following euthanasia, the right eye of each animal is enucleated and dissected into front (anterior) and back (posterior) sections around the lens. Each section is weighed and homogenised in 500 μL of sterile phosphate buffered saline followed by 20 minutes centrifugation at 12000 rpm at 4° C. The resulting supernatant is divided into 3 aliquots and stored at −80° C. until subsequent cytokine analysis by R&D DuoSet ELISA.

Summary of In Vitro and In Vivo Screening Results

TABLE 1a

Dissociation constants for selected kinases determined by LeadHunter Discover Services (DiscoveRx Corporation, Fremont, CA), using the KINOMEscan™ technology (NT = not tested).

| Test Compound Example No. | Dissociation Constant (nM) | | | |
|---|---|---|---|---|
| | Lck | p38 MAPK α | p38 MAPK β | Syk |
| Example 9 | 8.6 | 26 | 340 | 29 |
| Example 12 | 3.6 | 11 | 57 | 18 |
| Example 37 | 1.2 | 4.5 | NT | 5.1 |

TABLE 1b

Results from in vitro p38 MAPKα (Method 2), c-Src, Syk and GSK3α (Method 2) inhibition assays

| Test Compound Example No. | IC50 Values for Enzyme Inhibition (nM) | | | |
|---|---|---|---|---|
| | p38 MAPKα | c-Src | Syk | GSK3α |
| 1 | 34 | 9 | 30 | 330 |
| 2 | 51 | 11 | 53 | 2815 |
| 3 | 91 | 38 | >1217 | 4903 |
| 4 | — | — | — | 4102 |
| 5 | — | — | — | >9383 |
| 6 | 211 | 16 | 58 | 1201 |
| 7 | 108 | — | 57 | 1070 |
| 8 | 188 | 14 | 42 | 788 |
| 9 | 290 | 52 | 233 | >10660 |
| 10 | 45 | 16 | >887 | >8338 |
| 11 | 141 | 32 | 186 | 3826 |
| 12 | 193 | 201 | 656 | >9904 |
| 13 | 108 | 239 | 1387 | 7579 |
| 14 | 392 | 135 | 364 | >10112 |
| 15(a) | 177 | 28 | 134 | >12241 |
| 15(b) | 59 | 14 | 273 | 785 |
| 15(c) | 52 | 16 | 103 | 844 |
| 15(d) | — | 61 | 477 | 919 |
| 15(e) | 360 | 120 | 551 | 2894 |
| 15(f) | — | — | — | 3100 |
| 15(g) | — | — | — | 757 |
| 15(h) | — | — | — | 779 |
| 15(i) | — | — | — | 359 |
| 15(j) | 173 | 19 | 16 | 855 |
| 15(k) | — | — | — | 1171 |
| 15(l) | — | — | — | 8222 |
| 15(m) | 747 | — | — | >16374 |
| 15(n) | — | — | — | 1644 |
| 15(o) | — | — | — | 5803 |
| 15(p) | — | — | — | 1948 |
| 15(q) | — | 211 | >1635 | 3482 |
| 15(r) | — | — | — | 188 |
| 15(s) | — | — | — | 239 |
| 15(t) | — | — | — | 283 |
| 15(u) | — | — | — | 3061 |
| 15(v) | — | — | — | 302 |
| 15(w) | — | — | — | 1671 |
| 15(x) | 219 | 356 | >1627 | 4657 |
| 15(y) | — | — | — | 194 |
| 15(z) | — | — | — | 1497 |
| 15(aa) | — | 46 | 114 | 192 |
| 15(ab) | — | — | — | 97 |
| 15(ac) | — | — | — | >14677 |
| 15(ad) | 181 | 129 | 1004 | 1604 |
| 15(ae) | — | — | — | 871 |
| 15(af) | 226 | 77 | 278 | 9395 |
| 15(ag) | — | — | — | 5808 |
| 15(ah) | — | — | — | 602 |
| 15(ai) | — | — | — | 127 |
| 15(aj) | — | — | — | 68 |
| 15(ak) | 38 | >1781 | >1781 | >17806 |
| 15(al) | — | — | — | 339 |
| 15(am) | — | — | — | >11656 |
| 15(an) | 344 | 116 | 712 | >15228 |
| 15(ao) | — | — | — | 387 |
| 15(ap) | — | — | — | >16873 |
| 15(aq) | — | 160 | 1516 | 3288 |
| 15(ar) | — | — | — | 356 |
| 16 | 230 | 40 | 93 | 5668 |
| 17 | 68 | 30 | 134 | 10270 |
| 18 | 218 | 15 | 69 | 1311 |
| 19 | 208 | 145 | 189 | >16006 |
| 20 | 368 | 33 | 188 | 2061 |
| 21 | — | — | — | 282 |
| 22 | — | — | — | 280 |
| 23 | — | — | — | 7942 |
| 24 | 220 | 168 | 289 | 7450 |
| 25 | 323 | 224 | 724 | 9618 |
| 26 | — | — | — | 249 |
| 27 | 230 | 44 | 137 | 11252 |
| 28 | 254 | 48 | 157 | 8258 |
| 29 | 31 | 24 | 123 | 5470 |
| 30 | 132 | 60 | 708 | >15391 |
| 31 | — | — | — | 186 |
| 32 | 6 | 1110 | 1601 | 988 |
| 33 | 109 | 63 | 519 | 10524 |
| 34 | 56 | 43 | 228 | 1585 |
| 35 | 294 | 112 | 369 | >11821 |
| 36 | 31 | 27 | 54 | 1072 |
| 37 | 62 | 32 | 347 | 2158 |
| 38(a) | 119 | 74 | 54 | 3324 |
| 38(b1) | — | — | — | >9657 |
| 38(b2) | — | — | — | >11123 |
| 38(c) | 27 | 12 | 31 | 2224 |
| 38(d) | 13 | >1568 | >1654 | 2238 |
| 38(e) | 5 | 522 | >1603 | 1981 |
| 38(f) | 226 | 69 | 837 | 14790 |
| 38(g) | 9 | — | — | 2373 |
| 38(h) | 123 | 181 | 1075 | >14607 |
| 38(i) | — | — | — | >15438 |
| 38(j) | — | — | — | >14497 |
| 38(k) | 152 | 166 | >1611 | 2624 |
| 38(l) | — | — | — | 472 |
| 38(m) | 48 | 33 | 364 | 3376 |
| 38(n) | 43 | 95 | >1611 | 1199 |
| 38(o) | 9 | 47 | 381 | 1053 |
| 38(p) | — | — | — | >15829 |
| 38(q) | 6 | 383 | >1616 | 1500 |
| 38(r) | 151 | 94 | >1462 | 2206 |
| 38(s) | — | 363 | >1525 | >15251 |

TABLE 1b-continued

Results from in vitro p38 MAPKα (Method 2), c-Src, Syk and GSK3α (Method 2) inhibition assays

| Test Compound Example No. | IC50 Values for Enzyme Inhibition (nM) | | | |
|---|---|---|---|---|
| | p38 MAPKα | c-Src | Syk | GSK3α |
| 38(t) | — | — | — | 839 |
| 38(u) | 15 | 13 | — | 1067 |
| 38(v) | — | — | — | 1154 |
| 38(w) | — | — | — | >12709 |
| 38(x) | — | — | — | >12628 |
| 38(y) | 21 | 15 | 393 | 867 |
| 38(z) | — | — | — | 789 |
| 38(aa) | — | — | — | 8292 |
| 38(ab) | 50 | 61 | >1205 | 4833 |
| 38(ac) | — | — | — | 834 |
| 38(ad) | 87 | 155 | >1382 | 11004 |
| 38(ae) | — | — | — | 800 |
| 38(af) | — | 44 | 249 | 1011 |
| 38(ag) | — | — | — | 370 |
| 38(ah) | 619 | 311 | >1551 | 13941 |
| 38(ai) | — | — | — | 885 |
| 38(aj) | 295 | 220 | >1376 | >13233 |
| 38(ak) | — | — | — | 461 |
| 38(al) | 44 | — | — | 1970 |
| 38(am) | — | — | — | 1504 |
| 38(an) | 48 | 24 | 99 | 3600 |
| 38(ao) | — | — | — | 3272 |
| 38(ap) | — | — | — | >5805 |
| 39 | — | — | — | >12573 |
| 40 | 302 | 78 | 201 | >15272 |
| 41 | 179 | 72 | 247 | 10219 |
| 42 | 8 | >1640 | >1640 | 3408 |
| 43 | 129 | 54 | 132 | 7696 |
| 44 | 175 | 67 | 95 | >15066 |
| 45 | 21 | 12 | >706 | 1595 |
| 46 | 25 | 25 | 996 | 2058 |
| 47 | 36 | 34 | >1509 | 1464 |
| 48 | 25 | 37 | >1229 | 2673 |
| 49 | 124 | 39 | >1344 | 4509 |
| 50 | — | 40 | 799 | 3267 |
| 51 | 158 | 55 | >1335 | 8711 |
| 52 | >1249 | 235 | >1249 | >12486 |
| 53 | 12 | 22 | >1236 | 1559 |
| 54 | 63 | 43 | 590 | >5017 |
| 55 | 38 | 37 | >692 | 2478 |
| 56 | 188 | 83 | >1433 | 1597 |
| 57 | 209 | 98 | >1502 | 3866 |
| 58 | 527 | 101 | >1341 | 7103 |
| 59 | 127 | 43 | 560 | 2512 |
| 60 | 128 | 35 | 206 | 1698 |
| 61 | 211 | — | — | 1613 |
| 62 | 482 | 105 | 145 | >11423 |
| 63 | 811 | 98 | 154 | 7664 |
| 64 | 945 | 90 | 156 | 9392 |
| 65 | 17 | 15 | 190 | 1225 |
| 66 | 222 | 54 | 918 | 4281 |
| 67 | 284 | — | — | 4255 |
| 68 | 13 | 18 | 143 | 1324 |
| 69 | 16 | 12 | 124 | 1965 |
| 70 | 28 | — | — | 2281 |
| 71 | 25 | 14 | 26 | 1201 |
| 72 | 32 | 20 | 98 | 3665 |
| 73 | 31 | 29 | 120 | 1981 |
| 74 | — | — | — | 1228 |
| 75 | 134 | 78 | >1095 | 2317 |
| 76 | — | — | — | 70 |
| 77 | 20 | 17 | 51 | 2621 |
| 78 | — | — | — | 773 |
| 79(a) | — | — | — | 480 |
| 79(b) | — | — | — | 1880 |
| 79(c) | — | — | — | 1771 |
| 79(d) | 39 | 218 | >1164 | 3939 |
| 79(e) | 269 | 81 | >1194 | >13108 |
| 79(f) | — | — | — | 957 |
| 79(g) | — | 17 | 5 | — |
| 79(h) | — | — | — | — |
| 79(i) | — | — | — | — |
| 79(j) | — | — | — | — |
| 79(k) | — | — | — | — |
| 79(l) | — | — | — | — |
| 79(m) | 6 | 25 | 7 | — |
| 80 | — | — | — | — |
| 81 | — | — | — | — |
| 82 | — | — | — | — |
| 83 | — | — | — | — |
| 84 | — | — | — | — |

TABLE 2

Results from cellular assays in PBMCs and HT29 cells (the protocols for which are described by assays (b) to (d) above).

| Test Compound Example No. | IC$_{50}$ Values for Inhibition of Cytokine Release (nM) | | | |
|---|---|---|---|---|
| | PBMCs | | | HT29 cells |
| | IL-8 | IL-2 | IFNγ | IL-8 |
| 1 | 1.1 | 61.2 | 3.8 | — |
| 2 | 1.0 | 76.1 | 2.9 | 1.7 |
| 3 | 2.8 | 180.8 | 18.4 | 14.5 |
| 4 | 5.6 | — | — | — |
| 5 | 8.7 | — | — | 7.3 |
| 6 | 1.9 | — | 15.5 | 5.3 |
| 7 | 4.6 | — | — | — |
| 8 | 1.3 | 41.4 | 2.2 | — |
| 9 | 3.5 | 42.7 | 9.4 | 4.3 |
| 10 | 2.0 | 88.6 | 31.3 | 8.2 |
| 11 | 2.3 | 80.6 | 10.5 | 15.8 |
| 12 | 3.6 | 67.0 | 8.6 | 8.6 |
| 13 | 6.4 | 203.7 | 50.4 | 18.2 |
| 14 | 3.3 | 39.2 | 16.3 | — |
| 15(a) | 3.6 | 43.2 | 27.2 | 4.2 |
| 15(b) | 4.5 | — | — | — |
| 15(c) | 1.6 | — | — | 3.6 |
| 15(d) | 6.2 | — | — | — |
| 15(e) | 4.7 | 25.6 | 60.4 | — |
| 15(f) | 26.2 | — | — | — |
| 15(g) | 1.9 | — | — | — |
| 15(h) | 4.6 | — | — | — |
| 15(i) | 1.5 | — | — | — |
| 15(j) | 3.2 | — | — | — |
| 15(k) | 5.6 | — | — | — |
| 15(l) | 17.5 | — | — | — |
| 15(m) | 16.0 | — | — | — |
| 15(n) | 13.5 | — | — | — |
| 15(o) | 20.4 | — | — | — |
| 15(p) | 9.4 | — | — | — |
| 15(q) | 6.2 | — | 1635.0 | — |
| 15(r) | 4.8 | — | — | — |
| 15(s) | 1.4 | — | — | — |
| 15(t) | 0.5 | — | — | — |
| 15(u) | 7.9 | — | — | — |
| 15(v) | 2.8 | — | — | — |
| 15(w) | 10.5 | — | — | — |
| 15(x) | 6.1 | 623.7 | 35.9 | — |
| 15(y) | 0.9 | — | — | — |
| 15(z) | 36.1 | — | — | — |
| 15(aa) | 0.8 | 58.6 | 14.7 | — |
| 15(ab) | 5.5 | — | — | — |
| 15(ac) | 9.1 | — | — | — |
| 15(ad) | 3.7 | 1109.3 | 16.2 | — |
| 15(ae) | 3.9 | — | — | — |
| 15(af) | 2.7 | — | — | — |
| 15(ag) | 9.8 | — | — | — |
| 15(ah) | 299.3 | — | — | — |
| 15(ai) | 3.7 | — | — | — |
| 15(aj) | 1.8 | — | — | — |

TABLE 2-continued

Results from cellular assays in PBMCs and HT29 cells
(the protocols for which are described by assays (b) to (d) above).

| Test Compound Example No. | IC$_{50}$ Values for Inhibition of Cytokine Release (nM) | | | |
|---|---|---|---|---|
| | PBMCs | | | HT29 cells |
| | IL-8 | IL-2 | IFNγ | IL-8 |
| 15(ak) | 26.0 | — | — | — |
| 15(al) | 3.7 | — | — | — |
| 15(am) | 6.1 | — | — | — |
| 15(an) | 2.7 | 251.3 | 6.2 | — |
| 15(ao) | 4.1 | — | — | — |
| 15(ap) | 48.3 | — | — | — |
| 15(aq) | 4.4 | — | — | — |
| 15(ar) | 0.8 | — | — | — |
| 16 | 1.7 | 7.7 | 4.3 | 1.5 |
| 17 | 0.9 | 30.5 | 4.9 | 2.0 |
| 18 | 2.1 | 19.4 | 8.2 | — |
| 19 | 6.2 | 256.8 | 26.8 | 8.6 |
| 20 | 2.5 | 10.5 | 7.9 | 3.3 |
| 21 | 3.2 | — | — | — |
| 22 | 3.3 | — | — | — |
| 23 | 6.8 | — | — | — |
| 24 | 3.1 | 276.4 | 64.0 | — |
| 25 | 5.3 | 175.1 | 29.5 | — |
| 26 | 2.2 | — | — | — |
| 27 | 1.0 | — | — | — |
| 28 | 2.5 | 63.3 | 1.4 | — |
| 29 | 0.8 | — | — | — |
| 30 | 1.7 | 94.5 | 6.4 | — |
| 31 | 2.6 | — | — | — |
| 32 | 1.8 | — | — | — |
| 33 | 1.7 | 116.9 | 11.0 | — |
| 34 | 1.2 | — | — | — |
| 35 | 3.4 | 221.2 | 10.9 | — |
| 36 | 1.1 | — | — | — |
| 37 | 1.7 | 48.0 | 0.7 | — |
| 38(a) | 3.8 | — | — | 25.7 |
| 38(b1) | 8.3 | — | — | — |
| 38(b2) | 6.0 | — | — | — |
| 38(c) | 1.7 | — | — | 7.3 |
| 38(d) | 4.5 | 1653.7 | 105.8 | — |
| 38(e) | 2.9 | — | — | 15.9 |
| 38(f) | 5.5 | 75.8 | 16.5 | 4.8 |
| 38(g) | 3.3 | 1603.4 | 22.5 | — |
| 38(h) | 2.7 | 160.4 | 17.7 | — |
| 38(i) | 11.4 | — | — | — |
| 38(j) | 12.5 | — | — | — |
| 38(k) | 2.1 | 281.4 | 14.6 | — |
| 38(l) | 5.9 | — | — | — |
| 38(m) | 2.0 | 93.8 | 7.0 | — |
| 38(n) | 1.4 | 347.5 | 14.1 | — |
| 38(o) | 1.3 | 60.8 | 7.8 | — |
| 38(p) | 7.2 | — | — | — |
| 38(q) | 1.4 | 443.0 | 26.1 | — |
| 38(r) | 1.9 | 153.3 | 9.8 | 25.9 |
| 38(s) | 5.3 | 190.3 | 26.7 | — |
| 38(t) | 0.7 | 287.9 | 7.4 | — |
| 38(u) | 1.0 | 170.7 | 2.9 | 2.6 |
| 38(v) | 1.7 | 84.5 | 8.1 | — |
| 38(w) | 4.0 | — | — | — |
| 38(x) | 4.1 | — | — | — |
| 38(y) | 0.5 | 28.3 | 7.9 | — |
| 38(z) | 0.6 | — | — | — |
| 38(aa) | 2.5 | — | — | — |
| 38(ab) | 1.4 | 317.3 | 10.9 | — |
| 38(ac) | 0.4 | — | — | — |
| 38(ad) | 2.2 | 214.1 | 10.9 | — |
| 38(ae) | 1.2 | — | — | — |
| 38(af) | 2.6 | 63.3 | 4.5 | — |
| 38(ag) | 0.6 | — | — | — |
| 38(ah) | 2.3 | 350.1 | 10.6 | — |
| 38(ai) | 1.6 | 91.7 | 11.1 | — |
| 38(aj) | 2.1 | 340.5 | 9.6 | — |
| 38(ak) | 1.2 | — | — | — |
| 38(al) | 7.2 | — | — | — |
| 38(am) | 6.2 | — | — | — |
| 38(an) | 3.8 | 81.8 | 8.2 | — |
| 38(ao) | 2.7 | 219.4 | 15.7 | — |
| 38(ap) | 4.5 | — | — | — |
| 39 | 31.4 | — | — | — |
| 40 | 2.7 | 179.2 | 5.2 | 3.0 |
| 41 | 2.9 | 184.2 | 6.9 | 2.2 |
| 42 | 4.3 | — | — | 2.0 |
| 43 | 1.4 | 30.4 | 2.8 | 3.7 |
| 44 | 1.3 | 28.3 | 2.3 | 5.2 |
| 45 | 1.2 | 36.4 | 5.2 | 8.0 |
| 46 | 0.8 | 47.3 | 2.8 | 2.8 |
| 47 | 2.2 | 57.1 | 3.0 | 26.1 |
| 48 | 0.4 | 115.9 | 3.7 | — |
| 49 | 0.8 | 91.0 | 5.7 | — |
| 50 | 1.2 | 30.1 | 0.9 | — |
| 51 | 1.3 | 100.7 | 75.2 | — |
| 52 | 2.8 | 43.5 | 5.5 | — |
| 53 | 1.1 | 52.5 | 6.0 | — |
| 54 | 1.5 | 37.9 | 3.7 | — |
| 55 | 0.6 | 31.2 | 6.2 | — |
| 56 | 1.2 | 234.2 | 9.5 | — |
| 57 | 1.1 | 92.9 | 7.8 | — |
| 58 | 1.4 | 586.9 | 3.2 | — |
| 59 | 1.7 | 55.6 | 2.9 | — |
| 60 | 2.4 | 101.3 | 7.0 | — |
| 61 | 1.9 | 7.8 | 1.6 | — |
| 62 | 2.4 | 24.9 | 4.8 | — |
| 63 | 2.5 | 17.5 | 7.7 | — |
| 64 | 2.6 | 62.7 | 13.3 | — |
| 65 | 4.3 | 31.3 | 7.6 | — |
| 66 | 2.2 | 60.9 | 7.7 | — |
| 67 | 5.6 | — | — | — |
| 68 | 3.8 | 40.6 | 8.0 | — |
| 69 | 2.3 | 75.7 | 7.6 | — |
| 70 | 2.3 | 98.1 | 11.1 | — |
| 71 | 3.4 | 33.7 | 7.2 | — |
| 72 | 2.1 | 156.1 | 7.5 | — |
| 73 | 1.5 | 60.1 | 6.3 | — |
| 74 | 1.6 | — | — | — |
| 75 | 1.6 | 115.3 | 3.0 | — |
| 76 | 41.5 | — | — | — |
| 77 | 0.9 | 18.9 | 2.3 | — |
| 78 | 23.0 | — | — | — |
| 79(a) | 5.1 | — | — | — |
| 79(b) | 7.4 | — | — | — |
| 79(c) | 7.0 | — | — | — |
| 79(d) | 3.9 | 624.3 | 14.6 | — |
| 79(e) | 4.1 | 51.9 | 6.9 | — |
| 79(f) | 3.9 | — | — | — |
| 79(g) | 5.3 | — | — | — |
| 79(h) | 16.4 | — | — | — |
| 79(i) | 12.2 | — | — | — |
| 79(j) | 15.3 | — | — | — |
| 79(k) | 7.0 | — | — | — |
| 79(l) | 22.5 | — | — | — |
| 79(m) | 1.8 | — | — | — |
| 80 | 4.5 | 415.4 | 6.6 | — |
| 81 | 0.4 | — | — | — |
| 82 | 1.7 | — | — | — |
| 83 | 1.5 | — | — | — |
| 84 | 1.8 | — | — | — |

As illustrated in Table 3a below, compounds of the examples of the present invention are, for the most part, markedly less active than the Reference Compound (N-(4-(4-(3-(3-tert-butyl-1-p-tolyl-1H-pyrazol-5-yl)ureido)naphthalen-1-yloxy)pyridin-2-yl)-2-methoxyacetamide) in assay (g) above, which measures impact on cell division (mitosis) in PBMCs.

TABLE 3a

Effect of compounds of the examples on cell division in PBMCs
(NT = not tested)

| Test compound | % Inhibition of mitosis at 5 μg/mL |
|---|---|
| Reference compound | 87.8[a] |
| 1 | NT |
| 2 | 58.9 |
| 3 | 29.4 |
| 4 | NT |
| 5 | NT |
| 6 | 52.4 |
| 7 | NT |
| 8 | 58.1 |
| 9 | 50.8 |
| 10 | 39.3 |
| 11 | 61.0 |
| 12 | 23.2 |
| 13 | 13.9 |
| 14 | 51.9 |
| 15(a) | 56.8 |
| 15(b) | NT |
| 15(c) | NT |
| 15(d) | NT |
| 15(e) | NT |
| 15(f) | NT |
| 15(g) | NT |
| 15(h) | NT |
| 15(i) | NT |
| 15(j) | NT |
| 15(k) | NT |
| 15(l) | NT |
| 15(m) | NT |
| 15(n) | NT |
| 15(o) | NT |
| 15(p) | NT |
| 15(q) | 12.9 |
| 15(r) | NT |
| 15(s) | NT |
| 15(t) | NT |
| 15(u) | NT |
| 15(v) | NT |
| 15(w) | NT |
| 15(x) | 18.4 |
| 15(y) | NT |
| 15(z) | NT |
| 15(aa) | 98.1 |
| 15(ab) | NT |
| 15(ac) | NT |
| 15(ad) | 31.0 |
| 15(ae) | NT |
| 15(af) | NT |
| 15(ag) | NT |
| 15(ah) | NT |
| 15(ai) | NT |
| 15(aj) | NT |
| 15(ak) | NT |
| 15(al) | NT |
| 15(am) | NT |
| 15(an) | 50.3 |
| 15(ao) | NT |
| 15(ap) | NT |
| 15(aq) | NT |
| 15(ar) | NT |
| 16 | 43.3 |
| 17 | 41.3 |
| 18 | NT |
| 19 | 36.9 |
| 20 | 55.0 |
| 21 | NT |
| 22 | NT |
| 23 | NT |
| 24 | 37.9 |
| 25 | 24.5 |
| 26 | NT |
| 27 | 52.0 |
| 28 | 54.4 |
| 29 | 49.4 |
| 30 | 48.7 |
| 31 | NT |
| 32 | NT |
| 33 | 31.3 |
| 34 | 81.1 |
| 35 | 50.6 |
| 36 | 86.6 |
| 37 | 43.2 |
| 38(a) | 86.2 |
| 38(b1) | NT |
| 38(b2) | NT |
| 38(c) | 90.2 |
| 38(d) | 28.1 |
| 38(e) | 41.6 |
| 38(f) | 37.8 |
| 38(g) | 28.8 |
| 38(h) | 30.3 |
| 38(i) | NT |
| 38(j) | NT |
| 38(k) | 70.5 |
| 38(l) | NT |
| 38(m) | 77.4 |
| 38(n) | 66.1 |
| 38(o) | 83.2 |
| 38(p) | NT |
| 38(q) | 82.1 |
| 38(r) | 56.1 |
| 38(s) | NT |
| 38(t) | 77.3 |
| 38(u) | 72.2 |
| 38(v) | NT |
| 38(w) | 23.9 |
| 38(x) | 35.0 |
| 38(y) | 65.7 |
| 38(z) | NT |
| 38(aa) | NT |
| 38(ab) | 30.7 |
| 38(ac) | NT |
| 38(ad) | 14.5 |
| 38(ae) | NT |
| 38(af) | 89.3 |
| 38(ag) | NT |
| 38(ah) | 6.7 |
| 38(ai) | 67.6 |
| 38(aj) | −1.0 |
| 38(ak) | NT |
| 38(al) | NT |
| 38(am) | NT |
| 38(an) | 30.1 |
| 38(ao) | 78.0 |
| 38(ap) | NT |
| 39 | NT |
| 40 | 44.3 |
| 41 | 36.0 |
| 42 | 29.9 |
| 43 | 62.1 |
| 44 | 42.8 |
| 45 | 49.6 |
| 46 | 45.8 |
| 47 | 30.1 |
| 48 | 35.6 |
| 49 | 43.9 |
| 50 | 57.7 |
| 51 | 28.0 |
| 52 | 46.8 |
| 53 | 22.3 |
| 54 | 51.9 |
| 55 | 51.7 |
| 56 | 17.6 |
| 57 | 50.6 |
| 58 | 2.9 |
| 59 | 30.9 |
| 60 | 47.5 |
| 61 | 68.7 |
| 62 | 54.1 |
| 63 | 45.1 |
| 64 | 32.4 |

TABLE 3a-continued

Effect of compounds of the examples on cell division in PBMCs
(NT = not tested)

| Test compound | % Inhibition of mitosis at 5 μg/mL |
|---|---|
| 65 | 8.7 |
| 66 | 46.4 |
| 67 | NT |
| 68 | −0.6 |
| 69 | 8.9 |
| 70 | 62.8 |
| 71 | 48.3 |
| 72 | 36.8 |
| 73 | 19.8 |
| 74 | NT |
| 75 | 13.9 |
| 76 | NT |
| 77 | 58.7 |
| 78 | NT |
| 79(a) | NT |
| 79(b) | NT |
| 79(c) | NT |
| 79(d) | 19.9 |
| 79(e) | 72.4 |
| 79(f) | NT |
| 79(g) | NT |
| 79(h) | NT |
| 79(i) | NT |
| 79(j) | NT |
| 79(k) | NT |
| 79(l) | NT |
| 79(m) | NT |
| 80 | NT |
| 81 | NT |
| 82 | NT |
| 83 | NT |
| 84 | NT |

<sup>a</sup>See, for example, the value reported in WO 2013/050757.

As illustrated in Table 3b below, compounds of the examples of the present invention did not elicit any substantial β-catenin induction when studied in assay (m) above. Thus, the potential of those compounds to increase cellular concentrations of β-catenin was found to be negative in that their inductive effect at various test concentrations was substantially less than the effect produced by the Reference Compound at 1 μg/mL.

TABLE 3b

Effect of compounds of the examples on β-catenin induction, expressed as percentage relative to Reference Compound (NT = not tested) (the protocol for which is described by assay (m) above).

| Test compound | % β-catenin induction Concentration of test compound | | |
|---|---|---|---|
| | 1 μg/mL | 5 μg/mL | 10 μg/mL |
| Reference compound | 100 | NT | NT |
| 1 | NT | NT | NT |
| 2 | 4.0 | 32.5 | 31.5 |
| 3 | 5.7 | 9.7 | 7.3 |
| 4 | NT | NT | NT |
| 5 | NT | NT | NT |
| 6 | 1.0 | 29.0 | 65.0 |
| 7 | NT | NT | NT |
| 8 | 2.5 | 22.5 | 26.5 |
| 9 | 4.5 | 5.5 | 0.0 |
| 10 | −2.5 | −6.0 | −4.0 |
| 11 | 5.0 | 19.7 | 27.3 |
| 12 | −0.5 | 5.0 | 6.0 |
| 13 | −4.0 | 6.5 | 9.5 |
| 14 | −0.5 | 22.0 | 25.5 |
| 15(a) | −4.0 | −5.0 | −3.0 |
| 15(b) | NT | NT | NT |
| 15(c) | 5.5 | 36.0 | 33.0 |
| 15(d) | 11.0 | 92.0 | 31.0 |
| 15(e) | 2.0 | 20.5 | 32.5 |
| 15(f) | NT | NT | NT |
| 15(g) | 15.0 | 94.0 | 94.0 |
| 15(h) | NT | NT | NT |
| 15(i) | NT | NT | NT |
| 15(j) | NT | NT | NT |
| 15(k) | NT | NT | NT |
| 15(l) | NT | NT | NT |
| 15(m) | −3.0 | 5.0 | 5.0 |
| 15(n) | NT | NT | NT |
| 15(o) | NT | NT | NT |
| 15(p) | NT | NT | NT |
| 15(q) | 5.0 | 9.5 | 2.5 |
| 15(r) | NT | NT | NT |
| 15(s) | NT | NT | NT |
| 15(t) | NT | NT | NT |
| 15(u) | NT | NT | NT |
| 15(v) | NT | NT | NT |
| 15(w) | NT | NT | NT |
| 15(x) | 7.0 | 4.0 | 4.0 |
| 15(y) | NT | NT | NT |
| 15(z) | NT | NT | NT |
| 15(aa) | 50.5 | 58.5 | 49.5 |
| 15(ab) | NT | NT | NT |
| 15(ac) | NT | NT | NT |
| 15(ad) | 12.0 | 36.0 | 49.0 |
| 15(ae) | NT | NT | NT |
| 15(af) | −2.0 | 13.0 | 32.0 |
| 15(ag) | NT | NT | NT |
| 15(ah) | NT | NT | NT |
| 15(ai) | NT | NT | NT |
| 15(aj) | NT | NT | NT |
| 15(ak) | NT | NT | NT |
| 15(al) | NT | NT | NT |
| 15(am) | NT | NT | NT |
| 15(an) | 1.5 | 11.5 | 13.5 |
| 15(ao) | NT | NT | NT |
| 15(ap) | NT | NT | NT |
| 15(aq) | NT | NT | NT |
| 15(ar) | NT | NT | NT |
| 16 | 0.0 | −3.0 | −6.5 |
| 17 | −2.0 | −7.0 | −5.5 |
| 18 | 6.5 | 35.5 | 39.0 |
| 19 | 2.5 | 9.0 | 13.0 |
| 20 | 2.5 | 20.5 | 16.5 |
| 21 | NT | NT | NT |
| 22 | NT | NT | NT |
| 23 | NT | NT | NT |
| 24 | −3.0 | 13.0 | 16.5 |
| 25 | 1.0 | 8.0 | 17.5 |
| 26 | NT | NT | NT |
| 27 | 5.7 | 13.0 | 13.3 |
| 28 | 3.0 | 6.7 | 11.3 |
| 29 | 6.5 | 9.0 | 45.0 |
| 30 | 6.5 | 23.5 | 1.0 |
| 31 | NT | NT | NT |
| 32 | NT | NT | NT |
| 33 | −1.0 | 3.5 | 9.5 |
| 34 | 2.0 | 28.5 | 23.0 |
| 35 | 5.5 | 16.5 | 23.5 |
| 36 | 17.5 | 84.5 | 27.5 |
| 37 | 2.0 | 15.5 | 25.5 |
| 38(a) | 5.0 | 10.7 | 19.0 |
| 38(b1) | NT | NT | NT |
| 38(b2) | NT | NT | NT |
| 38(c) | 3.5 | 16.0 | 28.5 |
| 38(d) | 2.5 | 19.5 | 30.0 |
| 38(e) | 2.0 | 30.5 | 32.5 |
| 38(f) | 2.0 | 3.3 | 8.3 |
| 38(g) | 4.5 | 24.5 | 38.0 |

TABLE 3b-continued

Effect of compounds of the examples on β-catenin induction, expressed as percentage relative to Reference Compound (NT = not tested) (the protocol for which is described by assay (m) above).

| Test compound | % β-catenin induction Concentration of test compound | | |
|---|---|---|---|
| | 1 µg/mL | 5 µg/mL | 10 µg/mL |
| 38(h) | 1.5 | 4.0 | 6.0 |
| 38(i) | NT | NT | NT |
| 38(j) | NT | NT | NT |
| 38(k) | 10.5 | 39.5 | 52.0 |
| 38(l) | NT | NT | NT |
| 38(m) | 3.0 | 23.0 | 37.0 |
| 38(n) | 2.0 | 21.0 | 23.5 |
| 38(o) | 13.0 | 38.0 | 35.0 |
| 38(p) | NT | NT | NT |
| 38(q) | 11.5 | 41.5 | 57.5 |
| 38(r) | NT | NT | NT |
| 38(s) | NT | NT | NT |
| 38(t) | NT | NT | NT |
| 38(u) | NT | NT | NT |
| 38(v) | NT | NT | NT |
| 38(w) | NT | NT | NT |
| 38(x) | NT | NT | NT |
| 38(y) | NT | NT | NT |
| 38(z) | NT | NT | NT |
| 38(aa) | NT | NT | NT |
| 38(ab) | NT | NT | NT |
| 38(ac) | NT | NT | NT |
| 38(ad) | NT | NT | NT |
| 38(ae) | NT | NT | NT |
| 38(af) | NT | NT | NT |
| 38(ag) | NT | NT | NT |
| 38(ah) | NT | NT | NT |
| 38(ai) | NT | NT | NT |
| 38(aj) | NT | NT | NT |
| 38(ak) | NT | NT | NT |
| 38(al) | NT | NT | NT |
| 38(am) | NT | NT | NT |
| 38(an) | NT | NT | NT |
| 38(ao) | NT | NT | NT |
| 38(ap) | NT | NT | NT |
| 39 | NT | NT | NT |
| 40 | −2.0 | −2.0 | −0.5 |
| 41 | −1.0 | −1.5 | 1.5 |
| 42 | −5.0 | 12.0 | 20.5 |
| 43 | 7.5 | 19.5 | 20.5 |
| 44 | 5.0 | 8.0 | 11.0 |
| 45 | NT | NT | NT |
| 46 | NT | NT | NT |
| 47 | NT | NT | NT |
| 48 | NT | NT | NT |
| 49 | NT | NT | NT |
| 50 | NT | NT | NT |
| 51 | NT | NT | NT |
| 52 | NT | NT | NT |
| 53 | NT | NT | NT |
| 54 | NT | NT | NT |
| 55 | NT | NT | NT |
| 56 | NT | NT | NT |
| 57 | NT | NT | NT |
| 58 | NT | NT | NT |
| 59 | NT | NT | NT |
| 60 | NT | NT | NT |
| 61 | NT | NT | NT |
| 62 | NT | NT | NT |
| 63 | NT | NT | NT |
| 64 | NT | NT | NT |
| 65 | NT | NT | NT |
| 66 | NT | NT | NT |
| 67 | NT | NT | NT |
| 68 | NT | NT | NT |
| 69 | NT | NT | NT |
| 70 | NT | NT | NT |
| 71 | NT | NT | NT |
| 72 | NT | NT | NT |
| 73 | NT | NT | NT |
| 74 | NT | NT | NT |
| 75 | NT | NT | NT |
| 76 | NT | NT | NT |
| 77 | NT | NT | NT |
| 78 | NT | NT | NT |
| 79(a) | NT | NT | NT |
| 79(b) | NT | NT | NT |
| 79(c) | NT | NT | NT |
| 79(d) | NT | NT | NT |
| 79(e) | NT | NT | NT |
| 79(f) | NT | NT | NT |
| 79(g) | NT | NT | NT |
| 79(h) | NT | NT | NT |
| 79(i) | NT | NT | NT |
| 79(j) | NT | NT | NT |
| 79(k) | NT | NT | NT |
| 79(l) | NT | NT | NT |
| 79(m) | NT | NT | NT |
| 80 | NT | NT | NT |
| 81 | NT | NT | NT |
| 82 | NT | NT | NT |
| 83 | NT | NT | NT |
| 84 | NT | NT | NT |

As illustrated in Table 4 below, the compounds of Examples 9, 13, 14 and 30 were also screened in in vivo assay (iv) above, as conducted over 2 days, and employing a self-microemulsifying drug delivery system (SMEDDS) as vehicle comprising a defined mixture of one or more oils, surfactants, solvents and co-surfactants. Histopathology analysis revealed that the compounds of Examples 9, 13, 14 and 30 displayed significant activity in this in vivo model of colonic inflammation. In particular, the compounds of Examples 9, 13 and 30, when dosed orally at 5 mg/kg, demonstrated marked improvements in ulcer grade and epithelial repair compared to the vehicle control. Furthermore, the compounds of Examples 9, 13, 14 and 30 produced marked reductions in inflammatory cell infiltrate in the reticular and laminar propria zone.

TABLE 4

Effect of compounds of the examples on TNBS-induced colitis in mice.

| Experiment no. | Treatment group | TNBS | | |
|---|---|---|---|---|
| | | N | Ulcer grade | LP inflammation |
| 1 | Non-diseased | 1 | 0.2 ± 0.2 | 0.3 ± 0.2 |
| 1 | TNBS + Vehicle | 1 | 4.3 ± 0.2 | 4.6 ± 0.1 |
| 1 | TNBS + Example 9 (5 mg/kg) | 1 | 3.6 ± 0.3 | 2.9 ± 0.3 |
| 2 | Non-diseased | 6 | 0.0 ± 0.0 | 0.2 ± 0.2 |
| 2 | TNBS + Vehicle | 24 | 4.0 ± 0.4 | 4.8 ± 0.1 |
| 2 | TNBS + Example 13 (5 mg/kg) | 12 | 2.6 ± 0.7 | 2.8 ± 0.5 |
| 2 | TNBS + Example 14 (5 mg/kg) | 12 | 3.5 ± 0.5 | 3.6 ± 0.2 |
| 3 | Non-diseased | 6 | 0.0 ± 0.0 | 0.2 ± 0.2 |
| 3 | TNBS + Vehicle | 24 | 4.0 ± 0.3 | 4.5 ± 0.2 |
| 3 | TNBS + Example 30 (5 mg/kg) | 12 | 3.1 ± 0.4 | 2.5 ± 0.4 |

As illustrated in Table 5 below, the compound of Example 37 significantly reduced cytokine levels in both the anterior and posterior segments of the eyes of rats treated with intravitreal endotoxin LPS (see assay (vi) above).

TABLE 5

Effect of the compound of Example 37 on cytokine levels and cell counts in the eyes of LPS-stimulated rats.

| Treatment | n | IL-1β (pg/mL) Anterior tissue | IL-1β (pg/mL) Posterior tissue | Cell counts |
|---|---|---|---|---|
| Non-diseased | 5 | 8.2 ± 3.5 | 33.3 ± 19.0 | 2.4 ± 0.4 |
| Vehicle control | 8 | 1404.3 ± 238.4 | 777.3 ± 135.3 | 75.6 ± 16.5 |
| Dexamethasone (1 mg/mL) | 8 | 313.9 ± 109.6 | 215.2 ± 88.5 | 30.1 ± 6.4 |
| Example 37 (1 mg/mL) | 8 | 330.4 ± 94.2 | 285.8 ± 96.4 | 32.6 ± 9.5 |
| Example 37 (0.1 mg/mL) | 8 | 480.1 ± 113.7 | 319.6 ± 64.8 | 39.1 ± 7.1 |

Summary of Additional Studies

Determination of Solubilities in Fasted-State Simulated Colonic Fluid (FaSSCoF)

The solubilities of compounds of the invention in FaSS-CoF at pH 6.5 are determined using a modification of a previously-reported procedure (Vertzoni, M., et al. *Pharm. Res.* 2010, 27, 2187-2196). In place of the bile salt extract employed in the original procedure (which extract is no longer available), the modified procedure uses a mixture of sodium taurochlorate (0.15 g), glycocholic acid (0.15 g), ursodeoxycholic acid (0.05 g), cholic acid (0.05 g), and glycodeoxycholic acid (0.05 g). These five bile acids are ground together with a mortar and pestle to produce a fine white powder that is incorporated into the FaSSCoF, as outlined below.

FaSSCoF Medium:

Tris(hydroxymethyl)aminomethane (Tris; 0.275 g) and maleic acid (0.44 g) are dissolved in water (35 mL) to give a solution whose pH is adjusted to 6.5 by treatment with 0.5M NaOH (ca. 12 mL). The solution is then made up to 50 mL with water. A portion of this Tris/maleate buffer solution (ca. 25 mL) is added to a 0.5 L round-bottomed flask, before being treated with 0.00565 g of the bile acid mixture described above. Solutions of phosphatidylcholine (0.0111 g) in DCM (0.15 mL) and palmitic acid (0.0013 g) in DCM (0.15 mL) are added, then the organic solvent is evaporated off under reduced pressure at 40° C. until a clear solution, with no perceptible DCM odour, is achieved. The volume of the evaporated solution is adjusted to 50 mL by addition of the remainder of Tris/maleate buffer, then BSA (0.115 g) is added, before being dissolved by gentle agitation.

Solubility Determination:

Test compounds are suspended in the pH 6.5 FaSSCoF medium to give a maximum final concentration of ca. 6 mg/mL. The suspensions are equilibrated at 25° C. for 24 h, before being filtered through a glass fibre C filter. The filtrates are then diluted as appropriate for injection and quantification by HPLC with reference to a standard. Different volumes of the standard, diluted and undiluted sample solutions are injected and the solubilities are calculated using the peak areas determined by integration of the peak found at the same retention time as the principal peak in the standard injection.

As revealed below in Table 6, the compounds of Examples 72, 73, 77 and 84 exhibited solubilities in the FaSSCoF medium at pH 6.5 of in excess of 0.01 mg/mL.

TABLE 6

Solubilities measured for Examples 72, 73, 77 and 84 in FaSSCoF at pH 6.5.

| Test Compound | pH 6.5 FaSSCoF Solubility (mg/mL) | |
|---|---|---|
| Example No. | Run 1 | Run 2 |
| 72 | 0.0107 | 0.0112 |
| 73 | 0.0152 | 0.0166 |
| 77 | 0.0123 | 0.0130 |
| 84 | 0.015 | 0.016 |

ABBREVIATIONS

AcOH glacial acetic acid
aq Aqueous
5-ASA 5-aminosalicylic acid
ATP adenosine-5'-triphosphate
BALF bronchoalveolar lavage fluid
BID bis in die (twice-daily)
BINAP 2,2'-bis(diphenylphosphino)-1,1'-binaphthyl
BOP (benzotriazol-1-yloxy)tris(dimethylamino)phosphonium hexafluorophosphate
br broad
BrdU 5-bromo-2'-deoxyuridine
BSA bovine serum albumin
CatCart® catalytic cartridge
CDI 1,1-carbonyl-diimidazole
COPD chronic obstructive pulmonary disease
d doublet
dba dibenzylideneacetone
DBU 1,8-diazabicyclo[5.4.0]undec-7-ene
DCC dicyclohexylcarbodiimide
DCM dichloromethane
DIAD diisopropyl azodicarboxylate
DIPEA diisopropylethylamine
DMAP 4-dimethylaminopyridine
DMEM Dulbecco's modified eagle medium
DMF N,N-dimethylformamide
DMSO dimethyl sulfoxide
DPPA diphenylphosphoryl azide
d-U937 cells PMA differentiated U-937 cells
EDTA ethylenediaminetetraacetic acid
ELISA enzyme-linked immunosorbant assay
(ES⁻) electrospray ionization, negative mode
(ES⁺) electrospray ionization, positive mode
Et ethyl
Et$_3$N triethylamine
EtOAc ethyl acetate
EtOH ethanol
FACS fluorescence-activated cell sorting
FaSSCoF fasted state simulated colonic fluid
FBS foetal bovine serum
FCS foetal calf serum
fMLP formyl-methionyl-leucyl-phenylalanine
FRET fluorescence resonance energy transfer
GSK3α glycogen synthase kinase 3α
HATU 2-(1H-7-azabenzotriazol-1-yl)-1,1,3,3-tetramethyluronium hexafluorophosphate
HBEC primary human bronchial epithelial cells
HBSS Hank's balanced salt solution
HPLC high performance liquid chromatography
HPMC hydroxypropylmethylcellulose
h or hr hour(s)
HOAt 1-hydroxy-7-azabenzotriazole
HOBt hydroxybenzotriazole HRP horseradish peroxidise
HRV human rhinovirus
ICAM-1 inter-cellular adhesion molecule 1
IFNγ interferon-γ
IL interleukin
IPA isopropyl alcohol
iPrOAc isopropyl acetate
JNK c-Jun N-terminal kinase
LC liquid chromatography
Lck lymphocyte-specific protein tyrosine kinase
LPS lipopolysaccharide
m multiplet
(M+H)⁺ protonated molecular ion
MAPK mitogen-activated protein kinase
MAPKAP-K2 mitogen-activated protein kinase-activated protein kinase-2
mCPBA meta-chloroperbenzoic acid
Me methyl
MeCN acetonitrile
MeOH methanol
MHz megahertz
min or mins minute(s)
MMAD mass median aerodynamic diameter
MOI multiplicity of infection
MPO myeloperoxidase
MTT 3-(4,5-dimethylthiazol-2-yl)-2,5-diphenyltetrazolium bromide
MS mass spectrometry
m/z mass-to-charge ratio
NMP N-methyl pyrrolodinone
NMR nuclear magnetic resonance (spectroscopy)
OD optical density
PBMC peripheral blood mononuclear cell
PBS phosphate buffered saline
Ph phenyl
PHA phytohaemagglutinin
PMA phorbol myristate acetate
p-TsOH or pTSA 4-methylbenzenesulfonic acid (para-toluenesulfonic acid)
PyBOP (benzotriazol-1-yloxy)tripyrrolidinophosphonium hexafluorophosphate
q quartet
rt or RT room temperature
RP HPLC reverse phase high performance liquid chromatography
rpm revolutions per minute
RPMI Roswell Park Memorial Institute
RSV respiratory syncytical virus
s singlet
sat or satd saturated
SCID severe combined immunodeficiency
SCX solid supported cation exchange (resin)
SDS sodium dodecyl sulfate
$S_NAr$ nucleophilic aromatic substitution
Syk Spleen tyrosine kinase
t triplet
T3P 1-propanephosphonic acid cyclic anhydride
TBAF tetrabutylammonium fluoride
TBDMS tert-butyldimethylsilyl
$TCID_{50}$ 50% tissue culture infectious dose
TEA triethylamine
THF tetrahydrofuran
TFA trifluoroacetic acid
TGFβ transforming growth factor beta
TIPS triisopropylsilyl
TMB 3,3',5,5'-tetramethylbenzidine
TMS-Cl trimethylsilyl chloride
TNBS 2,4,6-trinitrobenzenesulfonic acid
TNFα tumor necrosis factor alpha
UV ultra violet
Prefixes n-, s-, i-, t- and tert- have their usual meanings: normal, secondary, iso, and tertiary.

What is claimed is:
1. A compound of formula I,

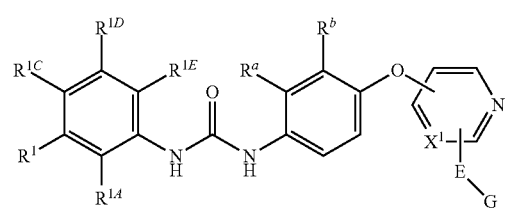

wherein
$R^1$ represents
  —$L^1$-C(O)N($R^{2a}$)$R^{2b}$,
  —$L^{2a}$-S(O)$_{0-1}$—$R^{2c1}$,
  —$L^{2b}$-S(O)$_2$—$R^{2c2}$,
  —$L^3$-P(O)$R^{2d}R^{2e}$,
  —CH$_2$N($R^{2d1}$)-Q-$R^{2f}$,
  —O—S(O)$_2$—N($R^{2g}$)$R^{2h}$,
  —N=S(O)(CH$_3$)$_2$,
  —S(=O)(=N$R^{2i}$)CH$_3$ or
  —O—C($R^{2x}$)($R^{2y}$)($R^{2z}$);
$L^1$, $L^{2a}$, $L^{2b}$ and $L^3$ independently represent a bond, —C($R^{3a}$)($R^{3b}$)— or —OC($R^{3a}$)($R^{3b}$)—, wherein the O-atom of the latter substituent is attached to the phenyl ring,
or $L^1$, $L^{2b}$ or $L^3$ represents O;
$R^{2a}$ represents —[C($R^{3a}$)($R^{3b}$)]—[C$_{1-4}$ alkylene]-$R^{3c}$ or, when $L^1$ is not a bond, $R^{2a}$ may alternatively represent H or $R^4$;
$R^{2b}$ represents H or C$_{1-6}$ alkyl,
or, when $L^1$ is not a bond, $R^{2a}$ and $R^{2b}$, together with the N-atom to which they are attached, may alternatively form a 4- to 7-membered heterocyclic group that is fully saturated or partially unsaturated and which heterocyclic group contains one N atom (the atom to which $R^{2a}$ and $R^{2b}$ are attached) and, optionally, one or more further heteroatoms selected from the group consisting of O, S and N, and which heterocyclic group is optionally substituted by one or more substituents selected from the group consisting of halo, OH, oxo, C$_{1-4}$ alkyl and C$_{1-4}$ alkoxy;
$R^{3c}$ represents [O—CH$_2$(CH$_2$)$_{0-1}$CH$_2$]$_{1-12}$—$R^{5a}$, Het$^1$ or Het$^2$;
$R^{2c1}$ and $R^{2c2}$ independently represent
  methyl optionally substituted by one or more halo groups,
  Het$^1$,
  Het$^2$ or
  C$_{3-7}$ cycloalkyl optionally substituted by one or more substituents selected from the group consisting of C$_{1-2}$ alkyl, halo, OH and C$_{1-2}$ alkoxy,
or, when $L^{2a}$ is not a bond, $R^{2c1}$ may alternatively represent $R^{2c3}$,
or, when $L^{2b}$ is not a bond, $R^{2c2}$ may alternatively represent $R^{2c3}$;
$R^{2c3}$ represents C$_{2-7}$ alkyl, C$_{2-7}$ alkenyl, C$_{2-7}$ alkynyl or phenyl, which latter four groups are optionally substituted by one or more substituents selected from the group consisting of $C_{1-2}$ alkyl, halo, OH and $C_{1-2}$ alkoxy;

$R^{2d}$ represents $C_{1-4}$ alkyl;

$R^{2e}$ represents $C_{1-4}$ alkyl, $C_{3-6}$ cycloalkyl, $C_{1-4}$ alkoxy or OH;

or $R^{2d}$ and $R^{2e}$ together combine to form $C_{3-6}$ alkylene;

$R^{2d1}$ represents H or $R^{2d}$;

Q represents C(O) or $S(O)_2$;

$R^{2f}$ represents $R^4$ or, when Q represents C(O), $R^{2f}$ may alternatively represent H;

$R^{2g}$ and $R^{2h}$ independently represent H or $R^4$;

$R^{2i}$ represents H or methyl;

$R^{2x}$ represents $C_{1-6}$ alkyl substituted by one or more OH groups;

$R^{2y}$ and $R^{2z}$ independently represent H or $C_{1-4}$ alkyl optionally substituted by OH;

$R^{3a}$ and $R^{3b}$ represent, independently at each occurrence, H or methyl;

$R^4$ represents, independently at each occurrence, $Het^1$, $Het^2$, $C_{1-6}$ alkyl, $C_{3-7}$ cycloalkyl or phenyl, which latter three groups are optionally substituted by one or more substituents selected from the group consisting of $C_{1-2}$ alkyl, halo, oxo, OH, $C_{1-2}$ alkoxy and $N(R^{4a})R^{4b}$;

$R^{5a}$ represents $OR^{5b}$ or $N(R^{5c})R^{5d}$;

$R^{4a}$, $R^{4b}$ and $R^{5b}$ to $R^{5d}$ independently represent H or $C_{1-4}$ alkyl optionally substituted by one or more halo or OH substituents, or $R^{5c}$ and $R^{5d}$ or $R^{4a}$ and $R^{4b}$, together with the N-atom to which they are attached, form a 4- to 7-membered heterocyclic group that is fully saturated, partially unsaturated or fully aromatic and which heterocyclic group contains one N atom (the atom to which $R^{5C}$ and $R^{5d}$ or $R^{4a}$ and $R^{4b}$ are attached) and, optionally, one or more further heteroatoms selected from the group consisting of O, S and N, and which heterocyclic group is optionally substituted by one or more substituents selected from the group consisting of halo, OH, oxo, $C_{1-4}$ alkyl and $C_{1-4}$ alkoxy;

$R^{1A}$ represents
H, OH, halo, cyano,
$C_{1-6}$ alkyl, $C_{2-6}$ alkenyl, $C_{2-6}$ alkynyl, $C_{1-6}$ alkoxy, which latter four groups are optionally substituted by one or more substituents selected from the group consisting of $C_{1-2}$ alkyl, halo, OH, and $C_{1-2}$ alkoxy,
$Het^1$ or phenyl, which latter group is optionally substituted with one or more substituents selected from the group consisting of halo, $C_{1-2}$ alkyl and $C_{1-2}$ alkoxy;

$R^{1C}$ and $R^{1E}$ independently represent H, halo, cyano or methyl;

$R^{1D}$ represents trimethylsilyl, $Het^1$, $Het^2$, trifluoromethyl, $C_{2-7}$ alkyl, $C_{2-7}$ alkenyl, $C_{2-7}$ alkynyl, $C_{3-7}$ cycloalkyl or phenyl, which latter five groups are optionally substituted by one or more substituents selected from the group consisting of $C_{1-2}$ alkyl, halo, OH and $C_{1-2}$ alkoxy;

$Het^1$ represents, independently at each occurrence, a 5- to 10-membered heterocyclic group that is fully aromatic, which group contains one or more heteroatoms selected from the group consisting of N, O and S and which group is optionally substituted by one or more substituents selected from the group consisting of OH, halo, $N(R^{4a})R^{4b}$, $C_{1-2}$ alkyl and $C_{1-2}$ alkoxy, which latter two groups are optionally substituted by one or more halo atoms;

$Het^2$ represents, independently at each occurrence, a 4- to 8-membered heterocyclic group that is fully saturated or partially unsaturated, which group contains one or more heteroatoms selected from the group consisting of N, O and S and which group is optionally substituted by one or more substituents selected from the group consisting of OH, oxo, $N(R^{4a})R^{4b}$, $C_{1-2}$ alkyl and $C_{1-2}$ alkoxy;

$R^a$ and $R^b$, together with the C-atoms to which they are attached, form a fused phenyl or pyridyl ring, which latter two rings are optionally substituted by one or more substituents selected from the group consisting of $C_{1-3}$ alkyl, $C_{1-3}$ haloalkyl, cyano and halo, or one of $R^a$ and $R^b$ represents H, halo, cyano, $C_{1-3}$ alkyl or $C_{1-3}$ haloalkyl and the other independently represents halo, cyano, $C_{1-3}$ alkyl or $C_{1-3}$ haloalkyl, or $R^a$ and $R^b$ together combine to form $C_{3-5}$ alkylene or $C_{3-5}$ alkenylene, which latter two groups are optionally substituted by one or more substituents selected from the group consisting of $C_{1-3}$ alkyl, $C_{1-3}$ haloalkyl, cyano and halo;

$X^1$ represents CH or N;

E represents $N(G^1)$, O or S;

G represents
phenyl optionally substituted by one or more $Y^1$,
$Het^3$ optionally substituted by one or more $Y^2$,
$R^{6a}$ or
$C(O)R^{6b}$;

$G^1$ represents H or $C_{1-3}$ alkyl;

or G and $G^1$ together combine to form
$C_{3-6}$ n-alkylene,
$C_{4-5}$ n-alkylene interrupted between C2 and C3 by —O—, —S(O)$_{0-2}$- or —N(R$^c$)— or
$C_6$ n-alkylene interrupted between C2 and C3, or between C3 and C4, by —O—, —S(O)$_{0-2}$- or —N(R$^c$)—, any of which n-alkylene groups are optionally substituted by one or more substituents selected from the group consisting of halo, OH, oxo, $C_{1-4}$ alkyl and $C_{1-4}$ alkoxy, which latter two groups are optionally substituted by one or more halo atoms or by OH;

each $Y^1$ is independently selected from the group consisting of
halo, OH, cyano, $SF_5$, $CO_2H$, —OC(O)NH$_2$,
$P(O)R^{6c}R^{6d}$,
$E^1$-N(R$^{6e}$)R$^{6f}$,
$E^2$-S(O)$_2$R$^{6g}$,
$E^3$-[C(R$^{3a}$)(R$^{3b}$)(CH$_2$)$_{0-1}$CH$_2$—O]$_{2-8}$—R$^{6h}$,
—C≡C—R$^{6i}$,
—N=S(O)R$^{6j}$R$^{6k}$,
$Het^a$,
$C_{1-6}$ alkyl, $C_{3-6}$ cycloalkyl, alkoxy, $C_{3-6}$ cycloalkoxy, —S(O)$_{0-1}$—C$_{1-6}$ alkyl and —S(O)$_{0-1}$—C$_{3-6}$ cycloalkyl which latter six groups are optionally substituted by one or more substituents selected from the group consisting of halo, OH, $C_{1-3}$ alkyl, $C_{1-3}$ alkoxy and $C_{3-6}$ cycloalkyl;

each $Y^2$ independently represents oxo or $Y^1$;

$E^1$ represents
a direct bond,
—C(O)—,
—S(O)$_2$—,
—[C(O)]$_p$—C$_{1-8}$ alkylene,
—C(O)—NR$^{7a}$—CH$_2$—[C$_{1-7}$ alkylene]-,
-Q$^1$-CH$_2$—[C$_{1-5}$ alkylene]-,
the alkylene parts of which latter three groups are optionally substituted by one or more substituents selected from the group consisting of halo, $C_{1-3}$ alkyl and OH;

$E^2$ represents
a direct bond,
—O—,
—$NR^{7a}$—
$C_{1-6}$ alkylene or
-$Q^2$-$CH_2$—[$C_{1-5}$ alkylene]-,
the alkylene parts of which latter two groups are optionally substituted by one or more substituents selected from the group consisting of halo, $C_{1-3}$ alkyl and OH;

$E^3$ represents —C(O)$NR^{7a}$, —O— or $S(O)_{0-2}$;

$Q^1$ and $Q^2$ independently represent O or $S(O)_{0-2}$;

p represents 0 or 1;

$R^{6a}$ represents $C_{1-8}$ alkyl, wherein one or two non-adjacent C-atoms of the alkyl group, that are not linked directly to E, are optionally replaced by heteroatoms independently selected from the group consisting of O and N and/or wherein the alkyl group is substituted by one or more $R^8$ substituents;

$R^{6b}$ represents $C_{1-8}$ alkyl, wherein one C-atom of the alkyl group is, or two non-adjacent C-atoms of the alkyl group are, optionally replaced by heteroatoms independently selected from the group consisting of O and N and/or wherein the alkyl group is substituted by one or more $R^8$ substituents;

$R^{6c}$ and $R^{6d}$ independently represent $C_{1-3}$ alkyl or $C_{1-3}$ alkoxy, or $R^{6c}$ and $R^{6d}$ together combine to form $C_{4-6}$ alkylene;

$R^{6e}$ and $R^{6f}$ independently represent H, $Het^4$ or $C_{1-8}$ alkyl, which latter two groups are optionally substituted by $R^{7b}$ and/or one or more substituents selected from the group consisting of $C_{1-2}$ alkyl, halo, N($R^{7c}$)$R^{7d}$ and OH, or $R^{6e}$ and $R^{6f}$, together with the N-atom to which they are attached, form a 4- to 7-membered heterocyclic group that is fully saturated, partially unsaturated or fully aromatic and which heterocyclic group contains one N atom (the atom to which $R^{6e}$ and $R^{6f}$ are attached) and, optionally, one or more further heteroatoms selected from the group consisting of O, S and N, and which heterocyclic group is optionally substituted by one or more substituents selected from the group consisting of halo, OH, oxo, $C_{1-4}$ alkyl, $C_{3-7}$ cycloalkyl and $C_{1-4}$ alkoxy;

$R^{6g}$ represents $C_{1-6}$ alkyl, $C_{3-6}$ cycloalkyl or phenyl, which latter three groups are optionally substituted by one or more substituents selected from the group consisting of halo, OH, $Het^5$, $C_{1-3}$ alkyl, $C_{1-3}$ alkoxy and $C_{3-6}$ cycloalkyl;

$R^{6h}$, $R^{6i}$, $R^{6j}$ and $R^{6k}$ independently represent $C_{1-4}$ alkyl optionally substituted by one or more halo atoms, or $R^{6h}$ and $R^{6i}$ independently represent H;

$R^c$, $R^{7a}$, $R^{7c}$ and $R^{7d}$ represent, independently at each occurrence, H or $C_{1-3}$ alkyl;

$R^{7b}$ represents $C_{1-4}$ alkoxy, —(S)$_{0-2}$—$C_{1-4}$ alkyl, —S(O)$_{1-2}$—$C_{1-4}$ alkyl, phenyl or $Het^6$, which latter two groups are optionally substituted by one or more substituents selected from the group consisting of halo, $C_{1-4}$ alkyl, $C_{1-4}$ haloalkyl, $C_{3-7}$ cycloalkyl, $C_{1-4}$ alkoxy, OH, amino and cyano, and which $Het^6$ group may also be substituted by oxo;

$R^8$ represents, independently on each occurrence, halo, OH, oxo, $C_{1-4}$ alkoxy, $C_{3-8}$ cycloalkyl, $Het^7$ or phenyl, which latter four groups are optionally substituted by one or more substituents selected from the group consisting of halo, $C_{1-4}$ alkyl, $C_{1-4}$ haloalkyl, $C_{1-4}$ alkoxy, OH, amino and cyano, and which $Het^7$ group may also be substituted by oxo;

$Het^3$, $Het^4$, $Het^5$, $Het^6$ and $Het^7$ independently represent 4- to 10-membered heterocyclic groups that are fully saturated, partially unsaturated or fully aromatic, which heterocyclic groups contain one or more heteroatoms selected from the group consisting of N, O and S; and $Het^a$ represents a 5- or 6-membered heterocyclic group that is fully saturated, partially unsaturated or fully aromatic, which group contains one or more heteroatoms selected from the group consisting of N, O and S, and which group is optionally substituted by one or more substituents selected from the group consisting of halo, OH, oxo, $C_{1-3}$ alkyl, $C_{1-3}$ alkoxy and $C_{3-6}$ cycloalkyl;

or a pharmaceutically acceptable salt, solvate or isotopic derivative thereof.

2. A compound according to claim 1 that is a compound of formula Ia, Ib or Ic,

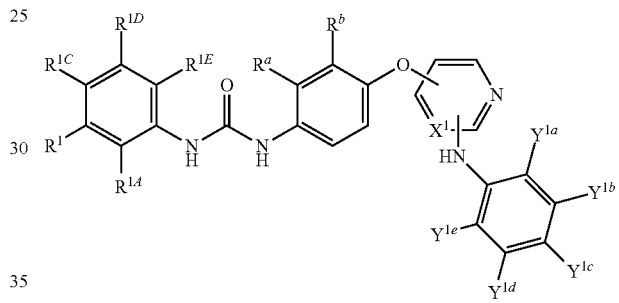

or a pharmaceutically acceptable salt, solvate or isotopic derivative thereof, wherein $R^1$, $R^{1A}$, $R^{1C}$, $R^{1D}$, $R^{1E}$, $R^a$, $R^b$, $X^1$, $Het^3$, $Y^2$ are $G^1$ as defined in claim 1 and:

$Y^{1a}$ to $Y^{1e}$ each independently represents H or $Y^1$ as defined in claim 1;

n represents 0, 1, 2, 3 or 4; and $R^6$ represents $CH_2$-phenyl, $C_{1-2}$ alkyl or —[C(O)]$_{0-1}$—$C_{1-4}$ alkylene-$Het^7$, wherein the $Het^7$ group is as defined in claim 1 and is optionally substituted by one or more substituents selected from the group consisting of halo, $C_{1-2}$ alkyl, $C_{1-2}$ haloalkyl and $C_{1-2}$ alkoxy.

3. A compound according to claim 1, wherein:
R$^1$ represents
-L$^1$-C(O)N(R$^{2a}$)R$^{2b}$,
-L$^{2a}$-S(O)—CH$_3$,
-L$^{2b}$-S(O)$_2$—CH$_3$,
-L$^3$-P(O)R$^{2d}$R$^{2e}$,
—OCH$_2$P(O)(CH$_3$)$_2$,
—O—S(O)$_2$—C$_{1-2}$ alkyl,
—CH$_2$N(R$^{2d1}$)-Q-C$_{1-3}$ alkyl,
—CH$_2$N(R$^{2d1}$)-Q-(CH$_2$)$_{1-3}$—N(R$^{4a}$)R$^{4b}$,
—O—CH$_2$CH$_2$—OH,
—O—CH(CH$_2$OH)$_2$, or
—O—CH$_2$C(CH$_2$OH)$_3$,
L$^1$, L$^{2a}$, L$^{2b}$ and L$^3$ independently represent a bond or —CH$_2$—;
R$^{2a}$ represents —[C(R$^{3a}$)(R$^{3b}$)]—[C$_{1-2}$ alkylene]-R$^{3c}$
or, when L$^1$ represents —CH$_2$—, R$^{2a}$ may alternatively represent H or C$_{1-2}$ alkyl, or R$^{2a}$ and R$^{2b}$, together with the N-atom to which they are attached, may form a 5- or 6-membered heterocyclic group that is fully saturated and which heterocyclic group contains one N atom (the atom to which R$^{2a}$ and R$^{2b}$ are attached) and, optionally, a further heteroatom selected from the group consisting of O, S and N, and which heterocyclic group is optionally substituted by one to three substituents selected from the group consisting of oxo and C$_{1-2}$ alkyl,
or R$^{2b}$ represents H or methyl;
R$^{2d1}$ represents H or methyl;
R$^{3b}$ and R$^{3b}$ independently represent H or methyl;
R$^{3c}$ represents Het$^1$, Het$^2$ or [O—CH$_2$CH$_2$]$_{2-5}$—R$^{5a}$;
R$^{2d}$ represents methyl or ethyl;
R$^{2e}$ represents methyl or ethyl,
or R$^{2d}$ and R$^{2e}$ together combine to form —(CH$_2$)$_{4-5}$-;
R$^{5a}$ represents N(R$^{5c}$)(R$^{5d}$) or O—C$_{1-2}$ alkyl; and/or
R$^{4a}$, R$^{4b}$, R$^{5c}$ and R$^{5d}$ independently represent H or methyl, or R$^{5c}$ and R$^{5d}$, together with the N-atom to which they are attached, form a 5- or 6-membered heterocyclic group that is fully saturated, partially unsaturated or fully aromatic and which heterocyclic group contains one N atom (the atom to which R$^{5c}$ and R$^{5d}$ are attached) and, optionally, one further heteroatom selected from the group consisting of O, S and N, and which heterocyclic group is optionally substituted by one or more substituents selected from the group consisting of OH, oxo and C$_{1-2}$ alkyl.

4. A compound as claimed in claim 1, wherein:
R$^{1A}$ represents H or C$_{1-2}$ alkoxy, which latter group is optionally substituted by one or more fluoro atoms;
R$^{1C}$ and R$^{1E}$ both represent H; and/or
R$^{1D}$ represents trimethylsilyl, —C(CH$_3$)$_2$—C≡CH, morpholinyl, C$_{3-6}$ alkyl or C$_{3-5}$ cycloalkyl, which latter group is optionally substituted by methyl.

5. A compound as claimed in claim 1, wherein:
Het$^1$ represents a 5- or 6-membered heterocyclic group that is fully aromatic, which group contains one N-atom and optionally contains one or two further heteroatoms selected from the group consisting of N, O and S, and which group is optionally substituted by one or more substituents selected from the group consisting of halo, methyl and methoxy; and/or
Het$^2$ represents a 4- to 6-membered heterocyclic group that is fully saturated or partially unsaturated, which group contains one or two heteroatoms selected from the group consisting of N, O and S and which group is optionally substituted by one or more substituents selected from the group consisting of oxo, methyl and methoxy.

6. A compound as claimed in claim 1, wherein X$^1$ represents CH and/or G$^1$ represents H or methyl.

7. A compound as claimed in claim 1, wherein R$^a$ and R$^b$, together with the C-atoms to which they are attached, form a fused phenyl ring.

8. A compound of formula 1 as claimed in claim 2, wherein:
at least two of Y$^{1a}$ to Y$^{1e}$ are H and the remainder of Y$^{1a}$ to Y$^{1e}$ are independently selected from the group consisting of H, halo, OH, cyano, —CH$_2$OH, —C(O)OH, —S(O)$_2$R$^{6g}$, —S(O)$_2$N(R$^{6e}$)R$^{6f}$—O—CH$_2$—[C$_{1-2}$ alkylene]-N(R$^{6e}$)R$^{6f}$, —P(O)(CH$_3$)$_2$, E$^1$-N(R$^{6e}$)R$^{6f}$, —C(O)N(R$^{6e}$)R$^{6f}$, —C(O)NH—CH$_2$—[C$_{1-2}$ alkylene]-N(R$^{6e}$)R$^{6f}$, —O—S(O)$_2$—C$_{1-4}$ alkyl, E$^3$-[CH$_2$CH$_2$—O]$_{2-5}$—R$^{6h}$, —C≡C—H, —N=S(O)(CH$_3$)$_2$ and C$_{1-2}$ alkyl or C$_{1-2}$ alkoxy, which latter two groups are optionally substituted by one or more fluoro atoms;
E$^1$ represents a direct bond or C$_{1-2}$ alkylene;
R$^{6e}$ and R$^{6f}$ independently represent
H,
C$_{1-5}$ alkyl optionally substituted by one to three OH groups or by Het$^6$ or
Het$^4$ optionally substituted by methyl,
or R$^{6e}$ and R$^{6f}$, together with the N-atom to which they are attached, form a 5- or 6-membered heterocyclic group that is fully saturated, partially unsaturated or fully aromatic and which heterocyclic group contains one N atom (the atom to which R$^{6e}$ and R$^{6f}$ are attached) and, optionally, one or two further heteroatoms selected from the group consisting of O, S and N, and which heterocyclic group is optionally substituted by one or more substituents selected from the group consisting of OH, oxo, methyl and methoxy;
E$^3$ represents —O— or —C(O)NH;
R$^{6g}$ represents C$_{1-2}$ alkyl or C$_{3-5}$ cycloalkyl; and/or
R$^{6h}$ represents H or methyl.

9. A compound according to claim 1, wherein:
Het$^3$ represents a 5- to 10-membered heterocyclic group that is partially unsaturated or fully aromatic, which heterocyclic group contains one to four heteroatoms selected from the group consisting of N, O and S,
or Het$^3$ represents a 5- or 6-membered heterocyclic group that is fully saturated, which heterocyclic group contains one or two heteroatoms selected from the group consisting of N, O and S;
each Y$^2$ independently represents oxo, OH, —N(R$^{6e}$)R$^{6f}$, C$_{1-2}$ alkoxy or C$_{1-2}$ alkyl, which latter two groups are optionally substituted by one or more fluoro atoms; and/or
n represents 0, 1 or 2.

10. A compound according to claim 2, wherein:
R$^6$ represents C$_{1-2}$ alkyl or —[C(O)]$_{0-1}$—(CH$_2$)$_{1-3}$-Het$^7$, wherein the Het$^7$ group is optionally substituted by one or more substituents selected from the group consisting of methyl and methoxy; and/or
Het$^7$ represents a 5- or 6-membered heterocyclic group that is fully saturated, partially unsaturated or fully aromatic, which heterocyclic group contains one to three heteroatoms selected from the group consisting of N, O and S.

11. A compound as claimed in claim 2 that is a compound of formula Ia1, Ib1 or Ic1,

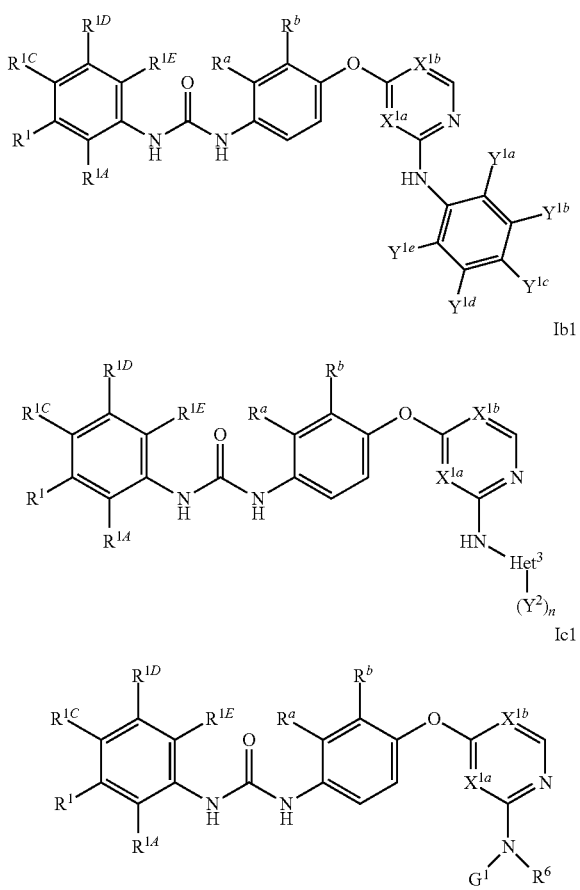

or a pharmaceutically acceptable salt, solvate or isotopic derivative thereof, wherein $R^1$, $R^{1A}$, $R^{1C}$, $R^{1D}$, $R^{1E}$, $R^a$, $R^b$, $Het^3$, $Y^{1a}$ to $Y^{1e}$, $Y^2$, $R^6$ and $G^1$ are as defined in claim 2;

$Y^{1a}$ to $Y^{1e}$ each independently represents H or $Y^1$ as defined in claim 2; and:

one of $X^{1a}$ and $X^{1b}$ represents CH and the other represents CH or N.

12. A compound of formula Ia according to claim 2, wherein either:

$Y^{1a}$ to $Y^{1e}$ are all H; or three or four of $Y^{1a}$ to $Y^{1e}$ are H the remainder of $Y^{1a}$ to $Y^{1e}$ are independently selected from the group consisting of fluoro, chloro, cyano, —S(O)$_2$N(R$^{6e}$)R$^{6f}$, —S(O)$_2$R$^{6g}$, —C(O)OH, —C$_{1-2}$ alkylene-N(R$^{6e}$)R$^{6f}$, —C(O)N(R$^{6e}$)R$^{6f}$, —C(O)N(H)—CH$_2$(CH$_2$)$_{1-2}$—N(R$^{6e}$)R$^{6f}$, —C(O)N(H)—[CH$_2$CH$_2$—O]$_{2-4}$—CH$_3$, —O—S(O)$_2$—CH$_3$, —O—CH$_2$(CH$_2$)$_{1-2}$—N(R$^{6e}$)R$^{6f}$, —O—[CH$_2$CH$_2$—O]$_{2-4}$—CH$_3$, —P(O)(CH$_3$)$_2$, —N=S(O)(CH$_3$)$_2$, —C≡C—H, —CH$_2$OH, methyl and methoxy, which latter two groups are optionally substituted by one or more fluoro atoms.

13. A compound as claimed in claim 1, wherein:
$R^1$ represents —C(O)N(H)—CH$_2$CH$_2$—R$^{3c}$, —CH$_2$—C(O)NH$_2$, —CH$_2$—C(O)N(H)CH$_3$, —CH$_2$—C(O)N(CH$_3$)$_2$, —CH$_2$—C(O)-(morpholin-4-yl)-S(O)—CH$_3$, —S(O)$_2$—CH$_3$, —CH$_2$—S(O)—CH$_3$, —CH$_2$—S(O)$_2$—CH$_3$, —O—S(O)$_2$—CH$_3$, —P(O)(CH$_3$)$_2$, —P(O)(CH$_2$CH$_3$)$_2$, —CH$_2$P(O)(CH$_3$)$_2$, —OCH$_2$P(O)(CH$_3$)$_2$, —CH$_2$NHC(O)CH$_3$, —CH$_2$N(CH$_3$)C(O)CH$_3$, —CH$_2$NHC(O)CH$_2$—N(CH$_3$)$_2$, —CH$_2$NHS(O)$_2$CH$_3$, —O—CH$_2$CH$_2$—OH, —O—CH(CH$_2$OH)$_2$, —O—CH$_2$C(CH$_2$OH)$_3$;

$R^{3c}$ represents [O—CH$_2$CH$_2$]$_{2-4}$—R$^{5a}$ or Het$^2$;

$R^{1A}$ represents H or methoxy, which latter group is optionally substituted by one or more fluoro atoms;

$R^{1C}$ and $R^{1E}$ both represent H;

$R^{1D}$ represents trimethylsilyl, —C(CH$_3$)$_2$—C≡CH, morpholino or C$_{3-5}$ alkyl; and/or Het$^2$ represents a 4-, 5- or 6-membered heterocyclic group that is fully saturated, which group contains one or two heteroatoms selected from the group consisting of N, O and S and which group is optionally substituted by oxo or by one or more methyl groups.

14. A compound as claimed in claim 1 which is a compound selected from the group consisting of:

1-(5-(tert-butyl)-3-(dimethylphosphoryl)-2-methoxyphenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

1-(5-(tert-butyl)-3-(dimethylphosphoryl)-2-methoxyphenyl)-3-(4-((2-((3-methoxy-5-(2-(2-(2-methoxyethoxy)ethoxy)ethoxy)phenyl)amino)pyridin-4-yl)oxy)naphthalen-1-yl)urea;

3-((4-((4-(3-(5-(tert-butyl)-3-(dimethylphosphoryl)-2-methoxyphenyl)ureido)naphthalen-1-yl)oxy)pyridin-2-yl)amino)-5-ethynyl-N-(2-(2-(2-methoxyethoxy)ethoxy)ethyl)benzamide;

1-(5-(tert-butyl)-3-(dimethylphosphoryl)-2-methoxyphenyl)-3-(4-((6-((3-methoxy-5-(2-(2-(2-methoxyethoxy)ethoxy)ethoxy)phenyl)amino)pyrimidin-4-yl)oxy)naphthalen-1-yl)urea;

5-(tert-butyl)-2-methoxy-3-(3-(4-((2-((3-methoxy-5-(2-(2-methoxyethoxy)ethoxy)-ethoxy)phenyl)amino)pyrimidin-4-yl)oxy)naphthalen-1-yl)ureido)phenyl methanesulfonate;

1-(5-(tert-butyl)-3-((dimethylphosphoryl)methoxy)-2-methoxyphenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

5-(tert-butyl)-2-methoxy-3-(3-(4-((2-((3-methoxy-5-(2-(2-methoxyethoxy)ethoxy)ethoxy)phenyl)amino)pyrimidin-4-yl)oxy)naphthalen-1-yl)ureido)-N-(2-(2-(2-methoxyethoxy)ethoxy)ethyl)benzamide;

5-(tert-butyl)-2-methoxy-3-(3-(4-((2-((3-methoxy-5-(2-(2-methoxyethoxy)ethoxy)-ethoxy)phenyl)amino)pyrimidin-4-yl)oxy)naphthalen-1-yl)ureido)-N-(2-morpholinoethyl)-benzamide;

1-(5-(tert-butyl)-2-methoxy-3-(methylsulfonyl)phenyl)-3-(4-((2-((3-methoxy-5-(2-(2-(2-methoxyethoxy)ethoxy)phenyl)amino)pyridin-4-yl)oxy)naphthalen-1-yl)urea;

1-(3-(tert-butyl)-5-(dimethylphosphoryl)phenyl)-3-(4-((2-((3-methoxy-5-(2-(2-(2-methoxy-ethoxy)ethoxy)ethoxy)phenyl)amino)pyridin-4-yl)oxy)naphthalen-1-yl)urea;

1-(5-(tert-butyl)-3-(dimethylphosphoryl)-2-methoxyphenyl)-3-(4-((2-(phenylamino)pyridin-4-yl)oxy)naphthalen-1-yl)urea;

1-(5-(tert-butyl)-2-methoxy-3-(methylsulfinyl)phenyl)-3-(4-((2-(phenylamino)pyridin-4-yl)oxy)naphthalen-1-yl)urea;

2-(5-(tert-butyl)-2-methoxy-3-(3-(4-((2-(phenylamino) pyridin-4-yl)oxy)naphthalen-1-yl)ureido)phenyl)acetamide;

5-(tert-butyl)-2-methoxy-N-(2-morpholinoethyl)-3-(3-(4-((2-(phenylamino)pyridin-4-yl)oxy)naphthalen-1-yl) ureido)benzamide;

1-(5-(tert-butyl)-2-methoxy-3-((methylsulfonyl)methyl) phenyl)-3-(4-((2-((3-methoxy-5-(2-(2-(2-methoxyethoxy)ethoxy)ethoxy)phenyl)amino)pyridin-4-yl) oxy)naphthalen-1-yl)urea;

1-(5-(tert-butyl)-3-(dimethylphosphoryl)-2-methoxyphenyl)-3-(4-((2-(phenylamino)-pyrimidin-4-yl)oxy)naphthalen-1-yl)urea;

5-(tert-butyl)-2-methoxy-3-(3-(4-((2-((3-methoxy-5-(2-(2-(2-methoxyethoxy)ethoxy)-ethoxy)phenyl)amino) pyridin-4-yl)oxy)naphthalen-1-yl)ureido)-N-(2-morpholinoethyl)benzamide;

2-(5-(tert-butyl)-2-methoxy-3-(3-(4-((2-((3-methoxy-5-(2-(2-(2-methoxyethoxy)ethoxy)-ethoxy)phenyl) amino)pyrimidin-4-yl)oxy)naphthalen-1-yl)ureido) phenyl)acetamide;

1-(5-(tert-butyl)-2-methoxy-3-(methylsulfinyl)phenyl)-3-(4-((2-((3-methoxy-5-(2-(2-(2-methoxyethoxy)ethoxy) ethoxy)phenyl)amino)pyridin-4-yl)oxy)naphthalen-1-yl)urea;

1-(5-(tert-butyl)-3-((dimethylphosphoryl)methoxy)-2-methoxyphenyl)-3-(4-((2-(phenylamino)pyrimidin-4-yl)oxy)naphthalen-1-yl)urea;

1-(5-(tert-butyl)-3-((dimethylphosphoryl)methoxy)-2-methoxyphenyl)-3-(4-((2-(phenylamino)pyridin-4-yl) oxy)naphthalen-1-yl)urea;

1-(5-(tert-butyl)-3-(dimethylphosphoryl)-2-methoxyphenyl)-3-(4-((2-((2-methoxy-phenyl)amino)pyrimidin-4-yl)oxy)naphthalen-1-yl)urea;

1-(5-(tert-butyl)-3-(dimethylphosphoryl)-2-methoxyphenyl)-3-(4-((2-((3-methoxy-phenyl)amino)pyrimidin-4-yl)oxy)naphthalen-1-yl)urea;

1-(5-(tert-butyl)-3-(dimethylphosphoryl)-2-methoxyphenyl)-3-(4-((2-((4-methoxy-phenyl)amino)pyrimidin-4-yl)oxy)naphthalen-1-yl)urea;

1-(5-(tert-butyl)-3-(dimethylphosphoryl)-2-methoxyphenyl)-3-(4-((2-((3,4-dimethoxyphenyl)amino)pyrimidin-4-yl)oxy)naphthalen-1-yl)urea;

1-(5-(tert-butyl)-3-(dimethylphosphoryl)-2-methoxyphenyl)-3-(4-((2-((3,5-dimethoxyphenyl)amino)pyrimidin-4-yl)oxy)naphthalen-1-yl)urea;

1-(5-(tert-butyl)-3-(dimethylphosphoryl)-2-methoxyphenyl)-3-(4-((2-((7-methyl-1H-indazol-5-yl)amino)pyrimidin-4-yl)oxy)naphthalen-1-yl)urea;

1-(5-(tert-butyl)-2-methoxy-3-(methylsulfinyl)phenyl)-3-(4-((2-(phenylamino)pyrimidin-4-yl)oxy)naphthalen-1-yl)urea;

1-(5-(tert-butyl)-2-methoxy-3-(methylsulfonyl)phenyl)-3-(4-((2-(phenylamino)pyrimidin-4-yl)oxy)naphthalen-1-yl)urea;

1-(5-(tert-butyl)-2-methoxy-3-(methylsulfonyl)phenyl)-3-(4-((2-(phenylamino)pyridin-4-yl)oxy)naphthalen-1-yl)urea;

1-(5-(tert-butyl)-2-methoxy-3-((methylsulfonyl)methyl) phenyl)-3-(4-((2-(phenylamino)-pyrimidin-4-yl)oxy) naphthalen-1-yl)urea;

1-(5-(tert-butyl)-2-methoxy-3-((methylsulfonyl)methyl) phenyl)-3-(4-((2-(phenylamino)-pyridin-4-yl)oxy) naphthalen-1-yl)urea;

1-(5-(tert-butyl)-3-(dimethylphosphoryl)-2-methoxyphenyl)-3-(4-((2-(pyridin-2-ylamino)pyrimidin-4-yl)oxy) naphthalen-1-yl)urea;

1-(5-(tert-butyl)-3-((dimethylphosphoryl)methoxy)-2-methoxyphenyl)-3-(4-((2-((3,5-dimethoxyphenyl) amino)pyrimidin-4-yl)oxy)naphthalen-1-yl)urea;

5-(tert-butyl)-2-methoxy-N-(2-morpholinoethyl)-3-(3-(4-((2-(phenylamino)pyrimidin-4-yl)oxy)naphthalen-1-yl)ureido)benzamide;

1-(5-(tert-butyl)-3-(dimethylphosphoryl)-2-methoxyphenyl)-3-(4-((2-(pyrazin-2-ylamino)pyrimidin-4-yl)oxy) naphthalen-1-yl)urea;

1-(5-(tert-butyl)-3-(dimethylphosphoryl)-2-methoxyphenyl)-3-(4-((2-(pyrimidin-5-ylamino)pyrimidin-4-yl) oxy)naphthalen-1-yl)urea;

1-(5-(tert-butyl)-3-(dimethylphosphoryl)-2-methoxyphenyl)-3-(4-((2-((1-methyl-1H-pyrazol-4-yl)amino)pyrimidin-4-yl)oxy)naphthalen-1-yl)urea;

3-((4-((4-(3-(5-(tert-butyl)-3-(dimethylphosphoryl)-2-methoxyphenyl)ureido)naphthalen-1-yl)oxy)pyrimidin-2-yl)amino)phenyl methanesulfonate;

5-(tert-butyl)-2-methoxy-3-(3-(4-((2-(phenylamino)pyrimidin-4-yl)oxy)naphthalen-1-yl)ureido)-N-(2-(pyrrolidin-1-yl)ethyl)benzamide;

1-(5-(tert-butyl)-3-(dimethylphosphoryl)-2-methoxyphenyl)-3-(4-((2-((2-oxoindolin-6-yl)amino)pyrimidin-4-yl)oxy)naphthalen-1-yl)urea;

1-(5-(tert-butyl)-3-(dimethylphosphoryl)-2-methoxyphenyl)-3-(4-((2-((2,3-dihydrobenzo[b][1,4]dioxin-6-yl) amino)pyrimidin-4-yl)oxy)naphthalen-1-yl)urea;

1-(5-(tert-butyl)-3-(dimethylphosphoryl)-2-methoxyphenyl)-3-(4-((2-((3-(dimethylphosphoryl)-5-methoxyphenyl)amino)pyrimidin-4-yl)oxy)naphthalen-1-yl) urea;

1-(5-(tert-butyl)-3-(dimethylphosphoryl)-2-methoxyphenyl)-3-(4-((2-((3-((dimethyl(oxo)-lambda-6-sulfanylidene)amino)phenyl)amino)pyrimidin-4-yl)oxy) naphthalen-1-yl)urea;

1-(5-(tert-butyl)-3-(dimethylphosphoryl)-2-methoxyphenyl)-3-(4-((2-((2-methyl-2H-1,2,3-triazol-4-yl)amino) pyrimidin-4-yl)oxy)naphthalen-1-yl)urea;

1-(5-(tert-butyl)-3-(dimethylphosphoryl)-2-methoxyphenyl)-3-(4-((2-((2,2-dioxido-1,3-dihydrobenzo[c]thiophen-5-yl)amino)pyrimidin-4-yl)oxy)naphthalen-1-yl) urea;

1-(5-(tert-butyl)-3-(dimethylphosphoryl)-2-methoxyphenyl)-3-(4-((2-(isoxazol-4-ylamino)pyrimidin-4-yl)oxy) naphthalen-1-yl)urea;

1-(5-(tert-butyl)-3-(dimethylphosphoryl)-2-methoxyphenyl)-3-(4-((2-(pyrazin-2-ylamino)pyridin-4-yl)oxy) naphthalen-1-yl)urea;

5-(tert-butyl)-2-methoxy-3-(3-(4-((2-(phenylamino)pyridin-4-yl)oxy)naphthalen-1-yl)ureido)-N-(2-(piperazin-1-yl)ethyl)benzamide;

1-(5-(tert-butyl)-3-(dimethylphosphoryl)-2-methoxyphenyl)-3-(4-((2-((3-oxoisoindolin-5-yl)amino)pyrimidin-4-yl)oxy)naphthalen-1-yl)urea;

1-(5-(tert-butyl)-3-(diethylphosphoryl)-2-methoxyphenyl)-3-(4-((2-(phenylamino)pyridin-4-yl)oxy)naphthalen-1-yl)urea;

1-(5-(tert-butyl)-3-((dimethylphosphoryl)methyl)-2-methoxyphenyl)-3-(4-((2-(phenylamino)pyridin-4-yl) oxy)naphthalen-1-yl)urea;

1-(5-(tert-butyl)-2-methoxy-3-((methylsulfinyl)methyl) phenyl)-3-(4-((2-(phenylamino)-pyridin-4-yl)oxy) naphthalen-1-yl)urea;

1-(5-(tert-butyl)-3-(dimethylphosphoryl)-2-methoxyphenyl)-3-(4-((2-(pyridin-3-ylamino)pyridin-4-yl)oxy) naphthalen-1-yl)urea;

1-(5-(tert-butyl)-3-(dimethylphosphoryl)-2-methoxyphenyl)-3-(4-((2-((6-(dimethylamino)pyrazin-2-yl)amino)pyridin-4-yl)oxy)naphthalen-1-yl)urea;

N-(4-((4-(3-(5-(tert-butyl)-3-(dimethylphosphoryl)-2-methoxyphenyl)ureido)naphthalen-1-yl)oxy)pyridin-2-yl)-2-((2S,6R)-2,6-dimethylmorpholino)acetamide;

1-(5-(tert-butyl)-3-(dimethylphosphoryl)-2-methoxyphenyl)-3-(4-((2-((3,5-dimethoxyphenyl)amino)pyridin-4-yl)oxy)naphthalen-1-yl)urea;

1-(5-(tert-butyl)-3-(dimethylphosphoryl)-2-methoxyphenyl)-3-(4-((2-((3-methoxy-phenyl)amino)pyridin-4-yl)oxy)naphthalen-1-yl)urea;

5-(tert-butyl)-2-methoxy-3-(3-(4-((2-(phenylamino)pyridin-4-yl)oxy)naphthalen-1-yl)ureido)-N-(2-(pyrrolidin-1-yl)ethyl)benzamide;

1-(5-(tert-butyl)-3-(dimethylphosphoryl)-2-methoxyphenyl)-3-(4-((2-((1-methylpiperidin-4-yl)amino)pyrimidin-4-yl)oxy)naphthalen-1-yl)urea;

(R)-1-(5-(tert-butyl)-3-(dimethylphosphoryl)-2-methoxyphenyl)-3-(4-((2-((tetrahydrofuran-3-yl)amino)pyrimidin-4-yl)oxy)naphthalen-1-yl)urea;

(S)-1-(5-(tert-butyl)-3-(dimethylphosphoryl)-2-methoxyphenyl)-3-(4-((2-((tetrahydrofuran-3-yl)amino)pyrimidin-4-yl)oxy)naphthalen-1-yl)urea;

1-(5-(tert-butyl)-3-(dimethylphosphoryl)-2-methoxyphenyl)-3-(4-((2-(dimethylamino)-pyrimidin-4-yl)oxy)naphthalen-1-yl)urea;

1-(5-(tert-butyl)-3-(dimethylphosphoryl)-2-methoxyphenyl)-3-(4-((2-((2-morpholinoethyl)amino)pyrimidin-4-yl)oxy)naphthalen-1-yl)urea;

1-(5-(tert-butyl)-3-(dimethylphosphoryl)-2-methoxyphenyl)-3-(4-((2-((3,5-dimethyl-phenyl)amino)pyridin-4-yl)oxy)naphthalen-1-yl)urea;

1-(5-(tert-butyl)-3-(dimethylphosphoryl)-2-methoxyphenyl)-3-(4-((2-((3-chloro-5-methylmethylphenyl)amino)pyridin-4-yl)oxy)naphthalen-1-yl)urea;

3-((4-((4-(3-(5-(tert-butyl)-3-(dimethylphosphoryl)-2-methoxyphenyl)ureido)naphthalen-1-yl)oxy)pyridin-2-yl)amino)-5-methoxybenzamide;

1-(5-(tert-butyl)-3-(dimethylphosphoryl)-2-methoxyphenyl)-3-(4-((2-((3-fluoro-5-methoxyphenyl)amino)pyridin-4-yl)oxy)naphthalen-1-yl)urea;

1-(5-(tert-butyl)-3-((dimethylphosphoryl)methyl)-2-methoxyphenyl)-3-(4-((2-((3-methoxy-5-(2-(2-(2-methoxyethoxy)ethoxy)ethoxy)phenyl)amino)pyridin-4-yl)oxy)-naphthalen-1-yl)urea;

2-(5-(tert-butyl)-3-(3-(4-((2-((3,5-dimethoxyphenyl)amino)pyridin-4-yl)oxy)naphthalen-1-yl)ureido)-2-methoxyphenyl)acetamide;

1-(5-(tert-butyl)-3-(dimethylphosphoryl)-2-methoxyphenyl)-3-(4-((2-((tetrahydro-2H-pyran-4-yl)amino)pyrimidin-4-yl)oxy)naphthalen-1-yl)urea;

1-(4-((2-((2-(1H-pyrazol-1-yl)ethyl)amino)pyrimidin-4-yl)oxy)naphthalen-1-yl)-3-(5-(tert-butyl)-3-(dimethylphosphoryl)-2-methoxyphenyl)urea;

1-(5-(tert-butyl)-3-(dimethylphosphoryl)-2-methoxyphenyl)-3-(4-((2-((pyridin-2-ylmethyl)amino)pyrimidin-4-yl)oxy)naphthalen-1-yl)urea;

1-(5-(tert-butyl)-3-(dimethylphosphoryl)-2-methylphenyl)-3-(4-((2-(phenylamino)pyridin-4-yl)oxy)naphthalen-1-yl)urea;

N-(5-(tert-butyl)-2-methoxy-3-(3-(4-((2-(phenylamino)pyridin-4-yl)oxy)naphthalen-1-yl)ureido)benzyl)methanesulfonamide;

2-(5-(tert-butyl)-2-methoxy-3-(3-(4-((2-((3-methoxyphenyl)amino)pyridin-4-yl)oxy)naphthalen-1-yl)ureido)phenyl)acetamide;

1-(5-(tert-butyl)-3-(dimethylphosphoryl)-2-methoxyphenyl)-3-(4-((2-((5-methoxypyridin-3-yl)amino)pyridin-4-yl)oxy)naphthalen-1-yl)urea;

N-(5-(tert-butyl)-2-methoxy-3-(3-(4-((2-(phenylamino)pyridin-4-yl)oxy)naphthalen-1-yl)ureido)benzyl)acetamide;

1-(5-(tert-butyl)-3-(dimethylphosphoryl)-2-methoxyphenyl)-3-(4-((2-((2-methyl-2H-1,2,3-triazol-4-yl)amino)pyridin-4-yl)oxy)naphthalen-1-yl)urea;

1-(5-(tert-butyl)-3-(dimethylphosphoryl)-2-methoxyphenyl)-3-(4-((2-((1-methyl-1H-pyrazol-3-yl)amino)pyridin-4-yl)oxy)naphthalen-1-yl)urea;

N-(2-(azetidin-1-yl)ethyl)-5-(tert-butyl)-2-methoxy-3-(3-(4-((2-(phenylamino)pyridin-4-yl)oxy)naphthalen-1-yl)ureido)benzamide;

(R)-1-(5-(tert-butyl)-2-methoxy-3-(methylsulfinyl)phenyl)-3-(4-((2-(phenylamino)pyridin-4-yl)oxy)naphthalen-1-yl)urea;

(S)-1-(5-(tert-butyl)-2-methoxy-3-(methylsulfinyl)phenyl)-3-(4-((2-(phenylamino)pyridin-4-yl)oxy)naphthalen-1-yl)urea;

1-(5-(tert-butyl)-3-(dimethylphosphoryl)-2-methoxyphenyl)-3-(4-((2-((3-(hydroxymethyl)-5-methoxyphenyl)amino)pyridin-4-yl)oxy)naphthalen-1-yl)urea;

2-(5-(tert-butyl)-2-methoxy-3-(3-(4-((2-((pyridin-2-ylmethyl)amino)pyridin-4-yl)oxy)naphthalen-1-yl)ureido)phenyl)acetamide;

1-(5-(tert-butyl)-3-(dimethylphosphoryl)-2-methoxyphenyl)-3-(4-((2-((pyridin-2-ylmethyl)amino)pyridin-4-yl)oxy)naphthalen-1-yl)urea;

2-(5-(tert-butyl)-3-(3-(4-((2-((3,5-dimethylphenyl)amino)pyridin-4-yl)oxy)naphthalen-1-yl)ureido)-2-methoxyphenyl)acetamide;

1-(4-((2-(benzylamino)pyrimidin-4-yl)oxy)naphthalen-1-yl)-3-(5-(tert-butyl)-3-(dimethylphosphoryl)-2-methoxyphenyl)urea;

2-(5-(tert-butyl)-2-methoxy-3-(3-(4-((2-((3-methoxyphenyl)amino)pyridin-4-yl)oxy)naphthalen-1-yl)ureido)phenyl)-N-methylacetamide;

2-(5-(tert-butyl)-2-methoxy-3-(3-(4-((2-((3-methoxyphenyl)amino)pyridin-4-yl)oxy)naphthalen-1-yl)ureido)phenyl)-N,N-dimethylacetamide;

1-(5-(tert-butyl)-2-methoxy-3-(2-morpholino-2-oxoethyl)phenyl)-3-(4-((2-((3-methoxyphenyl)amino)pyridin-4-yl)oxy)naphthalen-1-yl)urea;

2-(5-(tert-butyl)-2-methoxy-3-(3-(4-((2-((2-methoxypyridin-4-yl)amino)pyridin-4-yl)oxy)naphthalen-1-yl)ureido)phenyl)acetamide;

2-(5-(tert-butyl)-3-(3-(2,3-difluoro-4-((2-(phenylamino)pyridin-4-yl)oxy)phenyl)ureido)-2-methoxyphenyl)acetamide;

2-(5-(tert-butyl)-3-(3-(4-((2-((3-(hydroxymethyl)-5-methoxyphenyl)amino)pyridin-4-yl)oxy)naphthalen-1-yl)ureido)-2-methoxyphenyl)acetamide;

2-(5-(tert-butyl)-2-methoxy-3-(3-(4-((2-((5-methoxypyridin-3-yl)amino)pyridin-4-yl)oxy)naphthalen-1-yl)ureido)phenyl)acetamide;

2-(5-(tert-butyl)-2-methoxy-3-(3-(4-((2-((1-methyl-1H-pyrazol-3-yl)amino)pyridin-4-yl)oxy)naphthalen-1-yl)ureido)phenyl)acetamide;

N-(5-(tert-butyl)-3-(3-(4-((2-((3,5-dimethylphenyl)amino)pyridin-4-yl)oxy)naphthalen-1-yl)ureido)-2-methoxybenzyl)acetamide;

N-(5-(tert-butyl)-2-methoxy-3-(3-(4-((2-((pyridin-2-ylmethyl)amino)pyridin-4-yl)oxy)naphthalen-1-yl)ureido)benzyl)acetamide;

3-((4-((4-(3-(3-(2-amino-2-oxoethyl)-5-(tert-butyl)-2-methoxyphenyl)ureido)naphthalen-1-yl)oxy)pyridin-2-yl)amino)phenyl methanesulfonate;

2-(5-(tert-butyl)-3-(3-(4-((2-((3-(difluoromethoxy)phenyl)amino)pyridin-4-yl)oxy)naphthalen-1-yl)ureido)-2-methoxyphenyl)acetamide;

3-((4-((4-(3-(3-(acetamidomethyl)-5-(tert-butyl)-2-methoxyphenyl)ureido)naphthalen-1-yl)oxy)pyridin-2-yl)amino)-5-methoxy-N-(2-morpholinoethyl)benzamide;

3-((4-((4-(3-(5-(tert-butyl)-2-methoxy-3-((methylsulfinyl)methyl)phenyl)ureido)naphthalen-1-yl)oxy)pyridin-2-yl)amino)-5-methoxy-N-(2-morpholinoethyl)benzamide;

3-((4-((4-(3-(5-(tert-butyl)-3-((dimethylphosphoryl)methyl)-2-methoxyphenyl)ureido)-naphthalen-1-yl)oxy)pyridin-2-yl)amino)-5-methoxy-N-(2-morpholinoethyl)benzamide;

2-(5-(tert-butyl)-2-methoxy-3-(3-(4-((2-((3-(2-morpholinoethoxy)-5-(trifluoromethyl)-phenyl)amino)pyridin-4-yl)oxy)naphthalen-1-yl)ureido)phenyl)acetamide;

1-(5-(tert-butyl)-2-methoxy-3-(methylsulfinyl)phenyl)-3-(4-((2-((3-(2-morpholinoethoxy)-5-(trifluoromethyl)phenyl)amino)pyridin-4-yl)oxy)naphthalen-1-yl)urea;

3-((4-((4-(3-(3-(acetamidomethyl)-5-(tert-butyl)-2-methoxyphenyl)ureido)naphthalen-1-yl)oxy)pyridin-2-yl)amino)-5-methoxy-N-(2-(2-(2-methoxyethoxy)ethoxy)ethyl)benzamide;

3-((4-((4-(3-(5-(tert-butyl)-2-methoxy-3-((methylsulfinyl)methyl)phenyl)ureido)naphthalen-1-yl)oxy)pyridin-2-yl)amino)-5-methoxy-N-(2-(2-(2-methoxyethoxy)ethoxy)ethyl)benzamide;

N-(5-(tert-butyl)-2-methoxy-3-(3-(4-((2-(phenylamino)pyridin-4-yl)oxy)naphthalen-1-yl)ureido)benzyl)-N-methylacetamide;

3-((4-((4-(3-(5-(tert-butyl)-2-methoxy-3-(methylsulfonyl)phenyl)ureido)naphthalen-1-yl)oxy)pyridin-2-yl)amino)-5-methoxy-N-(2-(2-(2-methoxyethoxy)ethoxy)ethyl)benzamide;

3-((4-((4-(3-(3-(acetamidomethyl)-5-(tert-butyl)-2-methoxyphenyl)ureido)naphthalen-1-yl)oxy)pyridin-2-yl)amino)-5-methoxybenzamide;

2-(5-(tert-butyl)-3-(3-(4-((2-((3-(cyclopropylsulfonyl)-5-methoxyphenyl)amino)pyridin-4-yl)oxy)naphthalen-1-yl)ureido)-2-methoxyphenyl)acetamide;

2-(5-(tert-butyl)-3-(3-(4-((2-((3-(dimethylphosphoryl)-5-methoxyphenyl)amino)pyridin-4-yl)oxy)naphthalen-1-yl)ureido)-2-methoxyphenyl)acetamide;

2-(5-(tert-butyl)-3-(3-(2,3-dichloro-4-((2-((3-methoxyphenyl)amino)pyridin-4-yl)oxy)phenyl)ureido)-2-methoxyphenyl)acetamide;

3-((4-(4-(3-(3-(2-amino-2-oxoethyl)-5-(tert-butyl)-2-methoxyphenyl)ureido)-2,3-dichlorophenoxy)pyridin-2-yl)amino)-5-methoxy-N-(2-(2-(2-methoxyethoxy)ethoxy)ethyl)benzamide;

2-(5-(tert-butyl)-3-(3-(4-((2-((3-cyano-5-methoxyphenyl)amino)pyridin-4-yl)oxy)naphthalen-1-yl)ureido)-2-methoxyphenyl)acetamide;

2-(5-(tert-butyl)-2-methoxy-3-(3-(4-((2-((3-methoxy-5-sulfamoylphenyl)amino)pyridin-4-yl)oxy)naphthalen-1-yl)phenyl)acetamide;

2-(5-(tert-butyl)-3-(3-(4-((2-((3-(N,N-dimethylsulfamoyl)-5-methoxyphenyl)amino)pyridin-4-yl)oxy)naphthalen-1-yl)ureido)-2-methoxyphenyl)acetamide;

5-(tert-butyl)-2-methoxy-3-(3-(4-((2-((3-methoxy-5-((2-morpholinoethyl)carbamoyl)-phenyl)amino)pyrimidin-4-yl)oxy)naphthalen-1-yl)ureido)-N-(2-morpholinoethyl)benzamide;

3-((4-((4-(3-(3-(2-amino-2-oxoethyl)-5-(tert-butyl)-2-methoxyphenyl)ureido)naphthalen-1-yl)oxy)pyridin-2-yl)amino)-N-(3-hydroxy-2,2-bis(hydroxymethyl)propyl)-5-methoxybenzamide;

3-((4-((4-(3-(5-(tert-butyl)-3-(dimethylphosphoryl)-2-methoxyphenyl)ureido)naphthalen-1-yl)oxy)pyridin-2-yl)amino)-5-methoxy-N-(2-(1-oxidothiomorpholino)ethyl)benzamide;

3-((4-((4-(3-(5-(tert-butyl)-2-methoxy-3-(methylsulfonyl)phenyl)ureido)naphthalen-1-yl)oxy)pyridin-2-yl)amino)-5-methoxy-N-(2-(1-oxidothiomorpholino)ethyl)benzamide;

4-((4-((4-(3-(5-(tert-butyl)-3-(dimethylphosphoryl)-2-methoxyphenyl)ureido)naphthalen-1-yl)oxy)pyridin-2-yl)amino)-2-methoxy-N-(2-morpholinoethyl)benzamide 4-((4-((4-(3-(5-(tert-butyl)-2-methoxy-3-(methylsulfonyl)phenyl)ureido)naphthalen-1-yl)oxy)pyridin-2-yl)amino)-2-methoxy-N-(2-morpholinoethyl)benzamide 1-(5-(tert-butyl)-3-(dimethylphosphoryl)-2-hydroxyphenyl)-3-(4-((2-(phenylamino)pyridin-4-yl)oxy)naphthalen-1-yl)urea;

1-(5-(tert-butyl)-2-methoxy-3-(methylsulfinyl)phenyl)-3-(4-((2-((3,5-dimethoxyphenyl)amino)pyridin-4-yl)oxy)naphthalen-1-yl)urea;

1-(5-(tert-butyl)-2-methoxy-3-(methylsulfinyl)phenyl)-3-(4-((2-((3-methoxyphenyl)amino)pyridin-4-yl)oxy)naphthalen-1-yl)urea;

1-(5-(tert-butyl)-2-methoxy-3-(methylsulfinyl)phenyl)-3-(4-((2-((pyridin-2-ylmethyl)amino)pyridin-4-yl)oxy)naphthalen-1-yl)urea;

N-(5-(tert-butyl)-2-methoxy-3-(3-(4-((2-((3-methoxyphenyl)amino)pyridin-4-yl)oxy)naphthalen-1-yl)ureido)benzyl)acetamide;

N-(5-(tert-butyl)-3-(3-(4-((2-((3,5-dimethoxyphenyl)amino)pyridin-4-yl)oxy)naphthalen-1-yl)ureido)-2-methoxybenzyl)acetamide;

3-((4-((4-(3-(3-(2-amino-2-oxoethyl)-5-(tert-butyl)-2-methoxyphenyl)ureido)naphthalen-1-yl)oxy)pyridin-2-yl)amino)-5-methoxy-N-(2-morpholinoethyl)benzamide;

3-((4-((4-(3-(5-(tert-butyl)-2-methoxy-3-(methylsulfinyl)phenyl)ureido)naphthalen-1-yl)oxy)pyridin-2-yl)amino)-5-methoxy-N-(2-morpholinoethyl)benzamide;

3-((4-((4-(3-(3-(2-amino-2-oxoethyl)-5-(tert-butyl)-2-methoxyphenyl)ureido)naphthalen-1-yl)oxy)pyridin-2-yl)amino)-5-methoxybenzamide;

3-((4-((4-(3-(5-(tert-butyl)-2-methoxy-3-(methylsulfinyl)phenyl)ureido)naphthalen-1-yl)oxy)pyridin-2-yl)amino)-5-methoxy-N-(2-(2-(2-methoxyethoxy)ethoxy)ethyl)benzamide;

2-(5-(tert-butyl)-3-(3-(4-((2-((3-cyano-5-(2-morpholinoethoxy)phenyl)amino)pyridin-4-yl)oxy)naphthalen-1-yl)ureido)-2-methoxyphenyl)acetamide;

N-(5-(tert-butyl)-3-(3-(4-((2-((3-cyano-5-(2-morpholinoethoxy)phenyl)amino)pyridin-4-yl)oxy)naphthalen-1-yl)ureido)-2-methoxybenzyl)acetamide;

1-(5-(tert-butyl)-2-methoxy-3-(methylsulfinyl)phenyl)-3-(4-((2-((3-cyano-5-(2-morpholinoethoxy)phenyl)amino)pyridin-4-yl)oxy)naphthalen-1-yl)urea;

N-(5-(tert-butyl)-2-methoxy-3-(3-(4-((2-((3-(2-morpholinoethoxy)-5-(trifluoromethyl)phenyl)amino)pyridin-4-yl)oxy)naphthalen-1-yl)ureido)benzyl)acetamide;

3-((4-((4-(3-(2-amino-2-oxoethyl)-5-(tert-butyl)-2-methoxyphenyl)ureido)naphthalen-1-yl)oxy)pyridin-2-yl)amino)-5-methoxy-N-(2-(2-(2-methoxyethoxy)ethoxy)ethyl)benzamide;

3-((4-((4-(3-(5-(tert-butyl)-2-methoxy-3-(methylsulfonyl)phenyl)ureido)naphthalen-1-yl)oxy)pyridin-2-yl)amino)-5-methoxy-N-(2-morpholinoethyl)benzamide;

3-((4-((4-(3-(5-(tert-butyl)-2-methoxy-3-(methylsulfinyl)phenyl)ureido)naphthalen-1-yl)oxy)pyridin-2-yl)amino)-5-methoxybenzamide;

2-(5-(tert-butyl)-2-methoxy-3-(3-(4-((2-((3-methoxy-5-(methylsulfonyl)phenyl)amino)pyridin-4-yl)oxy)naphthalen-1-yl)ureido)phenyl)acetamide;

3-((4-((4-(3-(5-(tert-butyl)-3-(2-hydroxyethoxy)-2-methoxyphenyl)ureido)naphthalen-1-yl)oxy)pyridin-2-yl)amino)-5-methoxybenzamide;

3-((4-((4-(3-(5-(tert-butyl)-3-(dimethylphosphoryl)-2-methoxyphenyl)ureido)naphthalen-1-yl)oxy)pyridin-2-yl)amino)-5-methoxy-N,N-dimethylbenzenesulfonamide;

5-(tert-butyl)-2-methoxy-3-(3-(4-((2-((3-methoxy-5-((2-(2-(2-methoxyethoxy)ethoxy)ethyl)carbamoyl)phenyl)amino)pyridin-4-yl)oxy)naphthalen-1-yl)ureido)-N-(2-morpholinoethyl)benzamide;

5-(tert-butyl)-2-methoxy-3-(3-(4-((2-((3-methoxy-5-((2-morpholinoethyl)carbamoyl)phenyl)amino)pyridin-4-yl)oxy)naphthalen-1-yl)ureido)-N-(2-morpholinoethyl)benzamide;

5-(tert-butyl)-3-(3-(4-((2-((3-carbamoyl-5-methoxyphenyl)amino)pyridin-4-yl)oxy)naphthalen-1-yl)ureido)-2-methoxy-N-(2-morpholinoethyl)benzamide;

5-(tert-butyl)-3-(3-(4-((2-((3,5-dimethoxyphenyl)amino)pyridin-4-yl)oxy)naphthalen-1-yl)ureido)-2-methoxy-N-(2-morpholinoethyl)benzamide;

5-(tert-butyl)-2-methoxy-3-(3-(4-((2-((3-methoxyphenyl)amino)pyridin-4-yl)oxy)naphthalen-1-yl)ureido)-N-(2-morpholinoethyl)benzamide;

5-(tert-butyl)-3-(3-(4-((2-((3,5-dimethoxyphenyl)amino)pyridin-4-yl)oxy)naphthalen-1-yl)ureido)-2-methoxy-N-(2-(1-oxidothiomorpholino)ethyl)benzamide;

3-((4-((4-(3-(3-(2-amino-2-oxoethyl)-5-(tert-butyl)-2-methoxyphenyl)ureido)naphthalen-1-yl)oxy)pyridin-2-yl)amino)-5-methoxy-N-(2-(1-oxidothiomorpholino)ethyl)benzamide;

3-((4-((4-(3-(5-(tert-butyl)-3-((1,3-dihydroxypropan-2-yl)oxy)-2-methoxyphenyl)ureido)naphthalen-1-yl)oxy)pyridin-2-yl)amino)-5-methoxybenzamide;

3-((4-((4-(3-(5-(tert-butyl)-3-(3-hydroxy-2,2-bis(hydroxymethyl)propoxy)-2-methoxyphenyl)ureido)naphthalen-1-yl)oxy)pyridin-2-yl)amino)-5-methoxybenzamide;

3-((4-((4-(3-(3-(2-amino-2-oxoethyl)-5-(tert-butyl)-2-methoxyphenyl)ureido)naphthalen-1-yl)oxy)pyridin-2-yl)amino)-5-methoxy-N-(3-(1-oxidothiomorpholino)propyl)benzamide;

3-((4-((4-(3-(5-(tert-butyl)-2-methoxy-3-(methylsulfinyl)phenyl)ureido)naphthalen-1-yl)oxy)pyridin-2-yl)amino)-5-methoxy-N-(2-(1-oxidothiomorpholino)ethyl)benzamide;

4-((4-((4-(3-(3-(2-amino-2-oxoethyl)-5-(tert-butyl)-2-methoxyphenyl)ureido)naphthalen-1-yl)oxy)pyridin-2-yl)amino)-2-methoxy-N-(2-morpholinoethyl)benzamide;

3-((4-((4-(3-(3-(acetamidomethyl)-5-(tert-butyl)-2-methoxyphenyl)ureido)naphthalen-1-yl)oxy)pyridin-2-yl)amino)-5-methoxy-N-(2-(1-oxidothiomorpholino)ethyl)benzamide;

4-((4-((4-(3-(5-(tert-butyl)-2-methoxy-3-(methylsulfinyl)phenyl)ureido)naphthalen-1-yl)oxy)pyridin-2-yl)amino)-2-methoxy-N-(2-morpholinoethyl)benzamide;

4-((4-((4-(3-(3-(2-amino-2-oxoethyl)-5-(tert-butyl)-2-methoxyphenyl)ureido)naphthalen-1-yl)oxy)pyridin-2-yl)amino)-N-(3-hydroxy-2,2-bis(hydroxymethyl)propyl)-2-methoxybenzamide;

1-(5-(tert-butyl)-2-methoxy-3-(methylsulfinyl)phenyl)-3-(4-((2-((7-methyl-1H-indazol-5-yl)amino)pyrimidin-4-yl)oxy)naphthalen-1-yl)urea;

3-((4-((4-(3-(5-(tert-butyl)-3-(dimethylphosphoryl)-2-methoxyphenyl)ureido)naphthalen-1-yl)oxy)pyridin-2-yl)amino)-5-methoxy-N-methyl-N-(2-morpholinoethyl)benzenesulfonamide;

4-((4-((4-(3-(5-(tert-butyl)-3-(dimethylphosphoryl)-2-methoxyphenyl)ureido)naphthalen-1-yl)oxy)pyridin-2-yl)amino)-2-methoxybenzoic acid;

1-(5-tert-butyl-3-dimethylphosphoryl-2-methoxy-phenyl)-3-[4-[[2-[3-methoxy-4-(4-methylpiperazine-1-carbonyl)anilino]-4-pyridyl]oxy]-1-naphthyl]urea;

4-[[4-[[4-[(5-tert-butyl-3-dimethylphosphoryl-2-methoxy-phenyl)carbamoylamino]-1-naphthyl]oxy]-2-pyridyl]amino]-2-methoxy-N-(1-methyl-4-piperidyl)benzamide;

4-[[4-[[4-[(5-tert-butyl-3-dimethylphosphoryl-2-methoxy-phenyl)carbamoylamino]-1-naphthyl]oxy]-2-pyridyl]amino]-N-(2-dimethylaminoethyl)-2-methoxybenzamide;

1-(5-tert-butyl-3-dimethylphosphoryl-2-methoxy-phenyl)-3-[4-[[2-[3-methoxy-5-[methyl(3-morpholinopropyl)sulfamoyl]anilino]-4-pyridyl]oxy]-1-naphthyl]urea;

1-(5-tert-butyl-2-methoxy-3-methylsulfinyl-phenyl)-3-[4-[[2-[3-cyano-5-(3-morpholinopropoxy)anilino]-4-pyridyl]oxy]-1-naphthyl]urea;

3-[[4-[[4-[(5-tert-butyl-3-dimethylphosphoryl-2-methoxy-phenyl)carbamoylamino]-1-naphthyl]oxy]-2-pyridyl]amino]-N-methyl-5-(2-morpholinoethoxy)benzamide;

3-((4-((4-(3-(5-(tert-butyl)-3-((2-(dimethylamino)acetamido)methyl)-2-methoxyphenyl)ureido)-naphthalen-1-yl)oxy)pyridin-2-yl)amino)-5-methoxy-N-(2-(2-(2-methoxyethoxy)ethoxy)ethyl)-benzamide;

3-((4-((4-(3-(5-(tert-butyl)-3-(dimethylphosphoryl)-2-methoxyphenyl)ureido)naphthalen-1-yl)oxy)pyridin-2-yl)amino)-N-methyl-5-((4-methylpiperazin-1-yl)methyl)benzamide;

4-((4-((4-(3-(5-(tert-butyl)-2-methoxy-3-(methylsulfinyl)phenyl)ureido)naphthalen-1-yl)oxy)pyridin-2-yl)amino)-2-methoxybenzoic acid;

5-(tert-butyl)-3-(3-(4-((2-((3,5-dimethoxyphenyl)amino)pyridin-4-yl)oxy)naphthalen-1-yl)ureido)-2-methoxy-N-(2-(piperazin-1-yl)ethyl)benzamide;

4-((4-((4-(3-(5-(tert-butyl)-2-methoxy-3-(methylsulfonyl)phenyl)ureido)naphthalen-1-yl)oxy)pyrimidin-2-yl)amino)-2-methoxybenzoic acid;

4-((4-((4-(3-(5-(tert-butyl)-2-methoxy-3-(methylsulfinyl)phenyl)ureido)naphthalen-1-yl)oxy)pyrimidin-2-yl)amino)-2-methoxybenzoic acid;

3-((4-((4-(3-(5-(tert-butyl)-3-(dimethylphosphoryl)-2-methoxyphenyl)ureido)naphthalen-1-yl)oxy)pyridin-2-yl)amino)-5-methoxy-N-methyl-N-(2-(4-methylpiperazin-1-yl)ethyl)benzamide;

3-((4-((4-(3-(5-(tert-butyl)-3-(dimethylphosphoryl)-2-methoxyphenyl)ureido)naphthalen-1-yl)oxy)pyridin-2-yl)amino)-5-methoxy-N-methyl-N-(2-(1-methylpiperidin-4-yl)ethyl)benzamide;

3-((4-((4-(3-(5-(tert-Butyl)-3-(dimethylphosphoryl)-2-methoxyphenyl)ureido)naphthalen-1-yl)oxy)pyridin-2-yl)amino)-5-methoxy-N-methyl-N-(2-(4-methylpiperazin-1-yl)ethyl)benzene sulfonamide;

4-((4-((4-(3-(5-(tert-butyl)-2-methoxy-3-(methylsulfo-nyl)phenyl)ureido)naphthalen-1-yl)oxy)pyridin-2-yl)amino)-2-methoxybenzoic acid;

3-((4-((4-(3-(5-(tert-butyl)-3-((2-(dimethylamino)acet-amido)methyl)-2-methoxyphenyl)ureido)-naphthalen-1-yl)oxy)pyrimidin-2-yl)amino)-5-methoxy-N-(2-(2-(2-methoxyethoxy)ethoxy)-ethyl)benzamide;

3-((4-((4-(3-(5-(tert-butyl)-2-methoxy-3-(methylsulfinyl)phenyl)ureido)naphthalen-1-yl)oxy)pyrimidin-2-yl)amino)-5-methoxy-N-(2-(4-methylpiperazin-1-yl)ethyl)benzamide; and 3-((4-((4-(3-(5-(tert-butyl)-2-methoxy-3-(methylsulfinyl)phenyl)ureido)naphthalen-1-yl)oxy)pyridin-2-yl)amino)-5-methoxy-N-(2-(4-methylpiperazin-1-yl)ethyl)benzamide, or a pharmaceutically acceptable salt, solvate or isotopic derivative thereof.

15. A pharmaceutical formulation comprising a compound as defined in claim 1, or pharmaceutically acceptable salt, solvate or isotopic derivative thereof, in admixture with a pharmaceutically acceptable adjuvant, diluent or carrier.

16. A combination product comprising
(A) a compound as defined in claim 1, or pharmaceutically acceptable salt, solvate or isotopic derivative thereof, and
(B) another therapeutic agent,
wherein each of components (A) and (B) is formulated in admixture with a pharmaceutically-acceptable adjuvant, diluent or carrier.

17. A compound selected from the group consisting of:
methyl 4-((4-((4-(((tert-butoxycarbonyl)amino)naphthalen-1-yl)oxy)pyridin-2-yl)amino)-2-methoxybenzoate; and
methyl 4-((4-((4-aminonaphthalen-1-yl)oxy)pyridin-2-yl)amino)-2-methoxybenzoate.

18. A process for the preparation of a compound of formula I according to claim 1, which process comprises:
(a) reaction of a compound of formula II,

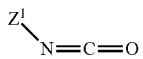

with a compound of formula III,

wherein one of $Z^1$ and $Z^2$ is a structural fragment of formula IV

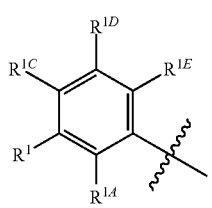

and the other of $Z^1$ and $Z^2$ is a structural fragment of formula V

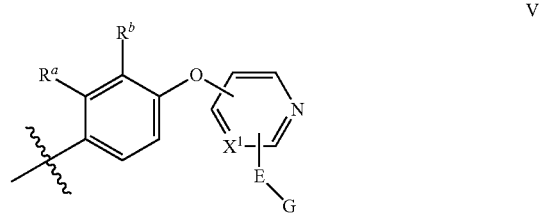

where $R^1$, $R^{1A}$, $R^{1C}$, $R^{1D}$, $R^{1E}$, $R^a$, $R^b$, $X^1$, E and G are as defined in claim 1;

(b) reaction of a compound of formula IIa,

wherein $Z^1$ is as defined above, with a suitable azide-forming agent,
which reaction is followed, without isolation, by thermal rearrangement of the intermediate acyl azide (of formula $Z^1$—C(O)—$N_3$) to provide, in situ, a compound of formula II, which compound is then reacted with a compound of formula III as defined above;

(c) reaction of a compound of formula IIb,

wherein $LG^1$ represents a leaving group and $Z^1$ is as defined above, with a compound of formula III, as defined above;

(d) reaction of a compound of formula VI,

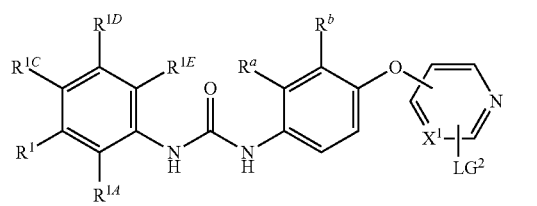

wherein $LG^2$ represents a leaving group and $R^1$, $R^{1A}$, $R^{1C}$, $R^{1D}$, $R^{1E}$, $R^a$, $R^b$ and $X^1$ are as defined in claim 1 with a compound of formula VII,

H-E-G    VII wherein E and G are as defined in claim 1;

(e) for compounds of formula I in which $R^1$ represents $-L^1$-C(O)N($R^{2a}$)$R^{2b}$, reaction of a compound of formula VIII,

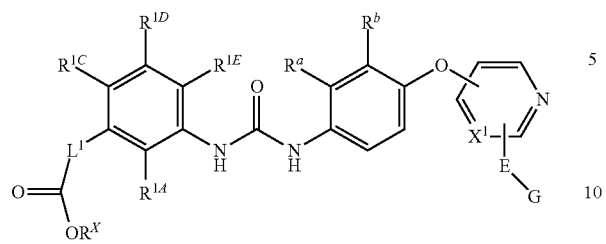

VIII wherein $R^{1A}$, $R^{1C}$, $R^{1D}$, $R^{1E}$, $R^a$, $R^b$, $X^1$, E and G are as defined in claim 1 and $R^X$ represents H or $C_{1-4}$ alkyl, with a compound of formula IX

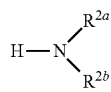

IX wherein $R^{2a}$ and $R^{2b}$ are as defined in claim 1; or (f) deprotection of a protected derivative of a compound of formula I, wherein the protected derivative bears a protecting group on an O- or N-atom of the compound of formula I.

* * * * *

UNITED STATES PATENT AND TRADEMARK OFFICE
CERTIFICATE OF CORRECTION

PATENT NO. : 9,890,185 B2
APPLICATION NO. : 15/105912
DATED : February 13, 2018
INVENTOR(S) : Matthew Colin Thor Fyfe et al.

Page 1 of 1

It is certified that error appears in the above-identified patent and that said Letters Patent is hereby corrected as shown below:

1. In Column 267 at Lines 31-36, replace the text in Claim 17:
"A compound selected from the group consisting of: methyl 4-((4-((4-(((tert-butoxycarbonyl)amino)naphthalen-1-yl)oxy)pyridin-2-yl)amino)-2-methoxybenzoate; and methyl 4-((4-((4-aminonaphthalen-1-yl)oxy)pyridin-2-yl)amino)-2-methoxybenzoate."

With:
--A method of treating an inflammatory disease, said method comprising administering to a subject an effective amount of:
    a compound as defined in claim 1, or a pharmaceutically acceptable salt, solvate or isotopic derivative thereof, or
    a pharmaceutical formulation comprising a compound as defined in claim 1, or a pharmaceutically acceptable salt, solvate or isotopic derivative thereof, in admixture with a pharmaceutically acceptable adjuvant, diluent or carrier, or
    a combination product comprising
        (A) a compound as defined in Claim 1, or pharmaceutically acceptable salt, solvate or isotopic derivative thereof, and
        (B) another therapeutic agent,
wherein each of components (A) and (B) is formulated in admixture with a pharmaceutically-acceptable adjuvant, diluent or carrier, wherein the inflammatory disease is ulcerative colitis, Crohn's disease, uveitis, asthma or COPD.--

Signed and Sealed this
Eighteenth Day of September, 2018

Andrei Iancu
*Director of the United States Patent and Trademark Office*